(12) United States Patent
Stahl et al.

(10) Patent No.: US 7,083,949 B2
(45) Date of Patent: Aug. 1, 2006

(54) RECEPTOR BASED ANTAGONISTS AND METHODS OF MAKING AND USING

(75) Inventors: Neil Stahl, Carmel, NY (US); George D. Yancopoulos, Yorktown Heights, NY (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 0 days.

(21) Appl. No.: 10/287,035

(22) Filed: Nov. 1, 2002

(65) Prior Publication Data

US 2003/0104567 A1 Jun. 5, 2003

Related U.S. Application Data

(63) Continuation-in-part of application No. 09/935,868, filed on Aug. 23, 2001, now abandoned, which is a continuation-in-part of application No. 09/787,835, filed as application No. PCT/US99/22045 on Sep. 22, 1999, now abandoned, which is a continuation-in-part of application No. 09/313,942, filed on May 19, 1999, now Pat. No. 6,472,179.

(60) Provisional application No. 60/101,858, filed on Sep. 25, 1998.

(51) Int. Cl.
*C12P 21/04* (2006.01)
*C07H 21/04* (2006.01)

(52) U.S. Cl. ............. 435/69.7; 435/320.1; 435/252.33; 435/361; 435/348; 435/255.1; 530/350; 536/23.5; 514/12

(58) Field of Classification Search ...................... None
See application file for complete search history.

(56) References Cited

U.S. PATENT DOCUMENTS 5,470,952 A    11/1995    Stahl et al.

6,210,661 B1 *    4/2001    Enssle et al. .............. 424/85.2
6,472,179 B1    10/2002    Stahl et al.

FOREIGN PATENT DOCUMENTS

| EP | 0835939 A2 | 6/1991 |
|---|---|---|
| EP | 0533006 A1 | 9/1992 |
| WO | WO93/19163 | 9/1993 |
| WO | WO93/19777 | 10/1993 |
| WO | WO94/22914 | 10/1994 |
| WO | WO95/06737 | 3/1995 |
| WO | WO96/11213 | 4/1996 |
| WO | WO96/23881 | 8/1996 |
| WO | WO96/35783 | 11/1996 |
| WO | WO97/15669 | 5/1997 |
| WO | WO97/31946 | 9/1997 |
| WO | WO99/37772 | 7/1999 |

OTHER PUBLICATIONS

Barnes, Journal of Clinical Immunology and Allergy. Aug. 2001, vol. 108, Issue 2, part 2, pp. S72-S76.*
The Physicians Desk Reference (PDR, electronic version).*
J. of Biol. Chem., 1995, Greenfeeder, S.A., et al., "Molecular Cloning and Characterization of a Second Subunit of the Interleukin 1 Receptor Complex", 270(23):13757-13765.
Biochem and Biophys Res Comm, 1997, Seipelt, I., et al., "Overexpression, Purification, and Use of a Soluble Human Interleukin-4 Receptor α-chain/Igγ1 Fusion Protein for Ligand Binding Studies," 239:534-542.
FASEB Journal, 1999, Stahl,N., et al., "Cytokine Traps: Heteromeric Receptor-Based Protein Therapeutics that Function as High-Affinity Blockers of Cytokine Action," Abstract, 1457.

* cited by examiner

*Primary Examiner*—Eileen B. O'Hara
(74) *Attorney, Agent, or Firm*—Valeta Gregg, Esq.

(57) ABSTRACT

The present invention provides a fusion polypeptide that forms a multimer that is capable of binding a cytokine to form a nonfunctional complex. It also provides a nucleic acid sequence encoding the fusion polypeptide and methods of making and uses for the fusion polypeptide.

81 Claims, 198 Drawing Sheets

Figure 4A

Amino acid sequence of human gp130-Fc-His6

```
         10          20          30          40          50          60
          *           *           *           *           *           *
MVTLQTWVVQALFIFLTTES TGELLDPCGYISPESPVVQL HSNFTAVCVLKEKCMDYFHV 70          80          90         100         110         120
          *           *           *           *           *           *
NANYIVWKTNHFTIPKEQYT IINRTASSVTFTDIASLNIQ LTCNILTFGQLEQNVYGITI 130         140         150         160         170         180
          *           *           *           *           *           *
ISGLPPEKPKNLSCIVNEGK KMRCEWDGGRETHLETNFTL KSEWATHKFADCKAKRDTPT 190         200         210         220         230         240
          *           *           *           *           *           *
SCTVDYSTVYFVNIEVWVEA ENALGKVTSDHINFDPVYKV KPNPPHNLSVINSEELSSIL 250         260         270         280         290         300
          *           *           *           *           *           *
KLTWTNPSIKSVIILKYNIQ YRTKDASTWSQIPPEDTAST RSSFTVQDLKPFTEYVFRIR 310         320         330         340         350         360
          *           *           *           *           *           *
CMKEDGKGYWSDWSEEASGI TYEDRPSKAPSFWYKIDPSH TQGYRTVQLVWKTLPPFEAN 370         380         390         400         410         420
          *           *           *           *           *           *
GKILDYEVTLTRWKSHLQNY TVNATKLTVNLTNDRYLATL TVRNLVGKSDAAVLTIPACD 430         440         450         460         470         480
          *           *           *           *           *           *
FQATHPVMDLKAFPKDNMLW VEWTTPRESVKKYILEWCVL SDKAPCITDWQQEDGTVHRT 490         500         510         520         530         540
          *           *           *           *           *           *
YLRGNLAESKCYLITVTPVY ADGPGSPESIKAYLKQAPPS KGPTVRTKKVGKNEAVLEWD 550         560         570         580         590         600
          *           *           *           *           *           *
QLPVDVQNGFIRNYTIFYRT IIGNETAVNVDSSHTEYTLS SLTSDTLYMVRMAAYTDEGG 610         620         630         640         650         660
          *           *         * †   †     *           *           *
KDGPEFTFTTPKFAQGEIES GEPKSCDKTHTCPPCPAPEL LGGPSVFLFPPKPKDTLMIS 670         680         690         700         710         720
          *           *           *           *           *           *
RTPEVTCVVVDVSHEDPEVK FNWYVDGVEVHNAKTKPREE QYNSTYRVVSVLTVLHQDWL 730         740         750         760         770         780
          *           *           *           *           *           *
```

Figure 4B

NGKEYKCKVSNKALPAPIEK TISKAKGQPREPQVYTLPPS RDELTKNQVSLTCLVKGFYP

```
       790               800               810               820               830               840
        *                 *                 *                 *                 *                 *
```
SDIAVEWESNGQPENNYKTT PPVLDSDGSFFLYSKLTVDK SRWQQGNVFSCSVMHEALHN

```
       850               860
        *                 *
```
HYTQKSLSLSPGKHHHHHH.

Figure 5

The amino acid sequence of human IL-6Rα-Fc

```
          10           20           30           40           50           60
          *            *            *            *            *            *
MVAVGCALLAALLAAPGAAL  APRRCPAQEVARGVLTSLPG  DSVTLTCPGVEPEDNATVHW 70           80           90          100          110          120
          *            *            *            *            *            *
VLRKPAAGSHPSRWAGMGRR  LLLRSVQLHDSGNYSCYRAG  RPAGTVHLLVDVPPEEPQLS 130          140          150          160          170          180
          *            *            *            *            *            *
CFRKSPLSNVVCEWGPRSTP  SLTTKAVLLVRKFQNSPAED  FQEPCQYSQESQKFSCQLAV 190          200          210          220          230          240
          *            *            *            *            *            *
PEGDSSFYIVSMCVASSVGS  KFSKTQTFQGCGILQPDPPA  NITVTAVARNPRWLSVTWQD 250          260          270          280          290          300
          *            *            *            *            *            *
PHSWNSSFYRLRFELRYRAE  RSKTFTTWMVKDLQHHCVIH  DAWSGLRHVVQLRAQEEFGQ 310          320          330          340          350          360
          *            *            *            *            *            *
GEWSEWSPEAMGTPWTESRS  PPAENEVSTPMQALTTNKDD  DNILFRDSANATSLPVQDAG
                                                 *
         370          380          390          400          410          420
         *†           †            *            *            *            *
EPKSCDKTHTCPPCPAPELL  GGPSVFLFPPKPKDTLMISR  TPEVTCVVVDVSHEDPEVKF 430          440          450          460          470          480
          *            *            *            *            *            *
NWYVDGVEVHNAKTKPREEQ  YNSTYRVVSVLTVLHQDWLN  GKEYKCKVSNKALPAPIEKT 490          500          510          520          530          540
          *            *            *            *            *            *
ISKAKGQPREPQVYTLPPSR  DELTKNQVSLTCLVKGFYPS  DIAVEWESNGQPENNYKTTP 550          560          570          580          590
          *            *            *            *            *
PVLDSDGSFFLYSKLTVDKS  RWQQGNVFSCSVMHEALHNH  YTQKSLSLSPGK.
```

Figure 9A

Amino acid sequence of gp130-Cγ1

```
         10         20         30         40         50         60
          *          *          *          *          *          *
MVTLQTWVVQALFIFLTTES  TGELLDPCGYISPESPVVQL  HSNFTAVCVLKEKCMDYFHV 70         80         90        100        110        120
          *          *          *          *          *          *
NANYIVWKTNHFTIPKEQYT  IINRTASSVTFTDIASLNIQ  LTCNILTFGQLEQNVYGITI 130        140        150        160        170        180
          *          *          *          *          *          *
ISGLPPEKPKNLSCIVNEGK  KMRCEWDGGRETHLETNFTL  KSEWATHKFADCKAKRDTPT 190        200        210        220        230        240
          *          *          *          *          *          *
SCTVDYSTVYFVNIEVWVEA  ENALGKVTSDHINFDPVYKV  KPNPPHNLSVINSEELSSIL 250        260        270        280        290        300
          *          *          *          *          *          *
KLTWTNPSIKSVIILKYNIQ  YRTKDASTWSQIPPEDTAST  RSSFTVQDLKPFTEYVFRIR 310        320        330        340        350        360
          *          *          *          *          *          *
CMKEDGKGYWSDWSEEASGI  TYEDRPSKAPSFWYKIDPSH  TQGYRTVQLVWKTLPPFEAN 370        380        390        400        410        420
          *          *          *          *          *          *
GKILDYEVTLTRWKSHLQNY  TVNATKLTVNLTNDRYLATL  TVRNLVGKSDAAVLTIPACD 430        440        450        460        470        480
          *          *          *          *          *          *
FQATHPVMDLKAFPKDNMLW  VEWTTPRESVKKYILEWCVL  SDKAPCITDWQQEDGTVHRT 490        500        510        520        530        540
          *          *          *          *          *          *
YLRGNLAESKCYLITVTPVY  ADGPGSPESIKAYLKQAPPS  KGPTVRTKKVGKNEAVLEWD 550        560        570        580        590        600
          *          *          *          *          *          *
QLPVDVQNGFIRNYTIFYRT  IIGNETAVNVDSSHTEYTLS  SLTSDTLYMVRMAAYTDEGG 610        620        630        640        650        660
          *          *          *          *          *          *
KDGPEPTFTTPKFAQGEIES  GASTKGPSVFPLAPSSKSTS  GGTAALGCLVKDYFPEPVTV 670        680        690        700        710        720
          *          *          *          *          *          *
SWNSGALTSGVHTFPAVLQS  SGLYSLSSVVTVPSSSLGTQ  TYICNVNHKPSNTKVDKKVE 730        740        750        760        770        780
          *          *          *          *          *          *
PKSCDKTHTCPPCPAPELLG  GPSVFLFPPKPKDTLMISRT  PEVTCVVVDVSHEDPEVKFN
```

Figure 9B

```
          790         800         810         820         830         840
           *           *           *           *           *           *
KYVDGVEVHNAKTKPREEQY NSTYRVVSVLTVLHQDWLNG KEYKCKVSNKALPAPIEKTI 850         860         870         880         890         900
           *           *           *           *           *           *
SKAKGQPREPQVYTLPPSRD ELTKNQVSLTCLVKGFYPSD IAVEWESNGQPENNYKTTPP 910         920         930         940         950
           *           *           *           *           *
VLDSDGSFFLYSKLTVDKSR WQQGNVFSCSVMHEALHNHY TQKSLSLSPGK*
```

Figure 10

Amino acid sequence of gp130Δ3fibro

```
         10          20         30         40         50         60
          *           *          *          *          *          *
MVTLQTWVVQALFIFLTTES TGELLDPCGYISPESPVVQL HSNFTAVCVLKEKCMDYFHV 70          80         90        100        110        120
          *           *          *          *          *          *
NANYIVWKTNHFTIPKEQYT IINRTASSVTFTDIASLNIQ LTCNILTFGQLEQNVYGITI 130         140        150        160        170        180
          *           *          *          *          *          *
ISGLPPEKPKNLSCIVNEGK KMRCEWDGGRETHLETNFTL KSEWATHKFADCKAKRDTPT 190         200        210        220        230        240
          *           *          *          *          *          *
SCTVDYSTVYFVNIEVWVEA ENALGKVTSDHINFDPVYKV KPNPPHNLSVINSEELSSIL 250         260        270        280        290        300
          *           *          *          *          *          *
KLTWTNPSIKSVIILKYNIQ YRTKDASTWSQIPPEDTAST RSSFTVQDLKPFTEYVFRIR 310         320        330
          *           *          *
CMKEDGKGYWSDWSEEASGI TYEDRPSKAPSG
```

Figure 11

Amino acid sequence of J-CH1

```
         10          20          30          40          50          60
          *           *           *           *           *           *
SGGQGTLVTVSSASTKGPSV FPLAPSSKSTSGGTAALGCL VKDYFPEPVTVSWNSGALTS 70          80          90         100         110         120
          *           *           *           *           *           *
GVHTFPAVLQSSGLYSLSSV VTVPSSSLGTQTYICNVNHK PSNTKVDKKVEPKSCDKTHT*
```

Figure 12
Amino acid sequence of Cγ4

```
              10           20           30           40           50           60
               *            *            *            *            *            *
     SGASTKGPSVFPLAPCSRST SESTAALGCLVKDYFPEPVT VSWNSGALTSGVHTFPAVLQ 70           80           90          100          110          120
               *            *            *            *            *            *
     SSGLYSLSSVVTVPSSSLGT KTYTCNVDHKPSNTKVDKRV ESKYGPPCPSCPAPEFLGGP 130          140          150          160          170          180
               *            *            *            *            *            *
     SVFLFPPKPKDTLMISRTPE VTCVVVDVSQEDPEVQFNWY VDGVEVHNAKTKPREEQFNS 190          200          210          220          230          240
               *            *            *            *            *            *
     TYRVVSVLTVLHQDWLNGKE YKCKVSNKGLPSSIEKTISK AKGQPREPQVYTLPPSQEEM 250          260          270          280          290          300
               *            *            *            *            *            *
     TKNQVSLTCLVKGFYPSDIA VEWESNGQPENNYKTTPPVL DSDGSFFLYSRLTVDKSRWQ 310          320          330
               *            *            *
     EGNVFSCSVMHEALHNHYTQ KSLSLSLGK*
```

Figure 13

Amino acid sequence of κ-domain

```
         10          20          30          40          50          60
          *           *           *           *           *           *
SGTVAAPSVFIPPPSDEQLK SGTASVVCLLNNFYPREAKV QWKVDNALQSGNSQESVTEQ 70          80          90         100
          *           *           *           *
DSKDSTYSLSSTLTLSKADY EKHKVYACEVTHQGLSSPVT KSFNRGEC*
```

Figure 14

Amino acid sequence of λ-domain:

```
         10         20         30         40         50         60
          *          *          *          *          *          *
SGPKAAPSVTLFPPSSEELQ ANKATLVCLISDFYPGAVTV AWKADSSPVKAGVETTTPSK 70         80         90        100
          *          *          *          *
QSNNKYAASSYLSLTPEQWK SHRSYSCQVTHEGSTVEKTV APTECS*
```

Figure 15

Amino acid sequence of the soluble IL-6Rα domain

```
          10         20         30         40         50         60
          *          *          *          *          *          *
MVAVGCALLAALLAAPGAAL APRRCPAQEVARGVLTSLPG DSVTLTCPGVEPEDNATVHW 70         80         90        100        110        120
          *          *          *          *          *          *
VLRKPAAGSHPSRWAGMGRR LLLRSVQLHDSGNYSCYRAG RPAGTVHLLVDVPPEEPQLS 130        140        150        160        170        180
          *          *          *          *          *          *
CFRKSPLSNVVCEWGPRSTP SLTTKAVLLVRKFQNSPAED FQEPCQYSQESQKFSCQLAV 190        200        210        220        230        240
          *          *          *          *          *          *
PEGDSSFYIVSMCVASSVGS KFSKTQTFQGCGILQPDPPA NITVTAVARNPRWLSVTWQD 250        260        270        280        290        300
          *          *          *          *          *          *
PHSWNSSFYRLRFELRYRAE RSKTFTTWMVKDLQHHCVIH DAWSGLRHVVQLRAQEEFGQ 310        320        330        340        350        360
          *          *          *          *          *          *
GEWSEWSPEAMGTPWTESRS PPAENEVSTPMQALTTNKDD DNILFRDSANATSLPVQDAG
```

Figure 16

Amino acid sequence of the soluble IL-6Rα313 domain

```
         10          20          30          40          50          60
          *           *           *           *           *           *
MVAVGCALLAALLAAPGAAL APRRCPAQEVARGVLTSLPG DSVTLTCPGVEPEDNATVHW 70          80          90         100         110         120
          *           *           *           *           *           *
VLRKPAAGSHPSRWAGMGRR LLLRSVQLHDSGNYSCYRAG RPAGTVHLLVDVPPEEPQLS 130         140         150         160         170         180
          *           *           *           *           *           *
CFRKSPLSNVVCEWGPRSTP SLTTKAVLLVRKFQNSPAED FQEPCQYSQESQKFSCQLAV 190         200         210         220         230         240
          *           *           *           *           *           *
PEGDSSFYIVSMCVASSVGS KFSKTQTFQGCGILQPDPPA NITVTAVARNPRWLSVTWQD 250         260         270         280         290         300
          *           *           *           *           *           *
PHSWNSSFYRLRFELRYRAE RSKTFTTWMVKDLQHHCVIH DAWSGLRHVVQLRAQEEFGQ

310
          *
GEWSEWSPEAMGTTG
```

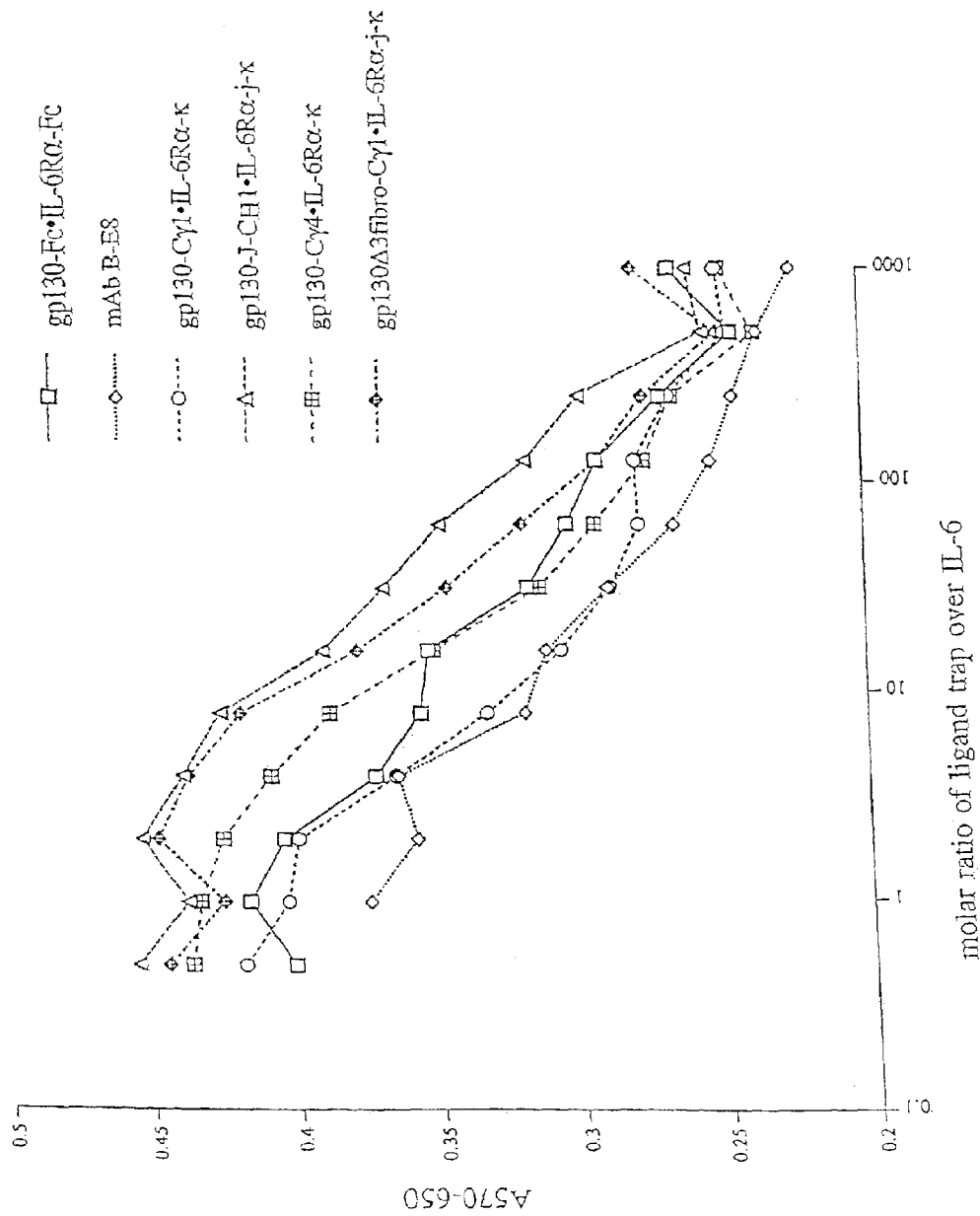

Figure 21A

```
         10             20             30             40
          *              *              *              *
ATG GTG AAG CCA TCA TTA CCA TTC ACA TCC CTC TTA TTC CTG CAG CTG
Met Val Lys Pro Ser Leu Pro Phe Thr Ser Leu Leu Phe Leu Gln Leu>

50             60             70             80             90
  *              *              *              *              *
CCC CTG CTG GGA GTG GGG CTG AAC ACG ACA ATT CTG ACG CCC AAT GGG
Pro Leu Leu Gly Val Gly Leu Asn Thr Thr Ile Leu Thr Pro Asn Gly>

100            110            120            130            140
     *              *              *              *              *
AAT GAA GAC ACC ACA GCT GAT TTC TTC CTG ACC ACT ATG CCC ACT GAC
Asn Glu Asp Thr Thr Ala Asp Phe Phe Leu Thr Thr Met Pro Thr Asp>

150            160            170            180            190
        *              *              *              *              *
TCC CTC AGT GTT TCC ACT CTG CCC CTC CCA GAG GTT CAG TGT TTT GTG
Ser Leu Ser Val Ser Thr Leu Pro Leu Pro Glu Val Gln Cys Phe Val>

200            210            220            230            240
           *              *              *              *              *
TTC AAT GTC GAG TAC ATG AAT TGC ACT TGG AAC AGC AGC TCT GAG CCC
Phe Asn Val Glu Tyr Met Asn Cys Thr Trp Asn Ser Ser Ser Glu Pro>

250            260            270            280
              *              *              *              *
CAG CCT ACC AAC CTC ACT CTG CAT TAT TGG TAC AAG AAC TCG GAT AAT
Gln Pro Thr Asn Leu Thr Leu His Tyr Trp Tyr Lys Asn Ser Asp Asn>

290            300            310            320            330
 *              *              *              *              *
GAT AAA GTC CAG AAG TGC AGC CAC TAT CTA TTC TCT GAA GAA ATC ACT
Asp Lys Val Gln Lys Cys Ser His Tyr Leu Phe Ser Glu Glu Ile Thr>

340            350            360            370            380
    *              *              *              *              *
TCT GGC TGT CAG TTG CAA AAA AAG GAG ATC CAC CTC TAC CAA ACA TTT
Ser Gly Cys Gln Leu Gln Lys Lys Glu Ile His Leu Tyr Gln Thr Phe>

390            400            410            420            430
       *              *              *              *              *
GTT GTT CAG CTC CAG GAC CCA CGG GAA CCC AGG AGA CAG GCC ACA CAG
Val Val Gln Leu Gln Asp Pro Arg Glu Pro Arg Arg Gln Ala Thr Gln>

440            450            460            470            480
          *              *              *              *              *
ATG CTA AAA CTG CAG AAT CTG GTG ATC CCC TGG GCT CCA GAG AAC CTA
Met Leu Lys Leu Gln Asn Leu Val Ile Pro Trp Ala Pro Glu Asn Leu>

490            500            510            520
             *              *              *              *
ACA CTT CAC AAA CTG AGT GAA TCC CAG CTA GAA CTG AAC TGG AAC AAC
Thr Leu His Lys Leu Ser Glu Ser Gln Leu Glu Leu Asn Trp Asn Asn>

530            540            550            560            570
 *              *              *              *              *
AGA TTC TTG AAC CAC TGT TTG GAG CAC TTG GTG CAG TAC CGG ACT GAC
Arg Phe Leu Asn His Cys Leu Glu His Leu Val Gln Tyr Arg Thr Asp>
```

Figure 21B

```
      580              590           600            610           620
       *       *        *      *      *      *       *      *      *
TGG GAC CAC AGC TGG ACT GAA CAA TCA GTG GAT TAT AGA CAT AAG TTC
Trp Asp His Ser Trp Thr Glu Gln Ser Val Asp Tyr Arg His Lys Phe>

630              640           650            660           670
       *       *        *      *      *      *       *      *      *
TCC TTG CCT AGT GTG GAT GGG CAG AAA CGC TAC ACG TTT CGT GTT CGG
Ser Leu Pro Ser Val Asp Gly Gln Lys Arg Tyr Thr Phe Arg Val Arg>

680              690           700            710           720
       *       *        *      *      *      *       *      *      *
AGC CGC TTT AAC CCA CTC TGT GGA AGT GCT CAG CAT TGG AGT GAA TGG
Ser Arg Phe Asn Pro Leu Cys Gly Ser Ala Gln His Trp Ser Glu Trp>

730              740           750            760
             *       *        *      *      *      *       *      *      *
AGC CAC CCA ATC CAC TGG GGG AGC AAT ACT TCA AAA GAG AAC GCG TCG
Ser His Pro Ile His Trp Gly Ser Asn Thr Ser Lys Glu Asn Ala Ser>

770              780           790            800           810
 *       *        *      *      *      *       *      *      *
TCT GGG AAC ATG AAG GTC CTG CAG GAG CCC ACC TGC GTC TCC GAC TAC
Ser Gly Asn Met Lys Val Leu Gln Glu Pro Thr Cys Val Ser Asp Tyr>

820              830           840            850           860
       *       *        *      *      *      *       *      *      *
ATG AGC ATC TCT ACT TGC GAG TGG AAG ATG AAT GGT CCC ACC AAT TGC
Met Ser Ile Ser Thr Cys Glu Trp Lys Met Asn Gly Pro Thr Asn Cys>

870              880           890            900           910
       *       *        *      *      *      *       *      *      *
AGC ACC GAG CTC CGC CTG TTG TAC CAG CTG GTT TTT CTG CTC TCC GAA
Ser Thr Glu Leu Arg Leu Leu Tyr Gln Leu Val Phe Leu Leu Ser Glu>

920              930           940            950           960
             *       *        *      *      *      *       *      *      *
GCC CAC ACG TGT ATC CCT GAG AAC AAC GGA GGC GCG GGG TGC GTG TGC
Ala His Thr Cys Ile Pro Glu Asn Asn Gly Gly Ala Gly Cys Val Cys>

970              980           990            1000
             *       *        *      *      *      *       *      *      *
CAC CTG CTC ATG GAT GAC GTG GTC AGT GCG GAT AAC TAT ACA CTG GAC
His Leu Leu Met Asp Asp Val Val Ser Ala Asp Asn Tyr Thr Leu Asp>

1010             1020          1030           1040          1050
 *       *        *      *      *      *       *      *      *
CTG TGG GCT GGG CAG CAG CTG CTG TGG AAG GGC TCC TTC AAG CCC AGC
Leu Trp Ala Gly Gln Gln Leu Leu Trp Lys Gly Ser Phe Lys Pro Ser>

1060             1070          1080           1090          1100
       *       *        *      *      *      *       *      *      *
GAG CAT GTG AAA CCC AGG GCC CCA GGA AAC CTG ACA GTT CAC ACC AAT
Glu His Val Lys Pro Arg Ala Pro Gly Asn Leu Thr Val His Thr Asn>

1110             1120          1130           1140          1150
             *       *        *      *      *      *       *      *      *
GTC TCC GAC ACT CTG CTG CTG ACC TGG AGC AAC CCG TAT CCC CCT GAC
Val Ser Asp Thr Leu Leu Leu Thr Trp Ser Asn Pro Tyr Pro Pro Asp>

```
AAT TAC CTG TAT AAT CAT CTC ACC TAT GCA GTC AAC ATT TGG AGT GAA
Asn Tyr Leu Tyr Asn His Leu Thr Tyr Ala Val Asn Ile Trp Ser Glu>

1210          1220          1230          1240
    *      *      *      *      *      *      *      *
AAC GAC CCG GCA GAT TTC AGA ATC TAT AAC GTG ACC TAC CTA GAA CCC
Asn Asp Pro Ala Asp Phe Arg Ile Tyr Asn Val Thr Tyr Leu Glu Pro>

1250         1260          1270          1280          1290
  *      *      *      *      *      *      *      *      *
TCC CTC CGC ATC GCA GCC AGC ACC CTG AAG TCT GGG ATT TCC TAC AGG
Ser Leu Arg Ile Ala Ala Ser Thr Leu Lys Ser Gly Ile Ser Tyr Arg>

1300          1310          1320          1330          1340
    *      *      *      *      *      *      *      *      *
GCA CGG GTG AGG GCC TGG GCT CAG TGC TAT AAC ACC ACC TGG AGT GAG
Ala Arg Val Arg Ala Trp Ala Gln Cys Tyr Asn Thr Thr Trp Ser Glu>

1350          1360          1370          1380          1390
    *      *      *      *      *      *      *      *      *
TGG AGC CCC AGC ACC AAG TGG CAC AAC TCC TAC AGG GAG CCC TTC GAG
Trp Ser Pro Ser Thr Lys Trp His Asn Ser Tyr Arg Glu Pro Phe Glu>

1400          1410          1420          1430          1440
    *      *      *      *      *      *      *      *      *
CAG TCC GGA GAC AAA ACT CAC ACA TGC CCA CCG TGC CCA GCA CCT GAA
Gln Ser Gly Asp Lys Thr His Thr Cys Pro Pro Cys Pro Ala Pro Glu>

1450          1460          1470          1480
    *      *      *      *      *      *      *      *      *
CTC CTG GGG GGA CCG TCA GTC TTC CTC TTC CCC CCA AAA CCC AAG GAC
Leu Leu Gly Gly Pro Ser Val Phe Leu Phe Pro Pro Lys Pro Lys Asp>

1490         1500          1510          1520          1530
  *      *      *      *      *      *      *      *      *
ACC CTC ATG ATC TCC CGG ACC CCT GAG GTC ACA TGC GTG GTG GTG GAC
Thr Leu Met Ile Ser Arg Thr Pro Glu Val Thr Cys Val Val Val Asp>

1540          1550          1560          1570          1580
    *      *      *      *      *      *      *      *      *
GTG AGC CAC GAA GAC CCT GAG GTC AAG TTC AAC TGG TAC GTG GAC GGC
Val Ser His Glu Asp Pro Glu Val Lys Phe Asn Trp Tyr Val Asp Gly>

1590          1600          1610          1620          1630
    *      *      *      *      *      *      *      *      *
GTG GAG GTG CAT AAT GCC AAG ACA AAG CCG CGG GAG GAG CAG TAC AAC
Val Glu Val His Asn Ala Lys Thr Lys Pro Arg Glu Glu Gln Tyr Asn>

1640          1650          1660          1670          1680
    *      *      *      *      *      *      *      *      *
AGC ACG TAC CGT GTG GTC AGC GTC CTC ACC GTC CTG CAC CAG GAC TGG
Ser Thr Tyr Arg Val Val Ser Val Leu Thr Val Leu His Gln Asp Trp>

1690          1700          1710          1720
    *      *      *      *      *      *      *      *      *
CTG AAT GGC AAG GAG TAC AAG TGC AAG GTC TCC AAC AAA GCC CTC CCA
Leu Asn Gly Lys Glu Tyr Lys Cys Lys Val Ser Asn Lys Ala Leu Pro>

1730         1740          1750          1760          1770
  *      *      *      *      *      *      *      *      *
GCC CCC ATC GAG AAA ACC ATC TCC AAA GCC AAA GGG CAG CCC CGA GAA
Ala Pro Ile Glu Lys Thr Ile Ser Lys Ala Lys Gly Gln Pro Arg Glu>
```

Figure 21D

```
         1780            1790            1800             1810            1820
           *               *               *    *           *              *  *
      CCA CAG GTG TAC ACC CTG CCC CCA TCC CGG GAG GAG ATG ACC AAG AAC
      Pro Gln Val Tyr Thr Leu Pro Pro Ser Arg Glu Glu Met Thr Lys Asn>

1830            1840            1850             1860            1870
         *   *             *               *   *            *   *            *
      CAG GTC AGC CTG ACC TGC CTG GTC AAA GGC TTC TAT CCC AGC GAC ATC
      Gln Val Ser Leu Thr Cys Leu Val Lys Gly Phe Tyr Pro Ser Asp Ile>

1880            1890            1900            1910            1920
           *   *           *   *            *    *          *   *          *   *
      GCC GTG GAG TGG GAG AGC AAT GGG CAG CCG GAG AAC AAC TAC AAG ACC
      Ala Val Glu Trp Glu Ser Asn Gly Gln Pro Glu Asn Asn Tyr Lys Thr>

1930            1940            1950            1960
             *     *           *     *          *    *          *    *         *
      ACG CCT CCC GTG CTG GAC TCC GAC GGC TCC TTC TTC CTC TAT AGC AAG
      Thr Pro Pro Val Leu Asp Ser Asp Gly Ser Phe Phe Leu Tyr Ser Lys>

1970            1980            1990            2000            2010
        *             *    *           *     *         *               *   *    *
      CTC ACC GTG GAC AAG AGC AGG TGG CAG CAG GGG AAC GTC TTC TCA TGC
      Leu Thr Val Asp Lys Ser Arg Trp Gln Gln Gly Asn Val Phe Ser Cys>

2020            2030            2040             2050            2060
           *               *               *    *           *               *
      TCC GTG ATG CAT GAG GCT CTG CAC AAC CAC TAC ACG CAG AAG AGC CTC
      Ser Val Met His Glu Ala Leu His Asn His Tyr Thr Gln Lys Ser Leu>

2070            2080
          *    *           *    *        *
      TCC CTG TCT CCG GGT AAA TGA
      Ser Leu Ser Pro Gly Lys ***>
```

Figure 22A

```
            10          20          30          40
             *           *           *           *
ATG GTG AAG CCA TCA TTA CCA TTC ACA TCC CTC TTA TTC CTG CAG CTG
Met Val Lys Pro Ser Leu Pro Phe Thr Ser Leu Leu Phe Leu Gln Leu>

50          60          70          80          90
  *           *           *           *           *
CCC CTG CTG GGA GTG GGG CTG AAC ACG ACA ATT CTG ACG CCC AAT GGG
Pro Leu Leu Gly Val Gly Leu Asn Thr Thr Ile Leu Thr Pro Asn Gly>

100         110         120         130         140
     *           *           *           *           *
AAT GAA GAC ACC ACA GCT GAT TTC TTC CTG ACC ACT ATG CCC ACT GAC
Asn Glu Asp Thr Thr Ala Asp Phe Phe Leu Thr Thr Met Pro Thr Asp>

150         160         170         180         190
        *           *           *           *           *
TCC CTC AGT GTT TCC ACT CTG CCC CTC CCA GAG GTT CAG TGT TTT GTG
Ser Leu Ser Val Ser Thr Leu Pro Leu Pro Glu Val Gln Cys Phe Val>

200         210         220         230         240
           *           *           *           *           *
TTC AAT GTC GAG TAC ATG AAT TGC ACT TGG AAC AGC AGC TCT GAG CCC
Phe Asn Val Glu Tyr Met Asn Cys Thr Trp Asn Ser Ser Ser Glu Pro>

250         260         270         280
              *           *           *           *
CAG CCT ACC AAC CTC ACT CTG CAT TAT TGG TAC AAG AAC TCG GAT AAT
Gln Pro Thr Asn Leu Thr Leu His Tyr Trp Tyr Lys Asn Ser Asp Asn>

290         300         310         320         330
  *           *           *           *           *
GAT AAA GTC CAG AAG TGC AGC CAC TAT CTA TTC TCT GAA GAA ATC ACT
Asp Lys Val Gln Lys Cys Ser His Tyr Leu Phe Ser Glu Glu Ile Thr>

340         350         360         370         380
     *           *           *           *           *
TCT GGC TGT CAG TTG CAA AAA AAG GAG ATC CAC CTC TAC CAA ACA TTT
Ser Gly Cys Gln Leu Gln Lys Lys Glu Ile His Leu Tyr Gln Thr Phe>

390         400         410         420         430
        *           *           *           *           *
GTT GTT CAG CTC CAG GAC CCA CGG GAA CCC AGG AGA CAG GCC ACA CAG
Val Val Gln Leu Gln Asp Pro Arg Glu Pro Arg Arg Gln Ala Thr Gln>

440         450         460         470         480
           *           *           *           *           *
ATG CTA AAA CTG CAG AAT CTG GTG ATC CCC TGG GCT CCA GAG AAC CTA
Met Leu Lys Leu Gln Asn Leu Val Ile Pro Trp Ala Pro Glu Asn Leu>

490         500         510         520
              *           *           *           *
ACA CTT CAC AAA CTG AGT GAA TCC CAG CTA GAA CTG AAC TGG AAC AAC
Thr Leu His Lys Leu Ser Glu Ser Gln Leu Glu Leu Asn Trp Asn Asn>

530         540         550         560         570
  *           *           *           *           *
AGA TTC TTG AAC CAC TGT TTG GAG CAC TTG GTG CAG TAC CGG ACT GAC
Arg Phe Leu Asn His Cys Leu Glu His Leu Val Gln Tyr Arg Thr Asp>
```

Figure 22B

```
       580           590           600           610           620
        *    *    *    *    *    *    *    *    *    *
TGG GAC CAC AGC TGG ACT GAA CAA TCA GTG GAT TAT AGA CAT AAG TTC
Trp Asp His Ser Trp Thr Glu Gln Ser Val Asp Tyr Arg His Lys Phe>

630           640           650           660           670
        *    *    *    *    *    *    *    *    *    *
TCC TTG CCT AGT GTG GAT GGG CAG AAA CGC TAC ACG TTT CGT GTT CGG
Ser Leu Pro Ser Val Asp Gly Gln Lys Arg Tyr Thr Phe Arg Val Arg>

680           690           700           710           720
        *    *    *    *    *    *    *    *    *    *
AGC CGC TTT AAC CCA CTC TGT GGA AGT GCT CAG CAT TGG AGT GAA TGG
Ser Arg Phe Asn Pro Leu Cys Gly Ser Ala Gln His Trp Ser Glu Trp>

730           740           750           760
        *    *    *    *    *    *    *    *    *
AGC CAC CCA ATC CAC TGG GGG AGC AAT ACT TCA AAA GAG AAC GGG AAC
Ser His Pro Ile His Trp Gly Ser Asn Thr Ser Lys Glu Asn Gly Asn>

770           780           790           800           810
 *    *    *    *    *    *    *    *    *    *
ATG AAG GTC CTG CAG GAG CCC ACC TGC GTC TCC GAC TAC ATG AGC ATC
Met Lys Val Leu Gln Glu Pro Thr Cys Val Ser Asp Tyr Met Ser Ile>

820           830           840           850           860
        *    *    *    *    *    *    *    *    *    *
TCT ACT TGC GAG TGG AAG ATG AAT GGT CCC ACC AAT TGC AGC ACC GAG
Ser Thr Cys Glu Trp Lys Met Asn Gly Pro Thr Asn Cys Ser Thr Glu>

870           880           890           900           910
        *    *    *    *    *    *    *    *    *    *
CTC CGC CTG TTG TAC CAG CTG GTT TTT CTG CTC TCC GAA GCC CAC ACG
Leu Arg Leu Leu Tyr Gln Leu Val Phe Leu Leu Ser Glu Ala His Thr>

920           930           940           950           960
        *    *    *    *    *    *    *    *    *    *
TGT ATC CCT GAG AAC AAC GGA GGC GCG GGG TGC GTG TGC CAC CTG CTC
Cys Ile Pro Glu Asn Asn Gly Gly Ala Gly Cys Val Cys His Leu Leu>

970           980           990          1000
        *    *    *    *    *    *    *    *    *
ATG GAT GAC GTG GTC AGT GCG GAT AAC TAT ACA CTG GAC CTG TGG GCT
Met Asp Asp Val Val Ser Ala Asp Asn Tyr Thr Leu Asp Leu Trp Ala>

1010          1020          1030          1040          1050
 *    *    *    *    *    *    *    *    *    *
GGG CAG CAG CTG CTG TGG AAG GGC TCC TTC AAG CCC AGC GAG CAT GTG
Gly Gln Gln Leu Leu Trp Lys Gly Ser Phe Lys Pro Ser Glu His Val>

1060          1070          1080          1090          1100
        *    *    *    *    *    *    *    *    *    *
AAA CCC AGG GCC CCA GGA AAC CTG ACA GTT CAC ACC AAT GTC TCC GAC
Lys Pro Arg Ala Pro Gly Asn Leu Thr Val His Thr Asn Val Ser Asp>

1110          1120          1130          1140          1150
        *    *    *    *    *    *    *    *    *    *
ACT CTG CTG CTG ACC TGG AGC AAC CCG TAT CCC CCT GAC AAT TAC CTG
Thr Leu Leu Leu Thr Trp Ser Asn Pro Tyr Pro Pro Asp Asn Tyr Leu>

```
TAT AAT CAT CTC ACC TAT GCA GTC AAC ATT TGG AGT GAA AAC GAC CCG
Tyr Asn His Leu Thr Tyr Ala Val Asn Ile Trp Ser Glu Asn Asp Pro>

1210          1220          1230          1240
           *             *             *             *     *
GCA GAT TTC AGA ATC TAT AAC GTG ACC TAC CTA GAA CCC TCC CTC CGC
Ala Asp Phe Arg Ile Tyr Asn Val Thr Tyr Leu Glu Pro Ser Leu Arg>

1250          1260          1270          1280          1290
   *             *             *             *             *
   ATC GCA GCC AGC ACC CTG AAG TCT GGG ATT TCC TAC AGG GCA CGG GTG
   Ile Ala Ala Ser Thr Leu Lys Ser Gly Ile Ser Tyr Arg Ala Arg Val>

1300          1310          1320          1330          1340
           *             *             *             *             *
AGG GCC TGG GCT CAG AGC TAT AAC ACC ACC TGG AGT GAG TGG AGC CCC
Arg Ala Trp Ala Gln Ser Tyr Asn Thr Thr Trp Ser Glu Trp Ser Pro>

1350          1360          1370          1380          1390
           *             *             *             *             *
AGC ACC AAG TGG CAC AAC TCC TAC AGG GAG CCC TTC GAG CAG TCC GGA
Ser Thr Lys Trp His Asn Ser Tyr Arg Glu Pro Phe Glu Gln Ser Gly>

1400          1410          1420          1430          1440
           *             *             *             *             *
GAC AAA ACT CAC ACA TGC CCA CCG TGC CCA GCA CCT GAA CTC CTG GGG
Asp Lys Thr His Thr Cys Pro Pro Cys Pro Ala Pro Glu Leu Leu Gly>

1450          1460          1470          1480
                *             *             *             *     *
       GGA CCG TCA GTC TTC CTC TTC CCC CCA AAA CCC AAG GAC ACC CTC ATG
       Gly Pro Ser Val Phe Leu Phe Pro Pro Lys Pro Lys Asp Thr Leu Met>

1490          1500          1510          1520          1530
  *             *             *             *             *     *
ATC TCC CGG ACC CCT GAG GTC ACA TGC GTG GTG GTG GAC GTG AGC CAC
Ile Ser Arg Thr Pro Glu Val Thr Cys Val Val Val Asp Val Ser His>

1540          1550          1560          1570          1580
      *             *             *             *             *
GAA GAC CCT GAG GTC AAG TTC AAC TGG TAC GTG GAC GGC GTG GAG GTG
Glu Asp Pro Glu Val Lys Phe Asn Trp Tyr Val Asp Gly Val Glu Val>

1590          1600          1610          1620          1630
           *             *             *             *             *
CAT AAT GCC AAG ACA AAG CCG CGG GAG GAG CAG TAC AAC AGC ACG TAC
His Asn Ala Lys Thr Lys Pro Arg Glu Glu Gln Tyr Asn Ser Thr Tyr>

1640          1650          1660          1670          1680
           *             *             *             *             *
CGT GTG GTC AGC GTC CTC ACC GTC CTG CAC CAG GAC TGG CTG AAT GGC
Arg Val Val Ser Val Leu Thr Val Leu His Gln Asp Trp Leu Asn Gly>

1690          1700          1710          1720
                *             *             *             *     *
     AAG GAG TAC AAG TGC AAG GTC TCC AAC AAA GCC CTC CCA GCC CCC ATC
     Lys Glu Tyr Lys Cys Lys Val Ser Asn Lys Ala Leu Pro Ala Pro Ile>

1730          1740          1750          1760          1770
           *             *             *             *             *
GAG AAA ACC ATC TCC AAA GCC AAA GGG CAG CCC CGA GAA CCA CAG GTG
Glu Lys Thr Ile Ser Lys Ala Lys Gly Gln Pro Arg Glu Pro Gln Val>
```

Figure 22D

```
              1780                1790                1800                1810                1820
               *                   *                   *                   *                   *
         TAC ACC CTG CCC CCA TCC CGG GAT GAG CTG ACC AAG AAC CAG GTC AGC
         Tyr Thr Leu Pro Pro Ser Arg Asp Glu Leu Thr Lys Asn Gln Val Ser>

1830                1840                1850                1860                1870
               *                   *                   *                   *                   *
         CTG ACC TGC CTG GTC AAA GGC TTC TAT CCC AGC GAC ATC GCC GTG GAG
         Leu Thr Cys Leu Val Lys Gly Phe Tyr Pro Ser Asp Ile Ala Val Glu>

1880                1890                1900                1910                1920
               *                   *                   *                   *                   *
         TGG GAG AGC AAT GGG CAG CCG GAG AAC AAC TAC AAG ACC ACG CCT CCC
         Trp Glu Ser Asn Gly Gln Pro Glu Asn Asn Tyr Lys Thr Thr Pro Pro>

1930                1940                1950                1960
               *                   *                   *                   *
         GTG CTG GAC TCC GAC GGC TCC TTC TTC CTC TAT AGC AAG CTC ACC GTG
         Val Leu Asp Ser Asp Gly Ser Phe Phe Leu Tyr Ser Lys Leu Thr Val>

1970                1980                1990                2000                2010
          *                   *                   *                   *                   *
         GAC AAG AGC AGG TGG CAG CAG GGG AAC GTC TTC TCA TGC TCC GTG ATG
         Asp Lys Ser Arg Trp Gln Gln Gly Asn Val Phe Ser Cys Ser Val Met>

2020                2030                2040                2050                2060
               *                   *                   *                   *                   *
         CAT GAG GCT CTG CAC AAC CAC TAC ACG CAG AAG AGC CTC TCC CTG TCT
         His Glu Ala Leu His Asn His Tyr Thr Gln Lys Ser Leu Ser Leu Ser>

2070
               *
         CCG GGT AAA TGA
         Pro Gly Lys ***>
```

Figure 23A

```
         10             20             30             40
          *              *              *              *              *
ATG GTG AAG CCA TCA TTA CCA TTC ACA TCC CTC TTA TTC CTG CAG CTG
Met Val Lys Pro Ser Leu Pro Phe Thr Ser Leu Leu Phe Leu Gln Leu>

50             60             70             80             90
   *              *              *              *              *              *
CCC CTG CTG GGA GTG GGG CTG AAC ACG ACA ATT CTG ACG CCC AAT GGG
Pro Leu Leu Gly Val Gly Leu Asn Thr Thr Ile Leu Thr Pro Asn Gly>

100            110            120            130            140
       *              *              *              *              *
AAT GAA GAC ACC ACA GCT GAT TTC TTC CTG ACC ACT ATG CCC ACT GAC
Asn Glu Asp Thr Thr Ala Asp Phe Phe Leu Thr Thr Met Pro Thr Asp>

150            160            170            180            190
          *              *              *              *              *              *
TCC CTC AGT GTT TCC ACT CTG CCC CTC CCA GAG GTT CAG TGT TTT GTG
Ser Leu Ser Val Ser Thr Leu Pro Leu Pro Glu Val Gln Cys Phe Val>

200            210            220            230            240
             *              *              *              *              *              *
TTC AAT GTC GAG TAC ATG AAT TGC ACT TGG AAC AGC AGC TCT GAG CCC
Phe Asn Val Glu Tyr Met Asn Cys Thr Trp Asn Ser Ser Ser Glu Pro>

250            260            270            280
                *              *              *              *              *
CAG CCT ACC AAC CTC ACT CTG CAT TAT TGG TAC AAG AAC TCG GAT AAT
Gln Pro Thr Asn Leu Thr Leu His Tyr Trp Tyr Lys Asn Ser Asp Asn>

290            300            310            320            330
   *              *              *              *              *              *
GAT AAA GTC CAG AAG TGC AGC CAC TAT CTA TTC TCT GAA GAA ATC ACT
Asp Lys Val Gln Lys Cys Ser His Tyr Leu Phe Ser Glu Glu Ile Thr>

340            350            360            370            380
       *              *              *              *              *
TCT GGC TGT CAG TTG CAA AAA AAG GAG ATC CAC CTC TAC CAA ACA TTT
Ser Gly Cys Gln Leu Gln Lys Lys Glu Ile His Leu Tyr Gln Thr Phe>

390            400            410            420            430
          *              *              *              *              *              *
GTT GTT CAG CTC CAG GAC CCA CGG GAA CCC AGG AGA CAG GCC ACA CAG
Val Val Gln Leu Gln Asp Pro Arg Glu Pro Arg Arg Gln Ala Thr Gln>

440            450            460            470            480
             *              *              *              *              *              *
ATG CTA AAA CTG CAG AAT CTG GTG ATC CCC TGG GCT CCA GAG AAC CTA
Met Leu Lys Leu Gln Asn Leu Val Ile Pro Trp Ala Pro Glu Asn Leu>

490            500            510            520
                *              *              *              *              *
ACA CTT CAC AAA CTG AGT GAA TCC CAG CTA GAA CTG AAC TGG AAC AAC
Thr Leu His Lys Leu Ser Glu Ser Gln Leu Glu Leu Asn Trp Asn Asn>

530            540            550            560            570
   *              *              *              *              *              *
AGA TTC TTG AAC CAC TGT TTG GAG CAC TTG GTG CAG TAC CGG ACT GAC
Arg Phe Leu Asn His Cys Leu Glu His Leu Val Gln Tyr Arg Thr Asp>
```

Figure 23B

```
         580            590            600            610            620
          *      *       *      *       *      *       *      *       *
TGG GAC CAC AGC TGG ACT GAA CAA TCA GTG GAT TAT AGA CAT AAG TTC
Trp Asp His Ser Trp Thr Glu Gln Ser Val Asp Tyr Arg His Lys Phe>

630            640            650            660            670
          *      *       *      *       *      *       *      *       *
TCC TTG CCT AGT GTG GAT GGG CAG AAA CGC TAC ACG TTT CGT GTT CGG
Ser Leu Pro Ser Val Asp Gly Gln Lys Arg Tyr Thr Phe Arg Val Arg>

680            690            700            710            720
          *      *       *      *       *      *       *      *       *
AGC CGC TTT AAC CCA CTC TGT GGA AGT GCT CAG CAT TGG AGT GAA TGG
Ser Arg Phe Asn Pro Leu Cys Gly Ser Ala Gln His Trp Ser Glu Trp>

730            740            750            760
          *      *       *      *       *      *       *      *       *
AGC CAC CCA ATC CAC TGG GGG AGC AAT ACT TCA AAA GAG AAC GCG TCG
Ser His Pro Ile His Trp Gly Ser Asn Thr Ser Lys Glu Asn Ala Ser>

770            780            790            800            810
 *      *       *      *       *      *       *      *       *
TCT GGG AAC ATG AAG GTC CTG CAG GAG CCC ACC TGC GTC TCC GAC TAC
Ser Gly Asn Met Lys Val Leu Gln Glu Pro Thr Cys Val Ser Asp Tyr>

820            830            840            850            860
          *      *       *      *       *      *       *      *       *
ATG AGC ATC TCT ACT TGC GAG TGG AAG ATG AAT GGT CCC ACC AAT TGC
Met Ser Ile Ser Thr Cys Glu Trp Lys Met Asn Gly Pro Thr Asn Cys>

870            880            890            900            910
          *      *       *      *       *      *       *      *       *
AGC ACC GAG CTC CGC CTG TTG TAC CAG CTG GTT TTT CTG CTC TCC GAA
Ser Thr Glu Leu Arg Leu Leu Tyr Gln Leu Val Phe Leu Leu Ser Glu>

920            930            940            950            960
          *      *       *      *       *      *       *      *       *
GCC CAC ACG TGT ATC CCT GAG AAC AAC GGA GGC GCG GGT GCG TGT GC
Ala His Thr Cys Ile Pro Glu Asn Asn Gly Gly Ala Gly Cys Val Cys>

970            980            990            1000
          *      *       *      *       *      *       *      *       *
CAC CTG CTC ATG GAT GAC GTG GTC AGT GCG GAT AAC TAT ACA CTG GAC
His Leu Leu Met Asp Asp Val Val Ser Ala Asp Asn Tyr Thr Leu Asp>

1010           1020           1030           1040           1050
 *      *       *      *       *      *       *      *       *
CTG TGG GCT GGG CAG CAG CTG CTG TGG AAG GGC TCC TTC AAG CCC AGC
Leu Trp Ala Gly Gln Gln Leu Leu Trp Lys Gly Ser Phe Lys Pro Ser>

1060           1070           1080           1090           1100
          *      *       *      *       *      *       *      *       *
GAG CAT GTG AAA CCC AGG GCC CCA GGA AAC CTG ACA GTT CAC ACC AAT
Glu His Val Lys Pro Arg Ala Pro Gly Asn Leu Thr Val His Thr Asn>

1110           1120           1130           1140           1150
          *      *       *      *       *      *       *      *       *
GTC TCC GAC ACT CTG CTG CTG ACC TGG AGC AAC CCG TAT CCC CCT GAC
Val Ser Asp Thr Leu Leu Leu Thr Trp Ser Asn Pro Tyr Pro Pro Asp>

```
AAT TAC CTG TAT AAT CAT CTC ACC TAT GCA GTC AAC ATT TGG AGT GAA
Asn Tyr Leu Tyr Asn His Leu Thr Tyr Ala Val Asn Ile Trp Ser Glu>

1210      1220      1230      1240
          *         *         *         *         *
AAC GAC CCG GCA GAT TTC AGA ATC TAT AAC GTG ACC TAC CTA GAA CCC
Asn Asp Pro Ala Asp Phe Arg Ile Tyr Asn Val Thr Tyr Leu Glu Pro>

1250      1260      1270      1280      1290
   *         *         *         *         *         *
TCC CTC CGC ATC GCA GCC AGC ACC CTG AAG TCT GGG ATT TCC TAC AGG
Ser Leu Arg Ile Ala Ala Ser Thr Leu Lys Ser Gly Ile Ser Tyr Arg>

1300      1310      1320      1330      1340
   *         *         *         *         *
GCA CGG GTG AGG GCC TGG GCT CAG AGC TAT AAC ACC ACC TGG AGT GAG
Ala Arg Val Arg Ala Trp Ala Gln Ser Tyr Asn Thr Thr Trp Ser Glu>

1350      1360      1370      1380      1390
          *         *         *         *         *
TGG AGC CCC AGC ACC AAG TGG CAC AAC TCC TAC AGG GAG CCC TTC GAG
Trp Ser Pro Ser Thr Lys Trp His Asn Ser Tyr Arg Glu Pro Phe Glu>

1400      1410      1420      1430      1440
          *         *         *         *         *
CAG TCC GGA GAC AAA ACT CAC ACA TGC CCA CCG TGC CCA GCA CCT GAA
Gln Ser Gly Asp Lys Thr His Thr Cys Pro Pro Cys Pro Ala Pro Glu>

1450      1460      1470      1480
          *         *         *         *         *
CTC CTG GGG GGA CCG TCA GTC TTC CTC TTC CCC CCA AAA CCC AAG GAC
Leu Leu Gly Gly Pro Ser Val Phe Leu Phe Pro Pro Lys Pro Lys Asp>

1490      1500      1510      1520      1530
   *         *         *         *         *         *
ACC CTC ATG ATC TCC CGG ACC CCT GAG GTC ACA TGC GTG GTG GTG GAC
Thr Leu Met Ile Ser Arg Thr Pro Glu Val Thr Cys Val Val Val Asp>

1540      1550      1560      1570      1580
   *         *         *         *         *
GTG AGC CAC GAA GAC CCT GAG GTC AAG TTC AAC TGG TAC GTG GAC GGC
Val Ser His Glu Asp Pro Glu Val Lys Phe Asn Trp Tyr Val Asp Gly>

1590      1600      1610      1620      1630
          *         *         *         *         *
GTG GAG GTG CAT AAT GCC AAG ACA AAG CCG CGG GAG GAG CAG TAC AAC
Val Glu Val His Asn Ala Lys Thr Lys Pro Arg Glu Glu Gln Tyr Asn>

1640      1650      1660      1670      1680
          *         *         *         *         *
AGC ACG TAC CGT GTG GTC AGC GTC CTC ACC GTC CTG CAC CAG GAC TGG
Ser Thr Tyr Arg Val Val Ser Val Leu Thr Val Leu His Gln Asp Trp>

1690      1700      1710      1720
          *         *         *         *         *
CTG AAT GGC AAG GAG TAC AAG TGC AAG GTC TCC AAC AAA GCC CTC CCA
Leu Asn Gly Lys Glu Tyr Lys Cys Lys Val Ser Asn Lys Ala Leu Pro>

1730      1740      1750      1760      1770
   *         *         *         *         *         *
GCC CCC ATC GAG AAA ACC ATC TCC AAA GCC AAA GGG CAG CCC CGA GAA
Ala Pro Ile Glu Lys Thr Ile Ser Lys Ala Lys Gly Gln Pro Arg Glu>
```

Figure 23D

```
        1780            1790            1800            1810            1820
          *               *               *               *               *
      CCA CAG GTG TAC ACC CTG CCC CCA TCC CGG GAT GAG CTG ACC AAG AAC
      Pro Gln Val Tyr Thr Leu Pro Pro Ser Arg Asp Glu Leu Thr Lys Asn>

1830            1840            1850            1860            1870
          *               *               *               *               *
      CAG GTC AGC CTG ACC TGC CTG GTC AAA GGC TTC TAT CCC AGC GAC ATC
      Gln Val Ser Leu Thr Cys Leu Val Lys Gly Phe Tyr Pro Ser Asp Ile>

1880            1890            1900            1910            1920
          *               *               *               *               *
      GCC GTG GAG TGG GAG AGC AAT GGG CAG CCG GAG AAC AAC TAC AAG ACC
      Ala Val Glu Trp Glu Ser Asn Gly Gln Pro Glu Asn Asn Tyr Lys Thr>

1930            1940            1950            1960
          *               *               *               *           *
      ACG CCT CCC GTG CTG GAC TCC GAC GGC TCC TTC TTC CTC TAT AGC AAG
      Thr Pro Pro Val Leu Asp Ser Asp Gly Ser Phe Phe Leu Tyr Ser Lys>

1970            1980            1990            2000            2010
     *               *               *               *               *
      CTC ACC GTG GAC AAG AGC AGG TGG CAG CAG GGG AAC GTC TTC TCA TGC
      Leu Thr Val Asp Lys Ser Arg Trp Gln Gln Gly Asn Val Phe Ser Cys>

2020            2030            2040            2050            2060
          *               *               *               *               *
      TCC GTG ATG CAT GAG GCT CTG CAC AAC CAC TAC ACG CAG AAG AGC CTC
      Ser Val Met His Glu Ala Leu His Asn His Tyr Thr Gln Lys Ser Leu>

2070            2080
          *               *           *
      TCC CTG TCT CCG GGT AAA TGA
      Ser Leu Ser Pro Gly Lys ***>
```

Figure 24A

```
             10             20             30             40
         *       *      *       *      *       *      *       *       *
ATG GTG GCC GTC GGC TGC GCG CTG CTG GCT GCC CTG CTG GCC GCG CCG
Met Val Ala Val Gly Cys Ala Leu Leu Ala Ala Leu Leu Ala Ala Pro>

50             60             70             80             90
  *       *      *       *      *       *      *       *      *       *
GGA GCG GCG CTG GCC CCA AGG CGC TGC CCT GCG CAG GAG GTG GCA AGA
Gly Ala Ala Leu Ala Pro Arg Arg Cys Pro Ala Gln Glu Val Ala Arg>

100            110            120            130            140
  *       *      *       *      *       *      *       *      *       *
GGC GTG CTG ACC AGT CTG CCA GGA GAC AGC GTG ACT CTG ACC TGC CCG
Gly Val Leu Thr Ser Leu Pro Gly Asp Ser Val Thr Leu Thr Cys Pro>

150            160            170            180            190
  *       *      *       *      *       *      *       *      *       *
GGG GTA GAG CCG GAA GAC AAT GCC ACT GTT CAC TGG GTG CTC AGG AAG
Gly Val Glu Pro Glu Asp Asn Ala Thr Val His Trp Val Leu Arg Lys>

200            210            220            230            240
  *       *      *       *      *       *      *       *      *       *
CCG GCT GCA GGC TCC CAC CCC AGC AGA TGG GCT GGC ATG GGA AGG AGG
Pro Ala Ala Gly Ser His Pro Ser Arg Trp Ala Gly Met Gly Arg Arg>

250            260            270            280
  *       *      *       *      *       *      *       *      *
CTG CTG CTG AGG TCG GTG CAG CTC CAC GAC TCT GGA AAC TAT TCA TGC
Leu Leu Leu Arg Ser Val Gln Leu His Asp Ser Gly Asn Tyr Ser Cys>

290            300            310            320            330
  *       *      *       *      *       *      *       *      *       *
TAC CGG GCC GGC CGC CCA GCT GGG ACT GTG CAC TTG CTG GTG GAT GTT
Tyr Arg Ala Gly Arg Pro Ala Gly Thr Val His Leu Leu Val Asp Val>

340            350            360            370            380
  *       *      *       *      *       *      *       *      *
CCC CCC GAG GAG CCC CAG CTC TCC TGC TTC CGG AAG AGC CCC CTC AGC
Pro Pro Glu Glu Pro Gln Leu Ser Cys Phe Arg Lys Ser Pro Leu Ser>

390            400            410            420            430
  *       *      *       *      *       *      *       *      *       *
AAT GTT GTT TGT GAG TGG GGT CCT CGG AGC ACC CCA TCC CTG ACG ACA
Asn Val Val Cys Glu Trp Gly Pro Arg Ser Thr Pro Ser Leu Thr Thr>

440            450            460            470            480
  *       *      *       *      *       *      *       *      *       *
AAG GCT GTG CTC TTG GTG AGG AAG TTT CAG AAC AGT CCG GCC GAA GAC
Lys Ala Val Leu Leu Val Arg Lys Phe Gln Asn Ser Pro Ala Glu Asp>

490            500            510            520
  *       *      *       *      *       *      *       *      *
TTC CAG GAG CCG TGC CAG TAT TCC CAG GAG TCC CAG AAG TTC TCC TGC
Phe Gln Glu Pro Cys Gln Tyr Ser Gln Glu Ser Gln Lys Phe Ser Cys>

530            540            550            560            570
  *       *      *       *      *       *      *       *      *       *
CAG TTA GCA GTC CCG GAG GGA GAC AGC TCT TTC TAC ATA GTG TCC ATG
Gln Leu Ala Val Pro Glu Gly Asp Ser Ser Phe Tyr Ile Val Ser Met>
```

Figure 24B

```
        580           590           600           610           620
   *     *     *     *     *     *     *     *     *     *
TGC GTC GCC AGT AGT GTC GGG AGC AAG TTC AGC AAA ACT CAA ACC TTT
Cys Val Ala Ser Ser Val Gly Ser Lys Phe Ser Lys Thr Gln Thr Phe>

630           640           650           660           670
     *     *     *     *     *     *     *     *     *     *
CAG GGT TGT GGA ATC TTG CAG CCT GAT CCG CCT GCC AAC ATC ACA GTC
Gln Gly Cys Gly Ile Leu Gln Pro Asp Pro Pro Ala Asn Ile Thr Val>

680           690           700           710           720
     *     *     *     *     *     *     *     *     *     *
ACT GCC GTG GCC AGA AAC CCC CGC TGG CTC AGT GTC ACC TGG CAA GAC
Thr Ala Val Ala Arg Asn Pro Arg Trp Leu Ser Val Thr Trp Gln Asp>

730           740           750           760
     *     *     *     *     *     *     *     *     *
CCC CAC TCC TGG AAC TCA TCT TTC TAC AGA CTA CGG TTT GAG CTC AGA
Pro His Ser Trp Asn Ser Ser Phe Tyr Arg Leu Arg Phe Glu Leu Arg>

770           780           790           800           810
   *     *     *     *     *     *     *     *     *     *
TAT CGG GCT GAA CGG TCA AAG ACA TTC ACA ACA TGG ATG GTC AAG GAC
Tyr Arg Ala Glu Arg Ser Lys Thr Phe Thr Thr Trp Met Val Lys Asp>

820           830           840           850           860
   *     *     *     *     *     *     *     *     *     *
CTC CAG CAT CAC TGT GTC ATC CAC GAC GCC TGG AGC GGC CTG AGG CAC
Leu Gln His His Cys Val Ile His Asp Ala Trp Ser Gly Leu Arg His>

870           880           890           900           910
     *     *     *     *     *     *     *     *     *     *
GTG GTG CAG CTT CGT GCC CAG GAG GAG TTC GGG CAA GGC GAG TGG AGC
Val Val Gln Leu Arg Ala Gln Glu Glu Phe Gly Gln Gly Glu Trp Ser>

920           930           940           950           960
         *     *     *     *     *     *     *     *     *     *
GAG TGG AGC CCG GAG GCC ATG GGC ACG CCT TGG ACA GAA TCC AGG AGT
Glu Trp Ser Pro Glu Ala Met Gly Thr Pro Trp Thr Glu Ser Arg Ser>

970           980           990           1000
     *     *     *     *     *     *     *     *     *
CCT CCA GCT GAG AAC GAG GTG TCC ACC CCC ATG ACC GGT GGC GCG CCT
Pro Pro Ala Glu Asn Glu Val Ser Thr Pro Met Thr Gly Gly Ala Pro>

1010          1020          1030          1040          1050
   *     *     *     *     *     *     *     *     *     *
TCA GGT GCT CAG CTG GAA CTT CTA GAC CCA TGT GGT TAT ATC AGT CCT
Ser Gly Ala Gln Leu Glu Leu Leu Asp Pro Cys Gly Tyr Ile Ser Pro>

1060          1070          1080          1090          1100
   *     *     *     *     *     *     *     *     *     *
GAA TCT CCA GTT GTA CAA CTT CAT TCT AAT TTC ACT GCA GTT TGT GTG
Glu Ser Pro Val Val Gln Leu His Ser Asn Phe Thr Ala Val Cys Val>

1110          1120          1130          1140          1150
     *     *     *     *     *     *     *     *     *     *
CTA AAG GAA AAA TGT ATG GAT TAT TTT CAT GTA AAT GCT AAT TAC ATT
Leu Lys Glu Lys Cys Met Asp Tyr Phe His Val Asn Ala Asn Tyr Ile>

```
         GTC TGG AAA ACA AAC CAT TTT ACT ATT CCT AAG GAG CAA TAT ACT ATC
         Val Trp Lys Thr Asn His Phe Thr Ile Pro Lys Glu Gln Tyr Thr Ile>

1210        1220        1230        1240
           *     *     *     *     *     *     *     *     *
         ATA AAC AGA ACA GCA TCC AGT GTC ACC TTT ACA GAT ATA GCT TCA TTA
         Ile Asn Arg Thr Ala Ser Ser Val Thr Phe Thr Asp Ile Ala Ser Leu>

1250        1260        1270        1280        1290
     *     *     *     *     *     *     *     *     *     *
         AAT ATT CAG CTC ACT TGC AAC ATT CTT ACA TTC GGA CAG CTT GAA CAG
         Asn Ile Gln Leu Thr Cys Asn Ile Leu Thr Phe Gly Gln Leu Glu Gln>

1300        1310        1320        1330        1340
           *     *     *     *     *     *     *     *     *     *
         AAT GTT TAT GGA ATC ACA ATA ATT TCA GGC TTG CCT CCA GAA AAA CCT
         Asn Val Tyr Gly Ile Thr Ile Ile Ser Gly Leu Pro Pro Glu Lys Pro>

1350        1360        1370        1380        1390
           *     *     *     *     *     *     *     *     *     *
         AAA AAT TTG AGT TGC ATT GTG AAC GAG GGG AAG AAA ATG AGG TGT GAG
         Lys Asn Leu Ser Cys Ile Val Asn Glu Gly Lys Lys Met Arg Cys Glu>

1400        1410        1420        1430        1440
           *     *     *     *     *     *     *     *     *     *
         TGG GAT GGT GGA AGG GAA ACA CAC TTG GAG ACA AAC TTC ACT TTA AAA
         Trp Asp Gly Gly Arg Glu Thr His Leu Glu Thr Asn Phe Thr Leu Lys>

1450        1460        1470        1480
                *     *     *     *     *     *     *     *     *
         TCT GAA TGG GCA ACA CAC AAG TTT GCT GAT TGC AAA GCA AAA CGT GAC
         Ser Glu Trp Ala Thr His Lys Phe Ala Asp Cys Lys Ala Lys Arg Asp>

1490        1500        1510        1520        1530
     *     *     *     *     *     *     *     *     *     *
         ACC CCC ACC TCA TGC ACT GTT GAT TAT TCT ACT GTG TAT TTT GTC AAC
         Thr Pro Thr Ser Cys Thr Val Asp Tyr Ser Thr Val Tyr Phe Val Asn>

1540        1550        1560        1570        1580
           *     *     *     *     *     *     *     *     *
         ATT GAA GTC TGG GTA GAA GCA GAG AAT GCC CTT GGG AAG GTT ACA TCA
         Ile Glu Val Trp Val Glu Ala Glu Asn Ala Leu Gly Lys Val Thr Ser>

1590        1600        1610        1620        1630
           *     *     *     *     *     *     *     *     *     *
         GAT CAT ATC AAT TTT GAT CCT GTA TAT AAA GTG AAG CCC AAT CCG CCA
         Asp His Ile Asn Phe Asp Pro Val Tyr Lys Val Lys Pro Asn Pro Pro>

1640        1650        1660        1670        1680
           *     *     *     *     *     *     *     *     *     *
         CAT AAT TTA TCA GTG ATC AAC TCA GAG GAA CTG TCT AGT ATC TTA AAA
         His Asn Leu Ser Val Ile Asn Ser Glu Glu Leu Ser Ser Ile Leu Lys>

1690        1700        1710        1720
                *     *     *     *     *     *     *     *     *
         TTG ACA TGG ACC AAC CCA AGT ATT AAG AGT GTT ATA ATA CTA AAA TAT
         Leu Thr Trp Thr Asn Pro Ser Ile Lys Ser Val Ile Ile Leu Lys Tyr>

1730        1740        1750        1760        1770
           *     *     *     *     *     *     *     *     *     *
         AAC ATT CAA TAT AGG ACC AAA GAT GCC TCA ACT TGG AGC CAG ATT CCT
         Asn Ile Gln Tyr Arg Thr Lys Asp Ala Ser Thr Trp Ser Gln Ile Pro>
```

Figure 24D

```
      1780          1790          1800          1810          1820
        *     *       *     *       *     *       *     *       *
CCT GAA GAC ACA GCA TCC ACC CGA TCT TCA TTC ACT GTC CAA GAC CTT
Pro Glu Asp Thr Ala Ser Thr Arg Ser Ser Phe Thr Val Gln Asp Leu>

1830          1840          1850          1860          1870
        *     *       *     *       *     *       *     *       *
AAA CCT TTT ACA GAA TAT GTG TTT AGG ATT CGC TGT ATG AAG GAA GAT
Lys Pro Phe Thr Glu Tyr Val Phe Arg Ile Arg Cys Met Lys Glu Asp>

1880          1890          1900          1910          1920
        *     *       *     *       *     *       *     *       *
GGT AAG GGA TAC TGG AGT GAC TGG AGT GAA GAA GCA AGT GGG ATC ACC
Gly Lys Gly Tyr Trp Ser Asp Trp Ser Glu Glu Ala Ser Gly Ile Thr>

1930          1940          1950          1960
        *       *     *       *     *       *     *       *     *
TAT GAA GAT AGA CCA TCT AAA GCA CCA AGT TTC TGG TAT AAA ATA GAT
Tyr Glu Asp Arg Pro Ser Lys Ala Pro Ser Phe Trp Tyr Lys Ile Asp>

1970          1980          1990          2000          2010
  *     *       *     *       *     *       *     *       *     *
CCA TCC CAT ACT CAA GGC TAC AGA ACT GTA CAA CTC GTG TGG AAG ACA
Pro Ser His Thr Gln Gly Tyr Arg Thr Val Gln Leu Val Trp Lys Thr>

2020          2030          2040          2050          2060
        *     *       *     *       *     *       *     *       *
TTG CCT CCT TTT GAA GCC AAT GGA AAA ATC TTG GAT TAT GAA GTG ACT
Leu Pro Pro Phe Glu Ala Asn Gly Lys Ile Leu Asp Tyr Glu Val Thr>

2070          2080          2090          2100          2110
        *     *       *     *       *     *       *     *       *
CTC ACA AGA TGG AAA TCA CAT TTA CAA AAT TAC ACA GTT AAT GCC ACA
Leu Thr Arg Trp Lys Ser His Leu Gln Asn Tyr Thr Val Asn Ala Thr>

2120          2130          2140          2150          2160
        *     *       *     *       *     *       *     *       *
AAA CTG ACA GTA AAT CTC ACA AAT GAT CGC TAT CTA GCA ACC CTA ACA
Lys Leu Thr Val Asn Leu Thr Asn Asp Arg Tyr Leu Ala Thr Leu Thr>

2170          2180          2190          2200
        *       *     *       *     *       *     *       *     *
GTA AGA AAT CTT GTT GGC AAA TCA GAT GCA GCT GTT TTA ACT ATC CCT
Val Arg Asn Leu Val Gly Lys Ser Asp Ala Ala Val Leu Thr Ile Pro>

2210          2220          2230          2240          2250
  *     *       *     *       *     *       *     *       *     *
GCC TGT GAC TTT CAA GCT ACT CAC CCT GTA ATG GAT CTT AAA GCA TTC
Ala Cys Asp Phe Gln Ala Thr His Pro Val Met Asp Leu Lys Ala Phe>

2260          2270          2280          2290          2300
        *     *       *     *       *     *       *     *       *
CCC AAA GAT AAC ATG CTT TGG GTG GAA TGG ACT ACT CCA AGG GAA TCT
Pro Lys Asp Asn Met Leu Trp Val Glu Trp Thr Thr Pro Arg Glu Ser>

2310          2320          2330          2340          2350
        *     *       *     *       *     *       *     *       *
GTA AAG AAA TAT ATA CTT GAG TGG TGT GTG TTA TCA GAT AAA GCA CCC
Val Lys Lys Tyr Ile Leu Glu Trp Cys Val Leu Ser Asp Lys Ala Pro>

```
TGT ATC ACA GAC TGG CAA CAA GAA GAT GGT ACC GTG CAT CGC ACC TAT
Cys Ile Thr Asp Trp Gln Gln Glu Asp Gly Thr Val His Arg Thr Tyr>

2410          2420          2430          2440
TTA AGA GGG AAC TTA GCA GAG AGC AAA TGC TAT TTG ATA ACA GTT ACT
Leu Arg Gly Asn Leu Ala Glu Ser Lys Cys Tyr Leu Ile Thr Val Thr>

2450          2460          2470          2480          2490
CCA GTA TAT GCT GAT GGA CCA GGA AGC CCT GAA TCC ATA AAG GCA TAC
Pro Val Tyr Ala Asp Gly Pro Gly Ser Pro Glu Ser Ile Lys Ala Tyr>

2500          2510          2520          2530          2540
CTT AAA CAA GCT CCA CCT TCC AAA GGA CCT ACT GTT CGG ACA AAA AAA
Leu Lys Gln Ala Pro Pro Ser Lys Gly Pro Thr Val Arg Thr Lys Lys>

2550          2560          2570          2580          2590
GTA GGG AAA AAC GAA GCT GTC TTA GAG TGG GAC CAA CTT CCT GTT GAT
Val Gly Lys Asn Glu Ala Val Leu Glu Trp Asp Gln Leu Pro Val Asp>

2600          2610          2620          2630          2640
GTT CAG AAT GGA TTT ATC AGA AAT TAT ACT ATA TTT TAT AGA ACC ATC
Val Gln Asn Gly Phe Ile Arg Asn Tyr Thr Ile Phe Tyr Arg Thr Ile>

2650          2660          2670          2680
ATT GGA AAT GAA ACT GCT GTG AAT GTG GAT TCT TCC CAC ACA GAA TAT
Ile Gly Asn Glu Thr Ala Val Asn Val Asp Ser Ser His Thr Glu Tyr>

2690          2700          2710          2720          2730
ACA TTG TCC TCT TTG ACT AGT GAC ACA TTG TAC ATG GTA CGA ATG GCA
Thr Leu Ser Ser Leu Thr Ser Asp Thr Leu Tyr Met Val Arg Met Ala>

2740          2750          2760          2770          2780
GCA TAC ACA GAT GAA GGT GGG AAG GAT GGT CCA GAA TTC ACT TTT ACT
Ala Tyr Thr Asp Glu Gly Gly Lys Asp Gly Pro Glu Phe Thr Phe Thr>

2790          2800          2810          2820          2830
ACC CCA AAG TTT GCT CAA GGA GAA ATT GAA TCC GGG GGC GAC AAA ACT
Thr Pro Lys Phe Ala Gln Gly Glu Ile Glu Ser Gly Gly Asp Lys Thr>

2840          2850          2860          2870          2880
CAC ACA TGC CCA CCG TGC CCA GCA CCT GAA CTC CTG GGG GGA CCG TCA
His Thr Cys Pro Pro Cys Pro Ala Pro Glu Leu Leu Gly Gly Pro Ser>

2890          2900          2910          2920
GTC TTC CTC TTC CCC CCA AAA CCC AAG GAC ACC CTC ATG ATC TCC CGG
Val Phe Leu Phe Pro Pro Lys Pro Lys Asp Thr Leu Met Ile Ser Arg>

2930          2940          2950          2960          2970
ACC CCT GAG GTC ACA TGC GTG GTG GTG GAC GTG AGC CAC GAA GAC CCT
```

Figure 24F

Thr Pro Glu Val Thr Cys Val Val Val Asp Val Ser His Glu Asp Pro>

```
       2980        2990        3000        3010        3020
         *           *           *           *           *
GAG GTC AAG TTC AAC TGG TAC GTG GAC GGC GTG GAG GTG CAT AAT GCC
Glu Val Lys Phe Asn Trp Tyr Val Asp Gly Val Glu Val His Asn Ala>

3030        3040        3050        3060        3070
         *           *           *           *           *
AAG ACA AAG CCG CGG GAG GAG CAG TAC AAC AGC ACG TAC CGT GTG GTC
Lys Thr Lys Pro Arg Glu Glu Gln Tyr Asn Ser Thr Tyr Arg Val Val>

3080        3090        3100        3110        3120
         *           *           *           *           *
AGC GTC CTC ACC GTC CTG CAC CAG GAC TGG CTG AAT GGC AAG GAG TAC
Ser Val Leu Thr Val Leu His Gln Asp Trp Leu Asn Gly Lys Glu Tyr>

3130        3140        3150        3160
         *           *           *           *
AAG TGC AAG GTC TCC AAC AAA GCC CTC CCA GCC CCC ATC GAG AAA ACC
Lys Cys Lys Val Ser Asn Lys Ala Leu Pro Ala Pro Ile Glu Lys Thr>

3170        3180        3190        3200        3210
  *           *           *           *           *
ATC TCC AAA GCC AAA GGG CAG CCC CGA GAA CCA CAG GTG TAC ACC CTG
Ile Ser Lys Ala Lys Gly Gln Pro Arg Glu Pro Gln Val Tyr Thr Leu>

3220        3230        3240        3250        3260
         *           *           *           *           *
CCC CCA TCC CGG GAT GAG CTG ACC AAG AAC CAG GTC AGC CTG ACC TGC
Pro Pro Ser Arg Asp Glu Leu Thr Lys Asn Gln Val Ser Leu Thr Cys>

3270        3280        3290        3300        3310
         *           *           *           *           *
CTG GTC AAA GGC TTC TAT CCC AGC GAC ATC GCC GTG GAG TGG GAG AGC
Leu Val Lys Gly Phe Tyr Pro Ser Asp Ile Ala Val Glu Trp Glu Ser>

3320        3330        3340        3350        3360
         *           *           *           *           *
AAT GGG CAG CCG GAG AAC AAC TAC AAG ACC ACG CCT CCC GTG CTG GAC
Asn Gly Gln Pro Glu Asn Asn Tyr Lys Thr Thr Pro Pro Val Leu Asp>

3370        3380        3390        3400
                *           *           *           *
TCC GAC GGC TCC TTC TTC CTC TAC AGC AAG CTC ACC GTG GAC AAG AGC
Ser Asp Gly Ser Phe Phe Leu Tyr Ser Lys Leu Thr Val Asp Lys Ser>

3410        3420        3430        3440        3450
  *           *           *           *           *
AGG TGG CAG CAG GGG AAC GTC TTC TCA TGC TCC GTG ATG CAT GAG GCT
Arg Trp Gln Gln Gly Asn Val Phe Ser Cys Ser Val Met His Glu Ala>

3460        3470        3480        3490        3500
         *           *           *           *           *
CTG CAC AAC CAC TAC ACG CAG AAG AGC CTC TCC CTG TCT CCG GGT AAA
Leu His Asn His Tyr Thr Gln Lys Ser Leu Ser Leu Ser Pro Gly Lys>

*
TGA
***>
```

Figure 25A

```
          10                  20                  30                  40
           *                   *                   *                   *
ATG GTG GCC GTC GGC TGC GCG CTG CTG GCT GCC CTG CTG GCC GCG CCG
Met Val Ala Val Gly Cys Ala Leu Leu Ala Ala Leu Leu Ala Ala Pro>

50                  60                  70                  80                  90
   *                   *                   *                   *                   *
GGA GCG GCG CTG GCC CCA AGG CGC TGC CCT GCG CAG GAG GTG GCA AGA
Gly Ala Ala Leu Ala Pro Arg Arg Cys Pro Ala Gln Glu Val Ala Arg>

100                 110                 120                 130                 140
      *                   *                   *                   *                   *
GGC GTG CTG ACC AGT CTG CCA GGA GAC AGC GTG ACT CTG ACC TGC CCG
Gly Val Leu Thr Ser Leu Pro Gly Asp Ser Val Thr Leu Thr Cys Pro>

150                 160                 170                 180                 190
         *                   *                   *                   *                   *
GGG GTA GAG CCG GAA GAC AAT GCC ACT GTT CAC TGG GTG CTC AGG AAG
Gly Val Glu Pro Glu Asp Asn Ala Thr Val His Trp Val Leu Arg Lys>

200                 210                 220                 230                 240
            *                   *                   *                   *                   *
CCG GCT GCA GGC TCC CAC CCC AGC AGA TGG GCT GGC ATG GGA AGG AGG
Pro Ala Ala Gly Ser His Pro Ser Arg Trp Ala Gly Met Gly Arg Arg>

250                 260                 270                 280
               *                   *                   *                   *
CTG CTG CTG AGG TCG GTG CAG CTC CAC GAC TCT GGA AAC TAT TCA TGC
Leu Leu Leu Arg Ser Val Gln Leu His Asp Ser Gly Asn Tyr Ser Cys>

290                 300                 310                 320                 330
  *                   *                   *                   *                   *
TAC CGG GCC GGC CGC CCA GCT GGG ACT GTG CAC TTG CTG GTG GAT GTT
Tyr Arg Ala Gly Arg Pro Ala Gly Thr Val His Leu Leu Val Asp Val>

340                 350                 360                 370                 380
     *                   *                   *                   *                   *
CCC CCC GAG GAG CCC CAG CTC TCC TGC TTC CGG AAG AGC CCC CTC AGC
Pro Pro Glu Glu Pro Gln Leu Ser Cys Phe Arg Lys Ser Pro Leu Ser>

390                 400                 410                 420                 430
        *                   *                   *                   *                   *
AAT GTT GTT TGT GAG TGG GGT CCT CGG AGC ACC CCA TCC CTG ACG ACA
Asn Val Val Cys Glu Trp Gly Pro Arg Ser Thr Pro Ser Leu Thr Thr>

440                 450                 460                 470                 480
           *                   *                   *                   *                   *
AAG GCT GTG CTC TTG GTG AGG AAG TTT CAG AAC AGT CCG GCC GAA GAC
Lys Ala Val Leu Leu Val Arg Lys Phe Gln Asn Ser Pro Ala Glu Asp>

490                 500                 510                 520
              *                   *                   *                   *
TTC CAG GAG CCG TGC CAG TAT TCC CAG GAG TCC CAG AAG TTC TCC TGC
Phe Gln Glu Pro Cys Gln Tyr Ser Gln Glu Ser Gln Lys Phe Ser Cys>

530                 540                 550                 560                 570
  *                   *                   *                   *                   *
CAG TTA GCA GTC CCG GAG GGA GAC AGC TCT TTC TAC ATA GTG TCC ATG
Gln Leu Ala Val Pro Glu Gly Asp Ser Ser Phe Tyr Ile Val Ser Met>
```

Figure 25B

```
       580           590           600           610           620
        *     *      *     *       *     *       *     *       *     *
TGC GTC GCC AGT AGT GTC GGG AGC AAG TTC AGC AAA ACT CAA ACC TTT
Cys Val Ala Ser Ser Val Gly Ser Lys Phe Ser Lys Thr Gln Thr Phe>

630           640           650           660           670
           *     *      *     *       *     *       *     *       *
CAG GGT TGT GGA ATC TTG CAG CCT GAT CCG CCT GCC AAC ATC ACA GTC
Gln Gly Cys Gly Ile Leu Gln Pro Asp Pro Pro Ala Asn Ile Thr Val>

680           690           700           710           720
              *     *      *     *       *     *       *     *       *
ACT GCC GTG GCC AGA AAC CCC CGC TGG CTC AGT GTC ACC TGG CAA GAC
Thr Ala Val Ala Arg Asn Pro Arg Trp Leu Ser Val Thr Trp Gln Asp>

730           740           750           760
                 *     *      *     *       *     *       *     *
CCC CAC TCC TGG AAC TCA TCT TTC TAC AGA CTA CGG TTT GAG CTC AGA
Pro His Ser Trp Asn Ser Ser Phe Tyr Arg Leu Arg Phe Glu Leu Arg>

770           780           790           800           810
   *     *      *     *       *     *       *     *       *     *
TAT CGG GCT GAA CGG TCA AAG ACA TTC ACA ACA TGG ATG GTC AAG GAC
Tyr Arg Ala Glu Arg Ser Lys Thr Phe Thr Thr Trp Met Val Lys Asp>

820           830           840           850           860
      *     *      *     *       *     *       *     *       *
CTC CAG CAT CAC TGT GTC ATC CAC GAC GCC TGG AGC GGC CTG AGG CAC
Leu Gln His His Cys Val Ile His Asp Ala Trp Ser Gly Leu Arg His>

870           880           890           900           910
         *     *      *     *       *     *       *     *       *
GTG GTG CAG CTT CGT GCC CAG GAG GAG TTC GGG CAA GGC GAG TGG AGC
Val Val Gln Leu Arg Ala Gln Glu Glu Phe Gly Gln Gly Glu Trp Ser>

920           930           940           950           960
            *     *      *     *       *     *       *     *       *
GAG TGG AGC CCG GAG GCC ATG GGC ACG CCT TGG ACA GAA TCG CGA TCG
Glu Trp Ser Pro Glu Ala Met Gly Thr Pro Trp Thr Glu Ser Arg Ser>

970           980           990           1000
               *     *      *     *       *     *       *     *
CCT CCA GCT GAG AAC GAG GTG TCC ACC CCC ATG GAA CTT CTA GAC CCA
Pro Pro Ala Glu Asn Glu Val Ser Thr Pro Met Glu Leu Leu Asp Pro>

1010          1020          1030          1040          1050
 *     *      *     *       *     *       *     *       *     *
TGT GGT TAT ATC AGT CCT GAA TCT CCA GTT GTA CAA CTT CAT TCT AAT
Cys Gly Tyr Ile Ser Pro Glu Ser Pro Val Val Gln Leu His Ser Asn>

1060          1070          1080          1090          1100
     *     *      *     *       *     *       *     *       *
TTC ACT GCA GTT TGT GTG CTA AAG GAA AAA TGT ATG GAT TAT TTT CAT
Phe Thr Ala Val Cys Val Leu Lys Glu Lys Cys Met Asp Tyr Phe His>

1110          1120          1130          1140          1150
        *     *      *     *       *     *       *     *       *
GTA AAT GCT AAT TAC ATT GTC TGG AAA ACA AAC CAT TTT ACT ATT CCT
Val Asn Ala Asn Tyr Ile Val Trp Lys Thr Asn His Phe Thr Ile Pro>

```
AAG GAG CAA TAT ACT ATC ATA AAC AGA ACA GCA TCC AGT GTC ACC TTT
Lys Glu Gln Tyr Thr Ile Ile Asn Arg Thr Ala Ser Ser Val Thr Phe>

1210        1220        1230        1240
          *           *           *           *           *
ACA GAT ATA GCT TCA TTA AAT ATT CAG CTC ACT TGC AAC ATT CTT ACA
Thr Asp Ile Ala Ser Leu Asn Ile Gln Leu Thr Cys Asn Ile Leu Thr>

1250        1260        1270        1280        1290
 *           *           *           *           *
TTC GGA CAG CTT GAA CAG AAT GTT TAT GGA ATC ACA ATA ATT TCA GGC
Phe Gly Gln Leu Glu Gln Asn Val Tyr Gly Ile Thr Ile Ile Ser Gly>

1300        1310        1320        1330        1340
      *           *           *           *           *
TTG CCT CCA GAA AAA CCT AAA AAT TTG AGT TGC ATT GTG AAC GAG GGG
Leu Pro Pro Glu Lys Pro Lys Asn Leu Ser Cys Ile Val Asn Glu Gly>

1350        1360        1370        1380        1390
          *           *           *           *           *
AAG AAA ATG AGG TGT GAG TGG GAT GGT GGA AGG GAA ACA CAC TTG GAG
Lys Lys Met Arg Cys Glu Trp Asp Gly Gly Arg Glu Thr His Leu Glu>

1400        1410        1420        1430        1440
           *           *           *           *           *
ACA AAC TTC ACT TTA AAA TCT GAA TGG GCA ACA CAC AAG TTT GCT GAT
Thr Asn Phe Thr Leu Lys Ser Glu Trp Ala Thr His Lys Phe Ala Asp>

1450        1460        1470        1480
              *           *           *           *           *
TGC AAA GCA AAA CGT GAC ACC CCC ACC TCA TGC ACT GTT GAT TAT TCT
Cys Lys Ala Lys Arg Asp Thr Pro Thr Ser Cys Thr Val Asp Tyr Ser>

1490        1500        1510        1520        1530
 *           *           *           *           *
ACT GTG TAT TTT GTC AAC ATT GAA GTC TGG GTA GAA GCA GAG AAT GCC
Thr Val Tyr Phe Val Asn Ile Glu Val Trp Val Glu Ala Glu Asn Ala>

1540        1550        1560        1570        1580
      *           *           *           *           *
CTT GGG AAG GTT ACA TCA GAT CAT ATC AAT TTT GAT CCT GTA TAT AAA
Leu Gly Lys Val Thr Ser Asp His Ile Asn Phe Asp Pro Val Tyr Lys>

1590        1600        1610        1620        1630
          *           *           *           *           *
GTG AAG CCC AAT CCG CCA CAT AAT TTA TCA GTG ATC AAC TCA GAG GAA
Val Lys Pro Asn Pro Pro His Asn Leu Ser Val Ile Asn Ser Glu Glu>

1640        1650        1660        1670        1680
              *           *           *           *           *
CTG TCT AGT ATC TTA AAA TTG ACA TGG ACC AAC CCA AGT ATT AAG AGT
Leu Ser Ser Ile Leu Lys Leu Thr Trp Thr Asn Pro Ser Ile Lys Ser>

1690        1700        1710        1720
                  *           *           *           *           *
GTT ATA ATA CTA AAA TAT AAC ATT CAA TAT AGG ACC AAA GAT GCC TCA
Val Ile Ile Leu Lys Tyr Asn Ile Gln Tyr Arg Thr Lys Asp Ala Ser>

1730        1740        1750        1760        1770
 *           *           *           *           *
ACT TGG AGC CAG ATT CCT CCT GAA GAC ACA GCA TCC ACC CGA TCT TCA
Thr Trp Ser Gln Ile Pro Pro Glu Asp Thr Ala Ser Thr Arg Ser Ser>
```

Figure 25D

```
       1780        1790        1800        1810        1820
         *           *           *           *           *
    TTC ACT GTC CAA GAC CTT AAA CCT TTT ACA GAA TAT GTG TTT AGG ATT
    Phe Thr Val Gln Asp Leu Lys Pro Phe Thr Glu Tyr Val Phe Arg Ile>

1830        1840        1850        1860        1870
         *           *           *           *           *
    CGC TGT ATG AAG GAA GAT GGT AAG GGA TAC TGG AGT GAC TGG AGT GAA
    Arg Cys Met Lys Glu Asp Gly Lys Gly Tyr Trp Ser Asp Trp Ser Glu>

1880        1890        1900        1910        1920
         *           *           *           *           *
    GAA GCA AGT GGG ATC ACC TAT GAA GAT AGA CCA TCT AAA GCA CCA AGT
    Glu Ala Ser Gly Ile Thr Tyr Glu Asp Arg Pro Ser Lys Ala Pro Ser>

1930        1940        1950        1960
                *           *           *           *
      TTC TGG TAT AAA ATA GAT CCA TCC CAT ACT CAA GGC TAC AGA ACT GTA
      Phe Trp Tyr Lys Ile Asp Pro Ser His Thr Gln Gly Tyr Arg Thr Val>

1970        1980        1990        2000        2010
   *           *           *           *           *
 CAA CTC GTG TGG AAG ACA TTG CCT CCT TTT GAA GCC AAT GGA AAA ATC
 Gln Leu Val Trp Lys Thr Leu Pro Pro Phe Glu Ala Asn Gly Lys Ile>

2020        2030        2040        2050        2060
        *           *           *           *           *
    TTG GAT TAT GAA GTG ACT CTC ACA AGA TGG AAA TCA CAT TTA CAA AAT
    Leu Asp Tyr Glu Val Thr Leu Thr Arg Trp Lys Ser His Leu Gln Asn>

2070        2080        2090        2100        2110
         *           *           *           *           *
    TAC ACA GTT AAT GCC ACA AAA CTG ACA GTA AAT CTC ACA AAT GAT CGC
    Tyr Thr Val Asn Ala Thr Lys Leu Thr Val Asn Leu Thr Asn Asp Arg>

2120        2130        2140        2150        2160
         *           *           *           *           *
    TAT CTA GCA ACC CTA ACA GTA AGA AAT CTT GTT GGC AAA TCA GAT GCA
    Tyr Leu Ala Thr Leu Thr Val Arg Asn Leu Val Gly Lys Ser Asp Ala>

2170        2180        2190        2200
                *           *           *           *
      GCT GTT TTA ACT ATC CCT GCC TGT GAC TTT CAA GCT ACT CAC CCT GTA
      Ala Val Leu Thr Ile Pro Ala Cys Asp Phe Gln Ala Thr His Pro Val>

2210        2220        2230        2240        2250
   *           *           *           *           *
 ATG GAT CTT AAA GCA TTC CCC AAA GAT AAC ATG CTT TGG GTG GAA TGG
 Met Asp Leu Lys Ala Phe Pro Lys Asp Asn Met Leu Trp Val Glu Trp>

2260        2270        2280        2290        2300
         *           *           *           *           *
    ACT ACT CCA AGG GAA TCT GTA AAG AAA TAT ATA CTT GAG TGG TGT GTG
    Thr Thr Pro Arg Glu Ser Val Lys Lys Tyr Ile Leu Glu Trp Cys Val>

2310        2320        2330        2340        2350
         *           *           *           *           *
    TTA TCA GAT AAA GCA CCC TGT ATC ACA GAC TGG CAA CAA GAA GAT GGT
    Leu Ser Asp Lys Ala Pro Cys Ile Thr Asp Trp Gln Gln Glu Asp Gly>

```
         *         *         *         *         *         *         *         *         *         *
        ACC GTG CAT CGC ACC TAT TTA AGA GGG AAC TTA GCA GAG AGC AAA TGC
        Thr Val His Arg Thr Tyr Leu Arg Gly Asn Leu Ala Glu Ser Lys Cys>

2410          2420          2430          2440
         *         *         *         *         *         *         *         *         *
        TAT TTG ATA ACA GTT ACT CCA GTA TAT GCT GAT GGA CCA GGA AGC CCT
        Tyr Leu Ile Thr Val Thr Pro Val Tyr Ala Asp Gly Pro Gly Ser Pro>

2450          2460          2470          2480          2490
    *         *         *         *         *         *         *         *         *         *
        GAA TCC ATA AAG GCA TAC CTT AAA CAA GCT CCA CCT TCC AAA GGA CCT
        Glu Ser Ile Lys Ala Tyr Leu Lys Gln Ala Pro Pro Ser Lys Gly Pro>

2500          2510          2520          2530          2540
         *         *         *         *         *         *         *         *         *         *
        ACT GTT CGG ACA AAA AAA GTA GGG AAA AAC GAA GCT GTC TTA GAG TGG
        Thr Val Arg Thr Lys Lys Val Gly Lys Asn Glu Ala Val Leu Glu Trp>

2550          2560          2570          2580          2590
         *         *         *         *         *         *         *         *         *         *
        GAC CAA CTT CCT GTT GAT GTT CAG AAT GGA TTT ATC AGA AAT TAT ACT
        Asp Gln Leu Pro Val Asp Val Gln Asn Gly Phe Ile Arg Asn Tyr Thr>

2600          2610          2620          2630          2640
         *         *         *         *         *         *         *         *         *         *
        ATA TTT TAT AGA ACC ATC ATT GGA AAT GAA ACT GCT GTG AAT GTG GAT
        Ile Phe Tyr Arg Thr Ile Ile Gly Asn Glu Thr Ala Val Asn Val Asp>

2650          2660          2670          2680
                 *         *         *         *         *         *         *         *         *
        TCT TCC CAC ACA GAA TAT ACA TTG TCC TCT TTG ACT AGT GAC ACA TTG
        Ser Ser His Thr Glu Tyr Thr Leu Ser Ser Leu Thr Ser Asp Thr Leu>

2690          2700          2710          2720          2730
    *         *         *         *         *         *         *         *         *         *
        TAC ATG GTA CGA ATG GCA GCA TAC ACA GAT GAA GGT GGG AAG GAT GGT
        Tyr Met Val Arg Met Ala Ala Tyr Thr Asp Glu Gly Gly Lys Asp Gly>

2740          2750          2760          2770          2780
         *         *         *         *         *         *         *         *         *
        CCA GAA TTC ACT TTT ACT ACC CCA AAG TTT GCT CAA GGA GAA ATT GAA
        Pro Glu Phe Thr Phe Thr Thr Pro Lys Phe Ala Gln Gly Glu Ile Glu>

2790          2800          2810          2820          2830
         *         *         *         *         *         *         *         *         *         *
        TCC GGG GGC GAC AAA ACT CAC ACA TGC CCA CCG TGC CCA GCA CCT GAA
        Ser Gly Gly Asp Lys Thr His Thr Cys Pro Pro Cys Pro Ala Pro Glu>

2840          2850          2860          2870          2880
         *         *         *         *         *         *         *         *         *         *
        CTC CTG GGG GGA CCG TCA GTC TTC CTC TTC CCC CCA AAA CCC AAG GAC
        Leu Leu Gly Gly Pro Ser Val Phe Leu Phe Pro Pro Lys Pro Lys Asp>

2890          2900          2910          2920
                 *         *         *         *         *         *         *         *         *
        ACC CTC ATG ATC TCC CGG ACC CCT GAG GTC ACA TGC GTG GTG GTG GAC
        Thr Leu Met Ile Ser Arg Thr Pro Glu Val Thr Cys Val Val Val Asp>

2930          2940          2950          2960          2970
    *         *         *         *         *         *         *         *         *         *
        GTG AGC CAC GAA GAC CCT GAG GTC AAG TTC AAC TGG TAC GTG GAC GGC
```

Figure 25F

Val Ser His Glu Asp Pro Glu Val Lys Phe Asn Trp Tyr Val Asp Gly>

```
       2980          2990          3000          3010          3020
         *             *             *             *             *
    GTG GAG GTG CAT AAT GCC AAG ACA AAG CCG CGG GAG GAG CAG TAC AAC
    Val Glu Val His Asn Ala Lys Thr Lys Pro Arg Glu Glu Gln Tyr Asn>

3030          3040          3050          3060          3070
         *             *             *             *             *
    AGC ACG TAC CGT GTG GTC AGC GTC CTC ACC GTC CTG CAC CAG GAC TGG
    Ser Thr Tyr Arg Val Val Ser Val Leu Thr Val Leu His Gln Asp Trp>

3080          3090          3100          3110          3120
         *             *             *             *             *
    CTG AAT GGC AAG GAG TAC AAG TGC AAG GTC TCC AAC AAA GCC CTC CCA
    Leu Asn Gly Lys Glu Tyr Lys Cys Lys Val Ser Asn Lys Ala Leu Pro>

3130          3140          3150          3160
         *             *             *             *             *
    GCC CCC ATC GAG AAA ACC ATC TCC AAA GCC AAA GGG CAG CCC CGA GAA
    Ala Pro Ile Glu Lys Thr Ile Ser Lys Ala Lys Gly Gln Pro Arg Glu>

3170          3180          3190          3200          3210
  *             *             *             *             *             *
    CCA CAG GTG TAC ACC CTG CCC CCA TCC CGG GAT GAG CTG ACC AAG AAC
    Pro Gln Val Tyr Thr Leu Pro Pro Ser Arg Asp Glu Leu Thr Lys Asn>

3220          3230          3240          3250          3260
         *             *             *             *             *
    CAG GTC AGC CTG ACC TGC CTG GTC AAA GGC TTC TAT CCC AGC GAC ATC
    Gln Val Ser Leu Thr Cys Leu Val Lys Gly Phe Tyr Pro Ser Asp Ile>

3270          3280          3290          3300          3310
         *             *             *             *             *
    GCC GTG GAG TGG GAG AGC AAT GGG CAG CCG GAG AAC AAC TAC AAG ACC
    Ala Val Glu Trp Glu Ser Asn Gly Gln Pro Glu Asn Asn Tyr Lys Thr>

3320          3330          3340          3350          3360
         *             *             *             *             *
    ACG CCT CCC GTG CTG GAC TCC GAC GGC TCC TTC TTC CTC TAC AGC AAG
    Thr Pro Pro Val Leu Asp Ser Asp Gly Ser Phe Phe Leu Tyr Ser Lys>

3370          3380          3390          3400
         *             *             *             *             *
    CTC ACC GTG GAC AAG AGC AGG TGG CAG CAG GGG AAC GTC TTC TCA TGC
    Leu Thr Val Asp Lys Ser Arg Trp Gln Gln Gly Asn Val Phe Ser Cys>

3410          3420          3430          3440          3450
  *             *             *             *             *             *
    TCC GTG ATG CAT GAG GCT CTG CAC AAC CAC TAC ACG CAG AAG AGC CTC
    Ser Val Met His Glu Ala Leu His Asn His Tyr Thr Gln Lys Ser Leu>

3460          3470
         *             *             *
    TCC CTG TCT CCG GGT AAA TGA
    Ser Leu Ser Pro Gly Lys ***>
```

Figure 26A

```
         10              20              30              40
          *               *               *               *
ATG GTG CTT CTG TGG TGT GTA GTG AGT CTC TAC TTT TAT GGA ATC CTG
Met Val Leu Leu Trp Cys Val Val Ser Leu Tyr Phe Tyr Gly Ile Leu>

50              60              70              80              90
      *               *               *               *               *
CAA AGT GAT GCC TCA GAA CGC TGC GAT GAC TGG GGA CTA GAC ACC ATG
Gln Ser Asp Ala Ser Glu Arg Cys Asp Asp Trp Gly Leu Asp Thr Met>

100             110             120             130             140
         *               *               *               *               *
AGG CAA ATC CAA GTG TTT GAA GAT GAG CCA GCT CGC ATC AAG TGC CCA
Arg Gln Ile Gln Val Phe Glu Asp Glu Pro Ala Arg Ile Lys Cys Pro>

150             160             170             180             190
         *               *               *               *               *
CTC TTT GAA CAC TTC TTG AAA TTC AAC TAC AGC ACA GCC CAT TCA GCT
Leu Phe Glu His Phe Leu Lys Phe Asn Tyr Ser Thr Ala His Ser Ala>

200             210             220             230             240
             *               *               *               *               *
GGC CTT ACT CTG ATC TGG TAT TGG ACT AGG CAG GAC CGG GAC CTT GAG
Gly Leu Thr Leu Ile Trp Tyr Trp Thr Arg Gln Asp Arg Asp Leu Glu>

250             260             270             280
             *               *               *               *
GAG CCA ATT AAC TTC CGC CTC CCC GAG AAC CGC ATT AGT AAG GAG AAA
Glu Pro Ile Asn Phe Arg Leu Pro Glu Asn Arg Ile Ser Lys Glu Lys>

290             300             310             320             330
     *               *               *               *               *
GAT GTG CTG TGG TTC CGG CCC ACT CTC CTC AAT GAC ACT GGC AAC TAT
Asp Val Leu Trp Phe Arg Pro Thr Leu Leu Asn Asp Thr Gly Asn Tyr>

340             350             360             370             380
         *               *               *               *               *
ACC TGC ATG TTA AGG AAC ACT ACA TAT TGC AGC AAA GTT GCA TTT CCC
Thr Cys Met Leu Arg Asn Thr Thr Tyr Cys Ser Lys Val Ala Phe Pro>

390             400             410             420             430
         *               *               *               *               *
TTG GAA GTT GTT CAA AAA GAC AGC TGT TTC AAT TCC CCA ATG AAA CTC
Leu Glu Val Val Gln Lys Asp Ser Cys Phe Asn Ser Pro Met Lys Leu>

440             450             460             470             480
         *               *               *               *               *
CCA GTG CAT AAA CTG TAT ATA GAA TAT GGC ATT CAG AGG ATC ACT TGT
Pro Val His Lys Leu Tyr Ile Glu Tyr Gly Ile Gln Arg Ile Thr Cys>

490             500             510             520
             *               *               *               *
CCA AAT GTA GAT GGA TAT TTT CCT TCC AGT GTC AAA CCG ACT ATC ACT
Pro Asn Val Asp Gly Tyr Phe Pro Ser Ser Val Lys Pro Thr Ile Thr>

530             540             550             560             570
 *               *               *               *               *
TGG TAT ATG GGC TGT TAT AAA ATA CAG AAT TTT AAT AAT GTA ATA CCC
Trp Tyr Met Gly Cys Tyr Lys Ile Gln Asn Phe Asn Asn Val Ile Pro>
```

Figure 26B

```
        580              590              600              610              620
          *       *       *       *       *       *       *       *       *
GAA GGT ATG AAC TTG AGT TTC CTC ATT GCC TTA ATT TCA AAT AAT GGA
Glu Gly Met Asn Leu Ser Phe Leu Ile Ala Leu Ile Ser Asn Asn Gly>

630              640              650              660              670
          *       *       *       *       *       *       *       *       *
AAT TAC ACA TGT GTT GTT ACA TAT CCA GAA AAT GGA CGT ACG TTT CAT
Asn Tyr Thr Cys Val Val Thr Tyr Pro Glu Asn Gly Arg Thr Phe His>

680              690              700              710              720
          *       *       *       *       *       *       *       *       *
CTC ACC AGG ACT CTG ACT GTA AAG GTA GTA GGC TCT CCA AAA AAT GCA
Leu Thr Arg Thr Leu Thr Val Lys Val Val Gly Ser Pro Lys Asn Ala>

730              740              750              760
          *       *       *       *       *       *       *       *
GTG CCC CCT GTG ATC CAT TCA CCT AAT GAT CAT GTG GTC TAT GAG AAA
Val Pro Pro Val Ile His Ser Pro Asn Asp His Val Val Tyr Glu Lys>

770              780              790              800              810
  *       *       *       *       *       *       *       *       *       *
GAA CCA GGA GAG GAG CTA CTC ATT CCC TGT ACG GTC TAT TTT AGT TTT
Glu Pro Gly Glu Glu Leu Leu Ile Pro Cys Thr Val Tyr Phe Ser Phe>

820              830              840              850              860
          *       *       *       *       *       *       *       *       *
CTG ATG GAT TCT CGC AAT GAG GTT TGG TGG ACC ATT GAT GGA AAA AAA
Leu Met Asp Ser Arg Asn Glu Val Trp Trp Thr Ile Asp Gly Lys Lys>

870              880              890              900              910
          *       *       *       *       *       *       *       *       *
CCT GAT GAC ATC ACT ATT GAT GTC ACC ATT AAC GAA AGT ATA AGT CAT
Pro Asp Asp Ile Thr Ile Asp Val Thr Ile Asn Glu Ser Ile Ser His>

920              930              940              950              960
          *       *       *       *       *       *       *       *       *
AGT AGA ACA GAA GAT GAA ACA AGA ACT CAG ATT TTG AGC ATC AAG AAA
Ser Arg Thr Glu Asp Glu Thr Arg Thr Gln Ile Leu Ser Ile Lys Lys>

970              980              990              1000
          *       *       *       *       *       *       *       *
GTT ACC TCT GAG GAT CTC AAG CGC AGC TAT GTC TGT CAT GCT AGA AGT
Val Thr Ser Glu Asp Leu Lys Arg Ser Tyr Val Cys His Ala Arg Ser>

1010             1020             1030             1040             1050
  *       *       *       *       *       *       *       *       *       *
GCC AAA GGC GAA GTT GCC AAA GCA GCC AAG GTG AAG CAG AAA GTG CCA
Ala Lys Gly Glu Val Ala Lys Ala Ala Lys Val Lys Gln Lys Val Pro>

1060             1070             1080             1090             1100
          *       *       *       *       *       *       *       *       *
GCT CCA AGA TAC ACA GTG TCC GGT GGC GCG CCT ATG CTG AGC GAG GCT
Ala Pro Arg Tyr Thr Val Ser Gly Gly Ala Pro Met Leu Ser Glu Ala>

1110             1120             1130             1140             1150
          *       *       *       *       *       *       *       *       *
GAT AAA TGC AAG GAA CGT GAA GAA AAA ATA ATT TTA GTG TCA TCT GCA
Asp Lys Cys Lys Glu Arg Glu Glu Lys Ile Ile Leu Val Ser Ser Ala>

```
AAT GAA ATT GAT GTT CGT CCC TGT CCT CTT AAC CCA AAT GAA CAC AAA
Asn Glu Ile Asp Val Arg Pro Cys Pro Leu Asn Pro Asn Glu His Lys>

1210          1220          1230          1240
          *    *    *    *    *    *    *    *    *
          GGC ACT ATA ACT TGG TAT AAG GAT GAC AGC AAG ACA CCT GTA TCT ACA
          Gly Thr Ile Thr Trp Tyr Lys Asp Asp Ser Lys Thr Pro Val Ser Thr>

1250          1260          1270          1280          1290
 *    *    *    *    *    *    *    *    *    *
          GAA CAA GCC TCC AGG ATT CAT CAA CAC AAA GAG AAA CTT TGG TTT GTT
          Glu Gln Ala Ser Arg Ile His Gln His Lys Glu Lys Leu Trp Phe Val>

1300          1310          1320          1330          1340
          *    *    *    *    *    *    *    *    *
          CCT GCT AAG GTG GAG GAT TCA GGA CAT TAC TAT TGC GTG GTA AGA AAT
          Pro Ala Lys Val Glu Asp Ser Gly His Tyr Tyr Cys Val Val Arg Asn>

1350          1360          1370          1380          1390
          *    *    *    *    *    *    *    *    *    *
          TCA TCT TAC TGC CTC AGA ATT AAA ATA AGT GCA AAA TTT GTG GAG AAT
          Ser Ser Tyr Cys Leu Arg Ile Lys Ile Ser Ala Lys Phe Val Glu Asn>

1400          1410          1420          1430          1440
          *    *    *    *    *    *    *    *    *    *
          GAG CCT AAC TTA TGT TAT AAT GCA CAA GCC ATA TTT AAG CAG AAA CTA
          Glu Pro Asn Leu Cys Tyr Asn Ala Gln Ala Ile Phe Lys Gln Lys Leu>

1450          1460          1470          1480
          *    *    *    *    *    *    *    *    *
          CCC GTT GCA GGA GAC GGA GGA CTT GTG TGC CCT TAT ATG GAG TTT TTT
          Pro Val Ala Gly Asp Gly Gly Leu Val Cys Pro Tyr Met Glu Phe Phe>

1490          1500          1510          1520          1530
 *    *    *    *    *    *    *    *    *    *
          AAA AAT GAA AAT AAT GAG TTA CCT AAA TTA CAG TGG TAT AAG GAT TGC
          Lys Asn Glu Asn Asn Glu Leu Pro Lys Leu Gln Trp Tyr Lys Asp Cys>

1540          1550          1560          1570          1580
          *    *    *    *    *    *    *    *    *
          AAA CCT CTA CTT CTT GAC AAT ATA CAC TTT AGT GGA GTC AAA GAT AGG
          Lys Pro Leu Leu Leu Asp Asn Ile His Phe Ser Gly Val Lys Asp Arg>

1590          1600          1610          1620          1630
          *    *    *    *    *    *    *    *    *    *
          CTC ATC GTG ATG AAT GTG GCT GAA AAG CAT AGA GGG AAC TAT ACT TGT
          Leu Ile Val Met Asn Val Ala Glu Lys His Arg Gly Asn Tyr Thr Cys>

1640          1650          1660          1670          1680
          *    *    *    *    *    *    *    *    *    *
          CAT GCA TCC TAC ACA TAC TTG GGC AAG CAA TAT CCT ATT ACC CGG GTA
          His Ala Ser Tyr Thr Tyr Leu Gly Lys Gln Tyr Pro Ile Thr Arg Val>

1690          1700          1710          1720
          *    *    *    *    *    *    *    *    *
          ATA GAA TTT ATT ACT CTA GAG GAA AAC AAA CCC ACA AGG CCT GTG ATT
          Ile Glu Phe Ile Thr Leu Glu Glu Asn Lys Pro Thr Arg Pro Val Ile>

1730          1740          1750          1760          1770
 *    *    *    *    *    *    *    *    *    *
          GTG AGC CCA GCT AAT GAG ACA ATG GAA GTA GAC TTG GGA TCC CAG ATA
          Val Ser Pro Ala Asn Glu Thr Met Glu Val Asp Leu Gly Ser Gln Ile>
```

Figure 26D

```
        1780          1790          1800          1810          1820
          *             *             *             *             *
    CAA TTG ATC TGT AAT GTC ACC GGC CAG TTG AGT GAC ATT GCT TAC TGG
    Gln Leu Ile Cys Asn Val Thr Gly Gln Leu Ser Asp Ile Ala Tyr Trp>

1830          1840          1850          1860          1870
            *             *             *             *             *
    AAG TGG AAT GGG TCA GTA ATT GAT GAA GAT GAC CCA GTG CTA GGG GAA
    Lys Trp Asn Gly Ser Val Ile Asp Glu Asp Asp Pro Val Leu Gly Glu>

1880          1890          1900          1910          1920
            *             *             *             *             *
    GAC TAT TAC AGT GTG GAA AAT CCT GCA AAC AAA AGA AGG AGT ACC CTC
    Asp Tyr Tyr Ser Val Glu Asn Pro Ala Asn Lys Arg Arg Ser Thr Leu>

1930          1940          1950          1960
                *             *             *             *
    ATC ACA GTG CTT AAT ATA TCG GAA ATT GAG AGT AGA TTT TAT AAA CAT
    Ile Thr Val Leu Asn Ile Ser Glu Ile Glu Ser Arg Phe Tyr Lys His>

1970          1980          1990          2000          2010
      *             *             *             *             *
    CCA TTT ACC TGT TTT GCC AAG AAT ACA CAT GGT ATA GAT GCA GCA TAT
    Pro Phe Thr Cys Phe Ala Lys Asn Thr His Gly Ile Asp Ala Ala Tyr>

2020          2030          2040          2050          2060
          *             *             *             *             *
    ATC CAG TTA ATA TAT CCA GTC ACT AAT TCC GGA GAC AAA ACT CAC ACA
    Ile Gln Leu Ile Tyr Pro Val Thr Asn Ser Gly Asp Lys Thr His Thr>

2070          2080          2090          2100          2110
            *             *             *             *             *
    TGC CCA CCG TGC CCA GCA CCT GAA CTC CTG GGG GGA CCG TCA GTC TTC
    Cys Pro Pro Cys Pro Ala Pro Glu Leu Leu Gly Gly Pro Ser Val Phe>

2120          2130          2140          2150          2160
                *             *             *             *             *
    CTC TTC CCC CCA AAA CCC AAG GAC ACC CTC ATG ATC TCC CGG ACC CCT
    Leu Phe Pro Pro Lys Pro Lys Asp Thr Leu Met Ile Ser Arg Thr Pro>

2170          2180          2190          2200
                    *             *             *             *
    GAG GTC ACA TGC GTG GTG GTG GAC GTG AGC CAC GAA GAC CCT GAG GTC
    Glu Val Thr Cys Val Val Val Asp Val Ser His Glu Asp Pro Glu Val>

2210          2220          2230          2240          2250
      *             *             *             *             *
    AAG TTC AAC TGG TAC GTG GAC GGC GTG GAG GTG CAT AAT GCC AAG ACA
    Lys Phe Asn Trp Tyr Val Asp Gly Val Glu Val His Asn Ala Lys Thr>

2260          2270          2280          2290          2300
          *             *             *             *             *
    AAG CCG CGG GAG GAG CAG TAC AAC AGC ACG TAC CGT GTG GTC AGC GTC
    Lys Pro Arg Glu Glu Gln Tyr Asn Ser Thr Tyr Arg Val Val Ser Val>

2310          2320          2330          2340          2350
              *             *             *             *             *
    CTC ACC GTC CTG CAC CAG GAC TGG CTG AAT GGC AAG GAG TAC AAG TGC
    Leu Thr Val Leu His Gln Asp Trp Leu Asn Gly Lys Glu Tyr Lys Cys>

```
       *         *         *         *         *         *         *         *         *         *
     AAG GTC TCC AAC AAA GCC CTC CCA GCC CCC ATC GAG AAA ACC ATC TCC
     Lys Val Ser Asn Lys Ala Leu Pro Ala Pro Ile Glu Lys Thr Ile Ser>

2410        2420        2430        2440
       *         *         *         *         *         *         *         *
     AAA GCC AAA GGG CAG CCC CGA GAA CCA CAG GTG TAC ACC CTG CCC CCA
     Lys Ala Lys Gly Gln Pro Arg Glu Pro Gln Val Tyr Thr Leu Pro Pro>

2450        2460        2470        2480        2490
  *         *         *         *         *         *         *         *         *         *
     TCC CGG GAG GAG ATG ACC AAG AAC CAG GTC AGC CTG ACC TGC CTG GTC
     Ser Arg Glu Glu Met Thr Lys Asn Gln Val Ser Leu Thr Cys Leu Val>

2500        2510        2520        2530        2540
       *         *         *         *         *         *         *         *         *
     AAA GGC TTC TAT CCC AGC GAC ATC GCC GTG GAG TGG GAG AGC AAT GGG
     Lys Gly Phe Tyr Pro Ser Asp Ile Ala Val Glu Trp Glu Ser Asn Gly>

2550        2560        2570        2580        2590
  *         *         *         *         *         *         *         *         *         *
     CAG CCG GAG AAC AAC TAC AAG ACC ACG CCT CCC GTG CTG GAC TCC GAC
     Gln Pro Glu Asn Asn Tyr Lys Thr Thr Pro Pro Val Leu Asp Ser Asp>

2600        2610        2620        2630        2640
       *         *         *         *         *         *         *         *         *         *
     GGC TCC TTC TTC CTC TAT AGC AAG CTC ACC GTG GAC AAG AGC AGG TGG
     Gly Ser Phe Phe Leu Tyr Ser Lys Leu Thr Val Asp Lys Ser Arg Trp>

2650        2660        2670        2680
       *         *         *         *         *         *         *         *         *
     CAG CAG GGG AAC GTC TTC TCA TGC TCC GTG ATG CAT GAG GCT CTG CAC
     Gln Gln Gly Asn Val Phe Ser Cys Ser Val Met His Glu Ala Leu His>

2690        2700        2710        2720        2730
  *         *         *         *         *         *         *         *         *
     AAC CAC TAC ACG CAG AAG AGC CTC TCC CTG TCT CCG GGT AAA TGA
     Asn His Tyr Thr Gln Lys Ser Leu Ser Leu Ser Pro Gly Lys ***>
```

Figure 31A

```
              10              20              30              40
         *         *     *         *     *         *     *         *     *
ATG GTG TGG CTT TGC TCT GGG CTC CTG TTC CCT GTG AGC TGC CTG GTC
TAC CAC ACC GAA ACG AGA CCC GAG GAC AAG GGA CAC TCG ACG GAC CAG
Met Val Trp Leu Cys Ser Gly Leu Leu Phe Pro Val Ser Cys Leu Val>

50              60              70              80              90
 *         *     *         *     *         *     *         *     *         *
CTG CTG CAG GTG GCA AGC TCT GGG AAC ATG AAG GTC TTG CAG GAG CCC
GAC GAC GTC CAC CGT TCG AGA CCC TTG TAC TTC CAG AAC GTC CTC GGG
Leu Leu Gln Val Ala Ser Ser Gly Asn Met Lys Val Leu Gln Glu Pro>

100             110             120             130             140
     *         *     *         *     *         *     *         *     *
ACC TGC GTC TCC GAC TAC ATG AGC ATC TCT ACT TGC GAG TGG AAG ATG
TGG ACG CAG AGG CTG ATG TAC TCG TAG AGA TGA ACG CTC ACC TTC TAC
Thr Cys Val Ser Asp Tyr Met Ser Ile Ser Thr Cys Glu Trp Lys Met>

150             160             170             180             190
 *         *     *         *     *         *     *         *     *         *
AAT GGT CCC ACC AAT TGC AGC ACC GAG CTC CGC CTG TTG TAC CAG CTG
TTA CCA GGG TGG TTA ACG TCG TGG CTC GAG GCG GAC AAC ATG GTC GAC
Asn Gly Pro Thr Asn Cys Ser Thr Glu Leu Arg Leu Leu Tyr Gln Leu>

200             210             220             230             240
     *         *     *         *     *         *     *         *     *
GTT TTT CTG CTC TCC GAA GCC CAC ACG TGT ATC CCT GAG AAC AAC GGA
CAA AAA GAC GAG AGG CTT CGG GTG TGC ACA TAG GGA CTC TTG TTG CCT
Val Phe Leu Leu Ser Glu Ala His Thr Cys Ile Pro Glu Asn Asn Gly>

250             260             270             280
         *         *     *         *     *         *     *         *     *
GGC GCG GGG TGC GTG TGC CAC CTG CTC ATG GAT GAC GTG GTC AGT GCG
CCG CGC CCC ACG CAC ACG GTG GAC GAG TAC CTA CTG CAC CAG TCA CGC
Gly Ala Gly Cys Val Cys His Leu Leu Met Asp Asp Val Val Ser Ala>

290             300             310             320             330
     *     *         *     *         *     *         *     *         *
GAT AAC TAT ACA CTG GAC CTG TGG GCT GGG CAG CAG CTG CTG TGG AAG
CTA TTG ATA TGT GAC CTG GAC ACC CGA CCC GTC GTC GAC GAC ACC TTC
Asp Asn Tyr Thr Leu Asp Leu Trp Ala Gly Gln Gln Leu Leu Trp Lys>

340             350             360             370             380
     *         *     *         *     *         *     *         *     *
GGC TCC TTC AAG CCC AGC GAG CAT GTG AAA CCC AGG GCC CCA GGA AAC
CCG AGG AAG TTC GGG TCG CTC GTA CAC TTT GGG TCC CGG GGT CCT TTG
Gly Ser Phe Lys Pro Ser Glu His Val Lys Pro Arg Ala Pro Gly Asn>
```

Figure 31B

```
            390             400             410             420             430
       *     *        *     *        *     *        *     *        *     *
      CTG ACA GTT CAC ACC AAT GTC TCC GAC ACT CTG CTG CTG ACC TGG AGC
      GAC TGT CAA GTG TGG TTA CAG AGG CTG TGA GAC GAC GAC TGG ACC TCG
      Leu Thr Val His Thr Asn Val Ser Asp Thr Leu Leu Leu Thr Trp Ser>

440             450             460             470             480
       *     *        *     *        *     *        *     *        *     *
      AAC CCG TAT CCC CCT GAC AAT TAC CTG TAT AAT CAT CTC ACC TAT GCA
      TTG GGC ATA GGG GGA CTG TTA ATG GAC ATA TTA GTA GAG TGG ATA CGT
      Asn Pro Tyr Pro Pro Asp Asn Tyr Leu Tyr Asn His Leu Thr Tyr Ala>

490             500             510             520
            *     *        *     *        *     *        *     *
      GTC AAC ATT TGG AGT GAA AAC GAC CCG GCA GAT TTC AGA ATC TAT AAC
      CAG TTG TAA ACC TCA CTT TTG CTG GGC CGT CTA AAG TCT TAG ATA TTG
      Val Asn Ile Trp Ser Glu Asn Asp Pro Ala Asp Phe Arg Ile Tyr Asn>

530             540             550             560             570
       *     *        *     *        *     *        *     *        *     *
      GTG ACC TAC CTA GAA CCC TCC CTC CGC ATC GCA GCC AGC ACC CTG AAG
      CAC TGG ATG GAT CTT GGG AGG GAG GCG TAG CGT CGG TCG TGG GAC TTC
      Val Thr Tyr Leu Glu Pro Ser Leu Arg Ile Ala Ala Ser Thr Leu Lys>

580             590             600             610             620
       *     *        *     *        *     *        *     *        *
      TCT GGG ATT TCC TAC AGG GCA CGG GTG AGG GCC TGG GCT CAG AGC TAT
      AGA CCC TAA AGG ATG TCC CGT GCC CAC TCC CGG ACC CGA GTC TCG ATA
      Ser Gly Ile Ser Tyr Arg Ala Arg Val Arg Ala Trp Ala Gln Ser Tyr>

630             640             650             660             670
       *     *        *     *        *     *        *     *        *     *
      AAC ACC ACC TGG AGT GAG TGG AGC CCC AGC ACC AAG TGG CAC AAC TCC
      TTG TGG TGG ACC TCA CTC ACC TCG GGG TCG TGG TTC ACC GTG TTG AGG
      Asn Thr Thr Trp Ser Glu Trp Ser Pro Ser Thr Lys Trp His Asn Ser>

680             690             700             710             720
       *     *        *     *        *     *        *     *        *     *
      TAC AGG GAG CCC TTC GAG CAG TCC GGT GGG GGC GGG GGC GCC GCG CCT
      ATG TCC CTC GGG AAG CTC GTC AGG CCA CCC CCG CCC CCG CGG CGC GGA
      Tyr Arg Glu Pro Phe Glu Gln Ser Gly Gly Gly Gly Gly Ala Ala Pro>

730             740             750             760
            *     *        *     *        *     *        *     *
      ACG GAA ACT CAG CCA CCT GTG ACA AAT TTG AGT GTC TCT GTT GAA AAC
      TGC CTT TGA GTC GGT GGA CAC TGT TTA AAC TCA CAG AGA CAA CTT TTG
      Thr Glu Thr Gln Pro Pro Val Thr Asn Leu Ser Val Ser Val Glu Asn>
```

Figure 31C

```
770         780         790         800         810
 *     *     *     *     *     *     *     *     *     *
CTC TGC ACA GTA ATA TGG ACA TGG AAT CCA CCC GAG GGA GCC AGC TCA
GAG ACG TGT CAT TAT ACC TGT ACC TTA GGT GGG CTC CCT CGG TCG AGT
Leu Cys Thr Val Ile Trp Thr Trp Asn Pro Pro Glu Gly Ala Ser Ser>

820         830         840         850         860
 *     *     *     *     *     *     *     *     *     *
AAT TGT AGT CTA TGG TAT TTT AGT CAT TTT GGC GAC AAA CAA GAT AAG
TTA ACA TCA GAT ACC ATA AAA TCA GTA AAA CCG CTG TTT GTT CTA TTC
Asn Cys Ser Leu Trp Tyr Phe Ser His Phe Gly Asp Lys Gln Asp Lys>

870         880         890         900         910
 *     *     *     *     *     *     *     *     *     *
AAA ATA GCT CCG GAA ACT CGT CGT TCA ATA GAA GTA CCC CTG AAT GAG
TTT TAT CGA GGC CTT TGA GCA GCA AGT TAT CTT CAT GGG GAC TTA CTC
Lys Ile Ala Pro Glu Thr Arg Arg Ser Ile Glu Val Pro Leu Asn Glu>

920         930         940         950         960
 *     *     *     *     *     *     *     *     *     *
AGG ATT TGT CTG CAA GTG GGG TCC CAG TGT AGC ACC AAT GAG AGT GAG
TCC TAA ACA GAC GTT CAC CCC AGG GTC ACA TCG TGG TTA CTC TCA CTC
Arg Ile Cys Leu Gln Val Gly Ser Gln Cys Ser Thr Asn Glu Ser Glu>

970         980         990         1000
 *     *     *     *     *     *     *     *     *     *
AAG CCT AGC ATT TTG GTT GAA AAA TGC ATC TCA CCC CCA GAA GGT GAT
TTC GGA TCG TAA AAC CAA CTT TTT ACG TAG AGT GGG GGT CTT CCA CTA
Lys Pro Ser Ile Leu Val Glu Lys Cys Ile Ser Pro Pro Glu Gly Asp>

1010        1020        1030        1040        1050
 *     *     *     *     *     *     *     *     *     *
CCT GAG TCT GCT GTG ACT GAG CTT CAA TGC ATT TGG CAC AAC CTG AGC
GGA CTC AGA CGA CAC TGA CTC GAA GTT ACG TAA ACC GTG TTG GAC TCG
Pro Glu Ser Ala Val Thr Glu Leu Gln Cys Ile Trp His Asn Leu Ser>

1060        1070        1080        1090        1100
 *     *     *     *     *     *     *     *     *     *
TAC ATG AAG TGT TCT TGG CTC CCT GGA AGG AAT ACC AGT CCC GAC ACT
ATG TAC TTC ACA AGA ACC GAG GGA CCT TCC TTA TGG TCA GGG CTG TGA
Tyr Met Lys Cys Ser Trp Leu Pro Gly Arg Asn Thr Ser Pro Asp Thr>

1110        1120        1130        1140        1150
 *     *     *     *     *     *     *     *     *     *
AAC TAT ACT CTC TAC TAT TGG CAC AGA AGC CTG GAA AAA ATT CAT CAA
TTG ATA TGA GAG ATG ATA ACC GTG TCT TCG GAC CTT TTT TAA GTA GTT
Asn Tyr Thr Leu Tyr Tyr Trp His Arg Ser Leu Glu Lys Ile His Gln>
```

Figure 31D

```
         1160          1170          1180          1190          1200
     *     *       *     *       *     *       *     *       *     *
    TGT GAA AAC ATC TTT AGA GAA GGC CAA TAC TTT GGT TGT TCC TTT GAT
    ACA CTT TTG TAG AAA TCT CTT CCG GTT ATG AAA CCA ACA AGG AAA CTA
    Cys Glu Asn Ile Phe Arg Glu Gly Gln Tyr Phe Gly Cys Ser Phe Asp>

1210          1220          1230          1240
            *     *       *     *       *     *       *     *     *
           CTG ACC AAA GTC AAG GAT TCC AGT TTT GAA CAA CAC AGT GTC CAA ATA
           GAC TGG TTT CAC TTC CTA AGG TCA AAA CTT GTT GTG TCA CAG GTT TAT
           Leu Thr Lys Val Lys Asp Ser Ser Phe Glu Gln His Ser Val Gln Ile>

1250          1260          1270          1280          1290
  *     *       *     *       *     *       *     *       *     *
 ATG GTC AAG GAT AAT GCA GGA AAA ATT AAA CCA TCC TTC AAT ATA GTG
 TAC CAG TTC CTA TTA CGT CCT TTT TAA TTT GGT AGG AAG TTA TAT CAC
 Met Val Lys Asp Asn Ala Gly Lys Ile Lys Pro Ser Phe Asn Ile Val>

1300          1310          1320          1330          1340
     *     *       *     *       *     *       *     *       *     *
    CCT TTA ACT TCC CGT GTG AAA CCT GAT CCT CCA CAT ATT AAA AAC CTC
    GGA AAT TGA AGG GCA CAC TTT GGA CTA GGA GGT GTA TAA TTT TTG GAG
    Pro Leu Thr Ser Arg Val Lys Pro Asp Pro Pro His Ile Lys Asn Leu>

1350          1360          1370          1380          1390
          *     *       *     *       *     *       *     *       *     *
         TCC TTC CAC AAT GAT GAC CTA TAT GTG CAA TGG GAG AAT CCA CAG AAT
         AGG AAG GTG TTA CTA CTG GAT ATA CAC GTT ACC CTC TTA GGT GTC TTA
         Ser Phe His Asn Asp Asp Leu Tyr Val Gln Trp Glu Asn Pro Gln Asn>

1400          1410          1420          1430          1440
              *     *       *     *       *     *       *     *       *     *
             TTT ATT AGC AGA TGC CTA TTT TAT GAA GTA GAA GTC AAT AAC AGC CAA
             AAA TAA TCG TCT ACG GAT AAA ATA CTT CAT CTT CAG TTA TTG TCG GTT
             Phe Ile Ser Arg Cys Leu Phe Tyr Glu Val Glu Val Asn Asn Ser Gln>

1450          1460          1470          1480
                   *     *       *     *       *     *       *     *     *
                  ACT GAG ACA CAT AAT GTT TTC TAC GTC CAA GAG GCT AAA TGT GAG AAT
                  TGA CTC TGT GTA TTA CAA AAG ATG CAG GTT CTC CGA TTT ACA CTC TTA
                  Thr Glu Thr His Asn Val Phe Tyr Val Gln Glu Ala Lys Cys Glu Asn>

1490          1500          1510          1520          1530
  *     *       *     *       *     *       *     *       *     *
 CCA GAA TTT GAG AGA AAT GTG GAG AAT ACA TCT TGT TTC ATG GTC CCT
 GGT CTT AAA CTC TCT TTA CAC CTC TTA TGT AGA ACA AAG TAC CAG GGA
 Pro Glu Phe Glu Arg Asn Val Glu Asn Thr Ser Cys Phe Met Val Pro>
```

Figure 31E

```
          1540            1550            1560            1570            1580
            *               *               *               *               *
       GGT GTT CTT CCT GAT ACT TTG AAC ACA GTC AGA ATA AGA GTC AAA ACA
       CCA CAA GAA GGA CTA TGA AAC TTG TGT CAG TCT TAT TCT CAG TTT TGT
       Gly Val Leu Pro Asp Thr Leu Asn Thr Val Arg Ile Arg Val Lys Thr>

1590            1600            1610            1620            1630
            *               *               *               *               *
       AAT AAG TTA TGC TAT GAG GAT GAC AAA CTC TGG AGT AAT TGG AGC CAA
       TTA TTC AAT ACG ATA CTC CTA CTG TTT GAG ACC TCA TTA ACC TCG GTT
       Asn Lys Leu Cys Tyr Glu Asp Asp Lys Leu Trp Ser Asn Trp Ser Gln>

1640            1650            1660            1670            1680
            *               *               *               *               *
       GAA ATG AGT ATA GGT AAG AAG CGC AAT TCC ACA ACC GGA GAC AAA ACT
       CTT TAC TCA TAT CCA TTC TTC GCG TTA AGG TGT TGG CCT CTG TTT TGA
       Glu Met Ser Ile Gly Lys Lys Arg Asn Ser Thr Thr Gly Asp Lys Thr>

1690            1700            1710            1720
            *               *               *               *               *
       CAC ACA TGC CCA CCG TGC CCA GCA CCT GAA CTC CTG GGG GGA CCG TCA
       GTG TGT ACG GGT GGC ACG GGT CGT GGA CTT GAG GAC CCC CCT GGC AGT
       His Thr Cys Pro Pro Cys Pro Ala Pro Glu Leu Leu Gly Gly Pro Ser>

1730            1740            1750            1760            1770
     *               *               *               *               *
   GTC TTC CTC TTC CCC CCA AAA CCC AAG GAC ACC CTC ATG ATC TCC CGG
   CAG AAG GAG AAG GGG GGT TTT GGG TTC CTG TGG GAG TAC TAG AGG GCC
   Val Phe Leu Phe Pro Pro Lys Pro Lys Asp Thr Leu Met Ile Ser Arg>

1780            1790            1800            1810            1820
            *               *               *               *               *
       ACC CCT GAG GTC ACA TGC GTG GTG GTG GAC GTG AGC CAC GAA GAC CCT
       TGG GGA CTC CAG TGT ACG CAC CAC CAC CTG CAC TCG GTG CTT CTG GGA
       Thr Pro Glu Val Thr Cys Val Val Val Asp Val Ser His Glu Asp Pro>

1830            1840            1850            1860            1870
            *               *               *               *               *
       GAG GTC AAG TTC AAC TGG TAC GTG GAC GGC GTG GAG GTG CAT AAT GCC
       CTC CAG TTC AAG TTG ACC ATG CAC CTG CCG CAC CTC CAC GTA TTA CGG
       Glu Val Lys Phe Asn Trp Tyr Val Asp Gly Val Glu Val His Asn Ala>

1880            1890            1900            1910            1920
            *               *               *               *               *
       AAG ACA AAG CCG CGG GAG GAG CAG TAC AAC AGC ACG TAC CGT GTG GTC
       TTC TGT TTC GGC GCC CTC CTC GTC ATG TTG TCG TGC ATG GCA CAC CAG
       Lys Thr Lys Pro Arg Glu Glu Gln Tyr Asn Ser Thr Tyr Arg Val Val>
```

Figure 31F

```
              1930          1940          1950          1960
               *     *       *     *       *     *       *     *       *
         AGC GTC CTC ACC GTC CTG CAC CAG GAC TGG CTG AAT GGC AAG GAG TAC
         TCG CAG GAG TGG CAG GAC GTG GTC CTG ACC GAC TTA CCG TTC CTC ATG
         Ser Val Leu Thr Val Leu His Gln Asp Trp Leu Asn Gly Lys Glu Tyr>

1970          1980          1990          2000          2010
        *     *       *     *       *     *       *     *       *     *
      AAG TGC AAG GTC TCC AAC AAA GCC CTC CCA GCC CCC ATC GAG AAA ACC
      TTC ACG TTC CAG AGG TTG TTT CGG GAG GGT CGG GGG TAG CTC TTT TGG
      Lys Cys Lys Val Ser Asn Lys Ala Leu Pro Ala Pro Ile Glu Lys Thr>

2020          2030          2040          2050          2060
           *     *       *     *       *     *       *     *       *
        ATC TCC AAA GCC AAA GGG CAG CCC CGA GAA CCA CAG GTG TAC ACC CTG
        TAG AGG TTT CGG TTT CCC GTC GGG GCT CTT GGT GTC CAC ATG TGG GAC
        Ile Ser Lys Ala Lys Gly Gln Pro Arg Glu Pro Gln Val Tyr Thr Leu>

2070          2080          2090          2100          2110
           *     *       *     *       *     *       *     *       *     *
        CCC CCA TCC CGG GAG GAG ATG ACC AAG AAC CAG GTC AGC CTG ACC TGC
        GGG GGT AGG GCC CTC CTC TAC TGG TTC TTG GTC CAG TCG GAC TGG ACG
        Pro Pro Ser Arg Glu Glu Met Thr Lys Asn Gln Val Ser Leu Thr Cys>

2120          2130          2140          2150          2160
              *     *       *     *       *     *       *     *       *     *
           CTG GTC AAA GGC TTC TAT CCC AGC GAC ATC GCC GTG GAG TGG GAG AGC
           GAC CAG TTT CCG AAG ATA GGG TCG CTG TAG CGG CAC CTC ACC CTC TCG
           Leu Val Lys Gly Phe Tyr Pro Ser Asp Ile Ala Val Glu Trp Glu Ser>

2170          2180          2190          2200
                  *     *       *     *       *     *       *     *       *
               AAT GGG CAG CCG GAG AAC AAC TAC AAG ACC ACG CCT CCC GTG CTG GAC
               TTA CCC GTC GGC CTC TTG TTG ATG TTC TGG TGC GGA GGG CAC GAC CTG
               Asn Gly Gln Pro Glu Asn Asn Tyr Lys Thr Thr Pro Pro Val Leu Asp>

2210          2220          2230          2240          2250
        *     *       *     *       *     *       *     *       *     *
      TCC GAC GGC TCC TTC TTC CTC TAT AGC AAG CTC ACC GTG GAC AAG AGC
      AGG CTG CCG AGG AAG AAG GAG ATA TCG TTC GAG TGG CAC CTG TTC TCG
      Ser Asp Gly Ser Phe Phe Leu Tyr Ser Lys Leu Thr Val Asp Lys Ser>

2260          2270          2280          2290          2300
           *     *       *     *       *     *       *     *       *
        AGG TGG CAG CAG GGG AAC GTC TTC TCA TGC TCC GTG ATG CAT GAG GCT
        TCC ACC GTC GTC CCC TTG CAG AAG AGT ACG AGG CAC TAC GTA CTC CGA
        Arg Trp Gln Gln Gly Asn Val Phe Ser Cys Ser Val Met His Glu Ala>
```

Figure 31G

```
         2310           2320           2330           2340           2350
   *       *      *       *      *       *      *       *      *       *
CTG CAC AAC CAC TAC ACG CAG AAG AGC CTC TCC CTG TCT CCG GGT AAA
GAC GTG TTG GTG ATG TGC GTC TTC TCG GAG AGG GAC AGA GGC CCA TTT
Leu His Asn His Tyr Thr Gln Lys Ser Leu Ser Leu Ser Pro Gly Lys>

*
TGA
ACT
* * *>
```

Figure 32A

```
                10                  20                  30                  40
         *       *       *       *       *       *       *       *       *
ATG GTG TGG CCG GCG CGG CTC TGC GGG CTG TGG GCG CTG CTG CTC TGC
TAC CAC ACC GGC CGC GCC GAG ACG CCC GAC ACC CGC GAC GAC GAG ACG
Met Val Trp Pro Ala Arg Leu Cys Gly Leu Trp Ala Leu Leu Leu Cys>

50                  60                  70                  80                  90
   *       *       *       *       *       *       *       *       *       *
GCC GGC GGC GGG GGC GGG GGC GGG GGC GCC GCG CCT ACG GAA ACT CAG
CGG CCG CCG CCC CCG CCC CCG CCC CCG CGG CGC GGA TGC CTT TGA GTC
Ala Gly Gly Gly Gly Gly Gly Gly Ala Ala Pro Thr Glu Thr Gln>

100                 110                 120                 130                 140
    *       *       *       *       *       *       *       *       *
CCA CCT GTG ACA AAT TTG AGT GTC TCT GTT GAA AAC CTC TGC ACA GTA
GGT GGA CAC TGT TTA AAC TCA CAG AGA CAA CTT TTG GAG ACG TGT CAT
Pro Pro Val Thr Asn Leu Ser Val Ser Val Glu Asn Leu Cys Thr Val>

150                 160                 170                 180                 190
    *       *       *       *       *       *       *       *       *       *
ATA TGG ACA TGG AAT CCA CCC GAG GGA GCC AGC TCA AAT TGT AGT CTA
TAT ACC TGT ACC TTA GGT GGG CTC CCT CGG TCG AGT TTA ACA TCA GAT
Ile Trp Thr Trp Asn Pro Pro Glu Gly Ala Ser Ser Asn Cys Ser Leu>

200                 210                 220                 230                 240
    *       *       *       *       *       *       *       *       *       *
TGG TAT TTT AGT CAT TTT GGC GAC AAA CAA GAT AAG AAA ATA GCT CCG
ACC ATA AAA TCA GTA AAA CCG CTG TTT GTT CTA TTC TTT TAT CGA GGC
Trp Tyr Phe Ser His Phe Gly Asp Lys Gln Asp Lys Lys Ile Ala Pro>

250                 260                 270                 280
        *       *       *       *       *       *       *       *       *
GAA ACT CGT CGT TCA ATA GAA GTA CCC CTG AAT GAG AGG ATT TGT CTG
CTT TGA GCA GCA AGT TAT CTT CAT GGG GAC TTA CTC TCC TAA ACA GAC
Glu Thr Arg Arg Ser Ile Glu Val Pro Leu Asn Glu Arg Ile Cys Leu>

290                 300                 310                 320                 330
*       *       *       *       *       *       *       *       *       *
CAA GTG GGG TCC CAG TGT AGC ACC AAT GAG AGT GAG AAG CCT AGC ATT
GTT CAC CCC AGG GTC ACA TCG TGG TTA CTC TCA CTC TTC GGA TCG TAA
Gln Val Gly Ser Gln Cys Ser Thr Asn Glu Ser Glu Lys Pro Ser Ile>

340                 350                 360                 370                 380
   *       *       *       *       *       *       *       *       *
TTG GTT GAA AAA TGC ATC TCA CCC CCA GAA GGT GAT CCT GAG TCT GCT
AAC CAA CTT TTT ACG TAG AGT GGG GGT CTT CCA CTA GGA CTC AGA CGA
Leu Val Glu Lys Cys Ile Ser Pro Pro Glu Gly Asp Pro Glu Ser Ala>
```

Figure 32B

```
         390         400         410         420         430
    *    *      *    *      *    *      *    *      *    *
GTG ACT GAG CTT CAA TGC ATT TGG CAC AAC CTG AGC TAC ATG AAG TGT
CAC TGA CTC GAA GTT ACG TAA ACC GTG TTG GAC TCG ATG TAC TTC ACA
Val Thr Glu Leu Gln Cys Ile Trp His Asn Leu Ser Tyr Met Lys Cys>

440         450         460         470         480
         *    *      *    *      *    *      *    *      *    *
TCT TGG CTC CCT GGA AGG AAT ACC AGT CCC GAC ACT AAC TAT ACT CTC
AGA ACC GAG GGA CCT TCC TTA TGG TCA GGG CTG TGA TTG ATA TGA GAG
Ser Trp Leu Pro Gly Arg Asn Thr Ser Pro Asp Thr Asn Tyr Thr Leu>

490         500         510         520
         *    *      *    *      *    *      *    *      *
TAC TAT TGG CAC AGA AGC CTG GAA AAA ATT CAT CAA TGT GAA AAC ATC
ATG ATA ACC GTG TCT TCG GAC CTT TTT TAA GTA GTT ACA CTT TTG TAG
Tyr Tyr Trp His Arg Ser Leu Glu Lys Ile His Gln Cys Glu Asn Ile>

530         540         550         560         570
    *    *      *    *      *    *      *    *      *    *
TTT AGA GAA GGC CAA TAC TTT GGT TGT TCC TTT GAT CTG ACC AAA GTG
AAA TCT CTT CCG GTT ATG AAA CCA ACA AGG AAA CTA GAC TGG TTT CAC
Phe Arg Glu Gly Gln Tyr Phe Gly Cys Ser Phe Asp Leu Thr Lys Val>

580         590         600         610         620
    *    *      *    *      *    *      *    *      *
AAG GAT TCC AGT TTT GAA CAA CAC AGT GTC CAA ATA ATG GTC AAG GAT
TTC CTA AGG TCA AAA CTT GTT GTG TCA CAG GTT TAT TAC CAG TTC CTA
Lys Asp Ser Ser Phe Glu Gln His Ser Val Gln Ile Met Val Lys Asp>

630         640         650         660         670
    *    *      *    *      *    *      *    *      *    *
AAT GCA GGA AAA ATT AAA CCA TCC TTC AAT ATA GTG CCT TTA ACT TCC
TTA CGT CCT TTT TAA TTT GGT AGG AAG TTA TAT CAC GGA AAT TGA AGG
Asn Ala Gly Lys Ile Lys Pro Ser Phe Asn Ile Val Pro Leu Thr Ser>

680         690         700         710         720
    *    *      *    *      *    *      *    *      *    *
CGT GTG AAA CCT GAT CCT CCA CAT ATT AAA AAC CTC TCC TTC CAC AAT
GCA CAC TTT GGA CTA GGA GGT GTA TAA TTT TTG GAG AGG AAG GTG TTA
Arg Val Lys Pro Asp Pro Pro His Ile Lys Asn Leu Ser Phe His Asn>

730         740         750         760
    *    *      *    *      *    *      *    *
GAT GAC CTA TAT GTG CAA TGG GAG AAT CCA CAG AAT TTT ATT AGC AGA
CTA CTG GAT ATA CAC GTT ACC CTC TTA GGT GTC TTA AAA TAA TCG TCT
Asp Asp Leu Tyr Val Gln Trp Glu Asn Pro Gln Asn Phe Ile Ser Arg>
```

Figure 32C

```
   770         780         790         800         810
    *     *     *     *     *     *     *     *     *     *
TGC CTA TTT TAT GAA GTA GAA GTC AAT AAC AGC CAA ACT GAG ACA CAT
ACG GAT AAA ATA CTT CAT CTT CAG TTA TTG TCG GTT TGA CTC TGT GTA
Cys Leu Phe Tyr Glu Val Glu Val Asn Asn Ser Gln Thr Glu Thr His>

820         830         840         850         860
    *     *     *     *     *     *     *     *     *
AAT GTT TTC TAC GTC CAA GAG GCT AAA TGT GAG AAT CCA GAA TTT GAG
TTA CAA AAG ATG CAG GTT CTC CGA TTT ACA CTC TTA GGT CTT AAA CTC
Asn Val Phe Tyr Val Gln Glu Ala Lys Cys Glu Asn Pro Glu Phe Glu>

870         880         890         900         910
    *     *     *     *     *     *     *     *     *     *
AGA AAT GTG GAG AAT ACA TCT TGT TTC ATG GTC CCT GGT GTT CTT CCT
TCT TTA CAC CTC TTA TGT AGA ACA AAG TAC CAG GGA CCA CAA GAA GGA
Arg Asn Val Glu Asn Thr Ser Cys Phe Met Val Pro Gly Val Leu Pro>

920         930         940         950         960
    *     *     *     *     *     *     *     *     *     *
GAT ACT TTG AAC ACA GTC AGA ATA AGA GTC AAA ACA AAT AAG TTA TGC
CTA TGA AAC TTG TGT CAG TCT TAT TCT CAG TTT TGT TTA TTC AAT ACG
Asp Thr Leu Asn Thr Val Arg Ile Arg Val Lys Thr Asn Lys Leu Cys>

970         980         990        1000
    *     *     *     *     *     *     *     *     *
TAT GAG GAT GAC AAA CTC TGG AGT AAT TGG AGC CAA GAA ATG AGT ATA
ATA CTC CTA CTG TTT GAG ACC TCA TTA ACC TCG GTT CTT TAC TCA TAT
Tyr Glu Asp Asp Lys Leu Trp Ser Asn Trp Ser Gln Glu Met Ser Ile>

1010        1020        1030        1040        1050
    *     *     *     *     *     *     *     *     *     *
GGT AAG AAG CGC AAT TCC ACA GGC GCG CCT AGT GGT GGA GGT GGC CGG
CCA TTC TTC GCG TTA AGG TGT CCG CGC GGA TCA CCA CCT CCA CCG GCC
Gly Lys Lys Arg Asn Ser Thr Gly Ala Pro Ser Gly Gly Gly Gly Arg>

1060        1070        1080        1090        1100
    *     *     *     *     *     *     *     *     *
CCC GCA AGC TCT GGG AAC ATG AAG GTC TTG CAG GAG CCC ACC TGC GTC
GGG CGT TCG AGA CCC TTG TAC TTC CAG AAC GTC CTC GGG TGG ACG CAG
Pro Ala Ser Ser Gly Asn Met Lys Val Leu Gln Glu Pro Thr Cys Val>

1110        1120        1130        1140        1150
    *     *     *     *     *     *     *     *     *     *
TCC GAC TAC ATG AGC ATC TCT ACT TGC GAG TGG AAG ATG AAT GGT CCC
AGG CTG ATG TAC TCG TAG AGA TGA ACG CTC ACC TTC TAC TTA CCA GGG
Ser Asp Tyr Met Ser Ile Ser Thr Cys Glu Trp Lys Met Asn Gly Pro>
```

Figure 32D

```
          1160           1170           1180           1190           1200
       *      *      *      *      *      *      *      *      *      *
      ACC AAT TGC AGC ACC GAG CTC CGC CTG TTG TAC CAG CTG GTT TTT CTG
      TGG TTA ACG TCG TGG CTC GAG GCG GAC AAC ATG GTC GAC CAA AAA GAC
      Thr Asn Cys Ser Thr Glu Leu Arg Leu Leu Tyr Gln Leu Val Phe Leu>

1210           1220           1230           1240
           *      *      *      *      *      *      *      *
          CTC TCC GAA GCC CAC ACG TGT ATC CCT GAG AAC AAC GGA GGC GCG GGG
          GAG AGG CTT CGG GTG TGC ACA TAG GGA CTC TTG TTG CCT CCG CGC CCC
          Leu Ser Glu Ala His Thr Cys Ile Pro Glu Asn Asn Gly Gly Ala Gly>

1250           1260           1270           1280           1290
   *      *      *      *      *      *      *      *      *      *
  TGC GTG TGC CAC CTG CTC ATG GAT GAC GTG GTC AGT GCG GAT AAC TAT
  ACG CAC ACG GTG GAC GAG TAC CTA CTG CAC CAG TCA CGC CTA TTG ATA
  Cys Val Cys His Leu Leu Met Asp Asp Val Val Ser Ala Asp Asn Tyr>

1300           1310           1320           1330           1340
       *      *      *      *      *      *      *      *      *      *
      ACA CTG GAC CTG TGG GCT GGG CAG CAG CTG CTG TGG AAG GGC TCC TTC
      TGT GAC CTG GAC ACC CGA CCC GTC GTC GAC GAC ACC TTC CCG AGG AAG
      Thr Leu Asp Leu Trp Ala Gly Gln Gln Leu Leu Trp Lys Gly Ser Phe>

1350           1360           1370           1380           1390
           *      *      *      *      *      *      *      *      *      *
          AAG CCC AGC GAG CAT GTG AAA CCC AGG GCC CCA GGA AAC CTG ACA GTT
          TTC GGG TCG CTC GTA CAC TTT GGG TCC CGG GGT CCT TTG GAC TGT CAA
          Lys Pro Ser Glu His Val Lys Pro Arg Ala Pro Gly Asn Leu Thr Val>

1400           1410           1420           1430           1440
               *      *      *      *      *      *      *      *      *      *
              CAC ACC AAT GTC TCC GAC ACT CTG CTG CTG ACC TGG AGC AAC CCG TAT
              GTG TGG TTA CAG AGG CTG TGA GAC GAC GAC TGG ACC TCG TTG GGC ATA
              His Thr Asn Val Ser Asp Thr Leu Leu Leu Thr Trp Ser Asn Pro Tyr>

1450           1460           1470           1480
                   *      *      *      *      *      *      *      *      *
                  CCC CCT GAC AAT TAC CTG TAT AAT CAT CTC ACC TAT GCA GTC AAC ATT
                  GGG GGA CTG TTA ATG GAC ATA TTA GTA GAG TGG ATA CGT CAG TTG TAA
                  Pro Pro Asp Asn Tyr Leu Tyr Asn His Leu Thr Tyr Ala Val Asn Ile>

1490           1500           1510           1520           1530
       *      *      *      *      *      *      *      *      *      *
      TGG AGT GAA AAC GAC CCG GCA GAT TTC AGA ATC TAT AAC GTG ACC TAC
      ACC TCA CTT TTG CTG GGC CGT CTA AAG TCT TAG ATA TTG CAC TGG ATG
      Trp Ser Glu Asn Asp Pro Ala Asp Phe Arg Ile Tyr Asn Val Thr Tyr>
```

Figure 32E

```
      1540           1550           1560           1570           1580
        *       *       *       *       *       *       *       *       *       *
CTA GAA CCC TCC CTC CGC ATC GCA GCC AGC ACC CTG AAG TCT GGG ATT
GAT CTT GGG AGG GAG GCG TAG CGT CGG TCG TGG GAC TTC AGA CCC TAA
Leu Glu Pro Ser Leu Arg Ile Ala Ala Ser Thr Leu Lys Ser Gly Ile>

1590           1600           1610           1620           1630
        *       *       *       *       *       *       *       *       *       *
TCC TAC AGG GCA CGG GTG AGG GCC TGG GCT CAG TGC TAT AAC ACC ACC
AGG ATG TCC CGT GCC CAC TCC CGG ACC CGA GTC ACG ATA TTG TGG TGG
Ser Tyr Arg Ala Arg Val Arg Ala Trp Ala Gln Cys Tyr Asn Thr Thr>

1640           1650           1660           1670           1680
        *       *       *       *       *       *       *       *       *       *
TGG AGT GAG TGG AGC CCC AGC ACC AAG TGG CAC AAC TCC TAC AGG GAG
ACC TCA CTC ACC TCG GGG TCG TGG TTC ACC GTG TTG AGG ATG TCC CTC
Trp Ser Glu Trp Ser Pro Ser Thr Lys Trp His Asn Ser Tyr Arg Glu>

1690           1700           1710           1720
        *       *       *       *       *       *       *       *       *
CCC TTC GAG CAG TCC GGA GAC AAA ACT CAC ACA TGC CCA CCG TGC CCA
GGG AAG CTC GTC AGG CCT CTG TTT TGA GTG TGT ACG GGT GGC ACG GGT
Pro Phe Glu Gln Ser Gly Asp Lys Thr His Thr Cys Pro Pro Cys Pro>

1730           1740           1750           1760           1770
   *       *       *       *       *       *       *       *       *       *
GCA CCT GAA CTC CTG GGG GGA CCG TCA GTC TTC CTC TTC CCC CCA AAA
CGT GGA CTT GAG GAC CCC CCT GGC AGT CAG AAG GAG AAG GGG GGT TTT
Ala Pro Glu Leu Leu Gly Gly Pro Ser Val Phe Leu Phe Pro Pro Lys>

1780           1790           1800           1810           1820
        *       *       *       *       *       *       *       *       *
CCC AAG GAC ACC CTC ATG ATC TCC CGG ACC CCT GAG GTC ACA TGC GTG
GGG TTC CTG TGG GAG TAC TAG AGG GCC TGG GGA CTC CAG TGT ACG CAC
Pro Lys Asp Thr Leu Met Ile Ser Arg Thr Pro Glu Val Thr Cys Val>

1830           1840           1850           1860           1870
        *       *       *       *       *       *       *       *       *       *
GTG GTG GAC GTG AGC CAC GAA GAC CCT GAG GTC AAG TTC AAC TGG TAC
CAC CAC CTG CAC TCG GTG CTT CTG GGA CTC CAG TTC AAG TTG ACC ATG
Val Val Asp Val Ser His Glu Asp Pro Glu Val Lys Phe Asn Trp Tyr>

1880           1890           1900           1910           1920
        *       *       *       *       *       *       *       *       *       *
GTG GAC GGC GTG GAG GTG CAT AAT GCC AAG ACA AAG CCG CGG GAG GAG
CAC CTG CCG CAC CTC CAC GTA TTA CGG TTC TGT TTC GGC GCC CTC CTC
Val Asp Gly Val Glu Val His Asn Ala Lys Thr Lys Pro Arg Glu Glu>
```

Figure 32F

```
              1930           1940           1950           1960
         *     *     *     *     *     *     *     *     *     *
        CAG   TAC   AAC   AGC   ACG   TAC   CGT   GTG   GTC   AGC   GTC   CTC   ACC   GTC   CTG   CAC
        GTC   ATG   TTG   TCG   TGC   ATG   GCA   CAC   CAG   TCG   CAG   GAG   TGG   CAG   GAC   GTG
        Gln   Tyr   Asn   Ser   Thr   Tyr   Arg   Val   Val   Ser   Val   Leu   Thr   Val   Leu   His>

1970           1980           1990           2000           2010
    *     *     *     *     *     *     *     *     *     *
   CAG   GAC   TGG   CTG   AAT   GGC   AAG   GAG   TAC   AAG   TGC   AAG   GTC   TCC   AAC   AAA
   GTC   CTG   ACC   GAC   TTA   CCG   TTC   CTC   ATG   TTC   ACG   TTC   CAG   AGG   TTG   TTT
   Gln   Asp   Trp   Leu   Asn   Gly   Lys   Glu   Tyr   Lys   Cys   Lys   Val   Ser   Asn   Lys>

2020           2030           2040           2050           2060
          *     *     *     *     *     *     *     *     *
         GCC   CTC   CCA   GCC   CCC   ATC   GAG   AAA   ACC   ATC   TCC   AAA   GCC   AAA   GGG   CAG
         CGG   GAG   GGT   CGG   GGG   TAG   CTC   TTT   TGG   TAG   AGG   TTT   CGG   TTT   CCC   GTC
         Ala   Leu   Pro   Ala   Pro   Ile   Glu   Lys   Thr   Ile   Ser   Lys   Ala   Lys   Gly   Gln>

2070           2080           2090           2100           2110
       *     *     *     *     *     *     *     *     *     *
       CCC   CGA   GAA   CCA   CAG   GTG   TAC   ACC   CTG   CCC   CCA   TCC   CGG   GAG   GAG   ATG
       GGG   GCT   CTT   GGT   GTC   CAC   ATG   TGG   GAC   GGG   GGT   AGG   GCC   CTC   CTC   TAC
       Pro   Arg   Glu   Pro   Gln   Val   Tyr   Thr   Leu   Pro   Pro   Ser   Arg   Glu   Glu   Met>

2120           2130           2140           2150           2160
          *     *     *     *     *     *     *     *     *     *
         ACC   AAG   AAC   CAG   GTC   AGC   CTG   ACC   TGC   CTG   GTC   AAA   GGC   TTC   TAT   CCC
         TGG   TTC   TTG   GTC   CAG   TCG   GAC   TGG   ACG   GAC   CAG   TTT   CCG   AAG   ATA   GGG
         Thr   Lys   Asn   Gln   Val   Ser   Leu   Thr   Cys   Leu   Val   Lys   Gly   Phe   Tyr   Pro>

2170           2180           2190           2200
         *     *     *     *     *     *     *     *     *
        AGC   GAC   ATC   GCC   GTG   GAG   TGG   GAG   AGC   AAT   GGG   CAG   CCG   GAG   AAC   AAC
        TCG   CTG   TAG   CGG   CAC   CTC   ACC   CTC   TCG   TTA   CCC   GTC   GGC   CTC   TTG   TTG
        Ser   Asp   Ile   Ala   Val   Glu   Trp   Glu   Ser   Asn   Gly   Gln   Pro   Glu   Asn   Asn>

2210           2220           2230           2240           2250
    *     *     *     *     *     *     *     *     *     *
   TAC   AAG   ACC   ACG   CCT   CCC   GTG   CTG   GAC   TCC   GAC   GGC   TCC   TTC   TTC   CTC
   ATG   TTC   TGG   TGC   GGA   GGG   CAC   GAC   CTG   AGG   CTG   CCG   AGG   AAG   AAG   GAG
   Tyr   Lys   Thr   Thr   Pro   Pro   Val   Leu   Asp   Ser   Asp   Gly   Ser   Phe   Phe   Leu>

2260           2270           2280           2290           2300
          *     *     *     *     *     *     *     *     *
         TAT   AGC   AAG   CTC   ACC   GTG   GAC   AAG   AGC   AGG   TGG   CAG   CAG   GGG   AAC   GTC
         ATA   TCG   TTC   GAG   TGG   CAC   CTG   TTC   TCG   TCC   ACC   GTC   GTC   CCC   TTG   CAG
         Tyr   Ser   Lys   Leu   Thr   Val   Asp   Lys   Ser   Arg   Trp   Gln   Gln   Gly   Asn   Val>
```

Figure 32G

```
         2310            2320            2330            2340            2350
    *       *       *       *       *       *       *       *       *       *
   TTC TCA TGC TCC GTG ATG CAT GAG GCT CTG CAC AAC CAC TAC ACG CAG
   AAG AGT ACG AGG CAC TAC GTA CTC CGA GAC GTG TTG GTG ATG TGC GTC
   Phe Ser Cys Ser Val Met His Glu Ala Leu His Asn His Tyr Thr Gln>

2360            2370            2380
    *       *       *       *       *       *
   AAG AGC CTC TCC CTG TCT CCG GGT AAA TGA
   TTC TCG GAG AGG GAC AGA GGC CCA TTT ACT
   Lys Ser Leu Ser Leu Ser Pro Gly Lys ***>
```

Figure 38A

```
              -70            -60            -50            -40
        *      *      *      *      *      *      *      *
ATG  GTG  TGG  CCG  GCG  CGG  CTC  TGC  GGG  CTG  TGG  GCG  CTG  CTG
TAC  CAC  ACC  GGC  CGC  GCC  GAG  ACG  CCC  GAC  ACC  CGC  GAC  GAC
Met  Val  Trp  Pro  Ala  Arg  Leu  Cys  Gly  Leu  Trp  Ala  Leu  Leu>
_____SIGNAL PEPTIDE_____>
_____IL13Rα1_____>

-30            -20            -10             1
     *    *      *      *      *      *      *      *      *
CTC  TGC  GCC  GGC  GGC  GGG  GGC  GGG  GGC  GGG  GGC  GCC  GCG  CCT
GAG  ACG  CGG  CCG  CCG  CCC  CCG  CCC  CCG  CCC  CCG  CGG  CGC  GGA
Leu  Cys  Ala  Gly  Gly  Gly  Gly  Gly  Gly  Gly  Gly  Ala  Ala  Pro>
_____SIGNAL PEPTIDE_____>
_____IL13Rα1_____>

10             20             30             40
     *     *      *      *      *      *      *     *
ACG  GAA  ACT  CAG  CCA  CCT  GTG  ACA  AAT  TTG  AGT  GTC  TCT  GTT
TGC  CTT  TGA  GTC  GGT  GGA  CAC  TGT  TTA  AAC  TCA  CAG  AGA  CAA
Thr  Glu  Thr  Gln  Pro  Pro  Val  Thr  Asn  Leu  Ser  Val  Ser  Val>
_____IL13Rα1_____>

50            60              70             80            90
  *      *      *      *      *      *      *      *      *
GAA  AAC  CTC  TGC  ACA  GTA  ATA  TGG  ACA  TGG  AAT  CCA  CCC  GAG
CTT  TTG  GAG  ACG  TGT  CAT  TAT  ACC  TGT  ACC  TTA  GGT  GGG  CTC
Glu  Asn  Leu  Cys  Thr  Val  Ile  Trp  Thr  Trp  Asn  Pro  Pro  Glu>
_____IL13Rα1_____>

100            110            120            130
     *      *      *      *      *      *      *      *
GGA  GCC  AGC  TCA  AAT  TGT  AGT  CTA  TGG  TAT  TTT  AGT  CAT  TTT
CCT  CGG  TCG  AGT  TTA  ACA  TCA  GAT  ACC  ATA  AAA  TCA  GTA  AAA
Gly  Ala  Ser  Ser  Asn  Cys  Ser  Leu  Trp  Tyr  Phe  Ser  His  Phe>
_____IL13Rα1_____>

140            150            160            170
     *      *      *      *      *      *      *      *
GGC  GAC  AAA  CAA  GAT  AAG  AAA  ATA  GCT  CCG  GAA  ACT  CGT  CGT
CCG  CTG  TTT  GTT  CTA  TTC  TTT  TAT  CGA  GGC  CTT  TGA  GCA  GCA
Gly  Asp  Lys  Gln  Asp  Lys  Lys  Ile  Ala  Pro  Glu  Thr  Arg  Arg>
_____IL13Rα1_____>

180            190            200            210
     *     *      *      *      *      *      *      *     *
TCA  ATA  GAA  GTA  CCC  CTG  AAT  GAG  AGG  ATT  TGT  CTG  CAA  GTG
AGT  TAT  CTT  CAT  GGG  GAC  TTA  CTC  TCC  TAA  ACA  GAC  GTT  CAC
Ser  Ile  Glu  Val  Pro  Leu  Asn  Glu  Arg  Ile  Cys  Leu  Gln  Val>
_____IL13Rα1_____>
```

Figure 38B

```
           220            230            240              250
            *       *      *       *       *       *       *       *
           GGG     TCC    CAG     TGT     AGC     ACC     AAT     GAG     AGT     GAG     AAG     CCT     AGC     ATT
           CCC     AGG    GTC     ACA     TCG     TGG     TTA     CTC     TCA     CTC     TTC     GGA     TCG     TAA
           Gly     Ser    Gln     Cys     Ser     Thr     Asn     Glu     Ser     Glu     Lys     Pro     Ser     Ile>
                                          _____IL13Rα1_____>

260            270            280              290            300
      *       *      *       *       *       *       *       *       *
     TTG     GTT    GAA     AAA     TGC     ATC     TCA     CCC     CCA     GAA     GGT     GAT     CCT     GAG
     AAC     CAA    CTT     TTT     ACG     TAG     AGT     GGG     GGT     CTT     CCA     CTA     GGA     CTC
     Leu     Val    Glu     Lys     Cys     Ile     Ser     Pro     Pro     Glu     Gly     Asp     Pro     Glu>
                                    _____IL13Rα1_____>

310            320            330              340
       *       *      *       *       *       *       *       *
      TCT     GCT    GTG     ACT     GAG     CTT     CAA     TGC     ATT     TGG     CAC     AAC     CTG     AGC
      AGA     CGA    CAC     TGA     CTC     GAA     GTT     ACG     TAA     ACC     GTG     TTG     GAC     TCG
      Ser     Ala    Val     Thr     Glu     Leu     Gln     Cys     Ile     Trp     His     Asn     Leu     Ser>
                                     _____IL13Rα1_____>

350            360            370              380
       *       *      *       *       *       *       *       *
      TAC     ATG    AAG     TGT     TCT     TGG     CTC     CCT     GGA     AGG     AAT     ACC     AGT     CCC
      ATG     TAC    TTC     ACA     AGA     ACC     GAG     GGA     CCT     TCC     TTA     TGG     TCA     GGG
      Tyr     Met    Lys     Cys     Ser     Trp     Leu     Pro     Gly     Arg     Asn     Thr     Ser     Pro>
                                     _____IL13Rα1_____>

390            400            410              420
       *       *      *       *       *       *       *       *       *
      GAC     ACT    AAC     TAT     ACT     CTC     TAC     TAT     TGG     CAC     AGA     AGC     CTG     GAA
      CTG     TGA    TTG     ATA     TGA     GAG     ATG     ATA     ACC     GTG     TCT     TCG     GAC     CTT
      Asp     Thr    Asn     Tyr     Thr     Leu     Tyr     Tyr     Trp     His     Arg     Ser     Leu     Glu>
                                     _____IL13Rα1_____>

430            440            450              460
       *       *      *       *       *       *       *       *
      AAA     ATT    CAT     CAA     TGT     GAA     AAC     ATC     TTT     AGA     GAA     GGC     CAA     TAC
      TTT     TAA    GTA     GTT     ACA     CTT     TTG     TAG     AAA     TCT     CTT     CCG     GTT     ATG
      Lys     Ile    His     Gln     Cys     Glu     Asn     Ile     Phe     Arg     Glu     Gly     Gln     Tyr>
                                     _____IL13Rα1_____>

470            480            490              500            510
      *       *      *       *       *       *       *       *       *
     TTT     GGT    TGT     TCC     TTT     GAT     CTG     ACC     AAA     GTG     AAG     GAT     TCC     AGT
     AAA     CCA    ACA     AGG     AAA     CTA     GAC     TGG     TTT     CAC     TTC     CTA     AGG     TCA
     Phe     Gly    Cys     Ser     Phe     Asp     Leu     Thr     Lys     Val     Lys     Asp     Ser     Ser>
                                    _____IL13Rα1_____>
```

Figure 38C

```
               520         530         540         550
          *     *     *     *     *     *     *     *
     TTT GAA CAA CAC AGT GTC CAA ATA ATG GTC AAG GAT AAT GCA
     AAA CTT GTT GTG TCA CAG GTT TAT TAC CAG TTC CTA TTA CGT
     Phe Glu Gln His Ser Val Gln Ile Met Val Lys Asp Asn Ala>
     ─────────────────────────IL13Rα1────────────────────────>

560         570         580         590
          *     *     *     *     *     *     *     *
     GGA AAA ATT AAA CCA TCC TTC AAT ATA GTG CCT TTA ACT TCC
     CCT TTT TAA TTT GGT AGG AAG TTA TAT CAC GGA AAT TGA AGG
     Gly Lys Ile Lys Pro Ser Phe Asn Ile Val Pro Leu Thr Ser>
     ─────────────────────────IL13Rα1────────────────────────>

600         610         620         630
          *     *     *     *     *     *     *     *
     CGT GTG AAA CCT GAT CCT CCA CAT ATT AAA AAC CTC TCC TTC
     GCA CAC TTT GGA CTA GGA GGT GTA TAA TTT TTG GAG AGG AAG
     Arg Val Lys Pro Asp Pro Pro His Ile Lys Asn Leu Ser Phe>
     ─────────────────────────IL13Rα1────────────────────────>

640         650         660         670
          *     *     *     *     *     *     *     *
     CAC AAT GAT GAC CTA TAT GTG CAA TGG GAG AAT CCA CAG AAT
     GTG TTA CTA CTG GAT ATA CAC GTT ACC CTC TTA GGT GTC TTA
     His Asn Asp Asp Leu Tyr Val Gln Trp Glu Asn Pro Gln Asn>
     ─────────────────────────IL13Rα1────────────────────────>

680         690         700         710         720
      *     *     *     *     *     *     *     *     *
     TTT ATT AGC AGA TGC CTA TTT TAT GAA GTA GAA GTC AAT AAC
     AAA TAA TCG TCT ACG GAT AAA ATA CTT CAT CTT CAG TTA TTG
     Phe Ile Ser Arg Cys Leu Phe Tyr Glu Val Glu Val Asn Asn>
     ─────────────────────────IL13Rα1────────────────────────>

730         740         750         760
          *     *     *     *     *     *     *     *
     AGC CAA ACT GAG ACA CAT AAT GTT TTC TAC GTC CAA GAG GCT
     TCG GTT TGA CTC TGT GTA TTA CAA AAG ATG CAG GTT CTC CGA
     Ser Gln Thr Glu Thr His Asn Val Phe Tyr Val Gln Glu Ala>
     ─────────────────────────IL13Rα1────────────────────────>

770         780         790         800
          *     *     *     *     *     *     *     *
     AAA TGT GAG AAT CCA GAA TTT GAG AGA AAT GTG GAG AAT ACA
     TTT ACA CTC TTA GGT CTT AAA CTC TCT TTA CAC CTC TTA TGT
     Lys Cys Glu Asn Pro Glu Phe Glu Arg Asn Val Glu Asn Thr>
     ─────────────────────────IL13Rα1────────────────────────>
```

Figure 38D

```
        810             820             830             840
    *       *       *       *       *       *       *       *       *
   TCT TGT TTC ATG GTC CCT GGT GTT CTT CCT GAT ACT TTG AAC
   AGA ACA AAG TAC CAG GGA CCA CAA GAA GGA CTA TGA AAC TTG
   Ser Cys Phe Met Val Pro Gly Val Leu Pro Asp Thr Leu Asn>
   _____IL13Rα1_____>

850             860             870             880
    *       *       *       *       *       *       *       *
   ACA GTC AGA ATA AGA GTC AAA ACA AAT AAG TTA TGC TAT GAG
   TGT CAG TCT TAT TCT CAG TTT TGT TTA TTC AAT ACG ATA CTC
   Thr Val Arg Ile Arg Val Lys Thr Asn Lys Leu Cys Tyr Glu>
   _____IL13Rα1_____>

890             900             910             920             930
    *       *       *       *       *       *       *       *       *
   GAT GAC AAA CTC TGG AGT AAT TGG AGC CAA GAA ATG AGT ATA
   CTA CTG TTT GAG ACC TCA TTA ACC TCG GTT CTT TAC TCA TAT
   Asp Asp Lys Leu Trp Ser Asn Trp Ser Gln Glu Met Ser Ile>
   _____IL13Rα1_____>

940             950             960             970
    *       *       *       *       *       *       *       *
   GGT AAG AAG CGC AAT TCC ACA GGG AAC ATG AAG GTC TTG CAG
   CCA TTC TTC GCG TTA AGG TGT CCC TTG TAC TTC CAG AAC GTC
                                   Gly Asn Met Lys Val Leu Gln>
                                   _____IL4Rα_____>
   Gly Lys Lys Arg Asn Ser Thr>
   _____IL13Rα1_____>

980             990             1000            1010
    *       *       *       *       *       *       *       *
   GAG CCC ACC TGC GTC TCC GAC TAC ATG AGC ATC TCT ACT TGC
   CTC GGG TGG ACG CAG AGG CTG ATG TAC TCG TAG AGA TGA ACG
   Glu Pro Thr Cys Val Ser Asp Tyr Met Ser Ile Ser Thr Cys>
   _____IL4Rα_____>

1020            1030            1040            1050
    *       *       *       *       *       *       *       *       *
   GAG TGG AAG ATG AAT GGT CCC ACC AAT TGC AGC ACC GAG CTC
   CTC ACC TTC TAC TTA CCA GGG TGG TTA ACG TCG TGG CTC GAG
   Glu Trp Lys Met Asn Gly Pro Thr Asn Cys Ser Thr Glu Leu>
   _____IL4Rα_____>

1060            1070            1080            1090
    *       *       *       *       *       *       *       *
   CGC CTG TTG TAC CAG CTG GTT TTT CTG CTC TCC GAA GCC CAC
   GCG GAC AAC ATG GTC GAC CAA AAA GAC GAG AGG CTT CGG GTG
   Arg Leu Leu Tyr Gln Leu Val Phe Leu Leu Ser Glu Ala His>
   _____IL4Rα_____>
```

Figure 38E

```
       1100          1110         1120          1130          1140
          *        *    *        *    *        *    *        *    *
    ACG TGT ATC CCT GAG AAC AAC GGA GGC GCG GGG TGC GTG TGC
    TGC ACA TAG GGA CTC TTG TTG CCT CCG CGC CCC ACG CAC ACG
    Thr Cys Ile Pro Glu Asn Asn Gly Gly Ala Gly Cys Val Cys>
    _____IL4Rα_____>

1150         1160          1170          1180
               *        *    *        *    *        *    *        *
    CAC CTG CTC ATG GAT GAC GTG GTC AGT GCG GAT AAC TAT ACA
    GTG GAC GAG TAC CTA CTG CAC CAG TCA CGC CTA TTG ATA TGT
    His Leu Leu Met Asp Asp Val Val Ser Ala Asp Asn Tyr Thr>
    _____IL4Rα_____>

1190         1200          1210          1220
               *        *    *        *    *        *    *        *
    CTG GAC CTG TGG GCT GGG CAG CAG CTG CTG TGG AAG GGC TCC
    GAC CTG GAC ACC CGA CCC GTC GTC GAC GAC ACC TTC CCG AGG
    Leu Asp Leu Trp Ala Gly Gln Gln Leu Leu Trp Lys Gly Ser>
    _____IL4Rα_____>

1230         1240          1250          1260
           *        *    *        *    *        *    *        *    *
    TTC AAG CCC AGC GAG CAT GTG AAA CCC AGG GCC CCA GGA AAC
    AAG TTC GGG TCG CTC GTA CAC TTT GGG TCC CGG GGT CCT TTG
    Phe Lys Pro Ser Glu His Val Lys Pro Arg Ala Pro Gly Asn>
    _____IL4Rα_____>

1270          1280         1290          1300
          *        *    *        *    *        *    *        *
    CTG ACA GTT CAC ACC AAT GTC TCC GAC ACT CTG CTG CTG ACC
    GAC TGT CAA GTG TGG TTA CAG AGG CTG TGA GAC GAC GAC TGG
    Leu Thr Val His Thr Asn Val Ser Asp Thr Leu Leu Leu Thr>
    _____IL4Rα_____>

1310         1320          1330          1340          1350
       *        *    *        *    *        *    *        *    *
    TGG AGC AAC CCG TAT CCC CCT GAC AAT TAC CTG TAT AAT CAT
    ACC TCG TTG GGC ATA GGG GGA CTG TTA ATG GAC ATA TTA GTA
    Trp Ser Asn Pro Tyr Pro Pro Asp Asn Tyr Leu Tyr Asn His>
    _____IL4Rα_____>

1360         1370          1380          1390
               *        *    *        *    *        *    *        *
    CTC ACC TAT GCA GTC AAC ATT TGG AGT GAA AAC GAC CCG GCA
    GAG TGG ATA CGT CAG TTG TAA ACC TCA CTT TTG CTG GGC CGT
    Leu Thr Tyr Ala Val Asn Ile Trp Ser Glu Asn Asp Pro Ala>
    _____IL4Rα_____>
```

Figure 38F

```
         1400           1410           1420           1430
          *      *       *      *       *      *       *      *
         GAT    TTC     AGA    ATC     TAT    AAC     GTG    ACC    TAC    CTA    GAA    CCC    TCC    CTC
         CTA    AAG     TCT    TAG     ATA    TTG     CAC    TGG    ATG    GAT    CTT    GGG    AGG    GAG
         Asp    Phe     Arg    Ile     Tyr    Asn     Val    Thr    Tyr    Leu    Glu    Pro    Ser    Leu>
                                             _____IL4Rα_____>

1440           1450           1460           1470
          *      *       *      *       *      *       *      *       *
         CGC    ATC     GCA    GCC     AGC    ACC     CTG    AAG    TCT    GGG    ATT    TCC    TAC    AGG
         GCG    TAG     CGT    CGG     TCG    TGG     GAC    TTC    AGA    CCC    TAA    AGG    ATG    TCC
         Arg    Ile     Ala    Ala     Ser    Thr     Leu    Lys    Ser    Gly    Ile    Ser    Tyr    Arg>
                                             _____IL4Rα_____>

>Mutation Cysteine to Serine
         1480           1490           1500   |       1510
          *      *       *      *       *     |  *     *      *       *
         GCA    CGC     GTA    CGG     GCC    TGG     GCT    CAG    AGC    TAT    AAC    ACC    ACC    TGG
         CGT    GCG     CAT    GCC     CGG    ACC     CGA    GTC    TCG    ATA    TTG    TGG    TGG    ACC
         Ala    Arg     Val    Arg     Ala    Trp     Ala    Gln    Ser    Tyr    Asn    Thr    Thr    Trp>
                                             _____IL4Rα_____>

1520           1530           1540           1550           1560
  *      *       *      *       *      *       *      *       *      *
 AGT    GAG     TGG    AGC     CCC    AGC     ACC    AAG    TGG    CAC    AAC    TCC    TAC    AGG
 TCA    CTC     ACC    TCG     GGG    TCG     TGG    TTC    ACC    GTG    TTG    AGG    ATG    TCC
 Ser    Glu     Trp    Ser     Pro    Ser     Thr    Lys    Trp    His    Asn    Ser    Tyr    Arg>
                                     _____IL4Rα_____>

1570           1580           1590           1600
          *      *       *      *       *      *       *      *
         GAG    CCC     TTC    GAG     CAG    TCC     GGA    GAC    AAA    ACT    CAC    ACA    TGC    CCA
         CTC    GGG     AAG    CTC     GTC    AGG     CCT    CTG    TTT    TGA    GTG    TGT    ACG    GGT
         Glu    Pro     Phe    Glu     Gln>
                ___IL4Rα___>
                                      Ser    Gly    Asp    Lys    Thr    His    Thr    Cys    Pro>
                                             _____FC-IgG1_____>

1610           1620           1630           1640
          *      *       *      *       *      *       *      *
         CCG    TGC     CCA    GCA     CCT    GAA     CTC    CTG    GGG    GGA    CCG    TCA    GTC    TTC
         GGC    ACG     GGT    CGT     GGA    CTT     GAG    GAC    CCC    CCT    GGC    AGT    CAG    AAG
         Pro    Cys     Pro    Ala     Pro    Glu     Leu    Leu    Gly    Gly    Pro    Ser    Val    Phe>
                                             _____FC-IgG1_____>

1650           1660           1670           1680
          *      *       *      *       *      *       *      *       *
         CTC    TTC     CCC    CCA     AAA    CCC     AAG    GAC    ACC    CTC    ATG    ATC    TCC    CGG
         GAG    AAG     GGG    GGT     TTT    GGG     TTC    CTG    TGG    GAG    TAC    TAG    AGG    GCC
         Leu    Phe     Pro    Pro     Lys    Pro     Lys    Asp    Thr    Leu    Met    Ile    Ser    Arg>
                                             _____FC-IgG1_____>
```

Figure 38G

```
          1690          1700          1710          1720
           *      *      *      *      *      *      *      *
          ACC   CCT   GAG   GTC   ACA   TGC   GTG   GTG   GTG   GAC   GTG   AGC   CAC   GAA
          TGG   GGA   CTC   CAG   TGT   ACG   CAC   CAC   CAC   CTG   CAC   TCG   GTG   CTT
          Thr   Pro   Glu   Val   Thr   Cys   Val   Val   Val   Asp   Val   Ser   His   Glu>
          _____FC-IgG1_____>

1730          1740          1750          1760          1770
    *      *      *      *      *      *      *      *      *
   GAC   CCT   GAG   GTC   AAG   TTC   AAC   TGG   TAC   GTG   GAC   GGC   GTG   GAG
   CTG   GGA   CTC   CAG   TTC   AAG   TTG   ACC   ATG   CAC   CTG   CCG   CAC   CTC
   Asp   Pro   Glu   Val   Lys   Phe   Asn   Trp   Tyr   Val   Asp   Gly   Val   Glu>
   _____FC-IgG1_____>

1780          1790          1800          1810
            *      *      *      *      *      *      *      *
           GTG   CAT   AAT   GCC   AAG   ACA   AAG   CCG   CGG   GAG   GAG   CAG   TAC   AAC
           CAC   GTA   TTA   CGG   TTC   TGT   TTC   GGC   GCC   CTC   CTC   GTC   ATG   TTG
           Val   His   Asn   Ala   Lys   Thr   Lys   Pro   Arg   Glu   Glu   Gln   Tyr   Asn>
           _____FC-IgG1_____>

1820          1830          1840          1850
           *      *      *      *      *      *      *      *
          AGC   ACG   TAC   CGT   GTG   GTC   AGC   GTC   CTC   ACC   GTC   CTG   CAC   CAG
          TCG   TGC   ATG   GCA   CAC   CAG   TCG   CAG   GAG   TGG   CAG   GAC   GTG   GTC
          Ser   Thr   Tyr   Arg   Val   Val   Ser   Val   Leu   Thr   Val   Leu   His   Gln>
          _____FC-IgG1_____>

1860          1870          1880          1890
       *      *      *      *      *      *      *      *      *
      GAC   TGG   CTG   AAT   GGC   AAG   GAG   TAC   AAG   TGC   AAG   GTC   TCC   AAC
      CTG   ACC   GAC   TTA   CCG   TTC   CTC   ATG   TTC   ACG   TTC   CAG   AGG   TTG
      Asp   Trp   Leu   Asn   Gly   Lys   Glu   Tyr   Lys   Cys   Lys   Val   Ser   Asn>
      _____FC-IgG1_____>

1900          1910          1920          1930
       *      *      *      *      *      *      *      *
      AAA   GCC   CTC   CCA   GCC   CCC   ATC   GAG   AAA   ACC   ATC   TCC   AAA   GCC
      TTT   CGG   GAG   GGT   CGG   GGG   TAG   CTC   TTT   TGG   TAG   AGG   TTT   CGG
      Lys   Ala   Leu   Pro   Ala   Pro   Ile   Glu   Lys   Thr   Ile   Ser   Lys   Ala>
      _____FC-IgG1_____>

1940          1950          1960          1970          1980
    *      *      *      *      *      *      *      *      *
   AAA   GGG   CAG   CCC   CGA   GAA   CCA   CAG   GTG   TAC   ACC   CTG   CCC   CCA
   TTT   CCC   GTC   GGG   GCT   CTT   GGT   GTC   CAC   ATG   TGG   GAC   GGG   GGT
   Lys   Gly   Gln   Pro   Arg   Glu   Pro   Gln   Val   Tyr   Thr   Leu   Pro   Pro>
   _____FC-IgG1_____>
```

Figure 38 H

```
            1990           2000            2010            2020
         *      *       *      *       *      *       *      *
       TCC CGG GAT GAG CTG ACC AAG AAC CAG GTC AGC CTG ACC TGC
       AGG GCC CTA CTC GAC TGG TTC TTG GTC CAG TCG GAC TGG ACG
       Ser Arg Asp Glu Leu Thr Lys Asn Gln Val Ser Leu Thr Cys>
       _____FC-IgG1_____>

2030            2040            2050       2060
         *       *       *      *       *      *       *      *
       CTG GTC AAA GGC TTC TAT CCC AGC GAC ATC GCC GTG GAG TGG
       GAC CAG TTT CCG AAG ATA GGG TCG CTG TAG CGG CAC CTC ACC
       Leu Val Lys Gly Phe Tyr Pro Ser Asp Ile Ala Val Glu Trp>
       _____FC-IgG1_____>

2070            2080            2090       2100
         *      *       *      *       *      *       *      *      *
       GAG AGC AAT GGG CAG CCG GAG AAC AAC TAC AAG ACC ACG CCT
       CTC TCG TTA CCC GTC GGC CTC TTG TTG ATG TTC TGG TGC GGA
       Glu Ser Asn Gly Gln Pro Glu Asn Asn Tyr Lys Thr Thr Pro>
       _____FC-IgG1_____>

2110           2120            2130            2140
         *      *       *      *       *      *       *      *
       CCC GTG CTG GAC TCC GAC GGC TCC TTC TTC CTC TAC AGC AAG
       GGG CAC GAC CTG AGG CTG CCG AGG AAG AAG GAG ATG TCG TTC
       Pro Val Leu Asp Ser Asp Gly Ser Phe Phe Leu Tyr Ser Lys>
       _____FC-IgG1_____>

2150            2160            2170            2180            2190
         *      *       *      *       *      *       *      *       *
       CTC ACC GTG GAC AAG AGC AGG TGG CAG CAG GGG AAC GTC TTC
       GAG TGG CAC CTG TTC TCG TCC ACC GTC GTC CCC TTG CAG AAG
       Leu Thr Val Asp Lys Ser Arg Trp Gln Gln Gly Asn Val Phe>
       _____FC-IgG1_____>

2200            2210            2220       2230
         *      *       *      *       *      *       *      *
       TCA TGC TCC GTG ATG CAT GAG GCT CTG CAC AAC CAC TAC ACG
       AGT ACG AGG CAC TAC GTA CTC CGA GAC GTG TTG GTG ATG TGC
       Ser Cys Ser Val Met His Glu Ala Leu His Asn His Tyr Thr>
       _____FC-IgG1_____>

2240           2250            2260
         *      *       *      *       *      *       *
       CAG AAG AGC CTC TCC CTG TCT CCG GGT AAA TGA
       GTC TTC TCG GAG AGG GAC AGA GGC CCA TTT ACT
       Gln Lys Ser Leu Ser Leu Ser Pro Gly Lys ***>
       _____FC-IgG1_____>
```

Figure 39A

```
            -60           -50           -40           -30
     *       *       *       *       *       *       *       *       *
    ATG GTG TGG CTT TGC TCT GGG CTC CTG TTC CCT GTG AGC TGC CTG GTC
    TAC CAC ACC GAA ACG AGA CCC GAG GAC AAG GGA CAC TCG ACG GAC CAG
    Met Val Trp Leu Cys Ser Gly Leu Leu Phe Pro Val Ser Cys Leu Val>
    _____SIGNAL PEPTIDE_____>

-20           -10            1            10            20
     *       *       *       *       *       *       *       *       *       *
    CTG CTG CAG GTG GCA AGC TCT GGG AAC ATG AAG GTC TTG CAG GAG CCC
    GAC GAC GTC CAC CGT TCG AGA CCC TTG TAC TTC CAG AAC GTC CTC GGG
                                    Gly Asn Met Lys Val Leu Gln Glu Pro>
                                    _____IL4Rα_____>
    Leu Leu Gln Val Ala Ser Ser>
    _____SIGNAL PEPTIDE_____>

30            40            50            60            70
     *       *       *       *       *       *       *       *       *       *
    ACC TGC GTC TCC GAC TAC ATG AGC ATC TCT ACT TGC GAG TGG AAG ATG
    TGG ACG CAG AGG CTG ATG TAC TCG TAG AGA TGA ACG CTC ACC TTC TAC
    Thr Cys Val Ser Asp Tyr Met Ser Ile Ser Thr Cys Glu Trp Lys Met>
    _____IL4Rα_____>

80            90           100           110           120
     *       *       *       *       *       *       *       *       *
    AAT GGT CCC ACC AAT TGC AGC ACC GAG CTC CGC CTG TTG TAC CAG CTG
    TTA CCA GGG TGG TTA ACG TCG TGG CTC GAG GCG GAC AAC ATG GTC GAC
    Asn Gly Pro Thr Asn Cys Ser Thr Glu Leu Arg Leu Leu Tyr Gln Leu>
    _____IL4Rα_____>

130           140           150           160           170
     *       *       *       *       *       *       *       *       *       *
    GTT TTT CTG CTC TCC GAA GCC CAC ACG TGT ATC CCT GAG AAC AAC GGA
    CAA AAA GAC GAG AGG CTT CGG GTG TGC ACA TAG GGA CTC TTG TTG CCT
    Val Phe Leu Leu Ser Glu Ala His Thr Cys Ile Pro Glu Asn Asn Gly>
    _____IL4Rα_____>

180           190           200           210
     *       *       *       *       *       *       *       *       *
    GGC GCG GGG TGC GTG TGC CAC CTG CTC ATG GAT GAC GTG GTC AGT GCG
    CCG CGC CCC ACG CAC ACG GTG GAC GAG TAC CTA CTG CAC CAG TCA CGC
    Gly Ala Gly Cys Val Cys His Leu Leu Met Asp Asp Val Val Ser Ala>
    _____IL4Rα_____>

220           230           240           250           260
     *       *       *       *       *       *       *       *       *       *
    GAT AAC TAT ACA CTG GAC CTG TGG GCT GGG CAG CAG CTG CTG TGG AAG
    CTA TTG ATA TGT GAC CTG GAC ACC CGA CCC GTC GTC GAC GAC ACC TTC
    Asp Asn Tyr Thr Leu Asp Leu Trp Ala Gly Gln Gln Leu Leu Trp Lys>
    _____IL4Rα_____>
```

Figure 39B

```
        270               280               290               300               310
         *         *       *         *       *         *       *         *       *         *
GGC TCC TTC AAG CCC AGC GAG CAT GTG AAA CCC AGG GCC CCA GGA AAC
CCG AGG AAG TTC GGG TCG CTC GTA CAC TTT GGG TCC CGG GGT CCT TTG
Gly Ser Phe Lys Pro Ser Glu His Val Lys Pro Arg Ala Pro Gly Asn>
_____IL4Rα_____>

320               330               340               350               360
         *         *       *         *       *         *       *         *       *
CTG ACA GTT CAC ACC AAT GTC TCC GAC ACT CTG CTG CTG ACC TGG AGC
GAC TGT CAA GTG TGG TTA CAG AGG CTG TGA GAC GAC GAC TGG ACC TCG
Leu Thr Val His Thr Asn Val Ser Asp Thr Leu Leu Leu Thr Trp Ser>
_____IL4Rα_____>

370               380               390               400               410
         *         *       *         *       *         *       *         *       *         *
AAC CCG TAT CCC CCT GAC AAT TAC CTG TAT AAT CAT CTC ACC TAT GCA
TTG GGC ATA GGG GGA CTG TTA ATG GAC ATA TTA GTA GAG TGG ATA CGT
Asn Pro Tyr Pro Pro Asp Asn Tyr Leu Tyr Asn His Leu Thr Tyr Ala>
_____IL4Rα_____>

420               430               440               450
         *         *       *         *       *         *       *         *       *
GTC AAC ATT TGG AGT GAA AAC GAC CCG GCA GAT TTC AGA ATC TAT AAC
CAG TTG TAA ACC TCA CTT TTG CTG GGC CGT CTA AAG TCT TAG ATA TTG
Val Asn Ile Trp Ser Glu Asn Asp Pro Ala Asp Phe Arg Ile Tyr Asn>
_____IL4Rα_____>

460              470               480               490               500
 *         *       *         *       *         *       *         *       *         *
GTG ACC TAC CTA GAA CCC TCC CTC CGC ATC GCA GCC AGC ACC CTG AAG
CAC TGG ATG GAT CTT GGG AGG GAG GCG TAG CGT CGG TCG TGG GAC TTC
Val Thr Tyr Leu Glu Pro Ser Leu Arg Ile Ala Ala Ser Thr Leu Lys>
_____IL4Rα_____>

Mutation Cysteine to Serine
                                                              |
        510               520               530               540               550
         *         *       *         *       *         *       *         *       *         *
TCT GGG ATT TCC TAC AGG GCA CGC GTA CGG GCC TGG GCT CAG AGC TAT
AGA CCC TAA AGG ATG TCC CGT GCG CAT GCC CGG ACC CGA GTC TCG ATA
Ser Gly Ile Ser Tyr Arg Ala Arg Val Arg Ala Trp Ala Gln Ser Tyr>
_____IL4Rα_____>

560               570               580               590               600
         *         *       *         *       *         *       *         *       *
AAC ACC ACC TGG AGT GAG TGG AGC CCC AGC ACC AAG TGG CAC AAC TCC
TTG TGG TGG ACC TCA CTC ACC TCG GGG TCG TGG TTC ACC GTG TTG AGG
Asn Thr Thr Trp Ser Glu Trp Ser Pro Ser Thr Lys Trp His Asn Ser>
_____IL4Rα_____>
```

Figure 39C

```
           610         620         630         640         650
            *     *     *     *     *     *     *     *     *     *
         TAC AGG GAG CCC TTC GAG CAG GCG CCT ACG GAA ACT CAG CCA CCT GTG
         ATG TCC CTC GGG AAG CTC GTC CGC GGA TGC CTT TGA GTC GGT GGA CAC
         Tyr Arg Glu Pro Phe Glu Gln>
         _____IL4Rα_____>
                                    Ala Pro Thr Glu Thr Gln Pro Pro Val>
                                        _____IL13Rα1_____>

660         670         680         690
            *     *     *     *     *     *     *     *     *
         ACA AAT TTG AGT GTC TCT GTT GAA AAC CTC TGC ACA GTA ATA TGG ACA
         TGT TTA AAC TCA CAG AGA CAA CTT TTG GAG ACG TGT CAT TAT ACC TGT
         Thr Asn Leu Ser Val Ser Val Glu Asn Leu Cys Thr Val Ile Trp Thr>
                           _____IL13Rα1_____>

700         710         720         730         740
   *     *     *     *     *     *     *     *     *     *
TGG AAT CCA CCC GAG GGA GCC AGC TCA AAT TGT AGT CTA TGG TAT TTT
ACC TTA GGT GGG CTC CCT CGG TCG AGT TTA ACA TCA GAT ACC ATA AAA
Trp Asn Pro Pro Glu Gly Ala Ser Ser Asn Cys Ser Leu Trp Tyr Phe>
                     _____IL13Rα1_____>

750         760         770         780         790
            *     *     *     *     *     *     *     *     *     *
         AGT CAT TTT GGC GAC AAA CAA GAT AAG AAA ATA GCT CCG GAA ACT CGT
         TCA GTA AAA CCG CTG TTT GTT CTA TTC TTT TAT CGA GGC CTT TGA GCA
         Ser His Phe Gly Asp Lys Gln Asp Lys Lys Ile Ala Pro Glu Thr Arg>
                                  _____IL13Rα1_____>

800         810         820         830         840
            *     *     *     *     *     *     *     *     *
         CGT TCA ATA GAA GTA CCC CTG AAT GAG AGG ATT TGT CTG CAA GTG GGG
         GCA AGT TAT CTT CAT GGG GAC TTA CTC TCC TAA ACA GAC GTT CAC CCC
         Arg Ser Ile Glu Val Pro Leu Asn Glu Arg Ile Cys Leu Gln Val Gly>
                             _____IL13Rα1_____>

850         860         870         880         890
            *     *     *     *     *     *     *     *     *     *
         TCC CAG TGT AGC ACC AAT GAG AGT GAG AAG CCT AGC ATT TTG GTT GAA
         AGG GTC ACA TCG TGG TTA CTC TCA CTC TTC GGA TCG TAA AAC CAA CTT
         Ser Gln Cys Ser Thr Asn Glu Ser Glu Lys Pro Ser Ile Leu Val Glu>
                                  _____IL13Rα1_____>

900         910         920         930
            *     *     *     *     *     *     *     *     *
         AAA TGC ATC TCA CCC CCA GAA GGT GAT CCT GAG TCT GCT GTG ACT GAG
         TTT ACG TAG AGT GGG GGT CTT CCA CTA GGA CTC AGA CGA CAC TGA CTC
         Lys Cys Ile Ser Pro Pro Glu Gly Asp Pro Glu Ser Ala Val Thr Glu>
                              _____IL13Rα1_____>
```

Figure 39D

```
       940            950            960            970            980
  *      *      *      *      *      *      *      *      *      *
 CTT    CAA    TGC    ATT    TGG    CAC    AAC    CTG    AGC    TAC    ATG    AAG    TGT    TCT    TGG    CTC
 GAA    GTT    ACG    TAA    ACC    GTG    TTG    GAC    TCG    ATG    TAC    TTC    ACA    AGA    ACC    GAG
 Leu    Gln    Cys    Ile    Trp    His    Asn    Leu    Ser    Tyr    Met    Lys    Cys    Ser    Trp    Leu>
 _____IL13Rα1_____>

990           1000           1010           1020           1030
  *      *      *      *      *      *      *      *      *      *
 CCT    GGA    AGG    AAT    ACC    AGT    CCC    GAC    ACT    AAC    TAT    ACT    CTC    TAC    TAT    TGG
 GGA    CCT    TCC    TTA    TGG    TCA    GGG    CTG    TGA    TTG    ATA    TGA    GAG    ATG    ATA    ACC
 Pro    Gly    Arg    Asn    Thr    Ser    Pro    Asp    Thr    Asn    Tyr    Thr    Leu    Tyr    Tyr    Trp>
 _____IL13Rα1_____>

1040           1050           1060           1070           1080
    *      *      *      *      *      *      *      *      *
 CAC    AGA    AGC    CTG    GAA    AAA    ATT    CAT    CAA    TGT    GAA    AAC    ATC    TTT    AGA    GAA
 GTG    TCT    TCG    GAC    CTT    TTT    TAA    GTA    GTT    ACA    CTT    TTG    TAG    AAA    TCT    CTT
 His    Arg    Ser    Leu    Glu    Lys    Ile    His    Gln    Cys    Glu    Asn    Ile    Phe    Arg    Glu>
 _____IL13Rα1_____>

1090           1100           1110           1120           1130
    *      *      *      *      *      *      *      *      *      *
 GGC    CAA    TAC    TTT    GGT    TGT    TCC    TTT    GAT    CTG    ACC    AAA    GTG    AAG    GAT    TCC
 CCG    GTT    ATG    AAA    CCA    ACA    AGG    AAA    CTA    GAC    TGG    TTT    CAC    TTC    CTA    AGG
 Gly    Gln    Tyr    Phe    Gly    Cys    Ser    Phe    Asp    Leu    Thr    Lys    Val    Lys    Asp    Ser>
 _____IL13Rα1_____>

1140           1150           1160           1170
    *      *      *      *      *      *      *      *      *
 AGT    TTT    GAA    CAA    CAC    AGT    GTC    CAA    ATA    ATG    GTC    AAG    GAT    AAT    GCA    GGA
 TCA    AAA    CTT    GTT    GTG    TCA    CAG    GTT    TAT    TAC    CAG    TTC    CTA    TTA    CGT    CCT
 Ser    Phe    Glu    Gln    His    Ser    Val    Gln    Ile    Met    Val    Lys    Asp    Asn    Ala    Gly>
 _____IL13Rα1_____>

1180           1190           1200           1210           1220
  *      *      *      *      *      *      *      *      *      *
 AAA    ATT    AAA    CCA    TCC    TTC    AAT    ATA    GTG    CCT    TTA    ACT    TCC    CGT    GTG    AAA
 TTT    TAA    TTT    GGT    AGG    AAG    TTA    TAT    CAC    GGA    AAT    TGA    AGG    GCA    CAC    TTT
 Lys    Ile    Lys    Pro    Ser    Phe    Asn    Ile    Val    Pro    Leu    Thr    Ser    Arg    Val    Lys>
 _____IL13Rα1_____>

1230           1240           1250           1260           1270
  *      *      *      *      *      *      *      *      *      *
 CCT    GAT    CCT    CCA    CAT    ATT    AAA    AAC    CTC    TCC    TTC    CAC    AAT    GAT    GAC    CTA
 GGA    CTA    GGA    GGT    GTA    TAA    TTT    TTG    GAG    AGG    AAG    GTG    TTA    CTA    CTG    GAT
 Pro    Asp    Pro    Pro    His    Ile    Lys    Asn    Leu    Ser    Phe    His    Asn    Asp    Asp    Leu>
 _____IL13Rα1_____>
```

Figure 39E

```
        1280           1290           1300           1310           1320
          *         *    *         *    *         *    *         *    *
     TAT GTG CAA TGG GAG AAT CCA CAG AAT TTT ATT AGC AGA TGC CTA TTT
     ATA CAC GTT ACC CTC TTA GGT GTC TTA AAA TAA TCG TCT ACG GAT AAA
     Tyr Val Gln Trp Glu Asn Pro Gln Asn Phe Ile Ser Arg Cys Leu Phe>
     _____IL13Rα1_____>

1330           1340           1350           1360           1370
          *    *         *    *         *    *         *    *         *    *
     TAT GAA GTA GAA GTC AAT AAC AGC CAA ACT GAG ACA CAT AAT GTT TTC
     ATA CTT CAT CTT CAG TTA TTG TCG GTT TGA CTC TGT GTA TTA CAA AAG
     Tyr Glu Val Glu Val Asn Asn Ser Gln Thr Glu Thr His Asn Val Phe>
     _____IL13Rα1_____>

1380           1390           1400           1410
                *    *         *    *         *    *         *    *    *
     TAC GTC CAA GAG GCT AAA TGT GAG AAT CCA GAA TTT GAG AGA AAT GTG
     ATG CAG GTT CTC CGA TTT ACA CTC TTA GGT CTT AAA CTC TCT TTA CAC
     Tyr Val Gln Glu Ala Lys Cys Glu Asn Pro Glu Phe Glu Arg Asn Val>
     _____IL13Rα1_____>

1420           1430           1440           1450           1460
   *         *    *         *    *         *    *         *    *    *
 GAG AAT ACA TCT TGT TTC ATG GTC CCT GGT GTT CTT CCT GAT ACT TTG
 CTC TTA TGT AGA ACA AAG TAC CAG GGA CCA CAA GAA GGA CTA TGA AAC
 Glu Asn Thr Ser Cys Phe Met Val Pro Gly Val Leu Pro Asp Thr Leu>
 _____IL13Rα1_____>

1470           1480           1490           1500           1510
          *    *         *    *         *    *         *    *         *    *
     AAC ACA GTC AGA ATA AGA GTC AAA ACA AAT AAG TTA TGC TAT GAG GAT
     TTG TGT CAG TCT TAT TCT CAG TTT TGT TTA TTC AAT ACG ATA CTC CTA
     Asn Thr Val Arg Ile Arg Val Lys Thr Asn Lys Leu Cys Tyr Glu Asp>
     _____IL13Rα1_____>

1520           1530           1540           1550           1560
          *    *         *    *         *    *         *    *         *
     GAC AAA CTC TGG AGT AAT TGG AGC CAA GAA ATG AGT ATA GGT AAG AAG
     CTG TTT GAG ACC TCA TTA ACC TCG GTT CTT TAC TCA TAT CCA TTC TTC
     Asp Lys Leu Trp Ser Asn Trp Ser Gln Glu Met Ser Ile Gly Lys Lys>
     _____IL13Rα1_____>

1570           1580           1590           1600           1610
          *    *         *    *         *    *         *    *         *    *
     CGC AAT TCC ACC GGT GAC AAA ACT CAC ACA TGC CCA CCG TGC CCA GCA
     GCG TTA AGG TGG CCA CTG TTT TGA GTG TGT ACG GGT GGC ACG GGT CGT
                 Gly Asp Lys Thr His Thr Cys Pro Pro Cys Pro Ala>
     _____FC-IgG1_____>
     Arg Asn Ser Thr>
     ____IL13Rα1_____>
```

Figure 39F

```
              1620        1630        1640        1650
         *     *     *     *     *     *     *     *     *
        CCT   GAA   CTC   CTG   GGG   GGA   CCG   TCA   GTC   TTC   CTC   TTC   CCC   CCA   AAA   CCC
        GGA   CTT   GAG   GAC   CCC   CCT   GGC   AGT   CAG   AAG   GAG   AAG   GGG   GGT   TTT   GGG
        Pro   Glu   Leu   Leu   Gly   Gly   Pro   Ser   Val   Phe   Leu   Phe   Pro   Pro   Lys   Pro>
        _____FC-IgG1_____>

1660        1670        1680        1690        1700
    *     *     *     *     *     *     *     *     *     *
   AAG   GAC   ACC   CTC   ATG   ATC   TCC   CGG   ACC   CCT   GAG   GTC   ACA   TGC   GTG   GTG
   TTC   CTG   TGG   GAG   TAC   TAG   AGG   GCC   TGG   GGA   CTC   CAG   TGT   ACG   CAC   CAC
   Lys   Asp   Thr   Leu   Met   Ile   Ser   Arg   Thr   Pro   Glu   Val   Thr   Cys   Val   Val>
   _____FC-IgG1_____>

1710        1720        1730        1740        1750
    *     *     *     *     *     *     *     *     *     *
   GTG   GAC   GTG   AGC   CAC   GAA   GAC   CCT   GAG   GTC   AAG   TTC   AAC   TGG   TAC   GTG
   CAC   CTG   CAC   TCG   GTG   CTT   CTG   GGA   CTC   CAG   TTC   AAG   TTG   ACC   ATG   CAC
   Val   Asp   Val   Ser   His   Glu   Asp   Pro   Glu   Val   Lys   Phe   Asn   Trp   Tyr   Val>
   _____FC-IgG1_____>

1760        1770        1780        1790        1800
         *     *     *     *     *     *     *     *     *
        GAC   GGC   GTG   GAG   GTG   CAT   AAT   GCC   AAG   ACA   AAG   CCG   CGG   GAG   GAG   CAG
        CTG   CCG   CAC   CTC   CAC   GTA   TTA   CGG   TTC   TGT   TTC   GGC   GCC   CTC   CTC   GTC
        Asp   Gly   Val   Glu   Val   His   Asn   Ala   Lys   Thr   Lys   Pro   Arg   Glu   Glu   Gln>
        _____FC-IgG1_____>

1810        1820        1830        1840        1850
         *     *     *     *     *     *     *     *     *     *
        TAC   AAC   AGC   ACG   TAC   CGT   GTG   GTC   AGC   GTC   CTC   ACC   GTC   CTG   CAC   CAG
        ATG   TTG   TCG   TGC   ATG   GCA   CAC   CAG   TCG   CAG   GAG   TGG   CAG   GAC   GTG   GTC
        Tyr   Asn   Ser   Thr   Tyr   Arg   Val   Val   Ser   Val   Leu   Thr   Val   Leu   His   Gln>
        _____FC-IgG1_____>

1860        1870        1880        1890
         *     *     *     *     *     *     *     *     *
        GAC   TGG   CTG   AAT   GGC   AAG   GAG   TAC   AAG   TGC   AAG   GTC   TCC   AAC   AAA   GCC
        CTG   ACC   GAC   TTA   CCG   TTC   CTC   ATG   TTC   ACG   TTC   CAG   AGG   TTG   TTT   CGG
        Asp   Trp   Leu   Asn   Gly   Lys   Glu   Tyr   Lys   Cys   Lys   Val   Ser   Asn   Lys   Ala>
        _____FC-IgG1_____>

1900        1910        1920        1930        1940
    *     *     *     *     *     *     *     *     *     *
   CTC   CCA   GCC   CCC   ATC   GAG   AAA   ACC   ATC   TCC   AAA   GCC   AAA   GGG   CAG   CCC
   GAG   GGT   CGG   GGG   TAG   CTC   TTT   TGG   TAG   AGG   TTT   CGG   TTT   CCC   GTC   GGG
   Leu   Pro   Ala   Pro   Ile   Glu   Lys   Thr   Ile   Ser   Lys   Ala   Lys   Gly   Gln   Pro>
   _____FC-IgG1_____>
```

Figure 39G

```
        1950            1960            1970            1980            1990
          *       *       *       *       *       *       *       *       *       *
        CGA GAA CCA CAG GTG TAC ACC CTG CCC CCA TCC CGG GAT GAG CTG ACC
        GCT CTT GGT GTC CAC ATG TGG GAC GGG GGT AGG GCC CTA CTC GAC TGG
        Arg Glu Pro Gln Val Tyr Thr Leu Pro Pro Ser Arg Asp Glu Leu Thr>
        _____FC-IgG1_____>

2000            2010            2020            2030            2040
          *       *       *       *       *       *       *       *       *
        AAG AAC CAG GTC AGC CTG ACC TGC CTG GTC AAA GGC TTC TAT CCC AGC
        TTC TTG GTC CAG TCG GAC TGG ACG GAC CAG TTT CCG AAG ATA GGG TCG
        Lys Asn Gln Val Ser Leu Thr Cys Leu Val Lys Gly Phe Tyr Pro Ser>
        _____FC-IgG1_____>

2050            2060            2070            2080            2090
          *       *       *       *       *       *       *       *       *       *
        GAC ATC GCC GTG GAG TGG GAG AGC AAT GGG CAG CCG GAG AAC AAC TAC
        CTG TAG CGG CAC CTC ACC CTC TCG TTA CCC GTC GGC CTC TTG TTG ATG
        Asp Ile Ala Val Glu Trp Glu Ser Asn Gly Gln Pro Glu Asn Asn Tyr>
        _____FC-IgG1_____>

2100            2110            2120            2130
          *       *       *       *       *       *       *       *       *
        AAG ACC ACG CCT CCC GTG CTG GAC TCC GAC GGC TCC TTC TTC CTC TAC
        TTC TGG TGC GGA GGG CAC GAC CTG AGG CTG CCG AGG AAG AAG GAG ATG
        Lys Thr Thr Pro Pro Val Leu Asp Ser Asp Gly Ser Phe Phe Leu Tyr>
        _____FC-IgG1_____>

2140            2150            2160            2170            2180
      *       *       *       *       *       *       *       *       *       *
    AGC AAG CTC ACC GTG GAC AAG AGC AGG TGG CAG CAG GGG AAC GTC TTC
    TCG TTC GAG TGG CAC CTG TTC TCG TCC ACC GTC GTC CCC TTG CAG AAG
    Ser Lys Leu Thr Val Asp Lys Ser Arg Trp Gln Gln Gly Asn Val Phe>
    _____FC-IgG1_____>

2190            2200            2210            2220            2230
          *       *       *       *       *       *       *       *       *       *
        TCA TGC TCC GTG ATG CAT GAG GCT CTG CAC AAC CAC TAC ACG CAG AAG
        AGT ACG AGG CAC TAC GTA CTC CGA GAC GTG TTG GTG ATG TGC GTC TTC
        Ser Cys Ser Val Met His Glu Ala Leu His Asn His Tyr Thr Gln Lys>
        _____FC-IgG1_____>

2240            2250            2260
          *       *       *       *       *
        AGC CTC TCC CTG TCT CCG GGT AAA TGA
        TCG GAG AGG GAC AGA GGC CCA TTT ACT
        Ser Leu Ser Leu Ser Pro Gly Lys ***>
        _____FC-IgG1_____>
```

Figure 40A

```
          -70              -60              -50              -40
    *      *      *      *      *      *      *      *
   ATG    GTG    TGG    CCG    GCG    CGG    CTC    TGC    GGG    CTG    TGG    GCG    CTG    CTG
   TAC    CAC    ACC    GGC    CGC    GCC    GAG    ACG    CCC    GAC    ACC    CGC    GAC    GAC
   Met    Val    Trp    Pro    Ala    Arg    Leu    Cys    Gly    Leu    Trp    Ala    Leu    Leu>
                        _____SIGNAL PEPTIDE_____>
   _____IL13Rα1_____>

-30              -20              -10               1
    *      *      *      *      *      *      *      *      *
   CTC    TGC    GCC    GGC    GGC    GGG    GGC    GGG    GGC    GGG    GGC    GCC    GCG    CCT
   GAG    ACG    CGG    CCG    CCG    CCC    CCG    CCC    CCG    CCC    CCG    CGG    CGC    GGA
   Leu    Cys    Ala    Gly    Gly    Gly    Gly    Gly    Gly    Gly    Gly    Ala    Ala    Pro>
   ___d_____SIGNAL PEPTIDE_____>
   _____IL13Rα1_____>

10               20               30               40
    *      *      *      *      *      *      *      *
   ACG    GAA    ACT    CAG    CCA    CCT    GTG    ACA    AAT    TTG    AGT    GTC    TCT    GTT
   TGC    CTT    TGA    GTC    GGT    GGA    CAC    TGT    TTA    AAC    TCA    CAG    AGA    CAA
   Thr    Glu    Thr    Gln    Pro    Pro    Val    Thr    Asn    Leu    Ser    Val    Ser    Val>
                        _____IL13Rα1_____>

>Mutation Cysteine to Serine
          |
    50    |60               70               80               90
    *   * | *      *      *      *      *      *      *
   GAA    AAC    CTC    AGC    ACA    GTA    ATA    TGG    ACA    TGG    AAT    CCA    CCC    GAG
   CTT    TTG    GAG    TCG    TGT    CAT    TAT    ACC    TGT    ACC    TTA    GGT    GGG    CTC
   Glu    Asn    Leu    Ser    Thr    Val    Ile    Trp    Thr    Trp    Asn    Pro    Pro    Glu>
                              _____IL13Rα1_____>

100              110              120              130
    *      *      *      *      *      *      *      *
   GGA    GCC    AGC    TCA    AAT    TGT    AGT    CTA    TGG    TAT    TTT    AGT    CAT    TTT
   CCT    CGG    TCG    AGT    TTA    ACA    TCA    GAT    ACC    ATA    AAA    TCA    GTA    AAA
   Gly    Ala    Ser    Ser    Asn    Cys    Ser    Leu    Trp    Tyr    Phe    Ser    His    Phe>
                              _____IL13Rα1_____>

140              150              160              170
    *      *      *      *      *      *      *      *
   GGC    GAC    AAA    CAA    GAT    AAG    AAA    ATA    GCT    CCG    GAA    ACT    CGT    CGT
   CCG    CTG    TTT    GTT    CTA    TTC    TTT    TAT    CGA    GGC    CTT    TGA    GCA    GCA
   Gly    Asp    Lys    Gln    Asp    Lys    Lys    Ile    Ala    Pro    Glu    Thr    Arg    Arg>
                              _____IL13Rα1_____>
```

Figure 40B

```
       180              190             200             210
    *    *     *    *     *     *    *    *     *
   TCA  ATA  GAA  GTA  CCC  CTG  AAT  GAG  AGG  ATT  TGT  CTG  CAA  GTG
   AGT  TAT  CTT  CAT  GGG  GAC  TTA  CTC  TCC  TAA  ACA  GAC  GTT  CAC
   Ser  Ile  Glu  Val  Pro  Leu  Asn  Glu  Arg  Ile  Cys  Leu  Gln  Val>
   _____IL13Rα1_____>

220             230             240           250
       *    *     *     *    *     *    *     *
   GGG  TCC  CAG  TGT  AGC  ACC  AAT  GAG  AGT  GAG  AAG  CCT  AGC  ATT
   CCC  AGG  GTC  ACA  TCG  TGG  TTA  CTC  TCA  CTC  TTC  GGA  TCG  TAA
   Gly  Ser  Gln  Cys  Ser  Thr  Asn  Glu  Ser  Glu  Lys  Pro  Ser  Ile>
   _____IL13Rα1_____>

260             270             280             290            300
    *         *     *    *     *    *     *     *    *     *
   TTG  GTT  GAA  AAA  TGC  ATC  TCA  CCC  CCA  GAA  GGT  GAT  CCT  GAG
   AAC  CAA  CTT  TTT  ACG  TAG  AGT  GGG  GGT  CTT  CCA  CTA  GGA  CTC
   Leu  Val  Glu  Lys  Cys  Ile  Ser  Pro  Pro  Glu  Gly  Asp  Pro  Glu>
   _____IL13Rα1_____>

310             320             330            340
          *    *     *     *    *     *    *     *
   TCT  GCT  GTG  ACT  GAG  CTT  CAA  TGC  ATT  TGG  CAC  AAC  CTG  AGC
   AGA  CGA  CAC  TGA  CTC  GAA  GTT  ACG  TAA  ACC  GTG  TTG  GAC  TCG
   Ser  Ala  Val  Thr  Glu  Leu  Gln  Cys  Ile  Trp  His  Asn  Leu  Ser>
   _____IL13Rα1_____>

350             360             370            380
          *    *     *     *    *     *    *     *
   TAC  ATG  AAG  TGT  TCT  TGG  CTC  CCT  GGA  AGG  AAT  ACC  AGT  CCC
   ATG  TAC  TTC  ACA  AGA  ACC  GAG  GGA  CCT  TCC  TTA  TGG  TCA  GGG
   Tyr  Met  Lys  Cys  Ser  Trp  Leu  Pro  Gly  Arg  Asn  Thr  Ser  Pro>
   _____IL13Rα1_____>

390             400             410            420
       *    *     *     *    *     *    *     *    *
   GAC  ACT  AAC  TAT  ACT  CTC  TAC  TAT  TGG  CAC  AGA  AGC  CTG  GAA
   CTG  TGA  TTG  ATA  TGA  GAG  ATG  ATA  ACC  GTG  TCT  TCG  GAC  CTT
   Asp  Thr  Asn  Tyr  Thr  Leu  Tyr  Tyr  Trp  His  Arg  Ser  Leu  Glu>
   _____IL13Rα1_____>

430             440             450           460
       *    *     *     *    *     *    *     *
   AAA  ATT  CAT  CAA  TGT  GAA  AAC  ATC  TTT  AGA  GAA  GGC  CAA  TAC
   TTT  TAA  GTA  GTT  ACA  CTT  TTG  TAG  AAA  TCT  CTT  CCG  GTT  ATG
   Lys  Ile  His  Gln  Cys  Glu  Asn  Ile  Phe  Arg  Glu  Gly  Gln  Tyr>
   _____IL13Rα1_____>
```

Figure 40C

```
       470           480           490           500           510
        *     *      *     *      *     *      *     *      *
       TTT GGT TGT TCC TTT GAT CTG ACC AAA GTG AAG GAT TCC AGT
       AAA CCA ACA AGG AAA CTA GAC TGG TTT CAC TTC CTA AGG TCA
       Phe Gly Cys Ser Phe Asp Leu Thr Lys Val Lys Asp Ser Ser>
       _____IL13Rα1_____>

520           530           540           550
              *     *     *      *     *      *     *      *
       TTT GAA CAA CAC AGT GTC CAA ATA ATG GTC AAG GAT AAT GCA
       AAA CTT GTT GTG TCA CAG GTT TAT TAC CAG TTC CTA TTA CGT
       Phe Glu Gln His Ser Val Gln Ile Met Val Lys Asp Asn Ala>
       _____IL13Rα1_____>

560           570           580           590
                 *     *     *      *     *      *     *      *
       GGA AAA ATT AAA CCA TCC TTC AAT ATA GTG CCT TTA ACT TCC
       CCT TTT TAA TTT GGT AGG AAG TTA TAT CAC GGA AAT TGA AGG
       Gly Lys Ile Lys Pro Ser Phe Asn Ile Val Pro Leu Thr Ser>
       _____IL13Rα1_____>

600           610           620           630
        *     *     *     *      *     *      *     *      *
       CGT GTG AAA CCT GAT CCT CCA CAT ATT AAA AAC CTC TCC TTC
       GCA CAC TTT GGA CTA GGA GGT GTA TAA TTT TTG GAG AGG AAG
       Arg Val Lys Pro Asp Pro Pro His Ile Lys Asn Leu Ser Phe>
       _____IL13Rα1_____>

640           650           660           670
        *     *     *     *      *     *      *     *
       CAC AAT GAT GAC CTA TAT GTG CAA TGG GAG AAT CCA CAG AAT
       GTG TTA CTA CTG GAT ATA CAC GTT ACC CTC TTA GGT GTC TTA
       His Asn Asp Asp Leu Tyr Val Gln Trp Glu Asn Pro Gln Asn>
       _____IL13Rα1_____>

680           690           700           710           720
        *     *      *     *      *     *      *     *      *
       TTT ATT AGC AGA TGC CTA TTT TAT GAA GTA GAA GTC AAT AAC
       AAA TAA TCG TCT ACG GAT AAA ATA CTT CAT CTT CAG TTA TTG
       Phe Ile Ser Arg Cys Leu Phe Tyr Glu Val Glu Val Asn Asn>
       _____IL13Rα1_____>

730           740           750           760
              *     *     *      *     *      *     *      *
       AGC CAA ACT GAG ACA CAT AAT GTT TTC TAC GTC CAA GAG GCT
       TCG GTT TGA CTC TGT GTA TTA CAA AAG ATG CAG GTT CTC CGA
       Ser Gln Thr Glu Thr His Asn Val Phe Tyr Val Gln Glu Ala>
       _____IL13Rα1_____>
```

Figure 40D

```
          770           780           790           800
    *      *      *      *      *      *      *      *
   AAA  TGT  GAG  AAT  CCA  GAA  TTT  GAG  AGA  AAT  GTG  GAG  AAT  ACA
   TTT  ACA  CTC  TTA  GGT  CTT  AAA  CTC  TCT  TTA  CAC  CTC  TTA  TGT
   Lys  Cys  Glu  Asn  Pro  Glu  Phe  Glu  Arg  Asn  Val  Glu  Asn  Thr>
   _____IL13Rα1_____>

810           820           830           840
    *      *      *      *      *      *      *      *      *
   TCT  TGT  TTC  ATG  GTC  CCT  GGT  GTT  CTT  CCT  GAT  ACT  TTG  AAC
   AGA  ACA  AAG  TAC  CAG  GGA  CCA  CAA  GAA  GGA  CTA  TGA  AAC  TTG
   Ser  Cys  Phe  Met  Val  Pro  Gly  Val  Leu  Pro  Asp  Thr  Leu  Asn>
   _____IL13Rα1_____>

850           860           870           880
    *    *      *      *      *      *      *      *
   ACA  GTC  AGA  ATA  AGA  GTC  AAA  ACA  AAT  AAG  TTA  TGC  TAT  GAG
   TGT  CAG  TCT  TAT  TCT  CAG  TTT  TGT  TTA  TTC  AAT  ACG  ATA  CTC
   Thr  Val  Arg  Ile  Arg  Val  Lys  Thr  Asn  Lys  Leu  Cys  Tyr  Glu>
   _____IL13Rα1_____>

890           900           910           920           930
   *     *      *      *      *      *      *      *      *
   GAT  GAC  AAA  CTC  TGG  AGT  AAT  TGG  AGC  CAA  GAA  ATG  AGT  ATA
   CTA  CTG  TTT  GAG  ACC  TCA  TTA  ACC  TCG  GTT  CTT  TAC  TCA  TAT
   Asp  Asp  Lys  Leu  Trp  Ser  Asn  Trp  Ser  Gln  Glu  Met  Ser  Ile>
   _____IL13Rα1_____>

940           950           960           970
    *       *      *      *      *      *      *      *      *
   GGT  AAG  AAG  CGC  AAT  TCC  ACA  GGG  AAC  ATG  AAG  GTC  TTG  CAG
   CCA  TTC  TTC  GCG  TTA  AGG  TGT  CCC  TTG  TAC  TTC  CAG  AAC  GTC
                                  Gly  Asn  Met  Lys  Val  Leu  Gln>
                                  _____IL4Rα_____>
   Gly  Lys  Lys  Arg  Asn  Ser  Thr>
   _____IL13Rα1_____>

980           990          1000          1010
    *      *      *      *      *      *      *      *
   GAG  CCC  ACC  TGC  GTC  TCC  GAC  TAC  ATG  AGC  ATC  TCT  ACT  TGC
   CTC  GGG  TGG  ACG  CAG  AGG  CTG  ATG  TAC  TCG  TAG  AGA  TGA  ACG
   Glu  Pro  Thr  Cys  Val  Ser  Asp  Tyr  Met  Ser  Ile  Ser  Thr  Cys>
   _____IL4Rα_____>

1020          1030          1040          1050
    *      *      *      *      *      *      *      *      *
   GAG  TGG  AAG  ATG  AAT  GGT  CCC  ACC  AAT  TGC  AGC  ACC  GAG  CTC
   CTC  ACC  TTC  TAC  TTA  CCA  GGG  TGG  TTA  ACG  TCG  TGG  CTC  GAG
   Glu  Trp  Lys  Met  Asn  Gly  Pro  Thr  Asn  Cys  Ser  Thr  Glu  Leu>
   _____IL4Rα_____>
```

Figure 40E

```
          1060           1070           1080           1090
            *      *       *      *       *      *       *      *
         CGC    CTG    TTG    TAC    CAG    CTG    GTT    TTT    CTG    CTC    TCC    GAA    GCC    CAC
         GCG    GAC    AAC    ATG    GTC    GAC    CAA    AAA    GAC    GAG    AGG    CTT    CGG    GTG
         Arg    Leu    Leu    Tyr    Gln    Leu    Val    Phe    Leu    Leu    Ser    Glu    Ala    His>
         ─────────────────────────────────────IL4Rα─────────────────────────────────────>

1100           1110           1120           1130           1140
     *      *       *      *       *      *       *      *       *
   ACG    TGT    ATC    CCT    GAG    AAC    AAC    GGA    GGC    GCG    GGG    TGC    GTG    TGC
   TGC    ACA    TAG    GGA    CTC    TTG    TTG    CCT    CCG    CGC    CCC    ACG    CAC    ACG
   Thr    Cys    Ile    Pro    Glu    Asn    Asn    Gly    Gly    Ala    Gly    Cys    Val    Cys>
   ─────────────────────────────────────IL4Rα─────────────────────────────────────>

1150           1160           1170           1180
                    *      *       *      *       *      *       *      *
                 CAC    CTG    CTC    ATG    GAT    GAC    GTG    GTC    AGT    GCG    GAT    AAC    TAT    ACA
                 GTG    GAC    GAG    TAC    CTA    CTG    CAC    CAG    TCA    CGC    CTA    TTG    ATA    TGT
                 His    Leu    Leu    Met    Asp    Asp    Val    Val    Ser    Ala    Asp    Asn    Tyr    Thr>
                 ─────────────────────────────────────IL4Rα─────────────────────────────────────>

1190           1200           1210           1220
                    *      *       *      *       *      *       *      *
                 CTG    GAC    CTG    TGG    GCT    GGG    CAG    CAG    CTG    CTG    TGG    AAG    GGC    TCC
                 GAC    CTG    GAC    ACC    CGA    CCC    GTC    GTC    GAC    GAC    ACC    TTC    CCG    AGG
                 Leu    Asp    Leu    Trp    Ala    Gly    Gln    Gln    Leu    Leu    Trp    Lys    Gly    Ser>
                 ─────────────────────────────────────IL4Rα─────────────────────────────────────>

1230           1240           1250           1260
             *      *       *      *       *      *       *      *       *
          TTC    AAG    CCC    AGC    GAG    CAT    GTG    AAA    CCC    AGG    GCC    CCA    GGA    AAC
          AAG    TTC    GGG    TCG    CTC    GTA    CAC    TTT    GGG    TCC    CGG    GGT    CCT    TTG
          Phe    Lys    Pro    Ser    Glu    His    Val    Lys    Pro    Arg    Ala    Pro    Gly    Asn>
          ─────────────────────────────────────IL4Rα─────────────────────────────────────>

1270           1280           1290           1300
             *      *       *      *       *      *       *      *
          CTG    ACA    GTT    CAC    ACC    AAT    GTC    TCC    GAC    ACT    CTG    CTG    CTG    ACC
          GAC    TGT    CAA    GTG    TGG    TTA    CAG    AGG    CTG    TGA    GAC    GAC    GAC    TGG
          Leu    Thr    Val    His    Thr    Asn    Val    Ser    Asp    Thr    Leu    Leu    Leu    Thr>
          ─────────────────────────────────────IL4Rα─────────────────────────────────────>

1310           1320           1330           1340           1350
     *      *       *      *       *      *       *      *       *
   TGG    AGC    AAC    CCG    TAT    CCC    CCT    GAC    AAT    TAC    CTG    TAT    AAT    CAT
   ACC    TCG    TTG    GGC    ATA    GGG    GGA    CTG    TTA    ATG    GAC    ATA    TTA    GTA
   Trp    Ser    Asn    Pro    Tyr    Pro    Pro    Asp    Asn    Tyr    Leu    Tyr    Asn    His>
   ─────────────────────────────────────IL4Rα─────────────────────────────────────>
```

Figure 40F

```
           1360           1370           1380           1390
       *      *      *      *      *      *      *      *
      CTC    ACC    TAT    GCA    GTC    AAC    ATT    TGG    AGT    GAA    AAC    GAC    CCG    GCA
      GAG    TGG    ATA    CGT    CAG    TTG    TAA    ACC    TCA    CTT    TTG    CTG    GGC    CGT
      Leu    Thr    Tyr    Ala    Val    Asn    Ile    Trp    Ser    Glu    Asn    Asp    Pro    Ala>
      _____IL4Rα_____>

1400           1410           1420           1430
       *      *      *      *      *      *      *      *
      GAT    TTC    AGA    ATC    TAT    AAC    GTG    ACC    TAC    CTA    GAA    CCC    TCC    CTC
      CTA    AAG    TCT    TAG    ATA    TTG    CAC    TGG    ATG    GAT    CTT    GGG    AGG    GAG
      Asp    Phe    Arg    Ile    Tyr    Asn    Val    Thr    Tyr    Leu    Glu    Pro    Ser    Leu>
      _____IL4Rα_____>

1440           1450           1460           1470
          *      *      *      *      *      *      *      *      *
         CGC    ATC    GCA    GCC    AGC    ACC    CTG    AAG    TCT    GGG    ATT    TCC    TAC    AGG
         GCG    TAG    CGT    CGG    TCG    TGG    GAC    TTC    AGA    CCC    TAA    AGG    ATG    TCC
         Arg    Ile    Ala    Ala    Ser    Thr    Leu    Lys    Ser    Gly    Ile    Ser    Tyr    Arg>
         _____IL4Rα_____>

>Mutation Cysteine to Serine
           1480           1490           1500   |       1510
       *      *      *      *      *   |    *      *      *
      GCA    CGC    GTA    CGG    GCC    TGG    GCT    CAG    AGC    TAT    AAC    ACC    ACC    TGG
      CGT    GCG    CAT    GCC    CGG    ACC    CGA    GTC    TCG    ATA    TTG    TGG    TGG    ACC
      Ala    Arg    Val    Arg    Ala    Trp    Ala    Gln    Ser    Tyr    Asn    Thr    Thr    Trp>
      _____IL4Rα_____>

1520           1530           1540           1550           1560
    *      *      *      *      *      *      *      *      *
   AGT    GAG    TGG    AGC    CCC    AGC    ACC    AAG    TGG    CAC    AAC    TCC    TAC    AGG
   TCA    CTC    ACC    TCG    GGG    TCG    TGG    TTC    ACC    GTG    TTG    AGG    ATG    TCC
   Ser    Glu    Trp    Ser    Pro    Ser    Thr    Lys    Trp    His    Asn    Ser    Tyr    Arg>
   _____IL4Rα_____>

1570           1580           1590           1600
          *      *      *      *      *      *      *      *
         GAG    CCC    TTC    GAG    CAG    TCC    GGA    GAC    AAA    ACT    CAC    ACA    TGC    CCA
         CTC    GGG    AAG    CTC    GTC    AGG    CCT    CTG    TTT    TGA    GTG    TGT    ACG    GGT
         Glu    Pro    Phe    Glu    Gln>
         _____IL4Rα_____>
                                    Ser    Gly    Asp    Lys    Thr    His    Thr    Cys    Pro>
                                    _____FC-IgG1_____>

1610           1620           1630           1640
          *      *      *      *      *      *      *      *
         CCG    TGC    CCA    GCA    CCT    GAA    CTC    CTG    GGG    GGA    CCG    TCA    GTC    TTC
         GGC    ACG    GGT    CGT    GGA    CTT    GAG    GAC    CCC    CCT    GGC    AGT    CAG    AAG
         Pro    Cys    Pro    Ala    Pro    Glu    Leu    Leu    Gly    Gly    Pro    Ser    Val    Phe>
         _____FC-IgG1_____>
```

Figure 40G

```
         1650           1660            1670          1680
          *      *       *      *        *      *      *      *       *
       CTC  TTC  CCC  CCA  AAA  CCC  AAG  GAC  ACC  CTC  ATG  ATC  TCC  CGG
       GAG  AAG  GGG  GGT  TTT  GGG  TTC  CTG  TGG  GAG  TAC  TAG  AGG  GCC
       Leu  Phe  Pro  Pro  Lys  Pro  Lys  Asp  Thr  Leu  Met  Ile  Ser  Arg>
                              _____FC-IgG1_____>

1690           1700            1710          1720
          *      *       *      *        *       *      *      *
       ACC  CCT  GAG  GTC  ACA  TGC  GTG  GTG  GTG  GAC  GTG  AGC  CAC  GAA
       TGG  GGA  CTC  CAG  TGT  ACG  CAC  CAC  CAC  CTG  CAC  TCG  GTG  CTT
       Thr  Pro  Glu  Val  Thr  Cys  Val  Val  Val  Asp  Val  Ser  His  Glu>
                              _____FC-IgG1_____>

1730           1740            1750          1760          1770
  *      *       *      *        *      *      *      *      *     *
GAC  CCT  GAG  GTC  AAG  TTC  AAC  TGG  TAC  GTG  GAC  GGC  GTG  GAG
CTG  GGA  CTC  CAG  TTC  AAG  TTG  ACC  ATG  CAC  CTG  CCG  CAC  CTC
Asp  Pro  Glu  Val  Lys  Phe  Asn  Trp  Tyr  Val  Asp  Gly  Val  Glu>
                      _____FC-IgG1_____>

1780           1790            1800          1810
          *      *       *      *        *      *      *      *
       GTG  CAT  AAT  GCC  AAG  ACA  AAG  CCG  CGG  GAG  GAG  CAG  TAC  AAC
       CAC  GTA  TTA  CGG  TTC  TGT  TTC  GGC  GCC  CTC  CTC  GTC  ATG  TTG
       Val  His  Asn  Ala  Lys  Thr  Lys  Pro  Arg  Glu  Glu  Gln  Tyr  Asn>
                              _____FC-IgG1_____>

1820           1830            1840          1850
          *      *       *      *        *      *      *      *
       AGC  ACG  TAC  CGT  GTG  GTC  AGC  GTC  CTC  ACC  GTC  CTG  CAC  CAG
       TCG  TGC  ATG  GCA  CAC  CAG  TCG  CAG  GAG  TGG  CAG  GAC  GTG  GTC
       Ser  Thr  Tyr  Arg  Val  Val  Ser  Val  Leu  Thr  Val  Leu  His  Gln>
                              _____FC-IgG1_____>

1860           1870            1880          1890
          *      *       *      *        *      *      *      *       *
       GAC  TGG  CTG  AAT  GGC  AAG  GAG  TAC  AAG  TGC  AAG  GTC  TCC  AAC
       CTG  ACC  GAC  TTA  CCG  TTC  CTC  ATG  TTC  ACG  TTC  CAG  AGG  TTG
       Asp  Trp  Leu  Asn  Gly  Lys  Glu  Tyr  Lys  Cys  Lys  Val  Ser  Asn>
                              _____FC-IgG1_____>

1900           1910            1920          1930
          *      *       *      *        *      *      *      *
       AAA  GCC  CTC  CCA  GCC  CCC  ATC  GAG  AAA  ACC  ATC  TCC  AAA  GCC
       TTT  CGG  GAG  GGT  CGG  GGG  TAG  CTC  TTT  TGG  TAG  AGG  TTT  CGG
       Lys  Ala  Leu  Pro  Ala  Pro  Ile  Glu  Lys  Thr  Ile  Ser  Lys  Ala>
                              _____FC-IgG1_____>
```

Figure 40H

```
      1940           1950           1960           1970           1980
   *             *         *         *         *         *         *         *         *
   AAA GGG CAG CCC CGA GAA CCA CAG GTG TAC ACC CTG CCC CCA
   TTT CCC GTC GGG GCT CTT GGT GTC CAC ATG TGG GAC GGG GGT
   Lys Gly Gln Pro Arg Glu Pro Gln Val Tyr Thr Leu Pro Pro>
   _____FC-IgG1_____>

1990           2000           2010           2020
      *         *         *         *         *         *         *         *
   TCC CGG GAT GAG CTG ACC AAG AAC CAG GTC AGC CTG ACC TGC
   AGG GCC CTA CTC GAC TGG TTC TTG GTC CAG TCG GAC TGG ACG
   Ser Arg Asp Glu Leu Thr Lys Asn Gln Val Ser Leu Thr Cys>
   _____FC-IgG1_____>

2030           2040           2050           2060
   *         *         *         *         *         *         *         *
   CTG GTC AAA GGC TTC TAT CCC AGC GAC ATC GCC GTG GAG TGG
   GAC CAG TTT CCG AAG ATA GGG TCG CTG TAG CGG CAC CTC ACC
   Leu Val Lys Gly Phe Tyr Pro Ser Asp Ile Ala Val Glu Trp>
   _____FC-IgG1_____>

2070           2080           2090           2100
   *         *         *         *         *         *         *         *         *
   GAG AGC AAT GGG CAG CCG GAG AAC AAC TAC AAG ACC ACG CCT
   CTC TCG TTA CCC GTC GGC CTC TTG TTG ATG TTC TGG TGC GGA
   Glu Ser Asn Gly Gln Pro Glu Asn Asn Tyr Lys Thr Thr Pro>
   _____FC-IgG1_____>

2110           2120           2130           2140
   *         *         *         *         *         *         *         *
   CCC GTG CTG GAC TCC GAC GGC TCC TTC TTC CTC TAC AGC AAG
   GGG CAC GAC CTG AGG CTG CCG AGG AAG AAG GAG ATG TCG TTC
   Pro Val Leu Asp Ser Asp Gly Ser Phe Phe Leu Tyr Ser Lys>
   _____FC-IgG1_____>

2150           2160           2170           2180           2190
   *         *         *         *         *         *         *         *         *
   CTC ACC GTG GAC AAG AGC AGG TGG CAG CAG GGG AAC GTC TTC
   GAG TGG CAC CTG TTC TCG TCC ACC GTC GTC CCC TTG CAG AAG
   Leu Thr Val Asp Lys Ser Arg Trp Gln Gln Gly Asn Val Phe>
   _____FC-IgG1_____>

2200           2210           2220           2230
      *         *         *         *         *         *         *         *
   TCA TGC TCC GTG ATG CAT GAG GCT CTG CAC AAC CAC TAC ACG
   AGT ACG AGG CAC TAC GTA CTC CGA GAC GTG TTG GTG ATG TGC
   Ser Cys Ser Val Met His Glu Ala Leu His Asn His Tyr Thr>
   _____FC-IgG1_____>
```

Figure 40I

```
          2240              2250              2260
  *        *        *        *        *        *        *
CAG AAG AGC CTC TCC CTG TCT CCG GGT AAA TGA
GTC TTC TCG GAG AGG GAC AGA GGC CCA TTT ACT
Gln Lys Ser Leu Ser Leu Ser Pro Gly Lys ***>
                         FC-IgG1                        >
```

Figure 41A

```
-60      -50           -40           -30
          *       *     *       *     *       *       *       *       *
         ATG GTG TGG CTT TGC TCT GGG CTC CTG TTC CCT GTG AGC TGC CTG GTC
         TAC CAC ACC GAA ACG AGA CCC GAG GAC AAG GGA CAC TCG ACG GAC CAG
         Met Val Trp Leu Cys Ser Gly Leu Leu Phe Pro Val Ser Cys Leu Val>
         _____SIGNAL PEPTIDE_____>

-20           -10            1            10             20
        *       *     *       *     *       *     *       *     *       *
       CTG CTG CAG GTG GCA AGC TCT GGG AAC ATG AAG GTC TTG CAG GAG CCC
       GAC GAC GTC CAC CGT TCG AGA CCC TTG TAC TTC CAG AAC GTC CTC GGG
       Leu Leu Gln Val Ala Ser Ser Gly Asn Met Lys Val Leu Gln Glu Pro>
                                            _____IL4Rα_____>
       Leu Leu Gln Val Ala Ser Ser>
       _____SIGNAL PEPTIDE_____>

30            40           50            60            70
          *       *     *       *     *       *     *       *     *       *
         ACC TGC GTC TCC GAC TAC ATG AGC ATC TCT ACT TGC GAG TGG AAG ATG
         TGG ACG CAG AGG CTG ATG TAC TCG TAG AGA TGA ACG CTC ACC TTC TAC
         Thr Cys Val Ser Asp Tyr Met Ser Ile Ser Thr Cys Glu Trp Lys Met>
         _____IL4Rα_____>

80            90           100           110           120
               *       *     *       *     *       *     *       *     *
              AAT GGT CCC ACC AAT TGC AGC ACC GAG CTC CGC CTG TTG TAC CAG CTG
              TTA CCA GGG TGG TTA ACG TCG TGG CTC GAG GCG GAC AAC ATG GTC GAC
              Asn Gly Pro Thr Asn Cys Ser Thr Glu Leu Arg Leu Leu Tyr Gln Leu>
              _____IL4Rα_____>

130           140           150           160           170
               *       *     *       *     *       *     *       *     *       *
              GTT TTT CTG CTC TCC GAA GCC CAC ACG TGT ATC CCT GAG AAC AAC GGA
              CAA AAA GAC GAG AGG CTT CGG GTG TGC ACA TAG GGA CTC TTG TTG CCT
              Val Phe Leu Leu Ser Glu Ala His Thr Cys Ile Pro Glu Asn Asn Gly>
              _____IL4Rα_____>

180           190           200           210
                    *       *     *       *     *       *     *       *     *
                   GGC GCG GGG TGC GTG TGC CAC CTG CTC ATG GAT GAC GTG GTC AGT GCG
                   CCG CGC CCC ACG CAC ACG GTG GAC GAG TAC CTA CTG CAC CAG TCA CGC
                   Gly Ala Gly Cys Val Cys His Leu Leu Met Asp Asp Val Val Ser Ala>
                   _____IL4Rα_____>

220           230           240           250           260
               *       *     *       *     *       *     *       *     *       *
              GAT AAC TAT ACA CTG GAC CTG TGG GCT GGG CAG CAG CTG CTG TGG AAG
              CTA TTG ATA TGT GAC CTG GAC ACC CGA CCC GTC GTC GAC GAC ACC TTC
              Asp Asn Tyr Thr Leu Asp Leu Trp Ala Gly Gln Gln Leu Leu Trp Lys>
              _____IL4Rα_____>
```

Figure 41B

```
           270              280              290              300              310
    *       *        *       *        *       *        *       *        *       *
   GGC TCC TTC AAG CCC AGC GAG CAT GTG AAA CCC AGG GCC CCA GGA AAC
   CCG AGG AAG TTC GGG TCG CTC GTA CAC TTT GGG TCC CGG GGT CCT TTG
   Gly Ser Phe Lys Pro Ser Glu His Val Lys Pro Arg Ala Pro Gly Asn>
   _____IL4Rα_____>

320              330              340              350              360
       *       *        *       *        *       *        *       *        *
      CTG ACA GTT CAC ACC AAT GTC TCC GAC ACT CTG CTG CTG ACC TGG AGC
      GAC TGT CAA GTG TGG TTA CAG AGG CTG TGA GAC GAC GAC TGG ACC TCG
      Leu Thr Val His Thr Asn Val Ser Asp Thr Leu Leu Leu Thr Trp Ser>
      _____IL4Rα_____>

370              380              390              400              410
         *       *        *       *        *       *        *       *        *
        AAC CCG TAT CCC CCT GAC AAT TAC CTG TAT AAT CAT CTC ACC TAT GCA
        TTG GGC ATA GGG GGA CTG TTA ATG GAC ATA TTA GTA GAG TGG ATA CGT
        Asn Pro Tyr Pro Pro Asp Asn Tyr Leu Tyr Asn His Leu Thr Tyr Ala>
        _____IL4Rα_____>

420              430              440              450
             *       *        *       *        *       *        *       *
            GTC AAC ATT TGG AGT GAA AAC GAC CCG GCA GAT TTC AGA ATC TAT AAC
            CAG TTG TAA ACC TCA CTT TTG CTG GGC CGT CTA AAG TCT TAG ATA TTG
            Val Asn Ile Trp Ser Glu Asn Asp Pro Ala Asp Phe Arg Ile Tyr Asn>
            _____IL4Rα_____>

460              470              480              490              500
    *       *        *       *        *       *        *       *        *       *
   GTG ACC TAC CTA GAA CCC TCC CTC CGC ATC GCA GCC AGC ACC CTG AAG
   CAC TGG ATG GAT CTT GGG AGG GAG GCG TAG CGT CGG TCG TGG GAC TTC
   Val Thr Tyr Leu Glu Pro Ser Leu Arg Ile Ala Ala Ser Thr Leu Lys>
   _____IL4Rα_____>

Mutation Cysteine to Serine
                                                                |
                                                                |
   510              520              530              540              550
    *       *        *       *        *       *        *       *        *       *
   TCT GGG ATT TCC TAC AGG GCA CGC GTA CGG GCC TGG GCT CAG AGC TAT
   AGA CCC TAA AGG ATG TCC CGT GCG CAT GCC CGG ACC CGA GTC TCG ATA
   Ser Gly Ile Ser Tyr Arg Ala Arg Val Arg Ala Trp Ala Gln Ser Tyr>
   _____IL4Rα_____>

560              570              580              590              600
       *       *        *       *        *       *        *       *        *
      AAC ACC ACC TGG AGT GAG TGG AGC CCC AGC ACC AAG TGG CAC AAC TCC
      TTG TGG TGG ACC TCA CTC ACC TCG GGG TCG TGG TTC ACC GTG TTG ACG
      Asn Thr Thr Trp Ser Glu Trp Ser Pro Ser Thr Lys Trp His Asn Ser>
      _____IL4Rα_____>
```

Figure 41C

```
              610            620            630            640            650
          *    *    *    *    *    *    *    *    *    *
        TAC  AGG  GAG  CCC  TTC  GAG  CAG  GCG  CCT  ACG  GAA  ACT  CAG  CCA  CCT  GTG
        ATG  TCC  CTC  GGG  AAG  CTC  GTC  CGC  GGA  TGC  CTT  TGA  GTC  GGT  GGA  CAC
        Tyr  Arg  Glu  Pro  Phe  Glu  Gln>
        _____IL4Rα_____>
                                          Ala  Pro  Thr  Glu  Thr  Gln  Pro  Pro  Val>
                                          _____IL13Rα1_____>

Mutation Cysteine to Serine
                                                    |
              660            670            680     |     690
          *    *    *    *    *    *    | *    *    *
        ACA  AAT  TTG  AGT  GTC  TCT  GTT  GAA  AAC  CTC  AGC  ACA  GTA  ATA  TGG  ACA
        TGT  TTA  AAC  TCA  CAG  AGA  CAA  CTT  TTG  GAG  TCG  TGT  CAT  TAT  ACC  TGT
        Thr  Asn  Leu  Ser  Val  Ser  Val  Glu  Asn  Leu  Ser  Thr  Val  Ile  Trp  Thr>
        _____IL13Rα1_____>

700            710            720            730            740
     *    *    *    *    *    *    *    *    *    *
   TGG  AAT  CCA  CCC  GAG  GGA  GCC  AGC  TCA  AAT  TGT  AGT  CTA  TGG  TAT  TTT
   ACC  TTA  GGT  GGG  CTC  CCT  CGG  TCG  AGT  TTA  ACA  TCA  GAT  ACC  ATA  AAA
   Trp  Asn  Pro  Pro  Glu  Gly  Ala  Ser  Ser  Asn  Cys  Ser  Leu  Trp  Tyr  Phe>
   _____IL13Rα1_____>

750            760            770            780            790
     *    *    *    *    *    *    *    *    *    *
   AGT  CAT  TTT  GGC  GAC  AAA  CAA  GAT  AAG  AAA  ATA  GCT  CCG  GAA  ACT  CGT
   TCA  GTA  AAA  CCG  CTG  TTT  GTT  CTA  TTC  TTT  TAT  CGA  GGC  CTT  TGA  GCA
   Ser  His  Phe  Gly  Asp  Lys  Gln  Asp  Lys  Lys  Ile  Ala  Pro  Glu  Thr  Arg>
   _____IL13Rα1_____>

800            810            820            830            840
          *    *    *    *    *    *    *    *    *
        CGT  TCA  ATA  GAA  GTA  CCC  CTG  AAT  GAG  AGG  ATT  TGT  CTG  CAA  GTG  GGG
        GCA  AGT  TAT  CTT  CAT  GGG  GAC  TTA  CTC  TCC  TAA  ACA  GAC  GTT  CAC  CCC
        Arg  Ser  Ile  Glu  Val  Pro  Leu  Asn  Glu  Arg  Ile  Cys  Leu  Gln  Val  Gly>
        _____IL13Rα1_____>

850            860            870            880            890
           *    *    *    *    *    *    *    *    *    *
         TCC  CAG  TGT  AGC  ACC  AAT  GAG  AGT  GAG  AAG  CCT  AGC  ATT  TTG  GTT  GAA
         AGG  GTC  ACA  TCG  TGG  TTA  CTC  TCA  CTC  TTC  GGA  TCG  TAA  AAC  CAA  CTT
         Ser  Gln  Cys  Ser  Thr  Asn  Glu  Ser  Glu  Lys  Pro  Ser  Ile  Leu  Val  Glu>
         _____IL13Rα1_____>

900            910            920            930
                 *    *    *    *    *    *    *    *    *
              AAA  TGC  ATC  TCA  CCC  CCA  GAA  GGT  GAT  CCT  GAG  TCT  GCT  GTG  ACT  GAG
              TTT  ACG  TAG  AGT  GGG  GGT  CTT  CCA  CTA  GGA  CTC  AGA  CGA  CAC  TGA  CTC
              Lys  Cys  Ile  Ser  Pro  Pro  Glu  Gly  Asp  Pro  Glu  Ser  Ala  Val  Thr  Glu>
              _____IL13Rα1_____>
```

Figure 41D

```
      940           950           960           970           980
       *       *     *       *     *       *     *       *     *       *
      CTT CAA TGC ATT TGG CAC AAC CTG AGC TAC ATG AAG TGT TCT TGG CTC
      GAA GTT ACG TAA ACC GTG TTG GAC TCG ATG TAC TTC ACA AGA ACC GAG
      Leu Gln Cys Ile Trp His Asn Leu Ser Tyr Met Lys Cys Ser Trp Leu>
      _____IL13Rα1_____>

990          1000          1010          1020          1030
       *       *     *       *     *       *     *       *     *       *
      CCT GGA AGG AAT ACC AGT CCC GAC ACT AAC TAT ACT CTC TAC TAT TGG
      GGA CCT TCC TTA TGG TCA GGG CTG TGA TTG ATA TGA GAG ATG ATA ACC
      Pro Gly Arg Asn Thr Ser Pro Asp Thr Asn Tyr Thr Leu Tyr Tyr Trp>
      _____IL13Rα1_____>

1040          1050          1060          1070          1080
            *     *       *     *       *     *       *     *       *
      CAC AGA AGC CTG GAA AAA ATT CAT CAA TGT GAA AAC ATC TTT AGA GAA
      GTG TCT TCG GAC CTT TTT TAA GTA GTT ACA CTT TTG TAG AAA TCT CTT
      His Arg Ser Leu Glu Lys Ile His Gln Cys Glu Asn Ile Phe Arg Glu>
      _____IL13Rα1_____>

1090          1100          1110          1120          1130
       *     *     *       *     *       *     *       *     *       *
      GGC CAA TAC TTT GGT TGT TCC TTT GAT CTG ACC AAA GTG AAG GAT TCC
      CCG GTT ATG AAA CCA ACA AGG AAA CTA GAC TGG TTT CAC TTC CTA AGG
      Gly Gln Tyr Phe Gly Cys Ser Phe Asp Leu Thr Lys Val Lys Asp Ser>
      _____IL13Rα1_____>

1140          1150          1160          1170
             *     *       *     *     *       *     *       *     *
      AGT TTT GAA CAA CAC AGT GTC CAA ATA ATG GTC AAG GAT AAT GCA GGA
      TCA AAA CTT GTT GTG TCA CAG GTT TAT TAC CAG TTC CTA TTA CGT CCT
      Ser Phe Glu Gln His Ser Val Gln Ile Met Val Lys Asp Asn Ala Gly>
      _____IL13Rα1_____>

1180          1190          1200         1210          1220
       *     *       *     *       *     *     *     *       *     *
      AAA ATT AAA CCA TCC TTC AAT ATA GTG CCT TTA ACT TCC CGT GTG AAA
      TTT TAA TTT GGT AGG AAG TTA TAT CAC GGA AAT TGA AGG GCA CAC TTT
      Lys Ile Lys Pro Ser Phe Asn Ile Val Pro Leu Thr Ser Arg Val Lys>
      _____IL13Rα1_____>

1230          1240          1250          1260          1270
            *     *     *     *       *     *     *       *     *       *
      CCT GAT CCT CCA CAT ATT AAA AAC CTC TCC TTC CAC AAT GAT GAC CTA
      GGA CTA GGA GGT GTA TAA TTT TTG GAG AGG AAG GTG TTA CTA CTG GAT
      Pro Asp Pro Pro His Ile Lys Asn Leu Ser Phe His Asn Asp Asp Leu>
      _____IL13Rα1_____>
```

Figure 41E

```
           1280        1290        1300        1310        1320
             *     *     *     *     *     *     *     *     *
         TAT GTG CAA TGG GAG AAT CCA CAG AAT TTT ATT AGC AGA TGC CTA TTT
         ATA CAC GTT ACC CTC TTA GGT GTC TTA AAA TAA TCG TCT ACG GAT AAA
         Tyr Val Gln Trp Glu Asn Pro Gln Asn Phe Ile Ser Arg Cys Leu Phe>
         _____IL13Rα1_____>

1330        1340        1350        1360        1370
             *     *     *     *     *     *     *     *     *     *
         TAT GAA GTA GAA GTC AAT AAC AGC CAA ACT GAG ACA CAT AAT GTT TTC
         ATA CTT CAT CTT CAG TTA TTG TCG GTT TGA CTC TGT GTA TTA CAA AAG
         Tyr Glu Val Glu Val Asn Asn Ser Gln Thr Glu Thr His Asn Val Phe>
         _____IL13Rα1_____>

1380        1390        1400        1410
                *     *     *     *     *     *     *     *     *
            TAC GTC CAA GAG GCT AAA TGT GAG AAT CCA GAA TTT GAG AGA AAT GTG
            ATG CAG GTT CTC CGA TTT ACA CTC TTA GGT CTT AAA CTC TCT TTA CAC
            Tyr Val Gln Glu Ala Lys Cys Glu Asn Pro Glu Phe Glu Arg Asn Val>
            _____IL13Rα1_____>

1420        1430        1440        1450        1460
        *     *     *     *     *     *     *     *     *     *
     GAG AAT ACA TCT TGT TTC ATG GTC CCT GGT GTT CTT CCT GAT ACT TTG
     CTC TTA TGT AGA ACA AAG TAC CAG GGA CCA CAA GAA GGA CTA TGA AAC
     Glu Asn Thr Ser Cys Phe Met Val Pro Gly Val Leu Pro Asp Thr Leu>
     _____IL13Rα1_____>

1470        1480        1490        1500        1510
            *     *     *     *     *     *     *     *     *     *
         AAC ACA GTC AGA ATA AGA GTC AAA ACA AAT AAG TTA TGC TAT GAG GAT
         TTG TGT CAG TCT TAT TCT CAG TTT TGT TTA TTC AAT ACG ATA CTC CTA
         Asn Thr Val Arg Ile Arg Val Lys Thr Asn Lys Leu Cys Tyr Glu Asp>
         _____IL13Rα1_____>

1520        1530        1540        1550        1560
               *     *     *     *     *     *     *     *     *
            GAC AAA CTC TGG AGT AAT TGG AGC CAA GAA ATG AGT ATA GGT AAG AAG
            CTG TTT GAG ACC TCA TTA ACC TCG GTT CTT TAC TCA TAT CCA TTC TTC
            Asp Lys Leu Trp Ser Asn Trp Ser Gln Glu Met Ser Ile Gly Lys Lys>
            _____IL13Rα1_____>

1570        1580        1590        1600        1610
                  *     *     *     *     *     *     *     *     *     *
               CGC AAT TCC ACC GGT GAC AAA ACT CAC ACA TGC CCA CCG TGC CCA GCA
               GCG TTA AGG TGG CCA CTG TTT TGA GTG TGT ACG GGT GGC ACG GGT CGT
                           Gly Asp Lys Thr His Thr Cys Pro Pro Cys Pro Ala>
                           _____FC-IgG1_____>
         Arg Asn Ser Thr>
         ____IL13Rα1____>
```

Figure 41F

```
            1620          1630          1640          1650
      *       *       *       *       *       *       *       *       *
    CCT GAA CTC CTG GGG GGA CCG TCA GTC TTC CTC TTC CCC CCA AAA CCC
    GGA CTT GAG GAC CCC CCT GGC AGT CAG AAG GAG AAG GGG GGT TTT GGG
    Pro Glu Leu Leu Gly Gly Pro Ser Val Phe Leu Phe Pro Pro Lys Pro>
    _____FC-IgG1_____>

1660          1670          1680          1690          1700
    *       *       *       *       *       *       *       *       *       *
    AAG GAC ACC CTC ATG ATC TCC CGG ACC CCT GAG GTC ACA TGC GTG GTG
    TTC CTG TGG GAG TAC TAG AGG GCC TGG GGA CTC CAG TGT ACG CAC CAC
    Lys Asp Thr Leu Met Ile Ser Arg Thr Pro Glu Val Thr Cys Val Val>
    _____FC-IgG1_____>

1710          1720          1730          1740          1750
      *       *       *       *       *       *       *       *       *       *
    GTG GAC GTG AGC CAC GAA GAC CCT GAG GTC AAG TTC AAC TGG TAC GTG
    CAC CTG CAC TCG GTG CTT CTG GGA CTC CAG TTC AAG TTG ACC ATG CAC
    Val Asp Val Ser His Glu Asp Pro Glu Val Lys Phe Asn Trp Tyr Val>
    _____FC-IgG1_____>

1760          1770          1780          1790          1800
         *       *       *       *       *       *       *       *       *
    GAC GGC GTG GAG GTG CAT AAT GCC AAG ACA AAG CCG CGG GAG GAG CAG
    CTG CCG CAC CTC CAC GTA TTA CGG TTC TGT TTC GGC GCC CTC CTC GTC
    Asp Gly Val Glu Val His Asn Ala Lys Thr Lys Pro Arg Glu Glu Gln>
    _____FC-IgG1_____>

1810          1820          1830          1840          1850
           *       *       *       *       *       *       *       *       *       *
    TAC AAC AGC ACG TAC CGT GTG GTC AGC GTC CTC ACC GTC CTG CAC CAG
    ATG TTG TCG TGC ATG GCA CAC CAG TCG CAG GAG TGG CAG GAC GTG GTC
    Tyr Asn Ser Thr Tyr Arg Val Val Ser Val Leu Thr Val Leu His Gln>
    _____FC-IgG1_____>

1860          1870          1880          1890
                *       *       *       *       *       *       *       *       *
    GAC TGG CTG AAT GGC AAG GAG TAC AAG TGC AAG GTC TCC AAC AAA GCC
    CTG ACC GAC TTA CCG TTC CTC ATG TTC ACG TTC CAG AGG TTG TTT CGG
    Asp Trp Leu Asn Gly Lys Glu Tyr Lys Cys Lys Val Ser Asn Lys Ala>
    _____FC-IgG1_____>

1900          1910          1920          1930          1940
    *       *       *       *       *       *       *       *       *       *
    CTC CCA GCC CCC ATC GAG AAA ACC ATC TCC AAA GCC AAA GGG CAG CCC
    GAG GGT CGG GGG TAG CTC TTT TGG TAG AGG TTT CGG TTT CCC GTC GGG
    Leu Pro Ala Pro Ile Glu Lys Thr Ile Ser Lys Ala Lys Gly Gln Pro>
    _____FC-IgG1_____>
```

Figure 41G

```
          1950                1960              1970              1980              1990
            *         *         *        *        *         *        *         *        *         *
         CGA  GAA  CCA  CAG  GTG  TAC  ACC  CTG  CCC  CCA  TCC  CGG  GAT  GAG  CTG  ACC
         GCT  CTT  GGT  GTC  CAC  ATG  TGG  GAC  GGG  GGT  AGG  GCC  CTA  CTC  GAC  TGG
         Arg  Glu  Pro  Gln  Val  Tyr  Thr  Leu  Pro  Pro  Ser  Arg  Asp  Glu  Leu  Thr>
                                         _____FC-IgG1_____>

2000                2010              2020              2030              2040
            *         *         *        *        *         *        *         *        *
         AAG  AAC  CAG  GTC  AGC  CTG  ACC  TGC  CTG  GTC  AAA  GGC  TTC  TAT  CCC  AGC
         TTC  TTG  GTC  CAG  TCG  GAC  TGG  ACG  GAC  CAG  TTT  CCG  AAG  ATA  GGG  TCG
         Lys  Asn  Gln  Val  Ser  Leu  Thr  Cys  Leu  Val  Lys  Gly  Phe  Tyr  Pro  Ser>
                                         _____FC-IgG1_____>

2050                2060              2070              2080              2090
            *         *         *        *        *         *        *         *        *
         GAC  ATC  GCC  GTG  GAG  TGG  GAG  AGC  AAT  GGG  CAG  CCG  GAG  AAC  AAC  TAC
         CTG  TAG  CGG  CAC  CTC  ACC  CTC  TCG  TTA  CCC  GTC  GGC  CTC  TTG  TTG  ATG
         Asp  Ile  Ala  Val  Glu  Trp  Glu  Ser  Asn  Gly  Gln  Pro  Glu  Asn  Asn  Tyr>
                                         _____FC-IgG1_____>

2100              2110              2120              2130
             *         *        *        *         *        *         *        *        *
         AAG  ACC  ACG  CCT  CCC  GTG  CTG  GAC  TCC  GAC  GGC  TCC  TTC  TTC  CTC  TAC
         TTC  TGG  TGC  GGA  GGG  CAC  GAC  CTG  AGG  CTG  CCG  AGG  AAG  AAG  GAG  ATG
         Lys  Thr  Thr  Pro  Pro  Val  Leu  Asp  Ser  Asp  Gly  Ser  Phe  Phe  Leu  Tyr>
                                         _____FC-IgG1_____>

2140               2150              2160              2170              2180
            *        *        *        *        *         *        *         *        *         *
         AGC  AAG  CTC  ACC  GTG  GAC  AAG  AGC  AGG  TGG  CAG  CAG  GGG  AAC  GTC  TTC
         TCG  TTC  GAG  TGG  CAC  CTG  TTC  TCG  TCC  ACC  GTC  GTC  CCC  TTG  CAG  AAG
         Ser  Lys  Leu  Thr  Val  Asp  Lys  Ser  Arg  Trp  Gln  Gln  Gly  Asn  Val  Phe>
                                         _____FC-IgG1_____>

2190              2200              2210              2220              2230
               *        *        *        *         *        *         *        *         *        *
         TCA  TGC  TCC  GTG  ATG  CAT  GAG  GCT  CTG  CAC  AAC  CAC  TAC  ACG  CAG  AAG
         AGT  ACG  AGG  CAC  TAC  GTA  CTC  CGA  GAC  GTG  TTG  GTG  ATG  TGC  GTC  TTC
         Ser  Cys  Ser  Val  Met  His  Glu  Ala  Leu  His  Asn  His  Tyr  Thr  Gln  Lys>
                                         _____FC-IgG1_____>

2240              2250              2260
               *         *        *        *         *
         AGC  CTC  TCC  CTG  TCT  CCG  GGT  AAA  TGA
         TCG  GAG  AGG  GAC  AGA  GGC  CCA  TTT  ACT
         Ser  Leu  Ser  Leu  Ser  Pro  Gly  Lys  ***>
                     _____FC-IgG1_____>
```

Figure 42A

```
              -70               -60              -50              -40
         *         *         *         *    *         *         *    *
ATG GTG TGG CCG GCG CGG CTC TGC GGG CTG TGG GCG CTG CTG
TAC CAC ACC GGC CGC GCC GAG ACG CCC GAC ACC CGC GAC GAC
Met Val Trp Pro Ala Arg Leu Cys Gly Leu Trp Ala Leu Leu>
_____SIGNAL PEPTIDE_____>
_____IL13Rα1_____>

-30              -20              -10               1
    *         *         *         *    *         *         *    *         *
CTC TGC GCC GGC GGC GGG GGC GGG GGC GGG GGC GCC GCG CCT
GAG ACG CGG CCG CCG CCC CCG CCC CCG CCC CCG CGG CGC GGA
Leu Cys Ala Gly Gly Gly Gly Gly Gly Gly Gly Ala Ala Pro>
____d_____SIGNAL PEPTIDE_____>
_____IL13Rα1_____>

10               20               30               40
    *         *         *         *    *         *         *         *
ACG GAA ACT CAG CCA CCT GTG ACA AAT TTG AGT GTC TCT GTT
TGC CTT TGA GTC GGT GGA CAC TGT TTA AAC TCA CAG AGA CAA
Thr Glu Thr Gln Pro Pro Val Thr Asn Leu Ser Val Ser Val>
_____IL13Rα1_____>

>Mutation Cysteine to Alanine
                  |
    50           |60             70             80             90
    *     *      |*        *         *         *         *         *         *
GAA AAC CTC GCG ACA GTA ATA TGG ACA TGG AAT CCA CCC GAG
CTT TTG GAG CGC TGT CAT TAT ACC TGT ACC TTA GGT GGG CTC
Glu Asn Leu Ala Thr Val Ile Trp Thr Trp Asn Pro Pro Glu>
_____IL13Rα1_____>

100             110             120             130
         *         *         *         *         *         *         *         *
GGA GCC AGC TCA AAT TGT AGT CTA TGG TAT TTT AGT CAT TTT
CCT CGG TCG AGT TTA ACA TCA GAT ACC ATA AAA TCA GTA AAA
Gly Ala Ser Ser Asn Cys Ser Leu Trp Tyr Phe Ser His Phe>
_____IL13Rα1_____>

140             150             160             170
    *         *         *         *         *         *         *         *
GGC GAC AAA CAA GAT AAG AAA ATA GCT CCG GAA ACT CGT CGT
CCG CTG TTT GTT CTA TTC TTT TAT CGA GGC CTT TGA GCA GCA
Gly Asp Lys Gln Asp Lys Lys Ile Ala Pro Glu Thr Arg Arg>
_____IL13Rα1_____>
```

Figure 42B

```
        180             190             200             210
 *       *       *       *       *       *       *       *       *
TCA ATA GAA GTA CCC CTG AAT GAG AGG ATT TGT CTG CAA GTG
AGT TAT CTT CAT GGG GAC TTA CTC TCC TAA ACA GAC GTT CAC
Ser Ile Glu Val Pro Leu Asn Glu Arg Ile Cys Leu Gln Val>
_____IL13Rα1_____>

220             230             240             250
 *       *       *       *       *       *       *       *
GGG TCC CAG TGT AGC ACC AAT GAG AGT GAG AAG CCT AGC ATT
CCC AGG GTC ACA TCG TGG TTA CTC TCA CTC TTC GGA TCG TAA
Gly Ser Gln Cys Ser Thr Asn Glu Ser Glu Lys Pro Ser Ile>
_____IL13Rα1_____>

260             270             280             290             300
 *       *       *       *       *       *       *       *       *
TTG GTT GAA AAA TGC ATC TCA CCC CCA GAA GGT GAT CCT GAG
AAC CAA CTT TTT ACG TAG AGT GGG GGT CTT CCA CTA GGA CTC
Leu Val Glu Lys Cys Ile Ser Pro Pro Glu Gly Asp Pro Glu>
_____IL13Rα1_____>

310             320             330             340
 *       *       *       *       *       *       *       *
TCT GCT GTG ACT GAG CTT CAA TGC ATT TGG CAC AAC CTG AGC
AGA CGA CAC TGA CTC GAA GTT ACG TAA ACC GTG TTG GAC TCG
Ser Ala Val Thr Glu Leu Gln Cys Ile Trp His Asn Leu Ser>
_____IL13Rα1_____>

350             360             370             380
 *       *       *       *       *       *       *       *
TAC ATG AAG TGT TCT TGG CTC CCT GGA AGG AAT ACC AGT CCC
ATG TAC TTC ACA AGA ACC GAG GGA CCT TCC TTA TGG TCA GGG
Tyr Met Lys Cys Ser Trp Leu Pro Gly Arg Asn Thr Ser Pro>
_____IL13Rα1_____>

390             400             410             420
 *       *       *       *       *       *       *       *       *
GAC ACT AAC TAT ACT CTC TAC TAT TGG CAC AGA AGC CTG GAA
CTG TGA TTG ATA TGA GAG ATG ATA ACC GTG TCT TCG GAC CTT
Asp Thr Asn Tyr Thr Leu Tyr Tyr Trp His Arg Ser Leu Glu>
_____IL13Rα1_____>

430             440             450             460
 *       *       *       *       *       *       *       *
AAA ATT CAT CAA TGT GAA AAC ATC TTT AGA GAA GGC CAA TAC
TTT TAA GTA GTT ACA CTT TTG TAG AAA TCT CTT CCG GTT ATG
Lys Ile His Gln Cys Glu Asn Ile Phe Arg Glu Gly Gln Tyr>
_____IL13Rα1_____>
```

Figure 42C

```
         470           480           490           500           510
  *       *     *       *     *       *     *       *     *       *
TTT GGT TGT TCC TTT GAT CTG ACC AAA GTG AAG GAT TCC AGT
AAA CCA ACA AGG AAA CTA GAC TGG TTT CAC TTC CTA AGG TCA
Phe Gly Cys Ser Phe Asp Leu Thr Lys Val Lys Asp Ser Ser>
                          _IL13Rα1_                       >

520           530           540           550
        *       *     *       *     *       *     *       *
TTT GAA CAA CAC AGT GTC CAA ATA ATG GTC AAG GAT AAT GCA
AAA CTT GTT GTG TCA CAG GTT TAT TAC CAG TTC CTA TTA CGT
Phe Glu Gln His Ser Val Gln Ile Met Val Lys Asp Asn Ala>
                          _IL13Rα1_                       >

560           570           580           590
  *     *     *     *       *     *       *     *       *
GGA AAA ATT AAA CCA TCC TTC AAT ATA GTG CCT TTA ACT TCC
CCT TTT TAA TTT GGT AGG AAG TTA TAT CAC GGA AAT TGA AGG
Gly Lys Ile Lys Pro Ser Phe Asn Ile Val Pro Leu Thr Ser>
                          _IL13Rα1_                       >

600           610           620           630
  *       *     *       *     *       *     *       *     *
CGT GTG AAA CCT GAT CCT CCA CAT ATT AAA AAC CTC TCC TTC
GCA CAC TTT GGA CTA GGA GGT GTA TAA TTT TTG GAG AGG AAG
Arg Val Lys Pro Asp Pro Pro His Ile Lys Asn Leu Ser Phe>
                          _IL13Rα1_                       >

640           650           660           670
  *       *     *       *     *       *     *       *
CAC AAT GAT GAC CTA TAT GTG CAA TGG GAG AAT CCA CAG AAT
GTG TTA CTA CTG GAT ATA CAC GTT ACC CTC TTA GGT GTC TTA
His Asn Asp Asp Leu Tyr Val Gln Trp Glu Asn Pro Gln Asn>
                          _IL13Rα1_                       >

680           690           700           710           720
  *     *       *     *       *     *       *     *       *
TTT ATT AGC AGA TGC CTA TTT TAT GAA GTA GAA GTC AAT AAC
AAA TAA TCG TCT ACG GAT AAA ATA CTT CAT CTT CAG TTA TTG
Phe Ile Ser Arg Cys Leu Phe Tyr Glu Val Glu Val Asn Asn>
                          _IL13Rα1_                       >

730           740           750           760
        *       *     *       *     *       *     *       *
AGC CAA ACT GAG ACA CAT AAT GTT TTC TAC GTC CAA GAG GCT
TCG GTT TGA CTC TGT GTA TTA CAA AAG ATG CAG GTT CTC CGA
Ser Gln Thr Glu Thr His Asn Val Phe Tyr Val Gln Glu Ala>
                          _IL13Rα1_                       >
```

Figure 42D

```
          770            780            790           800
    *      *      *      *      *      *      *      *
   AAA    TGT    GAG    AAT    CCA    GAA    TTT    GAG    AGA    AAT    GTG    GAG    AAT    ACA
   TTT    ACA    CTC    TTA    GGT    CTT    AAA    CTC    TCT    TTA    CAC    CTC    TTA    TGT
   Lys    Cys    Glu    Asn    Pro    Glu    Phe    Glu    Arg    Asn    Val    Glu    Asn    Thr>
   ─────────────────────────────────IL13Rα1──────────────────────────────────>

810            820            830           840
    *      *      *      *      *      *      *      *      *
   TCT    TGT    TTC    ATG    GTC    CCT    GGT    GTT    CTT    CCT    GAT    ACT    TTG    AAC
   AGA    ACA    AAG    TAC    CAG    GGA    CCA    CAA    GAA    GGA    CTA    TGA    AAC    TTG
   Ser    Cys    Phe    Met    Val    Pro    Gly    Val    Leu    Pro    Asp    Thr    Leu    Asn>
   ─────────────────────────────────IL13Rα1──────────────────────────────────>

850            860           870           880
    *      *      *      *      *      *      *      *
   ACA    GTC    AGA    ATA    AGA    GTC    AAA    ACA    AAT    AAG    TTA    TGC    TAT    GAG
   TGT    CAG    TCT    TAT    TCT    CAG    TTT    TGT    TTA    TTC    AAT    ACG    ATA    CTC
   Thr    Val    Arg    Ile    Arg    Val    Lys    Thr    Asn    Lys    Leu    Cys    Tyr    Glu>
   ─────────────────────────────────IL13Rα1──────────────────────────────────>

890            900            910            920            930
    *      *      *      *      *      *      *      *      *
   GAT    GAC    AAA    CTC    TGG    AGT    AAT    TGG    AGC    CAA    GAA    ATG    AGT    ATA
   CTA    CTG    TTT    GAG    ACC    TCA    TTA    ACC    TCG    GTT    CTT    TAC    TCA    TAT
   Asp    Asp    Lys    Leu    Trp    Ser    Asn    Trp    Ser    Gln    Glu    Met    Ser    Ile>
   ─────────────────────────────────IL13Rα1──────────────────────────────────>

940            950            960           970
          *      *      *      *      *      *      *      *
         GGT    AAG    AAG    CGC    AAT    TCC    ACA    GGG    AAC    ATG    AAG    GTC    TTG    CAG
         CCA    TTC    TTC    GCG    TTA    AGG    TGT    CCC    TTG    TAC    TTC    CAG    AAC    GTC
                                                   Gly    Asn    Met    Lys    Val    Leu    Gln>
                                                   ─────────────IL4Rα───────────────────>

Gly    Lys    Lys    Arg    Asn    Ser    Thr>
         ─────────IL13Rα1─────────>

980            990           1000           1010
          *      *      *      *      *      *      *      *
         GAG    CCC    ACC    TGC    GTC    TCC    GAC    TAC    ATG    AGC    ATC    TCT    ACT    TGC
         CTC    GGG    TGG    ACG    CAG    AGG    CTG    ATG    TAC    TCG    TAG    AGA    TGA    ACG
         Glu    Pro    Thr    Cys    Val    Ser    Asp    Tyr    Met    Ser    Ile    Ser    Thr    Cys>
         ─────────────────────────────IL4Rα──────────────────────────────>

1020           1030           1040          1050
          *      *      *      *      *      *      *      *      *
         GAG    TGG    AAG    ATG    AAT    GGT    CCC    ACC    AAT    TGC    AGC    ACC    GAG    CTC
         CTC    ACC    TTC    TAC    TTA    CCA    GGG    TGG    TTA    ACG    TCG    TGG    CTC    GAG
         Glu    Trp    Lys    Met    Asn    Gly    Pro    Thr    Asn    Cys    Ser    Thr    Glu    Leu>
         ─────────────────────────────IL4Rα──────────────────────────────>
```

Figure 42E

```
            1060           1070           1080           1090
              *              *              *              *       *
        CGC CTG TTG TAC CAG CTG GTT TTT CTG CTC TCC GAA GCC CAC
        GCG GAC AAC ATG GTC GAC CAA AAA GAC GAG AGG CTT CGG GTG
        Arg Leu Leu Tyr Gln Leu Val Phe Leu Leu Ser Glu Ala His>
        _____IL4Rα_____>

1100           1110           1120           1130           1140
  *              *    *         *    *         *    *         *    *
ACG TGT ATC CCT GAG AAC AAC GGA GGC GCG GGG TGC GTG TGC
TGC ACA TAG GGA CTC TTG TTG CCT CCG CGC CCC ACG CAC ACG
Thr Cys Ile Pro Glu Asn Asn Gly Gly Ala Gly Cys Val Cys>
_____IL4Rα_____>

1150           1160           1170           1180
          *    *    *         *    *    *         *    *         *
        CAC CTG CTC ATG GAT GAC GTG GTC AGT GCG GAT AAC TAT ACA
        GTG GAC GAG TAC CTA CTG CAC CAG TCA CGC CTA TTG ATA TGT
        His Leu Leu Met Asp Asp Val Val Ser Ala Asp Asn Tyr Thr>
        _____IL4Rα_____>

1190           1200           1210           1220
          *    *         *    *    *         *    *    *         *
        CTG GAC CTG TGG GCT GGG CAG CAG CTG CTG TGG AAG GGC TCC
        GAC CTG GAC ACC CGA CCC GTC GTC GAC GAC ACC TTC CCG AGG
        Leu Asp Leu Trp Ala Gly Gln Gln Leu Leu Trp Lys Gly Ser>
        _____IL4Rα_____>

1230           1240           1250           1260
          *    *         *    *    *         *    *    *         *
        TTC AAG CCC AGC GAG CAT GTG AAA CCC AGG GCC CCA GGA AAC
        AAG TTC GGG TCG CTC GTA CAC TTT GGG TCC CGG GGT CCT TTG
        Phe Lys Pro Ser Glu His Val Lys Pro Arg Ala Pro Gly Asn>
        _____IL4Rα_____>

1270           1280           1290           1300
          *    *         *    *    *         *    *    *         *
        CTG ACA GTT CAC ACC AAT GTC TCC GAC ACT CTG CTG CTG ACC
        GAC TGT CAA GTG TGG TTA CAG AGG CTG TGA GAC GAC GAC TGG
        Leu Thr Val His Thr Asn Val Ser Asp Thr Leu Leu Leu Thr>
        _____IL4Rα_____>

1310           1320           1330           1340           1350
      *    *    *         *    *    *         *    *    *         *    *
    TGG AGC AAC CCG TAT CCC CCT GAC AAT TAC CTG TAT AAT CAT
    ACC TCG TTG GGC ATA GGG GGA CTG TTA ATG GAC ATA TTA GTA
    Trp Ser Asn Pro Tyr Pro Pro Asp Asn Tyr Leu Tyr Asn His>
    _____IL4Rα_____>
```

Figure 42F

```
             1360          1370          1380          1390
        *     *     *     *     *     *     *     *
   CTC ACC TAT GCA GTC AAC ATT TGG AGT GAA AAC GAC CCG GCA
   GAG TGG ATA CGT CAG TTG TAA ACC TCA CTT TTG CTG GGC CGT
   Leu Thr Tyr Ala Val Asn Ile Trp Ser Glu Asn Asp Pro Ala>
   _____IL4Rα_____>

1400          1410          1420          1430
        *     *     *     *     *     *     *     *
   GAT TTC AGA ATC TAT AAC GTG ACC TAC CTA GAA CCC TCC CTC
   CTA AAG TCT TAG ATA TTG CAC TGG ATG GAT CTT GGG AGG GAG
   Asp Phe Arg Ile Tyr Asn Val Thr Tyr Leu Glu Pro Ser Leu>
   _____IL4Rα_____>

1440          1450          1460          1470
       *     *     *     *     *     *     *     *     *
   CGC ATC GCA GCC AGC ACC CTG AAG TCT GGG ATT TCC TAC AGG
   GCG TAG CGT CGG TCG TGG GAC TTC AGA CCC TAA AGG ATG TCC
   Arg Ile Ala Ala Ser Thr Leu Lys Ser Gly Ile Ser Tyr Arg>
   _____IL4Rα_____>

>Mutation Cysteine to Serine
             1480          1490          1500  |     1510
        *     *     *     *     *     *  |  *     *     *
   GCA CGC GTA CGG GCC TGG GCT CAG AGC TAT AAC ACC ACC TGG
   CGT GCG CAT GCC CGG ACC CGA GTC TCG ATA TTG TGG TGG ACC
   Ala Arg Val Arg Ala Trp Ala Gln Ser Tyr Asn Thr Thr Trp>
   _____IL4Rα_____>

1520          1530          1540          1550          1560
     *     *     *     *     *     *     *     *     *
   AGT GAG TGG AGC CCC AGC ACC AAG TGG CAC AAC TCC TAC AGG
   TCA CTC ACC TCG GGG TCG TGG TTC ACC GTG TTG AGG ATG TCC
   Ser Glu Trp Ser Pro Ser Thr Lys Trp His Asn Ser Tyr Arg>
   _____IL4Rα_____>

1570          1580          1590          1600
        *     *     *     *     *     *     *     *
   GAG CCC TTC GAG CAG TCC GGA GAC AAA ACT CAC ACA TGC CCA
   CTC GGG AAG CTC GTC AGG CCT CTG TTT TGA GTG TGT ACG GGT
   Glu Pro Phe Glu Gln>
   _____IL4Rα_____>
                          Ser Gly Asp Lys Thr His Thr Cys Pro>
                          _____FC-IgG1_____>

1610          1620          1630          1640
        *     *     *     *     *     *     *     *
   CCG TGC CCA GCA CCT GAA CTC CTG GGG GGA CCG TCA GTC TTC
   GGC ACG GGT CGT GGA CTT GAG GAC CCC CCT GGC AGT CAG AAG
   Pro Cys Pro Ala Pro Glu Leu Leu Gly Gly Pro Ser Val Phe>
   _____FC-IgG1_____>
```

Figure 42G

```
         1650        1660        1670        1680
          *     *     *     *     *     *     *     *     *
         CTC   TTC   CCC   CCA   AAA   CCC   AAG   GAC   ACC   CTC   ATG   ATC   TCC   CGG
         GAG   AAG   GGG   GGT   TTT   GGG   TTC   CTG   TGG   GAG   TAC   TAG   AGG   GCC
         Leu   Phe   Pro   Pro   Lys   Pro   Lys   Asp   Thr   Leu   Met   Ile   Ser   Arg>
                                       ___FC-IgG1_____>

1690        1700        1710        1720
          *     *     *     *     *     *     *     *
         ACC   CCT   GAG   GTC   ACA   TGC   GTG   GTG   GTG   GAC   GTG   AGC   CAC   GAA
         TGG   GGA   CTC   CAG   TGT   ACG   CAC   CAC   CAC   CTG   CAC   TCG   GTG   CTT
         Thr   Pro   Glu   Val   Thr   Cys   Val   Val   Val   Asp   Val   Ser   His   Glu>
                                       ___FC-IgG1_____>

1730        1740        1750        1760        1770
   *     *     *     *     *     *     *     *     *
  GAC   CCT   GAG   GTC   AAG   TTC   AAC   TGG   TAC   GTG   GAC   GGC   GTG   GAG
  CTG   GGA   CTC   CAG   TTC   AAG   TTG   ACC   ATG   CAC   CTG   CCG   CAC   CTC
  Asp   Pro   Glu   Val   Lys   Phe   Asn   Trp   Tyr   Val   Asp   Gly   Val   Glu>
                                ___FC-IgG1_____>

1780        1790        1800        1810
                *     *     *     *     *     *     *     *
               GTG   CAT   AAT   GCC   AAG   ACA   AAG   CCG   CGG   GAG   GAG   CAG   TAC   AAC
               CAC   GTA   TTA   CGG   TTC   TGT   TTC   GGC   GCC   CTC   CTC   GTC   ATG   TTG
               Val   His   Asn   Ala   Lys   Thr   Lys   Pro   Arg   Glu   Glu   Gln   Tyr   Asn>
                                             ___FC-IgG1_____>

1820        1830        1840        1850
                *     *     *     *     *     *     *     *
               AGC   ACG   TAC   CGT   GTG   GTC   AGC   GTC   CTC   ACC   GTC   CTG   CAC   CAG
               TCG   TGC   ATG   GCA   CAC   CAG   TCG   CAG   GAG   TGG   CAG   GAC   GTG   GTC
               Ser   Thr   Tyr   Arg   Val   Val   Ser   Val   Leu   Thr   Val   Leu   His   Gln>
                                             ___FC-IgG1_____>

1860        1870        1880        1890
               *     *     *     *     *     *     *     *     *
              GAC   TGG   CTG   AAT   GGC   AAG   GAG   TAC   AAG   TGC   AAG   GTC   TCC   AAC
              CTG   ACC   GAC   TTA   CCG   TTC   CTC   ATG   TTC   ACG   TTC   CAG   AGG   TTG
              Asp   Trp   Leu   Asn   Gly   Lys   Glu   Tyr   Lys   Cys   Lys   Val   Ser   Asn>
                                            ___FC-IgG1_____>

1900        1910        1920        1930
         *     *     *     *     *     *     *     *
        AAA   GCC   CTC   CCA   GCC   CCC   ATC   GAG   AAA   ACC   ATC   TCC   AAA   GCC
        TTT   CGG   GAG   GGT   CGG   GGG   TAG   CTC   TTT   TGG   TAG   AGG   TTT   CGG
        Lys   Ala   Leu   Pro   Ala   Pro   Ile   Glu   Lys   Thr   Ile   Ser   Lys   Ala>
                                      ___FC-IgG1_____>
```

Figure 42H

```
      1940          1950          1960          1970          1980
        *        *     *        *     *     *     *     *     *
      AAA  GGG  CAG  CCC  CGA  GAA  CCA  CAG  GTG  TAC  ACC  CTG  CCC  CCA
      TTT  CCC  GTC  GGG  GCT  CTT  GGT  GTC  CAC  ATG  TGG  GAC  GGG  GGT
      Lys  Gly  Gln  Pro  Arg  Glu  Pro  Gln  Val  Tyr  Thr  Leu  Pro  Pro>
      _____FC-IgG1_____>

1990          2000          2010          2020
              *     *     *     *     *     *     *     *
            TCC  CGG  GAT  GAG  CTG  ACC  AAG  AAC  CAG  GTC  AGC  CTG  ACC  TGC
            AGG  GCC  CTA  CTC  GAC  TGG  TTC  TTG  GTC  CAG  TCG  GAC  TGG  ACG
            Ser  Arg  Asp  Glu  Leu  Thr  Lys  Asn  Gln  Val  Ser  Leu  Thr  Cys>
            _____FC-IgG1_____>

2030          2040          2050          2060
        *     *     *     *     *     *     *     *
      CTG  GTC  AAA  GGC  TTC  TAT  CCC  AGC  GAC  ATC  GCC  GTG  GAG  TGG
      GAC  CAG  TTT  CCG  AAG  ATA  GGG  TCG  CTG  TAG  CGG  CAC  CTC  ACC
      Leu  Val  Lys  Gly  Phe  Tyr  Pro  Ser  Asp  Ile  Ala  Val  Glu  Trp>
      _____FC-IgG1_____>

2070          2080          2090          2100
        *     *     *     *     *     *     *     *     *
      GAG  AGC  AAT  GGG  CAG  CCG  GAG  AAC  AAC  TAC  AAG  ACC  ACG  CCT
      CTC  TCG  TTA  CCC  GTC  GGC  CTC  TTG  TTG  ATG  TTC  TGG  TGC  GGA
      Glu  Ser  Asn  Gly  Gln  Pro  Glu  Asn  Asn  Tyr  Lys  Thr  Thr  Pro>
      _____FC-IgG1_____>

2110          2120          2130          2140
        *     *     *     *     *     *     *     *
      CCC  GTG  CTG  GAC  TCC  GAC  GGC  TCC  TTC  TTC  CTC  TAC  AGC  AAG
      GGG  CAC  GAC  CTG  AGG  CTG  CCG  AGG  AAG  AAG  GAG  ATG  TCG  TTC
      Pro  Val  Leu  Asp  Ser  Asp  Gly  Ser  Phe  Phe  Leu  Tyr  Ser  Lys>
      _____FC-IgG1_____>

2150          2160          2170          2180          2190
      *     *     *     *     *     *     *     *     *
    CTC  ACC  GTG  GAC  AAG  AGC  AGG  TGG  CAG  CAG  GGG  AAC  GTC  TTC
    GAG  TGG  CAC  CTG  TTC  TCG  TCC  ACC  GTC  GTC  CCC  TTG  CAG  AAG
    Leu  Thr  Val  Asp  Lys  Ser  Arg  Trp  Gln  Gln  Gly  Asn  Val  Phe>
    _____FC-IgG1_____>

2200          2210          2220          2230
        *     *     *     *     *     *     *     *
      TCA  TGC  TCC  GTG  ATG  CAT  GAG  GCT  CTG  CAC  AAC  CAC  TAC  ACG
      AGT  ACG  AGG  CAC  TAC  GTA  CTC  CGA  GAC  GTG  TTG  GTG  ATG  TGC
      Ser  Cys  Ser  Val  Met  His  Glu  Ala  Leu  His  Asn  His  Tyr  Thr>
      _____FC-IgG1_____>
```

Figure 42I

```
          2240              2250                2260
  *         *         *        *          *         *        *
CAG       AAG       AGC      CTC        TCC       CTG      TCT   CCG   GGT   AAA   TGA
GTC       TTC       TCG      GAG        AGG       GAC      AGA   GGC   CCA   TTT   ACT
Gln       Lys       Ser      Leu        Ser       Leu      Ser   Pro   Gly   Lys   ***>
_____FC-IgG1_____>
```

Figure 43A

```
        -60            -50            -40            -30
          *       *      *       *      *       *      *       *
ATG GTG TGG CTT TGC TCT GGG CTC CTG TTC CCT GTG AGC TGC CTG GTC
TAC CAC ACC GAA ACG AGA CCC GAG GAC AAG GGA CAC TCG ACG GAC CAG
Met Val Trp Leu Cys Ser Gly Leu Leu Phe Pro Val Ser Cys Leu Val>
_____SIGNAL PEPTIDE_____>

-20            -10             1             10            20
    *       *      *       *      *       *      *       *      *
CTG CTG CAG GTG GCA AGC TCT GGG AAC ATG AAG GTC TTG CAG GAG CCC
GAC GAC GTC CAC CGT TCG AGA CCC TTG TAC TTC CAG AAC GTC CTC GGG
                            Gly Asn Met Lys Val Leu Gln Glu Pro>
                                        _____IL4Rα_____>
Leu Leu Gln Val Ala Ser Ser>
_____SIGNAL PEPTIDE_____>

30             40             50             60             70
    *       *      *       *      *       *      *       *      *
ACC TGC GTC TCC GAC TAC ATG AGC ATC TCT ACT TGC GAG TGG AAG ATG
TGG ACG CAG AGG CTG ATG TAC TCG TAG AGA TGA ACG CTC ACC TTC TAC
Thr Cys Val Ser Asp Tyr Met Ser Ile Ser Thr Cys Glu Trp Lys Met>
_____IL4Rα_____>

80             90            100            110            120
    *       *      *       *      *       *      *       *      *
AAT GGT CCC ACC AAT TGC AGC ACC GAG CTC CGC CTG TTG TAC CAG CTG
TTA CCA GGG TGG TTA ACG TCG TGG CTC GAG GCG GAC AAC ATG GTC GAC
Asn Gly Pro Thr Asn Cys Ser Thr Glu Leu Arg Leu Leu Tyr Gln Leu>
_____IL4Rα_____>

130            140            150            160            170
    *       *      *       *      *       *      *       *      *
GTT TTT CTG CTC TCC GAA GCC CAC ACG TGT ATC CCT GAG AAC AAC GGA
CAA AAA GAC GAG AGG CTT CGG GTG TGC ACA TAG GGA CTC TTG TTG CCT
Val Phe Leu Leu Ser Glu Ala His Thr Cys Ile Pro Glu Asn Asn Gly>
_____IL4Rα_____>

180            190            200            210
    *       *      *       *      *       *      *       *
GGC GCG GGG TGC GTG TGC CAC CTG CTC ATG GAT GAC GTG GTC AGT GCG
CCG CGC CCC ACG CAC ACG GTG GAC GAG TAC CTA CTG CAC CAG TCA CGC
Gly Ala Gly Cys Val Cys His Leu Leu Met Asp Asp Val Val Ser Ala>
_____IL4Rα_____>

220            230            240            250            260
  *       *      *       *      *       *      *       *      *
GAT AAC TAT ACA CTG GAC CTG TGG GCT GGG CAG CAG CTG CTG TGG AAG
CTA TTG ATA TGT GAC CTG GAC ACC CGA CCC GTC GTC GAC GAC ACC TTC
Asp Asn Tyr Thr Leu Asp Leu Trp Ala Gly Gln Gln Leu Leu Trp Lys>
_____IL4Rα_____>
```

Figure 43B

```
         270              280              290              300              310
          *        *       *        *       *        *       *        *       *        *
        GGC TCC  TTC AAG  CCC AGC  GAG CAT  GTG AAA  CCC AGG  GCC CCA  GGA AAC
        CCG AGG  AAG TTC  GGG TCG  CTC GTA  CAC TTT  GGG TCC  CGG GGT  CCT TTG
        Gly Ser  Phe Lys  Pro Ser  Glu His  Val Lys  Pro Arg  Ala Pro  Gly Asn>
        ─────────────────────────────────IL4Rα─────────────────────────────────>

320              330              340              350              360
          *        *       *        *       *        *       *        *       *
        CTG ACA  GTT CAC  ACC AAT  GTC TCC  GAC ACT  CTG CTG  CTG ACC  TGG AGC
        GAC TGT  CAA GTG  TGG TTA  CAG AGG  CTG TGA  GAC GAC  GAC TGG  ACC TCG
        Leu Thr  Val His  Thr Asn  Val Ser  Asp Thr  Leu Leu  Leu Thr  Trp Ser>
        ─────────────────────────────────IL4Rα─────────────────────────────────>

370              380              390              400              410
          *        *       *        *       *        *       *        *       *        *
        AAC CCG  TAT CCC  CCT GAC  AAT TAC  CTG TAT  AAT CAT  CTC ACC  TAT GCA
        TTG GGC  ATA GGG  GGA CTG  TTA ATG  GAC ATA  TTA GTA  GAG TGG  ATA CGT
        Asn Pro  Tyr Pro  Pro Asp  Asn Tyr  Leu Tyr  Asn His  Leu Thr  Tyr Ala>
        ─────────────────────────────────IL4Rα─────────────────────────────────>

420              430              440              450
           *       *        *       *        *       *        *       *       *
        GTC AAC  ATT TGG  AGT GAA  AAC GAC  CCG GCA  GAT TTC  AGA ATC  TAT AAC
        CAG TTG  TAA ACC  TCA CTT  TTG CTG  GGC CGT  CTA AAG  TCT TAG  ATA TTG
        Val Asn  Ile Trp  Ser Glu  Asn Asp  Pro Ala  Asp Phe  Arg Ile  Tyr Asn>
        ─────────────────────────────────IL4Rα─────────────────────────────────>

460              470              480              490              500
          *        *       *        *       *        *       *        *       *        *
        GTG ACC  TAC CTA  GAA CCC  TCC CTC  CGC ATC  GCA GCC  AGC ACC  CTG AAG
        CAC TGG  ATG GAT  CTT GGG  AGG GAG  GCG TAG  CGT CGG  TCG TGG  GAC TTC
        Val Thr  Tyr Leu  Glu Pro  Ser Leu  Arg Ile  Ala Ala  Ser Thr  Leu Lys>
        ─────────────────────────────────IL4Rα─────────────────────────────────>

Mutation Cysteine to Serine
                                                                |
         510              520              530              540              550
          *        *       *        *       *        *       *        *       *        *
        TCT GGG  ATT TCC  TAC AGG  GCA CGC  GTA CGG  GCC TGG  GCT CAG  AGC TAT
        AGA CCC  TAA AGG  ATG TCC  CGT GCG  CAT GCC  CGG ACC  CGA GTC  TCG ATA
        Ser Gly  Ile Ser  Tyr Arg  Ala Arg  Val Arg  Ala Trp  Ala Gln  Ser Tyr>
        ─────────────────────────────────IL4Rα─────────────────────────────────>

560              570              580              590              600
          *        *       *        *       *        *       *        *       *
        AAC ACC  ACC TGG  AGT GAG  TGG AGC  CCC AGC  ACC AAG  TGG CAC  AAC TCC
        TTG TGG  TGG ACC  TCA CTC  ACC TCG  GGG TCG  TGG TTC  ACC GTG  TTG AGG
        Asn Thr  Thr Trp  Ser Glu  Trp Ser  Pro Ser  Thr Lys  Trp His  Asn Ser>
        ─────────────────────────────────IL4Rα─────────────────────────────────>
```

Figure 43C

```
            610           620           630           640           650
       *     *     *     *     *     *     *     *     *     *
      TAC   AGG   GAG   CCC   TTC   GAG   CAG   GCG   CCT   ACG   GAA   ACT   CAG   CCA   CCT   GTG
      ATG   TCC   CTC   GGG   AAG   CTC   GTC   CGC   GGA   TGC   CTT   TGA   GTC   GGT   GGA   CAC
      Tyr   Arg   Glu   Pro   Phe   Glu   Gln>
            _____IL4Rα_____>
                                          Ala   Pro   Thr   Glu   Thr   Gln   Pro   Pro   Val>
                                                      _____IL13Rα1_____>

Mutation Cysteine to Alanine
                                             |
            660           670           680 |         690
       *     *     *     *     *     *     *|*     *     *
      ACA   AAT   TTG   AGT   GTC   TCT   GTT   GAA   AAC   CTC   GCG   ACA   GTA   ATA   TGG   ACA
      TGT   TTA   AAC   TCA   CAG   AGA   CAA   CTT   TTG   GAG   CGC   TGT   CAT   TAT   ACC   TGT
      Thr   Asn   Leu   Ser   Val   Ser   Val   Glu   Asn   Leu   Ala   Thr   Val   Ile   Trp   Thr>
                                  _____IL13Rα1_____                                         >

700           710           720           730           740
  *     *     *     *     *     *     *     *     *     *
 TGG   AAT   CCA   CCC   GAG   GGA   GCC   AGC   TCA   AAT   TGT   AGT   CTA   TGG   TAT   TTT
 ACC   TTA   GGT   GGG   CTC   CCT   CGG   TCG   AGT   TTA   ACA   TCA   GAT   ACC   ATA   AAA
 Trp   Asn   Pro   Pro   Glu   Gly   Ala   Ser   Ser   Asn   Cys   Ser   Leu   Trp   Tyr   Phe>
              _____IL13Rα1_____                                         >

750           760           770           780           790
       *     *     *     *     *     *     *     *     *     *
      AGT   CAT   TTT   GGC   GAC   AAA   CAA   GAT   AAG   AAA   ATA   GCT   CCG   GAA   ACT   CGT
      TCA   GTA   AAA   CCG   CTG   TTT   GTT   CTA   TTC   TTT   TAT   CGA   GGC   CTT   TGA   GCA
      Ser   His   Phe   Gly   Asp   Lys   Gln   Asp   Lys   Lys   Ile   Ala   Pro   Glu   Thr   Arg>
                                  _____IL13Rα1_____                                         >

800           810           820           830           840
        *     *     *     *     *     *     *     *     *
       CGT   TCA   ATA   GAA   GTA   CCC   CTG   AAT   GAG   AGG   ATT   TGT   CTG   CAA   GTG   GGG
       GCA   AGT   TAT   CTT   CAT   GGG   GAC   TTA   CTC   TCC   TAA   ACA   GAC   GTT   CAC   CCC
       Arg   Ser   Ile   Glu   Val   Pro   Leu   Asn   Glu   Arg   Ile   Cys   Leu   Gln   Val   Gly>
             _____IL13Rα1_____                                         >

850           860           870           880           890
       *     *     *     *     *     *     *     *     *     *
      TCC   CAG   TGT   AGC   ACC   AAT   GAG   AGT   GAG   AAG   CCT   AGC   ATT   TTG   GTT   GAA
      AGG   GTC   ACA   TCG   TGG   TTA   CTC   TCA   CTC   TTC   GGA   TCG   TAA   AAC   CAA   CTT
      Ser   Gln   Cys   Ser   Thr   Asn   Glu   Ser   Glu   Lys   Pro   Ser   Ile   Leu   Val   Glu>
                              _____IL13Rα1_____                       >

900           910           920           930
             *     *     *     *     *     *     *     *     *
            AAA   TGC   ATC   TCA   CCC   CCA   GAA   GGT   GAT   CCT   GAG   TCT   GCT   GTG   ACT   GAG
            TTT   ACG   TAG   AGT   GGG   GGT   CTT   CCA   CTA   GGA   CTC   AGA   CGA   CAC   TGA   CTC
            Lys   Cys   Ile   Ser   Pro   Pro   Glu   Gly   Asp   Pro   Glu   Ser   Ala   Val   Thr   Glu>
                              _____IL13Rα1_____                       >
```

Figure 43D

```
       940           950           960           970           980
  *     *     *     *     *     *     *     *     *     *
  CTT CAA TGC ATT TGG CAC AAC CTG AGC TAC ATG AAG TGT TCT TGG CTC
  GAA GTT ACG TAA ACC GTG TTG GAC TCG ATG TAC TTC ACA AGA ACC GAG
  Leu Gln Cys Ile Trp His Asn Leu Ser Tyr Met Lys Cys Ser Trp Leu>
  _____IL13Rα1_____>

990          1000          1010          1020          1030
  *     *     *     *     *     *     *     *     *     *
  CCT GGA AGG AAT ACC AGT CCC GAC ACT AAC TAT ACT CTC TAC TAT TGG
  GGA CCT TCC TTA TGG TCA GGG CTG TGA TTG ATA TGA GAG ATG ATA ACC
  Pro Gly Arg Asn Thr Ser Pro Asp Thr Asn Tyr Thr Leu Tyr Tyr Trp>
  _____IL13Rα1_____>

1040          1050          1060          1070          1080
  *     *     *     *     *     *     *     *     *
  CAC AGA AGC CTG GAA AAA ATT CAT CAA TGT GAA AAC ATC TTT AGA GAA
  GTG TCT TCG GAC CTT TTT TAA GTA GTT ACA CTT TTG TAG AAA TCT CTT
  His Arg Ser Leu Glu Lys Ile His Gln Cys Glu Asn Ile Phe Arg Glu>
  _____IL13Rα1_____>

1090          1100          1110          1120          1130
  *     *     *     *     *     *     *     *     *     *
  GGC CAA TAC TTT GGT TGT TCC TTT GAT CTG ACC AAA GTG AAG GAT TCC
  CCG GTT ATG AAA CCA ACA AGG AAA CTA GAC TGG TTT CAC TTC CTA AGG
  Gly Gln Tyr Phe Gly Cys Ser Phe Asp Leu Thr Lys Val Lys Asp Ser>
  _____IL13Rα1_____>

1140          1150          1160          1170
  *     *     *     *     *     *     *     *     *
  AGT TTT GAA CAA CAC AGT GTC CAA ATA ATG GTC AAG GAT AAT GCA GGA
  TCA AAA CTT GTT GTG TCA CAG GTT TAT TAC CAG TTC CTA TTA CGT CCT
  Ser Phe Glu Gln His Ser Val Gln Ile Met Val Lys Asp Asn Ala Gly>
  _____IL13Rα1_____>

1180          1190          1200          1210          1220
  *     *     *     *     *     *     *     *     *     *
  AAA ATT AAA CCA TCC TTC AAT ATA GTG CCT TTA ACT TCC CGT GTG AAA
  TTT TAA TTT GGT AGG AAG TTA TAT CAC GGA AAT TGA AGG GCA CAC TTT
  Lys Ile Lys Pro Ser Phe Asn Ile Val Pro Leu Thr Ser Arg Val Lys>
  _____IL13Rα1_____>

1230          1240          1250          1260          1270
  *     *     *     *     *     *     *     *     *     *
  CCT GAT CCT CCA CAT ATT AAA AAC CTC TCC TTC CAC AAT GAT GAC CTA
  GGA CTA GGA GGT GTA TAA TTT TTG GAG AGG AAG GTG TTA CTA CTG GAT
  Pro Asp Pro Pro His Ile Lys Asn Leu Ser Phe His Asn Asp Asp Leu>
  _____IL13Rα1_____>
```

Figure 43E

```
          1280                1290                1300                1310                1320
           *         *         *         *         *         *         *         *         *
      TAT GTG CAA TGG GAG AAT CCA CAG AAT TTT ATT AGC AGA TGC CTA TTT
      ATA CAC GTT ACC CTC TTA GGT GTC TTA AAA TAA TCG TCT ACG GAT AAA
      Tyr Val Gln Trp Glu Asn Pro Gln Asn Phe Ile Ser Arg Cys Leu Phe>
      _____IL13Rα1_____>

1330                1340                1350                1360                1370
           *         *         *         *         *         *         *         *         *         *
      TAT GAA GTA GAA GTC AAT AAC AGC CAA ACT GAG ACA CAT AAT GTT TTC
      ATA CTT CAT CTT CAG TTA TTG TCG GTT TGA CTC TGT GTA TTA CAA AAG
      Tyr Glu Val Glu Val Asn Asn Ser Gln Thr Glu Thr His Asn Val Phe>
      _____IL13Rα1_____>

1380                1390                1400                1410
                  *         *         *         *         *         *         *         *         *
             TAC GTC CAA GAG GCT AAA TGT GAG AAT CCA GAA TTT GAG AGA AAT GTG
             ATG CAG GTT CTC CGA TTT ACA CTC TTA GGT CTT AAA CTC TCT TTA CAC
             Tyr Val Gln Glu Ala Lys Cys Glu Asn Pro Glu Phe Glu Arg Asn Val>
             _____IL13Rα1_____>

1420                1430                1440                1450                1460
    *         *         *         *         *         *         *         *         *         *
GAG AAT ACA TCT TGT TTC ATG GTC CCT GGT GTT CTT CCT GAT ACT TTG
CTC TTA TGT AGA ACA AAG TAC CAG GGA CCA CAA GAA GGA CTA TGA AAC
Glu Asn Thr Ser Cys Phe Met Val Pro Gly Val Leu Pro Asp Thr Leu>
_____IL13Rα1_____>

1470                1480                1490                1500                1510
       *         *         *         *         *         *         *         *         *         *
   AAC ACA GTC AGA ATA AGA GTC AAA ACA AAT AAG TTA TGC TAT GAG GAT
   TTG TGT CAG TCT TAT TCT CAG TTT TGT TTA TTC AAT ACG ATA CTC CTA
   Asn Thr Val Arg Ile Arg Val Lys Thr Asn Lys Leu Cys Tyr Glu Asp>
   _____IL13Rα1_____>

1520                1530                1540                1550                1560
           *         *         *         *         *         *         *         *         *
      GAC AAA CTC TGG AGT AAT TGG AGC CAA GAA ATG AGT ATA GGT AAG AAG
      CTG TTT GAG ACC TCA TTA ACC TCG GTT CTT TAC TCA TAT CCA TTC TTC
      Asp Lys Leu Trp Ser Asn Trp Ser Gln Glu Met Ser Ile Gly Lys Lys>
      _____IL13Rα1_____>

1570                1580                1590                1600                1610
              *         *         *         *         *         *         *         *         *         *
         CGC AAT TCC ACC GGT GAC AAA ACT CAC ACA TGC CCA CCG TGC CCA GCA
         GCG TTA AGG TGG CCA CTG TTT TGA GTG TGT ACG GGT GGC ACG GGT CGT
                         Gly Asp Lys Thr His Thr Cys Pro Pro Cys Pro Ala>
                         _____FC-IgG1_____>
      Arg Asn Ser Thr>
      ____IL13Rα1____>
```

Figure 43F

```
             1620          1630          1640          1650
    *    *    *    *    *    *    *    *    *
    CCT  GAA  CTC  CTG  GGG  GGA  CCG  TCA  GTC  TTC  CTC  TTC  CCC  CCA  AAA  CCC
    GGA  CTT  GAG  GAC  CCC  CCT  GGC  AGT  CAG  AAG  GAG  AAG  GGG  GGT  TTT  GGG
    Pro  Glu  Leu  Leu  Gly  Gly  Pro  Ser  Val  Phe  Leu  Phe  Pro  Pro  Lys  Pro>
                             _____FC-IgG1_____>

1660          1670          1680          1690          1700
    *    *    *    *    *    *    *    *    *    *
    AAG  GAC  ACC  CTC  ATG  ATC  TCC  CGG  ACC  CCT  GAG  GTC  ACA  TGC  GTG  GTG
    TTC  CTG  TGG  GAG  TAC  TAG  AGG  GCC  TGG  GGA  CTC  CAG  TGT  ACG  CAC  CAC
    Lys  Asp  Thr  Leu  Met  Ile  Ser  Arg  Thr  Pro  Glu  Val  Thr  Cys  Val  Val>
                             _____FC-IgG1_____>

1710          1720          1730          1740          1750
    *    *    *    *    *    *    *    *    *    *
    GTG  GAC  GTG  AGC  CAC  GAA  GAC  CCT  GAG  GTC  AAG  TTC  AAC  TGG  TAC  GTG
    CAC  CTG  CAC  TCG  GTG  CTT  CTG  GGA  CTC  CAG  TTC  AAG  TTG  ACC  ATG  CAC
    Val  Asp  Val  Ser  His  Glu  Asp  Pro  Glu  Val  Lys  Phe  Asn  Trp  Tyr  Val>
                             _____FC-IgG1_____>

1760          1770          1780          1790          1800
    *    *    *    *    *    *    *    *    *
    GAC  GGC  GTG  GAG  GTG  CAT  AAT  GCC  AAG  ACA  AAG  CCG  CGG  GAG  GAG  CAG
    CTG  CCG  CAC  CTC  CAC  GTA  TTA  CGG  TTC  TGT  TTC  GGC  GCC  CTC  CTC  GTC
    Asp  Gly  Val  Glu  Val  His  Asn  Ala  Lys  Thr  Lys  Pro  Arg  Glu  Glu  Gln>
                             _____FC-IgG1_____>

1810          1820          1830          1840          1850
    *    *    *    *    *    *    *    *    *    *
    TAC  AAC  AGC  ACG  TAC  CGT  GTG  GTC  AGC  GTC  CTC  ACC  GTC  CTG  CAC  CAG
    ATG  TTG  TCG  TGC  ATG  GCA  CAC  CAG  TCG  CAG  GAG  TGG  CAG  GAC  GTG  GTC
    Tyr  Asn  Ser  Thr  Tyr  Arg  Val  Val  Ser  Val  Leu  Thr  Val  Leu  His  Gln>
                             _____FC-IgG1_____>

1860          1870          1880          1890
    *    *    *    *    *    *    *    *    *
    GAC  TGG  CTG  AAT  GGC  AAG  GAG  TAC  AAG  TGC  AAG  GTC  TCC  AAC  AAA  GCC
    CTG  ACC  GAC  TTA  CCG  TTC  CTC  ATG  TTC  ACG  TTC  CAG  AGG  TTG  TTT  CGG
    Asp  Trp  Leu  Asn  Gly  Lys  Glu  Tyr  Lys  Cys  Lys  Val  Ser  Asn  Lys  Ala>
                             _____FC-IgG1_____>

1900          1910          1920          1930          1940
    *    *    *    *    *    *    *    *    *    *
    CTC  CCA  GCC  CCC  ATC  GAG  AAA  ACC  ATC  TCC  AAA  GCC  AAA  GGG  CAG  CCC
    GAG  GGT  CGG  GGG  TAG  CTC  TTT  TGG  TAG  AGG  TTT  CGG  TTT  CCC  GTC  GGG
    Leu  Pro  Ala  Pro  Ile  Glu  Lys  Thr  Ile  Ser  Lys  Ala  Lys  Gly  Gln  Pro>
                             _____FC-IgG1_____>
```

Figure 43G

```
      1950          1960          1970          1980          1990
       *       *     *       *     *       *     *       *     *       *
    CGA GAA CCA CAG GTG TAC ACC CTG CCC CCA TCC CGG GAT GAG CTG ACC
    GCT CTT GGT GTC CAC ATG TGG GAC GGG GGT AGG GCC CTA CTC GAC TGG
    Arg Glu Pro Gln Val Tyr Thr Leu Pro Pro Ser Arg Asp Glu Leu Thr>
    _____FC-IgG1_____>

2000          2010          2020          2030          2040
          *     *       *     *       *     *       *     *       *
    AAG AAC CAG GTC AGC CTG ACC TGC CTG GTC AAA GGC TTC TAT CCC AGC
    TTC TTG GTC CAG TCG GAC TGG ACG GAC CAG TTT CCG AAG ATA GGG TCG
    Lys Asn Gln Val Ser Leu Thr Cys Leu Val Lys Gly Phe Tyr Pro Ser>
    _____FC-IgG1_____>

2050          2060          2070          2080          2090
       *     *       *     *       *     *       *     *       *     *
    GAC ATC GCC GTG GAG TGG GAG AGC AAT GGG CAG CCG GAG AAC AAC TAC
    CTG TAG CGG CAC CTC ACC CTC TCG TTA CCC GTC GGC CTC TTG TTG ATG
    Asp Ile Ala Val Glu Trp Glu Ser Asn Gly Gln Pro Glu Asn Asn Tyr>
    _____FC-IgG1_____>

2100          2110          2120          2130
       *     *       *     *       *     *       *     *       *
    AAG ACC ACG CCT CCC GTG CTG GAC TCC GAC GGC TCC TTC TTC CTC TAC
    TTC TGG TGC GGA GGG CAC GAC CTG AGG CTG CCG AGG AAG AAG GAG ATG
    Lys Thr Thr Pro Pro Val Leu Asp Ser Asp Gly Ser Phe Phe Leu Tyr>
    _____FC-IgG1_____>

2140          2150          2160          2170          2180
     *       *     *       *     *       *     *       *     *       *
    AGC AAG CTC ACC GTG GAC AAG AGC AGG TGG CAG CAG GGG AAC GTC TTC
    TCG TTC GAG TGG CAC CTG TTC TCG TCC ACC GTC GTC CCC TTG CAG AAG
    Ser Lys Leu Thr Val Asp Lys Ser Arg Trp Gln Gln Gly Asn Val Phe>
    _____FC-IgG1_____>

2190          2200          2210          2220          2230
     *       *     *       *     *       *     *       *     *       *
    TCA TGC TCC GTG ATG CAT GAG GCT CTG CAC AAC CAC TAC ACG CAG AAG
    AGT ACG AGG CAC TAC GTA CTC CGA GAC GTG TTG GTG ATG TGC GTC TTC
    Ser Cys Ser Val Met His Glu Ala Leu His Asn His Tyr Thr Gln Lys>
    _____FC-IgG1_____>

2240          2250          2260
       *     *       *     *       *
    AGC CTC TCC CTG TCT CCG GGT AAA TGA
    TCG GAG AGG GAC AGA GGC CCA TTT ACT
    Ser Leu Ser Leu Ser Pro Gly Lys ***>
    _____FC-IgG1_____>
```

Figure 44A

```
           -60              -50              -40              -30
            *        *       *        *       *        *       *        *
       ATG GTG TGG CTT TGC TCT GGG CTC CTG TTC CCT GTG AGC TGC
       TAC CAC ACC GAA ACG AGA CCC GAG GAC AAG GGA CAC TCG ACG
       Met Val Trp Leu Cys Ser Gly Leu Leu Phe Pro Val Ser Cys>
       _____SIGNAL PEPTIDE_____>
       _____IL4Rα_____

-20              -10               1               10
            *        *       *        *       *        *       *        *
       CTG GTC CTG CTG CAG GTG GCA AGC TCT GGG AAC ATG AAG GTC
       GAC CAG GAC GAC GTC CAC CGT TCG AGA CCC TTG TAC TTC CAG
       Leu Val Leu Leu Gln Val Ala Ser Ser Gly Asn Met Lys Val>
       _____SIGNAL PEPTIDE_____>
       _____IL4Rα_____>

20               30               40              50
             *        *       *        *       *        *       *        *
       TTG CAG GAG CCC ACC TGC GTC TCC GAC TAC ATG AGC ATC TCT
       AAC GTC CTC GGG TGG ACG CAG AGG CTG ATG TAC TCG TAG AGA
       Leu Gln Glu Pro Thr Cys Val Ser Asp Tyr Met Ser Ile Ser>
       _____IL4Rα_____>

60               70               80              90
             *        *       *        *       *        *       *
       ACT TGC GAG TGG AAG ATG AAT GGT CCC ACC AAT TGC AGC ACC
       TGA ACG CTC ACC TTC TAC TTA CCA GGG TGG TTA ACG TCG TGG
       Thr Cys Glu Trp Lys Met Asn Gly Pro Thr Asn Cys Ser Thr>
       _____IL4Rα_____>

100              110              120              130              140
        *        *       *        *       *        *       *        *       *
       GAG CTC CGC CTG TTG TAC CAG CTG GTT TTT CTG CTC TCC GAA
       CTC GAG GCG GAC AAC ATG GTC GAC CAA AAA GAC GAG AGG CTT
       Glu Leu Arg Leu Leu Tyr Gln Leu Val Phe Leu Leu Ser Glu>
       _____IL4Rα_____>

150              160              170              180
                  *        *       *        *       *        *       *        *
       GCC CAC ACG TGT ATC CCT GAG AAC AAC GGA GGC GCG GGG TGC
       CGG GTG TGC ACA TAG GGA CTC TTG TTG CCT CCG CGC CCC ACG
       Ala His Thr Cys Ile Pro Glu Asn Asn Gly Gly Ala Gly Cys>
       _____IL4Rα_____>

190              200              210              220
                  *        *       *        *       *        *       *        *
       GTG TGC CAC CTG CTC ATG GAT GAC GTG GTC AGT GCG GAT AAC
       CAC ACG GTG GAC GAG TAC CTA CTG CAC CAG TCA CGC CTA TTG
       Val Cys His Leu Leu Met Asp Asp Val Val Ser Ala Asp Asn>
       _____IL4Rα_____>
```

Figure 44B

```
          230            240             250             260
   *        *     *        *       *        *      *       *
  TAT ACA CTG GAC CTG TGG GCT GGG CAG CAG CTG CTG TGG AAG
  ATA TGT GAC CTG GAC ACC CGA CCC GTC GTC GAC GAC ACC TTC
  Tyr Thr Leu Asp Leu Trp Ala Gly Gln Gln Leu Leu Trp Lys>
  ─────────────────────────IL4Rα──────────────────────────>

270            280             290             300
   *        *     *        *       *        *      *       *
  GGC TCC TTC AAG CCC AGC GAG CAT GTG AAA CCC AGG GCC CCA
  CCG AGG AAG TTC GGG TCG CTC GTA CAC TTT GGG TCC CGG GGT
  Gly Ser Phe Lys Pro Ser Glu His Val Lys Pro Arg Ala Pro>
  ─────────────────────────IL4Rα──────────────────────────>

310            320            330            340             350
    *     *        *     *        *     *        *      *        *
   GGA AAC CTG ACA GTT CAC ACC AAT GTC TCC GAC ACT CTG CTG
   CCT TTG GAC TGT CAA GTG TGG TTA CAG AGG CTG TGA GAC GAC
   Gly Asn Leu Thr Val His Thr Asn Val Ser Asp Thr Leu Leu>
   ──────────────────────────IL4Rα──────────────────────────>

360            370            380            390
     *       *     *        *     *        *      *       *
    CTG ACC TGG AGC AAC CCG TAT CCC CCT GAC AAT TAC CTG TAT
    GAC TGG ACC TCG TTG GGC ATA GGG GGA CTG TTA ATG GAC ATA
    Leu Thr Trp Ser Asn Pro Tyr Pro Pro Asp Asn Tyr Leu Tyr>
    ─────────────────────────IL4Rα──────────────────────────>

400            410            420            430
     *       *     *        *     *        *      *       *       *
    AAT CAT CTC ACC TAT GCA GTC AAC ATT TGG AGT GAA AAC GAC
    TTA GTA GAG TGG ATA CGT CAG TTG TAA ACC TCA CTT TTG CTG
    Asn His Leu Thr Tyr Ala Val Asn Ile Trp Ser Glu Asn Asp>
    ─────────────────────────IL4Rα──────────────────────────>

440            450            460            470
     *       *     *        *     *        *      *       *
    CCG GCA GAT TTC AGA ATC TAT AAC GTG ACC TAC CTA GAA CCC
    GGC CGT CTA AAG TCT TAG ATA TTG CAC TGG ATG GAT CTT GGG
    Pro Ala Asp Phe Arg Ile Tyr Asn Val Thr Tyr Leu Glu Pro>
    ─────────────────────────IL4Rα──────────────────────────>

480            490            500            510
     *       *     *        *     *        *      *       *
    TCC CTC CGC ATC GCA GCC AGC ACC CTG AAG TCT GGG ATT TCC
    AGG GAG GCG TAG CGT CGG TCG TGG GAC TTC AGA CCC TAA AGG
    Ser Leu Arg Ile Ala Ala Ser Thr Leu Lys Ser Gly Ile Ser>
    ─────────────────────────IL4Rα──────────────────────────>
```

Figure 44C

>Mutation Cysteine to Serine

```
       520           530           540           550           560
        *      *      *      *      *      *      *      *      *
       TAC    AGG    GCA    CGC    GTA    CGG    GCC    TGG    GCT    CAG    AGC    TAT    AAC    ACC
       ATG    TCC    CGT    GCG    CAT    GCC    CGG    ACC    CGA    GTC    TCG    ATA    TTG    TGG
       Tyr    Arg    Ala    Arg    Val    Arg    Ala    Trp    Ala    Gln    Ser    Tyr    Asn    Thr>
       _____IL4Rα_____>

570           580           590           600
        *      *      *      *      *      *      *      *
       ACC    TGG    AGT    GAG    TGG    AGC    CCC    AGC    ACC    AAG    TGG    CAC    AAC    TCC
       TGG    ACC    TCA    CTC    ACC    TCG    GGG    TCG    TGG    TTC    ACC    GTG    TTG    AGG
       Thr    Trp    Ser    Glu    Trp    Ser    Pro    Ser    Thr    Lys    Trp    His    Asn    Ser>
       _____IL4Rα_____>

610           620           630           640
        *      *      *      *      *      *      *      *      *
       TAC    AGG    GAG    CCC    TTC    GAG    CAG    GCG    CCT    ACG    GAA    ACT    CAG    CCA
       ATG    TCC    CTC    GGG    AAG    CTC    GTC    CGC    GGA    TGC    CTT    TGA    GTC    GGT
       Tyr    Arg    Glu    Pro    Phe    Glu    Gln>
       _____IL4Rα_____>

Ala    Pro    Thr    Glu    Thr    Gln    Pro>
                                               _____IL13RA1_____>
```

>Mutation Cysteine to Alanine

```
              650           660           670           680
        *      *      *      *      *      *      *      *
       CCT    GTG    ACA    AAT    TTG    AGT    GTC    TCT    GTT    GAA    AAC    CTC    GCG    ACA
       GGA    CAC    TGT    TTA    AAC    TCA    CAG    AGA    CAA    CTT    TTG    GAG    CGC    TGT
       Pro    Val    Thr    Asn    Leu    Ser    Val    Ser    Val    Glu    Asn    Leu    Ala    Thr>
       _____IL13Rα1_____>

690           700           710           720
        *      *      *      *      *      *      *      *
       GTA    ATA    TGG    ACA    TGG    AAT    CCA    CCC    GAG    GGA    GCC    AGC    TCA    AAT
       CAT    TAT    ACC    TGT    ACC    TTA    GGT    GGG    CTC    CCT    CGG    TCG    AGT    TTA
       Val    Ile    Trp    Thr    Trp    Asn    Pro    Pro    Glu    Gly    Ala    Ser    Ser    Asn>
       _____IL13Rα1_____>

730           740           750           760           770
        *      *      *      *      *      *      *      *      *
       TGT    AGT    CTA    TGG    TAT    TTT    AGT    CAT    TTT    GGC    GAC    AAA    CAA    GAT
       ACA    TCA    GAT    ACC    ATA    AAA    TCA    GTA    AAA    CCG    CTG    TTT    GTT    CTA
       Cys    Ser    Leu    Trp    Tyr    Phe    Ser    His    Phe    Gly    Asp    Lys    Gln    Asp>
       _____IL13Rα1_____>
```

Figure 44D

```
         780            790            800            810
    *     *      *      *      *      *      *      *
AAG  AAA  ATA  GCT  CCG  GAA  ACT  CGT  CGT  TCA  ATA  GAA  GTA  CCC
TTC  TTT  TAT  CGA  GGC  CTT  TGA  GCA  GCA  AGT  TAT  CTT  CAT  GGG
Lys  Lys  Ile  Ala  Pro  Glu  Thr  Arg  Arg  Ser  Ile  Glu  Val  Pro>
_____IL13Rα1_____>

820            830            840            850
    *     *      *      *      *      *      *      *      *
CTG  AAT  GAG  AGG  ATT  TGT  CTG  CAA  GTG  GGG  TCC  CAG  TGT  AGC
GAC  TTA  CTC  TCC  TAA  ACA  GAC  GTT  CAC  CCC  AGG  GTC  ACA  TCG
Leu  Asn  Glu  Arg  Ile  Cys  Leu  Gln  Val  Gly  Ser  Gln  Cys  Ser>
_____IL13Rα1_____>

860            870            880            890
    *     *      *      *      *      *      *      *
ACC  AAT  GAG  AGT  GAG  AAG  CCT  AGC  ATT  TTG  GTT  GAA  AAA  TGC
TGG  TTA  CTC  TCA  CTC  TTC  GGA  TCG  TAA  AAC  CAA  CTT  TTT  ACG
Thr  Asn  Glu  Ser  Glu  Lys  Pro  Ser  Ile  Leu  Val  Glu  Lys  Cys>
_____IL13Rα1_____>

900            910            920            930
    *     *      *      *      *      *      *      *
ATC  TCA  CCC  CCA  GAA  GGT  GAT  CCT  GAG  TCT  GCT  GTG  ACT  GAG
TAG  AGT  GGG  GGT  CTT  CCA  CTA  GGA  CTC  AGA  CGA  CAC  TGA  CTC
Ile  Ser  Pro  Pro  Glu  Gly  Asp  Pro  Glu  Ser  Ala  Val  Thr  Glu>
_____IL13Rα1_____>

940            950            960            970            980
 *     *      *      *      *      *      *      *      *
CTT  CAA  TGC  ATT  TGG  CAC  AAC  CTG  AGC  TAC  ATG  AAG  TGT  TCT
GAA  GTT  ACG  TAA  ACC  GTG  TTG  GAC  TCG  ATG  TAC  TTC  ACA  AGA
Leu  Gln  Cys  Ile  Trp  His  Asn  Leu  Ser  Tyr  Met  Lys  Cys  Ser>
_____IL13Rα1_____>

990           1000           1010           1020
    *     *      *      *      *      *      *      *
TGG  CTC  CCT  GGA  AGG  AAT  ACC  AGT  CCC  GAC  ACT  AAC  TAT  ACT
ACC  GAG  GGA  CCT  TCC  TTA  TGG  TCA  GGG  CTG  TGA  TTG  ATA  TGA
Trp  Leu  Pro  Gly  Arg  Asn  Thr  Ser  Pro  Asp  Thr  Asn  Tyr  Thr>
_____IL13Rα1_____>

1030           1040           1050           1060
    *     *      *      *      *      *      *      *      *
CTC  TAC  TAT  TGG  CAC  AGA  AGC  CTG  GAA  AAA  ATT  CAT  CAA  TGT
GAG  ATG  ATA  ACC  GTG  TCT  TCG  GAC  CTT  TTT  TAA  GTA  GTT  ACA
Leu  Tyr  Tyr  Trp  His  Arg  Ser  Leu  Glu  Lys  Ile  His  Gln  Cys>
_____IL13Rα1_____>
```

Figure 44E

```
        1070           1080           1090           1100
          *       *      *      *      *       *      *      *
        GAA    AAC    ATC    TTT    AGA    GAA    GGC    CAA    TAC    TTT    GGT    TGT    TCC    TTT
        CTT    TTG    TAG    AAA    TCT    CTT    CCG    GTT    ATG    AAA    CCA    ACA    AGG    AAA
        Glu    Asn    Ile    Phe    Arg    Glu    Gly    Gln    Tyr    Phe    Gly    Cys    Ser    Phe>
        _____IL13Rα1_____>

1110           1120           1130           1140
          *       *      *      *      *       *      *      *
        GAT    CTG    ACC    AAA    GTG    AAG    GAT    TCC    AGT    TTT    GAA    CAA    CAC    AGT
        CTA    GAC    TGG    TTT    CAC    TTC    CTA    AGG    TCA    AAA    CTT    GTT    GTG    TCA
        Asp    Leu    Thr    Lys    Val    Lys    Asp    Ser    Ser    Phe    Glu    Gln    His    Ser>
        _____IL13Rα1_____>

1150           1160           1170           1180           1190
      *       *      *      *      *       *      *      *      *
    GTC    CAA    ATA    ATG    GTC    AAG    GAT    AAT    GCA    GGA    AAA    ATT    AAA    CCA
    CAG    GTT    TAT    TAC    CAG    TTC    CTA    TTA    CGT    CCT    TTT    TAA    TTT    GGT
    Val    Gln    Ile    Met    Val    Lys    Asp    Asn    Ala    Gly    Lys    Ile    Lys    Pro>
    _____IL13Rα1_____>

1200           1210           1220           1230
          *       *      *      *      *       *      *      *
        TCC    TTC    AAT    ATA    GTG    CCT    TTA    ACT    TCC    CGT    GTG    AAA    CCT    GAT
        AGG    AAG    TTA    TAT    CAC    GGA    AAT    TGA    AGG    GCA    CAC    TTT    GGA    CTA
        Ser    Phe    Asn    Ile    Val    Pro    Leu    Thr    Ser    Arg    Val    Lys    Pro    Asp>
        _____IL13Rα1_____>

1240           1250           1260           1270
          *       *      *      *      *       *      *      *      *
        CCT    CCA    CAT    ATT    AAA    AAC    CTC    TCC    TTC    CAC    AAT    GAT    GAC    CTA
        GGA    GGT    GTA    TAA    TTT    TTG    GAG    AGG    AAG    GTG    TTA    CTA    CTG    GAT
        Pro    Pro    His    Ile    Lys    Asn    Leu    Ser    Phe    His    Asn    Asp    Asp    Leu>
        _____IL13Rα1_____>

1280           1290           1300           1310
          *       *      *      *      *       *      *      *
        TAT    GTG    CAA    TGG    GAG    AAT    CCA    CAG    AAT    TTT    ATT    AGC    AGA    TGC
        ATA    CAC    GTT    ACC    CTC    TTA    GGT    GTC    TTA    AAA    TAA    TCG    TCT    ACG
        Tyr    Val    Gln    Trp    Glu    Asn    Pro    Gln    Asn    Phe    Ile    Ser    Arg    Cys>
        _____IL13Rα1_____>

1320           1330           1340           1350
          *       *      *      *      *       *      *      *
        CTA    TTT    TAT    GAA    GTA    GAA    GTC    AAT    AAC    AGC    CAA    ACT    GAG    ACA
        GAT    AAA    ATA    CTT    CAT    CTT    CAG    TTA    TTG    TCG    GTT    TGA    CTC    TGT
        Leu    Phe    Tyr    Glu    Val    Glu    Val    Asn    Asn    Ser    Gln    Thr    Glu    Thr>
        _____IL13Rα1_____>
```

Figure 44F

```
1360          1370          1380          1390          1400
  *      *      *      *      *      *      *      *      *
CAT AAT GTT TTC TAC GTC CAA GAG GCT AAA TGT GAG AAT CCA
GTA TTA CAA AAG ATG CAG GTT CTC CGA TTT ACA CTC TTA GGT
His Asn Val Phe Tyr Val Gln Glu Ala Lys Cys Glu Asn Pro>
_____IL13Rα1_____>

1410          1420          1430          1440
  *      *      *      *      *      *      *      *
GAA TTT GAG AGA AAT GTG GAG AAT ACA TCT TGT TTC ATG GTC
CTT AAA CTC TCT TTA CAC CTC TTA TGT AGA ACA AAG TAC CAG
Glu Phe Glu Arg Asn Val Glu Asn Thr Ser Cys Phe Met Val>
_____IL13Rα1_____>

1450          1460          1470          1480
  *      *      *      *      *      *      *      *      *
CCT GGT GTT CTT CCT GAT ACT TTG AAC ACA GTC AGA ATA AGA
GGA CCA CAA GAA GGA CTA TGA AAC TTG TGT CAG TCT TAT TCT
Pro Gly Val Leu Pro Asp Thr Leu Asn Thr Val Arg Ile Arg>
_____IL13Rα1_____>

1490          1500          1510          1520
  *      *      *      *      *      *      *      *
GTC AAA ACA AAT AAG TTA TGC TAT GAG GAT GAC AAA CTC TGG
CAG TTT TGT TTA TTC AAT ACG ATA CTC CTA CTG TTT GAG ACC
Val Lys Thr Asn Lys Leu Cys Tyr Glu Asp Asp Lys Leu Trp>
_____IL13Rα1_____>

1530          1540          1550          1560
  *      *      *      *      *      *      *      *
AGT AAT TGG AGC CAA GAA ATG AGT ATA GGT AAG AAG CGC AAT
TCA TTA ACC TCG GTT CTT TAC TCA TAT CCA TTC TTC GCG TTA
Ser Asn Trp Ser Gln Glu Met Ser Ile Gly Lys Lys Arg Asn>
_____IL13Rα1_____>

1570          1580          1590          1600          1610
  *      *      *      *      *      *      *      *      *
TCC ACC GGA GAG TCC AAA TAC GGT CCG CCA TGC CCA TCA TGC
AGG TGG CCT CTC AGG TTT ATG CCA GGC GGT ACG GGT AGT ACG
Ser Thr
_____>
        Gly>
        ___>
            Glu Ser Lys Tyr Gly Pro Pro Cys Pro Ser Cys>
                        _____FC-IgG4_____>

1620          1630          1640          1650
  *      *      *      *      *      *      *      *
CCA GCA CCT GAG TTC CTG GGG GGA CCA TCA GTC TTC CTG TTC
GGT CGT GGA CTC AAG GAC CCC CCT GGT AGT CAG AAG GAC AAG
Pro Ala Pro Glu Phe Leu Gly Gly Pro Ser Val Phe Leu Phe>
_____FC-IgG4_____>
```

Figure 44G

```
            1660              1670              1680              1690
       *      *      *      *      *      *      *      *      *
     CCC    CCA    AAA    CCC    AAG    GAC    ACT    CTC    ATG    ATC    TCC    CGG    ACC    CCT
     GGG    GGT    TTT    GGG    TTC    CTG    TGA    GAG    TAC    TAG    AGG    GCC    TGG    GGA
     Pro    Pro    Lys    Pro    Lys    Asp    Thr    Leu    Met    Ile    Ser    Arg    Thr    Pro>
     _____FC-IgG4_____>

1700              1710              1720              1730
       *      *      *      *      *      *      *      *
     GAG    GTC    ACG    TGC    GTG    GTG    GTG    GAC    GTG    AGC    CAG    GAA    GAC    CCC
     CTC    CAG    TGC    ACG    CAC    CAC    CAC    CTG    CAC    TCG    GTC    CTT    CTG    GGG
     Glu    Val    Thr    Cys    Val    Val    Val    Asp    Val    Ser    Gln    Glu    Asp    Pro>
     _____FC-IgG4_____>

1740              1750              1760              1770
       *      *      *      *      *      *      *      *
     GAG    GTC    CAG    TTC    AAC    TGG    TAC    GTG    GAT    GGC    GTG    GAG    GTG    CAT
     CTC    CAG    GTC    AAG    TTG    ACC    ATG    CAC    CTA    CCG    CAC    CTC    CAC    GTA
     Glu    Val    Gln    Phe    Asn    Trp    Tyr    Val    Asp    Gly    Val    Glu    Val    His>
     _____FC-IgG4_____>

1780              1790              1800              1810              1820
    *      *      *      *      *      *      *      *      *
  AAT    GCC    AAG    ACA    AAG    CCG    CGG    GAG    GAG    CAG    TTC    AAC    AGC    ACG
  TTA    CGG    TTC    TGT    TTC    GGC    GCC    CTC    CTC    GTC    AAG    TTG    TCG    TGC
  Asn    Ala    Lys    Thr    Lys    Pro    Arg    Glu    Glu    Gln    Phe    Asn    Ser    Thr>
  _____FC-IgG4_____>

1830              1840              1850              1860
       *      *      *      *      *      *      *      *
     TAC    CGT    GTG    GTC    AGC    GTC    CTC    ACC    GTC    CTG    CAC    CAG    GAC    TGG
     ATG    GCA    CAC    CAG    TCG    CAG    GAG    TGG    CAG    GAC    GTG    GTC    CTG    ACC
     Tyr    Arg    Val    Val    Ser    Val    Leu    Thr    Val    Leu    His    Gln    Asp    Trp>
     _____FC-IgG4_____>

1870              1880              1890              1900
       *      *      *      *      *      *      *      *      *
     CTG    AAC    GGC    AAG    GAG    TAC    AAG    TGC    AAG    GTC    TCC    AAC    AAA    GGC
     GAC    TTG    CCG    TTC    CTC    ATG    TTC    ACG    TTC    CAG    AGG    TTG    TTT    CCG
     Leu    Asn    Gly    Lys    Glu    Tyr    Lys    Cys    Lys    Val    Ser    Asn    Lys    Gly>
     _____FC-IgG4_____>

1910              1920              1930              1940
       *      *      *      *      *      *      *      *      *
     CTC    CCG    TCC    TCC    ATC    GAG    AAA    ACC    ATC    TCC    AAA    GCC    AAA    GGG
     GAG    GGC    AGG    AGG    TAG    CTC    TTT    TGG    TAG    AGG    TTT    CGG    TTT    CCC
     Leu    Pro    Ser    Ser    Ile    Glu    Lys    Thr    Ile    Ser    Lys    Ala    Lys    Gly>
     _____FC-IgG4_____>
```

Figure 44H

```
       1950           1960           1970           1980
         *      *      *      *      *      *      *      *
       CAG    CCC    CGA    GAG    CCA    CAG    GTG    TAC    ACC    CTG    CCC    CCA    TCC    CAG
       GTC    GGG    GCT    CTC    GGT    GTC    CAC    ATG    TGG    GAC    GGG    GGT    AGG    GTC
       Gln    Pro    Arg    Glu    Pro    Gln    Val    Tyr    Thr    Leu    Pro    Pro    Ser    Gln>
       _____FC-IgG4_____>

1990           2000           2010           2020           2030
     *      *      *      *      *      *      *      *      *
   GAG    GAG    ATG    ACC    AAG    AAC    CAG    GTC    AGC    CTG    ACC    TGC    CTG    GTC
   CTC    CTC    TAC    TGG    TTC    TTG    GTC    CAG    TCG    GAC    TGG    ACG    GAC    CAG
   Glu    Glu    Met    Thr    Lys    Asn    Gln    Val    Ser    Leu    Thr    Cys    Leu    Val>
   _____FC-IgG4_____>

2040           2050           2060           2070
             *      *      *      *      *      *      *      *
           AAA    GGC    TTC    TAC    CCC    AGC    GAC    ATC    GCC    GTG    GAG    TGG    GAG    AGC
           TTT    CCG    AAG    ATG    GGG    TCG    CTG    TAG    CGG    CAC    CTC    ACC    CTC    TCG
           Lys    Gly    Phe    Tyr    Pro    Ser    Asp    Ile    Ala    Val    Glu    Trp    Glu    Ser>
           _____FC-IgG4_____>

2080           2090           2100           2110
             *      *      *      *      *      *      *      *      *
           AAT    GGG    CAG    CCG    GAG    AAC    AAC    TAC    AAG    ACC    ACG    CCT    CCC    GTG
           TTA    CCC    GTC    GGC    CTC    TTG    TTG    ATG    TTC    TGG    TGC    GGA    GGG    CAC
           Asn    Gly    Gln    Pro    Glu    Asn    Asn    Tyr    Lys    Thr    Thr    Pro    Pro    Val>
           _____FC-IgG4_____>

2120           2130           2140           2150
             *      *      *      *      *      *      *      *
           CTG    GAC    TCC    GAC    GGC    TCC    TTC    TTC    CTC    TAC    AGC    AGG    CTA    ACC
           GAC    CTG    AGG    CTG    CCG    AGG    AAG    AAG    GAG    ATG    TCG    TCC    GAT    TGG
           Leu    Asp    Ser    Asp    Gly    Ser    Phe    Phe    Leu    Tyr    Ser    Arg    Leu    Thr>
           _____FC-IgG4_____>

2160           2170           2180           2190
             *      *      *      *      *      *      *      *
           GTG    GAC    AAG    AGC    AGG    TGG    CAG    GAG    GGG    AAT    GTC    TTC    TCA    TGC
           CAC    CTG    TTC    TCG    TCC    ACC    GTC    CTC    CCC    TTA    CAG    AAG    AGT    ACG
           Val    Asp    Lys    Ser    Arg    Trp    Gln    Glu    Gly    Asn    Val    Phe    Ser    Cys>
           _____FC-IgG4_____>

2200           2210           2220           2230           2240
         *      *      *      *      *      *      *      *      *
       TCC    GTG    ATG    CAT    GAG    GCT    CTG    CAC    AAC    CAC    TAC    ACA    CAG    AAG
       AGG    CAC    TAC    GTA    CTC    CGA    GAC    GTG    TTG    GTG    ATG    TGT    GTC    TTC
       Ser    Val    Met    His    Glu    Ala    Leu    His    Asn    His    Tyr    Thr    Gln    Lys>
       _____FC-IgG4_____>
```

Figure 44I

```
              2250                2260
       *       *       *       *       *
      AGC     CTC     TCC     CTG     TCT     CTG     GGT     AAA     TGA
      TCG     GAG     AGG     GAC     AGA     GAC     CCA     TTT     ACT
      Ser     Leu     Ser     Leu     Ser     Leu     Gly     Lys     ***>
                          _____FC-IgG4_____>
```

Figure 45A

```
         -70              -60             -50              -40
     *    *    *    *    *    *    *    *
ATG  GTG  TGG  CCG  GCG  CGG  CTC  TGC  GGG  CTG  TGG  GCG  CTG  CTG
TAC  CAC  ACC  GGC  CGC  GCC  GAG  ACG  CCC  GAC  ACC  CGC  GAC  GAC
Met  Val  Trp  Pro  Ala  Arg  Leu  Cys  Gly  Leu  Trp  Ala  Leu  Leu>
                         SIGNAL PEPTIDE                            >
                              IL13Rα1                              >

-30              -20             -10               1
     *    *    *    *    *    *    *    *    *
CTC  TGC  GCC  GGC  GGC  GGG  GGC  GGG  GGC  GGG  GGC  GCC  GCG  CCT
GAG  ACG  CGG  CCG  CCG  CCC  CCG  CCC  CCG  CCC  CCG  CGG  CGC  GGA
Leu  Cys  Ala  Gly  Gly  Gly  Gly  Gly  Gly  Gly  Gly  Ala  Ala  Pro>
     d            SIGNAL PEPTIDE                >
                          IL13Rα1                                  >

10              20              30              40
     *    *    *    *    *    *    *    *
ACG  GAA  ACT  CAG  CCA  CCT  GTG  ACA  AAT  TTG  AGT  GTC  TCT  GTT
TGC  CTT  TGA  GTC  GGT  GGA  CAC  TGT  TTA  AAC  TCA  CAG  AGA  CAA
Thr  Glu  Thr  Gln  Pro  Pro  Val  Thr  Asn  Leu  Ser  Val  Ser  Val>
                              IL13Rα1                              >

>Mutation Cysteine to Alanine
                    |
          50       |60              70              80              90
     *    *    |   *    *    *    *    *    *    *
GAA  AAC  CTC  GCG  ACA  GTA  ATA  TGG  ACA  TGG  AAT  CCA  CCC  GAG
CTT  TTG  GAG  CGC  TGT  CAT  TAT  ACC  TGT  ACC  TTA  GGT  GGG  CTC
Glu  Asn  Leu  Ala  Thr  Val  Ile  Trp  Thr  Trp  Asn  Pro  Pro  Glu>
                              IL13Rα1                              >

100              110             120             130
     *    *    *    *    *    *    *    *
GGA  GCC  AGC  TCA  AAT  TGT  AGT  CTA  TGG  TAT  TTT  AGT  CAT  TTT
CCT  CGG  TCG  AGT  TTA  ACA  TCA  GAT  ACC  ATA  AAA  TCA  GTA  AAA
Gly  Ala  Ser  Ser  Asn  Cys  Ser  Leu  Trp  Tyr  Phe  Ser  His  Phe>
                              IL13Rα1                              >

140              150             160             170
     *    *    *    *    *    *    *    *
GGC  GAC  AAA  CAA  GAT  AAG  AAA  ATA  GCT  CCG  GAA  ACT  CGT  CGT
CCG  CTG  TTT  GTT  CTA  TTC  TTT  TAT  CGA  GGC  CTT  TGA  GCA  GCA
Gly  Asp  Lys  Gln  Asp  Lys  Lys  Ile  Ala  Pro  Glu  Thr  Arg  Arg>
                              IL13Rα1                              >
```

Figure 45B

```
           180              190             200               210
      *      *      *         *       *      *        *       *       *
     TCA    ATA    GAA    GTA    CCC    CTG    AAT    GAG    AGG    ATT    TGT    CTG    CAA    GTG
     AGT    TAT    CTT    CAT    GGG    GAC    TTA    CTC    TCC    TAA    ACA    GAC    GTT    CAC
     Ser    Ile    Glu    Val    Pro    Leu    Asn    Glu    Arg    Ile    Cys    Leu    Gln    Val>
     ────────────────────────────────IL13Rα1──────────────────────────────────────>

220              230             240               250
      *      *      *         *       *      *        *       *
     GGG    TCC    CAG    TGT    AGC    ACC    AAT    GAG    AGT    GAG    AAG    CCT    AGC    ATT
     CCC    AGG    GTC    ACA    TCG    TGG    TTA    CTC    TCA    CTC    TTC    GGA    TCG    TAA
     Gly    Ser    Gln    Cys    Ser    Thr    Asn    Glu    Ser    Glu    Lys    Pro    Ser    Ile>
     ────────────────────────────────IL13Rα1──────────────────────────────────────>

260              270             280               290             300
     *     *      *      *         *      *       *       *       *       *
    TTG   GTT    GAA    AAA    TGC    ATC    TCA    CCC    CCA    GAA    GGT    GAT    CCT    GAG
    AAC   CAA    CTT    TTT    ACG    TAG    AGT    GGG    GGT    CTT    CCA    CTA    GGA    CTC
    Leu   Val    Glu    Lys    Cys    Ile    Ser    Pro    Pro    Glu    Gly    Asp    Pro    Glu>
    ────────────────────────────────IL13Rα1──────────────────────────────────────>

310              320             330               340
         *     *      *         *       *      *       *       *
        TCT   GCT    GTG    ACT    GAG    CTT    CAA    TGC    ATT    TGG    CAC    AAC    CTG    AGC
        AGA   CGA    CAC    TGA    CTC    GAA    GTT    ACG    TAA    ACC    GTG    TTG    GAC    TCG
        Ser   Ala    Val    Thr    Glu    Leu    Gln    Cys    Ile    Trp    His    Asn    Leu    Ser>
        ────────────────────────────────IL13Rα1──────────────────────────────────────>

350              360             370               380
         *     *      *         *       *      *       *       *
        TAC   ATG    AAG    TGT    TCT    TGG    CTC    CCT    GGA    AGG    AAT    ACC    AGT    CCC
        ATG   TAC    TTC    ACA    AGA    ACC    GAG    GGA    CCT    TCC    TTA    TGG    TCA    GGG
        Tyr   Met    Lys    Cys    Ser    Trp    Leu    Pro    Gly    Arg    Asn    Thr    Ser    Pro>
        ────────────────────────────────IL13Rα1──────────────────────────────────────>

390              400             410               420
         *     *      *         *       *      *       *       *      *
        GAC   ACT    AAC    TAT    ACT    CTC    TAC    TAT    TGG    CAC    AGA    AGC    CTG    GAA
        CTG   TGA    TTG    ATA    TGA    GAG    ATG    ATA    ACC    GTG    TCT    TCG    GAC    CTT
        Asp   Thr    Asn    Tyr    Thr    Leu    Tyr    Tyr    Trp    His    Arg    Ser    Leu    Glu>
        ────────────────────────────────IL13Rα1──────────────────────────────────────>

430              440             450               460
         *     *      *         *       *      *       *       *
        AAA   ATT    CAT    CAA    TGT    GAA    AAC    ATC    TTT    AGA    GAA    GGC    CAA    TAC
        TTT   TAA    GTA    GTT    ACA    CTT    TTG    TAG    AAA    TCT    CTT    CCG    GTT    ATG
        Lys   Ile    His    Gln    Cys    Glu    Asn    Ile    Phe    Arg    Glu    Gly    Gln    Tyr>
        ────────────────────────────────IL13Rα1──────────────────────────────────────>
```

Figure 45C

```
      470            480           490           500           510
        *        *     *       *     *       *     *       *     *
      TTT GGT TGT TCC TTT GAT CTG ACC AAA GTG AAG GAT TCC AGT
      AAA CCA ACA AGG AAA CTA GAC TGG TTT CAC TTC CTA AGG TCA
      Phe Gly Cys Ser Phe Asp Leu Thr Lys Val Lys Asp Ser Ser>
      _____IL13Rα1_____>

520           530           540           550
                 *       *     *       *     *       *     *
           TTT GAA CAA CAC AGT GTC CAA ATA ATG GTC AAG GAT AAT GCA
           AAA CTT GTT GTG TCA CAG GTT TAT TAC CAG TTC CTA TTA CGT
           Phe Glu Gln His Ser Val Gln Ile Met Val Lys Asp Asn Ala>
           _____IL13Rα1_____>

560           570           580           590
                 *       *     *       *     *       *     *
           GGA AAA ATT AAA CCA TCC TTC AAT ATA GTG CCT TTA ACT TCC
           CCT TTT TAA TTT GGT AGG AAG TTA TAT CAC GGA AAT TGA AGG
           Gly Lys Ile Lys Pro Ser Phe Asn Ile Val Pro Leu Thr Ser>
           _____IL13Rα1_____>

600           610           620           630
             *     *       *     *       *     *       *     *     *
           CGT GTG AAA CCT GAT CCT CCA CAT ATT AAA AAC CTC TCC TTC
           GCA CAC TTT GGA CTA GGA GGT GTA TAA TTT TTG GAG AGG AAG
           Arg Val Lys Pro Asp Pro Pro His Ile Lys Asn Leu Ser Phe>
           _____IL13Rα1_____>

640           650           660           670
              *     *       *     *       *     *       *     *
           CAC AAT GAT GAC CTA TAT GTG CAA TGG GAG AAT CCA CAG AAT
           GTG TTA CTA CTG GAT ATA CAC GTT ACC CTC TTA GGT GTC TTA
           His Asn Asp Asp Leu Tyr Val Gln Trp Glu Asn Pro Gln Asn>
           _____IL13Rα1_____>

680           690           700           710           720
           *       *     *       *     *       *     *       *     *
         TTT ATT AGC AGA TGC CTA TTT TAT GAA GTA GAA GTC AAT AAC
         AAA TAA TCG TCT ACG GAT AAA ATA CTT CAT CTT CAG TTA TTG
         Phe Ile Ser Arg Cys Leu Phe Tyr Glu Val Glu Val Asn Asn>
         _____IL13Rα1_____>

730           740           750           760
                     *       *     *       *     *       *     *
                AGC CAA ACT GAG ACA CAT AAT GTT TTC TAC GTC AAA GAG GCT
                TCG GTT TGA CTC TGT GTA TTA CAA AAG ATG CAG TTT CTC CGA
                Ser Gln Thr Glu Thr His Asn Val Phe Tyr Val Gln Glu Ala>
                _____IL13Rα1_____>
```

Figure 45D

```
            770              780              790              800
         *        *        *        *        *        *        *        *
       AAA TGT GAG AAT CCA GAA TTT GAG AGA AAT GTG GAG AAT ACA
       TTT ACA CTC TTA GGT CTT AAA CTC TCT TTA CAC CTC TTA TGT
       Lys Cys Glu Asn Pro Glu Phe Glu Arg Asn Val Glu Asn Thr>
       _____IL13Rα1_____>

810              820              830              840
         *        *        *        *        *        *        *        *        *
       TCT TGT TTC ATG GTC CCT GGT GTT CTT CCT GAT ACT TTG AAC
       AGA ACA AAG TAC CAG GGA CCA CAA GAA GGA CTA TGA AAC TTG
       Ser Cys Phe Met Val Pro Gly Val Leu Pro Asp Thr Leu Asn>
       _____IL13Rα1_____>

850              860              870              880
       *        *        *        *        *        *        *        *
       ACA GTC AGA ATA AGA GTC AAA ACA AAT AAG TTA TGC TAT GAG
       TGT CAG TCT TAT TCT CAG TTT TGT TTA TTC AAT ACG ATA CTC
       Thr Val Arg Ile Arg Val Lys Thr Asn Lys Leu Cys Tyr Glu>
       _____IL13Rα1_____>

890          900              910              920          930
     *        *        *        *        *        *        *        *        *
     GAT GAC AAA CTC TGG AGT AAT TGG AGC CAA GAA ATG AGT ATA
     CTA CTG TTT GAG ACC TCA TTA ACC TCG GTT CTT TAC TCA TAT
     Asp Asp Lys Leu Trp Ser Asn Trp Ser Gln Glu Met Ser Ile>
     _____IL13Rα1_____>

940              950              960              970
              *        *        *        *        *        *        *        *
            GGT AAG AAG CGC AAT TCC ACA GGG AAC ATG AAG GTC TTG CAG
            CCA TTC TTC GCG TTA AGG TGT CCC TTG TAC TTC CAG AAC GTC
                                            Gly Asn Met Lys Val Leu Gln>
                                            _____IL4Rα_____>
       Gly Lys Lys Arg Asn Ser Thr>
       _____IL13Rα1_____>

980              990              1000             1010
         *        *        *        *        *        *        *        *
       GAG CCC ACC TGC GTC TCC GAC TAC ATG AGC ATC TCT ACT TGC
       CTC GGG TGG ACG CAG AGG CTG ATG TAC TCG TAG AGA TGA ACG
       Glu Pro Thr Cys Val Ser Asp Tyr Met Ser Ile Ser Thr Cys>
       _____IL4Rα_____>

1020             1030             1040             1050
         *        *        *        *        *        *        *        *        *
       GAG TGG AAG ATG AAT GGT CCC ACC AAT TGC AGC ACC GAG CTC
       CTC ACC TTC TAC TTA CCA GGG TGG TTA ACG TCG TGG CTC GAG
       Glu Trp Lys Met Asn Gly Pro Thr Asn Cys Ser Thr Glu Leu>
       _____IL4Rα_____>
```

Figure 45E

```
       1060           1070           1080           1090
         *      *       *      *       *      *       *      *
       CGC CTG TTG TAC CAG CTG GTT TTT CTG CTC TCC GAA GCC CAC
       GCG GAC AAC ATG GTC GAC CAA AAA GAC GAG AGG CTT CGG GTG
       Arg Leu Leu Tyr Gln Leu Val Phe Leu Leu Ser Glu Ala His>
       _____IL4Rα_____>

1100           1110           1120           1130           1140
    *      *       *      *       *      *       *      *       *
  ACG TGT ATC CCT GAG AAC AAC GGA GGC GCG GGG TGC GTG TGC
  TGC ACA TAG GGA CTC TTG TTG CCT CCG CGC CCC ACG CAC ACG
  Thr Cys Ile Pro Glu Asn Asn Gly Gly Ala Gly Cys Val Cys>
  _____IL4Rα_____>

1150           1160           1170           1180
             *      *       *      *       *      *       *      *
           CAC CTG CTC ATG GAT GAC GTG GTC AGT GCG GAT AAC TAT ACA
           GTG GAC GAG TAC CTA CTG CAC CAG TCA CGC CTA TTG ATA TGT
           His Leu Leu Met Asp Asp Val Val Ser Ala Asp Asn Tyr Thr>
           _____IL4Rα_____>

1190           1200           1210           1220
             *      *       *      *       *      *       *      *
           CTG GAC CTG TGG GCT GGG CAG CAG CTG CTG TGG AAG GGC TCC
           GAC CTG GAC ACC CGA CCC GTC GTC GAC GAC ACC TTC CCG AGG
           Leu Asp Leu Trp Ala Gly Gln Gln Leu Leu Trp Lys Gly Ser>
           _____IL4Rα_____>

1230           1240           1250           1260
         *      *       *      *       *      *       *      *       *
       TTC AAG CCC AGC GAG CAT GTG AAA CCC AGG GCC CCA GGA AAC
       AAG TTC GGG TCG CTC GTA CAC TTT GGG TCC CGG GGT CCT TTG
       Phe Lys Pro Ser Glu His Val Lys Pro Arg Ala Pro Gly Asn>
       _____IL4Rα_____>

1270           1280           1290           1300
         *      *       *      *       *      *       *      *
       CTG ACA GTT CAC ACC AAT GTC TCC GAC ACT CTG CTG CTG ACC
       GAC TGT CAA GTG TGG TTA CAG AGG CTG TGA GAC GAC GAC TGG
       Leu Thr Val His Thr Asn Val Ser Asp Thr Leu Leu Leu Thr>
       _____IL4Rα_____>

1310           1320           1330           1340           1350
    *      *       *      *       *      *       *      *       *
  TGG AGC AAC CCG TAT CCC CCT GAC AAT TAC CTG TAT AAT CAT
  ACC TCG TTG GGC ATA GGG GGA CTG TTA ATG GAC ATA TTA GTA
  Trp Ser Asn Pro Tyr Pro Pro Asp Asn Tyr Leu Tyr Asn His>
  _____IL4Rα_____>
```

Figure 45F

```
            1360           1370          1380          1390
         *      *       *      *      *      *      *      *
       CTC  ACC  TAT  GCA  GTC  AAC  ATT  TGG  AGT  GAA  AAC  GAC  CCG  GCA
       GAG  TGG  ATA  CGT  CAG  TTG  TAA  ACC  TCA  CTT  TTG  CTG  GGC  CGT
       Leu  Thr  Tyr  Ala  Val  Asn  Ile  Trp  Ser  Glu  Asn  Asp  Pro  Ala>
       _____IL4Rα_____>

1400           1410          1420          1430
         *      *       *      *      *      *      *      *
       GAT  TTC  AGA  ATC  TAT  AAC  GTG  ACC  TAC  CTA  GAA  CCC  TCC  CTC
       CTA  AAG  TCT  TAG  ATA  TTG  CAC  TGG  ATG  GAT  CTT  GGG  AGG  GAG
       Asp  Phe  Arg  Ile  Tyr  Asn  Val  Thr  Tyr  Leu  Glu  Pro  Ser  Leu>
       _____IL4Rα_____>

1440           1450          1460          1470
         *      *       *      *      *      *      *      *      *
       CGC  ATC  GCA  GCC  AGC  ACC  CTG  AAG  TCT  GGG  ATT  TCC  TAC  AGG
       GCG  TAG  CGT  CGG  TCG  TGG  GAC  TTC  AGA  CCC  TAA  AGG  ATG  TCC
       Arg  Ile  Ala  Ala  Ser  Thr  Leu  Lys  Ser  Gly  Ile  Ser  Tyr  Arg>
       _____IL4Rα_____>

>Mutation Cysteine to Serine
            1480           1490          1500   |     1510
         *      *       *      *      *    |  *      *      *
       GCA  CGC  GTA  CGG  GCC  TGG  GCT  CAG  AGC  TAT  AAC  ACC  ACC  TGG
       CGT  GCG  CAT  GCC  CGG  ACC  CGA  GTC  TCG  ATA  TTG  TGG  TGG  ACC
       Ala  Arg  Val  Arg  Ala  Trp  Ala  Gln  Ser  Tyr  Asn  Thr  Thr  Trp>
       _____IL4Rα_____>

1520         1530          1540          1550          1560
     *      *      *      *      *      *      *      *      *
   AGT  GAG  TGG  AGC  CCC  AGC  ACC  AAG  TGG  CAC  AAC  TCC  TAC  AGG
   TCA  CTC  ACC  TCG  GGG  TCG  TGG  TTC  ACC  GTG  TTG  AGG  ATG  TCC
   Ser  Glu  Trp  Ser  Pro  Ser  Thr  Lys  Trp  His  Asn  Ser  Tyr  Arg>
   _____IL4Rα_____>

1570           1580          1590          1600
         *      *       *      *      *      *      *      *
       GAG  CCC  TTC  GAG  CAG  ACC  GGA  GAG  TCC  AAA  TAC  GGT  CCG  CCA
       CTC  GGG  AAG  CTC  GTC  TGG  CCT  CTC  AGG  TTT  ATG  CCA  GGC  GGT
                                               Thr  Gly>
                                               _____>
       Glu  Pro  Phe  Glu  Gln>
       _____IL4Rα_____>
                                          Glu  Ser  Lys  Tyr  Gly  Pro  Pro>
                                          _____FC-IgG4_____>
```

Figure 45G

```
        1610          1620          1630          1640
     *     *     *     *     *     *     *     *
    TGC   CCA   TCA   TGC   CCA   GCA   CCT   GAG   TTC   CTG   GGG   GGA   CCA   TCA
    ACG   GGT   AGT   ACG   GGT   CGT   GGA   CTC   AAG   GAC   CCC   CCT   GGT   AGT
    Cys   Pro   Ser   Cys   Pro   Ala   Pro   Glu   Phe   Leu   Gly   Gly   Pro   Ser>
                              _____FC-IgG4_____>

1650          1660          1670          1680
     *     *     *     *     *     *     *     *     *
    GTC   TTC   CTG   TTC   CCC   CCA   AAA   CCC   AAG   GAC   ACT   CTC   ATG   ATC
    CAG   AAG   GAC   AAG   GGG   GGT   TTT   GGG   TTC   CTG   TGA   GAG   TAC   TAG
    Val   Phe   Leu   Phe   Pro   Pro   Lys   Pro   Lys   Asp   Thr   Leu   Met   Ile>
                              _____FC-IgG4_____>

1690          1700          1710          1720
     *     *     *     *     *     *     *     *
    TCC   CGG   ACC   CCT   GAG   GTC   ACG   TGC   GTG   GTG   GTG   GAC   GTG   AGC
    AGG   GCC   TGG   GGA   CTC   CAG   TGC   ACG   CAC   CAC   CAC   CTG   CAC   TCG
    Ser   Arg   Thr   Pro   Glu   Val   Thr   Cys   Val   Val   Val   Asp   Val   Ser>
                              _____FC-IgG4_____>

1730          1740          1750          1760          1770
     *     *     *     *     *     *     *     *     *
    CAG   GAA   GAC   CCC   GAG   GTC   CAG   TTC   AAC   TGG   TAC   GTG   GAT   GGC
    GTC   CTT   CTG   GGG   CTC   CAG   GTC   AAG   TTG   ACC   ATG   CAC   CTA   CCG
    Gln   Glu   Asp   Pro   Glu   Val   Gln   Phe   Asn   Trp   Tyr   Val   Asp   Gly>
                              _____FC-IgG4_____>

1780          1790          1800          1810
           *     *     *     *     *     *     *     *
          GTG   GAG   GTG   CAT   AAT   GCC   AAG   ACA   AAG   CCG   CGG   GAG   GAG   CAG
          CAC   CTC   CAC   GTA   TTA   CGG   TTC   TGT   TTC   GGC   GCC   CTC   CTC   GTC
          Val   Glu   Val   His   Asn   Ala   Lys   Thr   Lys   Pro   Arg   Glu   Glu   Gln>
                                    _____FC-IgG4_____>

1820          1830          1840          1850
           *     *     *     *     *     *     *     *
          TTC   AAC   AGC   ACG   TAC   CGT   GTG   GTC   AGC   GTC   CTC   ACC   GTC   CTG
          AAG   TTG   TCG   TGC   ATG   GCA   CAC   CAG   TCG   CAG   GAG   TGG   CAG   GAC
          Phe   Asn   Ser   Thr   Tyr   Arg   Val   Val   Ser   Val   Leu   Thr   Val   Leu>
                                    _____FC-IgG4_____>

1860          1870          1880          1890
           *     *     *     *     *     *     *     *     *
          CAC   CAG   GAC   TGG   CTG   AAC   GGC   AAG   GAG   TAC   AAG   TGC   AAG   GTC
          GTG   GTC   CTG   ACC   GAC   TTG   CCG   TTC   CTC   ATG   TTC   ACG   TTC   CAG
          His   Gln   Asp   Trp   Leu   Asn   Gly   Lys   Glu   Tyr   Lys   Cys   Lys   Val>
                                    _____FC-IgG4_____>
```

Figure 45H

```
         1900            1910           1920             1930
           *       *       *       *      *       *       *       *
        TCC AAC AAA GGC CTC CCG TCC TCC ATC GAG AAA ACC ATC TCC
        AGG TTG TTT CCG GAG GGC AGG AGG TAG CTC TTT TGG TAG AGG
        Ser Asn Lys Gly Leu Pro Ser Ser Ile Glu Lys Thr Ile Ser>
                                    _FC-IgG4_                    >

1940             1950            1960          1970           1980
        *       *       *       *       *       *       *       *       *
     AAA GCC AAA GGG CAG CCC CGA GAG CCA CAG GTG TAC ACC CTG
     TTT CGG TTT CCC GTC GGG GCT CTC GGT GTC CAC ATG TGG GAC
     Lys Ala Lys Gly Gln Pro Arg Glu Pro Gln Val Tyr Thr Leu>
                           _FC-IgG4_                             >

1990           2000            2010           2020
                *       *       *       *       *       *       *       *
          CCC CCA TCC CAG GAG GAG ATG ACC AAG AAC CAG GTC AGC CTG
          GGG GGT AGG GTC CTC CTC TAC TGG TTC TTG GTC CAG TCG GAC
          Pro Pro Ser Gln Glu Glu Met Thr Lys Asn Gln Val Ser Leu>
                               _FC-IgG4_                          >

2030           2040          2050            2060
                *       *       *       *       *       *       *       *
          ACC TGC CTG GTC AAA GGC TTC TAC CCC AGC GAC ATC GCC GTG
          TGG ACG GAC CAG TTT CCG AAG ATG GGG TCG CTG TAG CGG CAC
          Thr Cys Leu Val Lys Gly Phe Tyr Pro Ser Asp Ile Ala Val>
                               _FC-IgG4_                          >

2070            2080           2090            2100
              *       *       *       *       *       *       *       *       *
         GAG TGG GAG AGC AAT GGG CAG CCG GAG AAC AAC TAC AAG ACC
         CTC ACC CTC TCG TTA CCC GTC GGC CTC TTG TTG ATG TTC TGG
         Glu Trp Glu Ser Asn Gly Gln Pro Glu Asn Asn Tyr Lys Thr>
                              _FC-IgG4_                          >

2110            2120           2130             2140
          *       *       *       *       *       *       *       *
      ACG CCT CCC GTG CTG GAC TCC GAC GGC TCC TTC TTC CTC TAC
      TGC GGA GGG CAC GAC CTG AGG CTG CCG AGG AAG AAG GAG ATG
      Thr Pro Pro Val Leu Asp Ser Asp Gly Ser Phe Phe Leu Tyr>
                             _FC-IgG4_                          >

2150          2160           2170            2180            2190
        *       *       *       *       *       *       *       *       *
     AGC AGG CTA ACC GTG GAC AAG AGC AGG TGG CAG GAG GGG AAT
     TCG TCC GAT TGG CAC CTG TTC TCG TCC ACC GTC CTC CCC TTA
     Ser Arg Leu Thr Val Asp Lys Ser Arg Trp Gln Glu Gly Asn>
                            _FC-IgG4_                          >
```

Figure 45I

```
              2200                2210                2220                2230
       *        *        *         *         *         *         *         *
     GTC      TTC      TCA      TGC      TCC      GTG      ATG      CAT      GAG      GCT      CTG      CAC      AAC      CAC
     CAG      AAG      AGT      ACG      AGG      CAC      TAC      GTA      CTC      CGA      GAC      GTG      TTG      GTG
     Val      Phe      Ser      Cys      Ser      Val      Met      His      Glu      Ala      Leu      His      Asn      His>
                                         _____FC-IgG4_____>

2240                2250                2260                2270
       *        *        *         *         *         *         *         *
     TAC      ACA      CAG      AAG      AGC      CTC      TCC      CTG      TCT      CTG      GGT      AAA      TGA
     ATG      TGT      GTC      TTC      TCG      GAG      AGG      GAC      AGA      GAC      CCA      TTT      ACT
     Tyr      Thr      Gln      Lys      Ser      Leu      Ser      Leu      Ser      Leu      Gly      Lys      ***>
                                         _____FC-IgG4_____>
```

Figure 46A

```
              -60              -50              -40              -30
        *      *       *        *       *        *       *        *
      ATG    GTG     TGG      CTT     TGC      TCT     GGG      CTC     CTG     TTC     CCT     GTG     AGC     TGC
      TAC    CAC     ACC      GAA     ACG      AGA     CCC      GAG     GAC     AAG     GGA     CAC     TCG     ACG
      Met    Val     Trp      Leu     Cys      Ser     Gly      Leu     Leu     Phe     Pro     Val     Ser     Cys>
      _____SIGNAL PEPTIDE_____>
      _____IL4Rα_____

-20              -10               1               10
        *       *       *       *        *       *       *        *       *
      CTG    GTC     CTG     CTG     CAG      GTG     GCA     AGC      TCT     GGG     AAC     ATG     AAG     GTC
      GAC    CAG     GAC     GAC     GTC      CAC     CGT     TCG      AGA     CCC     TTG     TAC     TTC     CAG
      Leu    Val     Leu     Leu     Gln      Val     Ala     Ser      Ser     Gly     Asn     Met     Lys     Val>
      _____SIGNAL PEPTIDE_____>
      _____IL4Rα_____>

20              30              40               50
        *        *       *       *       *       *        *       *
      TTG     CAG      GAG     CCC     ACC     TGC     GTC      TCC     GAC     TAC     ATG     AGC     ATC     TCT
      AAC     GTC      CTC     GGG     TGG     ACG     CAG      AGG     CTG     ATG     TAC     TCG     TAG     AGA
      Leu     Gln      Glu     Pro     Thr     Cys     Val      Ser     Asp     Tyr     Met     Ser     Ile     Ser>
      _____IL4Rα_____>

60              70              80               90
        *       *        *       *       *       *        *       *
      ACT     TGC     GAG      TGG     AAG     ATG     AAT      GGT     CCC     ACC     AAT     TGC     AGC     ACC
      TGA     ACG     CTC      ACC     TTC     TAC     TTA      CCA     GGG     TGG     TTA     ACG     TCG     TGG
      Thr     Cys     Glu      Trp     Lys     Met     Asn      Gly     Pro     Thr     Asn     Cys     Ser     Thr>
      _____IL4Rα_____>

100              110             120              130              140
     *       *       *        *       *       *        *       *        *
   GAG     CTC     CGC      CTG     TTG     TAC     CAG      CTG     GTT     TTT     CTG     CTC     TCC     GAA
   CTC     GAG     GCG      GAC     AAC     ATG     GTC      GAC     CAA     AAA     GAC     GAG     AGG     CTT
   Glu     Leu     Arg      Leu     Leu     Tyr     Gln      Leu     Val     Phe     Leu     Leu     Ser     Glu>
   _____IL4Rα_____>

150             160              170              180
        *       *       *        *       *       *        *       *
      GCC     CAC     ACG      TGT     ATC     CCT     GAG      AAC     AAC     GGA     GGC     GCG     GGG     TGC
      CGG     GTG     TGC      ACA     TAG     GGA     CTC      TTG     TTG     CCT     CCG     CGC     CCC     ACG
      Ala     His     Thr      Cys     Ile     Pro     Glu      Asn     Asn     Gly     Gly     Ala     Gly     Cys>
      _____IL4Rα_____>

190             200              210              220
        *       *       *       *        *       *       *        *       *
      GTG    TGC     CAC     CTG     CTC      ATG     GAT     GAC      GTG     GTC     AGT     GCG     GAT     AAC
      CAC    ACG     GTG     GAC     GAG      TAC     CTA     CTG      CAC     CAG     TCA     CGC     CTA     TTG
      Val    Cys     His     Leu     Leu      Met     Asp     Asp      Val     Val     Ser     Ala     Asp     Asn>
      _____IL4Rα_____>
```

Figure 46B

```
        230             240             250             260
         *       *       *       *       *       *       *       *
   TAT ACA CTG GAC CTG TGG GCT GGG CAG CAG CTG CTG TGG AAG
   ATA TGT GAC CTG GAC ACC CGA CCC GTC GTC GAC GAC ACC TTC
   Tyr Thr Leu Asp Leu Trp Ala Gly Gln Gln Leu Leu Trp Lys>
   _____IL4Rα_____>

270             280             290             300
         *       *       *       *       *       *       *       *
   GGC TCC TTC AAG CCC AGC GAG CAT GTG AAA CCC AGG GCC CCA
   CCG AGG AAG TTC GGG TCG CTC GTA CAC TTT GGG TCC CGG GGT
   Gly Ser Phe Lys Pro Ser Glu His Val Lys Pro Arg Ala Pro>
   _____IL4Rα_____>

310             320             330             340             350
  *       *       *       *       *       *       *       *       *
   GGA AAC CTG ACA GTT CAC ACC AAT GTC TCC GAC ACT CTG CTG
   CCT TTG GAC TGT CAA GTG TGG TTA CAG AGG CTG TGA GAC GAC
   Gly Asn Leu Thr Val His Thr Asn Val Ser Asp Thr Leu Leu>
   _____IL4Rα_____>

360             370             380             390
         *       *       *       *       *       *       *       *
   CTG ACC TGG AGC AAC CCG TAT CCC CCT GAC AAT TAC CTG TAT
   GAC TGG ACC TCG TTG GGC ATA GGG GGA CTG TTA ATG GAC ATA
   Leu Thr Trp Ser Asn Pro Tyr Pro Pro Asp Asn Tyr Leu Tyr>
   _____IL4Rα_____>

400             410             420             430
         *       *       *       *       *       *       *       *
   AAT CAT CTC ACC TAT GCA GTC AAC ATT TGG AGT GAA AAC GAC
   TTA GTA GAG TGG ATA CGT CAG TTG TAA ACC TCA CTT TTG CTG
   Asn His Leu Thr Tyr Ala Val Asn Ile Trp Ser Glu Asn Asp>
   _____IL4Rα_____>

440             450             460             470
         *       *       *       *       *       *       *       *
   CCG GCA GAT TTC AGA ATC TAT AAC GTG ACC TAC CTA GAA CCC
   GGC CGT CTA AAG TCT TAG ATA TTG CAC TGG ATG GAT CTT GGG
   Pro Ala Asp Phe Arg Ile Tyr Asn Val Thr Tyr Leu Glu Pro>
   _____IL4Rα_____>

480             490             500             510
         *       *       *       *       *       *       *       *
   TCC CTC CGC ATC GCA GCC AGC ACC CTG AAG TCT GGG ATT TCC
   AGG GAG GCG TAG CGT CGG TCG TGG GAC TTC AGA CCC TAA AGG
   Ser Leu Arg Ile Ala Ala Ser Thr Leu Lys Ser Gly Ile Ser>
   _____IL4Rα_____>
```

Figure 46C

```
                                        >Mutation Cysteine to Serine
                                                       |
 520           530           540           550           560
  *     *      *     *      *     *      *     *      *
 TAC   AGG   GCA   CGC   GTA   CGG   GCC   TGG   GCT   CAG   AGC   TAT   AAC   ACC
 ATG   TCC   CGT   GCG   CAT   GCC   CGG   ACC   CGA   GTC   TCG   ATA   TTG   TGG
 Tyr   Arg   Ala   Arg   Val   Arg   Ala   Trp   Ala   Gln   Ser   Tyr   Asn   Thr>
 _____IL4Rα_____>

570           580           590           600
    *      *     *      *     *      *     *      *
 ACC   TGG   AGT   GAG   TGG   AGC   CCC   AGC   ACC   AAG   TGG   CAC   AAC   TCC
 TGG   ACC   TCA   CTC   ACC   TCG   GGG   TCG   TGG   TTC   ACC   GTG   TTG   AGG
 Thr   Trp   Ser   Glu   Trp   Ser   Pro   Ser   Thr   Lys   Trp   His   Asn   Ser>
 _____IL4Rα_____>

610           620           630           640
    *      *     *      *     *      *     *      *     *
 TAC   AGG   GAG   CCC   TTC   GAG   CAG   GCG   CCT   ACG   GAA   ACT   CAG   CCA
 ATG   TCC   CTC   GGG   AAG   CTC   GTC   CGC   GGA   TGC   CTT   TGA   GTC   GGT
 Tyr   Arg   Glu   Pro   Phe   Glu   Gln>
 _____IL4Rα_____>
                                       Ala   Pro   Thr   Glu   Thr   Gln   Pro>
                                       _____IL13Rα1_____>

>Mutation Cysteine to Serine
                                                       |
          650           660           670           680    |
    *      *     *      *     *      *     *      *  |   *
 CCT   GTG   ACA   AAT   TTG   AGT   GTC   TCT   GTT   GAA   AAC   CTC   AGC   ACA
 GGA   CAC   TGT   TTA   AAC   TCA   CAG   AGA   CAA   CTT   TTG   GAG   TCG   TGT
 Pro   Val   Thr   Asn   Leu   Ser   Val   Ser   Val   Glu   Asn   Leu   Ser   Thr>
 _____IL13Rα1_____>

690           700           710           720
   *     *      *     *      *     *      *     *
 GTA   ATA   TGG   ACA   TGG   AAT   CCA   CCC   GAG   GGA   GCC   AGC   TCA   AAT
 CAT   TAT   ACC   TGT   ACC   TTA   GGT   GGG   CTC   CCT   CGG   TCG   AGT   TTA
 Val   Ile   Trp   Thr   Trp   Asn   Pro   Pro   Glu   Gly   Ala   Ser   Ser   Asn>
 _____IL13Rα1_____>

730           740           750           760           770
   *     *      *     *      *     *      *     *      *
 TGT   AGT   CTA   TGG   TAT   TTT   AGT   CAT   TTT   GGC   GAC   AAA   CAA   GAT
 ACA   TCA   GAT   ACC   ATA   AAA   TCA   GTA   AAA   CCG   CTG   TTT   GTT   CTA
 Cys   Ser   Leu   Trp   Tyr   Phe   Ser   His   Phe   Gly   Asp   Lys   Gln   Asp>
 _____IL13Rα1_____>
```

Figure 46D

```
             780             790             800             810
         *    *    *    *    *    *    *    *
    AAG AAA ATA GCT CCG GAA ACT CGT CGT TCA ATA GAA GTA CCC
    TTC TTT TAT CGA GGC CTT TGA GCA GCA AGT TAT CTT CAT GGG
    Lys Lys Ile Ala Pro Glu Thr Arg Arg Ser Ile Glu Val Pro>
    _____IL13Rα1_____>

820             830             840             850
         *    *    *    *    *    *    *    *    *
    CTG AAT GAG AGG ATT TGT CTG CAA GTG GGG TCC CAG TGT AGC
    GAC TTA CTC TCC TAA ACA GAC GTT CAC CCC AGG GTC ACA TCG
    Leu Asn Glu Arg Ile Cys Leu Gln Val Gly Ser Gln Cys Ser>
    _____IL13Rα1_____>

860             870             880             890
       *    *    *    *    *    *    *    *
    ACC AAT GAG AGT GAG AAG CCT AGC ATT TTG GTT GAA AAA TGC
    TGG TTA CTC TCA CTC TTC GGA TCG TAA AAC CAA CTT TTT ACG
    Thr Asn Glu Ser Glu Lys Pro Ser Ile Leu Val Glu Lys Cys>
    _____IL13Rα1_____>

900             910             920             930
      *    *    *    *    *    *    *    *
    ATC TCA CCC CCA GAA GGT GAT CCT GAG TCT GCT GTG ACT GAG
    TAG AGT GGG GGT CTT CCA CTA GGA CTC AGA CGA CAC TGA CTC
    Ile Ser Pro Pro Glu Gly Asp Pro Glu Ser Ala Val Thr Glu>
    _____IL13Rα1_____>

940          950             960             970             980
      *    *    *    *    *    *    *    *    *
    CTT CAA TGC ATT TGG CAC AAC CTG AGC TAC ATG AAG TGT TCT
    GAA GTT ACG TAA ACC GTG TTG GAC TCG ATG TAC TTC ACA AGA
    Leu Gln Cys Ile Trp His Asn Leu Ser Tyr Met Lys Cys Ser>
    _____IL13Rα1_____>

990            1000            1010            1020
         *    *    *    *    *    *    *    *
    TGG CTC CCT GGA AGG AAT ACC AGT CCC GAC ACT AAC TAT ACT
    ACC GAG GGA CCT TCC TTA TGG TCA GGG CTG TGA TTG ATA TGA
    Trp Leu Pro Gly Arg Asn Thr Ser Pro Asp Thr Asn Tyr Thr>
    _____IL13Rα1_____>

1030            1040            1050            1060
         *    *    *    *    *    *    *    *    *
    CTC TAC TAT TGG CAC AGA AGC CTG GAA AAA ATT CAT CAA TGT
    GAG ATG ATA ACC GTG TCT TCG GAC CTT TTT TAA GTA GTT ACA
    Leu Tyr Tyr Trp His Arg Ser Leu Glu Lys Ile His Gln Cys>
    _____IL13Rα1_____>
```

Figure 46E

```
         1070          1080          1090          1100
           *       *     *       *     *       *     *       *
         GAA AAC ATC TTT AGA GAA GGC CAA TAC TTT GGT TGT TCC TTT
         CTT TTG TAG AAA TCT CTT CCG GTT ATG AAA CCA ACA AGG AAA
         Glu Asn Ile Phe Arg Glu Gly Gln Tyr Phe Gly Cys Ser Phe>
         _____IL13Rα1_____>

1110          1120          1130          1140
           *       *     *       *     *       *     *       *
         GAT CTG ACC AAA GTG AAG GAT TCC AGT TTT GAA CAA CAC AGT
         CTA GAC TGG TTT CAC TTC CTA AGG TCA AAA CTT GTT GTG TCA
         Asp Leu Thr Lys Val Lys Asp Ser Ser Phe Glu Gln His Ser>
         _____IL13Rα1_____>

1150          1160          1170          1180          1190
    *       *     *       *     *       *     *       *     *
  GTC CAA ATA ATG GTC AAG GAT AAT GCA GGA AAA ATT AAA CCA
  CAG GTT TAT TAC CAG TTC CTA TTA CGT CCT TTT TAA TTT GGT
  Val Gln Ile Met Val Lys Asp Asn Ala Gly Lys Ile Lys Pro>
  _____IL13Rα1_____>

1200          1210          1220          1230
                  *       *     *       *     *       *     *       *
                TCC TTC AAT ATA GTG CCT TTA ACT TCC CGT GTG AAA CCT GAT
                AGG AAG TTA TAT CAC GGA AAT TGA AGG GCA CAC TTT GGA CTA
                Ser Phe Asn Ile Val Pro Leu Thr Ser Arg Val Lys Pro Asp>
                _____IL13Rα1_____>

1240          1250          1260          1270
                  *       *     *       *     *       *     *       *
                CCT CCA CAT ATT AAA AAC CTC TCC TTC CAC AAT GAT GAC CTA
                GGA GGT GTA TAA TTT TTG GAG AGG AAG GTG TTA CTA CTG GAT
                Pro Pro His Ile Lys Asn Leu Ser Phe His Asn Asp Asp Leu>
                _____IL13Rα1_____>

1280          1290          1300          1310
                  *       *     *       *     *       *     *       *
                TAT GTG CAA TGG GAG AAT CCA CAG AAT TTT ATT AGC AGA TGC
                ATA CAC GTT ACC CTC TTA GGT GTC TTA AAA TAA TCG TCT ACG
                Tyr Val Gln Trp Glu Asn Pro Gln Asn Phe Ile Ser Arg Cys>
                _____IL13Rα1_____>

1320          1330          1340          1350
                  *       *     *       *     *       *     *       *
                CTA TTT TAT GAA GTA GAA GTC AAT AAC AGC CAA ACT GAG ACA
                GAT AAA ATA CTT CAT CTT CAG TTA TTG TCG GTT TGA CTC TGT
                Leu Phe Tyr Glu Val Glu Val Asn Asn Ser Gln Thr Glu Thr>
                _____IL13Rα1_____>
```

Figure 46F

```
          1360           1370           1380           1390           1400
           *      *       *      *       *      *       *      *       *
         CAT AAT GTT TTC TAC GTC CAA GAG GCT AAA TGT GAG AAT CCA
         GTA TTA CAA AAG ATG CAG GTT CTC CGA TTT ACA CTC TTA GGT
         His Asn Val Phe Tyr Val Gln Glu Ala Lys Cys Glu Asn Pro>
         _____IL13Rα1_____>

1410           1420           1430           1440
              *      *       *      *       *      *       *      *
            GAA TTT GAG AGA AAT GTG GAG AAT ACA TCT TGT TTC ATG GTC
            CTT AAA CTC TCT TTA CAC CTC TTA TGT AGA ACA AAG TAC CAG
            Glu Phe Glu Arg Asn Val Glu Asn Thr Ser Cys Phe Met Val>
            _____IL13Rα1_____>

1450           1460           1470           1480
                 *      *       *      *       *      *       *      *      *
               CCT GGT GTT CTT CCT GAT ACT TTG AAC ACA GTC AGA ATA AGA
               GGA CCA CAA GAA GGA CTA TGA AAC TTG TGT CAG TCT TAT TCT
               Pro Gly Val Leu Pro Asp Thr Leu Asn Thr Val Arg Ile Arg>
               _____IL13Rα1_____>

1490           1500           1510           1520
              *      *       *      *       *      *       *      *
            GTC AAA ACA AAT AAG TTA TGC TAT GAG GAT GAC AAA CTC TGG
            CAG TTT TGT TTA TTC AAT ACG ATA CTC CTA CTG TTT GAG ACC
            Val Lys Thr Asn Lys Leu Cys Tyr Glu Asp Asp Lys Leu Trp>
            _____IL13Rα1_____>

1530           1540           1550           1560
          *      *       *      *       *      *       *      *
        AGT AAT TGG AGC CAA GAA ATG AGT ATA GGT AAG AAG CGC AAT
        TCA TTA ACC TCG GTT CTT TAC TCA TAT CCA TTC TTC GCG TTA
        Ser Asn Trp Ser Gln Glu Met Ser Ile Gly Lys Lys Arg Asn>
        _____IL13Rα1_____>

1570           1580           1590           1600           1610
              *      *       *      *       *      *       *      *       *
            TCC ACC GGA GAG TCC AAA TAC GGT CCG CCA TGC CCA TCA TGC
            AGG TGG CCT CTC AGG TTT ATG CCA GGC GGT ACG GGT AGT ACG
            Ser Thr Gly Glu Ser Lys Tyr Gly Pro Pro Cys Pro Ser Cys>
            _____>
                 ___>
                       _____FC-IgG4_____>

1620           1630           1640           1650
                 *      *       *      *       *      *       *      *
               CCA GCA CCT GAG TTC CTG GGG GGA CCA TCA GTC TTC CTG TTC
               GGT CGT GGA CTC AAG GAC CCC CCT GGT AGT CAG AAG GAC AAG
               Pro Ala Pro Glu Phe Leu Gly Gly Pro Ser Val Phe Leu Phe>
               _____FC-IgG4_____>
```

Figure 46G

```
        1660                1670                1680                1690
     *         *         *         *         *         *         *         *         *
    CCC CCA AAA CCC AAG GAC ACT CTC ATG ATC TCC CGG ACC CCT
    GGG GGT TTT GGG TTC CTG TGA GAG TAC TAG AGG GCC TGG GGA
    Pro Pro Lys Pro Lys Asp Thr Leu Met Ile Ser Arg Thr Pro>
                              _FC-IgG4_                              >

1700                1710                1720                1730
     *         *         *         *         *         *         *         *
    GAG GTC ACG TGC GTG GTG GTG GAC GTG AGC CAG GAA GAC CCC
    CTC CAG TGC ACG CAC CAC CAC CTG CAC TCG GTC CTT CTG GGG
    Glu Val Thr Cys Val Val Val Asp Val Ser Gln Glu Asp Pro>
                              _FC-IgG4_                              >

1740                1750                1770                1770
     *         *         *    *         *         *         *         *
    GAG GTC CAG TTC AAC TGG TAC GTG GAT GGC GTG GAG GTG CAT
    CTC CAG GTC AAG TTG ACC ATG CAC CTA CCG CAC CTC CAC GTA
    Glu Val Gln Phe Asn Trp Tyr Val Asp Gly Val Glu Val His>
                              _FC-IgG4_                              >

1780                1790                1800                1810                1820
     *         *         *         *         *         *         *         *         *
    AAT GCC AAG ACA AAG CCG CGG GAG GAG CAG TTC AAC AGC ACG
    TTA CGG TTC TGT TTC GGC GCC CTC CTC GTC AAG TTG TCG TGC
    Asn Ala Lys Thr Lys Pro Arg Glu Glu Gln Phe Asn Ser Thr>
                              _FC-IgG4_                              >

1830                1840                1850                1860
         *         *         *         *         *         *         *         *
    TAC CGT GTG GTC AGC GTC CTC ACC GTC CTG CAC CAG GAC TGG
    ATG GCA CAC CAG TCG CAG GAG TGG CAG GAC GTG GTC CTG ACC
    Tyr Arg Val Val Ser Val Leu Thr Val Leu His Gln Asp Trp>
                              _FC-IgG4_                              >

1870                1880                1890                1900
         *         *         *         *         *         *         *         *         *
    CTG AAC GGC AAG GAG TAC AAG TGC AAG GTC TCC AAC AAA GGC
    GAC TTG CCG TTC CTC ATG TTC ACG TTC CAG AGG TTG TTT CCG
    Leu Asn Gly Lys Glu Tyr Lys Cys Lys Val Ser Asn Lys Gly>
                              _FC-IgG4_                              >

1910                1920                1930                1940
         *         *         *         *         *         *         *         *
    CTC CCG TCC TCC ATC GAG AAA ACC ATC TCC AAA GCC AAA GGG
    GAG GGC AGG AGG TAG CTC TTT TGG TAG AGG TTT CGG TTT CCC
    Leu Pro Ser Ser Ile Glu Lys Thr Ile Ser Lys Ala Lys Gly>
                              _FC-IgG4_                              >
```

Figure 46H

```
       1950              1960              1970              1980
         *         *       *         *       *         *       *         *
       CAG CCC CGA GAG CCA CAG GTG TAC ACC CTG CCC CCA TCC CAG
       GTC GGG GCT CTC GGT GTC CAC ATG TGG GAC GGG GGT AGG GTC
       Gln Pro Arg Glu Pro Gln Val Tyr Thr Leu Pro Pro Ser Gln>
                                  _FC-IgG4_____>

1990              2000              2010              2020              2030
         *         *       *         *       *         *       *         *       *
       GAG GAG ATG ACC AAG AAC CAG GTC AGC CTG ACC TGC CTG GTC
       CTC CTC TAC TGG TTC TTG GTC CAG TCG GAC TGG ACG GAC CAG
       Glu Glu Met Thr Lys Asn Gln Val Ser Leu Thr Cys Leu Val>
                                  _FC-IgG4_____>

2040              2050              2060              2070
            *       *         *       *         *       *         *       *
       AAA GGC TTC TAC CCC AGC GAC ATC GCC GTG GAG TGG GAG AGC
       TTT CCG AAG ATG GGG TCG CTG TAG CGG CAC CTC ACC CTC TCG
       Lys Gly Phe Tyr Pro Ser Asp Ile Ala Val Glu Trp Glu Ser>
                                  _FC-IgG4_____>

2080              2090              2100              2110
            *       *         *       *         *       *         *       *         *
       AAT GGG CAG CCG GAG AAC AAC TAC AAG ACC ACG CCT CCC GTG
       TTA CCC GTC GGC CTC TTG TTG ATG TTC TGG TGC GGA GGG CAC
       Asn Gly Gln Pro Glu Asn Asn Tyr Lys Thr Thr Pro Pro Val>
                                  _FC-IgG4_____>

2120              2130              2140              2150
            *       *         *       *         *       *         *       *
       CTG GAC TCC GAC GGC TCC TTC TTC CTC TAC AGC AGG CTA ACC
       GAC CTG AGG CTG CCG AGG AAG AAG GAG ATG TCG TCC GAT TGG
       Leu Asp Ser Asp Gly Ser Phe Phe Leu Tyr Ser Arg Leu Thr>
                                  _FC-IgG4_____>

2160              2170              2180              2190
            *       *         *       *         *       *         *
       GTG GAC AAG AGC AGG TGG CAG GAG GGG AAT GTC TTC TCA TGC
       CAC CTG TTC TCG TCC ACC GTC CTC CCC TTA CAG AAG AGT ACG
       Val Asp Lys Ser Arg Trp Gln Glu Gly Asn Val Phe Ser Cys>
                                  _FC-IgG4_____>

2200              2210              2220              2230              2240
         *         *       *         *       *         *       *         *       *
       TCC GTG ATG CAT GAG GCT CTG CAC AAC CAC TAC ACA CAG AAG
       AGG CAC TAC GTA CTC CGA GAC GTG TTG GTG ATG TGT GTC TTC
       Ser Val Met His Glu Ala Leu His Asn His Tyr Thr Gln Lys>
                                  _FC-IgG4_____>
```

Figure 46I

```
              2250              2260
       *       *       *       *       *
AGC    CTC    TCC    CTG    TCT    CTG    GGT    AAA    TGA
TCG    GAG    AGG    GAC    AGA    GAC    CCA    TTT    ACT
Ser    Leu    Ser    Leu    Ser    Leu    Gly    Lys    ***>
_____FC-IgG4_____>
```

Figure 47A

```
            -70              -60              -50              -40
        *     *     *     *     *     *     *     *
      ATG   GTG   TGG   CCG   GCG   CGG   CTC   TGC   GGG   CTG   TGG   GCG   CTG   CTG
      TAC   CAC   ACC   GGC   CGC   GCC   GAG   ACG   CCC   GAC   ACC   CGC   GAC   GAC
      Met   Val   Trp   Pro   Ala   Arg   Leu   Cys   Gly   Leu   Trp   Ala   Leu   Leu>
                              _____SIGNAL PEPTIDE_____>
                              _____IL13Rα1_____>

-30              -20              -10               1
        *     *     *     *     *     *     *     *     *
      CTC   TGC   GCC   GGC   GGC   GGG   GGC   GGG   GGC   GGG   GGC   GCC   GCG   CCT
      GAG   ACG   CGG   CCG   CCG   CCC   CCG   CCC   CCG   CCC   CCG   CGG   CGC   GGA
      Leu   Cys   Ala   Gly   Gly   Gly   Gly   Gly   Gly   Gly   Gly   Ala   Ala   Pro>
      ___d_____SIGNAL PEPTIDE_____>
                              _____IL13Rα1_____>

10               20               30               40
         *     *     *     *     *     *     *     *
      ACG   GAA   ACT   CAG   CCA   CCT   GTG   ACA   AAT   TTG   AGT   GTC   TCT   GTT
      TGC   CTT   TGA   GTC   GGT   GGA   CAC   TGT   TTA   AAC   TCA   CAG   AGA   CAA
      Thr   Glu   Thr   Gln   Pro   Pro   Val   Thr   Asn   Leu   Ser   Val   Ser   Val>
                              _____IL13Rα1_____>

>Mutation Cysteine to Serine
                 |
       50       |60               70               80               90
         *    *  |  *     *     *     *     *     *     *
      GAA   AAC   CTC   AGC   ACA   GTA   ATA   TGG   ACA   TGG   AAT   CCA   CCC   GAG
      CTT   TTG   GAG   TCG   TGT   CAT   TAT   ACC   TGT   ACC   TTA   GGT   GGG   CTC
      Glu   Asn   Leu   Ser   Thr   Val   Ile   Trp   Thr   Trp   Asn   Pro   Pro   Glu>
                              _____IL13Rα1_____>

100              110              120              130
         *     *     *     *     *     *     *     *
      GGA   GCC   AGC   TCA   AAT   TGT   AGT   CTA   TGG   TAT   TTT   AGT   CAT   TTT
      CCT   CGG   TCG   AGT   TTA   ACA   TCA   GAT   ACC   ATA   AAA   TCA   GTA   AAA
      Gly   Ala   Ser   Ser   Asn   Cys   Ser   Leu   Trp   Tyr   Phe   Ser   His   Phe>
                              _____IL13Rα1_____>

140              150              160              170
         *     *     *     *     *     *     *     *
      GGC   GAC   AAA   CAA   GAT   AAG   AAA   ATA   GCT   CCG   GAA   ACT   CGT   CGT
      CCG   CTG   TTT   GTT   CTA   TTC   TTT   TAT   CGA   GGC   CTT   TGA   GCA   GCA
      Gly   Asp   Lys   Gln   Asp   Lys   Lys   Ile   Ala   Pro   Glu   Thr   Arg   Arg>
                              _____IL13Rα1_____>
```

Figure 47B

```
          180              190            200              210
     *     *     *     *     *     *     *     *     *
    TCA   ATA   GAA   GTA   CCC   CTG   AAT   GAG   AGG   ATT   TGT   CTG   CAA   GTG
    AGT   TAT   CTT   CAT   GGG   GAC   TTA   CTC   TCC   TAA   ACA   GAC   GTT   CAC
    Ser   Ile   Glu   Val   Pro   Leu   Asn   Glu   Arg   Ile   Cys   Leu   Gln   Val>
                                    __IL13Rα1__                              >

220              230            240              250
     *     *     *     *     *     *     *     *
    GGG   TCC   CAG   TGT   AGC   ACC   AAT   GAG   AGT   GAG   AAG   CCT   AGC   ATT
    CCC   AGG   GTC   ACA   TCG   TGG   TTA   CTC   TCA   CTC   TTC   GGA   TCG   TAA
    Gly   Ser   Gln   Cys   Ser   Thr   Asn   Glu   Ser   Glu   Lys   Pro   Ser   Ile>
                                    __IL13Rα1__                              >

260             270            280              290               300
     *     *     *     *     *     *     *     *     *
    TTG   GTT   GAA   AAA   TGC   ATC   TCA   CCC   CCA   GAA   GGT   GAT   CCT   GAG
    AAC   CAA   CTT   TTT   ACG   TAG   AGT   GGG   GGT   CTT   CCA   CTA   GGA   CTC
    Leu   Val   Glu   Lys   Cys   Ile   Ser   Pro   Pro   Glu   Gly   Asp   Pro   Glu>
                                    __IL13Rα1__                              >

310              320            330            340
        *     *     *     *     *     *     *     *
    TCT   GCT   GTG   ACT   GAG   CTT   CAA   TGC   ATT   TGG   CAC   AAC   CTG   AGC
    AGA   CGA   CAC   TGA   CTC   GAA   GTT   ACG   TAA   ACC   GTG   TTG   GAC   TCG
    Ser   Ala   Val   Thr   Glu   Leu   Gln   Cys   Ile   Trp   His   Asn   Leu   Ser>
                                    __IL13Rα1__                              >

350              360            370            380
        *     *     *     *     *     *     *     *
    TAC   ATG   AAG   TGT   TCT   TGG   CTC   CCT   GGA   AGG   AAT   ACC   AGT   CCC
    ATG   TAC   TTC   ACA   AGA   ACC   GAG   GGA   CCT   TCC   TTA   TGG   TCA   GGG
    Tyr   Met   Lys   Cys   Ser   Trp   Leu   Pro   Gly   Arg   Asn   Thr   Ser   Pro>
                                    __IL13Rα1__                              >

390              400            410            420
        *     *     *     *     *     *     *     *     *
    GAC   ACT   AAC   TAT   ACT   CTC   TAC   TAT   TGG   CAC   AGA   AGC   CTG   GAA
    CTG   TGA   TTG   ATA   TGA   GAG   ATG   ATA   ACC   GTG   TCT   TCG   GAC   CTT
    Asp   Thr   Asn   Tyr   Thr   Leu   Tyr   Tyr   Trp   His   Arg   Ser   Leu   Glu>
                                    __IL13Rα1__                              >

430              440            450            460
        *     *     *     *     *     *     *     *
    AAA   ATT   CAT   CAA   TGT   GAA   AAC   ATC   TTT   AGA   GAA   GGC   CAA   TAC
    TTT   TAA   GTA   GTT   ACA   CTT   TTG   TAG   AAA   TCT   CTT   CCG   GTT   ATG
    Lys   Ile   His   Gln   Cys   Glu   Asn   Ile   Phe   Arg   Glu   Gly   Gln   Tyr>
                                    __IL13Rα1__                              >
```

Figure 47C

```
          470              480             490              500              510
            *        *       *       *       *       *       *       *       *
         TTT      GGT     TGT     TCC     TTT     GAT     CTG     ACC     AAA     GTG     AAG     GAT     TCC     AGT
         AAA      CCA     ACA     AGG     AAA     CTA     GAC     TGG     TTT     CAC     TTC     CTA     AGG     TCA
         Phe      Gly     Cys     Ser     Phe     Asp     Leu     Thr     Lys     Val     Lys     Asp     Ser     Ser>
         _____IL13Rα1_____>

520             530              540              550
                    *       *       *       *       *       *       *       *
                 TTT     GAA     CAA     CAC     AGT     GTC     CAA     ATA     ATG     GTC     AAG     GAT     AAT     GCA
                 AAA     CTT     GTT     GTG     TCA     CAG     GTT     TAT     TAC     CAG     TTC     CTA     TTA     CGT
                 Phe     Glu     Gln     His     Ser     Val     Gln     Ile     Met     Val     Lys     Asp     Asn     Ala>
                 _____IL13Rα1_____>

560             570              580              590
              *       *       *       *       *       *       *       *
           GGA     AAA     ATT     AAA     CCA     TCC     TTC     AAT     ATA     GTG     CCT     TTA     ACT     TCC
           CCT     TTT     TAA     TTT     GGT     AGG     AAG     TTA     TAT     CAC     GGA     AAT     TGA     AGG
           Gly     Lys     Ile     Lys     Pro     Ser     Phe     Asn     Ile     Val     Pro     Leu     Thr     Ser>
           _____IL13Rα1_____>

600             610              620              630
              *       *       *       *       *       *       *       *       *
           CGT     GTG     AAA     CCT     GAT     CCT     CCA     CAT     ATT     AAA     AAC     CTC     TCC     TTC
           GCA     CAC     TTT     GGA     CTA     GGA     GGT     GTA     TAA     TTT     TTG     GAG     AGG     AAG
           Arg     Val     Lys     Pro     Asp     Pro     Pro     His     Ile     Lys     Asn     Leu     Ser     Phe>
           _____IL13Rα1_____>

640             650              660              670
              *       *       *       *       *       *       *       *
           CAC     AAT     GAT     GAC     CTA     TAT     GTG     CAA     TGG     GAG     AAT     CCA     CAG     AAT
           GTG     TTA     CTA     CTG     GAT     ATA     CAC     GTT     ACC     CTC     TTA     GGT     GTC     TTA
           His     Asn     Asp     Asp     Leu     Tyr     Val     Gln     Trp     Glu     Asn     Pro     Gln     Asn>
           _____IL13Rα1_____>

680             690              700              710              720
            *       *       *       *       *       *       *       *       *
         TTT     ATT     AGC     AGA     TGC     CTA     TTT     TAT     GAA     GTA     GAA     GTC     AAT     AAC
         AAA     TAA     TCG     TCT     ACG     GAT     AAA     ATA     CTT     CAT     CTT     CAG     TTA     TTG
         Phe     Ile     Ser     Arg     Cys     Leu     Phe     Tyr     Glu     Val     Glu     Val     Asn     Asn>
         _____IL13Rα1_____>

730             740              750              760
                    *       *       *       *       *       *       *       *
                 AGC     CAA     ACT     GAG     ACA     CAT     AAT     GTT     TTC     TAC     GTC     CAA     GAG     GCT
                 TCG     GTT     TGA     CTC     TGT     GTA     TTA     CAA     AAG     ATG     CAG     GTT     CTC     CGA
                 Ser     Gln     Thr     Glu     Thr     His     Asn     Val     Phe     Tyr     Val     Gln     Glu     Ala>
                 _____IL13Rα1_____>
```

Figure 47D

```
         770              780              790              800
    *     *     *     *     *     *     *     *
AAA TGT GAG AAT CCA GAA TTT GAG AGA AAT GTG GAG AAT ACA
TTT ACA CTC TTA GGT CTT AAA CTC TCT TTA CAC CTC TTA TGT
Lys Cys Glu Asn Pro Glu Phe Glu Arg Asn Val Glu Asn Thr>
_____IL13Rα1_____>

810              820              830              840
    *     *     *     *     *     *     *     *     *
TCT TGT TTC ATG GTC CCT GGT GTT CTT CCT GAT ACT TTG AAC
AGA ACA AAG TAC CAG GGA CCA CAA GAA GGA CTA TGA AAC TTG
Ser Cys Phe Met Val Pro Gly Val Leu Pro Asp Thr Leu Asn>
_____IL13Rα1_____>

850              860              870              880
    *     *     *     *     *     *     *     *
ACA GTC AGA ATA AGA GTC AAA ACA AAT AAG TTA TGC TAT GAG
TGT CAG TCT TAT TCT CAG TTT TGT TTA TTC AAT ACG ATA CTC
Thr Val Arg Ile Arg Val Lys Thr Asn Lys Leu Cys Tyr Glu>
_____IL13Rα1_____>

890              900              910              920              930
    *     *     *     *     *     *     *     *     *
GAT GAC AAA CTC TGG AGT AAT TGG AGC CAA GAA ATG AGT ATA
CTA CTG TTT GAG ACC TCA TTA ACC TCG GTT CTT TAC TCA TAT
Asp Asp Lys Leu Trp Ser Asn Trp Ser Gln Glu Met Ser Ile>
_____IL13Rα1_____>

940              950              960              970
          *     *     *     *     *     *     *     *
       GGT AAG AAG CGC AAT TCC ACA GGG AAC ATG AAG GTC TTG CAG
       CCA TTC TTC GCG TTA AGG TGT CCC TTG TAC TTC CAG AAC GTC
                                       Gly Asn Met Lys Val Leu Gln>
                                       _____IL4Rα_____>
Gly Lys Lys Arg Asn Ser Thr>
_____IL13Rα1_____>

980              990             1000             1010
    *     *     *     *     *     *     *     *
GAG CCC ACC TGC GTC TCC GAC TAC ATG AGC ATC TCT ACT TGC
CTC GGG TGG ACG CAG AGG CTG ATG TAC TCG TAG AGA TGA ACG
Glu Pro Thr Cys Val Ser Asp Tyr Met Ser Ile Ser Thr Cys>
_____IL4Rα_____>

1020             1030             1040             1050
    *     *     *     *     *     *     *     *     *
GAG TGG AAG ATG AAT GGT CCC ACC AAT TGC AGC ACC GAG CTC
CTC ACC TTC TAC TTA CCA GGG TGG TTA ACG TCG TGG CTC GAG
Glu Trp Lys Met Asn Gly Pro Thr Asn Cys Ser Thr Glu Leu>
_____IL4Rα_____>
```

Figure 47E

```
        1060              1070              1080              1090
          *        *        *        *        *        *        *        *
        CGC      CTG      TTG      TAC      CAG      CTG      GTT      TTT      CTG      CTC      TCC      GAA      GCC      CAC
        GCG      GAC      AAC      ATG      GTC      GAC      CAA      AAA      GAC      GAG      AGG      CTT      CGG      GTG
        Arg      Leu      Leu      Tyr      Gln      Leu      Val      Phe      Leu      Leu      Ser      Glu      Ala      His>
                                                    _IL4Rα_____>

1100              1110              1120              1130              1140
  *        *        *        *        *        *        *        *        *        *
ACG      TGT      ATC      CCT      GAG      AAC      AAC      GGA      GGC      GCG      GGG      TGC      GTG      TGC
TGC      ACA      TAG      GGA      CTC      TTG      TTG      CCT      CCG      CGC      CCC      ACG      CAC      ACG
Thr      Cys      Ile      Pro      Glu      Asn      Asn      Gly      Gly      Ala      Gly      Cys      Val      Cys>
                                        _IL4Rα_____>

1150              1160              1170              1180
              *        *        *        *        *        *        *        *
            CAC      CTG      CTC      ATG      GAT      GAC      GTG      GTC      AGT      GCG      GAT      AAC      TAT      ACA
            GTG      GAC      GAG      TAC      CTA      CTG      CAC      CAG      TCA      CGC      CTA      TTG      ATA      TGT
            His      Leu      Leu      Met      Asp      Asp      Val      Val      Ser      Ala      Asp      Asn      Tyr      Thr>
                                            _IL4Rα_____>

1190              1200              1210              1220
                  *        *        *        *        *        *        *        *
                CTG      GAC      CTG      TGG      GCT      GGG      CAG      CAG      CTG      CTG      TGG      AAG      GGC      TCC
                GAC      CTG      GAC      ACC      CGA      CCC      GTC      GTC      GAC      GAC      ACC      TTC      CCG      AGG
                Leu      Asp      Leu      Trp      Ala      Gly      Gln      Gln      Leu      Leu      Trp      Lys      Gly      Ser>
                                                _IL4Rα_____>

1230              1240              1250              1260
              *        *        *        *        *        *        *        *        *
            TTC      AAG      CCC      AGC      GAG      CAT      GTG      AAA      CCC      AGG      GCC      CCA      GGA      AAC
            AAG      TTC      GGG      TCG      CTC      GTA      CAC      TTT      GGG      TCC      CGG      GGT      CCT      TTG
            Phe      Lys      Pro      Ser      Glu      His      Val      Lys      Pro      Arg      Ala      Pro      Gly      Asn>
                                            _IL4Rα_____>

1270              1280              1290              1300
          *        *        *        *        *        *        *        *
        CTG      ACA      GTT      CAC      ACC      AAT      GTC      TCC      GAC      ACT      CTG      CTG      CTG      ACC
        GAC      TGT      CAA      GTG      TGG      TTA      CAG      AGG      CTG      TGA      GAC      GAC      GAC      TGG
        Leu      Thr      Val      His      Thr      Asn      Val      Ser      Asp      Thr      Leu      Leu      Leu      Thr>
                                        _IL4Rα_____>

1310              1320              1330              1340              1350
  *        *        *        *        *        *        *        *        *        *
TGG      AGC      AAC      CCG      TAT      CCC      CCT      GAC      AAT      TAC      CTG      TAT      AAT      CAT
ACC      TCG      TTG      GGC      ATA      GGG      GGA      CTG      TTA      ATG      GAC      ATA      TTA      GTA
Trp      Ser      Asn      Pro      Tyr      Pro      Pro      Asp      Asn      Tyr      Leu      Tyr      Asn      His>
                                        _IL4Rα_____>
```

Figure 47F

```
         1360            1370           1380            1390
          *      *    *    *      *      *      *        *
        CTC ACC TAT GCA GTC AAC ATT TGG AGT GAA AAC GAC CCG GCA
        GAG TGG ATA CGT CAG TTG TAA ACC TCA CTT TTG CTG GGC CGT
        Leu Thr Tyr Ala Val Asn Ile Trp Ser Glu Asn Asp Pro Ala>
        _____IL4Rα_____>

1400            1410           1420            1430
          *      *    *    *      *      *      *        *
        GAT TTC AGA ATC TAT AAC GTG ACC TAC CTA GAA CCC TCC CTC
        CTA AAG TCT TAG ATA TTG CAC TGG ATG GAT CTT GGG AGG GAG
        Asp Phe Arg Ile Tyr Asn Val Thr Tyr Leu Glu Pro Ser Leu>
        _____IL4Rα_____>

1440            1450            1460           1470
           *      *      *      *      *      *      *      *
        CGC ATC GCA GCC AGC ACC CTG AAG TCT GGG ATT TCC TAC AGG
        GCG TAG CGT CGG TCG TGG GAC TTC AGA CCC TAA AGG ATG TCC
        Arg Ile Ala Ala Ser Thr Leu Lys Ser Gly Ile Ser Tyr Arg>
        _____IL4Rα_____>

>Mutation Cysteine to Serine
          1480        1490          1500  |       1510
           *     *     *      *      *    |  *      *      *
        GCA CGC GTA CGG GCC TGG GCT CAG AGC TAT AAC ACC ACC TGG
        CGT GCG CAT GCC CGG ACC CGA GTC TCG ATA TTG TGG TGG ACC
        Ala Arg Val Arg Ala Trp Ala Gln Ser Tyr Asn Thr Thr Trp>
        _____IL4Rα_____>

1520         1530          1540          1550         1560
        *     *      *      *      *      *      *      *     *
        AGT GAG TGG AGC CCC AGC ACC AAG TGG CAC AAC TCC TAC AGG
        TCA CTC ACC TCG GGG TCG TGG TTC ACC GTG TTG AGG ATG TCC
        Ser Glu Trp Ser Pro Ser Thr Lys Trp His Asn Ser Tyr Arg>
        _____IL4Rα_____>

1570           1580           1590          1600
              *      *      *      *      *      *      *      *
        GAG CCC TTC GAG CAG ACC GGA GAG TCC AAA TAC GGT CCG CCA
        CTC GGG AAG CTC GTC TGG CCT CTC AGG TTT ATG CCA GGC GGT
        Glu Pro Phe Glu Gln>
        _____IL4Rα_____>
                              Thr Gly>
                              _____>
                                      Glu Ser Lys Tyr Gly Pro Pro>
                                      _____FC-IgG4_____>
```

Figure 47G

```
           1610            1620            1630            1640
    *       *       *       *       *       *       *       *
   TGC     CCA     TCA     TGC     CCA     GCA     CCT     GAG     TTC     CTG     GGG     GGA     CCA     TCA
   ACG     GGT     AGT     ACG     GGT     CGT     GGA     CTC     AAG     GAC     CCC     CCT     GGT     AGT
   Cys     Pro     Ser     Cys     Pro     Ala     Pro     Glu     Phe     Leu     Gly     Gly     Pro     Ser>
                                          _____FC-IgG4_____>

1650            1660            1670            1680
    *       *       *       *       *       *       *       *       *
   GTC     TTC     CTG     TTC     CCC     CCA     AAA     CCC     AAG     GAC     ACT     CTC     ATG     ATC
   CAG     AAG     GAC     AAG     GGG     GGT     TTT     GGG     TTC     CTG     TGA     GAG     TAC     TAG
   Val     Phe     Leu     Phe     Pro     Pro     Lys     Pro     Lys     Asp     Thr     Leu     Met     Ile>
                                          _____FC-IgG4_____>

1690            1700            1710            1720
    *       *       *       *       *       *       *       *
   TCC     CGG     ACC     CCT     GAG     GTC     ACG     TGC     GTG     GTG     GTG     GAC     GTG     AGC
   AGG     GCC     TGG     GGA     CTC     CAG     TGC     ACG     CAC     CAC     CAC     CTG     CAC     TCG
   Ser     Arg     Thr     Pro     Glu     Val     Thr     Cys     Val     Val     Val     Asp     Val     Ser>
                                          _____FC-IgG4_____>

1730            1740            1750            1760            1770
    *       *       *       *       *       *       *       *       *
   CAG     GAA     GAC     CCC     GAG     GTC     CAG     TTC     AAC     TGG     TAC     GTG     GAT     GGC
   GTC     CTT     CTG     GGG     CTC     CAG     GTC     AAG     TTG     ACC     ATG     CAC     CTA     CCG
   Gln     Glu     Asp     Pro     Glu     Val     Gln     Phe     Asn     Trp     Tyr     Val     Asp     Gly>
                                          _____FC-IgG4_____>

1780            1790            1800            1810
    *       *       *       *       *       *       *       *
   GTG     GAG     GTG     CAT     AAT     GCC     AAG     ACA     AAG     CCG     CGG     GAG     GAG     CAG
   CAC     CTC     CAC     GTA     TTA     CGG     TTC     TGT     TTC     GGC     GCC     CTC     CTC     GTC
   Val     Glu     Val     His     Asn     Ala     Lys     Thr     Lys     Pro     Arg     Glu     Glu     Gln>
                                          _____FC-IgG4_____>

1820            1830            1840            1850
    *       *       *       *       *       *       *       *
   TTC     AAC     AGC     ACG     TAC     CGT     GTG     GTC     AGC     GTC     CTC     ACC     GTC     CTG
   AAG     TTG     TCG     TGC     ATG     GCA     CAC     CAG     TCG     CAG     GAG     TGG     CAG     GAC
   Phe     Asn     Ser     Thr     Tyr     Arg     Val     Val     Ser     Val     Leu     Thr     Val     Leu>
                                          _____FC-IgG4_____>

1860            1870            1880            1890
    *       *       *       *       *       *       *       *       *
   CAC     CAG     GAC     TGG     CTG     AAC     GGC     AAG     GAG     TAC     AAG     TGC     AAG     GTC
   GTG     GTC     CTG     ACC     GAC     TTG     CCG     TTC     CTC     ATG     TTC     ACG     TTC     CAG
   His     Gln     Asp     Trp     Leu     Asn     Gly     Lys     Glu     Tyr     Lys     Cys     Lys     Val>
                                          _____FC-IgG4_____>
```

Figure 47H

```
          1900          1910           1920           1930
            *       *       *       *       *       *       *       *
         TCC AAC AAA GGC CTC CCG TCC TCC ATC GAG AAA ACC ATC TCC
         AGG TTG TTT CCG GAG GGC AGG AGG TAG CTC TTT TGG TAG AGG
         Ser Asn Lys Gly Leu Pro Ser Ser Ile Glu Lys Thr Ile Ser>
         _____FC-IgG4_____>

1940          1950          1960           1970           1980
     *       *       *       *       *       *       *       *       *
   AAA GCC AAA GGG CAG CCC CGA GAG CCA CAG GTG TAC ACC CTG
   TTT CGG TTT CCC GTC GGG GCT CTC GGT GTC CAC ATG TGG GAC
   Lys Ala Lys Gly Gln Pro Arg Glu Pro Gln Val Tyr Thr Leu>
   _____FC-IgG4_____>

1990          2000          2010          2020
                 *       *       *       *       *       *       *       *
               CCC CCA TCC CAG GAG GAG ATG ACC AAG AAC CAG GTC AGC CTG
               GGG GGT AGG GTC CTC CTC TAC TGG TTC TTG GTC CAG TCG GAC
               Pro Pro Ser Gln Glu Glu Met Thr Lys Asn Gln Val Ser Leu>
               _____FC-IgG4_____>

2030          2040          2050          2060
                     *       *       *       *       *       *       *       *
                   ACC TGC CTG GTC AAA GGC TTC TAC CCC AGC GAC ATC GCC GTG
                   TGG ACG GAC CAG TTT CCG AAG ATG GGG TCG CTG TAG CGG CAC
                   Thr Cys Leu Val Lys Gly Phe Tyr Pro Ser Asp Ile Ala Val>
                   _____FC-IgG4_____>

2070          2080          2090          2100
                *       *       *       *       *       *       *       *       *
              GAG TGG GAG AGC AAT GGG CAG CCG GAG AAC AAC TAC AAG ACC
              CTC ACC CTC TCG TTA CCC GTC GGC CTC TTG TTG ATG TTC TGG
              Glu Trp Glu Ser Asn Gly Gln Pro Glu Asn Asn Tyr Lys Thr>
              _____FC-IgG4_____>

2110          2120          2130           2140
           *       *       *       *       *       *       *       *
         ACG CCT CCC GTG CTG GAC TCC GAC GGC TCC TTC TTC CTC TAC
         TGC GGA GGG CAC GAC CTG AGG CTG CCG AGG AAG AAG GAG ATG
         Thr Pro Pro Val Leu Asp Ser Asp Gly Ser Phe Phe Leu Tyr>
         _____FC-IgG4_____>

2150          2160          2170          2180          2190
     *       *       *       *       *       *       *       *       *
   AGC AGG CTA ACC GTG GAC AAG AGC AGG TGG CAG GAG GGG AAT
   TCG TCC GAT TGG CAC CTG TTC TCG TCC ACC GTC CTC CCC TTA
   Ser Arg Leu Thr Val Asp Lys Ser Arg Trp Gln Glu Gly Asn>
   _____FC-IgG4_____>
```

Figure 47I

```
          2200           2210           2220           2230
      *        *      *        *      *        *      *        *
GTC TTC TCA TGC TCC GTG ATG CAT GAG GCT CTG CAC AAC CAC
CAG AAG AGT ACG AGG CAC TAC GTA CTC CGA GAC GTG TTG GTG
Val Phe Ser Cys Ser Val Met His Glu Ala Leu His Asn His>
_____FC-IgG4_____>

2240           2250           2260           2270
      *        *      *        *      *        *      *        *
TAC ACA CAG AAG AGC CTC TCC CTG TCT CTG GGT AAA TGA
ATG TGT GTC TTC TCG GAG AGG GAC AGA GAC CCA TTT ACT
Tyr Thr Gln Lys Ser Leu Ser Leu Ser Leu Gly Lys ***>
_____FC-IgG4_____>
```

Figure 52A

```
               -70              -60              -50              -40
          *      *      *      *      *      *      *      *
       ATG GTG TGG CCG GCG CGG CTC TGC GGG CTG TGG GCG CTG CTG
       TAC CAC ACC GGC CGC GCC GAG ACG CCC GAC ACC CGC GAC GAC
       Met Val Trp Pro Ala Arg Leu Cys Gly Leu Trp Ala Leu Leu>
       _____SIGNAL PEPTIDE_____>
       _____IL13Rα1_____>

-30              -20              -10               1
          *      *      *      *      *      *      *      *      *
       CTC TGC GCC GGC GGC GGG GGC GGG GGC GGG GGC GCC GCG CCT
       GAG ACG CGG CCG CCG CCC CCG CCC CCG CCC CCG CGG CGC GGA
       Leu Cys Ala Gly Gly Gly Gly Gly Gly Gly Gly Ala Ala Pro>
       ___d_____SIGNAL PEPTIDE_____>
       _____IL13Rα1_____>

10              20              30              40
          *      *      *      *      *      *      *      *
       ACG GAA ACT CAG CCA CCT GTG ACA AAT TTG AGT GTC TCT GTT
       TGC CTT TGA GTC GGT GGA CAC TGT TTA AAC TCA CAG AGA CAA
       Thr Glu Thr Gln Pro Pro Val Thr Asn Leu Ser Val Ser Val>
       _____IL13Rα1_____>

>Mutation Cysteine to Alanine
                |
       50       |60              70              80              90
          *      *  |  *      *      *      *      *      *      *
       GAA AAC CTC GCG ACA GTA ATA TGG ACA TGG AAT CCA CCC GAG
       CTT TTG GAG CGC TGT CAT TAT ACC TGT ACC TTA GGT GGG CTC
       Glu Asn Leu Ala Thr Val Ile Trp Thr Trp Asn Pro Pro Glu>
       _____IL13Rα1_____>

100             110             120             130
          *      *      *      *      *      *      *      *
       GGA GCC AGC TCA AAT TGT AGT CTA TGG TAT TTT AGT CAT TTT
       CCT CGG TCG AGT TTA ACA TCA GAT ACC ATA AAA TCA GTA AAA
       Gly Ala Ser Ser Asn Cys Ser Leu Trp Tyr Phe Ser His Phe>
       _____IL13Rα1_____>

140             150             160             170
          *      *      *      *      *      *      *      *
       GGC GAC AAA CAA GAT AAG AAA ATA GCT CCG GAA ACT CGT CGT
       CCG CTG TTT GTT CTA TTC TTT TAT CGA GGC CTT TGA GCA GCA
       Gly Asp Lys Gln Asp Lys Lys Ile Ala Pro Glu Thr Arg Arg>
       _____IL13Rα1_____>
```

Figure 52B

```
         180            190           200            210
     *     *      *     *     *      *     *     *      *
   TCA   ATA   GAA   GTA   CCC   CTG   AAT   GAG   AGG   ATT   TGT   CTG   CAA   GTG
   AGT   TAT   CTT   CAT   GGG   GAC   TTA   CTC   TCC   TAA   ACA   GAC   GTT   CAC
   Ser   Ile   Glu   Val   Pro   Leu   Asn   Glu   Arg   Ile   Cys   Leu   Gln   Val>
   _____IL13Rα1_____>

220            230           240            250
     *     *      *     *     *      *     *     *
   GGG   TCC   CAG   TGT   AGC   ACC   AAT   GAG   AGT   GAG   AAG   CCT   AGC   ATT
   CCC   AGG   GTC   ACA   TCG   TGG   TTA   CTC   TCA   CTC   TTC   GGA   TCG   TAA
   Gly   Ser   Gln   Cys   Ser   Thr   Asn   Glu   Ser   Glu   Lys   Pro   Ser   Ile>
   _____IL13Rα1_____>

260            270           280            290           300
    *     *     *     *      *     *     *      *     *     *
  TTG   GTT   GAA   AAA   TGC   ATC   TCA   CCC   CCA   GAA   GGT   GAT   CCT   GAG
  AAC   CAA   CTT   TTT   ACG   TAG   AGT   GGG   GGT   CTT   CCA   CTA   GGA   CTC
  Leu   Val   Glu   Lys   Cys   Ile   Ser   Pro   Pro   Glu   Gly   Asp   Pro   Glu>
  _____IL13Rα1_____>

310            320           330            340
     *      *     *     *      *     *     *      *     *
   TCT   GCT   GTG   ACT   GAG   CTT   CAA   TGC   ATT   TGG   CAC   AAC   CTG   AGC
   AGA   CGA   CAC   TGA   CTC   GAA   GTT   ACG   TAA   ACC   GTG   TTG   GAC   TCG
   Ser   Ala   Val   Thr   Glu   Leu   Gln   Cys   Ile   Trp   His   Asn   Leu   Ser>
   _____IL13Rα1_____>

350            360           370            380
     *      *     *     *      *     *     *      *
   TAC   ATG   AAG   TGT   TCT   TGG   CTC   CCT   GGA   AGG   AAT   ACC   AGT   CCC
   ATG   TAC   TTC   ACA   AGA   ACC   GAG   GGA   CCT   TCC   TTA   TGG   TCA   GGG
   Tyr   Met   Lys   Cys   Ser   Trp   Leu   Pro   Gly   Arg   Asn   Thr   Ser   Pro>
   _____IL13Rα1_____>

390            400           410            420
     *      *     *     *      *     *     *      *     *
   GAC   ACT   AAC   TAT   ACT   CTC   TAC   TAT   TGG   CAC   AGA   AGC   CTG   GAA
   CTG   TGA   TTG   ATA   TGA   GAG   ATG   ATA   ACC   GTG   TCT   TCG   GAC   CTT
   Asp   Thr   Asn   Tyr   Thr   Leu   Tyr   Tyr   Trp   His   Arg   Ser   Leu   Glu>
   _____IL13Rα1_____>

430            440           450            460
     *      *     *     *      *     *     *      *
   AAA   ATT   CAT   CAA   TGT   GAA   AAC   ATC   TTT   AGA   GAA   GGC   CAA   TAC
   TTT   TAA   GTA   GTT   ACA   CTT   TTG   TAG   AAA   TCT   CTT   CCG   GTT   ATG
   Lys   Ile   His   Gln   Cys   Glu   Asn   Ile   Phe   Arg   Glu   Gly   Gln   Tyr>
   _____IL13Rα1_____>
```

Figure 52C

```
           470          480          490          500          510
            *     *      *     *      *     *      *     *      *
           TTT   GGT   TGT   TCC   TTT   GAT   CTG   ACC   AAA   GTG   AAG   GAT   TCC   AGT
           AAA   CCA   ACA   AGG   AAA   CTA   GAC   TGG   TTT   CAC   TTC   CTA   AGG   TCA
           Phe   Gly   Cys   Ser   Phe   Asp   Leu   Thr   Lys   Val   Lys   Asp   Ser   Ser>
           _____IL13Rα1_____>

520          530          540          550
                         *     *      *     *      *     *      *     *
                        TTT   GAA   CAA   CAC   AGT   GTC   CAA   ATA   ATG   GTC   AAG   GAT   AAT   GCA
                        AAA   CTT   GTT   GTG   TCA   CAG   GTT   TAT   TAC   CAG   TTC   CTA   TTA   CGT
                        Phe   Glu   Gln   His   Ser   Val   Gln   Ile   Met   Val   Lys   Asp   Asn   Ala>
                        _____IL13Rα1_____>

560          570          580          590
                         *     *      *     *      *     *      *     *
                        GGA   AAA   ATT   AAA   CCA   TCC   TTC   AAT   ATA   GTG   CCT   TTA   ACT   TCC
                        CCT   TTT   TAA   TTT   GGT   AGG   AAG   TTA   TAT   CAC   GGA   AAT   TGA   AGG
                        Gly   Lys   Ile   Lys   Pro   Ser   Phe   Asn   Ile   Val   Pro   Leu   Thr   Ser>
                        _____IL13Rα1_____>

600          610          620          630
               *     *      *     *      *     *      *     *      *
              CGT   GTG   AAA   CCT   GAT   CCT   CCA   CAT   ATT   AAA   AAC   CTC   TCC   TTC
              GCA   CAC   TTT   GGA   CTA   GGA   GGT   GTA   TAA   TTT   TTG   GAG   AGG   AAG
              Arg   Val   Lys   Pro   Asp   Pro   Pro   His   Ile   Lys   Asn   Leu   Ser   Phe>
              _____IL13Rα1_____>

640          650          660          670
                  *     *      *     *      *     *      *     *
                 CAC   AAT   GAT   GAC   CTA   TAT   GTG   CAA   TGG   GAG   AAT   CCA   CAG   AAT
                 GTG   TTA   CTA   CTG   GAT   ATA   CAC   GTT   ACC   CTC   TTA   GGT   GTC   TTA
                 His   Asn   Asp   Asp   Leu   Tyr   Val   Gln   Trp   Glu   Asn   Pro   Gln   Asn>
                 _____IL13Rα1_____>

680          690          700          710          720
            *     *      *     *      *     *      *     *      *
           TTT   ATT   AGC   AGA   TGC   CTA   TTT   TAT   GAA   GTA   GAA   GTC   AAT   AAC
           AAA   TAA   TCG   TCT   ACG   GAT   AAA   ATA   CTT   CAT   CTT   CAG   TTA   TTG
           Phe   Ile   Ser   Arg   Cys   Leu   Phe   Tyr   Glu   Val   Glu   Val   Asn   Asn>
           _____IL13Rα1_____>

730          740          750          760
                         *     *      *     *      *     *      *     *
                        AGC   CAA   ACT   GAG   ACA   CAT   AAT   GTT   TTC   TAC   GTC   CAA   GAG   GCT
                        TCG   GTT   TGA   CTC   TGT   GTA   TTA   CAA   AAG   ATG   CAG   GTT   CTC   CGA
                        Ser   Gln   Thr   Glu   Thr   His   Asn   Val   Phe   Tyr   Val   Gln   Glu   Ala>
                        _____IL13Rα1_____>
```

Figure 52D

```
           770            780            790            800
       *    *    *    *    *    *    *    *
      AAA  TGT  GAG  AAT  CCA  GAA  TTT  GAG  AGA  AAT  GTG  GAG  AAT  ACA
      TTT  ACA  CTC  TTA  GGT  CTT  AAA  CTC  TCT  TTA  CAC  CTC  TTA  TGT
      Lys  Cys  Glu  Asn  Pro  Glu  Phe  Glu  Arg  Asn  Val  Glu  Asn  Thr>
      _____IL13Rα1_____>

810            820            830            840
       *    *    *    *    *    *    *    *    *
      TCT  TGT  TTC  ATG  GTC  CCT  GGT  GTT  CTT  CCT  GAT  ACT  TTG  AAC
      AGA  ACA  AAG  TAC  CAG  GGA  CCA  CAA  GAA  GGA  CTA  TGA  AAC  TTG
      Ser  Cys  Phe  Met  Val  Pro  Gly  Val  Leu  Pro  Asp  Thr  Leu  Asn>
      _____IL13Rα1_____>

850            860            870            880
       *    *    *    *    *    *    *    *
      ACA  GTC  AGA  ATA  AGA  GTC  AAA  ACA  AAT  AAG  TTA  TGC  TAT  GAG
      TGT  CAG  TCT  TAT  TCT  CAG  TTT  TGT  TTA  TTC  AAT  ACG  ATA  CTC
      Thr  Val  Arg  Ile  Arg  Val  Lys  Thr  Asn  Lys  Leu  Cys  Tyr  Glu>
      _____IL13Rα1_____>

890            900            910            920            930
   *    *    *    *    *    *    *    *    *
  GAT  GAC  AAA  CTC  TGG  AGT  AAT  TGG  AGC  CAA  GAA  ATG  AGT  ATA
  CTA  CTG  TTT  GAG  ACC  TCA  TTA  ACC  TCG  GTT  CTT  TAC  TCA  TAT
  Asp  Asp  Lys  Leu  Trp  Ser  Asn  Trp  Ser  Gln  Glu  Met  Ser  Ile>
  _____IL13Rα1_____>

940            950            960            970
       *    *    *    *    *    *    *    *
      GGT  AAG  AAG  CGC  AAT  TCC  ACA  GGG  AAC  ATG  AAG  GTC  TTG  CAG
      CCA  TTC  TTC  GCG  TTA  AGG  TGT  CCC  TTG  TAC  TTC  CAG  AAC  GTC
                                      Gly  Asn  Met  Lys  Val  Leu  Gln>
                                      _____IL4Rα_____>
      Gly  Lys  Lys  Arg  Asn  Ser  Thr>
      _____IL13Rα1_____>

980            990            1000           1010
       *    *    *    *    *    *    *    *
      GAG  CCC  ACC  TGC  GTC  TCC  GAC  TAC  ATG  AGC  ATC  TCT  ACT  TGC
      CTC  GGG  TGG  ACG  CAG  AGG  CTG  ATG  TAC  TCG  TAG  AGA  TGA  ACG
      Glu  Pro  Thr  Cys  Val  Ser  Asp  Tyr  Met  Ser  Ile  Ser  Thr  Cys>
      _____IL4Rα_____>

1020           1030           1040           1050
       *    *    *    *    *    *    *    *    *
      GAG  TGG  AAG  ATG  AAT  GGT  CCC  ACC  AAT  TGC  AGC  ACC  GAG  CTC
      CTC  ACC  TTC  TAC  TTA  CCA  GGG  TGG  TTA  ACG  TCG  TGG  CTC  GAG
      Glu  Trp  Lys  Met  Asn  Gly  Pro  Thr  Asn  Cys  Ser  Thr  Glu  Leu>
      _____IL4Rα_____>
```

Figure 52E

```
         1060           1070           1080           1090
          *      *       *      *       *      *       *       *
         CGC    CTG    TTG    TAC    CAG    CTG    GTT    TTT    CTG    CTC    TCC    GAA    GCC    CAC
         GCG    GAC    AAC    ATG    GTC    GAC    CAA    AAA    GAC    GAG    AGG    CTT    CGG    GTG
         Arg    Leu    Leu    Tyr    Gln    Leu    Val    Phe    Leu    Leu    Ser    Glu    Ala    His>
         _____IL4Rα_____>

1100           1110           1120           1130           1140
  *      *       *      *       *      *       *      *       *
 ACG    TGT    ATC    CCT    GAG    AAC    AAC    GGA    GGC    GCG    GGG    TGC    GTG    TGC
 TGC    ACA    TAG    GGA    CTC    TTG    TTG    CCT    CCG    CGC    CCC    ACG    CAC    ACG
 Thr    Cys    Ile    Pro    Glu    Asn    Asn    Gly    Gly    Ala    Gly    Cys    Val    Cys>
         _____IL4Rα_____>

1150           1160           1170           1180
          *      *       *      *       *      *       *      *
         CAC    CTG    CTC    ATG    GAT    GAC    GTG    GTC    AGT    GCG    GAT    AAC    TAT    ACA
         GTG    GAC    GAG    TAC    CTA    CTG    CAC    CAG    TCA    CGC    CTA    TTG    ATA    TGT
         His    Leu    Leu    Met    Asp    Asp    Val    Val    Ser    Ala    Asp    Asn    Tyr    Thr>
         _____IL4Rα_____>

1190           1200           1210           1220
              *      *       *      *       *      *       *      *
             CTG    GAC    CTG    TGG    GCT    GGG    CAG    CAG    CTG    CTG    TGG    AAG    GGC    TCC
             GAC    CTG    GAC    ACC    CGA    CCC    GTC    GTC    GAC    GAC    ACC    TTC    CCG    AGG
             Leu    Asp    Leu    Trp    Ala    Gly    Gln    Gln    Leu    Leu    Trp    Lys    Gly    Ser>
             _____IL4Rα_____>

1230           1240           1250           1260
          *      *       *      *       *      *       *      *       *
         TTC    AAG    CCC    AGC    GAG    CAT    GTG    AAA    CCC    AGG    GCC    CCA    GGA    AAC
         AAG    TTC    GGG    TCG    CTC    GTA    CAC    TTT    GGG    TCC    CGG    GGT    CCT    TTG
         Phe    Lys    Pro    Ser    Glu    His    Val    Lys    Pro    Arg    Ala    Pro    Gly    Asn>
         _____IL4Rα_____>

1270           1280           1290           1300
                  *      *       *      *       *      *       *      *
                 CTG    ACA    GTT    CAC    ACC    AAT    GTC    TCC    GAC    ACT    CTG    CTG    CTG    ACC
                 GAC    TGT    CAA    GTG    TGG    TTA    CAG    AGG    CTG    TGA    GAC    GAC    GAC    TGG
                 Leu    Thr    Val    His    Thr    Asn    Val    Ser    Asp    Thr    Leu    Leu    Leu    Thr>
                 _____IL4Rα_____>

1310           1320           1330           1340           1350
          *      *       *      *       *      *       *      *       *
         TGG    AGC    AAC    CCG    TAT    CCC    CCT    GAC    AAT    TAC    CTG    TAT    AAT    CAT
         ACC    TCG    TTG    GGC    ATA    GGG    GGA    CTG    TTA    ATG    GAC    ATA    TTA    GTA
         Trp    Ser    Asn    Pro    Tyr    Pro    Pro    Asp    Asn    Tyr    Leu    Tyr    Asn    His>
         _____IL4Rα_____>
```

Figure 52F

```
             1360           1370           1380           1390
         *       *       *       *       *       *       *       *
       CTC ACC TAT GCA GTC AAC ATT TGG AGT GAA AAC GAC CCG GCA
       GAG TGG ATA CGT CAG TTG TAA ACC TCA CTT TTG CTG GGC CGT
       Leu Thr Tyr Ala Val Asn Ile Trp Ser Glu Asn Asp Pro Ala>
       _____IL4Rα_____>

1400           1410           1420           1430
         *       *       *       *       *       *       *       *
       GAT TTC AGA ATC TAT AAC GTG ACC TAC CTA GAA CCC TCC CTC
       CTA AAG TCT TAG ATA TTG CAC TGG ATG GAT CTT GGG AGG GAG
       Asp Phe Arg Ile Tyr Asn Val Thr Tyr Leu Glu Pro Ser Leu>
       _____IL4Rα_____>

1440           1450           1460           1470
         *       *       *       *       *       *       *       *
       CGC ATC GCA GCC AGC ACC CTG AAG TCT GGG ATT TCC TAC AGG
       GCG TAG CGT CGG TCG TGG GAC TTC AGA CCC TAA AGG ATG TCC
       Arg Ile Ala Ala Ser Thr Leu Lys Ser Gly Ile Ser Tyr Arg>
       _____IL4Rα_____>

>Mutation Cysteine to Serine
             1480           1490           1500  |        1510
         *       *       *       *       *    |    *       *       *
       GCA CGC GTA CGG GCC TGG GCT CAG AGC TAT AAC ACC ACC TGG
       CGT GCG CAT GCC CGG ACC CGA GTC TCG ATA TTG TGG TGG ACC
       Ala Arg Val Arg Ala Trp Ala Gln Ser Tyr Asn Thr Thr Trp>
       _____IL4Rα_____>

1520           1530           1540           1550           1560
     *       *       *       *       *       *       *       *       *
   AGT GAG TGG AGC CCC AGC ACC AAG TGG CAC AAC TCC TAC AGG
   TCA CTC ACC TCG GGG TCG TGG TTC ACC GTG TTG AGG ATG TCC
   Ser Glu Trp Ser Pro Ser Thr Lys Trp His Asn Ser Tyr Arg>
   _____IL4Rα_____>

1570           1580           1590           1600
         *       *       *       *       *       *       *       *
       GAG CCC TTC GAG CAG ACC GGA GAG TCC AAA TAC GGT CCG CCA
       CTC GGG AAG CTC GTC TGG CCT CTC AGG TTT ATG CCA GGC GGT
                                   Thr Gly Glu Ser Lys Tyr Gly Pro Pro>
                                   _____>
       Glu Pro Phe Glu Gln>
       _____IL4Rα_____>
                                         _____FC-IgG4_____>
```

Figure 52G

>Mutation Serine to Proline

```
            1610              1620              1630              1640
     *       |*        *        *        *        *        *        *
    TGC     CCA      CCA      TGC      CCA      GCA      CCT      GAG      TTC      CTG      GGG      GGA      CCA      TCA
    ACG     GGT      GGT      ACG      GGT      CGT      GGA      CTC      AAG      GAC      CCC      CCT      GGT      AGT
    Cys     Pro      Pro      Cys      Pro      Ala      Pro      Glu      Phe      Leu      Gly      Gly      Pro      Ser>
    _____FC-IgG4_____>

1650              1660              1670              1680
     *        *        *        *        *        *        *        *        *
    GTC     TTC      CTG      TTC      CCC      CCA      AAA      CCC      AAG      GAC      ACT      CTC      ATG      ATC
    CAG     AAG      GAC      AAG      GGG      GGT      TTT      GGG      TTC      CTG      TGA      GAG      TAC      TAG
    Val     Phe      Leu      Phe      Pro      Pro      Lys      Pro      Lys      Asp      Thr      Leu      Met      Ile>
    _____FC-IgG4_____>

1690              1700              1710              1720
     *        *        *        *        *        *        *        *
    TCC     CGG      ACC      CCT      GAG      GTC      ACG      TGC      GTG      GTG      GTG      GAC      GTG      AGC
    AGG     GCC      TGG      GGA      CTC      CAG      TGC      ACG      CAC      CAC      CAC      CTG      CAC      TCG
    Ser     Arg      Thr      Pro      Glu      Val      Thr      Cys      Val      Val      Val      Asp      Val      Ser>
    _____FC-IgG4_____>

1730              1740              1750              1760              1770
  *        *        *        *        *        *        *        *        *
 CAG     GAA      GAC      CCC      GAG      GTC      CAG      TTC      AAC      TGG      TAC      GTG      GAT      GGC
 GTC     CTT      CTG      GGG      CTC      CAG      GTC      AAG      TTG      ACC      ATG      CAC      CTA      CCG
 Gln     Glu      Asp      Pro      Glu      Val      Gln      Phe      Asn      Trp      Tyr      Val      Asp      Gly>
    _____FC-IgG4_____>

1780              1790              1800              1810
        *        *        *        *        *        *        *        *
    GTG     GAG      GTG      CAT      AAT      GCC      AAG      ACA      AAG      CCG      CGG      GAG      GAG      CAG
    CAC     CTC      CAC      GTA      TTA      CGG      TTC      TGT      TTC      GGC      GCC      CTC      CTC      GTC
    Val     Glu      Val      His      Asn      Ala      Lys      Thr      Lys      Pro      Arg      Glu      Glu      Gln>
    _____FC-IgG4_____>

1820              1830              1840              1850
     *        *        *        *        *        *        *        *
    TTC     AAC      AGC      ACG      TAC      CGT      GTG      GTC      AGC      GTC      CTC      ACC      GTC      CTG
    AAG     TTG      TCG      TGC      ATG      GCA      CAC      CAG      TCG      CAG      GAG      TGG      CAG      GAC
    Phe     Asn      Ser      Thr      Tyr      Arg      Val      Val      Ser      Val      Leu      Thr      Val      Leu>
    _____FC-IgG4_____>

1860              1870              1880              1890
     *        *        *        *        *        *        *        *        *
    CAC     CAG      GAC      TGG      CTG      AAC      GGC      AAG      GAG      TAC      AAG      TGC      AAG      GTC
    GTG     GTC      CTG      ACC      GAC      TTG      CCG      TTC      CTC      ATG      TTC      ACG      TTC      CAG
    His     Gln      Asp      Trp      Leu      Asn      Gly      Lys      Glu      Tyr      Lys      Cys      Lys      Val>
    _____FC-IgG4_____>
```

Figure 52H

```
      1900            1910           1920           1930
       *       *       *       *      *      *      *      *
      TCC AAC AAA GGC CTC CCG TCC TCC ATC GAG AAA ACC ATC TCC
      AGG TTG TTT CCG GAG GGC AGG AGG TAG CTC TTT TGG TAG AGG
      Ser Asn Lys Gly Leu Pro Ser Ser Ile Glu Lys Thr Ile Ser>
                                    _FC-IgG4_____>

1940           1950           1960           1970           1980
       *      *       *      *       *      *       *      *       *
      AAA GCC AAA GGG CAG CCC CGA GAG CCA CAG GTG TAC ACC CTG
      TTT CGG TTT CCC GTC GGG GCT CTC GGT GTC CAC ATG TGG GAC
      Lys Ala Lys Gly Gln Pro Arg Glu Pro Gln Val Tyr Thr Leu>
                                    _FC-IgG4_____>

1990           2000           2010           2020
       *       *       *      *       *      *       *      *
      CCC CCA TCC CAG GAG GAG ATG ACC AAG AAC CAG GTC AGC CTG
      GGG GGT AGG GTC CTC CTC TAC TGG TTC TTG GTC CAG TCG GAC
      Pro Pro Ser Gln Glu Glu Met Thr Lys Asn Gln Val Ser Leu>
                                    _FC-IgG4_____>

2030           2040           2050           2060
       *      *       *      *       *      *       *      *
      ACC TGC CTG GTC AAA GGC TTC TAC CCC AGC GAC ATC GCC GTG
      TGG ACG GAC CAG TTT CCG AAG ATG GGG TCG CTG TAG CGG CAC
      Thr Cys Leu Val Lys Gly Phe Tyr Pro Ser Asp Ile Ala Val>
                                    _FC-IgG4_____>

2070           2080           2090           2100
       *      *       *      *       *      *       *      *      *
      GAG TGG GAG AGC AAT GGG CAG CCG GAG AAC AAC TAC AAG ACC
      CTC ACC CTC TCG TTA CCC GTC GGC CTC TTG TTG ATG TTC TGG
      Glu Trp Glu Ser Asn Gly Gln Pro Glu Asn Asn Tyr Lys Thr>
                                    _FC-IgG4_____>

2110           2120           2130           2140
       *      *       *      *       *      *       *      *
      ACG CCT CCC GTG CTG GAC TCC GAC GGC TCC TTC TTC CTC TAC
      TGC GGA GGG CAC GAC CTG AGG CTG CCG AGG AAG AAG GAG ATG
      Thr Pro Pro Val Leu Asp Ser Asp Gly Ser Phe Phe Leu Tyr>
                                    _FC-IgG4_____>

2150           2160           2170           2180           2190
       *      *       *      *       *      *       *      *       *
      AGC AGG CTA ACC GTG GAC AAG AGC AGG TGG CAG GAG GGG AAT
      TCG TCC GAT TGG CAC CTG TTC TCG TCC ACC GTC CTC CCC TTA
      Ser Arg Leu Thr Val Asp Lys Ser Arg Trp Gln Glu Gly Asn>
                                    _FC-IgG4_____>
```

Figure 52I

```
          2200          2210          2220          2230
       *     *     *     *     *     *     *     *
GTC TTC TCA TGC TCC GTG ATG CAT GAG GCT CTG CAC AAC CAC
CAG AAG AGT ACG AGG CAC TAC GTA CTC CGA GAC GTG TTG GTG
Val Phe Ser Cys Ser Val Met His Glu Ala Leu His Asn His>
                          ____FC-IgG4_____>

2240          2250          2260          2270
       *     *     *     *     *     *     *     *
TAC ACA CAG AAG AGC CTC TCC CTG TCT CTG GGT AAA TGA
ATG TGT GTC TTC TCG GAG AGG GAC AGA GAC CCA TTT ACT
Tyr Thr Gln Lys Ser Leu Ser Leu Ser Leu Gly Lys ***>
                          ____FC-IgG4_____>
```

Figure 53A

```
              -60            -50            -40            -30
           *          *          *          *          *          *          *
ATG GTG TGG CTT TGC TCT GGG CTC CTG TTC CCT GTG AGC TGC
TAC CAC ACC GAA ACG AGA CCC GAG GAC AAG GGA CAC TCG ACG
Met Val Trp Leu Cys Ser Gly Leu Leu Phe Pro Val Ser Cys>
                     ___SIGNAL PEPTIDE_____>
            _____IL4Rα_____

-20            -10             1             10
           *          *          *          *          *          *          *          *
CTG GTC CTG CTG CAG GTG GCA AGC TCT GGG AAC ATG AAG GTC
GAC CAG GAC GAC GTC CAC CGT TCG AGA CCC TTG TAC TTC CAG
Leu Val Leu Leu Gln Val Ala Ser Ser Gly Asn Met Lys Val>
           ____SIGNAL PEPTIDE_____>
            _____IL4Rα_____>

20             30             40             50
           *          *          *          *          *          *          *          *
TTG CAG GAG CCC ACC TGC GTC TCC GAC TAC ATG AGC ATC TCT
AAC GTC CTC GGG TGG ACG CAG AGG CTG ATG TAC TCG TAG AGA
Leu Gln Glu Pro Thr Cys Val Ser Asp Tyr Met Ser Ile Ser>
                          _____IL4Rα_____>

60             70             80             90
           *          *          *          *          *          *          *          *
ACT TGC GAG TGG AAG ATG AAT GGT CCC ACC AAT TGC AGC ACC
TGA ACG CTC ACC TTC TAC TTA CCA GGG TGG TTA ACG TCG TGG
Thr Cys Glu Trp Lys Met Asn Gly Pro Thr Asn Cys Ser Thr>
                          _____IL4Rα_____>

100            110            120            130            140
           *          *          *          *          *          *          *          *          *
GAG CTC CGC CTG TTG TAC CAG CTG GTT TTT CTG CTC TCC GAA
CTC GAG GCG GAC AAC ATG GTC GAC CAA AAA GAC GAG AGG CTT
Glu Leu Arg Leu Leu Tyr Gln Leu Val Phe Leu Leu Ser Glu>
                          _____IL4Rα_____>

150            160            170            180
           *          *          *          *          *          *          *          *
GCC CAC ACG TGT ATC CCT GAG AAC AAC GGA GGC GCG GGG TGC
CGG GTG TGC ACA TAG GGA CTC TTG TTG CCT CCG CGC CCC ACG
Ala His Thr Cys Ile Pro Glu Asn Asn Gly Gly Ala Gly Cys>
                          _____IL4Rα_____>

190            200            210            220
           *          *          *          *          *          *          *          *          *
GTG TGC CAC CTG CTC ATG GAT GAC GTG GTC AGT GCG GAT AAC
CAC ACG GTG GAC GAG TAC CTA CTG CAC CAG TCA CGC CTA TTG
Val Cys His Leu Leu Met Asp Asp Val Val Ser Ala Asp Asn>
                          _____IL4Rα_____>
```

Figure 53B

```
          230                 240                 250                 260
           *         *         *         *         *         *         *         *
         TAT  ACA  CTG  GAC  CTG  TGG  GCT  GGG  CAG  CAG  CTG  CTG  TGG  AAG
         ATA  TGT  GAC  CTG  GAC  ACC  CGA  CCC  GTC  GTC  GAC  GAC  ACC  TTC
         Tyr  Thr  Leu  Asp  Leu  Trp  Ala  Gly  Gln  Gln  Leu  Leu  Trp  Lys>
         _____IL4Rα_____>

270                 280                 290                 300
           *         *         *         *         *         *         *         *
         GGC  TCC  TTC  AAG  CCC  AGC  GAG  CAT  GTG  AAA  CCC  AGG  GCC  CCA
         CCG  AGG  AAG  TTC  GGG  TCG  CTC  GTA  CAC  TTT  GGG  TCC  CGG  GGT
         Gly  Ser  Phe  Lys  Pro  Ser  Glu  His  Val  Lys  Pro  Arg  Ala  Pro>
         _____IL4Rα_____>

310                 320                 330                 340                 350
    *         *         *         *         *         *         *         *         *
  GGA  AAC  CTG  ACA  GTT  CAC  ACC  AAT  GTC  TCC  GAC  ACT  CTG  CTG
  CCT  TTG  GAC  TGT  CAA  GTG  TGG  TTA  CAG  AGG  CTG  TGA  GAC  GAC
  Gly  Asn  Leu  Thr  Val  His  Thr  Asn  Val  Ser  Asp  Thr  Leu  Leu>
  _____IL4Rα_____>

360                 370                 380                 390
           *         *         *         *         *         *         *         *
         CTG  ACC  TGG  AGC  AAC  CCG  TAT  CCC  CCT  GAC  AAT  TAC  CTG  TAT
         GAC  TGG  ACC  TCG  TTG  GGC  ATA  GGG  GGA  CTG  TTA  ATG  GAC  ATA
         Leu  Thr  Trp  Ser  Asn  Pro  Tyr  Pro  Pro  Asp  Asn  Tyr  Leu  Tyr>
         _____IL4Rα_____>

400                 410                 420                 430
     *         *         *         *         *         *         *         *         *
   AAT  CAT  CTC  ACC  TAT  GCA  GTC  AAC  ATT  TGG  AGT  GAA  AAC  GAC
   TTA  GTA  GAG  TGG  ATA  CGT  CAG  TTG  TAA  ACC  TCA  CTT  TTG  CTG
   Asn  His  Leu  Thr  Tyr  Ala  Val  Asn  Ile  Trp  Ser  Glu  Asn  Asp>
         _____IL4Rα_____>

440                 450                 460                 470
           *         *         *         *         *         *         *         *
         CCG  GCA  GAT  TTC  AGA  ATC  TAT  AAC  GTG  ACC  TAC  CTA  GAA  CCC
         GGC  CGT  CTA  AAG  TCT  TAG  ATA  TTG  CAC  TGG  ATG  GAT  CTT  GGG
         Pro  Ala  Asp  Phe  Arg  Ile  Tyr  Asn  Val  Thr  Tyr  Leu  Glu  Pro>
         _____IL4Rα_____>

480                 490                 500                 510
           *         *         *         *         *         *         *         *
         TCC  CTC  CGC  ATC  GCA  GCC  AGC  ACC  CTG  AAG  TCT  GGG  ATT  TCC
         AGG  GAG  GCG  TAG  CGT  CGG  TCG  TGG  GAC  TTC  AGA  CCC  TAA  AGG
         Ser  Leu  Arg  Ile  Ala  Ala  Ser  Thr  Leu  Lys  Ser  Gly  Ile  Ser>
         _____IL4Rα_____>
```

Figure 53C

```
                                            >Mutation Cysteine to Serine
                                                           |
520          530          540          550          560
 *    *       *    *       *    *       *    *       *    *
TAC  AGG  GCA  CGC  GTA  CGG  GCC  TGG  GCT  CAG  AGC  TAT  AAC  ACC
ATG  TCC  CGT  GCG  CAT  GCC  CGG  ACC  CGA  GTC  TCG  ATA  TTG  TGG
Tyr  Arg  Ala  Arg  Val  Arg  Ala  Trp  Ala  Gln  Ser  Tyr  Asn  Thr>
_____IL4Rα_____>

570          580          590          600
      *    *    *       *    *       *    *       *    *
     ACC  TGG  AGT  GAG  TGG  AGC  CCC  AGC  ACC  AAG  TGG  CAC  AAC  TCC
     TGG  ACC  TCA  CTC  ACC  TCG  GGG  TCG  TGG  TTC  ACC  GTG  TTG  AGG
     Thr  Trp  Ser  Glu  Trp  Ser  Pro  Ser  Thr  Lys  Trp  His  Asn  Ser>
     _____IL4Rα_____>

610          620          630          640
      *    *    *       *    *    *       *    *       *    *    *
     TAC  AGG  GAG  CCC  TTC  GAG  CAG  GCG  CCT  ACG  GAA  ACT  CAG  CCA
     ATG  TCC  CTC  GGG  AAG  CTC  GTC  CGC  GGA  TGC  CTT  TGA  GTC  GGT
     Tyr  Arg  Glu  Pro  Phe  Glu  Gln>
     _____IL4Rα_____>
                                         Ala  Pro  Thr  Glu  Thr  Gln  Pro>
                                         _____IL13Rα1_____>

>Mutation Cysteine to Serine
                                                              |
           650          660          670          680          |
      *    *    *       *    *    *       *    *    *       *  |   *
     CCT  GTG  ACA  AAT  TTG  AGT  GTC  TCT  GTT  GAA  AAC  CTC  AGC  ACA
     GGA  CAC  TGT  TTA  AAC  TCA  CAG  AGA  CAA  CTT  TTG  GAG  TCG  TGT
     Pro  Val  Thr  Asn  Leu  Ser  Val  Ser  Val  Glu  Asn  Leu  Ser  Thr>
     _____IL13Rα1_____>

690          700          710          720
 *    *       *    *    *       *    *       *    *
GTA  ATA  TGG  ACA  TGG  AAT  CCA  CCC  GAG  GGA  GCC  AGC  TCA  AAT
CAT  TAT  ACC  TGT  ACC  TTA  GGT  GGG  CTC  CCT  CGG  TCG  AGT  TTA
Val  Ile  Trp  Thr  Trp  Asn  Pro  Pro  Glu  Gly  Ala  Ser  Ser  Asn>
_____IL13Rα1_____>

730          740          750          760          770
 *    *    *       *    *    *       *    *    *       *    *    *
TGT  AGT  CTA  TGG  TAT  TTT  AGT  CAT  TTT  GGC  GAC  AAA  CAA  GAT
ACA  TCA  GAT  ACC  ATA  AAA  TCA  GTA  AAA  CCG  CTG  TTT  GTT  CTA
Cys  Ser  Leu  Trp  Tyr  Phe  Ser  His  Phe  Gly  Asp  Lys  Gln  Asp>
_____IL13Rα1_____>
```

Figure 53D

```
          780            790             800            810
     *     *      *      *      *      *      *      *
    AAG    AAA    ATA    GCT    CCG    GAA    ACT    CGT    CGT    TCA    ATA    GAA    GTA    CCC
    TTC    TTT    TAT    CGA    GGC    CTT    TGA    GCA    GCA    AGT    TAT    CTT    CAT    GGG
    Lys    Lys    Ile    Ala    Pro    Glu    Thr    Arg    Arg    Ser    Ile    Glu    Val    Pro>
    _____IL13Rα1_____>

820            830             840            850
     *     *      *      *      *      *      *      *      *
    CTG    AAT    GAG    AGG    ATT    TGT    CTG    CAA    GTG    GGG    TCC    CAG    TGT    AGC
    GAC    TTA    CTC    TCC    TAA    ACA    GAC    GTT    CAC    CCC    AGG    GTC    ACA    TCG
    Leu    Asn    Glu    Arg    Ile    Cys    Leu    Gln    Val    Gly    Ser    Gln    Cys    Ser>
    _____IL13Rα1_____>

860            870             880            890
     *     *      *      *      *      *      *      *
    ACC    AAT    GAG    AGT    GAG    AAG    CCT    AGC    ATT    TTG    GTT    GAA    AAA    TGC
    TGG    TTA    CTC    TCA    CTC    TTC    GGA    TCG    TAA    AAC    CAA    CTT    TTT    ACG
    Thr    Asn    Glu    Ser    Glu    Lys    Pro    Ser    Ile    Leu    Val    Glu    Lys    Cys>
    _____IL13Rα1_____>

900            910             920            930
     *      *      *      *      *      *      *      *
    ATC    TCA    CCC    CCA    GAA    GGT    GAT    CCT    GAG    TCT    GCT    GTG    ACT    GAG
    TAG    AGT    GGG    GGT    CTT    CCA    CTA    GGA    CTC    AGA    CGA    CAC    TGA    CTC
    Ile    Ser    Pro    Pro    Glu    Gly    Asp    Pro    Glu    Ser    Ala    Val    Thr    Glu>
    _____IL13Rα1_____>

940            950             960            970            980
 *      *      *      *      *      *      *      *      *
CTT    CAA    TGC    ATT    TGG    CAC    AAC    CTG    AGC    TAC    ATG    AAG    TGT    TCT
GAA    GTT    ACG    TAA    ACC    GTG    TTG    GAC    TCG    ATG    TAC    TTC    ACA    AGA
Leu    Gln    Cys    Ile    Trp    His    Asn    Leu    Ser    Tyr    Met    Lys    Cys    Ser>
_____IL13Rα1_____>

990            1000            1010           1020
     *     *      *      *      *      *      *      *
    TGG    CTC    CCT    GGA    AGG    AAT    ACC    AGT    CCC    GAC    ACT    AAC    TAT    ACT
    ACC    GAG    GGA    CCT    TCC    TTA    TGG    TCA    GGG    CTG    TGA    TTG    ATA    TGA
    Trp    Leu    Pro    Gly    Arg    Asn    Thr    Ser    Pro    Asp    Thr    Asn    Tyr    Thr>
    _____IL13Rα1_____>

1030           1040            1050           1060
     *     *      *      *      *      *      *      *      *
    CTC    TAC    TAT    TGG    CAC    AGA    AGC    CTG    GAA    AAA    ATT    CAT    CAA    TGT
    GAG    ATG    ATA    ACC    GTG    TCT    TCG    GAC    CTT    TTT    TAA    GTA    GTT    ACA
    Leu    Tyr    Tyr    Trp    His    Arg    Ser    Leu    Glu    Lys    Ile    His    Gln    Cys>
    _____IL13Rα1_____>
```

Figure 53E

```
           1070           1080           1090           1100
            *        *     *        *     *     *        *        *
           GAA  AAC  ATC  TTT  AGA  GAA  GGC  CAA  TAC  TTT  GGT  TGT  TCC  TTT
           CTT  TTG  TAG  AAA  TCT  CTT  CCG  GTT  ATG  AAA  CCA  ACA  AGG  AAA
           Glu  Asn  Ile  Phe  Arg  Glu  Gly  Gln  Tyr  Phe  Gly  Cys  Ser  Phe>
           _____IL13Rα1_____>

1110           1120           1130           1140
        *        *     *        *     *     *        *        *
       GAT  CTG  ACC  AAA  GTG  AAG  GAT  TCC  AGT  TTT  GAA  CAA  CAC  AGT
       CTA  GAC  TGG  TTT  CAC  TTC  CTA  AGG  TCA  AAA  CTT  GTT  GTG  TCA
       Asp  Leu  Thr  Lys  Val  Lys  Asp  Ser  Ser  Phe  Glu  Gln  His  Ser>
       _____IL13Rα1_____>

1150           1160           1170           1180           1190
    *       *      *        *     *        *     *        *        *
   GTC  CAA  ATA  ATG  GTC  AAG  GAT  AAT  GCA  GGA  AAA  ATT  AAA  CCA
   CAG  GTT  TAT  TAC  CAG  TTC  CTA  TTA  CGT  CCT  TTT  TAA  TTT  GGT
   Val  Gln  Ile  Met  Val  Lys  Asp  Asn  Ala  Gly  Lys  Ile  Lys  Pro>
   _____IL13Rα1_____>

1200           1210           1220           1230
            *        *     *        *     *     *        *        *
           TCC  TTC  AAT  ATA  GTG  CCT  TTA  ACT  TCC  CGT  GTG  AAA  CCT  GAT
           AGG  AAG  TTA  TAT  CAC  GGA  AAT  TGA  AGG  GCA  CAC  TTT  GGA  CTA
           Ser  Phe  Asn  Ile  Val  Pro  Leu  Thr  Ser  Arg  Val  Lys  Pro  Asp>
           _____IL13Rα1_____>

1240           1250           1260           1270
            *        *     *        *     *     *        *        *
           CCT  CCA  CAT  ATT  AAA  AAC  CTC  TCC  TTC  CAC  AAT  GAT  GAC  CTA
           GGA  GGT  GTA  TAA  TTT  TTG  GAG  AGG  AAG  GTG  TTA  CTA  CTG  GAT
           Pro  Pro  His  Ile  Lys  Asn  Leu  Ser  Phe  His  Asn  Asp  Asp  Leu>
           _____IL13Rα1_____>

1280           1290           1300           1310
            *        *     *        *     *     *        *        *
           TAT  GTG  CAA  TGG  GAG  AAT  CCA  CAG  AAT  TTT  ATT  AGC  AGA  TGC
           ATA  CAC  GTT  ACC  CTC  TTA  GGT  GTC  TTA  AAA  TAA  TCG  TCT  ACG
           Tyr  Val  Gln  Trp  Glu  Asn  Pro  Gln  Asn  Phe  Ile  Ser  Arg  Cys>
           _____IL13Rα1_____>

1320           1330           1340           1350
        *        *     *        *     *     *        *        *
       CTA  TTT  TAT  GAA  GTA  GAA  GTC  AAT  AAC  AGC  CAA  ACT  GAG  ACA
       GAT  AAA  ATA  CTT  CAT  CTT  CAG  TTA  TTG  TCG  GTT  TGA  CTC  TGT
       Leu  Phe  Tyr  Glu  Val  Glu  Val  Asn  Asn  Ser  Gln  Thr  Glu  Thr>
       _____IL13Rα1_____>
```

Figure 53F

```
         1360           1370           1380           1390           1400
           *      *       *      *       *      *       *      *       *
         CAT  AAT  GTT  TTC  TAC  GTC  CAA  GAG  GCT  AAA  TGT  GAG  AAT  CCA
         GTA  TTA  CAA  AAG  ATG  CAG  GTT  CTC  CGA  TTT  ACA  CTC  TTA  GGT
         His  Asn  Val  Phe  Tyr  Val  Gln  Glu  Ala  Lys  Cys  Glu  Asn  Pro>
         _____IL13Rα1_____>

1410           1420           1430           1440
                   *      *       *      *       *      *       *      *
                 GAA  TTT  GAG  AGA  AAT  GTG  GAG  AAT  ACA  TCT  TGT  TTC  ATG  GTC
                 CTT  AAA  CTC  TCT  TTA  CAC  CTC  TTA  TGT  AGA  ACA  AAG  TAC  CAG
                 Glu  Phe  Glu  Arg  Asn  Val  Glu  Asn  Thr  Ser  Cys  Phe  Met  Val>
                 _____IL13Rα1_____>

1450           1460           1470           1480
           *      *       *      *       *      *       *      *       *
         CCT  GGT  GTT  CTT  CCT  GAT  ACT  TTG  AAC  ACA  GTC  AGA  ATA  AGA
         GGA  CCA  CAA  GAA  GGA  CTA  TGA  AAC  TTG  TGT  CAG  TCT  TAT  TCT
         Pro  Gly  Val  Leu  Pro  Asp  Thr  Leu  Asn  Thr  Val  Arg  Ile  Arg>
         _____IL13Rα1_____>

1490           1500           1510           1520
                   *      *       *      *       *      *       *      *
                 GTC  AAA  ACA  AAT  AAG  TTA  TGC  TAT  GAG  GAT  GAC  AAA  CTC  TGG
                 CAG  TTT  TGT  TTA  TTC  AAT  ACG  ATA  CTC  CTA  CTG  TTT  GAG  ACC
                 Val  Lys  Thr  Asn  Lys  Leu  Cys  Tyr  Glu  Asp  Asp  Lys  Leu  Trp>
                 _____IL13Rα1_____>

1530           1540           1550           1560
           *      *       *      *       *      *       *      *
         AGT  AAT  TGG  AGC  CAA  GAA  ATG  AGT  ATA  GGT  AAG  AAG  CGC  AAT
         TCA  TTA  ACC  TCG  GTT  CTT  TAC  TCA  TAT  CCA  TTC  TTC  GCG  TTA
         Ser  Asn  Trp  Ser  Gln  Glu  Met  Ser  Ile  Gly  Lys  Lys  Arg  Asn>
         _____IL13Rα1_____>

>Mutation Serine to Proline
                 1570           1580           1590           1600    |    1610
                   *      *       *      *       *      *       *     |     *
                 TCC  ACC  GGA  GAG  TCC  AAA  TAC  GGT  CCG  CCA  TGC  CCA  CCA  TGC
                 AGG  TGG  CCT  CTC  AGG  TTT  ATG  CCA  GGC  GGT  ACG  GGT  GGT  ACG
                 Ser  Thr  Gly  Glu  Ser  Lys  Tyr  Gly  Pro  Pro  Cys  Pro  Pro  Cys>
                 _____>
                      ___>
                              _____FC-IgG4_____>
```

Figure 53G

```
            1620              1630              1640              1650
        *         *       *         *       *         *       *         *
     CCA GCA CCT GAG TTC CTG GGG GGA CCA TCA GTC TTC CTG TTC
     GGT CGT GGA CTC AAG GAC CCC CCT GGT AGT CAG AAG GAC AAG
     Pro Ala Pro Glu Phe Leu Gly Gly Pro Ser Val Phe Leu Phe>
     _____FC-IgG4_____>

1660              1670              1680              1690
        *         *       *         *       *         *       *         *       *
     CCC CCA AAA CCC AAG GAC ACT CTC ATG ATC TCC CGG ACC CCT
     GGG GGT TTT GGG TTC CTG TGA GAG TAC TAG AGG GCC TGG GGA
     Pro Pro Lys Pro Lys Asp Thr Leu Met Ile Ser Arg Thr Pro>
     _____FC-IgG4_____>

1700              1710              1720              1730
     *         *       *         *       *         *       *         *
     GAG GTC ACG TGC GTG GTG GTG GAC GTG AGC CAG GAA GAC CCC
     CTC CAG TGC ACG CAC CAC CAC CTG CAC TCG GTC CTT CTG GGG
     Glu Val Thr Cys Val Val Val Asp Val Ser Gln Glu Asp Pro>
     _____FC-IgG4_____>

1740              1750              1760              1770
     *         *       *         *       *         *       *         *
     GAG GTC CAG TTC AAC TGG TAC GTG GAT GGC GTG GAG GTG CAT
     CTC CAG GTC AAG TTG ACC ATG CAC CTA CCG CAC CTC CAC GTA
     Glu Val Gln Phe Asn Trp Tyr Val Asp Gly Val Glu Val His>
     _____FC-IgG4_____>

1780              1790              1800              1810              1820
     *         *       *         *       *         *       *         *       *
     AAT GCC AAG ACA AAG CCG CGG GAG GAG CAG TTC AAC AGC ACG
     TTA CGG TTC TGT TTC GGC GCC CTC CTC GTC AAG TTG TCG TGC
     Asn Ala Lys Thr Lys Pro Arg Glu Glu Gln Phe Asn Ser Thr>
     _____FC-IgG4_____>

1830              1840              1850              1860
        *         *       *         *       *         *       *         *
     TAC CGT GTG GTC AGC GTC CTC ACC GTC CTG CAC CAG GAC TGG
     ATG GCA CAC CAG TCG CAG GAG TGG CAG GAC GTG GTC CTG ACC
     Tyr Arg Val Val Ser Val Leu Thr Val Leu His Gln Asp Trp>
     _____FC-IgG4_____>

1870              1880              1890              1900
        *         *       *         *       *         *       *         *       *
     CTG AAC GGC AAG GAG TAC AAG TGC AAG GTC TCC AAC AAA GGC
     GAC TTG CCG TTC CTC ATG TTC ACG TTC CAG AGG TTG TTT CCG
     Leu Asn Gly Lys Glu Tyr Lys Cys Lys Val Ser Asn Lys Gly>
     _____FC-IgG4_____>
```

Figure 53H

```
        1910              1920              1930              1940
          *       *         *       *         *       *         *       *
       CTC CCG TCC TCC ATC GAG AAA ACC ATC TCC AAA GCC AAA GGG
       GAG GGC AGG AGG TAG CTC TTT TGG TAG AGG TTT CGG TTT CCC
       Leu Pro Ser Ser Ile Glu Lys Thr Ile Ser Lys Ala Lys Gly>
                             _____FC-IgG4_____>

1950              1960              1970              1980
          *       *         *       *         *       *         *
       CAG CCC CGA GAG CCA CAG GTG TAC ACC CTG CCC CCA TCC CAG
       GTC GGG GCT CTC GGT GTC CAC ATG TGG GAC GGG GGT AGG GTC
       Gln Pro Arg Glu Pro Gln Val Tyr Thr Leu Pro Pro Ser Gln>
                             _____FC-IgG4_____>

1990              2000              2010              2020              2030
     *       *         *       *         *       *         *       *         *
  GAG GAG ATG ACC AAG AAC CAG GTC AGC CTG ACC TGC CTG GTC
  CTC CTC TAC TGG TTC TTG GTC CAG TCG GAC TGG ACG GAC CAG
  Glu Glu Met Thr Lys Asn Gln Val Ser Leu Thr Cys Leu Val>
                        _____FC-IgG4_____>

2040              2050              2060              2070
             *       *         *       *         *       *         *       *
          AAA GGC TTC TAC CCC AGC GAC ATC GCC GTG GAG TGG GAG AGC
          TTT CCG AAG ATG GGG TCG CTG TAG CGG CAC CTC ACC CTC TCG
          Lys Gly Phe Tyr Pro Ser Asp Ile Ala Val Glu Trp Glu Ser>
                                _____FC-IgG4_____>

2080              2090              2100              2110
             *       *         *       *         *       *         *       *         *
          AAT GGG CAG CCG GAG AAC AAC TAC AAG ACC ACG CCT CCC GTG
          TTA CCC GTC GGC CTC TTG TTG ATG TTC TGG TGC GGA GGG CAC
          Asn Gly Gln Pro Glu Asn Asn Tyr Lys Thr Thr Pro Pro Val>
                                _____FC-IgG4_____>

2120              2130              2140              2150
             *       *         *       *         *       *         *       *
          CTG GAC TCC GAC GGC TCC TTC TTC CTC TAC AGC AGG CTA ACC
          GAC CTG AGG CTG CCG AGG AAG AAG GAG ATG TCG TCC GAT TGG
          Leu Asp Ser Asp Gly Ser Phe Phe Leu Tyr Ser Arg Leu Thr>
                                _____FC-IgG4_____>

2160              2170              2180              2190
          *       *         *       *         *       *         *       *
       GTG GAC AAG AGC AGG TGG CAG GAG GGG AAT GTC TTC TCA TGC
       CAC CTG TTC TCG TCC ACC GTC CTC CCC TTA CAG AAG AGT ACG
       Val Asp Lys Ser Arg Trp Gln Glu Gly Asn Val Phe Ser Cys>
                             _____FC-IgG4_____>
```

Figure 53I

```
    2200        2210        2220        2230        2240
     *     *     *     *     *     *     *     *     *
    TCC GTG ATG CAT GAG GCT CTG CAC AAC CAC TAC ACA CAG AAG
    AGG CAC TAC GTA CTC CGA GAC GTG TTG GTG ATG TGT GTC TTC
    Ser Val Met His Glu Ala Leu His Asn His Tyr Thr Gln Lys>
    _____FC-IgG4_____>

2250        2260
     *     *     *     *     *
    AGC CTC TCC CTG TCT CTG GGT AAA TGA
    TCG GAG AGG GAC AGA GAC CCA TTT ACT
    Ser Leu Ser Leu Ser Leu Gly Lys ***>
    _____FC-IgG4_____>
```

Figure 54A

```
           -70             -60              -50              -40
            *      *        *       *        *       *        *       *
        ATG GTG TGG CCG GCG CGG CTC TGC GGG CTG TGG GCG CTG CTG
        TAC CAC ACC GGC CGC GCC GAG ACG CCC GAC ACC CGC GAC GAC
        Met Val Trp Pro Ala Arg Leu Cys Gly Leu Trp Ala Leu Leu>
        _____SIGNAL PEPTIDE_____>
        _____IL13Rα1_____>

-30             -20              -10              1
            *      *        *       *        *       *        *       *      *
        CTC TGC GCC GGC GGC GGG GGC GGG GGC GGG GGC GCC GCG CCT
        GAG ACG CGG CCG CCG CCC CCG CCC CCG CCC CCG CGG CGC GGA
        Leu Cys Ala Gly Gly Gly Gly Gly Gly Gly Gly Ala Ala Pro>
        ___d_____SIGNAL PEPTIDE_____>
        _____IL13Rα1_____>

10              20              30               40
            *      *        *       *        *       *        *       *
        ACG GAA ACT CAG CCA CCT GTG ACA AAT TTG AGT GTC TCT GTT
        TGC CTT TGA GTC GGT GGA CAC TGT TTA AAC TCA CAG AGA CAA
        Thr Glu Thr Gln Pro Pro Val Thr Asn Leu Ser Val Ser Val>
                               _____IL13Rα1_____>

>Mutation Cysteine to Serine
                     |
          50        |60              70              80              90
           *      *  |  *       *     *       *      *       *        *
        GAA AAC CTC AGC ACA GTA ATA TGG ACA TGG AAT CCA CCC GAG
        CTT TTG GAG TCG TGT CAT TAT ACC TGT ACC TTA GGT GGG CTC
        Glu Asn Leu Ser Thr Val Ile Trp Thr Trp Asn Pro Pro Glu>
                                _____IL13Rα1_____>

100             110             120              130
           *      *       *       *       *       *        *       *
        GGA GCC AGC TCA AAT TGT AGT CTA TGG TAT TTT AGT CAT TTT
        CCT CGG TCG AGT TTA ACA TCA GAT ACC ATA AAA TCA GTA AAA
        Gly Ala Ser Ser Asn Cys Ser Leu Trp Tyr Phe Ser His Phe>
                                _____IL13Rα1_____>

140             150             160              170
           *       *       *      *       *        *       *       *
        GGC GAC AAA CAA GAT AAG AAA ATA GCT CCG GAA ACT CGT CGT
        CCG CTG TTT GTT CTA TTC TTT TAT CGA GGC CTT TGA GCA GCA
        Gly Asp Lys Gln Asp Lys Lys Ile Ala Pro Glu Thr Arg Arg>
                                _____IL13Rα1_____>
```

Figure 54B

```
       180            190           200            210
   *    *    *    *    *    *    *    *    *    *
  TCA  ATA  GAA  GTA  CCC  CTG  AAT  GAG  AGG  ATT  TGT  CTG  CAA  GTG
  AGT  TAT  CTT  CAT  GGG  GAC  TTA  CTC  TCC  TAA  ACA  GAC  GTT  CAC
  Ser  Ile  Glu  Val  Pro  Leu  Asn  Glu  Arg  Ile  Cys  Leu  Gln  Val>
  _____IL13Rα1_____>

220           230           240           250
        *    *    *    *    *    *    *    *    *
       GGG  TCC  CAG  TGT  AGC  ACC  AAT  GAG  AGT  GAG  AAG  CCT  AGC  ATT
       CCC  AGG  GTC  ACA  TCG  TGG  TTA  CTC  TCA  CTC  TTC  GGA  TCG  TAA
       Gly  Ser  Gln  Cys  Ser  Thr  Asn  Glu  Ser  Glu  Lys  Pro  Ser  Ile>
       _____IL13Rα1_____>

260           270            280           290           300
    *    *    *    *    *    *    *    *    *    *
   TTG  GTT  GAA  AAA  TGC  ATC  TCA  CCC  CCA  GAA  GGT  GAT  CCT  GAG
   AAC  CAA  CTT  TTT  ACG  TAG  AGT  GGG  GGT  CTT  CCA  CTA  GGA  CTC
   Leu  Val  Glu  Lys  Cys  Ile  Ser  Pro  Pro  Glu  Gly  Asp  Pro  Glu>
   _____IL13Rα1_____>

310           320           330           340
         *    *    *    *    *    *    *    *    *
        TCT  GCT  GTG  ACT  GAG  CTT  CAA  TGC  ATT  TGG  CAC  AAC  CTG  AGC
        AGA  CGA  CAC  TGA  CTC  GAA  GTT  ACG  TAA  ACC  GTG  TTG  GAC  TCG
        Ser  Ala  Val  Thr  Glu  Leu  Gln  Cys  Ile  Trp  His  Asn  Leu  Ser>
        _____IL13Rα1_____>

350           360           370           380
        *    *    *    *    *    *    *    *
       TAC  ATG  AAG  TGT  TCT  TGG  CTC  CCT  GGA  AGG  AAT  ACC  AGT  CCC
       ATG  TAC  TTC  ACA  AGA  ACC  GAG  GGA  CCT  TCC  TTA  TGG  TCA  GGG
       Tyr  Met  Lys  Cys  Ser  Trp  Leu  Pro  Gly  Arg  Asn  Thr  Ser  Pro>
       _____IL13Rα1_____>

390           400           410           420
        *    *    *    *    *    *    *    *    *
       GAC  ACT  AAC  TAT  ACT  CTC  TAC  TAT  TGG  CAC  AGA  AGC  CTG  GAA
       CTG  TGA  TTG  ATA  TGA  GAG  ATG  ATA  ACC  GTG  TCT  TCG  GAC  CTT
       Asp  Thr  Asn  Tyr  Thr  Leu  Tyr  Tyr  Trp  His  Arg  Ser  Leu  Glu>
       _____IL13Rα1_____>

430           440           450           460
    *    *    *    *    *    *    *    *
   AAA  ATT  CAT  CAA  TGT  GAA  AAC  ATC  TTT  AGA  GAA  GGC  CAA  TAC
   TTT  TAA  GTA  GTT  ACA  CTT  TTG  TAG  AAA  TCT  CTT  CCG  GTT  ATG
   Lys  Ile  His  Gln  Cys  Glu  Asn  Ile  Phe  Arg  Glu  Gly  Gln  Tyr>
   _____IL13Rα1_____>
```

Figure 54C

```
       470         480         490         500         510
    *    *    *    *    *    *    *    *    *
   TTT  GGT  TGT  TCC  TTT  GAT  CTG  ACC  AAA  GTG  AAG  GAT  TCC  AGT
   AAA  CCA  ACA  AGG  AAA  CTA  GAC  TGG  TTT  CAC  TTC  CTA  AGG  TCA
   Phe  Gly  Cys  Ser  Phe  Asp  Leu  Thr  Lys  Val  Lys  Asp  Ser  Ser>
   _____IL13Rα1_____>

520         530         540         550
         *    *    *    *    *    *    *    *
   TTT  GAA  CAA  CAC  AGT  GTC  CAA  ATA  ATG  GTC  AAG  GAT  AAT  GCA
   AAA  CTT  GTT  GTG  TCA  CAG  GTT  TAT  TAC  CAG  TTC  CTA  TTA  CGT
   Phe  Glu  Gln  His  Ser  Val  Gln  Ile  Met  Val  Lys  Asp  Asn  Ala>
   _____IL13Rα1_____>

560         570         580         590
         *    *    *    *    *    *    *    *
   GGA  AAA  ATT  AAA  CCA  TCC  TTC  AAT  ATA  GTG  CCT  TTA  ACT  TCC
   CCT  TTT  TAA  TTT  GGT  AGG  AAG  TTA  TAT  CAC  GGA  AAT  TGA  AGG
   Gly  Lys  Ile  Lys  Pro  Ser  Phe  Asn  Ile  Val  Pro  Leu  Thr  Ser>
   _____IL13Rα1_____>

600         610         620         630
         *    *    *    *    *    *    *    *    *
   CGT  GTG  AAA  CCT  GAT  CCT  CCA  CAT  ATT  AAA  AAC  CTC  TCC  TTC
   GCA  CAC  TTT  GGA  CTA  GGA  GGT  GTA  TAA  TTT  TTG  GAG  AGG  AAG
   Arg  Val  Lys  Pro  Asp  Pro  Pro  His  Ile  Lys  Asn  Leu  Ser  Phe>
   _____IL13Rα1_____>

640         650         660         670
      *    *    *    *    *    *    *    *
   CAC  AAT  GAT  GAC  CTA  TAT  GTG  CAA  TGG  GAG  AAT  CCA  CAG  AAT
   GTG  TTA  CTA  CTG  GAT  ATA  CAC  GTT  ACC  CTC  TTA  GGT  GTC  TTA
   His  Asn  Asp  Asp  Leu  Tyr  Val  Gln  Trp  Glu  Asn  Pro  Gln  Asn>
   _____IL13Rα1_____>

680         690         700         710         720
    *    *    *    *    *    *    *    *    *    *
   TTT  ATT  AGC  AGA  TGC  CTA  TTT  TAT  GAA  GTA  GAA  GTC  AAT  AAC
   AAA  TAA  TCG  TCT  ACG  GAT  AAA  ATA  CTT  CAT  CTT  CAG  TTA  TTG
   Phe  Ile  Ser  Arg  Cys  Leu  Phe  Tyr  Glu  Val  Glu  Val  Asn  Asn>
   _____IL13Rα1_____>

730         740         750         760
         *    *    *    *    *    *    *    *
   AGC  CAA  ACT  GAG  ACA  CAT  AAT  GTT  TTC  TAC  GTC  CAA  GAG  GCT
   TCG  GTT  TGA  CTC  TGT  GTA  TTA  CAA  AAG  ATG  CAG  GTT  CTC  CGA
   Ser  Gln  Thr  Glu  Thr  His  Asn  Val  Phe  Tyr  Val  Gln  Glu  Ala>
   _____IL13Rα1_____>
```

Figure 54D

```
              770           780           790           800
         *     *     *     *     *     *     *     *
        AAA   TGT   GAG   AAT   CCA   GAA   TTT   GAG   AGA   AAT   GTG   GAG   AAT   ACA
        TTT   ACA   CTC   TTA   GGT   CTT   AAA   CTC   TCT   TTA   CAC   CTC   TTA   TGT
        Lys   Cys   Glu   Asn   Pro   Glu   Phe   Glu   Arg   Asn   Val   Glu   Asn   Thr>
        _____IL13Rα1_____>

810           820           830           840
         *     *     *     *     *     *     *     *     *
        TCT   TGT   TTC   ATG   GTC   CCT   GGT   GTT   CTT   CCT   GAT   ACT   TTG   AAC
        AGA   ACA   AAG   TAC   CAG   GGA   CCA   CAA   GAA   GGA   CTA   TGA   AAC   TTG
        Ser   Cys   Phe   Met   Val   Pro   Gly   Val   Leu   Pro   Asp   Thr   Leu   Asn>
        _____IL13Rα1_____>

850           860           870           880
         *     *     *     *     *     *     *     *     *
        ACA   GTC   AGA   ATA   AGA   GTC   AAA   ACA   AAT   AAG   TTA   TGC   TAT   GAG
        TGT   CAG   TCT   TAT   TCT   CAG   TTT   TGT   TTA   TTC   AAT   ACG   ATA   CTC
        Thr   Val   Arg   Ile   Arg   Val   Lys   Thr   Asn   Lys   Leu   Cys   Tyr   Glu>
        _____IL13Rα1_____>

890           900           910           920           930
         *     *     *     *     *     *     *     *     *
        GAT   GAC   AAA   CTC   TGG   AGT   AAT   TGG   AGC   CAA   GAA   ATG   AGT   ATA
        CTA   CTG   TTT   GAG   ACC   TCA   TTA   ACC   TCG   GTT   CTT   TAC   TCA   TAT
        Asp   Asp   Lys   Leu   Trp   Ser   Asn   Trp   Ser   Gln   Glu   Met   Ser   Ile>
        _____IL13Rα1_____>

940           950           960           970
         *     *     *     *     *     *     *     *
        GGT   AAG   AAG   CGC   AAT   TCC   ACA   GGG   AAC   ATG   AAG   GTC   TTG   CAG
        CCA   TTC   TTC   GCG   TTA   AGG   TGT   CCC   TTG   TAC   TTC   CAG   AAC   GTC
                                                Gly   Asn   Met   Lys   Val   Leu   Gln>
                                                _____IL4Rα_____>

Gly   Lys   Lys   Arg   Asn   Ser   Thr>
        _____IL13Rα1_____>

980           990           1000          1010
         *     *     *     *     *     *     *     *
        GAG   CCC   ACC   TGC   GTC   TCC   GAC   TAC   ATG   AGC   ATC   TCT   ACT   TGC
        CTC   GGG   TGG   ACG   CAG   AGG   CTG   ATG   TAC   TCG   TAG   AGA   TGA   ACG
        Glu   Pro   Thr   Cys   Val   Ser   Asp   Tyr   Met   Ser   Ile   Ser   Thr   Cys>
        _____IL4Rα_____>

1020          1030          1040          1050
         *     *     *     *     *     *     *     *     *
        GAG   TGG   AAG   ATG   AAT   GGT   CCC   ACC   AAT   TGC   AGC   ACC   GAG   CTC
        CTC   ACC   TTC   TAC   TTA   CCA   GGG   TGG   TTA   ACG   TCG   TGG   CTC   GAG
        Glu   Trp   Lys   Met   Asn   Gly   Pro   Thr   Asn   Cys   Ser   Thr   Glu   Leu>
        _____IL4Rα_____>
```

Figure 54E

```
         1060           1070           1080           1090
           *         *    *         *    *         *    *         *
         CGC CTG TTG TAC CAG CTG GTT TTT CTG CTC TCC GAA GCC CAC
         GCG GAC AAC ATG GTC GAC CAA AAA GAC GAG AGG CTT CGG GTG
         Arg Leu Leu Tyr Gln Leu Val Phe Leu Leu Ser Glu Ala His>
         _____IL4Rα_____>

1100           1110           1120           1130           1140
      *         *    *         *    *         *    *         *    *
    ACG TGT ATC CCT GAG AAC AAC GGA GGC GCG GGG TGC GTG TGC
    TGC ACA TAG GGA CTC TTG TTG CCT CCG CGC CCC ACG CAC ACG
    Thr Cys Ile Pro Glu Asn Asn Gly Gly Ala Gly Cys Val Cys>
    _____IL4Rα_____>

1150           1160           1170           1180
                 *         *    *         *    *         *    *         *
               CAC CTG CTC ATG GAT GAC GTG GTC AGT GCG GAT AAC TAT ACA
               GTG GAC GAG TAC CTA CTG CAC CAG TCA CGC CTA TTG ATA TGT
               His Leu Leu Met Asp Asp Val Val Ser Ala Asp Asn Tyr Thr>
               _____IL4Rα_____>

1190           1200           1210           1220
            *         *    *         *    *         *    *         *
          CTG GAC CTG TGG GCT GGG CAG CAG CTG CTG TGG AAG GGC TCC
          GAC CTG GAC ACC CGA CCC GTC GTC GAC GAC ACC TTC CCG AGG
          Leu Asp Leu Trp Ala Gly Gln Gln Leu Leu Trp Lys Gly Ser>
          _____IL4Rα_____>

1230           1240           1250           1260
            *         *    *         *    *         *    *         *
          TTC AAG CCC AGC GAG CAT GTG AAA CCC AGG GCC CCA GGA AAC
          AAG TTC GGG TCG CTC GTA CAC TTT GGG TCC CGG GGT CCT TTG
          Phe Lys Pro Ser Glu His Val Lys Pro Arg Ala Pro Gly Asn>
          _____IL4Rα_____>

1270           1280           1290           1300
            *         *    *         *    *         *    *         *
          CTG ACA GTT CAC ACC AAT GTC TCC GAC ACT CTG CTG CTG ACC
          GAC TGT CAA GTG TGG TTA CAG AGG CTG TGA GAC GAC GAC TGG
          Leu Thr Val His Thr Asn Val Ser Asp Thr Leu Leu Leu Thr>
          _____IL4Rα_____>

1310           1320           1330           1340           1350
       *         *    *         *    *         *    *         *    *
     TGG AGC AAC CCG TAT CCC CCT GAC AAT TAC CTG TAT AAT CAT
     ACC TCG TTG GGC ATA GGG GGA CTG TTA ATG GAC ATA TTA GTA
     Trp Ser Asn Pro Tyr Pro Pro Asp Asn Tyr Leu Tyr Asn His>
     _____IL4Rα_____>
```

Figure 54F

```
              1360            1370            1380            1390
          *       *       *       *       *       *       *       *
    CTC ACC TAT GCA GTC AAC ATT TGG AGT GAA AAC GAC CCG GCA
    GAG TGG ATA CGT CAG TTG TAA ACC TCA CTT TTG CTG GGC CGT
    Leu Thr Tyr Ala Val Asn Ile Trp Ser Glu Asn Asp Pro Ala>
    _____IL4Rα_____>

1400            1410            1420            1430
          *       *       *       *       *       *       *       *
    GAT TTC AGA ATC TAT AAC GTG ACC TAC CTA GAA CCC TCC CTC
    CTA AAG TCT TAG ATA TTG CAC TGG ATG GAT CTT GGG AGG GAG
    Asp Phe Arg Ile Tyr Asn Val Thr Tyr Leu Glu Pro Ser Leu>
    _____IL4Rα_____>

1440            1450            1460            1470
        *       *       *       *       *       *       *       *       *
    CGC ATC GCA GCC AGC ACC CTG AAG TCT GGG ATT TCC TAC AGG
    GCG TAG CGT CGG TCG TGG GAC TTC AGA CCC TAA AGG ATG TCC
    Arg Ile Ala Ala Ser Thr Leu Lys Ser Gly Ile Ser Tyr Arg>
    _____IL4Rα_____>

>Mutation Cysteine to Serine
              1480            1490           1500  |      1510
          *       *       *       *       *   |   *       *       *
    GCA CGC GTA CGG GCC TGG GCT CAG AGC TAT AAC ACC ACC TGG
    CGT GCG CAT GCC CGG ACC CGA GTC TCG ATA TTG TGG TGG ACC
    Ala Arg Val Arg Ala Trp Ala Gln Ser Tyr Asn Thr Thr Trp>
    _____IL4Rα_____>

1520            1530            1540            1550            1560
    *       *       *       *       *       *       *       *       *
    AGT GAG TGG AGC CCC AGC ACC AAG TGG CAC AAC TCC TAC AGG
    TCA CTC ACC TCG GGG TCG TGG TTC ACC GTG TTG AGG ATG TCC
    Ser Glu Trp Ser Pro Ser Thr Lys Trp His Asn Ser Tyr Arg>
    _____IL4Rα_____>

1570            1580            1590            1600
          *       *       *       *       *       *       *       *
    GAG CCC TTC GAG CAG ACC GGA GAG TCC AAA TAC GGT CCG CCA
    CTC GGG AAG CTC GTC TGG CCT CTC AGG TTT ATG CCA GGC GGT
                                            Thr Gly>
                                        _____>
    Glu Pro Phe Glu Gln>              Glu Ser Lys Tyr Gly Pro Pro>
    _____IL4Rα_____>            _____FC-IgG4_____>
```

Figure 54G

>Mutation Serine to Proline

```
              1610          1620          1630          1640
      *      |*     *       *      *      *      *       *
     TGC CCA CCA TGC CCA GCA CCT GAG TTC CTG GGG GGA CCA TCA
     ACG GGT GGT ACG GGT CGT GGA CTC AAG GAC CCC CCT GGT AGT
     Cys Pro Pro Cys Pro Ala Pro Glu Phe Leu Gly Gly Pro Ser>
                             __FC-IgG4_____>

1650          1660          1670          1680
     *      *      *      *      *      *      *      *      *
     GTC TTC CTG TTC CCC CCA AAA CCC AAG GAC ACT CTC ATG ATC
     CAG AAG GAC AAG GGG GGT TTT GGG TTC CTG TGA GAG TAC TAG
     Val Phe Leu Phe Pro Pro Lys Pro Lys Asp Thr Leu Met Ile>
                             __FC-IgG4_____>

1690          1700          1710          1720
     *      *      *      *      *      *      *      *
     TCC CGG ACC CCT GAG GTC ACG TGC GTG GTG GTG GAC GTG AGC
     AGG GCC TGG GGA CTC CAG TGC ACG CAC CAC CAC CTG CAC TCG
     Ser Arg Thr Pro Glu Val Thr Cys Val Val Val Asp Val Ser>
                             __FC-IgG4_____>

1730          1740          1750          1760          1770
    *      *      *      *      *      *      *      *      *
   CAG GAA GAC CCC GAG GTC CAG TTC AAC TGG TAC GTG GAT GGC
   GTC CTT CTG GGG CTC CAG GTC AAG TTG ACC ATG CAC CTA CCG
   Gln Glu Asp Pro Glu Val Gln Phe Asn Trp Tyr Val Asp Gly>
                             __FC-IgG4_____>

1780          1790          1800          1810
      *      *      *      *      *      *      *      *
     GTG GAG GTG CAT AAT GCC AAG ACA AAG CCG CGG GAG GAG CAG
     CAC CTC CAC GTA TTA CGG TTC TGT TTC GGC GCC CTC CTC GTC
     Val Glu Val His Asn Ala Lys Thr Lys Pro Arg Glu Glu Gln>
                             __FC-IgG4_____>

1820          1830          1840          1850
      *      *      *      *      *      *      *      *
     TTC AAC AGC ACG TAC CGT GTG GTC AGC GTC CTC ACC GTC CTG
     AAG TTG TCG TGC ATG GCA CAC CAG TCG CAG GAG TGG CAG GAC
     Phe Asn Ser Thr Tyr Arg Val Val Ser Val Leu Thr Val Leu>
                             __FC-IgG4_____>

1860          1870          1880          1890
     *      *      *      *      *      *      *      *      *
     CAC CAG GAC TGG CTG AAC GGC AAG GAG TAC AAG TGC AAG GTC
     GTG GTC CTG ACC GAC TTG CCG TTC CTC ATG TTC ACG TTC CAG
     His Gln Asp Trp Leu Asn Gly Lys Glu Tyr Lys Cys Lys Val>
                             __FC-IgG4_____>
```

Figure 54H

```
         1900           1910          1920          1930
          *       *      *       *     *      *      *       *
        TCC AAC AAA GGC CTC CCG TCC TCC ATC GAG AAA ACC ATC TCC
        AGG TTG TTT CCG GAG GGC AGG AGG TAG CTC TTT TGG TAG AGG
        Ser Asn Lys Gly Leu Pro Ser Ser Ile Glu Lys Thr Ile Ser>
                                 FC-IgG4                       >

1940          1950          1960          1970          1980
   *      *     *      *      *      *      *      *      *
 AAA GCC AAA GGG CAG CCC CGA GAG CCA CAG GTG TAC ACC CTG
 TTT CGG TTT CCC GTC GGG GCT CTC GGT GTC CAC ATG TGG GAC
 Lys Ala Lys Gly Gln Pro Arg Glu Pro Gln Val Tyr Thr Leu>
                           FC-IgG4                       >

1990          2000          2010          2020
             *      *      *      *      *      *      *      *
           CCC CCA TCC CAG GAG GAG ATG ACC AAG AAC CAG GTC AGC CTG
           GGG GGT AGG GTC CTC CTC TAC TGG TTC TTG GTC CAG TCG GAC
           Pro Pro Ser Gln Glu Glu Met Thr Lys Asn Gln Val Ser Leu>
                                   FC-IgG4                       >

2030          2040          2050          2060
               *      *      *      *      *      *      *      *
             ACC TGC CTG GTC AAA GGC TTC TAC CCC AGC GAC ATC GCC GTG
             TGG ACG GAC CAG TTT CCG AAG ATG GGG TCG CTG TAG CGG CAC
             Thr Cys Leu Val Lys Gly Phe Tyr Pro Ser Asp Ile Ala Val>
                                     FC-IgG4                       >

2070          2080          2090          2100
                  *      *      *      *      *      *      *      *      *
                GAG TGG GAG AGC AAT GGG CAG CCG GAG AAC AAC TAC AAG ACC
                CTC ACC CTC TCG TTA CCC GTC GGC CTC TTG TTG ATG TTC TGG
                Glu Trp Glu Ser Asn Gly Gln Pro Glu Asn Asn Tyr Lys Thr>
                                        FC-IgG4                       >

2110          2120          2130          2140
                     *      *      *      *      *      *      *      *
                   ACG CCT CCC GTG CTG GAC TCC GAC GGC TCC TTC TTC CTC TAC
                   TGC GGA GGG CAC GAC CTG AGG CTG CCG AGG AAG AAG GAG ATG
                   Thr Pro Pro Val Leu Asp Ser Asp Gly Ser Phe Phe Leu Tyr>
                                           FC-IgG4                       >

2150          2160          2170          2180          2190
           *      *      *      *      *      *      *      *      *
         AGC AGG CTA ACC GTG GAC AAG AGC AGG TGG CAG GAG GGG AAT
         TCG TCC GAT TGG CAC CTG TTC TCG TCC ACC GTC CTC CCC TTA
         Ser Arg Leu Thr Val Asp Lys Ser Arg Trp Gln Glu Gly Asn>
                                 FC-IgG4                       >
```

Figure 54I

```
             2200           2210            2220            2230
       *       *       *      *       *       *       *       *
GTC   TTC   TCA   TGC   TCC   GTG   ATG   CAT   GAG   GCT   CTG   CAC   AAC   CAC
CAG   AAG   AGT   ACG   AGG   CAC   TAC   GTA   CTC   CGA   GAC   GTG   TTG   GTG
Val   Phe   Ser   Cys   Ser   Val   Met   His   Glu   Ala   Leu   His   Asn   His>
_____FC-IgG4_____>

2240           2250            2260            2270
       *       *       *      *       *       *       *       *
TAC   ACA   CAG   AAG   AGC   CTC   TCC   CTG   TCT   CTG   GGT   AAA   TGA
ATG   TGT   GTC   TTC   TCG   GAG   AGG   GAC   AGA   GAC   CCA   TTT   ACT
Tyr   Thr   Gln   Lys   Ser   Leu   Ser   Leu   Ser   Leu   Gly   Lys   ***>
_____FC-IgG4_____>
```

Figure 55A

```
              -60           -50           -40           -30
         *         *    *         *    *         *    *         *
       ATG GTG TGG CTT TGC TCT GGG CTC CTG TTC CCT GTG AGC TGC
       TAC CAC ACC GAA ACG AGA CCC GAG GAC AAG GGA CAC TCG ACG
       Met Val Trp Leu Cys Ser Gly Leu Leu Phe Pro Val Ser Cys>
       _____SIGNAL PEPTIDE_____>
       _____IL4Rα_____

-20           -10             1            10
         *         *    *         *    *         *    *         *    *
       CTG GTC CTG CTG CAG GTG GCA AGC TCT GGG AAC ATG AAG GTC
       GAC CAG GAC GAC GTC CAC CGT TCG AGA CCC TTG TAC TTC CAG
       Leu Val Leu Leu Gln Val Ala Ser Ser Gly Asn Met Lys Val>
       _____SIGNAL PEPTIDE_____>
       _____IL4Rα_____>

20            30            40            50
         *         *    *         *    *         *    *         *
       TTG CAG GAG CCC ACC TGC GTC TCC GAC TAC ATG AGC ATC TCT
       AAC GTC CTC GGG TGG ACG CAG AGG CTG ATG TAC TCG TAG AGA
       Leu Gln Glu Pro Thr Cys Val Ser Asp Tyr Met Ser Ile Ser>
       _____IL4Rα_____>

60            70            80            90
         *         *    *         *    *         *    *         *
       ACT TGC GAG TGG AAG ATG AAT GGT CCC ACC AAT TGC AGC ACC
       TGA ACG CTC ACC TTC TAC TTA CCA GGG TGG TTA ACG TCG TGG
       Thr Cys Glu Trp Lys Met Asn Gly Pro Thr Asn Cys Ser Thr>
       _____IL4Rα_____>

100           110           120           130           140
         *         *    *         *    *         *    *         *    *
       GAG CTC CGC CTG TTG TAC CAG CTG GTT TTT CTG CTC TCC GAA
       CTC GAG GCG GAC AAC ATG GTC GAC CAA AAA GAC GAG AGG CTT
       Glu Leu Arg Leu Leu Tyr Gln Leu Val Phe Leu Leu Ser Glu>
       _____IL4Rα_____>

150           160           170           180
         *         *    *         *    *         *    *         *
       GCC CAC ACG TGT ATC CCT GAG AAC AAC GGA GGC GCG GGG TGC
       CGG GTG TGC ACA TAG GGA CTC TTG TTG CCT CCG CGC CCC ACG
       Ala His Thr Cys Ile Pro Glu Asn Asn Gly Gly Ala Gly Cys>
       _____IL4Rα_____>

190           200           210           220
         *         *    *         *    *         *    *         *
       GTG TGC CAC CTG CTC ATG GAT GAC GTG GTC AGT GCG GAT AAC
       CAC ACG GTG GAC GAG TAC CTA CTG CAC CAG TCA CGC CTA TTG
       Val Cys His Leu Leu Met Asp Asp Val Val Ser Ala Asp Asn>
       _____IL4Rα_____>
```

Figure 55B

```
         230                240                250                260
          *        *         *         *         *         *         *         *
        TAT  ACA  CTG  GAC  CTG  TGG  GCT  GGG  CAG  CAG  CTG  CTG  TGG  AAG
        ATA  TGT  GAC  CTG  GAC  ACC  CGA  CCC  GTC  GTC  GAC  GAC  ACC  TTC
        Tyr  Thr  Leu  Asp  Leu  Trp  Ala  Gly  Gln  Gln  Leu  Leu  Trp  Lys>
        _____IL4Rα_____>

270                280                290                300
          *         *         *         *         *         *         *         *
        GGC  TCC  TTC  AAG  CCC  AGC  GAG  CAT  GTG  AAA  CCC  AGG  GCC  CCA
        CCG  AGG  AAG  TTC  GGG  TCG  CTC  GTA  CAC  TTT  GGG  TCC  CGG  GGT
        Gly  Ser  Phe  Lys  Pro  Ser  Glu  His  Val  Lys  Pro  Arg  Ala  Pro>
        _____IL4Rα_____>

310                320                330                340                350
      *         *         *         *         *         *         *         *         *
    GGA  AAC  CTG  ACA  GTT  CAC  ACC  AAT  GTC  TCC  GAC  ACT  CTG  CTG
    CCT  TTG  GAC  TGT  CAA  GTG  TGG  TTA  CAG  AGG  CTG  TGA  GAC  GAC
    Gly  Asn  Leu  Thr  Val  His  Thr  Asn  Val  Ser  Asp  Thr  Leu  Leu>
    _____IL4Rα_____>

360                370                380                390
               *         *         *         *         *         *         *         *
            CTG  ACC  TGG  AGC  AAC  CCG  TAT  CCC  CCT  GAC  AAT  TAC  CTG  TAT
            GAC  TGG  ACC  TCG  TTG  GGC  ATA  GGG  GGA  CTG  TTA  ATG  GAC  ATA
            Leu  Thr  Trp  Ser  Asn  Pro  Tyr  Pro  Pro  Asp  Asn  Tyr  Leu  Tyr>
            _____IL4Rα_____>

400                410                420                430
               *         *         *         *         *         *         *         *         *
            AAT  CAT  CTC  ACC  TAT  GCA  GTC  AAC  ATT  TGG  AGT  GAA  AAC  GAC
            TTA  GTA  GAG  TGG  ATA  CGT  CAG  TTG  TAA  ACC  TCA  CTT  TTG  CTG
            Asn  His  Leu  Thr  Tyr  Ala  Val  Asn  Ile  Trp  Ser  Glu  Asn  Asp>
            _____IL4Rα_____>

440                450                460                470
               *         *         *         *         *         *         *         *
            CCG  GCA  GAT  TTC  AGA  ATC  TAT  AAC  GTG  ACC  TAC  CTA  GAA  CCC
            GGC  CGT  CTA  AAG  TCT  TAG  ATA  TTG  CAC  TGG  ATG  GAT  CTT  GGG
            Pro  Ala  Asp  Phe  Arg  Ile  Tyr  Asn  Val  Thr  Tyr  Leu  Glu  Pro>
            _____IL4Rα_____>

480                490                500                510
               *         *         *         *         *         *         *         *
            TCC  CTC  CGC  ATC  GCA  GCC  AGC  ACC  CTG  AAG  TCT  GGG  ATT  TCC
            AGG  GAG  GCG  TAG  CGT  CGG  TCG  TGG  GAC  TTC  AGA  CCC  TAA  AGG
            Ser  Leu  Arg  Ile  Ala  Ala  Ser  Thr  Leu  Lys  Ser  Gly  Ile  Ser>
            _____IL4Rα_____>
```

Figure 55C

```
                                         >Mutation Cysteine to Serine
                                                      |
    520           530           540           550           560
     *       *     *       *     *       *     *       *     *
    TAC AGG GCA CGC GTA CGG GCC TGG GCT CAG AGC TAT AAC ACC
    ATG TCC CGT GCG CAT GCC CGG ACC CGA GTC TCG ATA TTG TGG
    Tyr Arg Ala Arg Val Arg Ala Trp Ala Gln Ser Tyr Asn Thr>
    _____IL4Rα_____>

570           580           590           600
     *     *       *     *       *     *       *     *
    ACC TGG AGT GAG TGG AGC CCC AGC ACC AAG TGG CAC AAC TCC
    TGG ACC TCA CTC ACC TCG GGG TCG TGG TTC ACC GTG TTG AGG
    Thr Trp Ser Glu Trp Ser Pro Ser Thr Lys Trp His Asn Ser>
    _____IL4Rα_____>

610           620           630           640
     *     *       *     *       *     *       *     *      *
    TAC AGG GAG CCC TTC GAG CAG GCG CCT ACG GAA ACT CAG CCA
    ATG TCC CTC GGG AAG CTC GTC CGC GGA TGC CTT TGA GTC GGT
    Tyr Arg Glu Pro Phe Glu Gln>
    _____IL4Rα_____>
                                    Ala Pro Thr Glu Thr Gln Pro>
                                    _____IL13Rα1_____>

>Mutation Cysteine to Alanine
                                                      |
          650           660           670           680   |
     *     *       *     *       *     *       *     *    |  *
    CCT GTG ACA AAT TTG AGT GTC TCT GTT GAA AAC CTC GCG ACA
    GGA CAC TGT TTA AAC TCA CAG AGA CAA CTT TTG GAG CGC TGT
    Pro Val Thr Asn Leu Ser Val Ser Val Glu Asn Leu Ala Thr>
    _____IL13Rα1_____>

690           700           710           720
     *     *       *     *       *     *       *     *
    GTA ATA TGG ACA TGG AAT CCA CCC GAG GGA GCC AGC TCA AAT
    CAT TAT ACC TGT ACC TTA GGT GGG CTC CCT CGG TCG AGT TTA
    Val Ile Trp Thr Trp Asn Pro Pro Glu Gly Ala Ser Ser Asn>
    _____IL13Rα1_____>

730           740           750           760           770
     *     *       *     *       *     *       *     *       *
    TGT AGT CTA TGG TAT TTT AGT CAT TTT GGC GAC AAA CAA GAT
    ACA TCA GAT ACC ATA AAA TCA GTA AAA CCG CTG TTT GTT CTA
    Cys Ser Leu Trp Tyr Phe Ser His Phe Gly Asp Lys Gln Asp>
    _____IL13Rα1_____>
```

Figure 55D

```
            780              790              800              810
        *        *        *        *        *        *        *        *
    AAG AAA ATA GCT CCG GAA ACT CGT CGT TCA ATA GAA GTA CCC
    TTC TTT TAT CGA GGC CTT TGA GCA GCA AGT TAT CTT CAT GGG
    Lys Lys Ile Ala Pro Glu Thr Arg Arg Ser Ile Glu Val Pro>
    _____IL13Rα1_____>

820              830              840              850
        *        *        *        *        *        *        *        *        *
    CTG AAT GAG AGG ATT TGT CTG CAA GTG GGG TCC CAG TGT AGC
    GAC TTA CTC TCC TAA ACA GAC GTT CAC CCC AGG GTC ACA TCG
    Leu Asn Glu Arg Ile Cys Leu Gln Val Gly Ser Gln Cys Ser>
    _____IL13Rα1_____>

860              870              880              890
    *        *        *        *        *        *        *        *
    ACC AAT GAG AGT GAG AAG CCT AGC ATT TTG GTT GAA AAA TGC
    TGG TTA CTC TCA CTC TTC GGA TCG TAA AAC CAA CTT TTT ACG
    Thr Asn Glu Ser Glu Lys Pro Ser Ile Leu Val Glu Lys Cys>
    _____IL13Rα1_____>

900              910              920              930
*        *        *        *        *        *        *        *
    ATC TCA CCC CCA GAA GGT GAT CCT GAG TCT GCT GTG ACT GAG
    TAG AGT GGG GGT CTT CCA CTA GGA CTC AGA CGA CAC TGA CTC
    Ile Ser Pro Pro Glu Gly Asp Pro Glu Ser Ala Val Thr Glu>
    _____IL13Rα1_____>

940              950              960              970              980
*        *        *        *        *        *        *        *        *
    CTT CAA TGC ATT TGG CAC AAC CTG AGC TAC ATG AAG TGT TCT
    GAA GTT ACG TAA ACC GTG TTG GAC TCG ATG TAC TTC ACA AGA
    Leu Gln Cys Ile Trp His Asn Leu Ser Tyr Met Lys Cys Ser>
    _____IL13Rα1_____>

990              1000             1010             1020
        *        *        *        *        *        *        *        *
    TGG CTC CCT GGA AGG AAT ACC AGT CCC GAC ACT AAC TAT ACT
    ACC GAG GGA CCT TCC TTA TGG TCA GGG CTG TGA TTG ATA TGA
    Trp Leu Pro Gly Arg Asn Thr Ser Pro Asp Thr Asn Tyr Thr>
    _____IL13Rα1_____>

1030             1040             1050             1060
        *        *        *        *        *        *        *        *        *
    CTC TAC TAT TGG CAC AGA AGC CTG GAA AAA ATT CAT CAA TGT
    GAG ATG ATA ACC GTG TCT TCG GAC CTT TTT TAA GTA GTT ACA
    Leu Tyr Tyr Trp His Arg Ser Leu Glu Lys Ile His Gln Cys>
    _____IL13Rα1_____>
```

Figure 55E

```
        1070            1080            1090           1100
         *       *       *       *       *       *       *       *
        GAA AAC ATC TTT AGA GAA GGC CAA TAC TTT GGT TGT TCC TTT
        CTT TTG TAG AAA TCT CTT CCG GTT ATG AAA CCA ACA AGG AAA
        Glu Asn Ile Phe Arg Glu Gly Gln Tyr Phe Gly Cys Ser Phe>
        ──────────────────────IL13Rα1──────────────────────────>

1110            1120            1130           1140
   *       *       *       *       *       *       *       *
  GAT CTG ACC AAA GTG AAG GAT TCC AGT TTT GAA CAA CAC AGT
  CTA GAC TGG TTT CAC TTC CTA AGG TCA AAA CTT GTT GTG TCA
  Asp Leu Thr Lys Val Lys Asp Ser Ser Phe Glu Gln His Ser>
  ──────────────────────IL13Rα1──────────────────────────>

1150            1160            1170           1180           1190
 *      *       *       *       *       *       *       *       *
GTC CAA ATA ATG GTC AAG GAT AAT GCA GGA AAA ATT AAA CCA
CAG GTT TAT TAC CAG TTC CTA TTA CGT CCT TTT TAA TTT GGT
Val Gln Ile Met Val Lys Asp Asn Ala Gly Lys Ile Lys Pro>
──────────────────────IL13Rα1──────────────────────────>

1200            1210            1220           1230
         *       *       *       *       *       *       *       *
        TCC TTC AAT ATA GTG CCT TTA ACT TCC CGT GTG AAA CCT GAT
        AGG AAG TTA TAT CAC GGA AAT TGA AGG GCA CAC TTT GGA CTA
        Ser Phe Asn Ile Val Pro Leu Thr Ser Arg Val Lys Pro Asp>
        ──────────────────────IL13Rα1──────────────────────────>

1240            1250            1260           1270
         *       *       *       *       *       *       *       *
        CCT CCA CAT ATT AAA AAC CTC TCC TTC CAC AAT GAT GAC CTA
        GGA GGT GTA TAA TTT TTG GAG AGG AAG GTG TTA CTA CTG GAT
        Pro Pro His Ile Lys Asn Leu Ser Phe His Asn Asp Asp Leu>
        ──────────────────────IL13Rα1──────────────────────────>

1280            1290            1300           1310
         *       *       *       *       *       *       *       *
        TAT GTG CAA TGG GAG AAT CCA CAG AAT TTT ATT AGC AGA TGC
        ATA CAC GTT ACC CTC TTA GGT GTC TTA AAA TAA TCG TCT ACG
        Tyr Val Gln Trp Glu Asn Pro Gln Asn Phe Ile Ser Arg Cys>
        ──────────────────────IL13Rα1──────────────────────────>

1320            1330            1340           1350
         *       *       *       *       *       *       *       *
        CTA TTT TAT GAA GTA GAA GTC AAT AAC AGC CAA ACT GAG ACA
        GAT AAA ATA CTT CAT CTT CAG TTA TTG TCG GTT TGA CTC TGT
        Leu Phe Tyr Glu Val Glu Val Asn Asn Ser Gln Thr Glu Thr>
        ──────────────────────IL13Rα1──────────────────────────>
```

Figure 55F

```
       1360            1370           1380           1390           1400
         *        *      *       *      *       *      *       *      *
        CAT  AAT  GTT  TTC  TAC  GTC  CAA  GAG  GCT  AAA  TGT  GAG  AAT  CCA
        GTA  TTA  CAA  AAG  ATG  CAG  GTT  CTC  CGA  TTT  ACA  CTC  TTA  GGT
        His  Asn  Val  Phe  Tyr  Val  Gln  Glu  Ala  Lys  Cys  Glu  Asn  Pro>
        _____IL13Rα1_____>

1410           1420           1430           1440
                   *      *      *       *      *       *      *       *
        GAA  TTT  GAG  AGA  AAT  GTG  GAG  AAT  ACA  TCT  TGT  TTC  ATG  GTC
        CTT  AAA  CTC  TCT  TTA  CAC  CTC  TTA  TGT  AGA  ACA  AAG  TAC  CAG
        Glu  Phe  Glu  Arg  Asn  Val  Glu  Asn  Thr  Ser  Cys  Phe  Met  Val>
        _____IL13Rα1_____>

1450           1460           1470           1480
              *      *       *      *       *      *       *      *       *
        CCT  GGT  GTT  CTT  CCT  GAT  ACT  TTG  AAC  ACA  GTC  AGA  ATA  AGA
        GGA  CCA  CAA  GAA  GGA  CTA  TGA  AAC  TTG  TGT  CAG  TCT  TAT  TCT
        Pro  Gly  Val  Leu  Pro  Asp  Thr  Leu  Asn  Thr  Val  Arg  Ile  Arg>
        _____IL13Rα1_____>

1490           1500           1510           1520
              *      *       *      *       *      *       *      *
        GTC  AAA  ACA  AAT  AAG  TTA  TGC  TAT  GAG  GAT  GAC  AAA  CTC  TGG
        CAG  TTT  TGT  TTA  TTC  AAT  ACG  ATA  CTC  CTA  CTG  TTT  GAG  ACC
        Val  Lys  Thr  Asn  Lys  Leu  Cys  Tyr  Glu  Asp  Asp  Lys  Leu  Trp>
        _____IL13Rα1_____>

1530            1540           1550           1560
         *        *      *       *      *       *      *       *
        AGT  AAT  TGG  AGC  CAA  GAA  ATG  AGT  ATA  GGT  AAG  AAG  CGC  AAT
        TCA  TTA  ACC  TCG  GTT  CTT  TAC  TCA  TAT  CCA  TTC  TTC  GCG  TTA
        Ser  Asn  Trp  Ser  Gln  Glu  Met  Ser  Ile  Gly  Lys  Lys  Arg  Asn>
        _____IL13Rα1_____>

>Mutation Serine to Proline
       1570            1580           1590           1600      |    1610
         *        *      *       *      *       *      *       *  |    *
        TCC  ACC  GGA  GAG  TCC  AAA  TAC  GGT  CCG  CCA  TGC  CCA  CCA  TGC
        AGG  TGG  CCT  CTC  AGG  TTT  ATG  CCA  GGC  GGT  ACG  GGT  GGT  ACG
        Ser  Thr
        _____>
                  Gly>
                  ____>
                       Glu  Ser  Lys  Tyr  Gly  Pro  Pro  Cys  Pro  Pro  Cys>
                       _____FC-IgG4_____>
```

Figure 55G

```
          1620            1630            1640            1650
       *     *       *       *       *       *       *       *
      CCA GCA CCT GAG TTC CTG GGG GGA CCA TCA GTC TTC CTG TTC
      GGT CGT GGA CTC AAG GAC CCC CCT GGT AGT CAG AAG GAC AAG
      Pro Ala Pro Glu Phe Leu Gly Gly Pro Ser Val Phe Leu Phe>
                               ____FC-IgG4_____>

1660            1670            1680            1690
        *       *       *       *       *       *       *       *
       CCC CCA AAA CCC AAG GAC ACT CTC ATG ATC TCC CGG ACC CCT
       GGG GGT TTT GGG TTC CTG TGA GAG TAC TAG AGG GCC TGG GGA
       Pro Pro Lys Pro Lys Asp Thr Leu Met Ile Ser Arg Thr Pro>
       _____FC-IgG4_____>

1700            1710            1720            1730
       *       *       *       *       *       *       *       *
      GAG GTC ACG TGC GTG GTG GTG GAC GTG AGC CAG GAA GAC CCC
      CTC CAG TGC ACG CAC CAC CAC CTG CAC TCG GTC CTT CTG GGG
      Glu Val Thr Cys Val Val Val Asp Val Ser Gln Glu Asp Pro>
      _____FC-IgG4_____>

1740            1750            1760            1770
       *       *       *       *       *       *       *       *
      GAG GTC CAG TTC AAC TGG TAC GTG GAT GGC GTG GAG GTG CAT
      CTC CAG GTC AAG TTG ACC ATG CAC CTA CCG CAC CTC CAC GTA
      Glu Val Gln Phe Asn Trp Tyr Val Asp Gly Val Glu Val His>
      _____FC-IgG4_____>

1780            1790            1800            1810            1820
     *       *       *       *       *       *       *       *       *
    AAT GCC AAG ACA AAG CCG CGG GAG GAG CAG TTC AAC AGC ACG
    TTA CGG TTC TGT TTC GGC GCC CTC CTC GTC AAG TTG TCG TGC
    Asn Ala Lys Thr Lys Pro Arg Glu Glu Gln Phe Asn Ser Thr>
    _____FC-IgG4_____>

1830            1840            1850            1860
        *       *       *       *       *       *       *       *
       TAC CGT GTG GTC AGC GTC CTC ACC GTC CTG CAC CAG GAC TGG
       ATG GCA CAC CAG TCG CAG GAG TGG CAG GAC GTG GTC CTG ACC
       Tyr Arg Val Val Ser Val Leu Thr Val Leu His Gln Asp Trp>
       _____FC-IgG4_____>

1870            1880            1890            1900
        *       *       *       *       *       *       *       *       *
       CTG AAC GGC AAG GAG TAC AAG TGC AAG GTC TCC AAC AAA GGC
       GAC TTG CCG TTC CTC ATG TTC ACG TTC CAG AGG TTG TTT CCG
       Leu Asn Gly Lys Glu Tyr Lys Cys Lys Val Ser Asn Lys Gly>
       _____FC-IgG4_____>
```

Figure 55H

```
         1910              1920              1930              1940
          *        *        *        *        *        *        *        *
         CTC CCG TCC TCC ATC GAG AAA ACC ATC TCC AAA GCC AAA GGG
         GAG GGC AGG AGG TAG CTC TTT TGG TAG AGG TTT CGG TTT CCC
         Leu Pro Ser Ser Ile Glu Lys Thr Ile Ser Lys Ala Lys Gly>
                                     _FC-IgG4_____>

1950              1960              1970              1980
          *        *        *        *        *        *        *        *
         CAG CCC CGA GAG CCA CAG GTG TAC ACC CTG CCC CCA TCC CAG
         GTC GGG GCT CTC GGT GTC CAC ATG TGG GAC GGG GGT AGG GTC
         Gln Pro Arg Glu Pro Gln Val Tyr Thr Leu Pro Pro Ser Gln>
                                     _FC-IgG4_____>

1990              2000              2010              2020              2030
          *        *        *        *        *        *        *        *        *
         GAG GAG ATG ACC AAG AAC CAG GTC AGC CTG ACC TGC CTG GTC
         CTC CTC TAC TGG TTC TTG GTC CAG TCG GAC TGG ACG GAC CAG
         Glu Glu Met Thr Lys Asn Gln Val Ser Leu Thr Cys Leu Val>
                                     _FC-IgG4_____>

2040              2050              2060              2070
                    *        *        *        *        *        *        *        *
                   AAA GGC TTC TAC CCC AGC GAC ATC GCC GTG GAG TGG GAG AGC
                   TTT CCG AAG ATG GGG TCG CTG TAG CGG CAC CTC ACC CTC TCG
                   Lys Gly Phe Tyr Pro Ser Asp Ile Ala Val Glu Trp Glu Ser>
                                     _FC-IgG4_____>

2080              2090              2100              2110
                    *        *        *        *        *        *        *        *
                   AAT GGG CAG CCG GAG AAC AAC TAC AAG ACC ACG CCT CCC GTG
                   TTA CCC GTC GGC CTC TTG TTG ATG TTC TGG TGC GGA GGG CAC
                   Asn Gly Gln Pro Glu Asn Asn Tyr Lys Thr Thr Pro Pro Val>
                                     _FC-IgG4_____>

2120              2130              2140              2150
                    *        *        *        *        *        *        *        *
                   CTG GAC TCC GAC GGC TCC TTC TTC CTC TAC AGC AGG CTA ACC
                   GAC CTG AGG CTG CCG AGG AAG AAG GAG ATG TCG TCC GAT TGG
                   Leu Asp Ser Asp Gly Ser Phe Phe Leu Tyr Ser Arg Leu Thr>
                                     _FC-IgG4_____>

2160              2170              2180              2190
          *        *        *        *        *        *        *        *
         GTG GAC AAG AGC AGG TGG CAG GAG GGG AAT GTC TTC TCA TGC
         CAC CTG TTC TCG TCC ACC GTC CTC CCC TTA CAG AAG AGT ACG
         Val Asp Lys Ser Arg Trp Gln Glu Gly Asn Val Phe Ser Cys>
                                     _FC-IgG4_____>
```

Figure 55I

```
     2200           2210           2220           2230           2240
       *    *    *    *    *    *    *    *    *
     TCC  GTG  ATG  CAT  GAG  GCT  CTG  CAC  AAC  CAC  TAC  ACA  CAG  AAG
     AGG  CAC  TAC  GTA  CTC  CGA  GAC  GTG  TTG  GTG  ATG  TGT  GTC  TTC
     Ser  Val  Met  His  Glu  Ala  Leu  His  Asn  His  Tyr  Thr  Gln  Lys>
                                  _FC-IgG4_____>

2250           2260
              *    *    *    *    *
          AGC  CTC  TCC  CTG  TCT  CTG  GGT  AAA  TGA
          TCG  GAG  AGG  GAC  AGA  GAC  CCA  TTT  ACT
          Ser  Leu  Ser  Leu  Ser  Leu  Gly  Lys  ***>
                    _FC-IgG4_____>
```

RECEPTOR BASED ANTAGONISTS AND METHODS OF MAKING AND USING

This application is a Continuation-in-Part of U.S. application Ser. No. 09/935,868, filed Aug. 23, 2001 now abandoned, which is a Continuation-in-Part of U.S. application Ser. No. 09/787,835, filed Mar. 22, 2001 now abandoned, which is a §371 U.S. National Stage Application of International Application No. PCT/US99/22045, filed Sep. 22, 1999, which is a Continuation-in-Part of and claims priority of U.S. application Ser. No. 09/313,942, filed May 19, 1999, now U.S. Pat. No. 6,472,179, which claims priority of U.S. Provisional Application No. 60/101,858 filed Sep. 25, 1998, now abandoned. Throughout this application various publications are referenced. The disclosures of these publications in their entireties are hereby incorporated by reference into this application.

BACKGROUND OF THE INVENTION

Although discovered for varying biological activities, ciliary neurotrophic factor (CNTF), leukemia inhibitory factor (LIF), oncostatin M (OSM) and interleukin-6 (IL-6) comprise a defined family of cytokines (referred to herein as the "CNTF family" of cytokines). These cytokines are grouped together because of their distant structural similarities [Bazan, J. Neuron 7: 197–208 (1991); Rose and Bruce, Proc. Natl. Acad. Sci. USA 88: 8641–8645 (1991)], and, perhaps more importantly, because they share "β" signal-transducing receptor components [Baumann, et al., J. Biol. Chem. 265:19853–19862 (1993); Davis, et al., Science 260: 1805–1808 (1993); Gearing et al., Science 255:1434-1437 (1992); Ip et al., Cell 69: 1121–1132 (1992); Stahl, et al., J. Biol. Chem. 268: 7628–7631 (1993); Stahl and Yancopoulos, Cell 74: 587–590 (1993)]. Receptor activation by this family of cytokines results from either homo- or hetero-dimerization of these β components [Davis, et al. Science 260: 1805–1808 (1993), Murakami, et al., Science 260: 1808–1810 (1993); Stahl and Yancopoulos, Cell 74: 587–590 (1993)]. IL-6 receptor activation requires homodimerization of gp130 [Murakami, et al. Science 260: 1808–1810 (1993), Hibi, et al., Cell 63: 1149–1157 (1990)], a protein initially identified as the IL-6 signal transducer [Hibi, et al., Cell 63: 1149–1157 (1990)]. CNTF, LIF and OSM receptor activation results from heterodimerization between gp130 and a second gp130-related protein known as LIFRβ [Davis, et al., Science 260: 1805–1808 (1993)], that was initially identified by its ability to bind LIF [Gearing et al., EMBO J. 10: 2839–2848 (1991)].

In addition to the β components, some of these cytokines also require specificity-determining "α" components that are more limited in their tissue distribution than the β components, and thus determine the cellular targets of the particular cytokines [Stahl and Yancopoulos, Cell 74: 587–590 (1993)]. Thus, LIF and OSM are broadly acting factors that may only require the presence of gp130 and LIFRβ on responding cells, while CNTF requires CNTFRα [Stahl and Yancopoulos, Cell 74: 587–590 (1993)] and IL-6 requires IL-6Rα [Kishimoto, et al., Science 258: 593–597 (1992)]. Both CNTFRα (Davis et al., Science 259:1736–1739 (1993) and IL-6Rα [Hibi, et al. Cell 63:1149–1157, Murakami, et al., Science 260:1808–1810 (1990); Taga, et al., Cell 58:573–581 (1989)] can function as soluble proteins, consistent with the notion that they do not interact with intracellular signaling molecules but that they serve to help their ligands interact with the appropriate signal transducing β subunits [Stahl and Yancopoulos, Cell 74: 587–590 (1993)].

Additional evidence from other cytokine systems also supports the notion that dimerization provides a common mechanism by which all cytokine receptors initiate signal transduction. Growth hormone (GH) serves as perhaps the best example in this regard. Crystallographic studies have revealed that each GH molecule contains two distinct receptor binding sites, both of which are recognized by the same binding domain in the receptor, allowing a single molecule of GH to engage two receptor molecules [de Vos, et al., Science 255: 306–312 (1992)]. Dimerization occurs sequentially, with site 1 on the GH first binding to one receptor molecule, followed by the binding of site 2 to a second receptor molecule [Fuh, et al., Science 256: 1677–1680 (1992)]. Studies with the erythropoietin (EPO) receptor are also consistent with the importance of dimerization in receptor activation, as EPO receptors can be constitutively activated by a single amino acid change that introduces a cysteine residue and results in disulfide-linked homodimers [Watowich, et al., Proc. Natl. Acad. Sci. USA 89:2140–2144 (1992)].

In addition to homo- or hetero-dimerization of β subunits as the critical step for receptor activation, a second important feature is that formation of the final receptor complex by the CNTF family of cytokines occurs through a mechanism whereby the ligand successively binds to receptor components in an ordered manner [Davis, et al. Science 260: 1805–1818 (1993); Stahl and Yancopoulos, Cell 74: 587–590 (1993)]. Thus CNTF first binds to CNTFRα, forming a complex which then binds gp130 to form an intermediate (called here the αβ1 intermediate) that is not signaling competent because it has only a single β component, before finally recruiting LIFRβ to form a heterodimer of β components which then initiates signal transduction. Although a similar intermediate containing IL-6 bound to IL-6Rα and a single molecule of gp130 has not been directly isolated, we have postulated that it does exist by analogy to its distant relative, CNTF, as well as the fact that the final active IL-6 receptor complex recruits two gp130 monomers. Altogether, these findings led to a proposal for the structure of a generic cytokine receptor complex (FIG. 1) in which each cytokine can have up to 3 receptor binding sites: a site that binds to an optional α specificity-determining component (α site), a site that binds to the first β signal-transducing component (β1 site), and a site that binds to the second β signal-transducing component (β2 site) [Stahl and Yancopoulos, Cell 74: 587–590 (1993)]. These 3 sites are used in sequential fashion, with the last step in complex formation—resulting in β component dimerization—critical for initiating signal transduction [Davis, et al. Science 260: 1805–1818 (1993)]. Knowledge of the details of receptor activation and the existence of the non-functional β1 intermediate for CNTF has led to the finding that CNTF is a high affinity antagonist for IL-6 under certain circumstances, and provides the strategic basis for designing ligand or receptor-based antagonists for the CNTF family of cytokines as detailed below.

Once cytokine binding induces receptor complex formation, the dimerization of β components activates intracellular tyrosine kinase activity that results in phosphorylation of a wide variety of substrates [Ip, et al. Cell 69:121–1132 (1992)]. This activation of tyrosine kinase appears to be critical for downstream events since inhibitors that block the tyrosine phosphorylations also prevent later events such as gene inductions [Ip, et al., Cell 69:121–1132 (1992); Nakajima and Wall, Mol. Cell. Biol. 11:1409–1418 (1991)]. Recently, we have demonstrated that a newly discovered family of non-receptor tyrosine kinases that includes Jak1, Jak2, and Tyk2 (referred to as the Jak/Tyk kinases) [Firmbach-Kraft, et al., Oncogene 5:1329–1336 (1990); Wilks, et al., Mol. Cell. Biol. 11: 2057–2065 (1991] and that are involved in signal transduction with other cytokines [Argetsinger, et al., Cell 74:237–244 (1993); Silvennoinen, et al., Proc. Natl. Acad. Sci. USA 90:8429–8433 (1993); Velazquez, et al., Cell 70: 313-322 (1992); Witthuhn, et al., Cell 74:227–236 (1993)], preassociate with the cytoplasmic domains of the β subunits gp130 and LIFRβ in the absence of ligand, and become tyrosine phosphorylated and activated upon ligand addition [Stahl et al., Science 263:92–95 (1994)]. Therefore these kinases appear to be the most proximal step of intracellular signal transduction activated inside the cell as a result of ligand binding outside of the cell. Assay systems for screening collections of small molecules for specific agonist or antagonist activities based on this system are described below.

The CNTF family of cytokines play important roles in a wide variety of physiological processes that provide potential therapeutic applications for both antagonists and agonists.

SUMMARY OF THE INVENTION

An object of the present invention is the production of cytokine antagonists that are useful in the treatment of cytokine-related diseases or disorders.

Another object of the invention is the use of the disclosed cytokine antagonists for the treatment of cytokine-related diseases or disorders. For example, an IL-6 antagonist described herein may be used for the treatment of osteoporosis, the primary and second effects of cancers, including multiple myeloma, or cachexia.

Another object of the invention is the development of screening systems useful for identifying novel agonists and antagonists of cytokine receptors.

Another object of the invention is the development of screening systems useful for identifying small molecules that act as agonists or antagonists of the cytokines.

Another object of the invention is the development of screening systems useful for identifying novel agonists and antagonists of members of the CNTF family of cytokines.

Another object of the invention is the development of screening systems useful for identifying small molecules that act as agonists or antagonists of the CNTF family of cytokines.

BRIEF DESCRIPTION OF THE FIGURES

FIGS. 4A–4B (SEQ ID NO: 7). The amino acid sequence of human gp130-Fc-His$_6$(SEQ ID NO: 7). Amino acids 1 to 619 are from human gp130 (Hibi et al., Cell 63:1149–1157 (1990). Note that amino acid number 2 has been changed from a Leu to a Val in order to accommodate a Kozak sequence in the coding DNA sequence. The signal peptide of gp130-Fc-His$_6$ has been italicized (amino acids 1 to 22). The Ser-Gly bridge is shown in bold type (amino acids 620, 621). Amino acids 662 to 853 are from the Fc domain of human IgG1 (Lewis, et al., J. Immunol. 151:2829–2838 (1993). (+) mark the two cysteines (amino acids number 632 and 635) of the IgG hinge preceding the Fc that form the inter-chain disulfide bridges that link two Fc domains. The hexahistine tag is shown in bold/italic type (amino acids 854 to 859). (•) shows the position of the STOP codon.

FIG. 5 (SEQ ID NO: 8): The amino acid sequence of human IL-6Rα-Fc (SEQ ID NO: 8). Key: Amino acids 1 to 358 are from human IL-6Rα, (Yamasaki, et al., Science 241:825–828 (1988). Note that amino acid number 2 has been changed from a Leu to a Val in order to accommodate a Kozak sequence in the coding DNA sequence. The signal peptide of IL-6Rα-Fc has been italicized (amino acids 1 to 19). The Ala-Gly bridge is shown in bold type (amino acids 359, 360). Amino acids 361 to 592 are from the Fc domain of human IgG1 (Lewis et al., J. Immunol. 151:2829–2838 (1993). (+) mark the two cysteines (amino acids number 371 and 374) of the IgG hinge preceding the Fc that form the inter-chain disulfide bridges that link two Fc domains. (•) shows the position of the STOP codon.

FIGS. 9A–9B (SEQ ID NO: 9). Amino acid sequence of gp130-Cγ1 (SEQ ID NO: 9). Key: Amino acids 1 to 619 are from human gp130 (Hibi, et al., Cell 63:1149–1157 (1990). Ser-Gly bridge is shown in bold type. Amino acids 662 to 651 are from the constant region of human IgG1 (Lewis et al., J. Immunol. 151:2829–2838 (1993). (*) shows the position of the STOP codon.

FIG. 10 (SEQ ID NO: 10): Amino acid sequence of gp130Δ3fibro (SEQ ID NO: 10). Key: Amino acids 1 to 330 are from human gp130 (Hibi et al., Cell 63:1149–1157 (1990). Other symbols as described in FIG. 9.

FIG. 11 (SEQ ID NO: 11): Amino acid sequence of J-CH1 (SEQ ID NO: 11). Key: The Ser-Gly bridge is shown in bold, the J-peptide is shown in italics, the $C_H1$ domain is underlined.

FIG. 12 (SEQ ID NO: 12): Amino acid sequence of Cγ4 (SEQ ID NO: 12). Key: The Ser-Gly bridge is shown in bold type. Amino acids 2 to 239 comprise the Cγ4 sequence.

FIG. 13 (SEQ ID NO: 13): Amino acid sequence of κ-domain (SEQ ID NO: 13). Key: The Ser-Gly bridge is shown in bold type. Amino acids 2 to 108 comprise the κ domain. The C-terminal cysteine (amino acid 108) is that involved in the disulfide bond of the κ domain with the $C_H1$ domain of Cγ.

FIG. 14 (SEQ ID NO: 14): Amino acid sequence of λ-domain (SEQ ID NO: 14). Key: The Ser-Gly bridge is shown in bold type. Amino acids 2 to 106 comprise the λ domain (Cheung, et al., J. Virol. 66: 6714–6720 (1992). The C-terminal cysteine (amino acid 106) is that involved in the disulfide bond of the λ domain with the $C_H1$ domain of Cγ.

FIG. 15 (SEQ ID NO: 15): Amino acid sequence of the soluble IL-6Rα domain (SEQ ID NO: 15). Key: Amino acids 1 to 358 comprise the soluble IL-6Rα domain (Yamasaki, et al., Science 241:825–828 (1988). The Ala-Gly bridge is shown in bold type.

FIG. 16 (SEQ ID NO: 16): Amino acid sequence of the soluble IL-6Rα313 domain (SEQ ID NO: 16): Key: Amino acids 1 to 313 comprise the truncated IL-6Rα domain (IL-6Rα313). The Thr-Gly bridge is shown in bold type.

FIG. 20: Inhibition of IL-6-dependent XG-1 cell proliferation. XG-1 cells [Zhang, et al., Blood 83:3654–3663 (1994)] were prepared for a proliferation assay by starving the cells from IL-6 for 5 hours. Assays were set up in 96-well tissue culture dishes in RPMI +10% fetal calf serum+ penicillin/streptomycin+0.050 nM 2-mercaptoethanol+ glutamine. 0.1 ml of that media was used per well. Cells were suspended at a density of 250,000 per ml at the start of the assay. 72 hours post addition of IL-6±ligands Traps or antibodies, an MTT assay was performed as described (Panayotatos et al. Biochemistry 33:5813–5818 (1994). The different ligand Traps utilized are listed.

FIGS. 21A–21D (SEQ ID NOS: 17 and 18): Nucleotide (SEQ ID NO: 17) sequence encoding and deduced amino acid (SEQ ID NO: 18) sequence of fusion polypeptide designated 424 which is capable of binding the cytokine IL-4 to form a nonfunctional complex.

FIGS. 22A–22D (SEQ ID NOS: 19 and 20): Nucleotide (SEQ ID NO: 19) sequence encoding and deduced amino acid (SEQ ID NO: 20) sequence of fusion polypeptide designated 603 which is capable of binding the cytokine IL-4 to form a nonfunctional complex.

FIGS. 23A–23D (SEQ ID NOS: 21 and 22): Nucleotide (SEQ ID NO: 21) sequence encoding and deduced amino acid (SEQ ID NO: 22) sequence of fusion polypeptide designated 622 which is capable of binding the cytokine IL-4 to form a nonfunctional complex.

FIGS. 24A–24F (SEQ ID NOS: 23 and 24): Nucleotide (SEQ ID NO: 23) sequence encoding and deduced amino acid (SEQ ID NO: 24) sequence of fusion polypeptide designated 412 which is capable of binding the cytokine IL-6 to form a nonfunctional complex.

FIGS. 25A–25F (SEQ ID NOS: 25 and 26): Nucleotide (SEQ ID NO: 25) sequence encoding and deduced amino acid (SEQ ID NO: 26) sequence of fusion polypeptide designated 616 which is capable of binding the cytokine IL-6 to form a nonfunctional complex.

FIGS. 26A–26E (SEQ ID NOS: 27 and 28): Nucleotide (SEQ ID NO: 27) sequence encoding and deduced amino acid (SEQ ID NO: 28) sequence of fusion polypeptide designated 569 which is capable of binding the cytokine IL-1 to form a nonfunctional complex.

FIGS. 31A–31G (SEQ ID NOS: 29 and 30): The nucleotide (SEQ ID NO: 29) and encoded amino acid (SEQ ID NO: 30) sequence of the IL-4Rα.IL-13Rα1.Fc single chain Trap construct is set forth.

FIGS. 32A–32G (SEQ ID NOS: 31 and 32): The nucleotide (SEQ ID NO: 31) and encoded amino acid (SEQ ID NO: 32) sequence of the IL-13Rα1.IL-4Rα.Fc single chain Trap construct is set forth.

FIG. 36A: Cynomologus monkeys were treated in three parts as indicated. Human IL-4 (25 μg/kg) was injected subcutaneously twice daily for 4 days and human IL-4 Trap (8 mg/ml) and vehicle were given intravenously daily for 5 days, beginning 1 day prior to human IL-4 administration. Plasma was collected daily and assayed for MCP-1 levels. Results were expressed as mean +/−SEM; n=4. (ANOVA p<0.0007; Tukey-Kramer: Part 2 vs. Part 1, p,0.05; Part 2 vs. Part 3, p,0.05; Part 1 vs. Part 3, not significant.) FIG. 36B: Cynomologus monkeys were treated in three parts as indicated. Human IL-4 (25 μg/kg) was injected subcutaneously twice daily for 4 days and human IL-4 Trap (8 mg/ml) and vehicle were given intravenously daily for 5 days, beginning 1 day prior to human IL-4 administration. Whole blood was collected daily for flow cytometry analysis for CD16. Results were expressed as mean +/−SEM; n=4. (ANOVA p<0.042; Tukey-Kramer: Part 2 vs. Part 1, p<0.05; Part 2 vs. Part 3 and Part 1 vs. Part 3, not significant.)

FIGS. 38A–38H (SEQ ID NOS: 33 and 34): Nucleotide (SEQ ID NO: 33) and deduced amino acid (SEQ ID NO: 34) sequence of IL-4/IL-13 Trap 933.

FIGS. 39A–39G (SEQ ID NOS: 39 and 40): Nucleotide (SEQ ID NO: 39) and deduced amino acid (SEQ ID NO: 40) sequence of IL-4/IL-13 Trap 943.

FIGS. 40A–40I (SEQ ID NOS: 37 and 38): Nucleotide (SEQ ID NO: 37) and deduced amino acid (SEQ ID NO: 38) sequence of IL-4/IL-13 Trap 1126.

FIGS. 41A–41P (SEQ ID NOS: 35 and 36): Nucleotide (SEQ ID NO: 35) and deduced amino acid (SEQ ID NO: 36) sequence of IL-4/IL-13 Trap 1128.

FIGS. 42A–42I (SEQ ID NOS: 41 and 42): Nucleotide (SEQ ID NO: 41) and deduced amino acid (SEQ ID NO: 42) sequence of IL-4/IL-13 Trap 1130.

FIGS. 43A–43P (SEQ ID NOS: 43 and 44): Nucleotide (SEQ ID NO: 43) and deduced amino acid (SEQ ID NO: 44) sequence of IL-4/IL-13 Trap 1132.

FIGS. 44A–44I (SEQ ID NOS: 45 and 46): Nucleotide (SEQ ID NO: 45) and deduced amino acid (SEQ ID NO: 46) sequence of IL-4/IL-13 Trap 1199.

FIGS. 45A–45I (SEQ ID NOS: 47 and 48): Nucleotide (SEQ ID NO: 47) and deduced amino acid (SEQ ID NO: 48) sequence of IL-4/IL-13 Trap 1244.

FIGS. 46A–46I (SEQ ID NOS: 49 and 50): Nucleotide and deduced amino acid sequence of IL-4/IL-13 Trap 1245.

FIGS. 47A–47I (SEQ ID NOS: 51 and 52): Nucleotide (SEQ ID NO: 51) and deduced amino acid (SEQ ID NO: 52) sequence of IL-4/IL-13 Trap 1246.

FIGS. 52A–52H (SEQ ID NOS: 53 and 54): The nucleotide (SEQ ID NO: 53) and deduced amino acid (SEQ ID NO: 54) sequence of IL-4/IL-13 Trap 1244-B.

FIGS. 53A–53I (SEQ ID NOS: 55 and 56): The nucleotide (SEQ ID NO: 55) and deduced amino acid (SEQ ID NO: 56) sequence of IL-4/IL-13 Trap 1245-B.

FIGS. 54A–54H (SEQ ID NOS: 57 and 58): The nucleotide (SEQ ID NO: 57) and deduced amino acid (SEQ ID NO: 58) sequence of IL-4/IL-13 Trap 1246-B.

FIGS. 55A–55H (SEQ ID NOS: 59 and 60): The nucleotide (SEQ ID NO: 59) and deduced amino acid (SEQ ID NO: 60) sequence of IL-4/IL-13 Trap 1268.

DETAILED DESCRIPTION OF THE INVENTION

Figure 1:
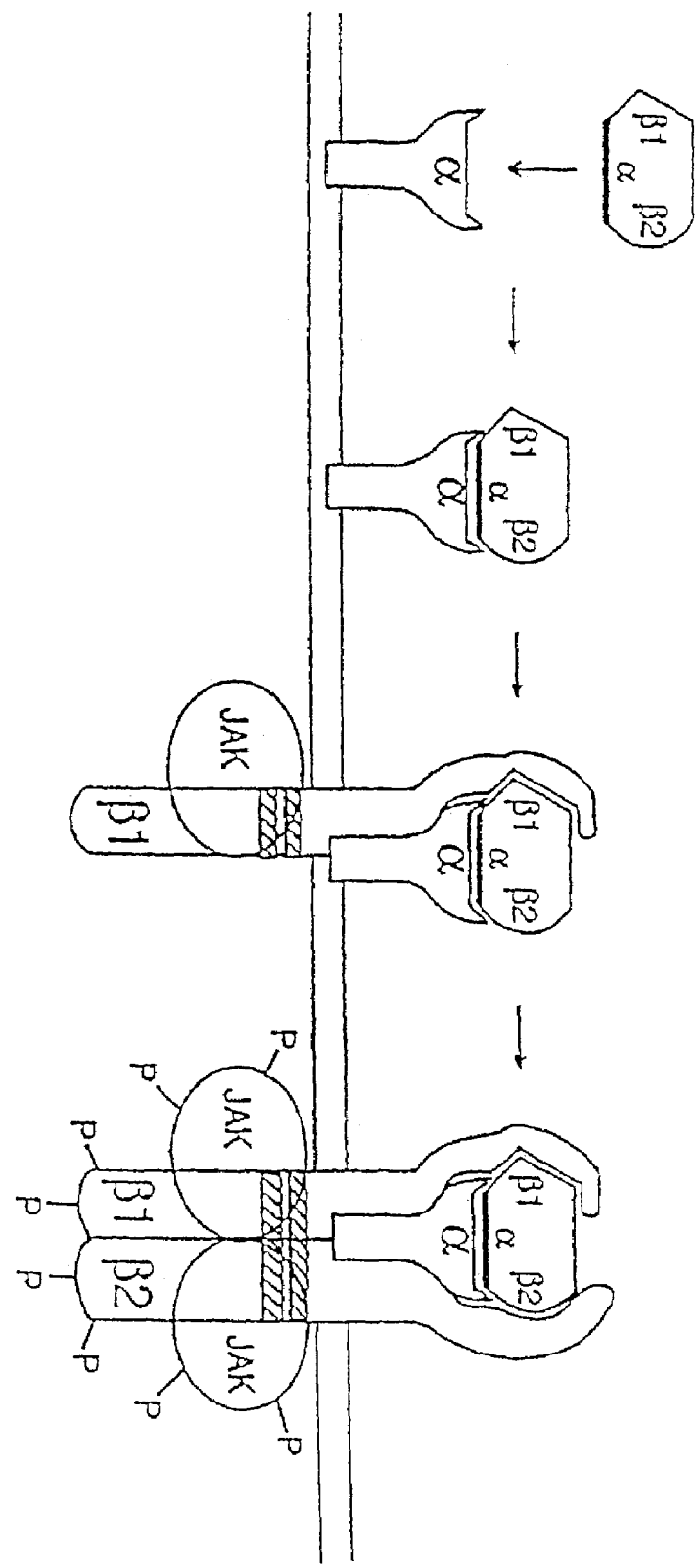
FIG. 1: Ordered binding of receptor components in a model of a generic cytokine receptor. The model indicates that cytokines contain up to 3 receptor binding sites and interact with their receptor components by binding first the optional α component, followed by binding to β1, and then β2. The β components for many cytokine receptors interact through membrane proximal regions (shaded boxes) with the Jak/Tyk family of cytoplasmic protein tyrosine kinases. Only upon dimerization of β components is signal transduction initiated, as schematized by the tyrosine phosphorylations (P) of the β components and the Jak/Tyk kinases.

The present invention provides an isolated nucleic acid molecule encoding a fusion polypeptide capable of binding a cytokine to form a nonfunctional complex comprising:
  a) a nucleotide sequence encoding a first fusion polypeptide component comprising the amino acid sequence of the cytokine binding portion of the extracellular domain of the specificity determining component of the cytokine's receptor;
  b) a nucleotide sequence encoding a second fusion polypeptide component comprising the amino acid sequence of the cytokine binding portion of the extracellular domain of the signal transducing component of the cytokine's receptor; and
  c) a nucleotide sequence encoding a third fusion polypeptide component comprising the amino acid sequence of a multimerizing component.

By "cytokine binding portion" what is meant is the minimal portion of the extracellular domain necessary to bind the cytokine. It is accepted by those of skill in the art that a defining characteristic of a cytokine receptor is the presence of the two fibronectin-like domains that contain canonical cysteines and of the WSXWS box (Bazan, J. F., 1990, PNAS 87: 6934–6938). Sequences encoding the extracellular domains of the binding component of the cytokine's receptor and of the signal transducing component of the cytokine's receptor may also be used to create the fusion polypeptide of the invention. Similarly, longer sequences encoding larger portions of the components of the cytokine's receptor may be used. However, it is contemplated that fragments smaller than the extracellular domain will function to bind the cytokine and therefore, the invention contemplates fusion polypeptides comprising the minimal portion of the extracellular domain necessary to bind the cytokine as the cytokine binding portion.

The invention comprises a "specificity determining component" of a cytokine's receptor and a "signal transducing component" of the cytokine's receptor. Regardless of the nomenclature used to designate a particular component or subunit of a cytokine receptor, one skilled in the art would recognize which component or subunit of a receptor is responsible for determining the cellular target of the cytokine, and thus would know which component constitutes the "specificity determining component."

Similarly, regardless of the nomenclature used, one of skill in the art would know which component or subunit of a receptor would constitute the "signal transducing component." As used herein, the "signal transducing component" is a component of the native receptor which is not the specificity determining component and which does not bind or weakly binds the cytokine in the absence of the specificity determining component. In the native receptor, the "signal transducing component" may participate in signaling.

For example, while some cytokine receptors have components designated α and β, the IL-4 receptor has a signal transducing component referred to as IL-2Rγ. However, regardless of what name is associated with that component, one skilled in the art would know which component of the IL-4 receptor is the signal transducing component. Thus to practice the present invention and create a high affinity Trap for IL-4, one of skill in the art would create an isolated nucleic acid comprising a nucleotide sequence encoding a first fusion polypeptide component comprising the amino acid sequence of the cytokine binding portion of the extracellular domain of the specificity determining component of the IL-4 receptor (IL-4Rα); a nucleotide sequence encoding a second fusion polypeptide component comprising the amino acid sequence of the cytokine binding portion of the extracellular domain of the signal transducing component of the IL-4 receptor (IL-2Rγ); and a nucleotide sequence encoding a third fusion polypeptide component comprising the amino acid sequence of a multimerizing component (for example, an Fc domain of IgG) to create a high affinity Trap for IL-4.

Some further examples of the receptor components that may be used to prepare cytokine antagonists according to the invention are set forth in Table 1. The Table 1 sets forth, by way of example but not by way of limitation, some of the varied nomenclature used in the scientific literature to describe those components which function as specificity determining components and those which function as signal transducing components of certain cytokine receptors.

Exhibit A

| Cytokine | Specificity determining Component | Signal transducing Component |
| --- | --- | --- |
| Interleukin-1 (IL-1) | Type I IL-1R[ref. 8]<br>Type II IL-1R[ref. 8]<br>IL-1RI[ref. 11]<br>IL-1RII[ref. 11] | IL-1R AcP[refs. 8, 11] |
| Interleukin-2 (IL-2) | α-subunit[ref. 2]<br>α-chain[ref. 3] | β-chain[ref. 3]<br>β-subunit[ref. 2] |

Exhibit A -continued

| Cytokine | Specificity determining Component | Signal transducing Component |
|---|---|---|
| | IL2Rα[ref. 1] | γ-chain[ref. 3]<br>IL-2Rβ[refs. 1, 10]<br>IL-2Rγ[refs. 1, 10] |
| Interleukin-3 (IL-3) | IL-3Rα[ref. 1]<br>α-subunit[ref. 2]<br>α-receptor component[ref. 5] | $\beta_c$[ref. 1]<br>β-subunit[ref. 2]<br>β-chain[ref. 3]<br>β-receptor component[ref. 5] |
| Interleukin-4 (IL-4) | IL-4R[ref. 1] | γ-chain[ref. 3]<br>IL-2Rγ[ref. 1] |
| Interleukin-5 (IL-5) | IL-5Rα[ref. 1]<br>α-subunit[ref. 2]<br>α-receptor compnent[ref. 5] | $\beta_c$[ref. 1]<br>β-subunit[ref. 2]<br>β-chain[ref. 3]<br>β-receptor component[ref. 5] |
| Granulocyte macro-page-colony stimulating factor (GM-SCF) | α-receptor component[ref. 5]<br>α-subunit[ref. 2]<br>GMRα[refs. 1, 2] | β-receptor component[ref. 5]<br>β-subunit[ref. 2]<br>β-chain[ref. 3]<br>$\beta_c$[ref. 1]<br>GMRβ[refs. 1, 2] |
| Leukemia inhibitory factor (LIF) | LIFBP[ref. 1]<br>α-receptor component[ref. 5] | gp130[refs. 1, 3]<br>β-receptor component[ref. 5] |
| Interleukin-11 (IL-11) | α-chain[ref. 4]<br>NR1[ref. 4] | gp130[ref. 4] |
| Interleukin-15 (IL-15) | IL-15Rα[ref. 10] | IL-2Rβ[ref. 10]<br>IL-2Rγ[ref. 10] |
| Interferon-γ (IFNγ) | IFN-γR[ref. 7]<br>IFN-γR1[ref. 7] | AF-1[ref. 7]<br>IFN-γR2[ref. 7] |
| TGFβ | Type II[refs. 6, 9] | Type I[refs. 6, 9] |

Only a few of the multitude of references are cited in Table 1, and they are set forth as follows:
1. Sato and Miyajima, Current Opinions in Cell Biology 6: 174–179 (1994)—See page 176, lines 9–16;
2. Miyajima, et al., Annual Review of Immunology 10: 295–331 (1992)—See page 295, line 4 to page 296, line 1; page 305, last paragraph;
3. Kondo, et al, Science 262: 1874–1877 (1993)—See page 1874, cols. 1 & 2;
4. Hilton, et al, EMBO Journal 13: 4765–4775 (1994)—See page 4766, col. 1, lines 20 24;
5. Stahl and Yancopoulos, Cell 74: 587–590 (1993)—See page 587, column 2, lines 15–22;
6. Bassing, et al, Journal of Biological Chemistry 269: 14861–14864 (1994)—See page 14861, col. 2, lines 1–9 and 21–28;
7. Kotenko, et al, Journal of Biological Science 270: 20915–20921 (1995)—See page 20915, lines 1–5 of the abstract;
8. Greenfeder, et al., Journal of Biological Chemistry 270: 13757–13765 (1995)—See page 13757, col. 1, line 6 to col. 2, line 3 and col. 2, lines 10–12; page 13764, col. 2, last 3 lines and page 13765, col. 1, lines 1–7;
9. Lebrun and Vale, Molecular Cell Biology 17: 1682–1691 (1997)—See page 1682, Abstract lines 2–6;
10. Kennedy and Park, Journal of Clinical Immunology 16: 134–143 (1996)—See page 134, lines 1–7 of the abstract; page 136, col 2., lines 1–5;
11. Wesche, et al., Journal of Biological Chemistry 272: 7727–7731 (1997) See page 7731, lines 20–26.

Kotenko, et al. recently identified the IL-10R2 (IL-10Rβ) chain which is reported to serve as an accessory chain that is essential for the active IL-10 receptor complex and for initiating IL-10 induced signal transduction events (S. V. Kotenko, et al., The EMBO Journal, 1997, Vol. 16: 5894–5903). Additional cytokines and their receptors are described in Appendix II, page A:9 of *Immunobiology, The Immune System In Health and Disease,* 2nd Edition, by Charles A. Janeway, Jr. and Paul Travers, published by Current Biology Ltd./Garland Publishing Inc., copyright 1996.

In preparing the nucleic acid sequence encoding the fusion polypeptide of the invention, the first, second, and third components of the fusion polypeptide are encoded in a single strand of nucleotides which, when expressed by a host vector system, produces a monomeric species of the fusion polypeptide. The monomers thus expressed then multimerize due to the interactions between the multimerizing components (the third fusion polypeptide components). Producing the fusion polypeptides in this manner avoids the need for purification of heterodimeric mixtures that would result if the first and second components were produced as separate molecules and then multimerized. For example, U.S. Pat. No. 5,470,952 issued Nov. 28, 1995 describes the production of heterodimeric proteins that function as CNTF or IL-6 antagonists. The heterodimers are purified from cell lines cotransfected with the appropriate alpha (α) and beta (β) components. Heterodimers are then separated from homodimers using methods such as passive elution from preparative, nondenaturing polyacrylamide gels or by using high pressure cation exchange chromatography. The need for this purification step is avoided by the methods of the present invention.

In addition, PCT International Application WO 96/11213 published Apr. 18, 1996 entitled Dimeric IL-4 Inhibitors states that the applicant has prepared homodimers in which two IL-4 receptors are bound by a polymeric spacer and has prepared heterodimers in which an IL-4 receptor is linked by a polymeric spacer to an IL-2 receptor gamma chain. The polymeric spacer described is polyethylene glycol (PEG). The two receptor components, IL-4R and IL-2Rgamma are separately expressed and purified. Pegylated homodimers and heterodimers are then produced by joining the components together using bi-functional PEG reagents. It is an advantage of the present invention that it avoids the need for such time consuming and costly purification and pegylation steps.

In one embodiment of the invention, the nucleotide sequence encoding the first component is upstream of the nucleotide sequence encoding the second component. In another embodiment of the invention, the nucleotide sequence encoding the first component is downstream of the nucleotide sequence encoding the second component. Further embodiments of the invention may be prepared in which the order of the first, second and third fusion polypeptide components are rearranged. For example, if the nucleotide sequence encoding the first component is designated 1, the nucleotide sequence encoding the second component is designated 2, and the nucleotide sequence of the third component is designated 3, then the order of the components in the isolated nucleic acid of the invention as read from 5' to 3' may be any of the following six combinations: 1,2,3; 1,3,2; 2,1,3; 2,3,1; 3,1,2; or 3,2,1.

In further embodiments of the invention, the cytokine bound by the fusion polypeptide may be a member of the hematopoietin family of cytokines selected from the group consisting of interleukin-2, interleukin-3, interleukin-4, interleukin-5, interleukin-6, interleukin-7, interleukin-9, interleukin-11, interleukin-13, interleukin-15, granulocyte macrophage colony stimulating factor, oncostatin M, leukemia inhibitory factor, and cardiotrophin-1.

In additional embodiments of the invention, the cytokine bound by the fusion polypeptide may be a member of the interferon family of cytokines selected from the group consisting of IFN-gamma, IFN-alpha, and IFN-beta.

In additional embodiments of the invention, the cytokine bound by the fusion polypeptide may be a member of the immunoglobulin superfamily of cytokines selected from the group consisting of B7.1 (CD80) and B7.2 (B70).

In still further embodiments of the invention, the cytokine bound by the fusion polypeptide may be a member of the TNF family of cytokines selected from the group consisting of TNF-alpha, TNF-beta, LT-beta, CD40 ligand, Fas ligand, CD 27 ligand, CD 30 ligand, and 4-1BBL.

In additional embodiments of the invention, the cytokine bound by the fusion polypeptide may be a cytokine selected from the group consisting of interleukin-1, interleukin-10, interleukin-12, interleukin-14, interleukin-18, and MIF.

Because specificity determination and signal transduction occurs by a similar mechanism in the TGF-β/BMP family of cytokines (See D. Kingsley, Genes & Development, 1994, 8: 133–146; J. Wrana, Miner Electrolyte Metab, 24: 120–130 (1998); R. Derynck and X. Feng, Biochimica et Biophysica Acta 1333 (1997) F105-F150; and J. Massague and F. Weis-Garcia, "Serine/threonine Kinase Receptors: Mediators of Transforming Growth Factor Beta Family Signals" In Cancer Surveys, Vol. 27: Cell Signaling, 1996, Imperial Cancer Research Fund) the present invention may be used to produce high affinity antagonists for cytokines that are members of the TGF-β/BMP family.

Therefore, in additional embodiments of the invention, the cytokine bound by the fusion polypeptide may be a member of the TGF-β/BMP family selected from the group consisting of TGF-β1, TGF-β2, TGF-β3, BMP-2, BMP-3a, BMP-3b, BMP-4, BMP-5, BMP-6, BMP-7, BMP-8a, BMP-8b, BMP-9, BMP-10, BMP-11, BMP-15, BMP-16, endometrial bleeding associated factor (EBAF), growth differentiation factor-1 (GDF-1), GDF-2, GDF-3, GDF-5, GDF-6, GDF-7, GDF-8, GDF-9, GDF-12, GDF-14, mullerian inhibiting substance (MIS), activin-1, activin-2, activin-3, activin-4, and activin-5.

In alternative embodiments of the invention, the specificity determining component, the signal transducing component, or both, may be substituted for by a single chain Fv. A single chain Fv (scFv) is a truncated Fab having only the V region of a heavy chain linked by a stretch of synthetic peptide to a V region of a light chain. See, for example, U.S. Pat. Nos. 5,565,332; 5,733,743; 5,837,242; 5,858,657; and 5,871,907 assigned to Cambridge Antibody Technology Limited incorporated by reference herein. Thus the present invention contemplates, for example, an isolated nucleic acid molecule encoding a fusion polypeptide capable of binding a cytokine to form a nonfunctional complex comprising a nucleotide sequence encoding a first fusion polypeptide component comprising the amino acid sequence of the cytokine binding portion of the extracellular domain of the specificity determining component of the cytokine's receptor; a nucleotide sequence encoding a second fusion polypeptide component comprising the amino acid sequence of an scFv capable of binding the cytokine at a site different from the site at which the cytokine binding portion of the extracellular domain of the specificity determining component of the cytokine's receptor binds; and a nucleotide sequence encoding a third fusion polypeptide component comprising the amino acid sequence of a multimerizing component. Alternatively, the specificity determining component may be substituted for by a scFv that binds to a site on the cytokine different from the site at which the signal transducing component binds. Thus the invention contemplates an isolated nucleic acid molecule encoding a fusion polypeptide capable of binding a cytokine to form a nonfunctional complex comprising a nucleotide sequence encoding a first fusion polypeptide component comprising the amino acid sequence of a scFv that binds to a site on the cytokine different from the site at which the cytokine binding portion of the extracellular domain of the signal transducing component of the cytokine's receptor binds; a nucleotide sequence encoding a second fusion polypeptide component comprising the amino acid sequence of the cytokine binding portion of the extracellular domain of the signal transducing component of the cytokine's receptor; and a nucleotide sequence encoding a third fusion polypeptide component comprising the amino acid sequence of a multimerizing component.

In another embodiment, the invention contemplates an isolated nucleic acid molecule encoding a fusion polypeptide capable of binding a cytokine to form a nonfunctional complex comprising a nucleotide sequence encoding a first fusion polypeptide component comprising the amino acid sequence of a first scFv that binds to a site on the cytokine; a nucleotide sequence encoding a second fusion polypeptide component comprising the amino acid sequence a second scFv that binds to a site on the cytokine different from the site at which the first scFv binds; and a nucleotide sequence encoding a third fusion polypeptide component comprising the amino acid sequence of a multimerizing component.

In all of the above described embodiments comprising scFv's, the invention also contemplates embodiments in which the nucleotide sequence encoding the first component is upstream of the nucleotide sequence encoding the second component; embodiments in which the nucleotide sequence encoding the first component is downstream of the nucleotide sequence encoding the second component; and further embodiments of the invention in which the order of the first, second and third fusion polypeptide components is rearranged. For example, if the nucleotide sequence encoding the first component is designated 1, the nucleotide sequence encoding the second component is designated 2, and the nucleotide sequence of the third component is designated 3, then the order of the components in the isolated nucleic acid of the invention as read from 5' to 3' may be any of the following six combinations: 1,2,3; 1,3,2; 2,1,3; 2,3,1; 3,1,2; or 3,2,1.

In preferred embodiments of the invention, the multimerizing component comprises an immunoglobulin derived domain. More specifically, the immunoglobulin derived domain may be selected from the group consisting of the Fc domain of IgG, the heavy chain of IgG, and the light chain of IgG. In another embodiment, the multimerizing component may be an Fc domain from which the first five amino acids (including a cysteine) have been removed to produce a multimerizing component referred to as Fc(ΔC1). Alternatively, the multimerizing component may be an Fc domain in which a cysteine within the first five amino acids has been substituted for by another amino acid such as, for example, serine or alanine.

The present invention also provides for fusion polypeptides encoded by the isolated nucleic acid molecules of the invention. Preferably, the fusion polypeptides are in multimeric form, due to the function of the third multimerizing component. In a preferred embodiment, the multimer is a dimer. Suitable multimerizing components are sequences encoding an immunoglobulin heavy chain hinge region (Takahashi et al., 1982, Cell 29:671–679); immunoglobulin gene sequences, and portions thereof. In a preferred embodiment of the invention, immunoglobulin gene sequences, especially one encoding the Fc domain, are used to encode the third multimerizing component.

The present invention also contemplates a vector which comprises the nucleic acid molecule of the invention as described herein.

Also provided is an expression vector comprising a nucleic acid molecule of the invention as described herein, wherein the nucleic acid molecule is operatively linked to an expression control sequence. Also provided is a host-vector system for the production of a fusion polypeptide which comprises the expression vector of the invention which has been introduced into a host cell suitable for expression of the fusion polypeptide. The suitable host cell may be a bacterial cell such as *E. coli*, a yeast cell, such as *Pichia pastoris*, an insect cell, such as *Spodoptera frugiperda*, or a mammalian cell, such as a COS, CHO, 293, BHK or NS0 cell.

The present invention also provides for methods of producing the fusion polypeptides of the invention by growing cells of the host-vector systems described herein, under conditions permitting production of the fusion polypeptide and recovering the fusion polypeptide so produced.

The present invention provides novel antagonists which are based on receptor components that are shared by cytokines such as the CNTF family of cytokines.

The invention described herein contemplates the production of antagonists to any cytokine that utilizes an α specificity determining component which, when combined with the cytokine, binds to a first β signal transducing component to form a nonfunctional intermediate which then binds to a second β signal transducing component causing β-receptor dimerization and consequent signal transduction. According to the invention, the soluble α specificity determining component of the receptor (sRα) and the extracellular domain of the first β signal transducing component of the cytokine receptor (β1) are combined to form heterodimers (sRα:β1) that act as antagonists to the cytokine by binding the cytokine to form a nonfunctional complex.

As described in Example 1, CNTF and IL-6 share the β1 receptor component gp130. The fact that CNTF forms an intermediate with CNTFRα and gp130 can be demonstrated (Example 1) in cells lacking LIFRβ, where the complex of CNTF and CNTFRα binds gp130, and prevents homodimerization of gp130 by IL-6 and IL-6Rα, thereby blocking signal transduction. These studies provide the basis for the development of the IL-6 antagonists described herein, as they show that if, in the presence of a ligand, a nonfunctional intermediate complex, consisting of the ligand, its α receptor component and its β1 receptor component, can be formed, it will effectively block the action of the ligand. Other cytokines may use other β1 receptor components, such as LIFRβ, which may also be used to produce antagonists according to the present invention.

Thus for example, in one embodiment of the invention, effective antagonists of IL-6 or CNTF consist of heterodimers of the extracellular domains of the α specificity determining components of their receptors (sIL-6Rα and sCNTFRα, respectively) and the extracellular domain of gp130. The resultant heterodimers, which are referred to hereinafter as sIL-6Rα:β1 and sCNTFRα:β1, respectively, function as high-affinity Traps for IL-6 or CNTF, respectively, thus rendering the cytokine inaccessible to form a signal transducing complex with the native membrane-bound forms of their receptors.

Although soluble ligand binding domains from the extracellular portion of receptors have proven to be somewhat effective as Traps for their ligands and thus act as antagonists [Bargetzi, et al., Cancer Res. 53:4010–4013 (1993);, et al., Proc. Natl. Acad. Sci. USA 89: 8616–8620 (1992); Mohler, et al., J. Immunol. 151: 1548–1561 (1993); Narazaki, et al., Blood 82: 1120–1126 (1993)], the IL-6 and CNTF receptors are unusual in that the α receptor components constitute ligand binding domains that, in concert with their ligands, function effectively in soluble form as receptor agonists [Davis, et al. Science 259:1736–1739 (1993); Taga, et al., Cell 58: 573–581 (1989)]. The sRα:β1 heterodimers prepared according to the present invention provide effective Traps for their ligands, binding these ligands with affinities in the picomolar range (based on binding studies for CNTF to PC12D cells) without creating functional intermediates. The technology described herein may be applied to develop a cytokine Trap for any cytokine that utilizes an α-component that confers specificity, as well as a β component which, when bound to the α-specificity component, has a higher affinity for the cytokine than either component alone. Accordingly, antagonists according to the invention include antagonists of interleukins 1 through 5 [IL-1, Greenfeder, et al. J. Biol. Chem. 270:13757–13765 (1995); Guo, et al. J. Biol. Chem. 270:27562–27568 (1995)], IL-2; [Taniguchi, et al. European Patent Nos. 0386289-A and 0386304-A (1990); Takeshita, et al. Science 257:379–382 (1992)]; IL-3; [Kitamura, et al. Cell 66:1165-1174 (1991)], IL-4; [Idzerda, et al. J. Exp. Med. 171:861–873 (1990)], IL-5; [Taverneir, et al. Cell 66:1175–1184 (1991)], IL-11 [(Cherel, et al. Direct Submission to EMBL/GenBank/DDBJ databases; accession No. Z38102)], interleukin 15 [IL-15; Hemar, et al. J. Cell Biol. 1295:55–64 (1995); Taniguchi, et al. European Patent Nos. 0386289-A and 0386304-A (1990); Takeshita, et al. Science 257:379–382 (1992)], granulocyte-macrophage colony stimulating factor [GM-CSF; Hayashida, et al. Proc. Natl. Acad. Sci. U.S.A. 97:9655–9659 (1990)], LIF, gamma interferon [IFNγ; Aguet, et al. Cell 55:273–280 (1988); Soh, et al. Cell 76:793–802 (1994)], and transforming growth factor beta [TGFβ; Inagaki, et al. Proc. Natl. Acad. Sci. USA 90:5359–5363 (1993)].

The α and β receptor extracellular domains may be prepared using methods known to those skilled in the art.

The CNTFRα receptor has been cloned, sequenced and expressed [Davis, et al. (1991) Science 253:59–63 which is incorporated by reference in its entirety herein]. The cloning of LIFRβ and gp130 are described in Gearing et al. in EMBO J. 10:2839–2848 (1991), Hibi, et al. Cell 63:1149–1157 (1990) and in published PCT application WO 93/10151 published May 27, 1993, all of which are incorporated by reference in their entirety herein.

The receptor molecules useful for practicing the present invention may be prepared by cloning and expression in a prokaryotic or eukaryotic expression system. The recombinant receptor gene may be expressed and purified utilizing any number of methods. The gene encoding the factor may be subcloned into a bacterial expression vector, such as for example, but not by way of limitation, pCP110.

The recombinant factors may be purified by any technique which allows for the subsequent formation of a stable, biologically active protein. For example, and not by way of limitation, the factors may be recovered from cells either as soluble proteins or as inclusion bodies, from which they may be extracted quantitatively by 8M guanidinium hydrochloride and dialysis. In order to further purify the factors, conventional ion exchange chromatography, hydrophobic interaction chromatography, reverse phase chromatography or gel filtration may be used.

The sRα:β heterodimeric receptors may be engineered using known fusion regions, as described in published PCT application WO 93/10151 published May 27, 1993 entitled "Receptor for Oncostatin M and Leukemia Inhibitory Factor" which describes production of β receptor heterodimers, or they may be prepared by crosslinking of extracellular domains by chemical means. The domains utilized may consist of the entire extracellular domain of the α and β components, or they may consist of mutants or fragments thereof that maintain the ability to form a complex with its ligand and other components in the sRα:β1 complex. For example, as described below in Example 4, IL-6 antagonists have been prepared using gp130 that is lacking its three fibronectin-like domains.

In one embodiment of the invention, the extracellular domains are engineered using leucine zippers. The leucine zipper domains of the human transcription factors c-jun and c-fos have been shown to form stable heterodimers [Busch and Sassone-Corsi, Trends Genetics 6: 36–40 (1990); Gentz, et al., Science 243: 1695–1699 (1989)] with a 1:1 stoichiometry. Although jun-jun homodimers have also been shown to form, they are about 1000-fold less stable than jun-fos heterodimers. Fos-fos homodimers have not been detected.

The leucine zipper domain of either c-jun or c-fos are fused in frame at the C-terminus of the soluble or extracellular domains of the above mentioned receptor components by genetically engineering chimeric genes. The fusions may be direct or they may employ a flexible linker domain, such as the hinge region of human IgG, or polypeptide linkers consisting of small amino acids such as glycine, serine, threonine or alanine, at various lengths and combinations. Additionally, the chimeric proteins may be tagged by His-His-His-His-His-His (His6),[SEQ. ID NO. 1] to allow rapid purification by metal-chelate chromatography, and/or by epitopes to which antibodies are available, to allow for detection on western blots, immunoprecipitation, or activity depletion/blocking in bioassays.

In another embodiment, as described below in Example 3, the srα: β1 heterodimer is prepared using a similar method, but using the Fc-domain of human IgG1 [Aruffo, et al., Cell 67:35–44 (1991)]. In contrast to the latter, formation of heterodimers must be biochemically achieved, as chimeric molecules carrying the Fc-domain will be expressed as disulfide-linked homodimers. Thus, homodimers may be reduced under conditions that favor the disruption of interchain disulfides but do not effect intra-chain disulfides. Then monomers with different extracellular portions are mixed in equimolar amounts and oxidized to form a mixture of homo- and heterodimers. The components of this mixture are separated by chromatographic techniques. Alternatively, the formation of this type of heterodimers may be biased by genetically engineering and expressing molecules that consist of the soluble or extracellular portion of the receptor components followed by the Fc-domain of hIgG, followed by either the c-jun or the c-fos leucine zippers described above [Kostelny, et al., J. Immunol. 148: 1547–1553 (1992)]. Since these leucine zippers form predominately heterodimers, they may be used to drive formation of the heterodimers where desired. As for the chimeric proteins described using leucine zippers, these may also be tagged with metal chelates or an epitope. This tagged domain can be used for rapid purification by metal-chelate chromatography, and/or by antibodies, to allow for detection on western blots, immunoprecipitation, or activity depletion/blocking in bioassays.

In additional embodiments, heterodimers may be prepared using other immunoglobulin derived domains that drive the formation of dimers. Such domains include, for example, the heavy chains of IgG (Cγ1 and Cγ4), as well as the constant regions of kappa (κ) and lambda (λ) light chains of human immunoglobulins. The heterodimerization of Cγ with the light chain occurs between the CH1 domain of Cγ and the constant region of the light chain (CL), and is stabilized by covalent linking of the two domains via a single disulfide bridge. Accordingly, as described in Example 4, constructs may be prepared using these immunoglobulin domains. Alternatively, the immunoglobulin domains include domains that may be derived from T cell receptor components which drive dimerization.

In another embodiment of the invention, the sRα:β1 heterodimers are prepared by expression as chimeric molecules utilizing flexible linker loops. A DNA construct encoding the chimeric protein is designed such that it expresses two soluble or extracellular domains fused together in tandem ("head to head") by a flexible loop. This loop may be entirely artificial (e.g. polyglycine repeats interrupted by serine or threonine at a certain interval) or "borrowed" from naturally occurring proteins (e.g. the hinge region of hIgG). Molecules may be engineered in which the order of the soluble or extracellular domains fused is switched (e.g. sIL6Rα/loop/sgp130 or sgp130/loop/sIL-6Rα) and/or in which the length and composition of the loop is varied, to allow for selection of molecules with desired characteristics.

Alternatively, the heterodimers made according to the present invention may be purified from cell lines cotransfected with the appropriate α and β components. Heterodimers may be separated from homodimers using methods available to those skilled in the art. For example, limited quantities of heterodimers may be recovered by passive elution from preparative, nondenaturing polyacrylamide gels. Alternatively, heterodimers may be purified using high pressure cation exchange chromatography. Excellent purification has been obtained using a Mono S cation exchange column.

In addition to sRα:β1 heterodimers that act as antagonists by binding free CNTF or IL-6, the present invention also contemplates the use of engineered, mutated versions of IL-6 with novel properties that allow it to bind to IL-6Rα and a single gp130 molecule, but fail to engage the second gp130 to complete β component homodimerization, and thus act as an effective IL-6 antagonist on any IL-6 responsive cell. Our model for the structure of the IL-6 and CNTF receptor complexes indicates that these cytokines have distinct sites for binding the α, β1, and β2 receptor components [Stahl and Yancopoulos, Cell 74: 587–590 (1993)]. Mutations of critical amino acid residues comprising each of these sites gives rise to novel molecules which have the desired antagonistic properties. Ablation of the β1 site would give a molecule which could still bind to the α receptor component but not the β1 component, and thereby comprise an antagonist with nanomolar affinity. Mutations of critical amino acid residues comprising the β2 site of IL-6 (IL-6β2$^-$) would give a molecule that would bind to IL-6Rα and the first gp130 monomer, but fail to engage the second gp130 and thus be functionally inactive. Similarly, mutations of the CNTF β2 site would give a molecule (CNTFβ2$^{-1}$) that would bind CNTFRα and gp130, but fail to engage LIFRβ, thereby antagonizing CNTF action by forming the non-functional β1 intermediate. Based on the binding results described above where CNTF forms the β1 intermediate with high affinity, both CNTFβ2$^-$ and IL-6β2$^-$ would constitute antagonists with affinity in the range of 10 pM.

A variety of means are used to generate and identify mutations of IL-6 or CNTF that have the desired properties. Random mutagenesis by standard methods of the DNA encoding IL-6 or CNTF may be used, followed by analysis of the collection of products to identify mutated cytokines having the desired novel properties as outlined below. Mutagenesis by genetic engineering has been used extensively in order to elucidate the structural organization of functional domains of recombinant proteins. Several different approaches have been described in the literature for carrying out deletion or substitution mutagenesis. The most successful appear to be alanine scanning mutagenesis [Cunningham and Wells (1989), Science 244: 1081–1085] and homolog-scanning mutagenesis [Cunningham, et al., (1989), Science 243:1330–1336].

Targeted mutagenesis of the IL-6 or CNTF nucleic acid sequences using such methods can be used to generate CNTFβ2- or IL-6β2-candidates. The choice of regions appropriate for targeted mutagenesis is done systematically, or determined from studies whereby panels of monoclonal antibodies against each factor are used to map regions of the cytokine that might be exposed after binding of the cytokine to the α receptor component alone, or to the αβ1 heterodimeric soluble receptors described above. Similarly, chemical modification or limited proteolysis of the cytokine alone or in a complex bound to the α receptor component or the αβ1 heterodimeric soluble receptors described above, followed by analysis of the protected and exposed regions could reveal potential β2 binding sites.

Assays for identifying CNTF or IL-6 mutants with the desired properties involve the ability to block with high affinity the action of IL-6 or CNTF on appropriately responsive cell lines [Davis, et al., Science 259: 1736–1739 (1993); Murakami, et al., Proc. Natl. Acad. Sci. USA 88: 11349–11353 (1991)]. Such assays include cell proliferation, survival, or DNA synthesis driven by CNTF or IL-6, or the construction of cell lines where binding of factor induces production of reporters such as CAT or β-galactosidase [Savino, et al., Proc. Natl. Acad. Sci. USA 90: 4067–4071 (1993)].

Alternatively, the properties of various mutants may be assessed with a receptor-based assay. One such assay consists of screening mutants for their ability to bind the sRα:β1 receptor heterodimers described above using epitope-tagged [Davis et al., Science 253: 59–63 (1991)] sRα:β1 reagents. Furthermore, one can probe for the presence or absence of the β2 site by assessing whether an epitope-tagged soluble β2 reagent will bind to the cytokine in the presence of the β1 heterodimer. For example, CNTF only binds to LIFRβ (the β2 component) in the presence of both CNTFRα and gp130 [Davis, et al. Science 260: 1805–1808 (1993); Stahl, et al. J. Biol. Chem. 268: 7628–7631 (1993)]. Thus a soluble LIFRβ reagent would only bind to CNTF in the presence of the soluble sRα,β1 dimer sCNTFRα:β1. For IL-6, the sRα:β1 reagent would be IL-6Rα:β1, and the probe for the β2 site would be epitope-tagged sgp130. Thus β2$^-$ mutants of CNTF would be identified as those that bound the sRα:β1 reagent, demonstrating that the α and β1 site of the cytokine were intact, yet failed to bind the β2 reagent.

In addition, the present invention provides for methods of detecting or measuring the activity of potential β2$^-$ mutants by measuring the phosphorylation of a β-receptor component or a signal transduction component selected from the group consisting of Jak1, Jak2 and Tyk2 or any other signal transduction component, such as the CLIPs, that are determined to be phosphorylated in response to a member of the CNTF family of cytokines.

A cell that expresses the signal transduction component(s) described herein may either do so naturally or be genetically engineered to do so. For example, Jak1 and Tyk-2-encoding nucleic acid sequences obtained as described in Velazquez, et al., Cell, Vol. 70:313–322 (1992), may be introduced into a cell by transduction, transfection, microinjection, electroporation, via a transgenic animal, etc., using any known method known in the art.

According to the invention, cells are exposed to a potential antagonist and the tyrosine phosphorylation of either the β-component(s) or the signal transduction component(s) are compared to the tyrosine phosphorylation of the same component(s) in the absence of the potential antagonist. In another embodiment of the invention, the tyrosine phosphorylation that results from contacting the above cells with the potential antagonist is compared to the tyrosine phosphorylation of the same cells exposed to the parental CNTF family member. In such assays, the cell must either express the extracellular receptor (α-component) or the cells may be exposed to the test agent in the presence of the soluble receptor component. Thus, for example, in an assay system designed to identify agonists or antagonists of CNTF, the cell may express the α-component CNTFRα, the β-components gp130 and LIFRβ and a signal transducing component such as Jak1. The cell is exposed to test agents, and the tyrosine phosphorylation of either the β-components or the signal transducing component is compared to the phosphorylation pattern produced in the presence of CNTF. Alternatively, the tyrosine phosphorylation which results from exposure to a test agent is compared to the phosphorylation which occurs in the absence of the test agent. Alternatively, an assay system, for example, for IL-6 may involve exposing a cell that expresses the β-component gp130 and a signal transducing protein such as Jak1, Jak2 or Tyk2 to a test agent in conjunction with the soluble IL-6 receptor.

In another embodiment of the invention the above approaches are used to develop a method for screening for small molecule antagonists that act at various steps in the process of ligand binding, receptor complex formation, and subsequent signal transduction. Molecules that potentially interfere with ligand-receptor interactions are screened by assessing interference of complex formation between the soluble receptors and ligand as described above. Alternatively, cell-based assays in which IL-6 or CNTF induce response of a reporter gene are screened against libraries of small molecules or natural products to identify potential antagonists. Those molecules showing antagonist activity are rescreened on cell-based assays responding to other factors (such as GM-CSF or factors like Neurotrophin-3 that activate receptor tyrosine kinases) to evaluate their specificity against the CNTF/IL-6/OSM/LIF family of factors. Such cell-based screens are used to identify antagonists that inhibit any of numerous targets in the signal transduction process.

In one such assay system, the specific target for antagonists is the interaction of the Jak/Tyk family of kinases [Firmbach-Kraft, Oncogene 5: 1329–1336 (1990); Wilks, et al., Mol. Cell. Biol. 11:2057–2065 (1991)] with the receptor β subunits. As described above, LIFRβ and gp130 preassociate with members of the Jak/Tyk family of cytoplasmic protein tyrosine kinases, which become activated in response to ligand-induced β component dimerization Stahl, et al. Science 263:92–95 (1993). Thus small molecules that could enter the cell cytoplasm and disrupt the interaction between the β component and the Jak/Tyk kinase could potentially block all subsequent intracellular signaling. Such activity could be screened with an in vitro scheme that assessed the ability of small molecules to block the interaction between the relevant binding domains of purified β component and Jak/Tyk kinase. Alternatively, one could easily screen for molecules that could inhibit a yeast-based assay of β component binding to Jak/Tyk kinases using the two-hybrid interaction system [Chien, et al., Proc. Natl. Acad. Sci. 88: 9578–9582 (1991)]. In such a system, the interaction between two proteins (β component and Jak/Tyk kinase or relevant domains thereof in this example) induces production of a convenient marker such as β-galactosidase. Collections of small molecules are tested for their ability to disrupt the desired interaction without inhibiting the interaction between two control proteins. The advantage of this screen would be the requirement that the test compounds enter the cell before inhibiting the interaction between the β component and the Jak/Tyk kinase.

The CNTF family antagonists described herein either bind to, or compete with the cytokines CNTF and IL-6. Accordingly, they are useful for treating diseases or disorders mediated by CNTF or IL-6. For example, therapeutic uses of IL-6 antagonists would include the following:

1) In osteoporosis, which can be exacerbated by lowering of estrogen levels in post-menopausal women or through ovariectomy, IL-6 appears to be a critical mediator of osteoclastogenesis, leading to bone resorption [Horowitz, Science 260: 626–627 (1993); Jilka, et al., Science 257: 88–91 (1992)]. Importantly, IL-6 only appears to play a major role in the estrogen-depleted state, and apparently is minimally involved in normal bone maintenance. Consistent with this, experimental evidence indicates that function-blocking antibodies to IL-6 can reduce the number of osteoclasts [Jilka, et al. Science 257: 88–91 (1992)]. While estrogen replacement therapy is also used, there appear to be side effects that may include increased risk of endometrial and breast cancer. Thus, IL-6 antagonists as described herein would be more specific to reduce osteoclastogenesis to normal levels.

2) IL-6 appears to be directly involved in multiple myeloma by acting in either an autocrine or paracrine fashion to promote tumor formation [van Oers, et al., Ann Hematol. 66: 219–223 (1993)]. Furthermore, the elevated IL-6 levels create undesirable secondary effects such as bone resorption, hypercalcemia, and cachexia; in limited studies function-blocking antibodies to IL-6 or IL-6Ra have some efficacy [Klein, et al., Blood 78: 1198–1204 (1991); Suzuki, et al., Eur. J. Immunol. 22:1989–1993 (1992)]. Therefore, IL-6 antagonists as described herein would be beneficial for both the secondary effects as well as for inhibiting tumor growth.

3) IL-6 may be a mediator of tumor necrosis factor (TNF) that leads to cachexia associated with AIDS and cancer [Strassmann, et al., J. Clin. Invest. 89: 1681–1684 (1992)], perhaps by reducing lipoprotein lipase activity in adipose tissue [Greenberg, et al., Cancer Research 52: 4113–4116 (1992)].

Accordingly, antagonists described herein would be useful in alleviating or reducing cachexia in such patients.

Effective doses useful for treating these or other CNTF family related diseases or disorders may be determined using methods known to one skilled in the art [see, for example, Fingl, et al., The Pharmacological Basis of Therapeutics, Goodman and Gilman, eds. Macmillan Publishing Co., New York, pp. 1–46 ((1975)]. Pharmaceutical compositions for use according to the invention include the antagonists described above in a pharmacologically acceptable liquid, solid or semi-solid carrier, linked to a carrier or targeting molecule (e.g., antibody, hormone, growth factor, etc.) and/or incorporated into liposomes, microcapsules, and controlled release preparation (including antagonist expressing cells) prior to administration in vivo. For example, the pharmaceutical composition may comprise one or more of the antagonists in an aqueous solution, such as sterile water, saline, phosphate buffer or dextrose solution. Alternatively, the active agents may be comprised in a solid (e.g. wax) or semi-solid (e.g. gelatinous) formulation that may be implanted into a patient in need of such treatment. The administration route may be any mode of administration known in the art, including but not limited to intravenously, intrathecally, subcutaneously, by injection into involved tissue, intraarterially, intranasally, orally, or via an implanted device.

Administration may result in the distribution of the active agent of the invention throughout the body or in a localized area. For example, in some conditions which involve distant regions of the nervous system, intravenous or intrathecal administration of agent may be desirable. In some situations, an implant containing active agent may be placed in or near the lesioned area. Suitable implants include, but are not limited to, gelfoam, wax, or microparticle-based implants.

EXAMPLES

Example 1

CNTF Competes with IL-6 for Binding to gp130

Materials and Methods

Materials. A clone of PC12 cells that respond to IL-6 (PC12D) was obtained from DNAX. Rat CNTF was prepared as described [Masiakowski, et al., J. Neurochem. 57:1003–10012 (1991)]. IL-6 and sIL-6Rα were purchased from R & D Systems. Antisera was raised in rabbits against a peptide derived from a region near the C-terminus of gp130 (sequence: CGTEGQVERFETVGME) [SEQ. ID. NO. 2] by the method described (Stahl, et al. J. Biol. Chem.

268:7628–7631 (1993). Anti-phosphotyrosine monoclonal 4G10 was purchased from UBI, and reagents for ECL from Amersham.

Signal Transduction Assays. Plates (10 cm) of PC12D were starved in serum-free medium (RPMI 1640+ glutamine) for 1 hour, then incubated with IL-6 (50 ng/mL)+ sIL-6R (1 mg/mL) in the presence or absence of added rat CNTF at the indicated concentrations for 5 minutes at 37° C. Samples were then subjected to anti-gp130 immunoprecipitation, SDS PAGE, and anti-phosphotyrosine immunoblotting as described (Stahl, et al. J. Biol. Chem. 268:7628–7631 (1993).

Results

Figure 2:
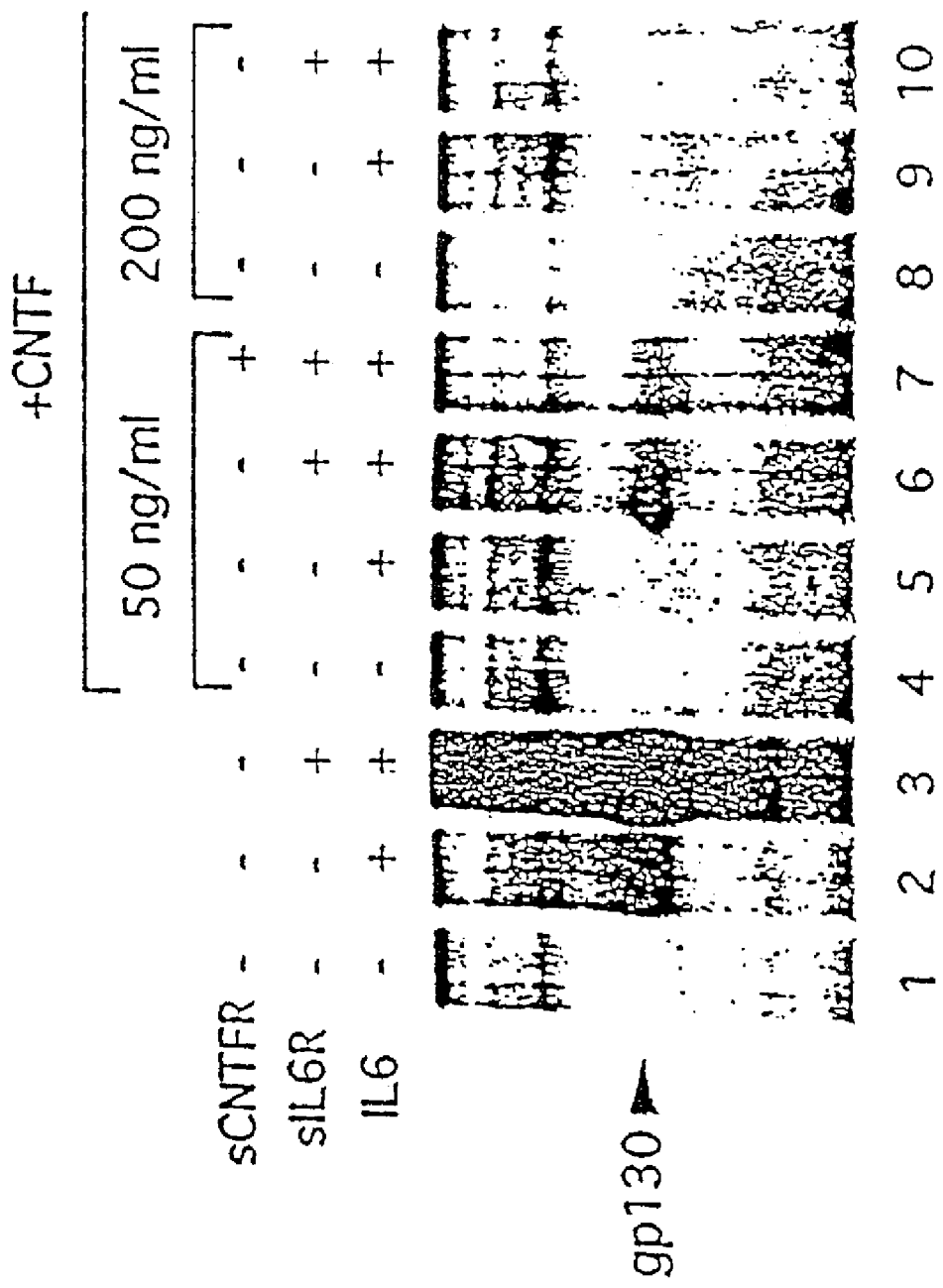
FIG. 2: CNTF inhibits IL-6 responses in a PC12 cell line (called PC12D) that expresses IL6Rα, gp130, CNTFRα, but not LIFRβ. Serum-deprived PC12D cells were incubated +IL-6 (50 ng/mL) in the presence or absence of CNTF as indicated. Some plates also received soluble IL6Rα (1 mg/mL) or soluble CNTFRα (1 mg/mL) as indicated. Cell lysates were subjected to immunoprecipitation with anti-gp130 and immunoblotted with anti-phosphotyrosine. Tyrosine phosphorylation of gp130 is indicative of IL-6 induced activation of the IL-6 receptor system, which is blocked upon coaddition of CNTF.

The ability of CNTF to block IL-6 responses was measured using a PC12 cell line (called PC12D) that expresses IL-6Rα, gp130, and CNTFRα, but not LIFRα. As one would predict, these cells respond to IL-6, but not to CNTF (FIG. 2) since LIFRβ is a required component for CNTF signal transduction [Davis, et al., Science 260: 59–63 (1993)]. In accordance with results on other cell lines [Ip, et al., Cell 69: 1121–1132 (1992)], PC12D cells give tyrosine phosphorylation of gp130 (as well as a variety of other proteins called CLIPs) in response to 2 nM IL-6 (FIG. 2). Addition of recombinant soluble IL-6Rα (sIL-6Rα) enhances the level of gp130 tyrosine phosphorylation, as has been reported in some other systems [(Taga, et al., Cell 58: 573–581 (1989)]. However, addition of 2 nM CNTF simultaneously with IL-6 severely diminishes the tyrosine phosphorylation of gp130. Although a slight gp130 phosphorylation response remains in the presence of CNTF, IL-6, and sIL-6Rα, it is eliminated if the CNTF concentration is increased fourfold to 8 nM. Thus, in IL-6 responsive cells that contain CNTFRα but no LIFRβ, CNTF is a rather potent antagonist of IL-6 action.

Example 2

Binding of CNTF to the CNTFRα:β

Materials and Methods

Scatchard Analysis of CNTF Binding. $^{125}$I-CNTF was prepared and purified as described [Stahl et al. JBC 268: 7628–7631 (1993)]. Saturation binding studies were carried out in PC12 cells, using concentrations of $^{125}$I-CNTF ranging from 20 pM to 10 nM. Binding was performed directly on a monolayer of cells. Medium was removed from wells and cells were washed once with assay buffer consisting of phosphate buffered saline (PBS; pH 7.4), 0.1 mM bacitracin, 1 mM PMSF, 1 mg/ml leupeptin, and 1 mg/ml BSA. Cells were incubated in $^{125}$I-CNTF for 2 hours at room temperature, followed by 2 quick washes with assay buffer. Cells were lysed with PBS containing 1% SDS and counted in a Packard Gamma Counter at 90–95% efficiency. Non-specific binding was defined by the presence of 100-fold excess of unlabelled CNTF. Specific binding ranged from 70% to 95%.

Results

Figure 3:
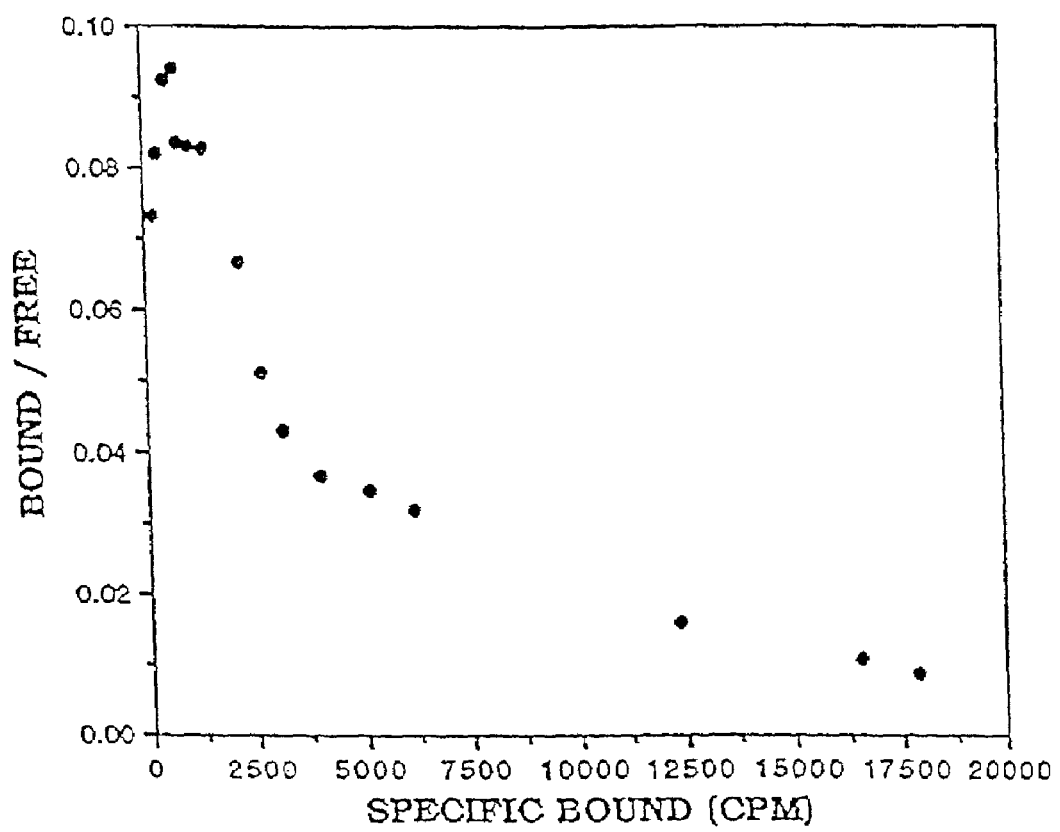
FIG. 3: Scatchard analysis of iodinated CNTF binding on PC12D cells. PC12D cells were incubated with various concentrations of iodinated CNTF in the presence or absence of excess non-radioactive competitor to determine the specific binding. The figure shows a Scatchard plot of the amount of iodinated CNTF specifically bound, and gives data consistent with two binding sites with dissociation constants of 9 pM and 3.4 nM.

The equilibrium constant for binding of CNTF to CNTFRα:β1 was estimated from Scatchard analysis of iodinated CNTF binding on PC12D cells (FIG. 3). The data is consistent with a 2 site fit having dissociation constants of 9 pM and 3.4 nM. The low affinity site corresponds to interaction of CNTF with CNTFRα, which has a Kd near 3 nM [(Panayotatos, et al., J. Biol. Chem. 268: 19000–19003 (1993)]. We interpret the high affinity complex as the intermediate containing CNTF, CNTFRα, and gp130. A Ewing sarcoma cell line (EW-1) which does contain CNTFRα, gp130, and LIFRβ, and therefore gives robust tyrosine phosphorylation in response to CNTF, displays a very similar two site fit with dissociation constants of 1 nM and 10. Thus it is apparent that CNTF binds with equally high affinity to a complex containing only CNTFRα and gp130, as it does to a complex which additionally contains LIFRβ, thus demonstrating the feasibility of creating the sRα:β antagonists described herein.

Example 3

Methods of Producing Cytokine Ligand Traps

Virus Stock Production

SF21 insect cells obtained from *Spodoptera frugiperda* were grown at 27° C. in Gibco SF900 II medium to a density of 1×10$^6$ cells/mL. The individual virus stock for either GP130-Fc-His$_6$ (FIGS. 4A–4B, [SEQ ID NO: 7]) or IL6Ra-Fc (FIG. 5, [SEQ ID NO: 8]) was added to the bioreactor to a low multiplicity 0.01–0.1 PFU/cell to begin the infection. The infection process was allowed to continue for 5–7 days allowing maximum virus replication without incurring substantial cell lysis. The cell suspension was aseptically aliquoted into sterile centrifuge bottles and the cells removed by centrifugation. The cell-free supernatant was collected in sterile bottles and stored at 4° C. until further use.

The virus titer was determined by plaque assay as described by O'Reilly, Miller and Luckow. The method is carried out in 60 mm tissue-culture dishes which are seeded with 2×10$^6$ cells. Serial dilutions of the virus stock are added to the attached cells and the mixture incubated with rocking to allow the virus to adsorb to individual cells. An agar overlay is added and plates incubated for 5–7 days at 27° C. Staining of viable cells with neutral red revealed circular plaques resulting which were counted to give the virus titer.

Coinfection of Cells for Protein Production

Uninfected SF21 Cells were grown in a 60L ABEC bioreactor containing 40L of SF900 11 medium. Temperature was controlled at 27° C. and the dissolved oxygen level was maintained at 50% of saturation by controlling the flowrate of oxygen in the inlet gas stream. When a density of 2×10$^6$ cells/mL was reached, the cells were concentrated within the bioreactor to a volume of 20L using a low shear steam sterilizable pump with a tangential flow filtration device with Millipore Prostak 0.65 micron membranes. After concentration fresh sterile growth medium is slowly added to the bioreactor while the filtration system continues to remove the spent growth medium by diafiltration. After two volume exchanges (40L) have been carried out an additional 20L of fresh medium was added to the bioreactor to resuspend the cells to the original volume of 40L. The cell density was determined once again by counting viable cells using a hemacytometer.

The required amount of each virus stock was calculated based on the cell density, virus titer and the desired multiplicity of infection (MOI). Virus stock ratios of 5:1, 5:2, 10:2 and 10:4, IL6Rα-Fc to GP130-Fc-His$_6$ all resulted in production of significant amounts of heterodimer. The ideal virus stock ratio is highly dependent on the ease of purification of the heterodimer from each of the two homodimers. The IL6Rα-Fc homodimer is relatively easy to remove downstream by immobilized metal affinity chromatography. Virus infection ratios have been chosen to minimize the formation of the GP130-Fc-His$_6$ homodimer which is more difficult to clear downstream. The relative amount of GP130-Fc-His$_6$ virus stock chosen for infection has increased with successive batches as the purification method for clearing the resultant homodimer has improved.

The virus stocks were aseptically mixed in a single vessel then transferred to the bioreactor. This results in synchronous infection of the SF21 cells. The infection is allowed to proceed for three to four days, allowing sufficient time for maximal production of the heterodimer protein.

Recovery and Protein A Chromatographic Purification

At the conclusion of the infection phase of the bioreactor process the cells were concentrated in the bioreactor using a 10 ft$^2$ Millipore Prostak filter (0.65 micron) pore size. The cell-free permeate passing through the filter was collected in a clean process vessel. At the conclusion of the filtration operation the pH of permeate stream, containing the protein product, was adjusted to 8.0 with 10N NaOH. The resultant precipitate was removed by forcing the extract through a 0.8 micron depth filter (Sartorious), followed by a 0.2 micron filter. Sufficient 0.5M EDTA stock was added to give a final concentration of 5 mM. The filtered protein solution was loaded onto a 10 cm diameter column containing 100–200 mL of Pharmacia Protein A Sepharose 4 Fast Flow, equilibrated with PBS. Protein A has a very high affinity for the Fc—Fc domain of each of the 3 recombinant protein products, allowing them to bind while other proteins in the cell-free extract flow through the column. After loading the column was washed to baseline with PBS containing an additional 350 mM NaCl. The IgG-Fc tagged proteins were eluted at low pH, either with 0.5M acetic acid or with a decreasing pH gradient of 0.1M citric acid and 0.2M disodium phosphate buffers. Tris base or disodium phosphate was added to the eluted protein to avoid prolonged exposure to low pH conditions.

The pooled protein was diafiltered into PBS or HEPES buffer and derivitized with 1 mM iodoacetamide to protect the exposed sulfhydryl group on the free cysteine near the hinge region of each Fc domain. This prevents disulfide mediated aggregation of proteins. A 6 ft$^2$ Millipore spiral wound ultrafiltration membrane with nominal 30 kiloDalton cutoff was used to perform the buffer exchange. The total protein was determined by UV absorbance at 280 nm using the diafiltration buffer as a blank. The relative amounts of heterodimer and two homodimer proteins were determined by SDS PAGE gel electrophoresis using a 6% Tris-Glycine gel (Novex). Gels were Coomassie-stained then transferred into destain solution overnight. A Shimadzu scanning densitometer was used to determine the relative intensity of the individual protein bands on the SDS PAGE gel. The peak area ratios are used to compute the fraction of heterodimer and each of the homodimers in the column pool fractions.

Immobilized Metal Affinity Chromatographic Purification

The six histidine residues on the C-terminus of the GP130-Fc-His$_6$ fusion protein provides an excellent molecular handle for separation of the heterodimeric IL6 antagonist from the two homodimers. The imidazole group on each of the C-terminal histidines of the GP130-Fc-His$_6$ moiety has a strong binding constant with several divalent metals, including copper, nickel, zinc, cobalt, iron and calcium. Since the IL6Rα-Fc homodimer has no C-terminal histidine residues, it clearly has the lowest affinity. The IL6Rα-Fc-GP130-Fc-His$_6$ heterodimer has a single stand set six histidines giving it greater affinity for the metal, while the GP130-Fc-His$_6$ homodimer has two sets of six histidines each giving it the highest affinity of the three IgG tagged proteins to the metal affinity column. Selective elution of the three proteins with increasing amounts of imidazole in the elution buffer therefore elutes the proteins in the following order:

1. IL6Rα-Fc homodimer
2. IL6Rα-Fc-GP130-Fc-His heterodimer
3. GP130-Fc-His homodimer A 26 mm diameter column containing 100 mL of Pharmacia Chelating Sepharose Fast Flow was saturated with a solution of nickel sulfate until a significant green color is observed in the column eluate. The column is then washed with several column volumes of deionized water, then equilibrated with 50 mM HEPES, 40 mM imidazole, pH 8.0. The binding of imidazole to the immobilized nickel results in a green to blue color change. Imidazole was added to the protein load to a final concentration of 40 mM. Addition of imidazole to the protein load reduces the binding of IL6Rα-Fc homodimer, increasing the surface area available for the remaining two species. After loading, the column was washed with several column volumes of 50 mM HEPES, 80 mM imidazole, pH 8.0 until a steady baseline was reestablished. The heterodimer was selectively eluted with 50 mM HEPES, 150 mM imidazole, pH 8.0 over several column volumes. The protein fractions were pooled and diafiltered into PBS as described in the section above.

Example 4

Alternative Methods of Constructing Ligand Traps

Figure 6:
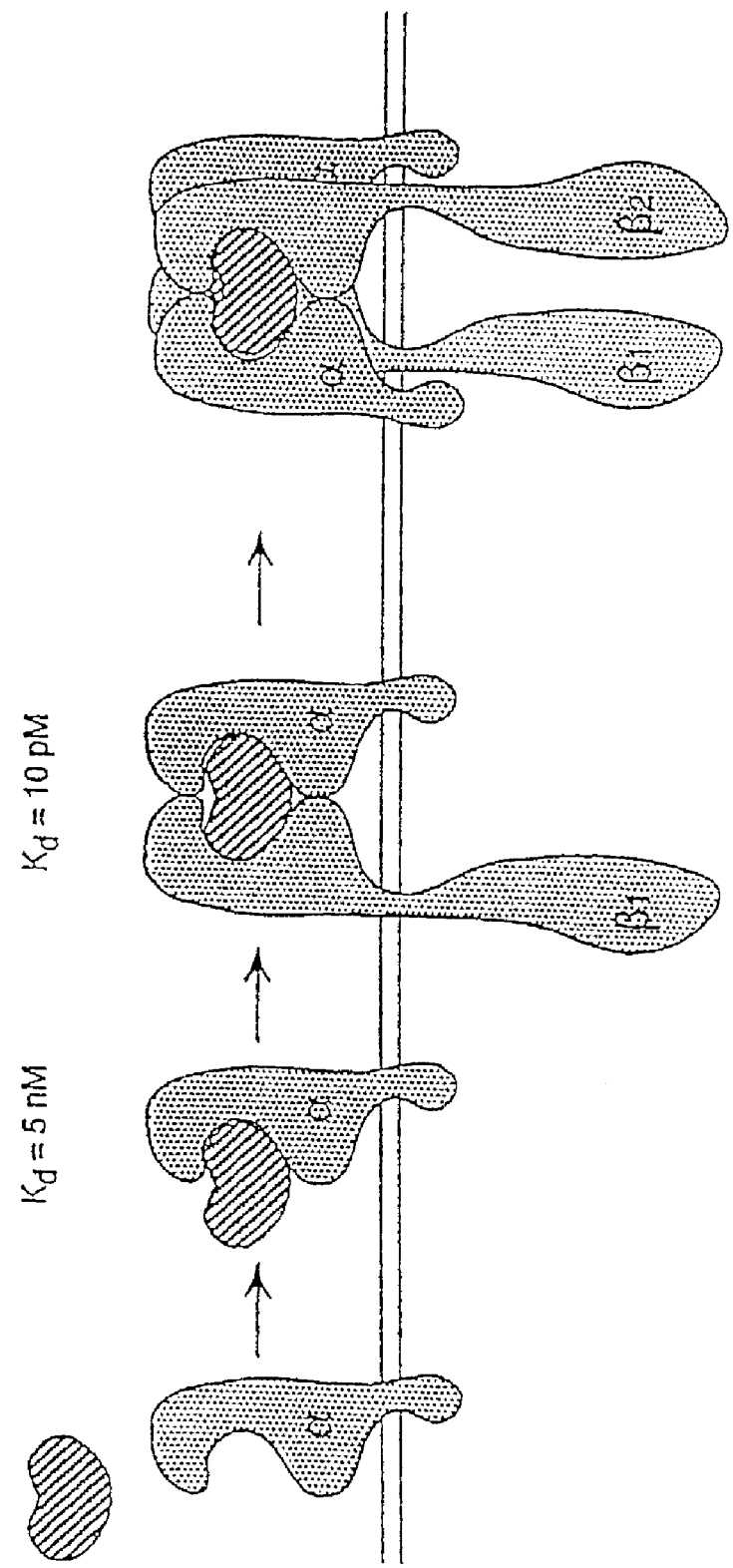
FIG. 6: The CNTF/IL-6/IL-11 receptor system. The ordered formation of the hexameric signal transducing receptor complex is depicted schematically. The cytokine associates with the Rα component to form an obligatory cytokine•Rα complex (Kd is about 5 nM). This low affinity complex next associates with the first signal transducing component, marked β1, to form a high affinity cytokine•Rα•β1 complex (Kd is about 10 pM). In the case of IL-6Rα, this component is gp130. This trimeric high affinity complex subsequently associates with another such complex. Formation of this complex results in signal transduction as it involves dimerization of two signal transducing components, marked β1 and β2 respectively (adapted from (Ward et al., J. Bio. Chem. 269:23286–23289 (1994); Stahl and Yancopoulos, J. Neurobiology 25:1454–1466 (1994); Stahl and Yancopoulos, Cell 74:587–590 (1993).

As described above, receptor activation by CNTF, and analogously by IL-6 and IL-11, follows an ordered sequence of binding events (FIG. 6). The cytokine initially binds to its cognate Rα with low affinity (Kd=3 to 10 nM); this is a required step—cells which do not express the cognate Rα do not respond to the cognate cytokine. The cytokine•Rα complex associates with the first signal transducing component, gp130, to form a high affinity complex (Kd in the order of 10 pM for the CNTF•CNTFRα•gp130 complex). This complex does not transduce signal, as it is the dimerization of the signal transducing components that brings about signaling (Stahl and Yancopoulos, J. Neurobiology 25: 1454–1466 (1994); Stahl et al., Science 267:1349–1353 (1995); Davis et al., Science 260:1805–1808 (1993); Stahl et al., Science 263:92–95 (1994); Murakami, et al. Science 260:1808–1810 (1993). At least in the case of IL-6, the cytokine•Rα•signal transducer heterotrimeric complex subsequently associates with another like complex, to form a hexameric complex (FIG. 6) (Ward et al., J. Biol. Chem. 269:23286–23289 (1994). The resulting dimerization of the signal transducers—gp130 in the case of IL-6 (Murakami et al., Science 260:1808–1810 (1993) and IL-11, gp130 and LIFR in the case of CNTF (Davis et al., Science 260: 1805–1808 (1993)—brings about signal transduction.

Figure 7:
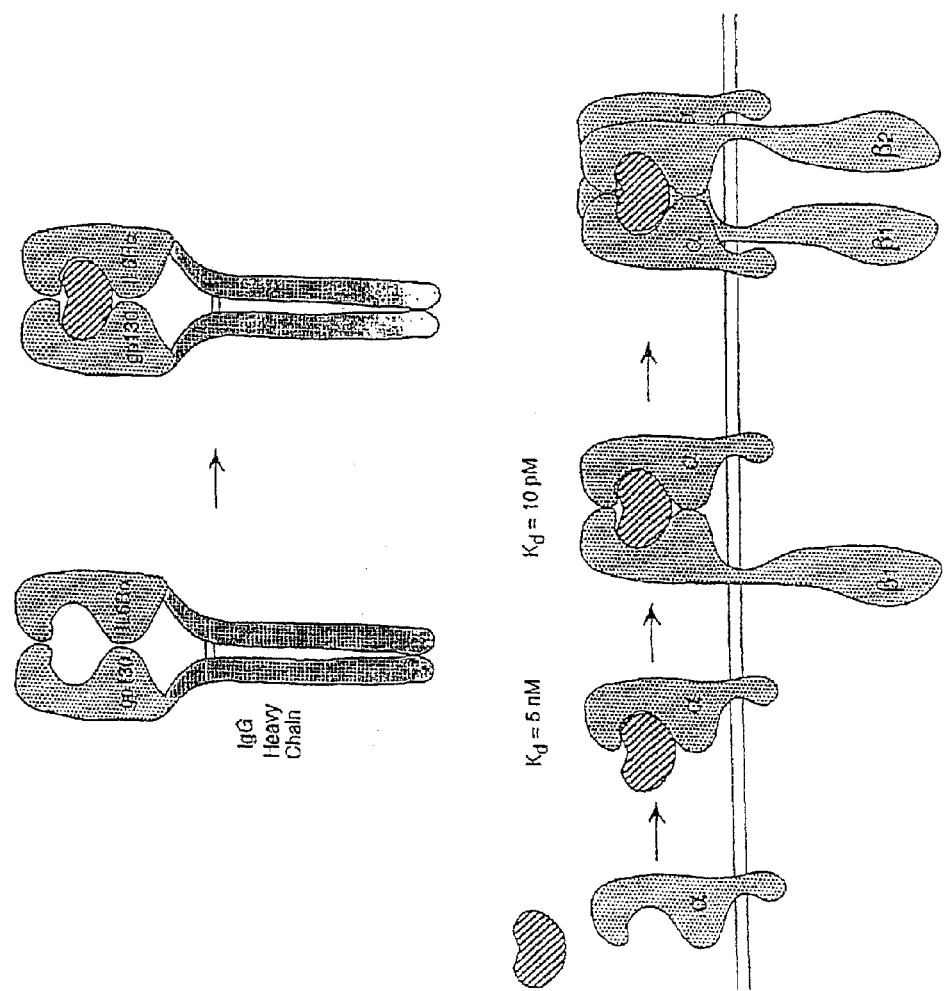
FIG. 7: Design of heterodimeric receptor-based ligand Traps for IL-6. The heterodimeric ligand Trap is comprised of two interdisulfide linked proteins, gp130-Fc and IL-6Rα-Fc. The gp130-Fc•IL-6Rα-Fc complex (upper panel) is shown to mimic the high affinity cytokine•Rα•β1 complex (lower panel). The ligand Trap functions as an antagonist by sequestering IL-6 and thus rendering unavailable to interact with the native receptors on IL-6-responsive cells.

The initial heterodimeric molecules made comprised a soluble Rα-component linked to the extracellular domain of gp130. These molecules were shown to mimic the high affinity cytokine•Rα•gp130 complex and behave as a high affinity antagonist of their cognate cytokine (FIG. 7). To make these molecules, the extracellular domain of gp130 was paired with the extracellular domain of the α-receptor components for IL-6 and CNTF, IL-6Rα and CNTFRα respectively. To link the Rα with the extracellular domain of gp130, the soluble Rα-components and gp130 were fused to the Fc portion of human IgG1 to produce Rα-Fc and gp130-Fc respectively. The Fc domain was chosen primarily but not solely because it naturally forms disulfide-linked dimers. Heterodimeric molecules comprising Rα-Fc•gp130-

Fc were expressed, purified and shown to behave as highly potent antagonists of their cognate ligand. Furthermore, these molecules were found to be highly specific for their cognate cytokine since it is the choice of the α-receptor component which specifies which cytokine is bound and trapped (there is no measurable binding of the cytokine to gp130 in the absence of the appropriate Rα).

Here we describe an extension of this technology which allows the engineering of different heteromeric soluble receptor ligand Traps which by virtue of their design may have additional beneficial characteristics such as stability, Fc-receptor-mediated clearance, or reduced effector functions (such as complement fixation). Furthermore, the technology described should prove suitable for the engineering of any heteromeric protein in mammalian or other suitable protein expression systems, including but not limited to heteromeric molecules which employ receptors, ligands, and catalytic components such as enzymes or catalytic antibodies.

Materials And Methods

Genetic Engineering of Heteromeric Immunoglobulin Heavy/Light Chain Soluble Receptor-Based Ligand Traps for IL-6.

Figure 8:
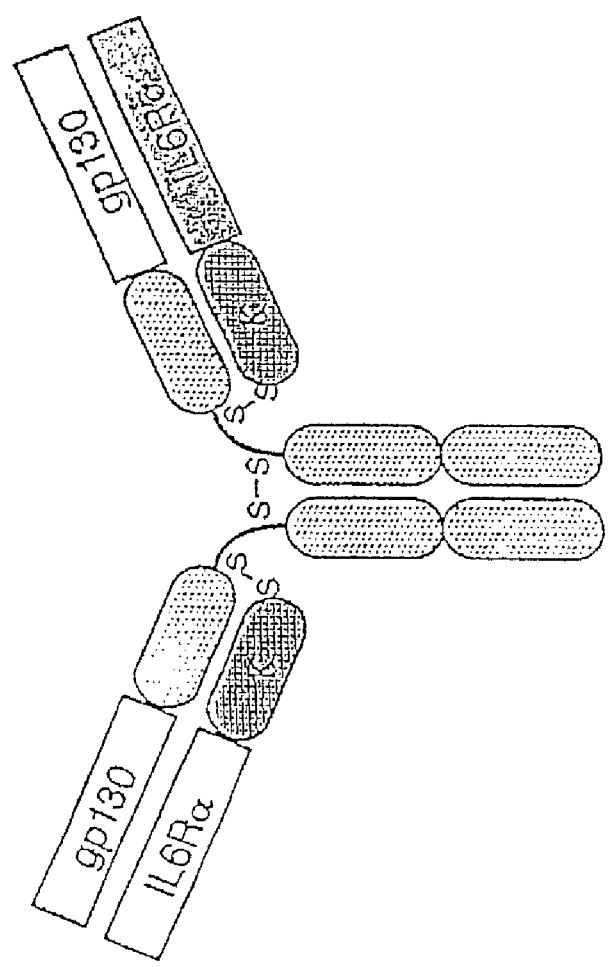
FIG. 8. Heteromeric immunoglobulin Heavy/Light Chain Receptor Fusions. An example of a heavy/light chain receptor fusion molecule is schematically depicted. The extracellular domain of gp130 is fused to Cγ, whereas the extracellular domain of IL-6Rα is fused to the constant region of the kappa chain (κ). The inter-chain disulfide bridges are also depicted (S-S).

The IL-6 Traps described here were engineered using human gp130, human IL-6 α-receptor (IL-6Rα), the constant region of the heavy chains (Cγ) of human IgG1 (Cγ1) (Lewis et al., Journal of Immunology 151:2829–2838 (1993) or IgG4 (Cγ4) with or without a join-region (J), and the constant regions of kappa (κ) and lambda (λ) (Cheung, et al., Journal of Virology 66:6714–6720 (1992) light chains of human immunoglobulin (Ig), also with or without a different j-peptide (j). This design takes advantage of the natural ability of the Cγ domain to heterodimerize with κ or λ light chains. The heterodimerization of Cγ with the light chain occurs between the CH1 domain of Cγ and the constant region of the light chain ($C_L$), and is stabilized by covalent linking of the two domains via a single disulfide bridge. We reasoned that, like the Fc domain of human IgG1, the combination of Cγ with $C_L$ could be used to produce disulfide linked heteromeric proteins comprised of the extracellular domain of gp130 on one chain and the extracellular domain of IL-6Rα on the other chain. Like their Fc-based counterparts, such proteins were postulated to be high affinity ligand Traps for IL-6 and as a result to inhibit the interaction of IL-6 with the native receptor on IL-6-responsive cells, thus functioning as IL-6 antagonists. Furthermore, constructs employing the full length Cγ region would, much like antibodies, form homodimers of the Cγ chain, giving rise to antibody-like molecules comprising of two "light chains" and two "heavy chains" (FIG. 8). The potential advantage of this design is that it may more closely mimic the IL-6•IL-6Rα•gp130 complex and may display a higher affinity for the ligand than comparable single heterodimers. An additional design is incorporated by using truncated versions of Cγ, comprised only of the $C_H1$ domain. These will form heterodimeric molecules with receptor-κ fusion proteins, and will thus resemble the Fab fragment of antibodies.

All the soluble receptor-Ig chimeric genes may be engineered in plasmid vectors including, but not limited to, vectors suitable for mammalian expression (COS monkey kidney cells, Chinese Hamster Ovary cells [CHO], and ras-transformed fibroblasts [MG-ras]) and include a Kozak sequence (CGC CGC CAC CAT GGT G) (SEQ ID NO: 3) at the beginning of each chimeric gene for efficient translation. Engineering was performed using standard genetic engineering methodology. Each construct was verified by DNA sequencing, mammalian expression followed by western blotting with suitable antibodies, biophysical assays that determine ligand binding and dissociation, and by growth inhibition assays (XG-1, as described later). Since the domains utilized to engineer these chimeric proteins are flanked by appropriate restriction sites, it is possible to use these domains to engineer other chimeric proteins, including chimeras employing the extracellular domains of the receptors for factors such as IL-1, IL-2, IL-3, IL-4, IL-5, GM-CSF, LIF, IL-11, IL-15, IFNγ, TGFβ, and others. The amino acid coordinates for each component utilized in making the IL-6 Traps are listed below (Note: numbering starts with the initiating methionine as #1; long sequences are listed using the single letter code for the twenty amino acids):

(a) Constructs Employing Human gp130:
(i) gp130-Cγ1 was engineered by fusing in frame the extracellular domain of gp130 (amino acids 1 to 619) to a Ser-Gly bridge, followed by the 330 amino acids which comprise Cγ1 and a termination codon (FIGS. 9A–9B, SEQ ID NO: 9).
(ii) gp130-J-Cγ1 was engineered in the same manner as gp130-Cγ1 except that a J-peptide (amino acid sequence: GQGTLVTVSS, SEQ ID NO: 4) was inserted between the Ser-Gly bridge and the sequence of Cγ1 (see FIGS. 9A–9B, SEQ ID NO: 9).
(iii) gp130Δ3fibro-Cγ1 was engineered by fusing in frame the extracellular domain of gp130 without its three fibronectin-like domains (FIG. 10, SEQ ID NO: 10). The remaining part of this chimeric protein is identical to gp130-Cγ1.
(iv) gp130-J-$C_H1$ was engineered in a manner identical for that described for gp130-Cγ1, except that in place of the Cγ1 region only the $C_H1$ part of Cγ1 has been used (FIG. 11, SEQ ID NO: 11). The C-terminal domain of this construct includes the part of the hinge that contains the cysteine residue responsible for heterodimerization of the heavy chain of IgG with a light chain. The part of the hinge that contains the two cysteines involved in Cγ1 homodimerization has been deleted along with the $C_H2$ and $C_H3$ domains.
(v) gp130 -Cγ4 was engineered in a manner identical to that described for gp130-Cγ1, except that Cγ4 was used in place of Cγ1 (FIG. 12, SEQ ID NO: 12). In addition, an RsrII DNA restriction site was engineered at the hinge region of the Cγ4 domain by introducing two silent base mutations. The RsrsII site allows for other desired genetic engineering manipulations, such as the construction of the $C_H1$ equivalent of gp130-Cγ4.
(vi) gp130-κ was engineered in a manner identical to that described for gp130-Cγ1, except that the constant region of the κ light chain of human Ig was used in place of Cγ1 (FIG. 13, SEQ ID NO: 13).
(vi) gp130-J-κ was engineered in a manner identical to that described for gp130-J-κ, except that a j-peptide (amino acid sequence: TFGQGTKVEIK, SEQ ID NO: 5) was inserted between the Ser-Gly bridge and the κ-region.
(viii) gp130-λ was engineered in a manner identical to that described for gp130O-Cγ1, except that the constant region of the λ light chain (Cheung, et al., Journal of Virology 66:6714–6720 (1992) of human Ig was used in place of Cγ1 (FIG. 14, SEQ ID NO: 14).

(b) Constructs employing human IL-6Rα:
(i) IL6Rα-Cγ1 was engineered by fusing in frame amino acids 1 to 358 of IL-6Rα (Yamasaki et al., Science 241:825–828 (1988), which comprise the extracellular domain of IL-6Rα (FIG. 15, SEQ ID NO: 15), to an Ala-Gly bridge, followed by the 330 amino acids which comprise Cγ1 and a termination codon.

(ii) IL6Rα-κ was engineered as described for IL6Rα-Cγ1, except that the κ-domain (FIG. 13, SEQ ID NO: 13) utilized for gp130-κ was used in place of Cγ1.

(iii) IL6Rα-j-κ was engineered as described for IL6Rα-κ except that the j-peptide described for gp130-j-κ was placed between the Ala-Gly bridge and the κ-domain.

(iv) Three additional constructs, IL6Rα313-Cγ1, IL6Rα313-κ, and IL6Rα313-j-κ, were engineered as using a truncated form of IL-6Rα comprised of amino acids 1 to 313 (FIG. 16, SEQ ID NO: 16). Each of these constructs were made by fusing in frame IL6Rα313 with a Thr-Gly bridge followed by the Cγ1, κ-, and j-κ-domains described above. These constructs were engineered in order to complement the gp130Δ3fibro-derived constructs.

Expression and Purification of Ligand Traps

To produce covalently linked heterodimers of soluble gp130 and soluble IL-6Rα, gp130-Ig chimeric proteins were co-expressed with appropriate IL-6Rα-Ig chimeric proteins in complementing pairs. Co-expression was achieved by co-transfecting the corresponding expression vectors into suitable mammalian cell lines, either stably or transiently. The resulting disulfide-linked heterodimers were purified from conditioned media by several different methods, including but not limited to affinity chromatography on immobilized Protein A or Protein G, ligand-based affinity chromatography, ion exchange, and gel filtration.

Figure 17:
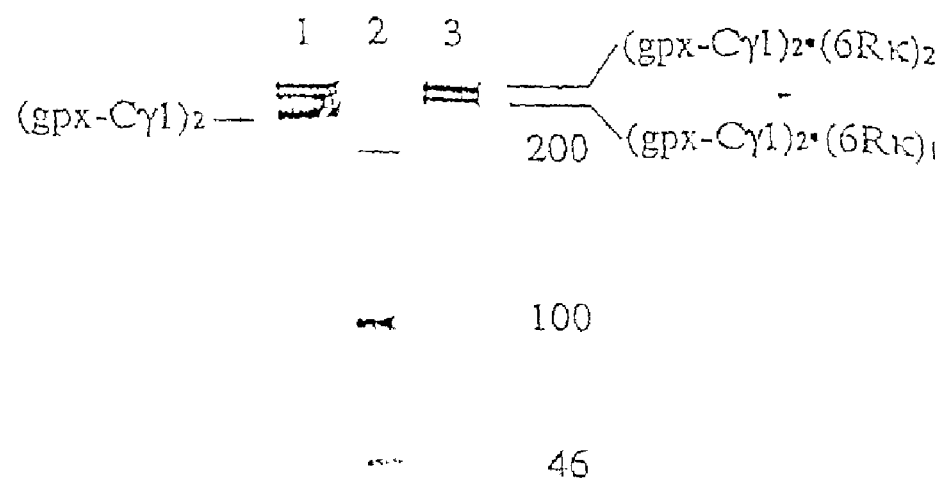
FIG. 17: Purification of gp130-Cγ1•IL-6Rα-κ. 4% to 12% SDS-PAGE gradient gel run under non-reducing conditions. Proteins were visualized by staining with silver. Lane 1: approximately 100 ng of material purified over Protein A Sepharose (Pharmacia). Lane 2: Molecular size standards (Amersham). Lane 3: The Protein A-purified material shown here after further purification over an IL-6 affinity chromatography step. The positions of the gp130-Cγ1 dimer [(gp130-Cγ1)$_2$], the gp130-Cγ1 dimer associated with one IL-6Rα-κ [(gp130-Cγ1)$_2$•(IL-6Rα-κ)$_1$], and the gp130-Cγ1 dimer associated with two IL-6Rα-κ [(gp130-Cγ1)$_2$•(IL-6Rα-κ)$_2$] are shown, as well as the sizes for the molecular size standards in kilodaltons (200, 100, and 46).

An example of the type of methods used for purification of a heavy/light receptor fusion protein is as follows: gp130-Cγ1•IL-6Rα-κ was expressed in COS cells by co-transfecting two different vectors, encoding gp130-Cγ1 and IL-6Rα-κ respectively. Serum-free conditioned media (400 ml) were collected two days post-transfection and Cγ1-bearing proteins were purified by affinity chromatography over a 1 ml Protein A Sepharose (Pharmacia). The material generated in this step was further purified by a second affinity chromatography step over a 1 ml NHS-activated Sepharose (Pharmacia) which was derivatized with recombinant human IL-6, in order to remove gp130-Cγ1 dimer from gp130-Cγ1•IL-6Rα-κ complexes (the gp130-Cγ1 dimer does not bind IL-6). Proteins generated by this method were more than 90% pure, as evidenced by SDS-PAGE followed by silver-staining (FIG. 17). Similar protocols have been employed successfully towards the purification of other heavy/light receptor heterodimers.

Results

Figure 18:
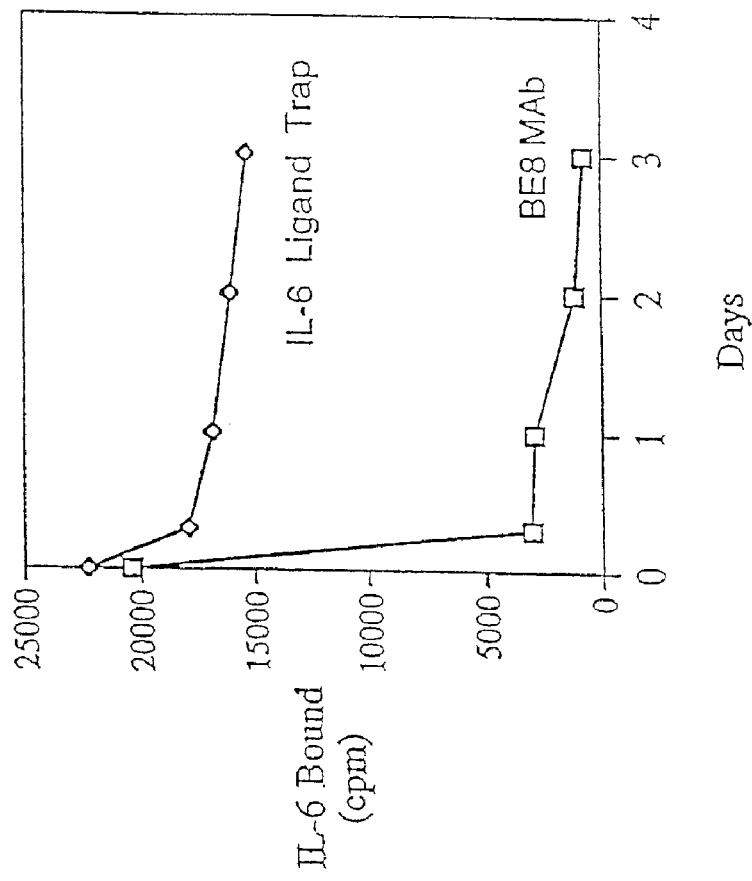
FIG. 18: IL-6 dissociates slowly from the ligand Trap. The dissociation rate of IL-6 from a heavy/light chain receptor-based ligand Trap (gp130-Cγ1•IL-6Rα-κ) was compared to that obtained with the neutralizing monoclonal antibody B-E8 (BE8 MAb).

Biological Activity of Immunoglobulin Heavy/Light Chain Receptor Fusion Antagonists The purified ligand Traps were tested for their ability to bind IL-6 in a variety of different assays. For example, the dissociation rate of IL-6 bound to the ligand Trap was measured in parallel with the dissociation rate of IL-6 from the anti-IL-6 monoclonal neutralizing antibody B-E8 [Brochier, et al., Int. J. Immunopharmacology 17:41–48 (1995), and references within]. An example of this type of experiment is shown in FIG. 18. In this experiment 20 pM $^{125}$I-IL-6 (1000 μCi/mmol; Amersham) was preincubated with 500 pM of either gp130-Cγ1•IL-6Rα-κ or mAb B-E8 for 20 hours. At this point a 1000-fold excess (20 nM) of "cold" IL-6 was added. Periodically, aliquots of the reaction were removed, the ligand Trap or B-E8 were precipitated with Protein G-Sepharose, and the number of cpm of $^{125}$I-IL-6 that remained bound was determined. Clearly, the dissociation rate of human $^{125}$I-IL6 from the ligand Trap was very slow—after three days, approximately 75% of the initial counts were still bound to the ligand Trap. In contrast, less than 5% of the counts remained associated with the antibody after three days. This result demonstrates that the dissociation rate of the ligand from these ligand Traps is very slow.

Figure 19:
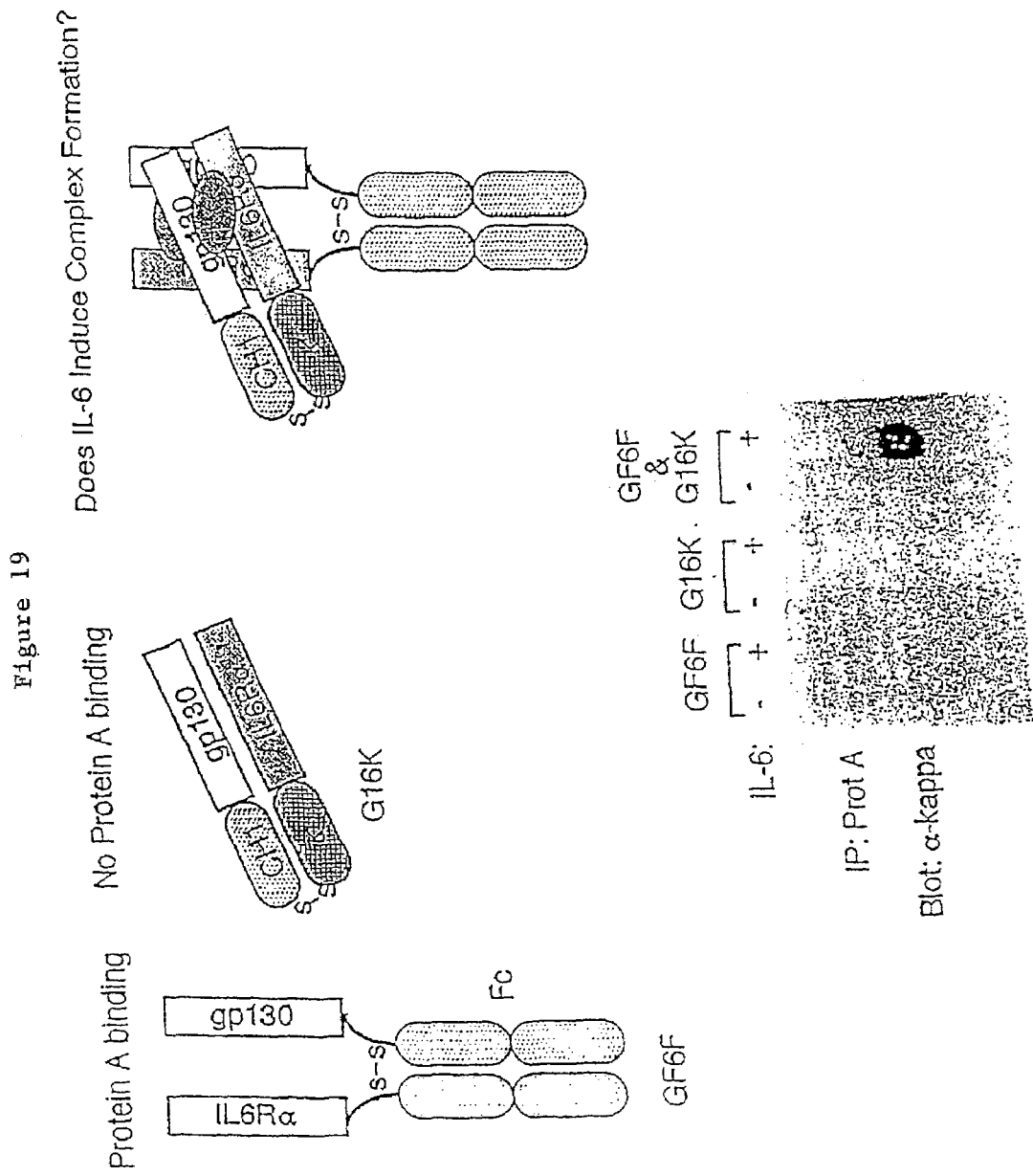
FIG. 19: IL-6 can induce multimerization of the ligand Trap. (A) Two different ligand Traps are depicted schematically and listed according to their ability to bind protein A. gp130-Fc•IL-6Rα-Fc (GF6F) binds protein A via its Fc-domains, whereas gp130-$C_H1$•IL-6Rα-κ (G16K) does not bind to protein A. (B) Anti-kappa western blotting of proteins precipitated with Protein A-Sepharose from mixtures of GF6F±IL-6, G16K±IL-6, or GF6F plus G16K±IL-6, as marked.

In a different set of experiments the ability of the ligand Traps to multimerize in the presence of ligand was tested. An example of this is shown in FIGS. 19A–19B. IL-6-induced association of gp130-Fc•IL-6Rα-Fc with gp130-$C_H$1•IL-6Rα-κ was determined by testing whether gp130-$C_H$1•IL-6Rα-κ, which does not by itself bind Protein A, could be precipitated by Protein A-Sepharose in the presence of gp130-Fc-IL-6Rα-Fc in an IL-6-depended manner (FIGS. 9A–9B, SEQ ID NO: 9). Precipitation of gp130-$C_H$1•IL-6Rα-κ by Protein A-Sepharose was determined by western blotting with an anti-kappa specific HRP conjugate, which does not detect gp130-Fc•IL-6Rα-Fc. gp130-$C_H$1•IL-6Rα-κ could be precipitated by Protein A-Sepharose only when both gp130-Fc•IL-6Rα-Fc and IL-6 were present. This result conclusively indicates that IL-6 can induce ligand Trap multimerization, and further indicate that the ligand Trap can mimic the hexameric cytokine•Rα•signal transducer complex (FIG. 1). Ligand-induced multimerization may play a significant role in the clearance of cytokine•ligand Trap complexes in vivo.

The biological activity of the different ligand Traps may be further tested in assays which measure ligand-depended cell proliferation. Several cell proliferation assays exist for IL-6 and they employ cell lines such as B9, CESS, or XG-1. An example of this type of assay using the XG-1 cell line is presented below: XG-1 is a cell line derived from a human multiple myeloma (Zhang, et al., Blood 83:3654–3663 (1994). XG-1 depends on exogenously supplied human IL-6 for survival and proliferation. The $EC_{50}$ of IL-6 for the XG-1 line is approximately 50 pmoles/ml. The ability of several different IL-6 Traps to block IL-6-depended proliferation of XG-1 cells was tested by incubating increasing amounts of purified ligand Traps with 50 pg/ml IL-6 in XG-1 cultures. The ligand Traps which were tested had been expressed and purified by methods similar to those described above. All of the ligand Traps tested were found to inhibit IL-6-dependent proliferation of XG-1 in a dose dependent manner (FIG. 20). Of the five different Traps tested gp130-Cγ1•IL-6Rα-κ was the most active and essentially display the same neutralizing activity towards IL-6 as the antibody B-E8. As little as a 10-fold molar excess of either gp130-Cγ1•IL-6Rα-κ or B-E8 completely blocked the activity of IL-6 (a reading of A570–650=0.3 AU corresponds to no proliferation of the XG-1 cells). At a 100-fold molar excess all of the ligand Traps tested completely blocked the activity of IL-6. This observed inhibition is highly selective as neither a gp130-Fc-CNTFRα-Fc ligand Trap which blocks CNTF activity, nor gp130-Fc homodimer exhibit any blocking activity towards IL-6 even when used at a 1000-fold molar excess over IL-6 (data not shown). This data demonstrates that the heteromeric immunoglobulin heavy/light chain receptor-based ligand Traps function as selective high affinity antagonists of their cognate ligand.

Example 5

Cloning of Fusion Polypeptide Components

The extracellular domains of the human cytokine receptors were obtained by standard PCR techniques using tissue cDNAs (CLONTECH), cloned into the expression vector, pMT21 (Genetics Institute, Inc.), and the sequences were sequenced by standard techniques using an ABI 373A DNA sequencer and Taq Dideoxy Terminator Cycle Sequencing Kit (Applied Biosystems, Inc., Foster City, Calif.). For the IL-4Rα, nucleotides 241 through 868 (corresponding to the amino acids 24–231) from the Genbank sequence, X52425, were cloned. For the IL-2Rγ, nucleotides 15 through 776 (corresponding to amino acids 1–233) from the Genbank sequence, D11086, were cloned. For the IL-6Rα, nucleotides 52 through 1044 (corresponding to the amino acids 1–331) from the Genbank sequence, X52425, were cloned. For gp130, nucleotides 322 through 2112 (corresponding to the amino acids 30–619) from the Genbank sequence, M57230, were cloned. For the IL-1RAcP, nucleotides 1 through 1074 (corresponding to the amino acids 1–358) from the Genbank sequence, AB006357, were cloned. For the IL-1RI, nucleotides 55 through 999 (corresponding to the amino acids 19–333) from the Genbank sequence, X16896, were cloned.

Example 6

Production of Fusion Polypeptides (Cytokine Traps)

The nucleotide sequences encoding the cytokine Traps were constructed from the individual cloned DNAs (described supra) by standard cloning and PCR techniques. In each case, the sequences were constructed in frame such that the sequence encoding the first fusion polypeptide component was fused to the sequence encoding the second fusion polypeptide component followed by an Fc domain (hinge, CH2 and CH3 region of human IgG1) as the multimerizing component. In some cases extra nucleotides were inserted in frame between sequences encoding the first and second fusion polypeptide components to add a linker region between the two components (See FIG. 21A–FIG. 21D, SEQ ID NO: 17-Trap 424; FIG. 24A–FIG. 24F, SEQ ID NO: 23-Trap 412; and FIG. 26A–FIG. 26E, SEQ ID NO: 27-Trap 569).

For the IL-4 Traps, 424 (FIG. 21A–FIG. 21D, SEQ ID NO: 17), 603 (FIG. 22A–FIG. 22D, SEQ ID NO: 19) and 622 (FIG. 23A–FIG. 23D, SEQ ID NO: 21), the IL-2Rγ component is 5', followed by the IL4Rα component and then the Fc component. For the IL-6 Traps, 412 (FIG. 24A–FIG. 24F, SEQ ID NO: 23) and 616 (FIG. 25A–FIG. 25F, SEQ ID NO: 25), the IL-6Rα component is 5' followed by the gp130 component and then the Fc domain. For the IL-1 Trap 569 (FIG. 26A–FIG. 26E, SEQ ID NO: 27), the IL-1RAcP component is 5' followed by the IL-1RI component and then the Fc domain. The final constructs were cloned into the mammalian expression vector pCDNA3.1 (STRATAGENE).

In the 569 sequence (FIG. 26A–FIG. 26E, SEQ ID NO: 27), nucleotides 1–1074 encode the IL1RAcP component, nucleotides 1075–1098 encode a linker region, nucleotides 1099–2043 encode the IL1RI component and nucleotides 2044–2730 encode the Fc domain.

In the 412 sequence (FIG. 24A–FIG. 24F, SEQ ID NO: 23), nucleotides 1–993 encode the IL6Rα component, nucleotides 994–1023 encode a linker region, nucleotides 1024–2814 encode the gp130 component and nucleotides 2815–3504 encode the Fc domain.

In the 616 sequence (FIG. 25A–FIG. 25F, SEQ ID NO: 25), nucleotides 1–993 encode the IL6Rα component, nucleotides 994–2784 encode the gp130 component and nucleotides 2785–3474 encode the Fc domain.

In the 424 (FIG. 21A–FIG. 21D) and 622 (FIG. 23A–FIG. 23D, SEQ ID NO: 17) sequences, nucleotides 1–762 encode the IL2Rγ component, nucleotides 763–771 encode a linker region, nucleotides 772–1395 encode the IL4Rα component and nucleotides 1396–2082 encode the Fc domain.

Finally, in the 603 sequence (FIG. 22A–FIG. 22D, SEQ ID NO: 19), nucleotides 1–762 encode the IL2Rγ component, nucleotides 763–1386 encode the IL4Rα component and nucleotides 1387–2073 encode the Fc domain.

DNA constructs were either transiently transfected into COS cells or stably transfected into CHO cells by standard techniques well known to one of skill in the art. Supernatants were collected and purified by Protein A affinity chromatography and size exclusion chromatography by standard techniques. (See for example Harlow and Lane, Antibodies—A Laboratory Manual, Cold Spring Harbor Laboratory, 1988).

Example 7

IL-4 Bioassay Protocol Using TF-1 (ATCC) Cells

Reagents and Equipment Needed

MTT Dye Solution:
MTT(3-[4,5-Dimethylthiazole-2-yl]) (Sigma catalog# M2128)
Working concentration: Dissolve 5 mg of anhydrous MTT in 200 ml PBS without $Ca^{+2}$, $Mg^{+}2$.
Sterile filter and store aliquoted at $-20°$ C.

Solubilization Solution:
For 1000 ml, combine 100 g SDS, 950 ml $dH_2O$, 50 ml Dimethyl Formamide, and 850 μl concentrated HCl.
Filter sterilize with a 0.45 μm filter unit.
Store at room temperature TF-1 cell Growth Medium:
RPMI 1640, 10% FBS, Pen/Strep, 2 mM L-glutamine Other:
0.4% Trypan Blue Stain, sterile tubes for dilutions, sterile 96 well cell culture plates (Falcon #3072), hemacytometer, centrifuge, ELISA plate reader, multichannel pipet for 15, 25, 50 and 100 μl volume, sterile reagent reservoirs, sterile pipet tips, gloves.

Assay Protocol

A. Preparation of Assay plates

1. Prepare sterile 96 well tissue culture plates to contain 50 μl of growth medium per well with various concentrations of IL-4 and 10 nM IL-4 antagonist. This can be done by preparing a working dilution of IL-4 that is 4 times the highest concentration to be assayed. In separate tubes, do a two-fold serial dilution of the IL-4. Add 25 μl of each dilution to one row across the plate (i.e. row A gets highest concentration, row G gets lowest concentration). Add 25 μl of growth medium without IL-4 to row H. Prepare the antagonists to be tested by making a stock that is 4 times the final concentration. Add 25 μl to a triplicate set of IL-4 containing wells (columns 1,2,3, A through H). Be sure to include antagonist in row H.

2. As a positive control, leave one set with no antagonist. These wells will contain IL-4 and media only.
3. Incubate the plate for 1–2 hours at 37° C. in a humidified 5% $CO_2$ incubator before preparing cells to be used for assay.

B. Preparation of Cells

4. Wash cells twice by centrifugation in assay medium free of growth factor.
5. Determine cell number and trypan blue viability and suspend cells to a final concentration of $8 \times 10^5$/ml in assay medium.
6. Dispense 50 µl of the cell suspension (40,000 cells) into all wells of the plates. Total volume should now be 100 µl/well.
7. Incubate the plate at 37° C. for 68 hours in a humidified 5% $CO_2$ incubator.

C. Color Development

8. After incubating for 68 hours, add 15 µl of the MTT dye solution to each well.
9. Incubate the plate at 37° C. for 4 hours in a humidified 5% $CO_2$ incubator.
10. After 4 hours, add 100 µl of the solubilization solution to each well. Allow the plate to stand overnight in a sealed container to completely solubilize the formazan crystals.
11. Record the absorbance at 570/650 nm.

Results

Figure 27:
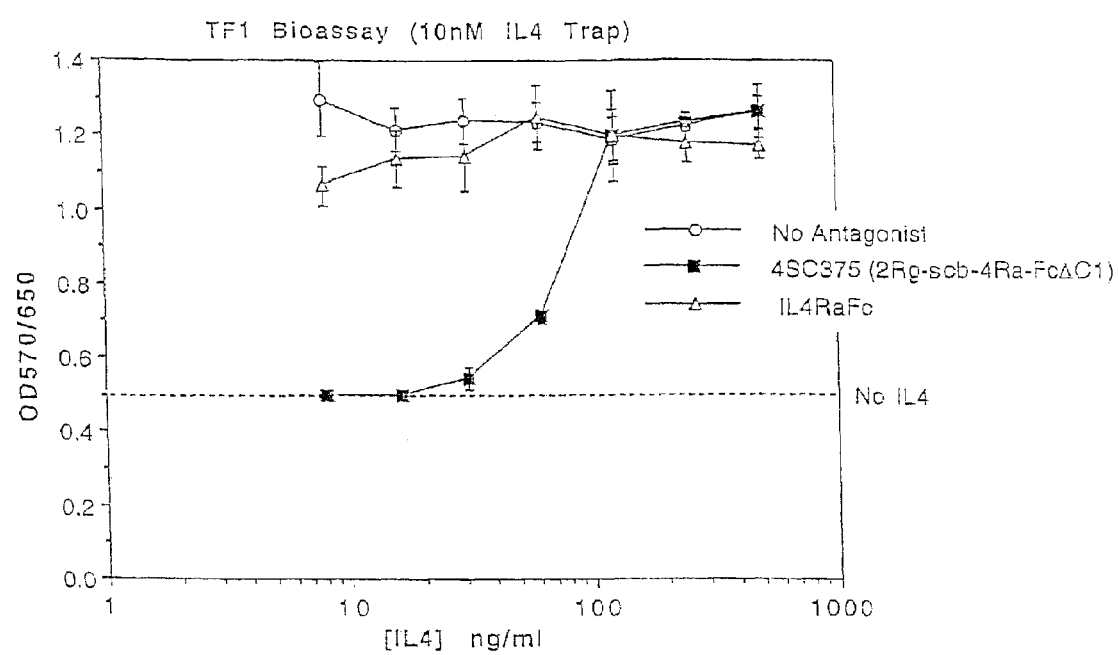
FIG. 27: Shows that an IL-4 Trap designated 4SC375, which is a fusion polypeptide of IL-2Rγ-scb-IL4Rα-FcΔC1, is several orders of magnitude better as an IL-4 antagonist than IL4RαFcΔC1 alone in the TF1 cell bioassay.

FIG. 27 shows that an IL-4 Trap designated 4SC375, which is a fusion polypeptide of IL-2Rγ-scb-IL4Rα-FcΔC1, is several orders of magnitude better as an IL-4 antagonist than IL4RαFcΔC1 alone in the TF1 cell bioassay.

Figure 28:
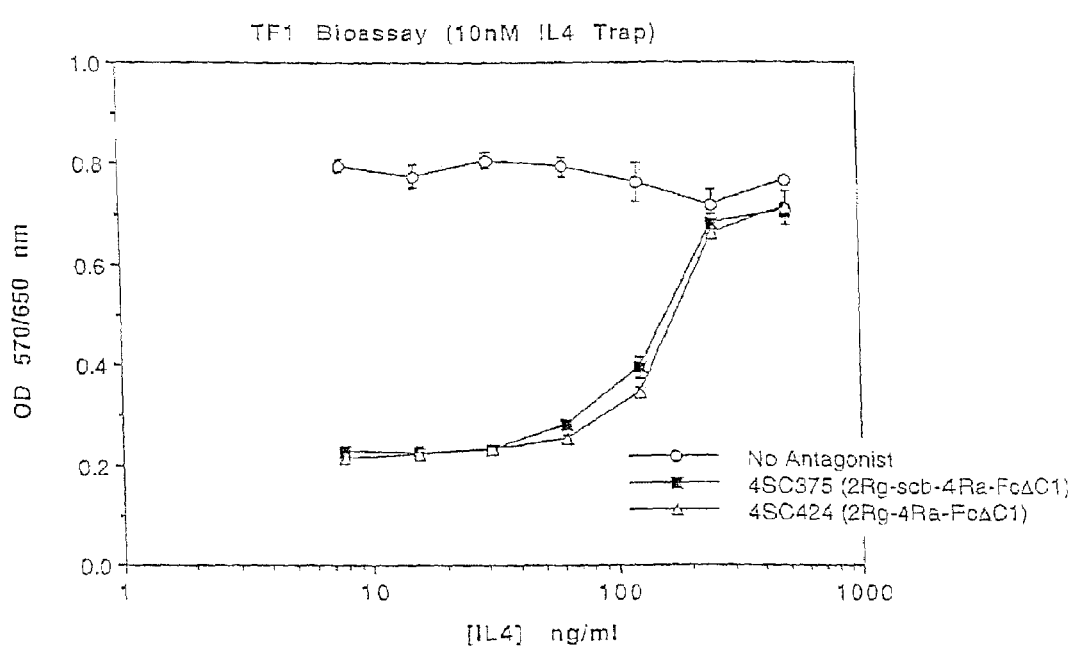
FIG. 28: Shows that an IL-4 Trap designated 4SC375 displays antagonistic activity in the TF1 cell bioassay equivalent to an IL-4 Trap designated 4SC424 (described in FIGS. 21A–21D) which is a fusion polypeptide of IL-2Rγ-IL4Rα-FcΔC1 having the IL-2Rγ component flush with the IL-4Rα component.

FIG. 28 shows that the IL-4 Trap designated 4SC375 shows antagonistic activity in the TF1 cell bioassay equivalent to an IL-4 Trap designated 4SC424 which is a fusion polypeptide of IL-2Rγ-IL4Rα-FcΔC1 having the IL-2Rγ component flush with the IL-4Rα component.

Example 8

IL-6 Bioassay Protocol using XG-1 Cells

Reagents and Equipment Needed

MTT Dye Solution:
MTT(3-[4,5-Dimethylthiazole-2-yl]) (Sigma catalog# M2128)
Working concentration: Dissolve 5 mg of anhydrous MTT in 200 ml PBS without $Ca^{+2}$, $Mg^{+2}$.
Sterile filter and store aliquoted at −20° C.

Solubilization Solution:
For 1000 ml, combine 100 g SDS, 950 ml $dH_2O$, 50 ml Dimethyl Formamide, and 850 µl concentrated HCl.
Filter sterilize with at 0.45 µm filter unit.
Store at room temperature Assay Medium:
RPMI 1640, 10%FBS, Pen/Strep, 2 mM L-glutamine, 50 µM mercapto-ethanol.

Other:
0.4% Trypan Blue Stain, sterile tubes for dilutions, sterile 96 well cell culture plates (Falcon#3072), hemacytometer, centrifuge, ELISA plate reader, multichannel pipet for 15, 25, 50 and 100 µl volume, sterile reagent reservoirs, sterile pipet tips, gloves.

Assay Protocol

A. Preparation of Assay Plates

1. Prepare sterile 96 well tissue culture plates to contain 50 µl of growth medium per well with various concentrations of IL-6 and 10 nM IL-6 antagonist. This can be done by preparing a working dilution of IL-6 that is 4 times the highest concentration to be assayed. In separate tubes, do a two-fold serial dilution of the IL-6. Add 25 µl of each dilution to one row across the plate (i.e. row A gets highest concentration, row G gets lowest concentration). Add 25 µl of growth medium without IL-6 to row H. Prepare the antagonists to be tested by making a stock that is 4 times the final concentration. Add 25 µl to a triplicate set of IL-6 containing wells (columns 1,2,3, A through H). Be sure to include antagonist in row H. A typical IL-6 titration starts at 200 ng/ml down to 3.1 ng/ml.
2. As a positive control, leave one set with no antagonist. These wells contain IL-6 and media in place of antagonist.
3. Incubate the plate 1–2 hours at 37° C. in a humidified 5% $CO_2$ incubator before preparing cells to be used for assay.

B. Preparation of Cells

4. Wash cells twice by centrifugation (5 min at 1000 RPM) in assay medium free of growth factor.
5. Determine cell number and trypan blue viability and suspend cells to a final concentration of $8 \times 10^5$/ml in assay medium.
6. Dispense 50 µl of the cell suspension (40000 cells) into all wells of the plates. Total volume should now be 100 µl/well.
7. Incubate the plate at 37° C. for 68 hours in a humidified 5% $CO_2$ incubator.

C. Color Development

8. At 68 hours add 15 µl of the dye solution to each well.
9. Incubate the plate at 37° C. for 4 hours in a humidified 5% $CO_2$ incubator.
10. After 4 hours, add 100 µl of the solubilization solution to each well. Allow the plate to stand overnight in a sealed container to completely solubilize the formazan crystals.
11. Record the absorbance at 570/650 nm.

Results

Figure 29:
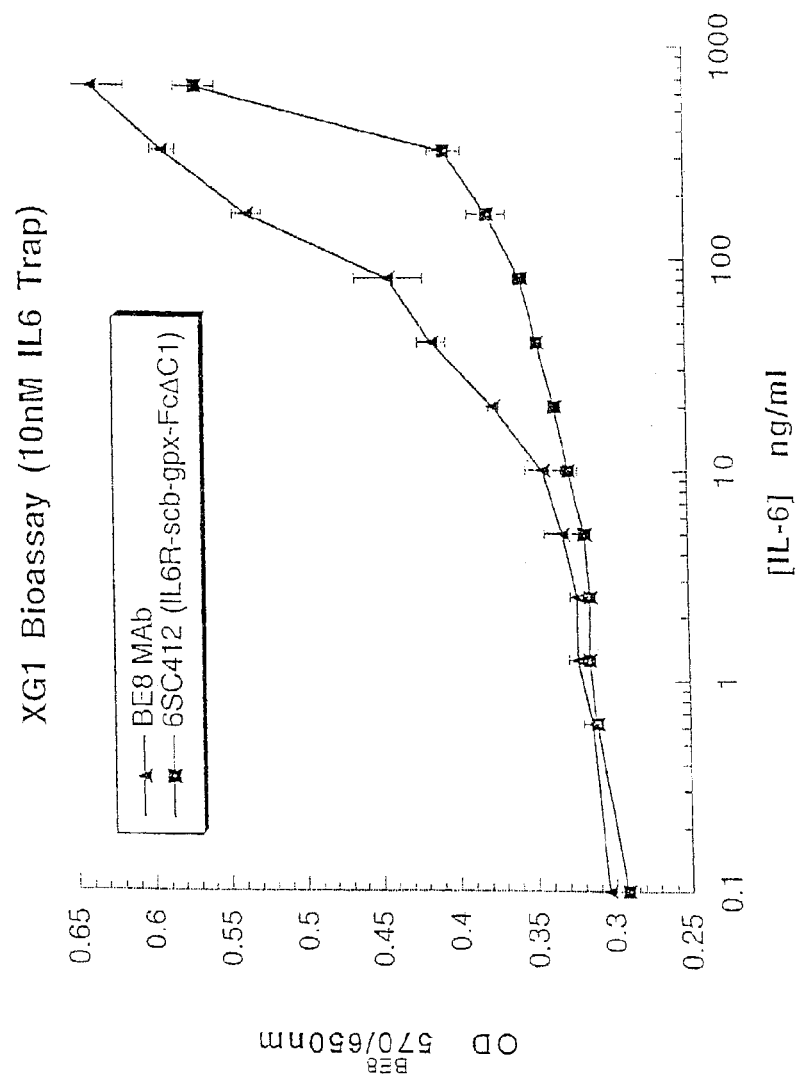
FIG. 29: Shows that the IL6 Trap (6SC412 IL6R-scb-gpx-FcΔC1) described in FIGS. 24A–24F is a better antagonist of IL-6 in the XG1 bioassay than the neutralizing monoclonal antibody to human IL-6-BE8.

FIG. 29 shows that the IL6 Trap (6SC412 IL6R-scb-gpx-FcΔC1) described in FIG. 24A–FIG. 24F (SEQ ID NOS: 23 and 24) is a better antagonist of IL-6 in the XG1 bioassay than the neutralizing monoclonal antibody to human IL-6-BE8.

Example 9

MRC5 Bioassay for IL1 Traps

MRC5 human lung fibroblast cells respond to IL-1 by secreting IL-6 and thus were utilized to assay the ability of IL-1 Traps to block the IL-1-dependent production of IL-6. IL1 Trap 1SC569 (FIG. 26A–FIG. 26E, SEQ ID NOS: 27 and 28) was tested against IL-1-RI.Fc which is the extracellular domain of the IL-1 Type I receptor fused to an Fc domain.

MRC5 cells are suspended at $1 \times 10^5$ cells per ml in medium and 0.1 ml of cells are plated (10,000 cells per well) into the wells of a 96 well tissue culture plate. Plates are incubated for 24 hours at 37° C. in a humidified 5% $CO_2$ incubator.

IL-1 Trap and recombinant human IL-1 at varying doses are pre-incubated in a 96 well tissue culture dish and incubated for 2 hours at 37° C. 0.1 ml of this mixture is then added to the 96 well plate containing the MRC5 cells such that the final concentration of IL-1 Trap is 10 nM and the final concentrations of the IL-1 ranges from 2.4 pM to 5 nM. Control wells contain Trap alone or nothing.

Plates are then incubated at 37° C. for 24 hours in a humidified 5% $CO_2$ incubator. Supernatant is collected and assayed for levels of IL-6 using R&D Systems Quantikine Immunoassay Kit according to the manufacturer's instructions.

Results

Figure 30:
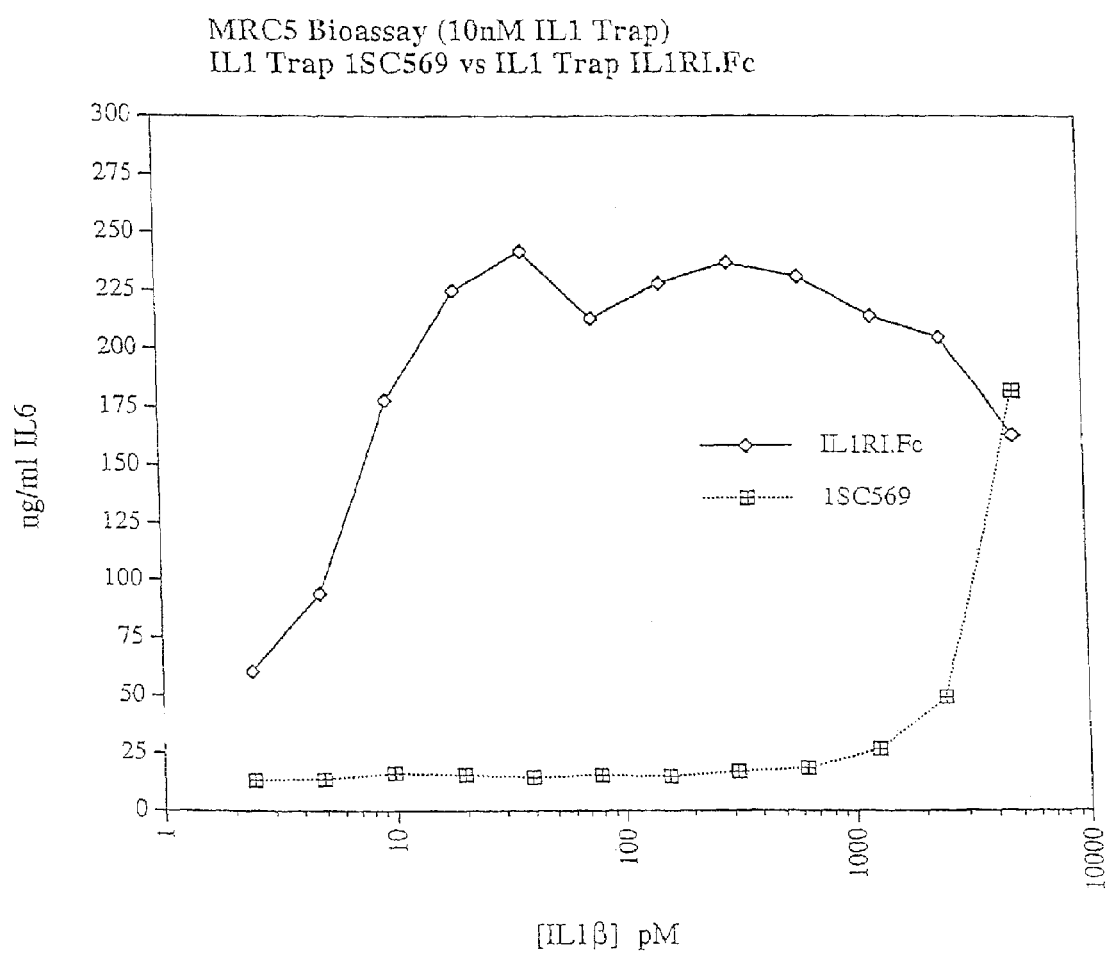
FIG. 30: Shows that the Trap 1SC569 (described in FIGS. 26A–26E) is able to antagonize the effects of IL-1 and block the IL-6 production from MRC 5 cells upon treatment with IL-1.

FIG. 30 shows that the Trap 569 (FIG. 26A–FIG. 26E, SEQ ID NOS: 27 and 28) is able to antagonize the effects of IL-1 and block the IL-6 production from MRC 5 cells upon treatment with IL-1. At a concentration of 10 nM, the Trap 569 is able to block the production of IL-6 up to an IL-1 concentration of 3 nM. In contrast, the IL-1RI.Fc is a much poorer antagonist of IL-1. It is only able to block the effects of IL-1 up to about 10–20 pM. Thus, the Trap 569 is approximately 100× better at blocking IL-1 than IL1RI.Fc.

Example 10

Construction of IL-13/IL-4 Single Chain Traps

1. To create the IL-13/IL-4 dual Trap designated IL-4Rα.IL-13Rα1.Fc, the human IL-4Rα extracellular domain (corresponding to nucleotides 1–693 of FIGS. 31A–31G, SEQ ID NO: 29) and the human IL-13Rα1 extracellular domain (corresponding to nucleotides 700–1665 of FIGS. 31A–31G, SEQ ID NO: 29) were amplified by standard PCR techniques and ligated into an expression vector pMT21 which contained the human Fc sequence (corresponding to nucleotides 1671–2355 of FIGS. 31A–31G, SEQ ID NO: 29), thus creating a fusion protein consisting of the IL-4Rα, IL-13Rα1, and the hinge, CH2 and CH3 region of human IgG1 from the N to C terminus. In addition, a two amino acid linker (corresponding to nucleotides 694–699 of FIGS. 31A–31G, SEQ ID NO: 29) with the amino acid sequence SerGly was constructed in frame between the IL-4Rα and the IL-13Rα1 and a two amino acid linker (corresponding to nucleotides 1666–1671 of FIGS. 31A–31G, SEQ ID NO: 29) with the amino acid sequence ThrGly was constructed in frame between the IL-13Rα1 and the Fc portion. All sequences were sequence-verified by standard techniques. The IL-4Rα.IL-13Rα1.Fc coding sequence was then subcloned into the expression vector pCDNA3.1 (Stratagene) using standard molecular biology techniques.
2. To create the IL-13/IL-4 dual Trap designated IL-13Rα1.1L-4Rα.Fc, the IL-13Rα1 extracellular domain (corresponding to nucleotides 1–1029 of FIGS. 32A–32G, SEQ ID NO: 31) and the human IL-4Rα (corresponding to nucleotides 1060–1692 of FIGS. 32A–32G, SEQ ID NO: 31) were amplified by standard PCR techniques and ligated into the expression vector pjFE14, which contains the human Fc sequence (corresponding to nucleotides 1699–2382 of FIGS. 32A–32G, SEQ ID NO: 31) to create a fusion protein consisting of the IL-13Rα1, IL-4Rα, and the hinge, CH2 and CH3 region of human IgG1 from the N to C terminus. In addition, a ten amino acid linker with the amino acid sequence GlyAlaProSerGlyGlyGlyGlyArgPro (SEQ ID NO: 6) (corresponding to nucleotide 1030–1059 of FIGS. 32A–32G, SEQ ID NO: 31) was constructed in frame between the IL-13Rα1 and the IL-4Rα. and a two amino acid linker (corresponding to nucleotides 1693–1698 of FIGS. 32A–32G, SEQ ID NO: 31) with the amino acid sequence SerGly was constructed in frame between IL-4Rα and the Fc portion. All sequences were sequence-verified using standard techniques. The coding sequence of IL-13Rα1.IL-4Rα.Fc was then subcloned into the expression vector pCDNA3.1 (Stratagene) using standard molecular biology techniques.

Example 11

Expression of IL-4Rα.IL-13Rα1.Fc and IL-13Rα1.IL-4Rα.Fc

Large scale (1L) cultures of the pCAE801 (the DNA vector construct encoding IL-4Rα.IL-13Rα1.Fc) and pCAE802 (the DNA plasmid construct encoding IL-13Rα1.IL-4Rα.Fc) in DH10B cells were grown overnight in LB+ampicillin and the plasmid DNA was extracted using a Qiagen Endofree Mega Kit following the manufacturer's protocol. The concentration of the purified plasmid DNA was determined in a UV spectrophotometer and fluorometer. The plasmid DNA was also verified by digestion of aliquots with BbsI, XmnI and NcoI restriction enzymes. All restriction enzyme digest fragments corresponded to the predicted sizes in a 1% agarose gel.

Forty 15 cm petri plates were seeded with CHO-K1/E1A cells at a density of $4\times10^6$ cells/plate. Plating media was Gibco Ham's F-12 w/10% Hyclone Fetal Bovine Serum (FBS)+penicillin/streptomycin and supplemented with glutamine. The following day each plate was transfected with 6 µg of pCAE801, or pCAE802, using Gibco Optimem and Gibco Lipofectamine in 12 ml volume, following the manufacturer's protocol. Four hours after adding the transfection mix to the cells 12 ml/plate of Optimem w/10% FBS was added. Plates were incubated at 37° C. in a 5% $CO_2$ incubator overnight. The following day the media was removed from each plate and 25 ml expression media (Gibco CHO-S-SFM II w/glutamine +1 mM sodium butyrate) was added. The plates were incubated at 37° C. for 3 days.

After 3 days of incubation the media was removed from each plate and centrifuged at 400 rpm in a swinging bucket rotor to pellet cells. The supernatant was decanted into sterile 1L bottles and expressed protein was purified as described infra.

Example 12

Purification of IL-4Rα.IL-13Rα1.Fc AND IL-13Rα1.IL-4Rα.Fc Protein from Culture Media 1. Purification of IL-4Rα.IL-13Rα1.Fc.

Human IL-4Rα.IL-13Rα1.Fc was transiently expressed in CHO cells and supernatants were harvested from plate transfections as described supra. Expression of the secreted protein was determined by a sandwich ELISA using goat anti-hIgG (γ chain specific; Sigma 1–3382) and goat anti-hIgG (Fc specific)-FITC conjugate (Sigma F9512) capture and report antibodies, respectively. The yield ranged from 5.8 to 9.2 mg (average of 7.5 mg) per liter of conditioned media. Complete™ protease inhibitor tablets (Roche Diagnostics Corp.) were dissolved into the media (1 tablet/L). The conditioned media was sterile filtered (0.22 µm pore size) prior to loading onto a pre-equilibrated, 5 mL HiTrap® Protein A affinity column (Amersham Pharmacia Biotech) in Dulbecco's PBS buffer (Life Technologies), pH 7.4 at 4° C.

The flow rate was ~1–2 mL/min. The column was extensively washed with PBS buffer to remove nonspecifically bound proteins from the column. IL-4Rα.IL-13Rα1.Fc was eluted using 20 mM sodium citrate, 150 mM NaCl, pH 3.5. The eluate was immediately neutralized by titrating with 1 M Tris-OH. The fractions containing protein were pooled and immediately dialyzed in PBS buffer, pH 7.4 at 4° C. The recovery from Protein A purification was 6.8 mg (73%). IL-4Rα.IL-13Rα1.Fc was further purified by size exclusion chromatography using a superose 6 column (25 mL bed volume; Amersham Pharmacia Biotech) pre-equilibrated in PBS, 5% v/v glycerol, pH 7.4 at ambient temperature. The flow rate was 0.5 mL/min. Protein fractions were assessed from a Coomassie stained non-reduced and reduced SDS-PAGE (Novex NuPAGE 4–12% Bis-Tris gels). Fractions were conservatively pooled to reduce the amount of aggregated protein. The overall yield was 51% (4.4 mg) with a purity of 97% as judged by SDS-PAGE. Purified IL-4Rα.IL-13Rα1.Fc was analyzed by non-reduced and reduced SDS-PAGE (4–12% Bis-Tris), analytical size exclusion chromatography (Tosohaas TSKG4000SWXL), N-terminal sequencing, and immunoblotting with goat anti-hIgG-HRP conjugate (Promega W403B), and also mouse monoclonal anti-hIL-4R (R&D MAB230) followed by anti-mIgG-HRP conjugate (Promega W402B) as the secondary antibody.

2. Purification of IL-13Rα1. IL-4Rα.Fc

Human IL-13Rα1.IL-4Rα.Fc was transiently expressed in CHO cells and supernatants were harvested from plate transfections as described supra. Expression of the secreted protein was determined by a sandwich ELISA using goat anti-hIgG (γ chain specific; Sigma 1–3382) and goat anti-hIgG (Fc specific)-FITC conjugate (Sigma F9512) capture and report antibodies, respectively. The yield was 8.8 mg per liter of conditioned media. Complete™ protease inhibitor tablets (Roche Diagnostics Corp.) were dissolved into the media (1 tablet/L). The conditioned media was sterile filtered (0.22 μm pore size) prior to loading onto a pre-equilibrated, 5 mL HiTrap® Protein A affinity column (Amersham Pharmacia Biotech) in Dulbecco's PBS buffer (Life Technologies), pH 7.4 at 4° C. The flow rate was ~1–2 mL/min. The column was extensively washed with PBS buffer to remove nonspecifically bound proteins from the column. IL-13Rα1. IL-4Rα.Fc was eluted using 20 mM sodium citrate, 150 mM NaCl, pH 3.5. The eluate was immediately neutralized by titrating with 1 M Tris-OH. The fractions containing protein were pooled and immediately dialyzed in PBS buffer, pH 7.4 at 4° C. The recovery from Protein A purification was 3.8 mg (43%). IL-13Rα1. IL-4Rα.Fc was further purified by size exclusion chromatography using a superose 6 column (25 mL bed volume; Amersham Pharmacia Biotech) pre-equilibrated in PBS, 5% v/v glycerol, pH 7.4 at ambient temperature. The flow rate was 0.5 mL/min. Protein fractions were assessed from a Coomassie stained non-reduced and reduced SDS-PAGE (Novex NuPAGE 4–12% Bis-Tris gels). Fractions were conservatively pooled to reduce the amount of aggregated protein. The overall yield was 17% (1.5 mg) with a purity of 95% as judged by SDS-PAGE. Purified IL-13Rα1. IL-4Rα.Fc was analyzed by non-reduced and reduced SDS-PAGE (4–12% Bis-Tris), analytical size exclusion chromatography (Tosohaas TSKG4000SWXL), N-terminal sequencing, and immunoblotting with goat anti-hIgG-HRP conjugate (Promega W403B), and also mouse monoclonal anti-hIL-4Rα (R&D MAB230) followed by anti-mIgG-HRP conjugate (Promega W402B) as the secondary antibody.

Example 13

Blocking of IL-4 and IL-13 by IL-4Rα.IL-13Rα1.Fc and IL-13Rα1. IL-4Rα.Fc

Materials and Methods

TF1 Bioassay. TF1 cells were maintained in growth media (10 ng/ml GM-CSF, RPMI 1640, 10% FBS, L-glutamine, Penicillin, Streptomycin). For the bioassay, cells were washed 2 times in assay media (as above but without GM-CSF) and then plated at $2 \times 10^5$ cells in 50 μl of assay media. The purified IL-4Rα.IL-13Rα1.Fc and IL-13Rα1. IL-4Rα.Fc proteins were diluted into assay media at a concentration of 40 nM. 25 ul of each of the Traps was added to the cells. Either IL-13 or IL-4 were diluted to 40 nM in assay media and then 2-fold dilution series in assay media were made. 25 μl of either IL-13 or IL-4 was then added to the wells containing the cells and the Traps. Cells were then incubated at 37° C., 5% $CO_2$ for ~70 hrs. The extent of TF1 cell proliferation was measured by the MTS assay according to the manufacturer's protocol (Promega, Inc.).

Results

Figure 33:
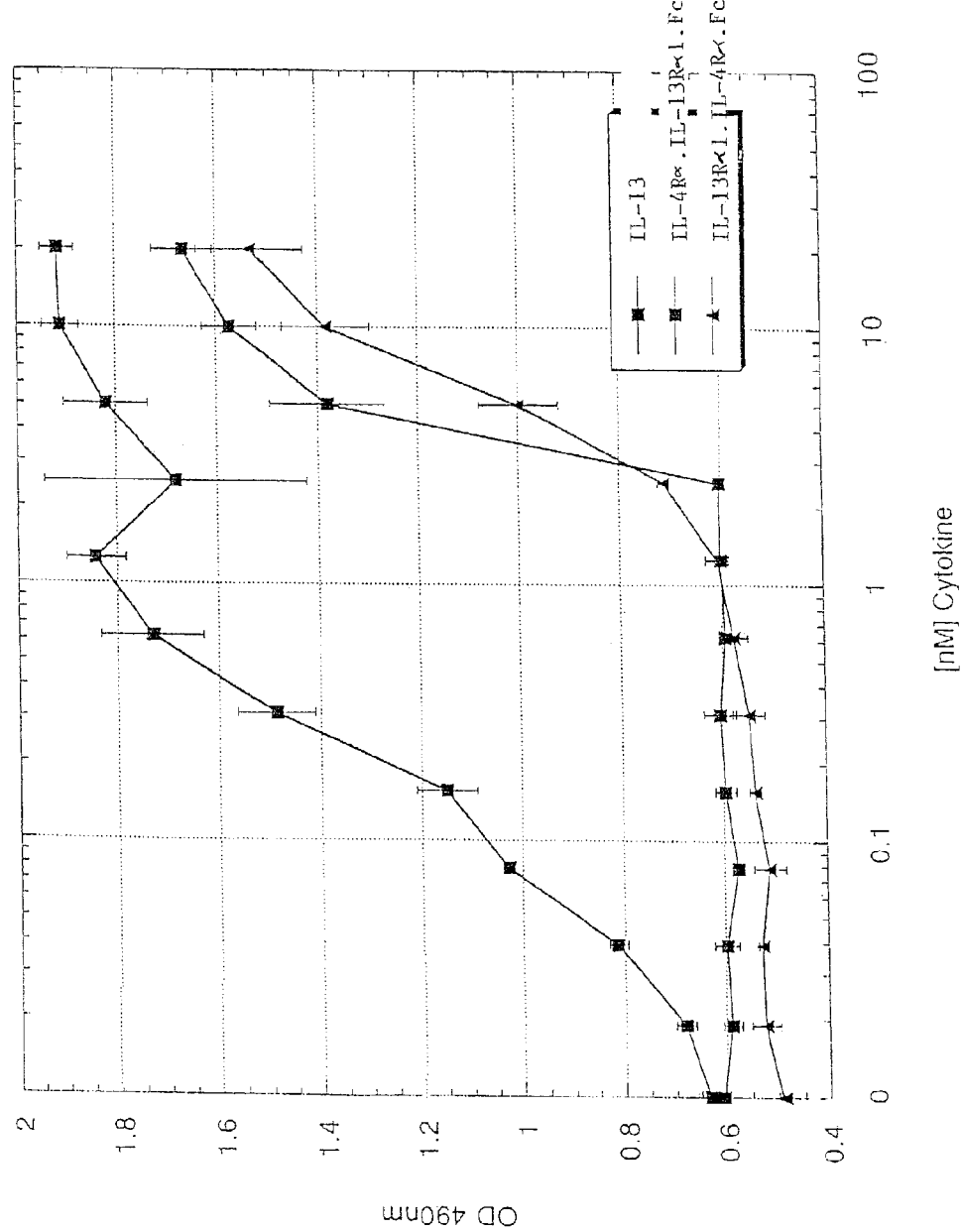
FIG. 33: Blocking of IL-13 by IL-4Rα.IL-13Rα1.Fc and IL-13Rα1.IL-4Rα.Fc. Addition of either IL-4Rα.IL-13Rα1.Fc or IL-13Rα1.IL-4Rα.Fc Trap at a concentration of 10 nM blocks IL-13-induced growth up to ~2 nM. At an IL-13 concentration of ~4–5 nM the growth of TF1 cells is inhibited by 50%.
Figure 34:
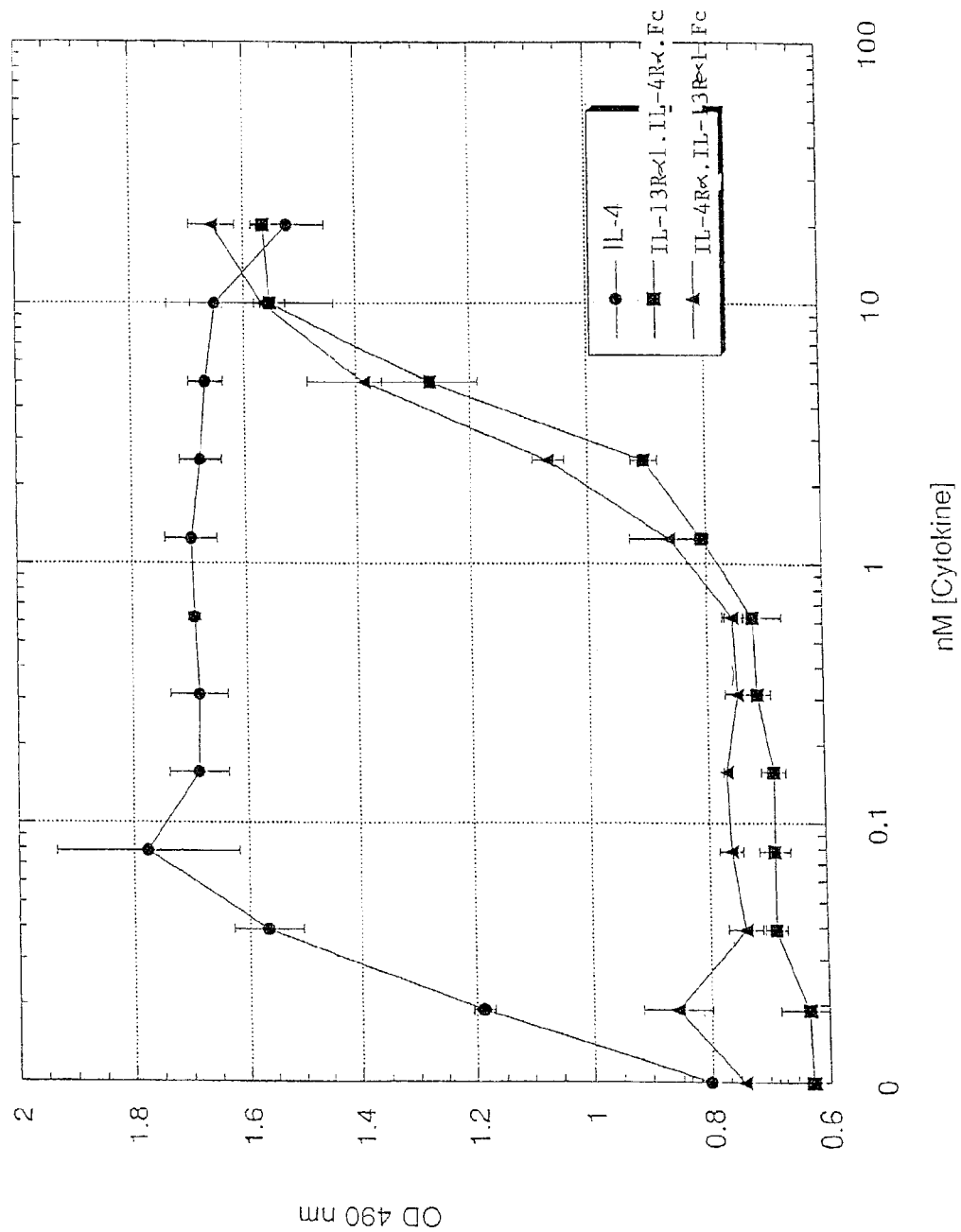
FIG. 34: Blocking of IL-4 by IL-4Rα.IL-13Rα1.Fc and IL-13Rα1.IL-4Rα.Fc. Addition of either IL-4Rα.IL-13Rα1.Fc or IL-13Rα1.IL-4Rα.Fc at a concentration of 10 nM blocks IL-4-induced growth up to ~1 nM. At an IL-4 concentration of ~3–4 nM the growth of TF1 cells is inhibited by 50%.

The ability of the IL-4Rα.IL-13Rα1.Fc and IL-13Rα.IL-4Rα.Fc Traps to block both human IL-13 and human IL-4 activity was measured in the TF1 bioassay described supra. IL-13 stimulates proliferation of TF1 cells, with half-maximal growth at a concentration of 0.2 nM. Addition of either IL-4Rα.IL-13Rα1.Fc or IL-13Rα1. IL-4Rα.Fc Trap at a concentration of 10 nM blocks IL-13-induced growth up to ~2 nM (FIG. 33). At an IL-13 concentration of ~4–5 nM the growth of TF1 cells is inhibited by 50%. TF1 cells are more sensitive to IL-4, which stimulates their proliferation with half-maximal growth at ~0.02 nM. Addition of either IL-4Rα.IL-13Rα1.Fc or IL-13Rα1. IL-4Rα.Fc at a concentration of 10 nM blocks IL-4-induced growth up to ~1 nM (FIG. 34). At an IL-4 concentration of ~3–4 nM the growth of TF1 cells is inhibited by 50%. These results show that both IL-4Rα.IL-13Rα1.Fc and IL-13Rα1.IL-4Rα.Fc can block the ability of both IL-13 and IL-4 to stimulate cellular responses.

Example 14

Blocking of Injected IL-1 by IL-1 Trap In Vivo

IL-1 is a pro-inflammatory cytokine. Systemic administration of IL-1 has been shown to elicit acute responses in animals, including transient hyperglycemia, hypoinsulinemia, fever, anorexia, and increased serum levels of interleukin-6 (IL-6) (Reimers, 1998). Since mice are responsive to both murine and human IL-1, human IL-1 can be used and in vivo binding effects of human specific IL-1 antagonists can be evaluated. This acute mouse model was used to determine the ability of a human IL-1 Trap to antagonize the in vivo effects of exogenously administered human IL-1. This provides a rapid indication of in vivo efficacy of the human IL-1 Trap and can be used as an assay to help molecule selection.

Experimental Design:

Mice were given subcutaneous injections of human IL-1 (0.3 μg/kg). Twenty-four hours prior to human IL-1 injection, the animals were pre-treated with either vehicle or 150-fold molar excess of human IL-1 Trap (0.54 mg/kg). Two hours prior to sacrifice (26 hrs), the mice were given a second injection of human IL-1 (0.3 µg/kg). Blood samples were collected at various time points and sera were assayed for IL-6 levels.

Results

Figure 35:
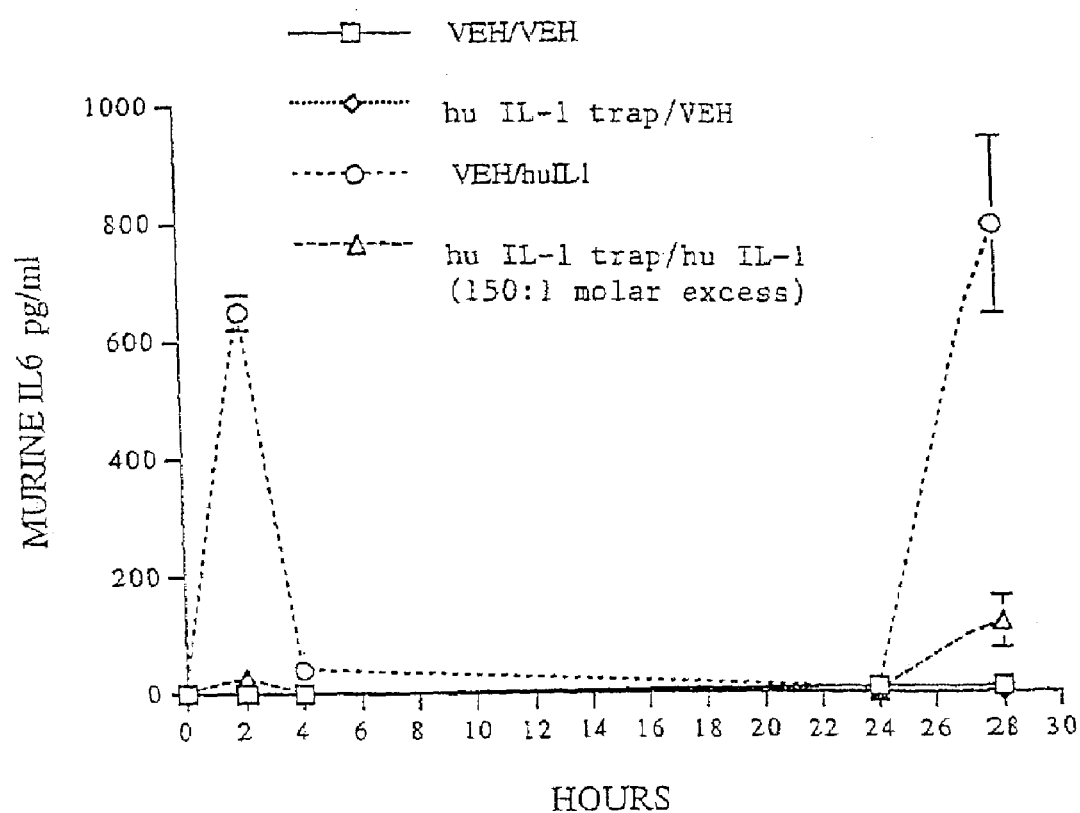
FIG. 35: Human IL-1 Trap blocks the in vivo effects of exogenously administered huIL-1. BALB/c mice were given subcutaneous injection of huIL-1 (0.3 μg/kg) at time 0. Twenty-four hours prior to huIL-1 injection, the animals were pre-treated with either vehicle or 150-fold molar excess of huIL-1 Trap. Two hours prior to sacrifice (26 hrs), the mice were re-challenged with a second injection of huIL-1 (0.3 μg/kg, s.c.). Blood samples were collected at various time points and sera were assayed for IL-1 levels (expressed as mean +/−SEM; n=5 per group).

Exogenous administration of human IL-1 resulted a dramatic induction of serum IL-6 levels. At 150-fold molar excess, the human IL-1 Trap completely blocked the IL-6 increase (FIG. 35). Furthermore, the effects of the human IL-1 Trap persisted for at least another 24 hours, preventing an IL-6 increase even when IL-1 was re-administered (FIG. 35). Such long-lasting efficacy suggests that daily injection of an IL-1 Trap may not be necessary for chronic applications.

Example 15

Evaluating the Ability of an IL-4 Trap to Block the Physiological Responses to Human IL-4 In Cynomologus Monkeys.

Systemic administration of human IL-4 elicits systemic responses in Cynomologus monkeys (Gundel et al., 1996). Thus, the effectiveness of the IL-4 Trap in blocking human IL-4 can be demonstrated by measuring these responses.

Experimental Design:

The experiment consisted of 3 parts: human IL-4+vehicle (part 1), human IL-4+IL-4 Trap (part 2), and human IL-4+ vehicle (part 3). Human IL-4 (25 µg/kg) was injected subcutaneously twice daily for 4 days and IL-4 Trap (8 mg/kg) and vehicle were given intravenously daily for 5 days, beginning 1 day prior to human IL-4 administration. Whole blood was collected daily for flow cytometry analysis for CD16 and plasma was obtained to assay for the cytokine monocyte chemotactic protein 1 (MCP-1). CD16 and MCP-1 are markers of IL-4-mediated inflammation in both humans and monkeys.

Results

Figure 36A:
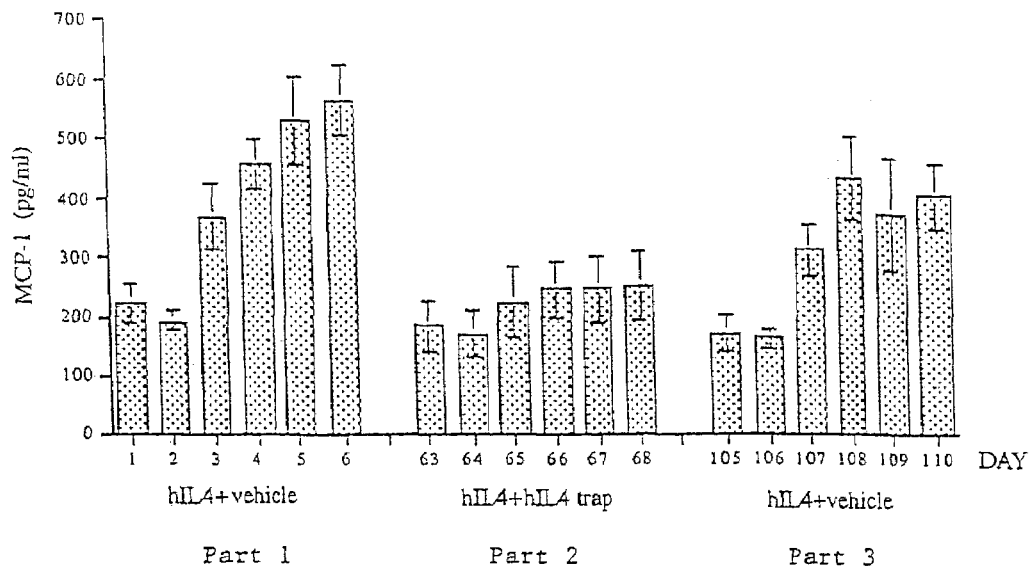
FIGS. 36A–36B: Human IL-4 Trap antagonizes the effects of human IL-4 in monkeys.
Figure 36B:
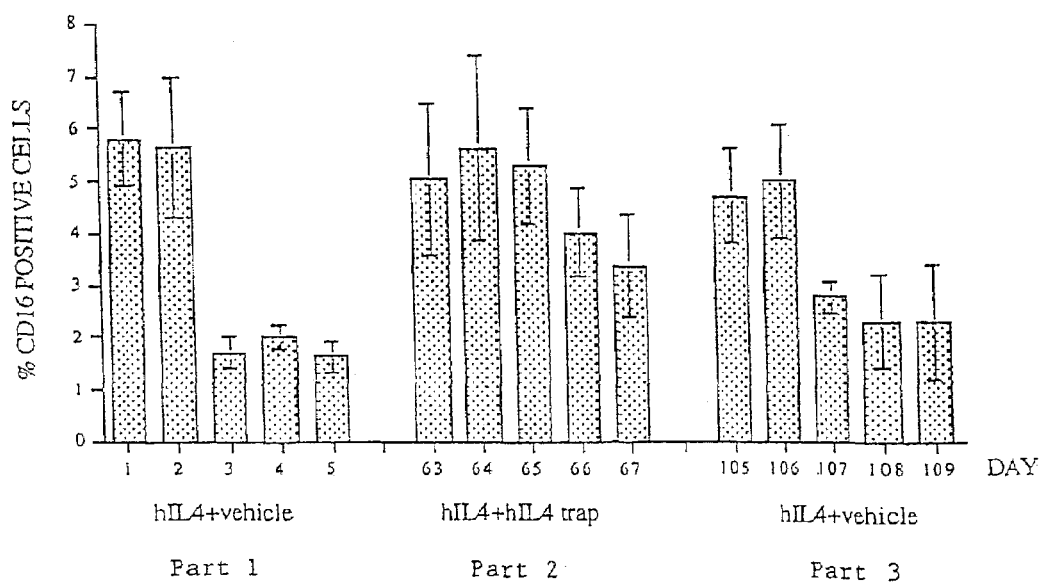

In the presence of human IL-4, MCP-1 increased 2.5-fold and was significantly blocked by the IL-4 Trap (FIG. 36A). Similarly, the decrease in the percent of CD16 positive lymphocytes in peripheral blood was attenuated by the IL-4 Trap (FIG. 36B). After a rest period, the monkeys were re-injected with human IL-4 and the responsiveness of the animals to human IL-4 was re-confirmed (FIGS. 36A and 36B), suggesting that inhibition of the MCP-1 and CD 16 responses is specifically mediated by the IL-4 Trap.

Example 16

The Effects of IL-4 Trap on IL-4-Induced IgE

Secretion

It has been shown that injection of anti-mouse IgD antibody stimulates an IL-4-mediated IgE increase in normal mice. This model has been widely used to evaluate IL-4 antagonists, such as soluble IL-4 receptor and anti-IL-4 monoclonal antibodies (Sato et al., 1993). We decided to use this model to evaluate the ability if the IL-4 Trap to block IL-4-mediated increases of IgE.

Experimental Design:

BALB/C mice injected with anti-mouse IgD (100 µl/mouse, s.c.) were randomly divided into 3 groups. Each received (on days 3–5) either vehicle, murine IL-4 Trap (1 mg/kg, s.c.), or a monoclonal antibody to mouse IL-4 (1 mg/kg, s.c.). Serum was collected at various time points and assayed for IgE levels.

Results

Figure 37:
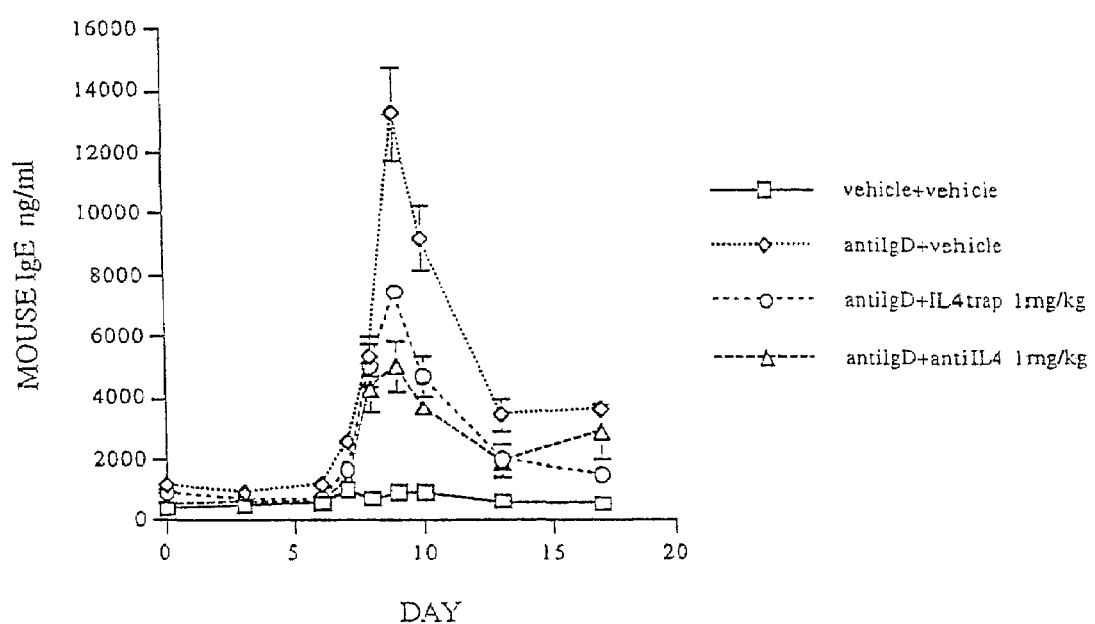
FIG. 37: Murine IL-4 Trap partially prevented IL-4-mediated IgE increase in mice. BALB/C mice injected with anti-mouse IgD (100 μl/mouse, s.c.) were randomly divided into 3 groups, each received (on days 3–5) either vehicle, murine IL-4 Trap (1 mg/kg, s.c.), or a monoclonal antibody to mouse IL-4 (1 mg/kg, s.c.). Sera were collected at various time points and assayed for IgE levels. Results were expressed as mean+/−SEM (n=5 per group). (ANOVA p=0.0002; Tukey-Kramer: vehicle vs. IL-4 Trap, p<0.01; vehicle vs. IL-4 antibody, p<0.001; IL-4 Trap vs. IL-4 antibody, not significant).

Treatment with the murine IL-4 Trap or the mouse IL-4 antibody both significantly antagonized the IL-4-mediated IgE increase in this mouse model (FIG. 37). This suggests that the murine IL-4 Trap binds murine IL-4 and antagonizes physiological responses elicited by endogenous IL-4 in vivo.

Example 17

Construction of Additional IL-4/IL-13 Traps

The following IL-4/IL-13 Traps were constructed using standard molecular biology techniques familiar to the skilled artisan.

IL-4/IL-13 Trap 933

The IL-4/IL-13 Trap 933 sequence consists of the extracellular domain of human IL-13Rα1 (nucleotides −78 to 951 of FIGS. 38A–38H, SEQ ID NO: 33), followed by the extracellular domain of human IL-4Rα (nucleotides 952–1575 of FIGS. 38A–38H, SEQ ID NO: 33) containing a mutation at nucleotide 1501 (T->A) to change a cysteine to a serine, followed by part of the hinge region, the CH2 and CH3 domains of human IgG1 (nucleotides 1576–2265 of FIGS. 38A–38H, SEQ ID NO: 33) containing a mutation at nucleotides 1579–1581 (TGT->GGA) to change a cysteine to a glycine. FIGS. 38A–38H sets forth the deduced amino acid sequence (SEQ ID NO: 34) of IL-4/IL-13 Trap 933.

IL-4/IL-13 Trap 943

The IL-4/IL-13 Trap 943 sequence consists of the extracellular domain of human IL-4Rα (nucleotides −69 to 624 of FIGS. 39A–39G, SEQ ID NO: 39) containing a mutation at nucleotide 550 (T->A) to change a cysteine to a serine, followed by the extracellular domain of human IL-13Rα1 (nucleotides 625–1575 of FIGS. 39A–39G, SEQ ID NO: 39) followed by part of the hinge region, the CH2 and CH3 domains of human IgG1 (nucleotides 1576–2262 of FIGS. 39A–39G, SEQ ID NO: 39) containing a mutation at nucleotides 1576–1578 (TGT->GGT) to change a cysteine to a glycine. FIGS. 39A–39G sets forth the deduced amino acid sequence (SEQ ID NO: 40) of IL-4/IL-13 Trap 943.

IL-4/IL-13 Trap 1126

The IL-4/IL-13 Trap 1126 sequence consists of the extracellular domain of human IL-13Rα1 (nucleotides −78 to 951 of FIGS. 40A–40I, SEQ ID NO: 37), containing a mutation at nucleotide58 (T->A) to change a cysteine to a serine, followed by the extracellular domain of human IL-4Rα (nucleotides 952–1575 of FIGS. 40A–40I, SEQ ID NO: 37) containing a mutation at nucleotide 1501 (T->A) to change a cysteine to a serine, followed by part of the hinge region, the CH2 and CH3 domains of human IgG1 (nucleotides 1576–2265 of FIGS. 40A–40I, SEQ ID NO: 37) containing a mutation at nucleotides 1579–1581 (TGT->GGA) to change a cysteine to a glycine. FIGS. 40A–40I sets forth the deduced amino acid sequence (SEQ ID NO: 38) of IL-4/IL-13 Trap 1126.

IL-4/IL-13 Trap 1128

The IL-4/IL-13 Trap 1128 sequence consists of the extracellular domain of human IL-4Rα (nucleotides −69 to 624 of FIGS. 41A–41P, SEQ ID NO: 35) containing a mutation at nucleotide 550 (T->A) to change a cysteine to a serine, followed by the extracellular domain of human IL-13Rα1

(nucleotides 625–1575 of FIGS. 41A–41P, SEQ ID NO: 35) containing a mutation at nucleotide 682 (T->A) to change a cysteine to a serine, followed by part of the hinge region, the CH2 and CH3 domains of human IgG1 (nucleotides 1576–2262 of FIGS. 41A–41P, SEQ ID NO: 35) containing a mutation at nucleotides 1576–1578 (TGT->GGT) to change a cysteine to a glycine. FIGS. 41A–41P sets forth the deduced amino acid sequence (SEQ ID NO: 36) of IL-4/IL-13 Trap 1128.

IL-4/IL-13 Trap 1130

The IL-4/IL-13 Trap 1130 sequence consists of the extracellular domain of human IL-13Rα1 (nucleotides –78 to 951 of FIGS. 42A–42I, SEQ ID NO: 41), containing a mutation at nucleotides 58–60 (TGC->GCG) to change a cysteine to an alanine, followed by the extracellular domain of human IL-4Rα (nucleotides 952–1575 of FIGS. 42A–42I, SEQ ID NO: 41), containing a mutation at nucleotide 1501 (T->A) to change a cysteine to a serine, followed by part of the hinge region, the CH2 and CH3 domains of human IgG1 (nucleotides 1576–2265 of FIGS. 42A–42I, SEQ ID NO: 41) containing a mutation at nucleotides 1579–1581 (TGT->GGA) to change a cysteine to a glycine. FIGS. 42A–42I sets forth the deduced amino acid sequence (SEQ ID NO: 42) of IL-4/IL-13 Trap 1130.

IL-4/IL-13 Trap 1132

The IL-4/IL-13 Trap 1132 sequence consists of the extracellular domain of human IL-4Rα (nucleotides –69 to 624 of FIGS. 43A–43P, SEQ ID NO: 43) containing a mutation at nucleotide 550 (T->A) to change a cysteine to a serine, followed by the extracellular domain of human IL-13Rα1 (nucleotides 625–1575 of FIGS. 43A–43P, SEQ ID NO: 43) containing a mutation at nucleotides 682–684 (TGC->GCG) to change a cysteine to an alanine, followed by part of the hinge region, the CH2 and CH3 domains of human IgG1 (nucleotides 1576–2262 of FIGS. 43A–43P, SEQ ID NO: 43) containing a mutation at nucleotides 1576–1578 (TGT->GGT) to change a cysteine to a glycine. FIGS. 43A–43P sets forth the deduced amino acid sequence (SEQ ID NO: 44) of IL-4/IL-13 Trap 1132.

IL-4/IL-13 Trap 1199

The IL-4/IL-13 Trap 1199 sequence consists of the extracellular domain of human IL-4Rα (nucleotides –69 to 624 of FIGS. 44A–44I, SEQ ID NO: 45) containing a mutation at nucleotide 550 (T->A) to change a cysteine to a serine, followed by the extracellular domain of human IL-13Rα1 (nucleotides 625–1575 of FIGS. 44A–44I, SEQ ID NO: 45) containing a mutation at nucleotide 682–684 (TGC->GCG) to change a cysteine to an alanine, followed by a stretch of amino acids (nucleotides 1576–1578 of FIGS. 44A–44I, SEQ ID NO: 45), followed by the hinge region, the CH2 and CH3 domains of human IgG4 (nucleotides 1579–2268 of FIGS. 44A–44I, SEQ ID NO: 45). FIGS. 44A–44I sets forth the deduced amino acid sequence (SEQ ID NO: 46) of IL-4/IL-13 Trap 1199.

IL-4/IL-13 Trap 1244

The IL-4/IL-13 Trap 1244 sequence consists of the extracellular domain of human IL-13Rα1 (nucleotides –78 to 951 of FIGS. 45A–45I, SEQ ID NO: 47), containing a mutation at nucleotide 58–60 (TGC->GCG) to change a cysteine to an alanine, followed by the extracellular domain of human IL-4Rα (nucleotides 952–1575 of FIGS. 45A–45I, SEQ ID NO: 47) containing a mutation at nucleotide 1501 (T->A) to change a cysteine to a serine, followed by a stretch of amino acids (nucleotides 1576–1581 of FIGS. 45A–45I, SEQ ID NO: 47), followed by the hinge region, the CH2 and CH3 domains of human IgG4 (nucleotides 1582–2271 of FIGS. 45A–45I, SEQ ID NO: 47). FIGS. 45A–45I sets forth the deduced amino acid sequence Trap 1244.

IL-4/IL-13 Trap 1245

The IL-4/IL-13 Trap 1245 sequence consists of the extracellular domain of human IL-4Rα (nucleotides –69 to 624 of FIGS. 46A–46I, SEQ ID NO: 49) containing a mutation at nucleotide 550 (T->A) to change a cysteine to a serine, followed by the extracellular domain of human IL-13Rα1 (nucleotides 625–1575 of FIGS. 46A–46I, SEQ ID NO: 49) containing a mutation at nucleotide 682 (T->A) to change a cysteine to an serine, followed by a stretch of amino acids (nucleotides 1576–1578 of FIGS. 46A–46I, SEQ ID NO: 49), followed by the hinge region, the CH2 and CH3 domains of human IgG4 (nucleotides 1579–2268 of FIGS. 46A–46I, SEQ ID NO: 49). FIGS. 46A–46I sets forth the deduced amino acid sequence (SEQ ID NO: 50) of IL-4/IL-13 Trap 1245.

IL-4/IL-13 Trap 1246

The IL-4/IL-13 Trap 1246 sequence consists of the extracellular domain of human IL-13Rα1 (nucleotides –78 to 951 of FIGS. 47A–47I, SEQ ID NO: 51) containing a mutation at nucleotide 58 (T->A) to change a cysteine to a serine, followed by the extracellular domain of human IL-4Rα (nucleotides 952–1575 of FIGS. 47A–47I, SEQ ID NO: 51) containing a mutation at nucleotide 1501 (T->A) to change a cysteine to a serine, followed by a stretch of amino acids (nucleotides 1576–1581 of FIGS. 47A–47I, SEQ ID NO: 51), followed by the hinge region, the CH2 and CH3 domains of human IgG4 (nucleotides 1582-2271 of FIGS. 47A–47I, SEQ ID NO: 51). FIGS. 47A–47I sets forth the deduced amino acid sequence (SEQ ID NO: 52) of IL-4/IL-13 Trap 1246.

IL-4/IL-13 Trap 1244-B

The IL-4/IL-13 Trap 1244-B sequence consists of the extracellular domain of human IL-13Rα1 (nucleotides –78 to 951 of FIGS. 52A–52H, SEQ ID NO: 53), containing a mutation at nucleotide 58–60 (TGC->GCG) to change a cysteine to an alanine, followed by the extracellular domain of human IL-4Rα (nucleotides 952–1575 of FIGS. 52A–52H, SEQ ID NO: 53) containing a mutation at nucleotide 1501 (T->A) to change a cysteine to a serine, followed by a stretch of amino acids (nucleotides 1576–1581 of FIGS. 52A–52H, SEQ ID NO: 53), followed by the hinge region, the CH2 and CH3 domains of human IgG4 (nucleotides 1582–2271 of FIGS. 52A–52H, SEQ ID NO: 53) containing a mutation at nucleotide 1609 (T->C) to change a serine to a proline. FIGS. 52A–52H sets forth the deduced amino acid sequence (SEQ ID NO: 54) of IL-4/IL-13 Trap 1244-B.

IL-4/IL-13 Trap 1245-B

The IL-4/IL-13 Trap 1245-B sequence consists of the extracellular domain of human IL-4Rα (nucleotides –69 to 624 of FIGS. 53A–53I, SEQ ID NO: 55) containing a mutation at nucleotide 550 (T->A) to change a cysteine to a serine, followed by the extracellular domain of human IL-13Rα1 (nucleotides 625–1575 of FIGS. 53A–53I, SEQ ID NO: 55) containing a mutation at nucleotide 682 (T->A) to change a cysteine to an serine, followed by a stretch of amino acids (nucleotides 1576–1578 of FIGS. 53A–53I, SEQ ID NO: 55), followed by the hinge region, the CH2 and CH3 domains of human IgG4 (nucleotides 1579–2268 of FIGS. 53A–53I, SEQ ID NO: 55) containing a mutation at nucleotide 1606 (T->C) to change a serine to a proline. FIGS. 53A–53I sets forth the deduced amino acid sequence (SEQ ID NO: 56) of IL-4/IL-13 Trap 1245-B.

IL-4/IL-13 Trap 1246-B

The IL-4/IL-13 Trap 1246-B sequence consists of the extracellular domain of human IL-13Rα1 (nucleotides −78 to 951 of FIGS. 54A–54H, SEQ ID NO: 57) containing a mutation at nucleotide 58 (T->A) to change a cysteine to a serine, followed by the extracellular domain of human IL-4Rα (nucleotides 952–1575 of FIGS. 54A–54H, SEQ ID NO: 57) containing a mutation at nucleotide 1501 (T->A) to change a cysteine to a serine, followed by a stretch of amino acids (nucleotides 1576–1581 of FIGS. 54A–54H, SEQ ID NO: 57), followed by the hinge region, the CH2 and CH3 domains of human IgG4 (nucleotides 1582–2271 of FIGS. 54A–54H, SEQ ID NO: 57) containing a mutation at nucleotide 1609 (T->C) to change a serine to a proline. FIGS. 54A–54H sets forth the deduced amino acid sequence (SEQ ID NO: 58) of IL-4/IL-13 Trap 1246-B.

IL-4/IL-13 Trap 1268

The IL-4/IL-13 Trap 1268 sequence consists of the extracellular domain of human IL-4Rα (nucleotides −69 to 624 of FIGS. 55A–55H, SEQ ID NO: 59) containing a mutation at nucleotide 550 (T->A) to change a cysteine to a serine, followed by the extracellular domain of human IL-13Rα1 (nucleotides 625–1575 of FIGS. 55A–55H, SEQ ID NO: 59) containing a mutation at nucleotide 682–684 (TGC->GCG) to change a cysteine to an alanine, followed by a stretch of amino acids (nucleotides 1576–1578 of FIGS. 55A–55H, SEQ ID NO: 59),followed by the hinge region, the CH2 and CH3 domains of human IgG4 (nucleotides 1579–2268 of FIGS. 55A–55H, SEQ ID NO: 59) containing a mutation at nucleotide 1606 (T->C) to change a serine to a proline. FIGS. 55A–55H sets forth the deduced amino acid sequence (SEQ ID NO: 60) of IL-4/IL-13 Trap 1268.

In addition to the sequences described supra and in the associated figures, the following modifications to those sequences are also contemplated by the subject invention:

SG Insertion:

For IL-4/IL-13 Traps 943, 1132, 1199, 1268, 1128, 1245, and 1245-B an insertion of the nucleotides TCC GGA between nucleotides 624 and 625 would add a Ser Gly stretch of amino acids between the two receptor domains of the Trap.

For IL-4/IL-13 Traps 933, 1130, 1244, 1244-B, 1126, 1246, and 1246-B, an insertion of the nucleotides TCC GGA between nucleotides 951 and 952 would add a Ser Gly stretch of amino acids between the two receptor domains of the Trap.

IL13Rα1 Alternative:

For IL-4/IL-13 Traps 943, 1132, 1199, 1268, 1128, 1245, and 1245-B a change at nucleotide 935 from C to T would change the amino acid from Thr to Ile.

For IL-4/IL-13 Traps 933, 1130, 1244, 1244-B, 1126, 1246, and 1246-B, a change at nucleotide 311 from C to T would change the amino acid from Thr to II e.

IL4Rα Alternative:

For IL-4/IL-13 Traps 943, 1132, 1199, 1268, 1128, 1245, and 1245-B, a change at nucleotide 154 from A to G would change the amino acid from Ile to Val.

For IL-4/IL-13 Traps 933, 1130, 1244, 1244-B, 1126, 1246, and 1246-B, a change at nucleotide 1105 from A to G would change the amino acid from Ile to Val.

The skilled artisan will recognize that any combination of the above-described modifications within a Trap are also contemplated by the present invention even if each and every combination is not explicitly set forth herein.

Example 18

IL-4/IL-13 Trap Properties

The IL-4/IL-13 Trap 943 blocked IL-4 and IL-13 in a TF1 bioassay more potently than the IL-4/IL-13 Trap 933. In addition, in CHO transient transfection systems, IL-4/IL-13 Trap 943 had a slightly higher protein expression level.

Disulfide mapping and stoichiometry using standard BIAcore methodologies suggested that the IL-4/IL-13 Trap 933 and IL-4/IL-13 Trap 943 molecules were misfolded. Therefore, second generation of IL-4/IL-13 Traps were constructed. It was found that the IL-4/IL-13 Trap constructs 1126, 1128, 1130, and 1132, in which the cysteine at position 20 of mature human IL-13Rα1 was mutated to either an alanine or a serine, exhibited less aggregation upon expression, had ~2 to 3-fold better activity than IL-4/IL-13 Trap 943 in the TF1 bioassay in blocking both IL-4 and IL-13, and exhibited a consistent and homogenous pattern of disulfide formation.

The IL-4/IL-13 Trap 1132 molecule had additional advantages over IL-4/IL-13 Traps 1126, 1128, and 1130. A higher percentage of the total protein (>95%) had the correct N-terminal sequence as compared to the IL-4/IL-13 Traps 1126 or 1130 (80–90%). Stoichiometric studies indicated a stoichiometry of 1 for the IL-4/IL-13 Trap 1132 whereas the IL-4/IL-13 Trap 1130 showed a stoichiometry of 1.5. Preliminary mouse pharmacokinetic experiments suggest that the IL-4/IL-13 Trap 1132 molecule has a higher Cmax (maximal serum concentration) and a longer $t_{1/2}$ (serum half-life) than the others. The IgG4 versions of the IL-4/IL-13 Traps containing the cysteine mutations may be preferred if it is desired to reduce the effector functions of the Fc portion of the Traps. The cysteine to serine mutation in IL-4/IL-13 Traps 1126 and 1128 molecules creates a novel N-glycosylation site which may be desirable in certain circumstances.

Example 19

IL-4/IL-13 Traps Potently Block both IL-4 and IL-13 in TF1 Bioassays.

Figure 48:
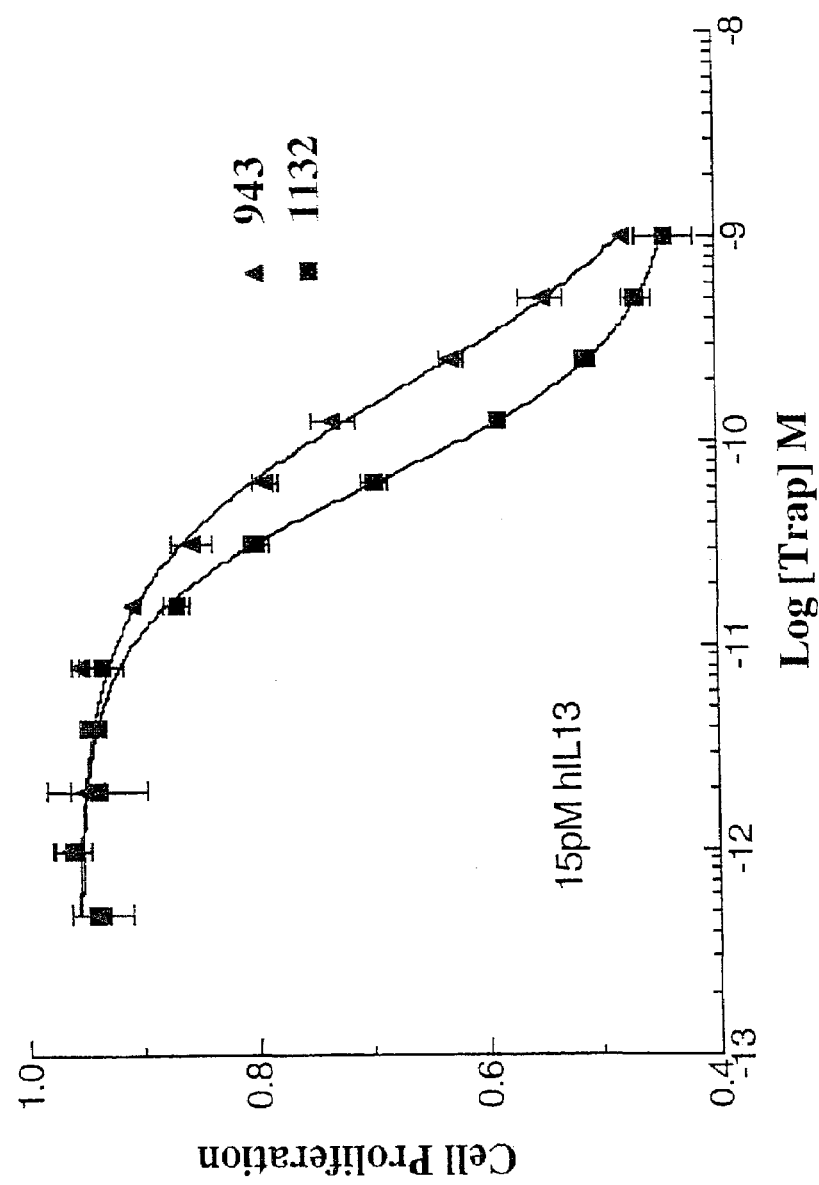
FIG. 48: The IL-4/IL-13 Trap 1132 can block IL-13 more potently than the IL-4/IL-13 Trap 943. Triplicate plates of TF1 cells (20,000 cells/well) were incubated with 15 pM recombinant human IL-13 (*E. coli*; Preprotech) and varying concentrations of IL-4/IL-13 Trap 943 or 1132 for ~3 days at 37° C., 5% $CO_2$. MTS was added to each well, incubated at 37° C., 5% $CO_2$ for 4 hrs. and cell proliferation was measured as OD at 490 nm. IL-4/IL-13 Trap 1132 exhibits an $IC_{50}$ of 64 pM as compared to 184 pM for Trap 943.

Triplicate plates of TF1 cells (20,000 cells/well) were incubated with 15 pM recombinant human IL-13 (*E. coli*; Preprotech) and varying concentrations of IL-4/IL-13 Trap 943 or 1132 for ~3 days at 37° C., 5% $CO_2$. MTS was added to each well as described supra, incubated at 37° C., 5% $CO_2$ for 4 hrs. and cell proliferation was measured as OD at 490 nm. FIG. 48 shows the results of this experiment. The IL-4/IL-13 Trap 1132 can block IL-13 more potently than the IL-4/IL-13 Trap 943. IL-4/IL-13 Trap 1132 exhibits an $IC_{50}$ of 64 pM as compared to 184 pM for Trap 943.

The above experiment was performed with *E. coli*-produced IL-13. To confirm that the IL-4/IL-13 Trap will bind human IL-13 in vivo, IL-13 was produced and purified from a mammalian cell line (CHO). The CHO-derived human IL-13 was then utilized in the TF1 bioassay to determine the ability of the IL-4/IL-13 Trap to bind and block activity. The IL-4/IL-13 Trap 1132 displays a higher affinity for human IL-13 produced by CHO cells ($IC_{50}$=17 pM) than for human IL-13 made in *E. coli* (64 pM). This result predicts that the IL-4/IL-13 Trap will successfully bind human IL-13 with high affinity in vivo.

Figure 49:
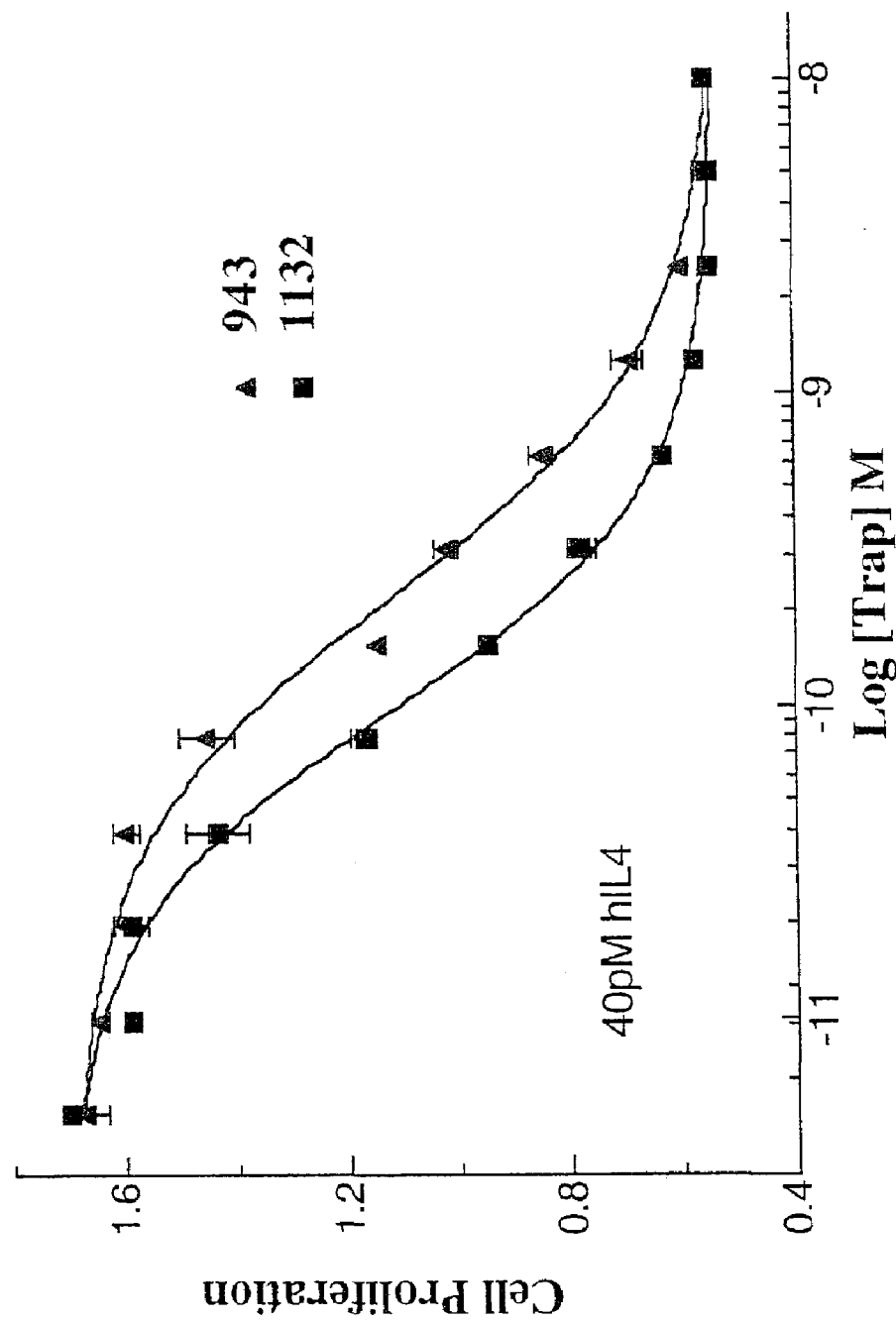
FIG. 49: The IL-4/IL-13 Trap 1132 can block IL-4 more potently than the IL-4/IL-13 Trap 943. Triplicate plates of TF1 cells (20,000 cells/well) were incubated with 40 pM recombinant human IL-4 (*E. coli*; Applicants' own material) and varying concentrations of IL-4/IL-13 Trap 943 or 1132 for ~3 days at 37° C., 5% $CO_2$. MTS was added to each well, incubated at 37° C., 5% $CO_2$ for 4 hrs. and cell proliferation was measured as OD at 490 nm. IL-4/IL-13 Trap 1132 exhibits an $IC_{50}$ of 95 pM as compared to 222 pM for Trap 943.

Triplicate plates of TF1 cells (20,000 cells/well) were incubated with 40 pM recombinant human IL-4 (*E. coli*; Applicants' own material) and varying concentrations of IL-4/IL-13 Trap 943 or 1132 for ~3 days at 37° C., 5% $CO_2$. MTS was added to each well, incubated at 37° C., 5% $CO_2$ for 4 hrs. and cell proliferation was measured as OD at 490 nm. FIG. 49 shows the results of this experiment. The IL-4/IL-13 Trap 1132 can block IL-4 more potently than the IL-4/IL-13 Trap 943. IL-4/IL-13 Trap 1132 exhibits an $IC_{50}$ of 95 pM as compared to 222 pM for Trap 943.

Figure 50:
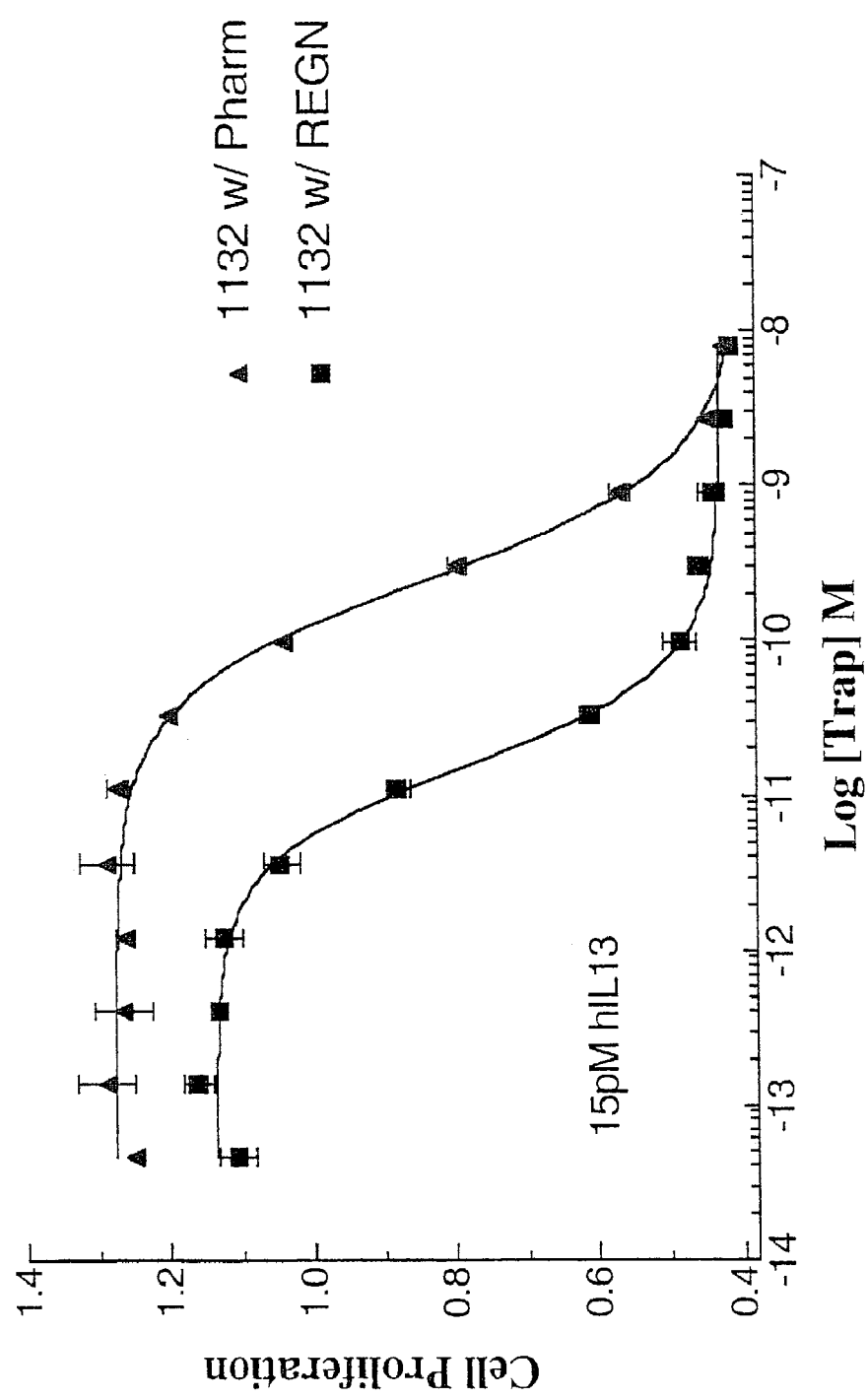
FIG. 50: IL-4/IL-13 Trap 1132 displays a higher affinity for Applicants' rhIL13. Triplicate plates of TF1 cells (20,000 cells/well) were incubated with 15 pM recombinant human IL-13 Applicants' own material (CHO) or Pharmingen (*E. coli*) and varying concentrations of IL-4/IL-13 Trap 943 or 1132 for ~3 days at 37° C., 5% $CO_2$. MTS was added to each well, incubated at 37° C., 5% $CO_2$ for 4 hrs. and cell proliferation was measured as OD at 490 nm. IL-4/IL-13 Trap 1132 has an $IC_{50}$ of 16 pM which indicates a Kd of ~9 pM.

As shown in FIG. 50, IL-4/IL-13 Trap 1132 displays a higher affinity for Applicants' rhIL13. Triplicate plates of TF1 cells (20,000 cells/well) were incubated with 15 pM recombinant human IL-13 Applicants' own material (CHO) or Pharmingen (*E. coli*) and varying concentrations of IL-4/IL-13 Trap 943 or 1132 for ~3 days at 37° C., 5% $CO_2$. MTS was added to each well, incubated at 37° C., 5% $CO_2$ for 4 hrs. and cell proliferation was measured as OD at 490 nm. IL-4/IL-13 Trap 1132 has an $IC_{50}$ of 16 pM which indicates a Kd of ~9 pM.

Figure 51:
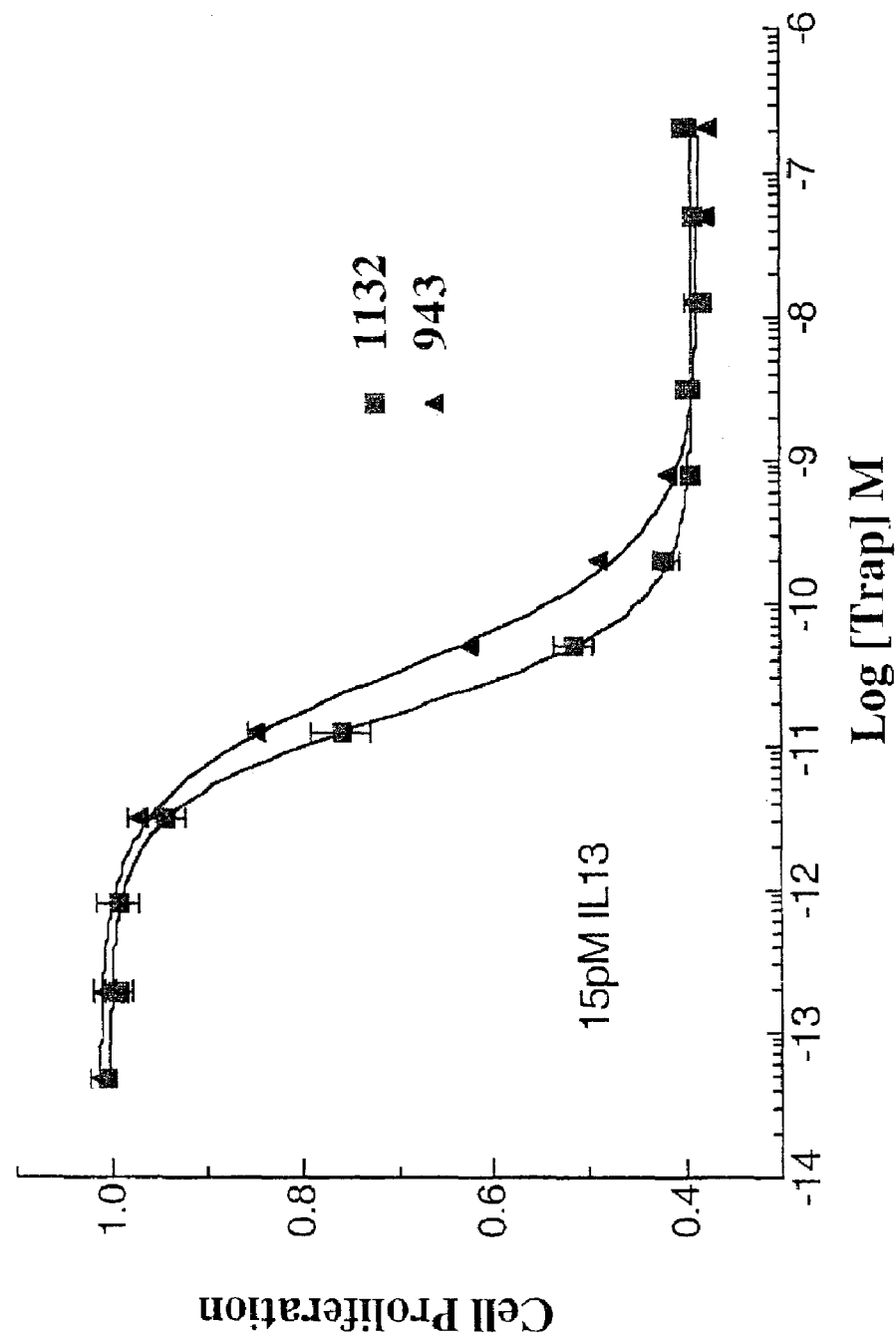
FIG. 51: IL-4/IL-13 Trap 1132 can block hIL13 more potently than IL-4/IL-13 Trap 943 with Applicants' rhIL13. Triplicate plates of TF1 cells (20,000 cells/well) were incubated with 15 pM recombinant human IL-13 (CHO; Applicants' own material) and varying concentrations of IL-4/IL-13 Trap 943 or 1132 for ~3 days at 37° C., 5% $CO_2$. MTS was added to each well, incubated at 37° C., 5% $CO_2$ for 4 hrs. and cell proliferation was measured as OD at 490 nm. IL-4/IL-13 Trap 1132 has an $IC_{50}$ of 17 pM as compared to 33 pM for 943.

As shown in FIG. 51, IL-4/IL-13 Trap 1132 can block hIL13 more potently than IL-4/IL-13 Trap 943 with Applicants' own rhIL13. Triplicate plates of TF1 cells (20,000 cells/well) were incubated with 15 pM recombinant human IL-13 (CHO; Applicants' own material) and varying concentrations of IL-4/IL-13 Trap 943 or 1132 for ~3 days at 37° C., 5% $CO_2$. MTS was added to each well, incubated at 37° C., 5% $CO_2$ for 4 hrs. and cell proliferation was measured as OD at 490 nm. IL-4/IL-13 Trap 1132 has an $IC_{50}$ of 17 pM as compared to 33 pM for 943.

Figure 56:
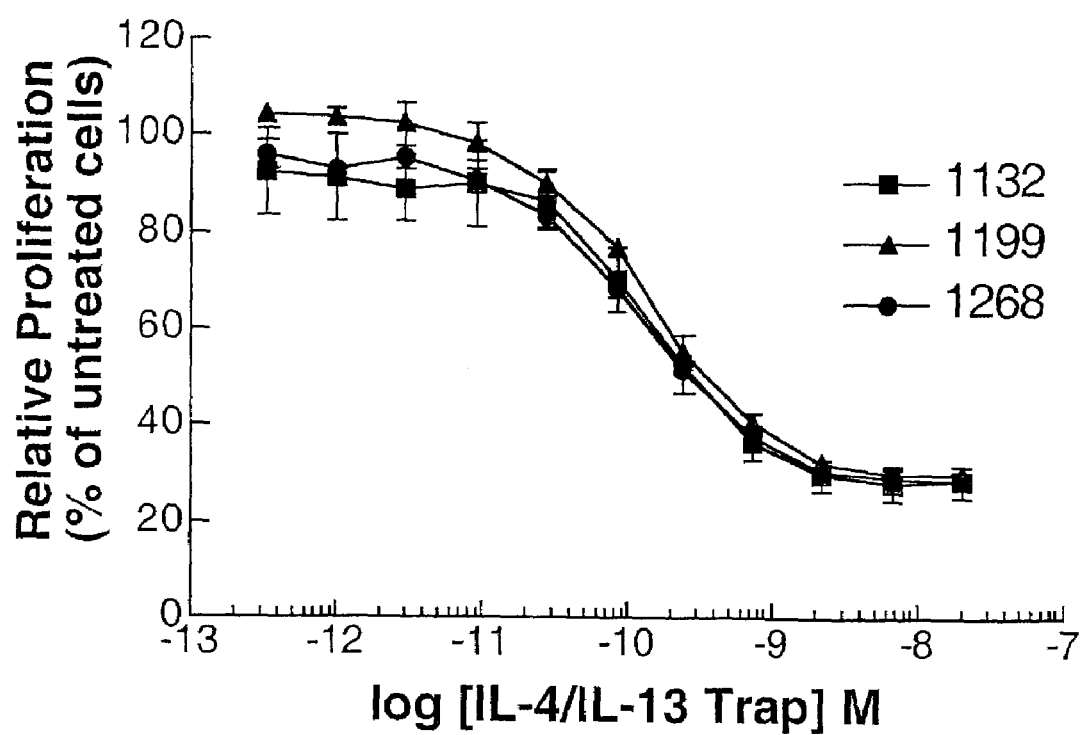
FIG. 56: IL-4/IL-13 Trap 1132, IL-4/IL-13 Trap 1199 and IL-4/IL-13 Trap 1268 are equally potent in blocking IL13. Triplicate plates of TF1 cells (20,000 cells/well) were incubated with 15 pM recombinant human IL-13 and varying concentrations of IL-4/IL-13 Trap 1132, 1199 or 1268 for ~3 days at 37° C., 5% $CO_2$. MTS was added to each well, incubated at 37° C., 5% $CO_2$ for 4 hrs. and cell proliferation was measured as OD at 490 nm. Relative cell proliferation as a percentage of the proliferation of cells in the absence of IL-4/IL-13 Trap is plotted on the y-axis. The IL-4/IL-13 Traps 1132, 1199 and 1268 all block IL-13 with the same potency, indicating that the isotype of the Fc portion does not affect the ability of IL-4/IL-13 Trap to block IL-13 in vitro.

As shown in FIG. 56, IL-4/IL-13 Trap 1132, IL-4/IL-13 Trap 1199 and IL-4/IL-13 Trap 1268 are equally potent in blocking IL13. Triplicate plates of TF1 cells (20,000 cells/well) were incubated with 15 pM recombinant human IL-13 (*E. coli*; Pharmingen) and varying concentrations of IL-4/IL-13 Trap 1132, 1199 or 1268 for ~3 days at 37° C., 5% $CO_2$. MTS was added to each well, incubated at 37° C., 5% $CO_2$ for 4 hrs. and cell proliferation was measured as OD at 490 nm. Relative cell proliferation as a percentage of the proliferation of cells in the absence of IL-4/IL-13 Trap is plotted on the y-axis. The IL-4/IL-13 Traps 1132, 1199 and 1268 all block IL-13 with the same potency, indicating that the isotype of the Fc portion does not affect the ability of IL-4/IL-13 Trap to block IL-13 in vitro.

The present invention is not to be limited in scope by the specific embodiments described herein. Indeed, various modifications of the invention in addition to those described herein will become apparent to those skilled in the art from the foregoing description and accompanying figures. Such modifications are intended to fall within the scope of the appended claims.

SEQUENCE LISTING

```
<160> NUMBER OF SEQ ID NOS: 60

<210> SEQ ID NO 1
<211> LENGTH: 6
<212> TYPE: PRT
<213> ORGANISM: Artificial Sequence
<220> FEATURE:
<223> OTHER INFORMATION: Tag sequence

<400> SEQUENCE: 1

His His His His His His
1               5

<210> SEQ ID NO 2
<211> LENGTH: 16
<212> TYPE: PRT
<213> ORGANISM: Artificial Sequence
<220> FEATURE:
<223> OTHER INFORMATION: peptide derived from region near C-terminus of
      gp130

<400> SEQUENCE: 2

Cys Gly Thr Glu Gly Gln Val Glu Arg Phe Glu Thr Val Gly Met Glu
1               5                   10                  15

<210> SEQ ID NO 3
<211> LENGTH: 16
<212> TYPE: DNA
<213> ORGANISM: Artificial Sequence
<220> FEATURE:
<223> OTHER INFORMATION: Kozak sequence

<400> SEQUENCE: 3
cgccgccacc atggtg                                                       16

<210> SEQ ID NO 4
<211> LENGTH: 10
<212> TYPE: PRT
<213> ORGANISM: Artificial Sequence
```

-continued

```
<220> FEATURE:
<223> OTHER INFORMATION: J peptide

<400> SEQUENCE: 4

Gly Gln Gly Thr Leu Val Thr Val Ser Ser
1               5                   10

<210> SEQ ID NO 5
<211> LENGTH: 11
<212> TYPE: PRT
<213> ORGANISM: Artificial Sequence
<220> FEATURE:
<223> OTHER INFORMATION: J peptide

<400> SEQUENCE: 5

Thr Phe Gly Gln Gly Thr Lys Val Glu Ile Lys
1               5                   10

<210> SEQ ID NO 6
<211> LENGTH: 10
<212> TYPE: PRT
<213> ORGANISM: Artificial Sequence
<220> FEATURE:
<223> OTHER INFORMATION: linker sequence

<400> SEQUENCE: 6

Gly Ala Pro Ser Gly Gly Gly Gly Arg Pro
1               5                   10

<210> SEQ ID NO 7
<211> LENGTH: 859
<212> TYPE: PRT
<213> ORGANISM: Homo sapiens

<400> SEQUENCE: 7

Met Val Thr Leu Gln Thr Trp Val Val Gln Ala Leu Phe Ile Phe Leu
1               5                   10                  15

Thr Thr Glu Ser Thr Gly Glu Leu Leu Asp Pro Cys Gly Tyr Ile Ser
                20                  25                  30

Pro Glu Ser Pro Val Val Gln Leu His Ser Asn Phe Thr Ala Val Cys
            35                  40                  45

Val Leu Lys Glu Lys Cys Met Asp Tyr Phe His Val Asn Ala Asn Tyr
        50                  55                  60

Ile Val Trp Lys Thr Asn His Phe Thr Ile Pro Lys Glu Gln Tyr Thr
65                  70                  75                  80

Ile Ile Asn Arg Thr Ala Ser Ser Val Thr Phe Thr Asp Ile Ala Ser
                85                  90                  95

Leu Asn Ile Gln Leu Thr Cys Asn Ile Leu Thr Phe Gly Gln Leu Glu
            100                 105                 110

Gln Asn Val Tyr Gly Ile Thr Ile Ile Ser Gly Leu Pro Pro Glu Lys
        115                 120                 125

Pro Lys Asn Leu Ser Cys Ile Val Asn Glu Gly Lys Lys Met Arg Cys
    130                 135                 140

Glu Trp Asp Gly Gly Arg Glu Thr His Leu Glu Thr Asn Phe Thr Leu
145                 150                 155                 160

Lys Ser Glu Trp Ala Thr His Lys Phe Ala Asp Cys Lys Ala Lys Arg
                165                 170                 175

Asp Thr Pro Thr Ser Cys Thr Val Asp Tyr Ser Thr Val Tyr Phe Val
            180                 185                 190

Asn Ile Glu Val Trp Val Glu Ala Glu Asn Ala Leu Gly Lys Val Thr
```

-continued

```
            195                 200                 205
Ser Asp His Ile Asn Phe Asp Pro Val Tyr Lys Val Lys Pro Asn Pro
    210                 215                 220

Pro His Asn Leu Ser Val Ile Asn Ser Glu Glu Leu Ser Ser Ile Leu
225                 230                 235                 240

Lys Leu Thr Trp Thr Asn Pro Ser Ile Lys Ser Val Ile Ile Leu Lys
                    245                 250                 255

Tyr Asn Ile Gln Tyr Arg Thr Lys Asp Ala Ser Thr Trp Ser Gln Ile
                260                 265                 270

Pro Pro Glu Asp Thr Ala Ser Thr Arg Ser Ser Phe Thr Val Gln Asp
            275                 280                 285

Leu Lys Pro Phe Thr Glu Tyr Val Phe Arg Ile Arg Cys Met Lys Glu
        290                 295                 300

Asp Gly Lys Gly Tyr Trp Ser Asp Trp Ser Glu Ala Ser Gly Ile
305                 310                 315                 320

Thr Tyr Glu Asp Arg Pro Ser Lys Ala Pro Ser Phe Trp Tyr Lys Ile
                    325                 330                 335

Asp Pro Ser His Thr Gln Gly Tyr Arg Thr Val Gln Leu Val Trp Lys
                340                 345                 350

Thr Leu Pro Pro Phe Glu Ala Asn Gly Lys Ile Leu Asp Tyr Glu Val
            355                 360                 365

Thr Leu Thr Arg Trp Lys Ser His Leu Gln Asn Tyr Thr Val Asn Ala
        370                 375                 380

Thr Lys Leu Thr Val Asn Leu Thr Asn Asp Arg Tyr Leu Ala Thr Leu
385                 390                 395                 400

Thr Val Arg Asn Leu Val Gly Lys Ser Asp Ala Ala Val Leu Thr Ile
                    405                 410                 415

Pro Ala Cys Asp Phe Gln Ala Thr His Pro Val Met Asp Leu Lys Ala
                420                 425                 430

Phe Pro Lys Asp Asn Met Leu Trp Val Glu Trp Thr Thr Pro Arg Glu
            435                 440                 445

Ser Val Lys Lys Tyr Ile Leu Glu Trp Cys Val Leu Ser Asp Lys Ala
        450                 455                 460

Pro Cys Ile Thr Asp Trp Gln Gln Glu Asp Gly Thr Val His Arg Thr
465                 470                 475                 480

Tyr Leu Arg Gly Asn Leu Ala Glu Ser Lys Cys Tyr Leu Ile Thr Val
                    485                 490                 495

Thr Pro Val Tyr Ala Asp Gly Pro Gly Ser Pro Glu Ser Ile Lys Ala
                500                 505                 510

Tyr Leu Lys Gln Ala Pro Pro Ser Lys Gly Pro Thr Val Arg Thr Lys
            515                 520                 525

Lys Val Gly Lys Asn Glu Ala Val Leu Glu Trp Asp Gln Leu Pro Val
        530                 535                 540

Asp Val Gln Asn Gly Phe Ile Arg Asn Tyr Thr Ile Phe Tyr Arg Thr
545                 550                 555                 560

Ile Ile Gly Asn Glu Thr Ala Val Asn Val Asp Ser Ser His Thr Glu
                    565                 570                 575

Tyr Thr Leu Ser Ser Leu Thr Ser Asp Thr Leu Tyr Met Val Arg Met
                580                 585                 590

Ala Ala Tyr Thr Asp Glu Gly Gly Lys Asp Gly Pro Glu Phe Thr Phe
            595                 600                 605

Thr Thr Pro Lys Phe Ala Gln Gly Glu Ile Glu Ser Gly Glu Pro Lys
        610                 615                 620
```

Ser Cys Asp Lys Thr His Thr Cys Pro Pro Cys Pro Ala Pro Glu Leu
625                 630                 635                 640

Leu Gly Gly Pro Ser Val Phe Leu Phe Pro Pro Lys Pro Lys Asp Thr
            645                 650                 655

Leu Met Ile Ser Arg Thr Pro Glu Val Thr Cys Val Val Val Asp Val
            660                 665                 670

Ser His Glu Asp Pro Glu Val Lys Phe Asn Trp Tyr Val Asp Gly Val
            675                 680                 685

Glu Val His Asn Ala Lys Thr Lys Pro Arg Glu Glu Gln Tyr Asn Ser
        690                 695                 700

Thr Tyr Arg Val Val Ser Val Leu Thr Val Leu His Gln Asp Trp Leu
705                 710                 715                 720

Asn Gly Lys Glu Tyr Lys Cys Lys Val Ser Asn Lys Ala Leu Pro Ala
                725                 730                 735

Pro Ile Glu Lys Thr Ile Ser Lys Ala Lys Gly Gln Pro Arg Glu Pro
            740                 745                 750

Gln Val Tyr Thr Leu Pro Pro Ser Arg Asp Glu Leu Thr Lys Asn Gln
            755                 760                 765

Val Ser Leu Thr Cys Leu Val Lys Gly Phe Tyr Pro Ser Asp Ile Ala
770                 775                 780

Val Glu Trp Glu Ser Asn Gly Gln Pro Glu Asn Asn Tyr Lys Thr Thr
785                 790                 795                 800

Pro Pro Val Leu Asp Ser Asp Gly Ser Phe Phe Leu Tyr Ser Lys Leu
                805                 810                 815

Thr Val Asp Lys Ser Arg Trp Gln Gln Gly Asn Val Phe Ser Cys Ser
            820                 825                 830

Val Met His Glu Ala Leu His Asn His Tyr Thr Gln Lys Ser Leu Ser
            835                 840                 845

Leu Ser Pro Gly Lys His His His His His
    850                 855

<210> SEQ ID NO 8
<211> LENGTH: 592
<212> TYPE: PRT
<213> ORGANISM: Homo sapiens

<400> SEQUENCE: 8

Met Val Ala Val Gly Cys Ala Leu Leu Ala Ala Leu Leu Ala Ala Pro
1               5                   10                  15

Gly Ala Ala Leu Ala Pro Arg Arg Cys Pro Ala Gln Glu Val Ala Arg
            20                  25                  30

Gly Val Leu Thr Ser Leu Pro Gly Asp Ser Val Thr Leu Thr Cys Pro
        35                  40                  45

Gly Val Glu Pro Glu Asp Asn Ala Thr Val His Trp Val Leu Arg Lys
    50                  55                  60

Pro Ala Ala Gly Ser His Pro Ser Arg Trp Ala Gly Met Gly Arg Arg
65                  70                  75                  80

Leu Leu Leu Arg Ser Val Gln Leu His Asp Ser Gly Asn Tyr Ser Cys
                85                  90                  95

Tyr Arg Ala Gly Arg Pro Ala Gly Thr Val His Leu Leu Val Asp Val
            100                 105                 110

Pro Pro Glu Glu Pro Gln Leu Ser Cys Phe Arg Lys Ser Pro Leu Ser
            115                 120                 125

Asn Val Val Cys Glu Trp Gly Pro Arg Ser Thr Pro Ser Leu Thr Thr

-continued

```
            130                 135                 140
Lys Ala Val Leu Leu Val Arg Lys Phe Gln Asn Ser Pro Ala Glu Asp
145                 150                 155                 160

Phe Gln Glu Pro Cys Gln Tyr Ser Gln Glu Ser Gln Lys Phe Ser Cys
                165                 170                 175

Gln Leu Ala Val Pro Glu Gly Asp Ser Ser Phe Tyr Ile Val Ser Met
            180                 185                 190

Cys Val Ala Ser Ser Val Gly Ser Lys Phe Ser Lys Thr Gln Thr Phe
        195                 200                 205

Gln Gly Cys Gly Ile Leu Gln Pro Asp Pro Ala Asn Ile Thr Val
210                 215                 220

Thr Ala Val Ala Arg Asn Pro Arg Trp Leu Ser Val Thr Trp Gln Asp
225                 230                 235                 240

Pro His Ser Trp Asn Ser Ser Phe Tyr Arg Leu Arg Phe Glu Leu Arg
                245                 250                 255

Tyr Arg Ala Glu Arg Ser Lys Thr Phe Thr Thr Trp Met Val Lys Asp
                260                 265                 270

Leu Gln His His Cys Val Ile His Asp Ala Trp Ser Gly Leu Arg His
            275                 280                 285

Val Val Gln Leu Arg Ala Gln Glu Glu Phe Gly Gln Gly Glu Trp Ser
        290                 295                 300

Glu Trp Ser Pro Glu Ala Met Gly Thr Pro Trp Thr Glu Ser Arg Ser
305                 310                 315                 320

Pro Pro Ala Glu Asn Glu Val Ser Thr Pro Met Gln Ala Leu Thr Thr
                325                 330                 335

Asn Lys Asp Asp Asp Asn Ile Leu Phe Arg Asp Ser Ala Asn Ala Thr
                340                 345                 350

Ser Leu Pro Val Gln Asp Ala Gly Glu Pro Lys Ser Cys Asp Lys Thr
            355                 360                 365

His Thr Cys Pro Pro Cys Pro Ala Pro Glu Leu Leu Gly Gly Pro Ser
            370                 375                 380

Val Phe Leu Phe Pro Pro Lys Pro Lys Asp Thr Leu Met Ile Ser Arg
385                 390                 395                 400

Thr Pro Glu Val Thr Cys Val Val Val Asp Val Ser His Glu Asp Pro
                405                 410                 415

Glu Val Lys Phe Asn Trp Tyr Val Asp Gly Val Glu Val His Asn Ala
                420                 425                 430

Lys Thr Lys Pro Arg Glu Glu Gln Tyr Asn Ser Thr Tyr Arg Val Val
            435                 440                 445

Ser Val Leu Thr Val Leu His Gln Asp Trp Leu Asn Gly Lys Glu Tyr
450                 455                 460

Lys Cys Lys Val Ser Asn Lys Ala Leu Pro Ala Pro Ile Glu Lys Thr
465                 470                 475                 480

Ile Ser Lys Ala Lys Gly Gln Pro Arg Glu Pro Gln Val Tyr Thr Leu
                485                 490                 495

Pro Pro Ser Arg Asp Glu Leu Thr Lys Asn Gln Val Ser Leu Thr Cys
            500                 505                 510

Leu Val Lys Gly Phe Tyr Pro Ser Asp Ile Ala Val Glu Trp Glu Ser
            515                 520                 525

Asn Gly Gln Pro Glu Asn Asn Tyr Lys Thr Thr Pro Pro Val Leu Asp
            530                 535                 540

Ser Asp Gly Ser Phe Phe Leu Tyr Ser Lys Leu Thr Val Asp Lys Ser
545                 550                 555                 560
```

-continued

Arg Trp Gln Gln Gly Asn Val Phe Ser Cys Ser Val Met His Glu Ala
              565                 570                 575

Leu His Asn His Tyr Thr Gln Lys Ser Leu Ser Leu Ser Pro Gly Lys
              580                 585                 590

<210> SEQ ID NO 9
<211> LENGTH: 951
<212> TYPE: PRT
<213> ORGANISM: Homo sapiens

<400> SEQUENCE: 9

Met Val Thr Leu Gln Thr Trp Val Val Gln Ala Leu Phe Ile Phe Leu
 1               5                  10                  15

Thr Thr Glu Ser Thr Gly Glu Leu Leu Asp Pro Cys Gly Tyr Ile Ser
             20                  25                  30

Pro Glu Ser Pro Val Val Gln Leu His Ser Asn Phe Thr Ala Val Cys
         35                  40                  45

Val Leu Lys Glu Lys Cys Met Asp Tyr Phe His Val Asn Ala Asn Tyr
     50                  55                  60

Ile Val Trp Lys Thr Asn His Phe Thr Ile Pro Lys Glu Gln Tyr Thr
 65                  70                  75                  80

Ile Ile Asn Arg Thr Ala Ser Ser Val Thr Phe Thr Asp Ile Ala Ser
                 85                  90                  95

Leu Asn Ile Gln Leu Thr Cys Asn Ile Leu Thr Phe Gly Gln Leu Glu
            100                 105                 110

Gln Asn Val Tyr Gly Ile Thr Ile Ile Ser Gly Leu Pro Pro Glu Lys
        115                 120                 125

Pro Lys Asn Leu Ser Cys Ile Val Asn Glu Gly Lys Lys Met Arg Cys
    130                 135                 140

Glu Trp Asp Gly Gly Arg Glu Thr His Leu Glu Thr Asn Phe Thr Leu
145                 150                 155                 160

Lys Ser Glu Trp Ala Thr His Lys Phe Ala Asp Cys Lys Ala Lys Arg
                165                 170                 175

Asp Thr Pro Thr Ser Cys Thr Val Asp Tyr Ser Thr Val Tyr Phe Val
            180                 185                 190

Asn Ile Glu Val Trp Val Glu Ala Glu Asn Ala Leu Gly Lys Val Thr
        195                 200                 205

Ser Asp His Ile Asn Phe Asp Pro Val Tyr Lys Val Lys Pro Asn Pro
    210                 215                 220

Pro His Asn Leu Ser Val Ile Asn Ser Glu Glu Leu Ser Ser Ile Leu
225                 230                 235                 240

Lys Leu Thr Trp Thr Asn Pro Ser Ile Lys Ser Val Ile Ile Leu Lys
                245                 250                 255

Tyr Asn Ile Gln Tyr Arg Thr Lys Asp Ala Ser Thr Trp Ser Gln Ile
            260                 265                 270

Pro Pro Glu Asp Thr Ala Ser Thr Arg Ser Ser Phe Thr Val Gln Asp
        275                 280                 285

Leu Lys Pro Phe Thr Glu Tyr Val Phe Arg Ile Arg Cys Met Lys Glu
    290                 295                 300

Asp Gly Lys Gly Tyr Trp Ser Asp Trp Ser Glu Glu Ala Ser Gly Ile
305                 310                 315                 320

Thr Tyr Glu Asp Arg Pro Ser Lys Ala Pro Ser Phe Trp Tyr Lys Ile
                325                 330                 335

Asp Pro Ser His Thr Gln Gly Tyr Arg Thr Val Gln Leu Val Trp Lys

-continued

```
                340             345             350
Thr Leu Pro Pro Phe Glu Ala Asn Gly Lys Ile Leu Asp Tyr Glu Val
            355                 360             365
Thr Leu Thr Arg Trp Lys Ser His Leu Gln Asn Tyr Thr Val Asn Ala
        370                 375             380
Thr Lys Leu Thr Val Asn Leu Thr Asn Asp Arg Tyr Leu Ala Thr Leu
385                 390             395                 400
Thr Val Arg Asn Leu Val Gly Lys Ser Asp Ala Ala Val Leu Thr Ile
                405             410                 415
Pro Ala Cys Asp Phe Gln Ala Thr His Pro Val Met Asp Leu Lys Ala
            420                 425             430
Phe Pro Lys Asp Asn Met Leu Trp Val Glu Trp Thr Thr Pro Arg Glu
        435                 440             445
Ser Val Lys Lys Tyr Ile Leu Glu Trp Cys Val Leu Ser Asp Lys Ala
        450                 455             460
Pro Cys Ile Thr Asp Trp Gln Gln Glu Asp Gly Thr Val His Arg Thr
465                 470             475                 480
Tyr Leu Arg Gly Asn Leu Ala Glu Ser Lys Cys Tyr Leu Ile Thr Val
                485             490                 495
Thr Pro Val Tyr Ala Asp Gly Pro Gly Ser Pro Glu Ser Ile Lys Ala
            500                 505             510
Tyr Leu Lys Gln Ala Pro Pro Ser Lys Gly Pro Thr Val Arg Thr Lys
        515                 520             525
Lys Val Gly Lys Asn Glu Ala Val Leu Glu Trp Asp Gln Leu Pro Val
        530                 535             540
Asp Val Gln Asn Gly Phe Ile Arg Asn Tyr Thr Ile Phe Tyr Arg Thr
545                 550             555                 560
Ile Ile Gly Asn Glu Thr Ala Val Asn Val Asp Ser Ser His Thr Glu
                565             570                 575
Tyr Thr Leu Ser Ser Leu Thr Ser Asp Thr Leu Tyr Met Val Arg Met
            580                 585             590
Ala Ala Tyr Thr Asp Glu Gly Gly Lys Asp Gly Pro Glu Phe Thr Phe
        595                 600             605
Thr Thr Pro Lys Phe Ala Gln Gly Glu Ile Glu Ser Gly Ala Ser Thr
610                 615             620
Lys Gly Pro Ser Val Phe Pro Leu Ala Pro Ser Ser Lys Ser Thr Ser
625                 630             635                 640
Gly Gly Thr Ala Ala Leu Gly Cys Leu Val Lys Asp Tyr Phe Pro Glu
            645                 650             655
Pro Val Thr Val Ser Trp Asn Ser Gly Ala Leu Thr Ser Gly Val His
                660             665             670
Thr Phe Pro Ala Val Leu Gln Ser Ser Gly Leu Tyr Ser Leu Ser Ser
            675                 680             685
Val Val Thr Val Pro Ser Ser Ser Leu Gly Thr Gln Thr Tyr Ile Cys
        690                 695             700
Asn Val Asn His Lys Pro Ser Asn Thr Lys Val Asp Lys Lys Val Glu
705                 710             715                 720
Pro Lys Ser Cys Asp Lys Thr His Thr Cys Pro Pro Cys Pro Ala Pro
                725             730                 735
Glu Leu Leu Gly Gly Pro Ser Val Phe Leu Phe Pro Pro Lys Pro Lys
            740                 745             750
Asp Thr Leu Met Ile Ser Arg Thr Pro Glu Val Thr Cys Val Val Val
        755                 760             765
```

```
Asp Val Ser His Glu Asp Pro Glu Val Lys Phe Asn Trp Tyr Val Asp
    770                 775                 780
Gly Val Glu Val His Asn Ala Lys Thr Lys Pro Arg Glu Glu Gln Tyr
785                 790                 795                 800
Asn Ser Thr Tyr Arg Val Val Ser Val Leu Thr Val Leu His Gln Asp
                805                 810                 815
Trp Leu Asn Gly Lys Glu Tyr Lys Cys Lys Val Ser Asn Lys Ala Leu
            820                 825                 830
Pro Ala Pro Ile Glu Lys Thr Ile Ser Lys Ala Lys Gly Gln Pro Arg
        835                 840                 845
Glu Pro Gln Val Tyr Thr Leu Pro Pro Ser Arg Asp Glu Leu Thr Lys
    850                 855                 860
Asn Gln Val Ser Leu Thr Cys Leu Val Lys Gly Phe Tyr Pro Ser Asp
865                 870                 875                 880
Ile Ala Val Glu Trp Glu Ser Asn Gly Gln Pro Glu Asn Asn Tyr Lys
                885                 890                 895
Thr Thr Pro Pro Val Leu Asp Ser Asp Gly Ser Phe Phe Leu Tyr Ser
            900                 905                 910
Lys Leu Thr Val Asp Lys Ser Arg Trp Gln Gln Gly Asn Val Phe Ser
        915                 920                 925
Cys Ser Val Met His Glu Ala Leu His Asn His Tyr Thr Gln Lys Ser
930                 935                 940
Leu Ser Leu Ser Pro Gly Lys
945                 950

<210> SEQ ID NO 10
<211> LENGTH: 332
<212> TYPE: PRT
<213> ORGANISM: Homo sapiens

<400> SEQUENCE: 10

Met Val Thr Leu Gln Thr Trp Val Val Gln Ala Leu Phe Ile Phe Leu
1               5                   10                  15
Thr Thr Glu Ser Thr Gly Glu Leu Leu Asp Pro Cys Gly Tyr Ile Ser
            20                  25                  30
Pro Glu Ser Pro Val Val Gln Leu His Ser Asn Phe Thr Ala Val Cys
        35                  40                  45
Val Leu Lys Glu Lys Cys Met Asp Tyr Phe His Val Asn Ala Asn Tyr
    50                  55                  60
Ile Val Trp Lys Thr Asn His Phe Thr Ile Pro Lys Glu Gln Tyr Thr
65                  70                  75                  80
Ile Ile Asn Arg Thr Ala Ser Ser Val Thr Phe Thr Asp Ile Ala Ser
                85                  90                  95
Leu Asn Ile Gln Leu Thr Cys Asn Ile Leu Thr Phe Gly Gln Leu Glu
            100                 105                 110
Gln Asn Val Tyr Gly Ile Thr Ile Ile Ser Gly Leu Pro Pro Glu Lys
        115                 120                 125
Pro Lys Asn Leu Ser Cys Ile Val Asn Glu Gly Lys Lys Met Arg Cys
    130                 135                 140
Glu Trp Asp Gly Gly Arg Glu Thr His Leu Glu Thr Asn Phe Thr Leu
145                 150                 155                 160
Lys Ser Glu Trp Ala Thr His Lys Phe Ala Asp Cys Lys Ala Lys Arg
                165                 170                 175
Asp Thr Pro Thr Ser Cys Thr Val Asp Tyr Ser Thr Val Tyr Phe Val
```

```
                    180                 185                 190
Asn Ile Glu Val Trp Val Glu Ala Glu Asn Ala Leu Gly Lys Val Thr
            195                 200                 205

Ser Asp His Ile Asn Phe Asp Pro Val Tyr Lys Val Lys Pro Asn Pro
        210                 215                 220

Pro His Asn Leu Ser Val Ile Asn Ser Glu Glu Leu Ser Ser Ile Leu
225                 230                 235                 240

Lys Leu Thr Trp Thr Asn Pro Ser Ile Lys Ser Val Ile Ile Leu Lys
                245                 250                 255

Tyr Asn Ile Gln Tyr Arg Thr Lys Asp Ala Ser Thr Trp Ser Gln Ile
            260                 265                 270

Pro Pro Glu Asp Thr Ala Ser Thr Arg Ser Ser Phe Thr Val Gln Asp
        275                 280                 285

Leu Lys Pro Phe Thr Glu Tyr Val Phe Arg Ile Arg Cys Met Lys Glu
290                 295                 300

Asp Gly Lys Gly Tyr Trp Ser Asp Trp Ser Glu Ala Ser Gly Ile
305                 310                 315                 320

Thr Tyr Glu Asp Arg Pro Ser Lys Ala Pro Ser Gly
                325                 330

<210> SEQ ID NO 11
<211> LENGTH: 120
<212> TYPE: PRT
<213> ORGANISM: Homo sapiens

<400> SEQUENCE: 11

Ser Gly Gly Gln Gly Thr Leu Val Thr Val Ser Ser Ala Ser Thr Lys
1               5                   10                  15

Gly Pro Ser Val Phe Pro Leu Ala Pro Ser Ser Lys Ser Thr Ser Gly
            20                  25                  30

Gly Thr Ala Ala Leu Gly Cys Leu Val Lys Asp Tyr Phe Pro Glu Pro
        35                  40                  45

Val Thr Val Ser Trp Asn Ser Gly Ala Leu Thr Ser Gly Val His Thr
    50                  55                  60

Phe Pro Ala Val Leu Gln Ser Ser Gly Leu Tyr Ser Leu Ser Ser Val
65                  70                  75                  80

Val Thr Val Pro Ser Ser Ser Leu Gly Thr Gln Thr Tyr Ile Cys Asn
                85                  90                  95

Val Asn His Lys Pro Ser Asn Thr Lys Val Asp Lys Lys Val Glu Pro
            100                 105                 110

Lys Ser Cys Asp Lys Thr His Thr
        115                 120

<210> SEQ ID NO 12
<211> LENGTH: 329
<212> TYPE: PRT
<213> ORGANISM: Homo sapiens

<400> SEQUENCE: 12

Ser Gly Ala Ser Thr Lys Gly Pro Ser Val Phe Pro Leu Ala Pro Cys
1               5                   10                  15

Ser Arg Ser Thr Ser Glu Ser Thr Ala Ala Leu Gly Cys Leu Val Lys
            20                  25                  30

Asp Tyr Phe Pro Glu Pro Val Thr Val Ser Trp Asn Ser Gly Ala Leu
        35                  40                  45

Thr Ser Gly Val His Thr Phe Pro Ala Val Leu Gln Ser Ser Gly Leu
```

```
                    50                  55                  60
Tyr Ser Leu Ser Ser Val Val Thr Val Pro Ser Ser Leu Gly Thr
 65                  70                  75                  80

Lys Thr Tyr Thr Cys Asn Val Asp His Lys Pro Ser Asn Thr Lys Val
                 85                  90                  95

Asp Lys Arg Val Glu Ser Lys Tyr Gly Pro Pro Cys Pro Ser Cys Pro
            100                 105                 110

Ala Pro Glu Phe Leu Gly Gly Pro Ser Val Phe Leu Phe Pro Pro Lys
        115                 120                 125

Pro Lys Asp Thr Leu Met Ile Ser Arg Thr Pro Glu Val Thr Cys Val
    130                 135                 140

Val Val Asp Val Ser Gln Glu Asp Pro Glu Val Gln Phe Asn Trp Tyr
145                 150                 155                 160

Val Asp Gly Val Glu Val His Asn Ala Lys Thr Lys Pro Arg Glu Glu
                165                 170                 175

Gln Phe Asn Ser Thr Tyr Arg Val Val Ser Val Leu Thr Val Leu His
            180                 185                 190

Gln Asp Trp Leu Asn Gly Lys Glu Tyr Lys Cys Lys Val Ser Asn Lys
        195                 200                 205

Gly Leu Pro Ser Ser Ile Glu Lys Thr Ile Ser Lys Ala Lys Gly Gln
    210                 215                 220

Pro Arg Glu Pro Gln Val Tyr Thr Leu Pro Pro Ser Gln Glu Glu Met
225                 230                 235                 240

Thr Lys Asn Gln Val Ser Leu Thr Cys Leu Val Lys Gly Phe Tyr Pro
                245                 250                 255

Ser Asp Ile Ala Val Glu Trp Glu Ser Asn Gly Gln Pro Glu Asn Asn
            260                 265                 270

Tyr Lys Thr Thr Pro Pro Val Leu Asp Ser Asp Gly Ser Phe Phe Leu
        275                 280                 285

Tyr Ser Arg Leu Thr Val Asp Lys Ser Arg Trp Gln Glu Gly Asn Val
    290                 295                 300

Phe Ser Cys Ser Val Met His Glu Ala Leu His Asn His Tyr Thr Gln
305                 310                 315                 320

Lys Ser Leu Ser Leu Ser Leu Gly Lys
                325

<210> SEQ ID NO 13
<211> LENGTH: 108
<212> TYPE: PRT
<213> ORGANISM: Homo sapiens

<400> SEQUENCE: 13

Ser Gly Thr Val Ala Ala Pro Ser Val Phe Ile Phe Pro Pro Ser Asp
  1               5                  10                  15

Glu Gln Leu Lys Ser Gly Thr Ala Ser Val Val Cys Leu Leu Asn Asn
             20                  25                  30

Phe Tyr Pro Arg Glu Ala Lys Val Gln Trp Lys Val Asp Asn Ala Leu
         35                  40                  45

Gln Ser Gly Asn Ser Gln Glu Ser Val Thr Glu Gln Asp Ser Lys Asp
    50                  55                  60

Ser Thr Tyr Ser Leu Ser Ser Thr Leu Thr Leu Ser Lys Ala Asp Tyr
 65                  70                  75                  80

Glu Lys His Lys Val Tyr Ala Cys Glu Val Thr His Gln Gly Leu Ser
             85                  90                  95
```

```
Ser Pro Val Thr Lys Ser Phe Asn Arg Gly Glu Cys
        100                 105
```

<210> SEQ ID NO 14
<211> LENGTH: 106
<212> TYPE: PRT
<213> ORGANISM: Homo sapiens

<400> SEQUENCE: 14

```
Ser Gly Pro Lys Ala Ala Pro Ser Val Thr Leu Phe Pro Pro Ser Ser
1               5                   10                  15

Glu Glu Leu Gln Ala Asn Lys Ala Thr Leu Val Cys Leu Ile Ser Asp
            20                  25                  30

Phe Tyr Pro Gly Ala Val Thr Val Ala Trp Lys Ala Asp Ser Ser Pro
        35                  40                  45

Val Lys Ala Gly Val Glu Thr Thr Pro Ser Lys Gln Ser Asn Asn
50                  55                  60

Lys Tyr Ala Ala Ser Ser Tyr Leu Ser Leu Thr Pro Glu Gln Trp Lys
65                  70                  75                  80

Ser His Arg Ser Tyr Ser Cys Gln Val Thr His Glu Gly Ser Thr Val
                85                  90                  95

Glu Lys Thr Val Ala Pro Thr Glu Cys Ser
            100                 105
```

<210> SEQ ID NO 15
<211> LENGTH: 360
<212> TYPE: PRT
<213> ORGANISM: Homo sapiens

<400> SEQUENCE: 15

```
Met Val Ala Val Gly Cys Ala Leu Leu Ala Ala Leu Leu Ala Ala Pro
1               5                   10                  15

Gly Ala Ala Leu Ala Pro Arg Arg Cys Pro Ala Gln Glu Val Ala Arg
            20                  25                  30

Gly Val Leu Thr Ser Leu Pro Gly Asp Ser Val Thr Leu Thr Cys Pro
        35                  40                  45

Gly Val Glu Pro Glu Asp Asn Ala Thr Val His Trp Val Leu Arg Lys
50                  55                  60

Pro Ala Ala Gly Ser His Pro Ser Arg Trp Ala Gly Met Gly Arg Arg
65                  70                  75                  80

Leu Leu Leu Arg Ser Val Gln Leu His Asp Ser Gly Asn Tyr Ser Cys
                85                  90                  95

Tyr Arg Ala Gly Arg Pro Ala Gly Thr Val His Leu Leu Val Asp Val
                100                 105                 110

Pro Pro Glu Glu Pro Gln Leu Ser Cys Phe Arg Lys Ser Pro Leu Ser
            115                 120                 125

Asn Val Val Cys Glu Trp Gly Pro Arg Ser Thr Pro Ser Leu Thr Thr
        130                 135                 140

Lys Ala Val Leu Leu Val Arg Lys Phe Gln Asn Ser Pro Ala Glu Asp
145                 150                 155                 160

Phe Gln Glu Pro Cys Gln Tyr Ser Gln Glu Ser Gln Lys Phe Ser Cys
                165                 170                 175

Gln Leu Ala Val Pro Glu Gly Asp Ser Ser Phe Tyr Ile Val Ser Met
                180                 185                 190

Cys Val Ala Ser Ser Val Gly Ser Lys Phe Ser Lys Thr Gln Thr Phe
            195                 200                 205
```

```
Gln Gly Cys Gly Ile Leu Gln Pro Asp Pro Ala Asn Ile Thr Val
    210                 215                 220

Thr Ala Val Ala Arg Asn Pro Arg Trp Leu Ser Val Thr Trp Gln Asp
225                 230                 235                 240

Pro His Ser Trp Asn Ser Ser Phe Tyr Arg Leu Arg Phe Glu Leu Arg
                245                 250                 255

Tyr Arg Ala Glu Arg Ser Lys Thr Phe Thr Thr Trp Met Val Lys Asp
            260                 265                 270

Leu Gln His His Cys Val Ile His Asp Ala Trp Ser Gly Leu Arg His
        275                 280                 285

Val Val Gln Leu Arg Ala Gln Glu Phe Gly Gln Gly Glu Trp Ser
290                 295                 300

Glu Trp Ser Pro Glu Ala Met Gly Thr Pro Trp Thr Glu Ser Arg Ser
305                 310                 315                 320

Pro Pro Ala Glu Asn Glu Val Ser Thr Pro Met Gln Ala Leu Thr Thr
                325                 330                 335

Asn Lys Asp Asp Asp Asn Ile Leu Phe Arg Asp Ser Ala Asn Ala Thr
            340                 345                 350

Ser Leu Pro Val Gln Asp Ala Gly
        355                 360

<210> SEQ ID NO 16
<211> LENGTH: 315
<212> TYPE: PRT
<213> ORGANISM: Homo sapiens

<400> SEQUENCE: 16

Met Val Ala Val Gly Cys Ala Leu Leu Ala Ala Leu Leu Ala Ala Pro
1               5                   10                  15

Gly Ala Ala Leu Ala Pro Arg Arg Cys Pro Ala Gln Glu Val Ala Arg
            20                  25                  30

Gly Val Leu Thr Ser Leu Pro Gly Asp Ser Val Thr Leu Thr Cys Pro
        35                  40                  45

Gly Val Glu Pro Glu Asp Asn Ala Thr Val His Trp Val Leu Arg Lys
    50                  55                  60

Pro Ala Ala Gly Ser His Pro Ser Arg Trp Ala Gly Met Gly Arg Arg
65                  70                  75                  80

Leu Leu Leu Arg Ser Val Gln Leu His Asp Ser Gly Asn Tyr Ser Cys
                85                  90                  95

Tyr Arg Ala Gly Arg Pro Ala Gly Thr Val His Leu Leu Val Asp Val
            100                 105                 110

Pro Pro Glu Glu Pro Gln Leu Ser Cys Phe Arg Lys Ser Pro Leu Ser
        115                 120                 125

Asn Val Val Cys Glu Trp Gly Pro Arg Ser Thr Pro Ser Leu Thr Thr
    130                 135                 140

Lys Ala Val Leu Leu Val Arg Lys Phe Gln Asn Ser Pro Ala Glu Asp
145                 150                 155                 160

Phe Gln Glu Pro Cys Gln Tyr Ser Gln Glu Ser Gln Lys Phe Ser Cys
                165                 170                 175

Gln Leu Ala Val Pro Glu Gly Asp Ser Ser Phe Tyr Ile Val Ser Met
            180                 185                 190

Cys Val Ala Ser Ser Val Gly Ser Lys Phe Ser Lys Thr Gln Thr Phe
        195                 200                 205

Gln Gly Cys Gly Ile Leu Gln Pro Asp Pro Pro Ala Asn Ile Thr Val
    210                 215                 220
```

```
Thr Ala Val Ala Arg Asn Pro Arg Trp Leu Ser Val Thr Trp Gln Asp
225                 230                 235                 240

Pro His Ser Trp Asn Ser Ser Phe Tyr Arg Leu Arg Phe Glu Leu Arg
            245                 250                 255

Tyr Arg Ala Glu Arg Ser Lys Thr Phe Thr Thr Trp Met Val Lys Asp
        260                 265                 270

Leu Gln His His Cys Val Ile His Asp Ala Trp Ser Gly Leu Arg His
        275                 280                 285

Val Val Gln Leu Arg Ala Gln Glu Glu Phe Gly Gln Gly Glu Trp Ser
290                 295                 300

Glu Trp Ser Pro Glu Ala Met Gly Thr Thr Gly
305                 310                 315

<210> SEQ ID NO 17
<211> LENGTH: 2085
<212> TYPE: DNA
<213> ORGANISM: Homo sapiens
<220> FEATURE:
<221> NAME/KEY: CDS
<222> LOCATION: (1)...(2082)

<400> SEQUENCE: 17 atg gtg aag cca tca tta cca ttc aca tcc ctc tta ttc ctg cag ctg      48
Met Val Lys Pro Ser Leu Pro Phe Thr Ser Leu Leu Phe Leu Gln Leu
1               5                   10                  15 ccc ctg ctg gga gtg ggg ctg aac acg aca att ctg acg ccc aat ggg      96
Pro Leu Leu Gly Val Gly Leu Asn Thr Thr Ile Leu Thr Pro Asn Gly
            20                  25                  30 aat gaa gac acc aca gct gat ttc ttc ctg acc act atg ccc act gac     144
Asn Glu Asp Thr Thr Ala Asp Phe Phe Leu Thr Thr Met Pro Thr Asp
        35                  40                  45 tcc ctc agt gtt tcc act ctg ccc ctc cca gag gtt cag tgt ttt gtg     192
Ser Leu Ser Val Ser Thr Leu Pro Leu Pro Glu Val Gln Cys Phe Val
    50                  55                  60 ttc aat gtc gag tac atg aat tgc act tgg aac agc agc tct gag ccc     240
Phe Asn Val Glu Tyr Met Asn Cys Thr Trp Asn Ser Ser Ser Glu Pro
65                  70                  75                  80 cag cct acc aac ctc act ctg cat tat tgg tac aag aac tcg gat aat     288
Gln Pro Thr Asn Leu Thr Leu His Tyr Trp Tyr Lys Asn Ser Asp Asn
                85                  90                  95 gat aaa gtc cag aag tgc agc cac tat cta ttc tct gaa gaa atc act     336
Asp Lys Val Gln Lys Cys Ser His Tyr Leu Phe Ser Glu Glu Ile Thr
            100                 105                 110 tct ggc tgt cag ttg caa aaa aag gag atc cac ctc tac caa aca ttt     384
Ser Gly Cys Gln Leu Gln Lys Lys Glu Ile His Leu Tyr Gln Thr Phe
        115                 120                 125 gtt gtt cag ctc cag gac cca cgg gaa ccc agg aga cag gcc aca cag     432
Val Val Gln Leu Gln Asp Pro Arg Glu Pro Arg Arg Gln Ala Thr Gln
    130                 135                 140 atg cta aaa ctg cag aat ctg gtg atc ccc tgg gct cca gag aac cta     480
Met Leu Lys Leu Gln Asn Leu Val Ile Pro Trp Ala Pro Glu Asn Leu
145                 150                 155                 160 aca ctt cac aaa ctg agt gaa tcc cag cta gaa ctg aac tgg aac aac     528
Thr Leu His Lys Leu Ser Glu Ser Gln Leu Glu Leu Asn Trp Asn Asn
                165                 170                 175 aga ttc ttg aac cac tgt ttg gag cac ttg gtg cag tac cgg act gac     576
Arg Phe Leu Asn His Cys Leu Glu His Leu Val Gln Tyr Arg Thr Asp
            180                 185                 190 tgg gac cac agc tgg act gaa caa tca gtg gat tat aga cat aag ttc     624
```

```
                                                                                -continued Trp Asp His Ser Trp Thr Glu Gln Ser Val Asp Tyr Arg His Lys Phe
        195                 200                 205 tcc ttg cct agt gtg gat ggg cag aaa cgc tac acg ttt cgt gtt cgg       672
Ser Leu Pro Ser Val Asp Gly Gln Lys Arg Tyr Thr Phe Arg Val Arg
    210                 215                 220 agc cgc ttt aac cca ctc tgt gga agt gct cag cat tgg agt gaa tgg       720
Ser Arg Phe Asn Pro Leu Cys Gly Ser Ala Gln His Trp Ser Glu Trp
225                 230                 235                 240 agc cac cca atc cac tgg ggg agc aat act tca aaa gag aac gcg tcg       768
Ser His Pro Ile His Trp Gly Ser Asn Thr Ser Lys Glu Asn Ala Ser
                245                 250                 255 tct ggg aac atg aag gtc ctg cag gag ccc acc tgc gtc tcc gac tac       816
Ser Gly Asn Met Lys Val Leu Gln Glu Pro Thr Cys Val Ser Asp Tyr
            260                 265                 270 atg agc atc tct act tgc gag tgg aag atg aat ggt ccc acc aat tgc       864
Met Ser Ile Ser Thr Cys Glu Trp Lys Met Asn Gly Pro Thr Asn Cys
        275                 280                 285 agc acc gag ctc cgc ctg ttg tac cag ctg gtt ttt ctg ctc tcc gaa       912
Ser Thr Glu Leu Arg Leu Leu Tyr Gln Leu Val Phe Leu Leu Ser Glu
    290                 295                 300 gcc cac acg tgt atc cct gag aac aac gga ggc gcg ggg tgc gtg tgc       960
Ala His Thr Cys Ile Pro Glu Asn Asn Gly Gly Ala Gly Cys Val Cys
305                 310                 315                 320 cac ctg ctc atg gat gac gtg gtc agt gcg gat aac tat aca ctg gac      1008
His Leu Leu Met Asp Asp Val Val Ser Ala Asp Asn Tyr Thr Leu Asp
                325                 330                 335 ctg tgg gct ggg cag cag ctg ctg tgg aag ggc tcc ttc aag ccc agc      1056
Leu Trp Ala Gly Gln Gln Leu Leu Trp Lys Gly Ser Phe Lys Pro Ser
            340                 345                 350 gag cat gtg aaa ccc agg gcc cca gga aac ctg aca gtt cac acc aat      1104
Glu His Val Lys Pro Arg Ala Pro Gly Asn Leu Thr Val His Thr Asn
        355                 360                 365 gtc tcc gac act ctg ctg ctg acc tgg agc aac ccg tat ccc cct gac      1152
Val Ser Asp Thr Leu Leu Leu Thr Trp Ser Asn Pro Tyr Pro Pro Asp
    370                 375                 380 aat tac ctg tat aat cat ctc acc tat gca gtc aac att tgg agt gaa      1200
Asn Tyr Leu Tyr Asn His Leu Thr Tyr Ala Val Asn Ile Trp Ser Glu
385                 390                 395                 400 aac gac ccg gca gat ttc aga atc tat aac gtg acc tac cta gaa ccc      1248
Asn Asp Pro Ala Asp Phe Arg Ile Tyr Asn Val Thr Tyr Leu Glu Pro
                405                 410                 415 tcc ctc cgc atc gca gcc agc acc ctg aag tct ggg att tcc tac agg      1296
Ser Leu Arg Ile Ala Ala Ser Thr Leu Lys Ser Gly Ile Ser Tyr Arg
            420                 425                 430 gca cgg gtg agg gcc tgg gct cag tgc tat aac acc acc tgg agt gag      1344
Ala Arg Val Arg Ala Trp Ala Gln Cys Tyr Asn Thr Thr Trp Ser Glu
        435                 440                 445 tgg agc ccc agc acc aag tgg cac aac tcc tac agg gag ccc ttc gag      1392
Trp Ser Pro Ser Thr Lys Trp His Asn Ser Tyr Arg Glu Pro Phe Glu
    450                 455                 460 cag tcc gga gac aaa act cac aca tgc cca ccg tgc cca gca cct gaa      1440
Gln Ser Gly Asp Lys Thr His Thr Cys Pro Pro Cys Pro Ala Pro Glu
465                 470                 475                 480 ctc ctg ggg gga ccg tca gtc ttc ctc ttc ccc cca aaa ccc aag gac      1488
Leu Leu Gly Gly Pro Ser Val Phe Leu Phe Pro Pro Lys Pro Lys Asp
                485                 490                 495 acc ctc atg atc tcc cgg acc cct gag gtc aca tgc gtg gtg gtg gac      1536
Thr Leu Met Ile Ser Arg Thr Pro Glu Val Thr Cys Val Val Val Asp
            500                 505                 510
```

-continued

```
gtg agc cac gaa gac cct gag gtc aag ttc aac tgg tac gtg gac ggc   1584
Val Ser His Glu Asp Pro Glu Val Lys Phe Asn Trp Tyr Val Asp Gly
        515                 520                 525 gtg gag gtg cat aat gcc aag aca aag ccg cgg gag gag cag tac aac   1632
Val Glu Val His Asn Ala Lys Thr Lys Pro Arg Glu Glu Gln Tyr Asn
    530                 535                 540 agc acg tac cgt gtg gtc agc gtc ctc acc gtc ctg cac cag gac tgg   1680
Ser Thr Tyr Arg Val Val Ser Val Leu Thr Val Leu His Gln Asp Trp
545                 550                 555                 560 ctg aat ggc aag gag tac aag tgc aag gtc tcc aac aaa gcc ctc cca   1728
Leu Asn Gly Lys Glu Tyr Lys Cys Lys Val Ser Asn Lys Ala Leu Pro
                565                 570                 575 gcc ccc atc gag aaa acc atc tcc aaa gcc aaa ggg cag ccc cga gaa   1776
Ala Pro Ile Glu Lys Thr Ile Ser Lys Ala Lys Gly Gln Pro Arg Glu
            580                 585                 590 cca cag gtg tac acc ctg ccc cca tcc cgg gag gag atg acc aag aac   1824
Pro Gln Val Tyr Thr Leu Pro Pro Ser Arg Glu Glu Met Thr Lys Asn
        595                 600                 605 cag gtc agc ctg acc tgc ctg gtc aaa ggc ttc tat ccc agc gac atc   1872
Gln Val Ser Leu Thr Cys Leu Val Lys Gly Phe Tyr Pro Ser Asp Ile
    610                 615                 620 gcc gtg gag tgg gag agc aat ggg cag ccg gag aac aac tac aag acc   1920
Ala Val Glu Trp Glu Ser Asn Gly Gln Pro Glu Asn Asn Tyr Lys Thr
625                 630                 635                 640 acg cct ccc gtg ctg gac tcc gac ggc tcc ttc ttc ctc tat agc aag   1968
Thr Pro Pro Val Leu Asp Ser Asp Gly Ser Phe Phe Leu Tyr Ser Lys
                645                 650                 655 ctc acc gtg gac aag agc agg tgg cag cag ggg aac gtc ttc tca tgc   2016
Leu Thr Val Asp Lys Ser Arg Trp Gln Gln Gly Asn Val Phe Ser Cys
            660                 665                 670 tcc gtg atg cat gag gct ctg cac aac cac tac acg cag aag agc ctc   2064
Ser Val Met His Glu Ala Leu His Asn His Tyr Thr Gln Lys Ser Leu
        675                 680                 685 tcc ctg tct ccg ggt aaa tga                                       2085
Ser Leu Ser Pro Gly Lys
    690
```

<210> SEQ ID NO 18
<211> LENGTH: 694
<212> TYPE: PRT
<213> ORGANISM: Homo sapiens

<400> SEQUENCE: 18

```
Met Val Lys Pro Ser Leu Pro Phe Thr Ser Leu Leu Phe Leu Gln Leu
1               5                   10                  15

Pro Leu Leu Gly Val Gly Leu Asn Thr Thr Ile Leu Thr Pro Asn Gly
            20                  25                  30

Asn Glu Asp Thr Thr Ala Asp Phe Phe Leu Thr Thr Met Pro Thr Asp
        35                  40                  45

Ser Leu Ser Val Ser Thr Leu Pro Leu Pro Glu Val Gln Cys Phe Val
    50                  55                  60

Phe Asn Val Glu Tyr Met Asn Cys Thr Trp Asn Ser Ser Ser Glu Pro
65                  70                  75                  80

Gln Pro Thr Asn Leu Thr Leu His Tyr Trp Tyr Lys Asn Ser Asp Asn
                85                  90                  95

Asp Lys Val Gln Lys Cys Ser His Tyr Leu Phe Ser Glu Glu Ile Thr
            100                 105                 110

Ser Gly Cys Gln Leu Gln Lys Lys Glu Ile His Leu Tyr Gln Thr Phe
        115                 120                 125
```

-continued

```
Val Val Gln Leu Gln Asp Pro Arg Glu Pro Arg Gln Ala Thr Gln
    130                 135                 140
Met Leu Lys Leu Gln Asn Leu Val Ile Pro Trp Ala Pro Glu Asn Leu
145                 150                 155                 160
Thr Leu His Lys Leu Ser Glu Ser Gln Leu Glu Leu Asn Trp Asn Asn
                165                 170                 175
Arg Phe Leu Asn His Cys Leu Glu His Leu Val Gln Tyr Arg Thr Asp
                180                 185                 190
Trp Asp His Ser Trp Thr Glu Gln Ser Val Asp Tyr Arg His Lys Phe
                195                 200                 205
Ser Leu Pro Ser Val Asp Gly Gln Lys Arg Tyr Thr Phe Arg Val Arg
    210                 215                 220
Ser Arg Phe Asn Pro Leu Cys Gly Ser Ala Gln His Trp Ser Glu Trp
225                 230                 235                 240
Ser His Pro Ile His Trp Gly Ser Asn Thr Ser Lys Glu Asn Ala Ser
                245                 250                 255
Ser Gly Asn Met Lys Val Leu Gln Glu Pro Thr Cys Val Ser Asp Tyr
                260                 265                 270
Met Ser Ile Ser Thr Cys Glu Trp Lys Met Asn Gly Pro Thr Asn Cys
                275                 280                 285
Ser Thr Glu Leu Arg Leu Leu Tyr Gln Leu Val Phe Leu Leu Ser Glu
    290                 295                 300
Ala His Thr Cys Ile Pro Glu Asn Asn Gly Gly Ala Gly Cys Val Cys
305                 310                 315                 320
His Leu Leu Met Asp Asp Val Val Ser Ala Asp Asn Tyr Thr Leu Asp
                325                 330                 335
Leu Trp Ala Gly Gln Gln Leu Leu Trp Lys Gly Ser Phe Lys Pro Ser
                340                 345                 350
Glu His Val Lys Pro Arg Ala Pro Gly Asn Leu Thr Val His Thr Asn
                355                 360                 365
Val Ser Asp Thr Leu Leu Leu Thr Trp Ser Asn Pro Tyr Pro Pro Asp
    370                 375                 380
Asn Tyr Leu Tyr Asn His Leu Thr Tyr Ala Val Asn Ile Trp Ser Glu
385                 390                 395                 400
Asn Asp Pro Ala Asp Phe Arg Ile Tyr Asn Val Thr Tyr Leu Glu Pro
                405                 410                 415
Ser Leu Arg Ile Ala Ala Ser Thr Leu Lys Ser Gly Ile Ser Tyr Arg
                420                 425                 430
Ala Arg Val Arg Ala Trp Ala Gln Cys Tyr Asn Thr Thr Trp Ser Glu
                435                 440                 445
Trp Ser Pro Ser Thr Lys Trp His Asn Ser Tyr Arg Glu Pro Phe Glu
    450                 455                 460
Gln Ser Gly Asp Lys Thr His Thr Cys Pro Pro Cys Pro Ala Pro Glu
465                 470                 475                 480
Leu Leu Gly Gly Pro Ser Val Phe Leu Phe Pro Pro Lys Pro Lys Asp
                485                 490                 495
Thr Leu Met Ile Ser Arg Thr Pro Glu Val Thr Cys Val Val Val Asp
                500                 505                 510
Val Ser His Glu Asp Pro Glu Val Lys Phe Asn Trp Tyr Val Asp Gly
                515                 520                 525
Val Glu Val His Asn Ala Lys Thr Lys Pro Arg Glu Glu Gln Tyr Asn
    530                 535                 540
```

-continued

```
Ser Thr Tyr Arg Val Val Ser Val Leu Thr Val Leu His Gln Asp Trp
545                 550                 555                 560

Leu Asn Gly Lys Glu Tyr Lys Cys Lys Val Ser Asn Lys Ala Leu Pro
                565                 570                 575

Ala Pro Ile Glu Lys Thr Ile Ser Lys Ala Lys Gly Gln Pro Arg Glu
            580                 585                 590

Pro Gln Val Tyr Thr Leu Pro Pro Ser Arg Glu Glu Met Thr Lys Asn
        595                 600                 605

Gln Val Ser Leu Thr Cys Leu Val Lys Gly Phe Tyr Pro Ser Asp Ile
    610                 615                 620

Ala Val Glu Trp Glu Ser Asn Gly Gln Pro Glu Asn Asn Tyr Lys Thr
625                 630                 635                 640

Thr Pro Pro Val Leu Asp Ser Asp Gly Ser Phe Phe Leu Tyr Ser Lys
                645                 650                 655

Leu Thr Val Asp Lys Ser Arg Trp Gln Gln Gly Asn Val Phe Ser Cys
                660                 665                 670

Ser Val Met His Glu Ala Leu His Asn His Tyr Thr Gln Lys Ser Leu
            675                 680                 685

Ser Leu Ser Pro Gly Lys
        690

<210> SEQ ID NO 19
<211> LENGTH: 2076
<212> TYPE: DNA
<213> ORGANISM: Homo sapiens
<220> FEATURE:
<221> NAME/KEY: CDS
<222> LOCATION: (1)...(2073)

<400> SEQUENCE: 19 atg gtg aag cca tca tta cca ttc aca tcc ctc tta ttc ctg cag ctg      48
Met Val Lys Pro Ser Leu Pro Phe Thr Ser Leu Leu Phe Leu Gln Leu
1               5                   10                  15 ccc ctg ctg gga gtg ggg ctg aac acg aca att ctg acg ccc aat ggg      96
Pro Leu Leu Gly Val Gly Leu Asn Thr Thr Ile Leu Thr Pro Asn Gly
            20                  25                  30 aat gaa gac acc aca gct gat ttc ttc ctg acc act atg ccc act gac     144
Asn Glu Asp Thr Thr Ala Asp Phe Phe Leu Thr Thr Met Pro Thr Asp
        35                  40                  45 tcc ctc agt gtt tcc act ctg ccc ctc cca gag gtt cag tgt ttt gtg     192
Ser Leu Ser Val Ser Thr Leu Pro Leu Pro Glu Val Gln Cys Phe Val
    50                  55                  60 ttc aat gtc gag tac atg aat tgc act tgg aac agc agc tct gag ccc     240
Phe Asn Val Glu Tyr Met Asn Cys Thr Trp Asn Ser Ser Ser Glu Pro
65                  70                  75                  80 cag cct acc aac ctc act ctg cat tat tgg tac aag aac tcg gat aat     288
Gln Pro Thr Asn Leu Thr Leu His Tyr Trp Tyr Lys Asn Ser Asp Asn
                85                  90                  95 gat aaa gtc cag aag tgc agc cac tat cta ttc tct gaa gaa atc act     336
Asp Lys Val Gln Lys Cys Ser His Tyr Leu Phe Ser Glu Glu Ile Thr
            100                 105                 110 tct ggc tgt cag ttg caa aaa aag gag atc cac ctc tac caa aca ttt     384
Ser Gly Cys Gln Leu Gln Lys Lys Glu Ile His Leu Tyr Gln Thr Phe
        115                 120                 125 gtt gtt cag ctc cag gac cca cgg gaa ccc agg aga cag gcc aca cag     432
Val Val Gln Leu Gln Asp Pro Arg Glu Pro Arg Arg Gln Ala Thr Gln
    130                 135                 140 atg cta aaa ctg cag aat ctg gtg atc ccc tgg gct cca gag aac cta     480
Met Leu Lys Leu Gln Asn Leu Val Ile Pro Trp Ala Pro Glu Asn Leu
```

```
                    145                 150                 155                 160
aca ctt cac aaa ctg agt gaa tcc cag cta gaa ctg aac tgg aac aac       528
Thr Leu His Lys Leu Ser Glu Ser Gln Leu Glu Leu Asn Trp Asn Asn
                165                 170                 175 aga ttc ttg aac cac tgt ttg gag cac ttg gtg cag tac cgg act gac       576
Arg Phe Leu Asn His Cys Leu Glu His Leu Val Gln Tyr Arg Thr Asp
            180                 185                 190 tgg gac cac agc tgg act gaa caa tca gtg gat tat aga cat aag ttc       624
Trp Asp His Ser Trp Thr Glu Gln Ser Val Asp Tyr Arg His Lys Phe
        195                 200                 205 tcc ttg cct agt gtg gat ggg cag aaa cgc tac acg ttt cgt gtt cgg       672
Ser Leu Pro Ser Val Asp Gly Gln Lys Arg Tyr Thr Phe Arg Val Arg
    210                 215                 220 agc cgc ttt aac cca ctc tgt gga agt gct cag cat tgg agt gaa tgg       720
Ser Arg Phe Asn Pro Leu Cys Gly Ser Ala Gln His Trp Ser Glu Trp
225                 230                 235                 240 agc cac cca atc cac tgg ggg agc aat act tca aaa gag aac ggg aac       768
Ser His Pro Ile His Trp Gly Ser Asn Thr Ser Lys Glu Asn Gly Asn
                245                 250                 255 atg aag gtc ctg cag gag ccc acc tgc gtc tcc gac tac atg agc atc       816
Met Lys Val Leu Gln Glu Pro Thr Cys Val Ser Asp Tyr Met Ser Ile
            260                 265                 270 tct act tgc gag tgg aag atg aat ggt ccc acc aat tgc agc acc gag       864
Ser Thr Cys Glu Trp Lys Met Asn Gly Pro Thr Asn Cys Ser Thr Glu
        275                 280                 285 ctc cgc ctg ttg tac cag ctg gtt ttt ctg ctc tcc gaa gcc cac acg       912
Leu Arg Leu Leu Tyr Gln Leu Val Phe Leu Leu Ser Glu Ala His Thr
    290                 295                 300 tgt atc cct gag aac aac gga ggc gcg ggg tgc gtg tgc cac ctg ctc       960
Cys Ile Pro Glu Asn Asn Gly Gly Ala Gly Cys Val Cys His Leu Leu
305                 310                 315                 320 atg gat gac gtg gtc agt gcg gat aac tat aca ctg gac ctg tgg gct      1008
Met Asp Asp Val Val Ser Ala Asp Asn Tyr Thr Leu Asp Leu Trp Ala
                325                 330                 335 ggg cag cag ctg ctg tgg aag ggc tcc ttc aag ccc agc gag cat gtg      1056
Gly Gln Gln Leu Leu Trp Lys Gly Ser Phe Lys Pro Ser Glu His Val
            340                 345                 350 aaa ccc agg gcc cca gga aac ctg aca gtt cac acc aat gtc tcc gac      1104
Lys Pro Arg Ala Pro Gly Asn Leu Thr Val His Thr Asn Val Ser Asp
        355                 360                 365 act ctg ctg ctg acc tgg agc aac ccg tat ccc cct gac aat tac ctg      1152
Thr Leu Leu Leu Thr Trp Ser Asn Pro Tyr Pro Pro Asp Asn Tyr Leu
    370                 375                 380 tat aat cat ctc acc tat gca gtc aac att tgg agt gaa aac gac ccg      1200
Tyr Asn His Leu Thr Tyr Ala Val Asn Ile Trp Ser Glu Asn Asp Pro
385                 390                 395                 400 gca gat ttc aga atc tat aac gtg acc tac cta gaa ccc tcc ctc cgc      1248
Ala Asp Phe Arg Ile Tyr Asn Val Thr Tyr Leu Glu Pro Ser Leu Arg
                405                 410                 415 atc gca gcc agc acc ctg aag tct ggg att tcc tac agg gca cgg gtg      1296
Ile Ala Ala Ser Thr Leu Lys Ser Gly Ile Ser Tyr Arg Ala Arg Val
            420                 425                 430 agg gcc tgg gct cag agc tat aac acc acc tgg agt gag tgg agc ccc      1344
Arg Ala Trp Ala Gln Ser Tyr Asn Thr Thr Trp Ser Glu Trp Ser Pro
        435                 440                 445 agc acc aag tgg cac aac tcc tac agg gag ccc ttc gag cag tcc gga      1392
Ser Thr Lys Trp His Asn Ser Tyr Arg Glu Pro Phe Glu Gln Ser Gly
    450                 455                 460 gac aaa act cac aca tgc cca ccg tgc cca gca cct gaa ctc ctg ggg      1440
Asp Lys Thr His Thr Cys Pro Pro Cys Pro Ala Pro Glu Leu Leu Gly
```

```
Asp Lys Thr His Thr Cys Pro Pro Cys Pro Ala Pro Glu Leu Leu Gly
465                 470                 475                 480 gga ccg tca gtc ttc ctc ttc ccc cca aaa ccc aag gac acc ctc atg      1488
Gly Pro Ser Val Phe Leu Phe Pro Pro Lys Pro Lys Asp Thr Leu Met
                    485                 490                 495 atc tcc cgg acc cct gag gtc aca tgc gtg gtg gtg gac gtg agc cac      1536
Ile Ser Arg Thr Pro Glu Val Thr Cys Val Val Val Asp Val Ser His
                500                 505                 510 gaa gac cct gag gtc aag ttc aac tgg tac gtg gac ggc gtg gag gtg      1584
Glu Asp Pro Glu Val Lys Phe Asn Trp Tyr Val Asp Gly Val Glu Val
            515                 520                 525 cat aat gcc aag aca aag ccg cgg gag gag cag tac aac agc acg tac      1632
His Asn Ala Lys Thr Lys Pro Arg Glu Glu Gln Tyr Asn Ser Thr Tyr
        530                 535                 540 cgt gtg gtc agc gtc ctc acc gtc ctg cac cag gac tgg ctg aat ggc      1680
Arg Val Val Ser Val Leu Thr Val Leu His Gln Asp Trp Leu Asn Gly
545                 550                 555                 560 aag gag tac aag tgc aag gtc tcc aac aaa gcc ctc cca gcc ccc atc      1728
Lys Glu Tyr Lys Cys Lys Val Ser Asn Lys Ala Leu Pro Ala Pro Ile
                565                 570                 575 gag aaa acc atc tcc aaa gcc aaa ggg cag ccc cga gaa cca cag gtg      1776
Glu Lys Thr Ile Ser Lys Ala Lys Gly Gln Pro Arg Glu Pro Gln Val
            580                 585                 590 tac acc ctg ccc cca tcc cgg gat gag ctg acc aag aac cag gtc agc      1824
Tyr Thr Leu Pro Pro Ser Arg Asp Glu Leu Thr Lys Asn Gln Val Ser
        595                 600                 605 ctg acc tgc ctg gtc aaa ggc ttc tat ccc agc gac atc gcc gtg gag      1872
Leu Thr Cys Leu Val Lys Gly Phe Tyr Pro Ser Asp Ile Ala Val Glu
610                 615                 620 tgg gag agc aat ggg cag ccg gag aac aac tac aag acc acg cct ccc      1920
Trp Glu Ser Asn Gly Gln Pro Glu Asn Asn Tyr Lys Thr Thr Pro Pro
625                 630                 635                 640 gtg ctg gac tcc gac ggc tcc ttc ttc ctc tat agc aag ctc acc gtg      1968
Val Leu Asp Ser Asp Gly Ser Phe Phe Leu Tyr Ser Lys Leu Thr Val
                645                 650                 655 gac aag agc agg tgg cag cag ggg aac gtc ttc tca tgc tcc gtg atg      2016
Asp Lys Ser Arg Trp Gln Gln Gly Asn Val Phe Ser Cys Ser Val Met
            660                 665                 670 cat gag gct ctg cac aac cac tac acg cag aag agc ctc tcc ctg tct      2064
His Glu Ala Leu His Asn His Tyr Thr Gln Lys Ser Leu Ser Leu Ser
        675                 680                 685 ccg ggt aaa tga                                                       2076
Pro Gly Lys
    690

<210> SEQ ID NO 20
<211> LENGTH: 691
<212> TYPE: PRT
<213> ORGANISM: Homo sapiens

<400> SEQUENCE: 20

Met Val Lys Pro Ser Leu Pro Phe Thr Ser Leu Leu Phe Leu Gln Leu
1               5                   10                  15

Pro Leu Leu Gly Val Gly Leu Asn Thr Thr Ile Leu Thr Pro Asn Gly
                20                  25                  30

Asn Glu Asp Thr Thr Ala Asp Phe Phe Leu Thr Thr Met Pro Thr Asp
            35                  40                  45

Ser Leu Ser Val Ser Thr Leu Pro Leu Pro Glu Val Gln Cys Phe Val
        50                  55                  60
```

```
Phe Asn Val Glu Tyr Met Asn Cys Thr Trp Asn Ser Ser Glu Pro
 65                  70                  75                  80

Gln Pro Thr Asn Leu Thr Leu His Tyr Trp Tyr Lys Asn Ser Asp Asn
                 85                  90                  95

Asp Lys Val Gln Lys Cys Ser His Tyr Leu Phe Ser Glu Glu Ile Thr
            100                 105                 110

Ser Gly Cys Gln Leu Gln Lys Lys Glu Ile His Leu Tyr Gln Thr Phe
        115                 120                 125

Val Val Gln Leu Gln Asp Pro Arg Glu Pro Arg Arg Gln Ala Thr Gln
    130                 135                 140

Met Leu Lys Leu Gln Asn Leu Val Ile Pro Trp Ala Pro Glu Asn Leu
145                 150                 155                 160

Thr Leu His Lys Leu Ser Glu Ser Gln Leu Glu Leu Asn Trp Asn Asn
                165                 170                 175

Arg Phe Leu Asn His Cys Leu Glu His Leu Val Gln Tyr Arg Thr Asp
            180                 185                 190

Trp Asp His Ser Trp Thr Glu Gln Ser Val Asp Tyr Arg His Lys Phe
        195                 200                 205

Ser Leu Pro Ser Val Asp Gly Gln Lys Arg Tyr Thr Phe Arg Val Arg
    210                 215                 220

Ser Arg Phe Asn Pro Leu Cys Gly Ser Ala Gln His Trp Ser Glu Trp
225                 230                 235                 240

Ser His Pro Ile His Trp Gly Ser Asn Thr Ser Lys Glu Asn Gly Asn
            245                 250                 255

Met Lys Val Leu Gln Glu Pro Thr Cys Val Ser Asp Tyr Met Ser Ile
        260                 265                 270

Ser Thr Cys Glu Trp Lys Met Asn Gly Pro Thr Asn Cys Ser Thr Glu
    275                 280                 285

Leu Arg Leu Leu Tyr Gln Leu Val Phe Leu Leu Ser Glu Ala His Thr
290                 295                 300

Cys Ile Pro Glu Asn Asn Gly Gly Ala Gly Cys Val Cys His Leu Leu
305                 310                 315                 320

Met Asp Asp Val Val Ser Ala Asp Asn Tyr Thr Leu Asp Leu Trp Ala
            325                 330                 335

Gly Gln Gln Leu Leu Trp Lys Gly Ser Phe Lys Pro Ser Glu His Val
        340                 345                 350

Lys Pro Arg Ala Pro Gly Asn Leu Thr Val His Thr Asn Val Ser Asp
    355                 360                 365

Thr Leu Leu Leu Thr Trp Ser Asn Pro Tyr Pro Pro Asp Asn Tyr Leu
370                 375                 380

Tyr Asn His Leu Thr Tyr Ala Val Asn Ile Trp Ser Glu Asn Asp Pro
385                 390                 395                 400

Ala Asp Phe Arg Ile Tyr Asn Val Thr Tyr Leu Glu Pro Ser Leu Arg
            405                 410                 415

Ile Ala Ala Ser Thr Leu Lys Ser Gly Ile Ser Tyr Arg Ala Arg Val
        420                 425                 430

Arg Ala Trp Ala Gln Ser Tyr Asn Thr Thr Trp Ser Glu Trp Ser Pro
    435                 440                 445

Ser Thr Lys Trp His Asn Ser Tyr Arg Glu Pro Phe Glu Gln Ser Gly
450                 455                 460

Asp Lys Thr His Thr Cys Pro Pro Cys Pro Ala Pro Glu Leu Leu Gly
465                 470                 475                 480

Gly Pro Ser Val Phe Leu Phe Pro Pro Lys Pro Lys Asp Thr Leu Met
```

```
                     485                 490                 495
Ile Ser Arg Thr Pro Glu Val Thr Cys Val Val Asp Val Ser His
        500                 505                 510

Glu Asp Pro Glu Val Lys Phe Asn Trp Tyr Val Asp Gly Val Glu Val
        515                 520                 525

His Asn Ala Lys Thr Lys Pro Arg Glu Glu Gln Tyr Asn Ser Thr Tyr
        530                 535                 540

Arg Val Val Ser Val Leu Thr Val Leu His Gln Asp Trp Leu Asn Gly
545                 550                 555                 560

Lys Glu Tyr Lys Cys Lys Val Ser Asn Lys Ala Leu Pro Ala Pro Ile
                565                 570                 575

Glu Lys Thr Ile Ser Lys Ala Lys Gly Gln Pro Arg Glu Pro Gln Val
            580                 585                 590

Tyr Thr Leu Pro Pro Ser Arg Asp Glu Leu Thr Lys Asn Gln Val Ser
        595                 600                 605

Leu Thr Cys Leu Val Lys Gly Phe Tyr Pro Ser Asp Ile Ala Val Glu
    610                 615                 620

Trp Glu Ser Asn Gly Gln Pro Glu Asn Asn Tyr Lys Thr Thr Pro Pro
625                 630                 635                 640

Val Leu Asp Ser Asp Gly Ser Phe Phe Leu Tyr Ser Lys Leu Thr Val
                645                 650                 655

Asp Lys Ser Arg Trp Gln Gln Gly Asn Val Phe Ser Cys Ser Val Met
            660                 665                 670

His Glu Ala Leu His Asn His Tyr Thr Gln Lys Ser Leu Ser Leu Ser
        675                 680                 685

Pro Gly Lys
        690

<210> SEQ ID NO 21
<211> LENGTH: 2085
<212> TYPE: DNA
<213> ORGANISM: Homo sapiens
<220> FEATURE:
<221> NAME/KEY: CDS
<222> LOCATION: (1)...(2082)

<400> SEQUENCE: 21 atg gtg aag cca tca tta cca ttc aca tcc ctc tta ttc ctg cag ctg      48
Met Val Lys Pro Ser Leu Pro Phe Thr Ser Leu Leu Phe Leu Gln Leu
1               5                   10                  15 ccc ctg ctg gga gtg ggg ctg aac acg aca att ctg acg ccc aat ggg      96
Pro Leu Leu Gly Val Gly Leu Asn Thr Thr Ile Leu Thr Pro Asn Gly
            20                  25                  30 aat gaa gac acc aca gct gat ttc ttc ctg acc act atg ccc act gac    144
Asn Glu Asp Thr Thr Ala Asp Phe Phe Leu Thr Thr Met Pro Thr Asp
        35                  40                  45 tcc ctc agt gtt tcc act ctg ccc ctc cca gag gtt cag tgt ttt gtg    192
Ser Leu Ser Val Ser Thr Leu Pro Leu Pro Glu Val Gln Cys Phe Val
    50                  55                  60 ttc aat gtc gag tac atg aat tgc act tgg aac agc agc tct gag ccc    240
Phe Asn Val Glu Tyr Met Asn Cys Thr Trp Asn Ser Ser Ser Glu Pro
65                  70                  75                  80 cag cct acc aac ctc act ctg cat tat tgg tac aag aac tcg gat aat    288
Gln Pro Thr Asn Leu Thr Leu His Tyr Trp Tyr Lys Asn Ser Asp Asn
                85                  90                  95 gat aaa gtc cag aag tgc agc cac tat cta ttc tct gaa gaa atc act    336
Asp Lys Val Gln Lys Cys Ser His Tyr Leu Phe Ser Glu Glu Ile Thr
            100                 105                 110
```

```
tct ggc tgt cag ttg caa aaa aag gag atc cac ctc tac caa aca ttt      384
Ser Gly Cys Gln Leu Gln Lys Lys Glu Ile His Leu Tyr Gln Thr Phe
        115                 120                 125 gtt gtt cag ctc cag gac cca cgg gaa ccc agg aga cag gcc aca cag      432
Val Val Gln Leu Gln Asp Pro Arg Glu Pro Arg Arg Gln Ala Thr Gln
130                 135                 140 atg cta aaa ctg cag aat ctg gtg atc ccc tgg gct cca gag aac cta      480
Met Leu Lys Leu Gln Asn Leu Val Ile Pro Trp Ala Pro Glu Asn Leu
145                 150                 155                 160 aca ctt cac aaa ctg agt gaa tcc cag cta gaa ctg aac tgg aac aac      528
Thr Leu His Lys Leu Ser Glu Ser Gln Leu Glu Leu Asn Trp Asn Asn
                165                 170                 175 aga ttc ttg aac cac tgt ttg gag cac ttg gtg cag tac cgg act gac      576
Arg Phe Leu Asn His Cys Leu Glu His Leu Val Gln Tyr Arg Thr Asp
            180                 185                 190 tgg gac cac agc tgg act gaa caa tca gtg gat tat aga cat aag ttc      624
Trp Asp His Ser Trp Thr Glu Gln Ser Val Asp Tyr Arg His Lys Phe
        195                 200                 205 tcc ttg cct agt gtg gat ggg cag aaa cgc tac acg ttt cgt gtt cgg      672
Ser Leu Pro Ser Val Asp Gly Gln Lys Arg Tyr Thr Phe Arg Val Arg
210                 215                 220 agc cgc ttt aac cca ctc tgt gga agt gct cag cat tgg agt gaa tgg      720
Ser Arg Phe Asn Pro Leu Cys Gly Ser Ala Gln His Trp Ser Glu Trp
225                 230                 235                 240 agc cac cca atc cac tgg ggg agc aat act tca aaa gag aac gcg tcg      768
Ser His Pro Ile His Trp Gly Ser Asn Thr Ser Lys Glu Asn Ala Ser
                245                 250                 255 tct ggg aac atg aag gtc ctg cag gag ccc acc tgc gtc tcc gac tac      816
Ser Gly Asn Met Lys Val Leu Gln Glu Pro Thr Cys Val Ser Asp Tyr
            260                 265                 270 atg agc atc tct act tgc gag tgg aag atg aat ggt ccc acc aat tgc      864
Met Ser Ile Ser Thr Cys Glu Trp Lys Met Asn Gly Pro Thr Asn Cys
        275                 280                 285 agc acc gag ctc cgc ctg ttg tac cag ctg gtt ttt ctg ctc tcc gaa      912
Ser Thr Glu Leu Arg Leu Leu Tyr Gln Leu Val Phe Leu Leu Ser Glu
    290                 295                 300 gcc cac acg tgt atc cct gag aac aac gga ggc gcg ggg tgc gtg tgc      960
Ala His Thr Cys Ile Pro Glu Asn Asn Gly Gly Ala Gly Cys Val Cys
305                 310                 315                 320 cac ctg ctc atg gat gac gtg gtc agt gcg gat aac tat aca ctg gac     1008
His Leu Leu Met Asp Asp Val Val Ser Ala Asp Asn Tyr Thr Leu Asp
                325                 330                 335 ctg tgg gct ggg cag cag ctg ctg tgg aag ggc tcc ttc aag ccc agc     1056
Leu Trp Ala Gly Gln Gln Leu Leu Trp Lys Gly Ser Phe Lys Pro Ser
            340                 345                 350 gag cat gtg aaa ccc agg gcc cca gga aac ctg aca gtt cac acc aat     1104
Glu His Val Lys Pro Arg Ala Pro Gly Asn Leu Thr Val His Thr Asn
        355                 360                 365 gtc tcc gac act ctg ctg ctg acc tgg agc aac ccg tat ccc cct gac     1152
Val Ser Asp Thr Leu Leu Leu Thr Trp Ser Asn Pro Tyr Pro Pro Asp
370                 375                 380 aat tac ctg tat aat cat ctc acc tat gca gtc aac att tgg agt gaa     1200
Asn Tyr Leu Tyr Asn His Leu Thr Tyr Ala Val Asn Ile Trp Ser Glu
385                 390                 395                 400 aac gac ccg gca gat ttc aga atc tat aac gtg acc tac cta gaa ccc     1248
Asn Asp Pro Ala Asp Phe Arg Ile Tyr Asn Val Thr Tyr Leu Glu Pro
                405                 410                 415 tcc ctc cgc atc gca gcc agc acc ctg aag tct ggg att tcc tac agg     1296
Ser Leu Arg Ile Ala Ala Ser Thr Leu Lys Ser Gly Ile Ser Tyr Arg
```

```
                    420                 425                 430
gca cgg gtg agg gcc tgg gct cag agc tat aac acc acc tgg agt gag      1344
Ala Arg Val Arg Ala Trp Ala Gln Ser Tyr Asn Thr Thr Trp Ser Glu
            435                 440                 445 tgg agc ccc agc acc aag tgg cac aac tcc tac agg gag ccc ttc gag      1392
Trp Ser Pro Ser Thr Lys Trp His Asn Ser Tyr Arg Glu Pro Phe Glu
        450                 455                 460 cag tcc gga gac aaa act cac aca tgc cca ccg tgc cca gca cct gaa      1440
Gln Ser Gly Asp Lys Thr His Thr Cys Pro Pro Cys Pro Ala Pro Glu
465                 470                 475                 480 ctc ctg ggg gga ccg tca gtc ttc ctc ttc ccc cca aaa ccc aag gac      1488
Leu Leu Gly Gly Pro Ser Val Phe Leu Phe Pro Pro Lys Pro Lys Asp
                485                 490                 495 acc ctc atg atc tcc cgg acc cct gag gtc aca tgc gtg gtg gtg gac      1536
Thr Leu Met Ile Ser Arg Thr Pro Glu Val Thr Cys Val Val Val Asp
            500                 505                 510 gtg agc cac gaa gac cct gag gtc aag ttc aac tgg tac gtg gac ggc      1584
Val Ser His Glu Asp Pro Glu Val Lys Phe Asn Trp Tyr Val Asp Gly
        515                 520                 525 gtg gag gtg cat aat gcc aag aca aag ccg cgg gag gag cag tac aac      1632
Val Glu Val His Asn Ala Lys Thr Lys Pro Arg Glu Glu Gln Tyr Asn
530                 535                 540 agc acg tac cgt gtg gtc agc gtc ctc acc gtc ctg cac cag gac tgg      1680
Ser Thr Tyr Arg Val Val Ser Val Leu Thr Val Leu His Gln Asp Trp
545                 550                 555                 560 ctg aat ggc aag gag tac aag tgc aag gtc tcc aac aaa gcc ctc cca      1728
Leu Asn Gly Lys Glu Tyr Lys Cys Lys Val Ser Asn Lys Ala Leu Pro
                565                 570                 575 gcc ccc atc gag aaa acc atc tcc aaa gcc aaa ggg cag ccc cga gaa      1776
Ala Pro Ile Glu Lys Thr Ile Ser Lys Ala Lys Gly Gln Pro Arg Glu
            580                 585                 590 cca cag gtg tac acc ctg ccc cca tcc cgg gat gag ctg acc aag aac      1824
Pro Gln Val Tyr Thr Leu Pro Pro Ser Arg Asp Glu Leu Thr Lys Asn
        595                 600                 605 cag gtc agc ctg acc tgc ctg gtc aaa ggc ttc tat ccc agc gac atc      1872
Gln Val Ser Leu Thr Cys Leu Val Lys Gly Phe Tyr Pro Ser Asp Ile
610                 615                 620 gcc gtg gag tgg gag agc aat ggg cag ccg gag aac aac tac aag acc      1920
Ala Val Glu Trp Glu Ser Asn Gly Gln Pro Glu Asn Asn Tyr Lys Thr
625                 630                 635                 640 acg cct ccc gtg ctg gac tcc gac ggc tcc ttc ttc ctc tat agc aag      1968
Thr Pro Pro Val Leu Asp Ser Asp Gly Ser Phe Phe Leu Tyr Ser Lys
                645                 650                 655 ctc acc gtg gac aag agc agg tgg cag cag ggg aac gtc ttc tca tgc      2016
Leu Thr Val Asp Lys Ser Arg Trp Gln Gln Gly Asn Val Phe Ser Cys
            660                 665                 670 tcc gtg atg cat gag gct ctg cac aac cac tac acg cag aag agc ctc      2064
Ser Val Met His Glu Ala Leu His Asn His Tyr Thr Gln Lys Ser Leu
        675                 680                 685 tcc ctg tct ccg ggt aaa tga                                          2085
Ser Leu Ser Pro Gly Lys
    690

<210> SEQ ID NO 22
<211> LENGTH: 694
<212> TYPE: PRT
<213> ORGANISM: Homo sapiens

<400> SEQUENCE: 22

Met Val Lys Pro Ser Leu Pro Phe Thr Ser Leu Leu Phe Leu Gln Leu
```

```
  1               5                  10                 15
Pro Leu Leu Gly Val Gly Leu Asn Thr Thr Ile Leu Thr Pro Asn Gly
                20                  25                 30

Asn Glu Asp Thr Thr Ala Asp Phe Phe Leu Thr Thr Met Pro Thr Asp
                35                  40                 45

Ser Leu Ser Val Ser Thr Leu Pro Leu Pro Glu Val Gln Cys Phe Val
 50                  55                 60

Phe Asn Val Glu Tyr Met Asn Cys Thr Trp Asn Ser Ser Ser Glu Pro
 65                  70                 75                 80

Gln Pro Thr Asn Leu Thr Leu His Tyr Trp Tyr Lys Asn Ser Asp Asn
                85                  90                 95

Asp Lys Val Gln Lys Cys Ser His Tyr Leu Phe Ser Glu Glu Ile Thr
                100                 105                110

Ser Gly Cys Gln Leu Gln Lys Lys Glu Ile His Leu Tyr Gln Thr Phe
                115                 120                125

Val Val Gln Leu Gln Asp Pro Arg Glu Pro Arg Arg Gln Ala Thr Gln
                130                 135                140

Met Leu Lys Leu Gln Asn Leu Val Ile Pro Trp Ala Pro Glu Asn Leu
145                 150                 155                160

Thr Leu His Lys Leu Ser Glu Ser Gln Leu Glu Leu Asn Trp Asn Asn
                165                 170                175

Arg Phe Leu Asn His Cys Leu Glu His Leu Val Gln Tyr Arg Thr Asp
                180                 185                190

Trp Asp His Ser Trp Thr Glu Gln Ser Val Asp Tyr Arg His Lys Phe
                195                 200                205

Ser Leu Pro Ser Val Asp Gly Gln Lys Arg Tyr Thr Phe Arg Val Arg
                210                 215                220

Ser Arg Phe Asn Pro Leu Cys Gly Ser Ala Gln His Trp Ser Glu Trp
225                 230                 235                240

Ser His Pro Ile His Trp Gly Ser Asn Thr Ser Lys Glu Asn Ala Ser
                245                 250                255

Ser Gly Asn Met Lys Val Leu Gln Glu Pro Thr Cys Val Ser Asp Tyr
                260                 265                270

Met Ser Ile Ser Thr Cys Glu Trp Lys Met Asn Gly Pro Thr Asn Cys
                275                 280                285

Ser Thr Glu Leu Arg Leu Leu Tyr Gln Leu Val Phe Leu Leu Ser Glu
                290                 295                300

Ala His Thr Cys Ile Pro Glu Asn Asn Gly Gly Ala Gly Cys Val Cys
305                 310                 315                320

His Leu Leu Met Asp Asp Val Val Ser Ala Asp Asn Tyr Thr Leu Asp
                325                 330                335

Leu Trp Ala Gly Gln Gln Leu Leu Trp Lys Gly Ser Phe Lys Pro Ser
                340                 345                350

Glu His Val Lys Pro Arg Ala Pro Gly Asn Leu Thr Val His Thr Asn
                355                 360                365

Val Ser Asp Thr Leu Leu Leu Thr Trp Ser Asn Pro Tyr Pro Pro Asp
                370                 375                380

Asn Tyr Leu Tyr Asn His Leu Thr Tyr Ala Val Asn Ile Trp Ser Glu
385                 390                 395                400

Asn Asp Pro Ala Asp Phe Arg Ile Tyr Asn Val Thr Tyr Leu Glu Pro
                405                 410                415

Ser Leu Arg Ile Ala Ala Ser Thr Leu Lys Ser Gly Ile Ser Tyr Arg
                420                 425                430
```

```
Ala Arg Val Arg Ala Trp Ala Gln Ser Tyr Asn Thr Thr Trp Ser Glu
            435                 440                 445

Trp Ser Pro Ser Thr Lys Trp His Asn Ser Tyr Arg Glu Pro Phe Glu
        450                 455                 460

Gln Ser Gly Asp Lys Thr His Thr Cys Pro Cys Pro Ala Pro Glu
465                 470                 475                 480

Leu Leu Gly Gly Pro Ser Val Phe Leu Phe Pro Pro Lys Pro Lys Asp
                485                 490                 495

Thr Leu Met Ile Ser Arg Thr Pro Glu Val Thr Cys Val Val Val Asp
                500                 505                 510

Val Ser His Glu Asp Pro Glu Val Lys Phe Asn Trp Tyr Val Asp Gly
            515                 520                 525

Val Glu Val His Asn Ala Lys Thr Lys Pro Arg Glu Glu Gln Tyr Asn
        530                 535                 540

Ser Thr Tyr Arg Val Val Ser Val Leu Thr Val Leu His Gln Asp Trp
545                 550                 555                 560

Leu Asn Gly Lys Glu Tyr Lys Cys Lys Val Ser Asn Lys Ala Leu Pro
                565                 570                 575

Ala Pro Ile Glu Lys Thr Ile Ser Lys Ala Lys Gly Gln Pro Arg Glu
                580                 585                 590

Pro Gln Val Tyr Thr Leu Pro Pro Ser Arg Asp Glu Leu Thr Lys Asn
            595                 600                 605

Gln Val Ser Leu Thr Cys Leu Val Lys Gly Phe Tyr Pro Ser Asp Ile
        610                 615                 620

Ala Val Glu Trp Glu Ser Asn Gly Gln Pro Glu Asn Asn Tyr Lys Thr
625                 630                 635                 640

Thr Pro Pro Val Leu Asp Ser Asp Gly Ser Phe Phe Leu Tyr Ser Lys
                645                 650                 655

Leu Thr Val Asp Lys Ser Arg Trp Gln Gln Gly Asn Val Phe Ser Cys
                660                 665                 670

Ser Val Met His Glu Ala Leu His Asn His Tyr Thr Gln Lys Ser Leu
            675                 680                 685

Ser Leu Ser Pro Gly Lys
            690

<210> SEQ ID NO 23
<211> LENGTH: 3507
<212> TYPE: DNA
<213> ORGANISM: Homo sapiens
<220> FEATURE:
<221> NAME/KEY: CDS
<222> LOCATION: (1)...(3504)

<400> SEQUENCE: 23 atg gtg gcc gtc ggc tgc gcg ctg ctg gct gcc ctg ctg gcc gcg ccg      48
Met Val Ala Val Gly Cys Ala Leu Leu Ala Ala Leu Leu Ala Ala Pro
 1               5                  10                  15 gga gcg gcg ctg gcc cca agg cgc tgc cct gcg cag gag gtg gca aga      96
Gly Ala Ala Leu Ala Pro Arg Arg Cys Pro Ala Gln Glu Val Ala Arg
             20                  25                  30 ggc gtg ctg acc agt ctg cca gga gac agc gtg act ctg acc tgc ccg     144
Gly Val Leu Thr Ser Leu Pro Gly Asp Ser Val Thr Leu Thr Cys Pro
         35                  40                  45 ggg gta gag ccg gaa gac aat gcc act gtt cac tgg gtg ctc agg aag     192
Gly Val Glu Pro Glu Asp Asn Ala Thr Val His Trp Val Leu Arg Lys
     50                  55                  60
```

-continued

| | |
|---|---|
| ccg gct gca ggc tcc cac ccc agc aga tgg gct ggc atg gga agg agg<br>Pro Ala Ala Gly Ser His Pro Ser Arg Trp Ala Gly Met Gly Arg Arg<br>65                        70                   75                     80 | 240 |
| ctg ctg ctg agg tcg gtg cag ctc cac gac tct gga aac tat tca tgc<br>Leu Leu Leu Arg Ser Val Gln Leu His Asp Ser Gly Asn Tyr Ser Cys<br>                   85                   90                   95 | 288 |
| tac cgg gcc ggc cgc cca gct ggg act gtg cac ttg ctg gtg gat gtt<br>Tyr Arg Ala Gly Arg Pro Ala Gly Thr Val His Leu Leu Val Asp Val<br>               100                    105                110 | 336 |
| ccc ccc gag gag ccc cag ctc tcc tgc ttc cgg aag agc ccc ctc agc<br>Pro Pro Glu Glu Pro Gln Leu Ser Cys Phe Arg Lys Ser Pro Leu Ser<br>            115                120                125 | 384 |
| aat gtt gtt tgt gag tgg ggt cct cgg agc acc cca tcc ctg acg aca<br>Asn Val Val Cys Glu Trp Gly Pro Arg Ser Thr Pro Ser Leu Thr Thr<br>130                       135                140 | 432 |
| aag gct gtg ctc ttg gtg agg aag ttt cag aac agt ccg gcc gaa gac<br>Lys Ala Val Leu Leu Val Arg Lys Phe Gln Asn Ser Pro Ala Glu Asp<br>145                      150                155                160 | 480 |
| ttc cag gag ccg tgc cag tat tcc cag gag tcc cag aag ttc tcc tgc<br>Phe Gln Glu Pro Cys Gln Tyr Ser Gln Glu Ser Gln Lys Phe Ser Cys<br>               165                    170                175 | 528 |
| cag tta gca gtc ccg gag gga gac agc tct ttc tac ata gtg tcc atg<br>Gln Leu Ala Val Pro Glu Gly Asp Ser Ser Phe Tyr Ile Val Ser Met<br>            180                    185                190 | 576 |
| tgc gtc gcc agt agt gtc ggg agc aag ttc agc aaa act caa acc ttt<br>Cys Val Ala Ser Ser Val Gly Ser Lys Phe Ser Lys Thr Gln Thr Phe<br>               195                    200                205 | 624 |
| cag ggt tgt gga atc ttg cag cct gat ccg cct gcc aac atc aca gtc<br>Gln Gly Cys Gly Ile Leu Gln Pro Asp Pro Pro Ala Asn Ile Thr Val<br>210                       215                220 | 672 |
| act gcc gtg gcc aga aac ccc cgc tgg ctc agt gtc acc tgg caa gac<br>Thr Ala Val Ala Arg Asn Pro Arg Trp Leu Ser Val Thr Trp Gln Asp<br>225                      230                235                240 | 720 |
| ccc cac tcc tgg aac tca tct ttc tac aga cta cgg ttt gag ctc aga<br>Pro His Ser Trp Asn Ser Ser Phe Tyr Arg Leu Arg Phe Glu Leu Arg<br>               245                    250                255 | 768 |
| tat cgg gct gaa cgg tca aag aca ttc aca aca tgg atg gtc aag gac<br>Tyr Arg Ala Glu Arg Ser Lys Thr Phe Thr Thr Trp Met Val Lys Asp<br>            260                    265                270 | 816 |
| ctc cag cat cac tgt gtc atc cac gac gcc tgg agc ggc ctg agg cac<br>Leu Gln His His Cys Val Ile His Asp Ala Trp Ser Gly Leu Arg His<br>               275                    280                285 | 864 |
| gtg gtg cag ctt cgt gcc cag gag gag ttc ggg caa ggc gag tgg agc<br>Val Val Gln Leu Arg Ala Gln Glu Glu Phe Gly Gln Gly Glu Trp Ser<br>            290                    295                300 | 912 |
| gag tgg agc ccg gag gcc atg ggc acg cct tgg aca gaa tcc agg agt<br>Glu Trp Ser Pro Glu Ala Met Gly Thr Pro Trp Thr Glu Ser Arg Ser<br>305                       310                315                320 | 960 |
| cct cca gct gag aac gag gtg tcc acc ccc atg acc ggt ggc gcg cct<br>Pro Pro Ala Glu Asn Glu Val Ser Thr Pro Met Thr Gly Gly Ala Pro<br>               325                    330                335 | 1008 |
| tca ggt gct cag ctg gaa ctt cta gac cca tgt ggt tat atc agt cct<br>Ser Gly Ala Gln Leu Glu Leu Leu Asp Pro Cys Gly Tyr Ile Ser Pro<br>            340                    345                350 | 1056 |
| gaa tct cca gtt gta caa ctt cat tct aat ttc act gca gtt tgt gtg<br>Glu Ser Pro Val Val Gln Leu His Ser Asn Phe Thr Ala Val Cys Val<br>               355                    360                365 | 1104 |
| cta aag gaa aaa tgt atg gat tat ttt cat gta aat gct aat tac att<br>Leu Lys Glu Lys Cys Met Asp Tyr Phe His Val Asn Ala Asn Tyr Ile<br>370                       375                380 | 1152 |

-continued

```
gtc tgg aaa aca aac cat ttt act att cct aag gag caa tat act atc    1200
Val Trp Lys Thr Asn His Phe Thr Ile Pro Lys Glu Gln Tyr Thr Ile
385                 390                 395                 400 ata aac aga aca gca tcc agt gtc acc ttt aca gat ata gct tca tta    1248
Ile Asn Arg Thr Ala Ser Ser Val Thr Phe Thr Asp Ile Ala Ser Leu
                405                 410                 415 aat att cag ctc act tgc aac att ctt aca ttc gga cag ctt gaa cag    1296
Asn Ile Gln Leu Thr Cys Asn Ile Leu Thr Phe Gly Gln Leu Glu Gln
            420                 425                 430 aat gtt tat gga atc aca ata att tca ggc ttg cct cca gaa aaa cct    1344
Asn Val Tyr Gly Ile Thr Ile Ile Ser Gly Leu Pro Pro Glu Lys Pro
        435                 440                 445 aaa aat ttg agt tgc att gtg aac gag ggg aag aaa atg agg tgt gag    1392
Lys Asn Leu Ser Cys Ile Val Asn Glu Gly Lys Lys Met Arg Cys Glu
450                 455                 460 tgg gat ggt gga agg gaa aca cac ttg gag aca aac ttc act tta aaa    1440
Trp Asp Gly Gly Arg Glu Thr His Leu Glu Thr Asn Phe Thr Leu Lys
465                 470                 475                 480 tct gaa tgg gca aca cac aag ttt gct gat tgc aaa gca aaa cgt gac    1488
Ser Glu Trp Ala Thr His Lys Phe Ala Asp Cys Lys Ala Lys Arg Asp
                485                 490                 495 acc ccc acc tca tgc act gtt gat tat tct act gtg tat ttt gtc aac    1536
Thr Pro Thr Ser Cys Thr Val Asp Tyr Ser Thr Val Tyr Phe Val Asn
            500                 505                 510 att gaa gtc tgg gta gaa gca gag aat gcc ctt ggg aag gtt aca tca    1584
Ile Glu Val Trp Val Glu Ala Glu Asn Ala Leu Gly Lys Val Thr Ser
        515                 520                 525 gat cat atc aat ttt gat cct gta tat aaa gtg aag ccc aat ccg cca    1632
Asp His Ile Asn Phe Asp Pro Val Tyr Lys Val Lys Pro Asn Pro Pro
530                 535                 540 cat aat tta tca gtg atc aac tca gag gaa ctg tct agt atc tta aaa    1680
His Asn Leu Ser Val Ile Asn Ser Glu Glu Leu Ser Ser Ile Leu Lys
545                 550                 555                 560 ttg aca tgg acc aac cca agt att aag agt gtt ata ata cta aaa tat    1728
Leu Thr Trp Thr Asn Pro Ser Ile Lys Ser Val Ile Ile Leu Lys Tyr
                565                 570                 575 aac att caa tat agg acc aaa gat gcc tca act tgg agc cag att cct    1776
Asn Ile Gln Tyr Arg Thr Lys Asp Ala Ser Thr Trp Ser Gln Ile Pro
            580                 585                 590 cct gaa gac aca gca tcc acc cga tct tca ttc act gtc caa gac ctt    1824
Pro Glu Asp Thr Ala Ser Thr Arg Ser Ser Phe Thr Val Gln Asp Leu
        595                 600                 605 aaa cct ttt aca gaa tat gtg ttt agg att cgc tgt atg aag gaa gat    1872
Lys Pro Phe Thr Glu Tyr Val Phe Arg Ile Arg Cys Met Lys Glu Asp
610                 615                 620 ggt aag gga tac tgg agt gac tgg agt gaa gaa gca agt ggg atc acc    1920
Gly Lys Gly Tyr Trp Ser Asp Trp Ser Glu Glu Ala Ser Gly Ile Thr
625                 630                 635                 640 tat gaa gat aga cca tct aaa gca cca agt ttc tgg tat aaa ata gat    1968
Tyr Glu Asp Arg Pro Ser Lys Ala Pro Ser Phe Trp Tyr Lys Ile Asp
                645                 650                 655 cca tcc cat act caa ggc tac aga act gta caa ctc gtg tgg aag aca    2016
Pro Ser His Thr Gln Gly Tyr Arg Thr Val Gln Leu Val Trp Lys Thr
            660                 665                 670 ttg cct cct ttt gaa gcc aat gga aaa atc ttg gat tat gaa gtg act    2064
Leu Pro Pro Phe Glu Ala Asn Gly Lys Ile Leu Asp Tyr Glu Val Thr
        675                 680                 685 ctc aca aga tgg aaa tca cat tta caa aat tac aca gtt aat gcc aca    2112
Leu Thr Arg Trp Lys Ser His Leu Gln Asn Tyr Thr Val Asn Ala Thr
```

```
          690                 695                 700
aaa ctg aca gta aat ctc aca aat gat cgc tat cta gca acc cta aca    2160
Lys Leu Thr Val Asn Leu Thr Asn Asp Arg Tyr Leu Ala Thr Leu Thr
705                 710                 715                 720 gta aga aat ctt gtt ggc aaa tca gat gca gct gtt tta act atc cct    2208
Val Arg Asn Leu Val Gly Lys Ser Asp Ala Ala Val Leu Thr Ile Pro
                725                 730                 735 gcc tgt gac ttt caa gct act cac cct gta atg gat ctt aaa gca ttc    2256
Ala Cys Asp Phe Gln Ala Thr His Pro Val Met Asp Leu Lys Ala Phe
            740                 745                 750 ccc aaa gat aac atg ctt tgg gtg gaa tgg act act cca agg gaa tct    2304
Pro Lys Asp Asn Met Leu Trp Val Glu Trp Thr Thr Pro Arg Glu Ser
        755                 760                 765 gta aag aaa tat ata ctt gag tgg tgt gtg tta tca gat aaa gca ccc    2352
Val Lys Lys Tyr Ile Leu Glu Trp Cys Val Leu Ser Asp Lys Ala Pro
    770                 775                 780 tgt atc aca gac tgg caa caa gaa gat ggt acc gtg cat cgc acc tat    2400
Cys Ile Thr Asp Trp Gln Gln Glu Asp Gly Thr Val His Arg Thr Tyr
785                 790                 795                 800 tta aga ggg aac tta gca gag agc aaa tgc tat ttg ata aca gtt act    2448
Leu Arg Gly Asn Leu Ala Glu Ser Lys Cys Tyr Leu Ile Thr Val Thr
                805                 810                 815 cca gta tat gct gat gga cca gga agc cct gaa tcc ata aag gca tac    2496
Pro Val Tyr Ala Asp Gly Pro Gly Ser Pro Glu Ser Ile Lys Ala Tyr
            820                 825                 830 ctt aaa caa gct cca cct tcc aaa gga cct act gtt cgg aca aaa aaa    2544
Leu Lys Gln Ala Pro Pro Ser Lys Gly Pro Thr Val Arg Thr Lys Lys
        835                 840                 845 gta ggg aaa aac gaa gct gtc tta gag tgg gac caa ctt cct gtt gat    2592
Val Gly Lys Asn Glu Ala Val Leu Glu Trp Asp Gln Leu Pro Val Asp
    850                 855                 860 gtt cag aat gga ttt atc aga aat tat act ata ttt tat aga acc atc    2640
Val Gln Asn Gly Phe Ile Arg Asn Tyr Thr Ile Phe Tyr Arg Thr Ile
865                 870                 875                 880 att gga aat gaa act gct gtg aat gtg gat tct tcc cac aca gaa tat    2688
Ile Gly Asn Glu Thr Ala Val Asn Val Asp Ser Ser His Thr Glu Tyr
                885                 890                 895 aca ttg tcc tct ttg act agt gac aca ttg tac atg gta cga atg gca    2736
Thr Leu Ser Ser Leu Thr Ser Asp Thr Leu Tyr Met Val Arg Met Ala
            900                 905                 910 gca tac aca gat gaa ggt ggg aag gat ggt cca gaa ttc act ttt act    2784
Ala Tyr Thr Asp Glu Gly Gly Lys Asp Gly Pro Glu Phe Thr Phe Thr
        915                 920                 925 acc cca aag ttt gct caa gga gaa att gaa tcc ggg ggc gac aaa act    2832
Thr Pro Lys Phe Ala Gln Gly Glu Ile Glu Ser Gly Gly Asp Lys Thr
    930                 935                 940 cac aca tgc cca ccg tgc cca gca cct gaa ctc ctg ggg gga ccg tca    2880
His Thr Cys Pro Pro Cys Pro Ala Pro Glu Leu Leu Gly Gly Pro Ser
945                 950                 955                 960 gtc ttc ctc ttc ccc cca aaa ccc aag gac acc ctc atg atc tcc cgg    2928
Val Phe Leu Phe Pro Pro Lys Pro Lys Asp Thr Leu Met Ile Ser Arg
                965                 970                 975 acc cct gag gtc aca tgc gtg gtg gtg gac gtg agc cac gaa gac cct    2976
Thr Pro Glu Val Thr Cys Val Val Val Asp Val Ser His Glu Asp Pro
            980                 985                 990 gag gtc aag ttc aac tgg tac gtg gac ggc gtg gag gtg cat aat gcc    3024
Glu Val Lys Phe Asn Trp Tyr Val Asp Gly Val Glu Val His Asn Ala
        995                 1000                1005 aag aca aag ccg cgg gag gag cag tac aac agc acg tac cgt gtg gtc    3072
```

```
Lys Thr Lys Pro Arg Glu Glu Gln Tyr Asn Ser Thr Tyr Arg Val Val
    1010                1015                1020 agc gtc ctc acc gtc ctg cac cag gac tgg ctg aat ggc aag gag tac      3120
Ser Val Leu Thr Val Leu His Gln Asp Trp Leu Asn Gly Lys Glu Tyr
1025                1030                1035                1040 aag tgc aag gtc tcc aac aaa gcc ctc cca gcc ccc atc gag aaa acc      3168
Lys Cys Lys Val Ser Asn Lys Ala Leu Pro Ala Pro Ile Glu Lys Thr
                1045                1050                1055 atc tcc aaa gcc aaa ggg cag ccc cga gaa cca cag gtg tac acc ctg      3216
Ile Ser Lys Ala Lys Gly Gln Pro Arg Glu Pro Gln Val Tyr Thr Leu
            1060                1065                1070 ccc cca tcc cgg gat gag ctg acc aag aac cag gtc agc ctg acc tgc      3264
Pro Pro Ser Arg Asp Glu Leu Thr Lys Asn Gln Val Ser Leu Thr Cys
        1075                1080                1085 ctg gtc aaa ggc ttc tat ccc agc gac atc gcc gtg gag tgg gag agc      3312
Leu Val Lys Gly Phe Tyr Pro Ser Asp Ile Ala Val Glu Trp Glu Ser
    1090                1095                1100 aat ggg cag ccg gag aac aac tac aag acc acg cct ccc gtg ctg gac      3360
Asn Gly Gln Pro Glu Asn Asn Tyr Lys Thr Thr Pro Pro Val Leu Asp
1105                1110                1115                1120 tcc gac ggc tcc ttc ttc ctc tac agc aag ctc acc gtg gac aag agc      3408
Ser Asp Gly Ser Phe Phe Leu Tyr Ser Lys Leu Thr Val Asp Lys Ser
                1125                1130                1135 agg tgg cag cag ggg aac gtc ttc tca tgc tcc gtg atg cat gag gct      3456
Arg Trp Gln Gln Gly Asn Val Phe Ser Cys Ser Val Met His Glu Ala
            1140                1145                1150 ctg cac aac cac tac acg cag aag agc ctc tcc ctg tct ccg ggt aaa      3504
Leu His Asn His Tyr Thr Gln Lys Ser Leu Ser Leu Ser Pro Gly Lys
        1155                1160                1165 tga                                                                  3507

<210> SEQ ID NO 24
<211> LENGTH: 1168
<212> TYPE: PRT
<213> ORGANISM: Homo sapiens

<400> SEQUENCE: 24

Met Val Ala Val Gly Cys Ala Leu Leu Ala Ala Leu Leu Ala Ala Pro
1               5                   10                  15

Gly Ala Ala Leu Ala Pro Arg Arg Cys Pro Ala Gln Glu Val Ala Arg
                20                  25                  30

Gly Val Leu Thr Ser Leu Pro Gly Asp Ser Val Thr Leu Thr Cys Pro
            35                  40                  45

Gly Val Glu Pro Glu Asp Asn Ala Thr Val His Trp Val Leu Arg Lys
        50                  55                  60

Pro Ala Ala Gly Ser His Pro Ser Arg Trp Ala Gly Met Gly Arg Arg
65                  70                  75                  80

Leu Leu Leu Arg Ser Val Gln Leu His Asp Ser Gly Asn Tyr Ser Cys
                85                  90                  95

Tyr Arg Ala Gly Arg Pro Ala Gly Thr Val His Leu Leu Val Asp Val
                100                 105                 110

Pro Pro Glu Glu Pro Gln Leu Ser Cys Phe Arg Lys Ser Pro Leu Ser
            115                 120                 125

Asn Val Val Cys Glu Trp Gly Pro Arg Ser Thr Pro Ser Leu Thr Thr
        130                 135                 140

Lys Ala Val Leu Leu Val Arg Lys Phe Gln Asn Ser Pro Ala Glu Asp
145                 150                 155                 160
```

-continued

```
Phe Gln Glu Pro Cys Gln Tyr Ser Gln Glu Ser Gln Lys Phe Ser Cys
                165                 170                 175
Gln Leu Ala Val Pro Glu Gly Asp Ser Ser Phe Tyr Ile Val Ser Met
            180                 185                 190
Cys Val Ala Ser Ser Val Gly Ser Lys Phe Ser Lys Thr Gln Thr Phe
        195                 200                 205
Gln Gly Cys Gly Ile Leu Gln Pro Asp Pro Ala Asn Ile Thr Val
    210                 215                 220
Thr Ala Val Ala Arg Asn Pro Arg Trp Leu Ser Val Thr Trp Gln Asp
225                 230                 235                 240
Pro His Ser Trp Asn Ser Ser Phe Tyr Arg Leu Arg Phe Glu Leu Arg
                245                 250                 255
Tyr Arg Ala Glu Arg Ser Lys Thr Phe Thr Thr Trp Met Val Lys Asp
            260                 265                 270
Leu Gln His His Cys Val Ile His Asp Ala Trp Ser Gly Leu Arg His
        275                 280                 285
Val Val Gln Leu Arg Ala Gln Glu Glu Phe Gly Gln Gly Glu Trp Ser
    290                 295                 300
Glu Trp Ser Pro Glu Ala Met Gly Thr Pro Trp Thr Glu Ser Arg Ser
305                 310                 315                 320
Pro Pro Ala Glu Asn Glu Val Ser Thr Pro Met Thr Gly Gly Ala Pro
                325                 330                 335
Ser Gly Ala Gln Leu Glu Leu Leu Asp Pro Cys Gly Tyr Ile Ser Pro
            340                 345                 350
Glu Ser Pro Val Val Gln Leu His Ser Asn Phe Thr Ala Val Cys Val
        355                 360                 365
Leu Lys Glu Lys Cys Met Asp Tyr Phe His Val Asn Ala Asn Tyr Ile
    370                 375                 380
Val Trp Lys Thr Asn His Phe Thr Ile Pro Lys Glu Gln Tyr Thr Ile
385                 390                 395                 400
Ile Asn Arg Thr Ala Ser Ser Val Thr Phe Thr Asp Ile Ala Ser Leu
                405                 410                 415
Asn Ile Gln Leu Thr Cys Asn Ile Leu Thr Phe Gly Gln Leu Glu Gln
            420                 425                 430
Asn Val Tyr Gly Ile Thr Ile Ile Ser Gly Leu Pro Pro Glu Lys Pro
        435                 440                 445
Lys Asn Leu Ser Cys Ile Val Asn Glu Gly Lys Lys Met Arg Cys Glu
    450                 455                 460
Trp Asp Gly Gly Arg Glu Thr His Leu Glu Thr Asn Phe Thr Leu Lys
465                 470                 475                 480
Ser Glu Trp Ala Thr His Lys Phe Ala Asp Cys Lys Ala Lys Arg Asp
                485                 490                 495
Thr Pro Thr Ser Cys Thr Val Asp Tyr Ser Thr Val Tyr Phe Val Asn
            500                 505                 510
Ile Glu Val Trp Val Glu Ala Glu Asn Ala Leu Gly Lys Val Thr Ser
        515                 520                 525
Asp His Ile Asn Phe Asp Pro Val Tyr Lys Val Lys Pro Asn Pro Pro
    530                 535                 540
His Asn Leu Ser Val Ile Asn Ser Glu Glu Leu Ser Ser Ile Leu Lys
545                 550                 555                 560
Leu Thr Trp Thr Asn Pro Ser Ile Lys Ser Val Ile Ile Leu Lys Tyr
                565                 570                 575
Asn Ile Gln Tyr Arg Thr Lys Asp Ala Ser Thr Trp Ser Gln Ile Pro
```

-continued

```
            580                 585                 590
Pro Glu Asp Thr Ala Ser Thr Arg Ser Ser Phe Thr Val Gln Asp Leu
            595                 600                 605
Lys Pro Phe Thr Glu Tyr Val Phe Arg Ile Arg Cys Met Lys Glu Asp
            610                 615                 620
Gly Lys Gly Tyr Trp Ser Asp Trp Ser Glu Glu Ala Ser Gly Ile Thr
625                 630                 635                 640
Tyr Glu Asp Arg Pro Ser Lys Ala Pro Ser Phe Trp Tyr Lys Ile Asp
                    645                 650                 655
Pro Ser His Thr Gln Gly Tyr Arg Thr Val Gln Leu Val Trp Lys Thr
                660                 665                 670
Leu Pro Pro Phe Glu Ala Asn Gly Lys Ile Leu Asp Tyr Glu Val Thr
            675                 680                 685
Leu Thr Arg Trp Lys Ser His Leu Gln Asn Tyr Thr Val Asn Ala Thr
            690                 695                 700
Lys Leu Thr Val Asn Leu Thr Asn Asp Arg Tyr Leu Ala Thr Leu Thr
705                 710                 715                 720
Val Arg Asn Leu Val Gly Lys Ser Asp Ala Ala Val Leu Thr Ile Pro
                    725                 730                 735
Ala Cys Asp Phe Gln Ala Thr His Pro Val Met Asp Leu Lys Ala Phe
                740                 745                 750
Pro Lys Asp Asn Met Leu Trp Val Glu Trp Thr Thr Pro Arg Glu Ser
            755                 760                 765
Val Lys Lys Tyr Ile Leu Glu Trp Cys Val Leu Ser Asp Lys Ala Pro
            770                 775                 780
Cys Ile Thr Asp Trp Gln Gln Glu Asp Gly Thr Val His Arg Thr Tyr
785                 790                 795                 800
Leu Arg Gly Asn Leu Ala Glu Ser Lys Cys Tyr Leu Ile Thr Val Thr
                    805                 810                 815
Pro Val Tyr Ala Asp Gly Pro Gly Ser Pro Glu Ser Ile Lys Ala Tyr
                820                 825                 830
Leu Lys Gln Ala Pro Pro Ser Lys Gly Pro Thr Val Arg Thr Lys Lys
            835                 840                 845
Val Gly Lys Asn Glu Ala Val Leu Glu Trp Asp Gln Leu Pro Val Asp
850                 855                 860
Val Gln Asn Gly Phe Ile Arg Asn Tyr Thr Ile Phe Tyr Arg Thr Ile
865                 870                 875                 880
Ile Gly Asn Glu Thr Ala Val Asn Val Asp Ser Ser His Thr Glu Tyr
                    885                 890                 895
Thr Leu Ser Ser Leu Thr Ser Asp Thr Leu Tyr Met Val Arg Met Ala
                900                 905                 910
Ala Tyr Thr Asp Glu Gly Gly Lys Asp Gly Pro Glu Phe Thr Phe Thr
            915                 920                 925
Thr Pro Lys Phe Ala Gln Gly Glu Ile Glu Ser Gly Gly Asp Lys Thr
            930                 935                 940
His Thr Cys Pro Pro Cys Pro Ala Pro Glu Leu Leu Gly Gly Pro Ser
945                 950                 955                 960
Val Phe Leu Phe Pro Pro Lys Pro Lys Asp Thr Leu Met Ile Ser Arg
                    965                 970                 975
Thr Pro Glu Val Thr Cys Val Val Val Asp Val Ser His Glu Asp Pro
                980                 985                 990
Glu Val Lys Phe Asn Trp Tyr Val Asp Gly Val Glu Val His Asn Ala
            995                 1000                1005
```

```
Lys Thr Lys Pro Arg Glu Glu Gln Tyr Asn Ser Thr Tyr Arg Val Val
    1010                1015                1020

Ser Val Leu Thr Val Leu His Gln Asp Trp Leu Asn Gly Lys Glu Tyr
1025                1030                1035                1040

Lys Cys Lys Val Ser Asn Lys Ala Leu Pro Ala Pro Ile Glu Lys Thr
                1045                1050                1055

Ile Ser Lys Ala Lys Gly Gln Pro Arg Glu Pro Gln Val Tyr Thr Leu
            1060                1065                1070

Pro Pro Ser Arg Asp Glu Leu Thr Lys Asn Gln Val Ser Leu Thr Cys
        1075                1080                1085

Leu Val Lys Gly Phe Tyr Pro Ser Asp Ile Ala Val Glu Trp Glu Ser
    1090                1095                1100

Asn Gly Gln Pro Glu Asn Asn Tyr Lys Thr Thr Pro Pro Val Leu Asp
1105                1110                1115                1120

Ser Asp Gly Ser Phe Phe Leu Tyr Ser Lys Leu Thr Val Asp Lys Ser
                1125                1130                1135

Arg Trp Gln Gln Gly Asn Val Phe Ser Cys Ser Val Met His Glu Ala
            1140                1145                1150

Leu His Asn His Tyr Thr Gln Lys Ser Leu Ser Leu Ser Pro Gly Lys
        1155                1160                1165

<210> SEQ ID NO 25
<211> LENGTH: 3477
<212> TYPE: DNA
<213> ORGANISM: Homo sapiens
<220> FEATURE:
<221> NAME/KEY: CDS
<222> LOCATION: (1)...(3474)

<400> SEQUENCE: 25 atg gtg gcc gtc ggc tgc gcg ctg ctg gct gcc ctg ctg gcc gcg ccg      48
Met Val Ala Val Gly Cys Ala Leu Leu Ala Ala Leu Leu Ala Ala Pro
  1               5                  10                  15 gga gcg gcg ctg gcc cca agg cgc tgc cct gcg cag gag gtg gca aga      96
Gly Ala Ala Leu Ala Pro Arg Arg Cys Pro Ala Gln Glu Val Ala Arg
             20                  25                  30 ggc gtg ctg acc agt ctg cca gga gac agc gtg act ctg acc tgc ccg     144
Gly Val Leu Thr Ser Leu Pro Gly Asp Ser Val Thr Leu Thr Cys Pro
         35                  40                  45 ggg gta gag ccg gaa gac aat gcc act gtt cac tgg gtg ctc agg aag     192
Gly Val Glu Pro Glu Asp Asn Ala Thr Val His Trp Val Leu Arg Lys
     50                  55                  60 ccg gct gca ggc tcc cac ccc agc aga tgg gct ggc atg gga agg agg     240
Pro Ala Ala Gly Ser His Pro Ser Arg Trp Ala Gly Met Gly Arg Arg
 65                  70                  75                  80 ctg ctg ctg agg tcg gtg cag ctc cac gac tct gga aac tat tca tgc     288
Leu Leu Leu Arg Ser Val Gln Leu His Asp Ser Gly Asn Tyr Ser Cys
                 85                  90                  95 tac cgg gcc ggc cgc cca gct ggg act gtg cac ttg ctg gtg gat gtt     336
Tyr Arg Ala Gly Arg Pro Ala Gly Thr Val His Leu Leu Val Asp Val
            100                 105                 110 ccc ccc gag gag ccc cag ctc tcc tgc ttc cgg aag agc ccc ctc agc     384
Pro Pro Glu Glu Pro Gln Leu Ser Cys Phe Arg Lys Ser Pro Leu Ser
        115                 120                 125 aat gtt gtt tgt gag tgg ggt cct cgg agc acc cca tcc ctg acg aca     432
Asn Val Val Cys Glu Trp Gly Pro Arg Ser Thr Pro Ser Leu Thr Thr
    130                 135                 140 aag gct gtg ctc ttg gtg agg aag ttt cag aac agt ccg gcc gaa gac     480
Lys Ala Val Leu Leu Val Arg Lys Phe Gln Asn Ser Pro Ala Glu Asp
```

```
Lys Ala Val Leu Leu Val Arg Lys Phe Gln Asn Ser Pro Ala Glu Asp
145                 150                 155                 160 ttc cag gag ccg tgc cag tat tcc cag gag tcc cag aag ttc tcc tgc    528
Phe Gln Glu Pro Cys Gln Tyr Ser Gln Glu Ser Gln Lys Phe Ser Cys
                    165                 170                 175 cag tta gca gtc ccg gag gga gac agc tct ttc tac ata gtg tcc atg    576
Gln Leu Ala Val Pro Glu Gly Asp Ser Ser Phe Tyr Ile Val Ser Met
                180                 185                 190 tgc gtc gcc agt agt gtc ggg agc aag ttc agc aaa act caa acc ttt    624
Cys Val Ala Ser Ser Val Gly Ser Lys Phe Ser Lys Thr Gln Thr Phe
            195                 200                 205 cag ggt tgt gga atc ttg cag cct gat ccg cct gcc aac atc aca gtc    672
Gln Gly Cys Gly Ile Leu Gln Pro Asp Pro Pro Ala Asn Ile Thr Val
        210                 215                 220 act gcc gtg gcc aga aac ccc cgc tgg ctc agt gtc acc tgg caa gac    720
Thr Ala Val Ala Arg Asn Pro Arg Trp Leu Ser Val Thr Trp Gln Asp
225                 230                 235                 240 ccc cac tcc tgg aac tca tct ttc tac aga cta cgg ttt gag ctc aga    768
Pro His Ser Trp Asn Ser Ser Phe Tyr Arg Leu Arg Phe Glu Leu Arg
                    245                 250                 255 tat cgg gct gaa cgg tca aag aca ttc aca aca tgg atg gtc aag gac    816
Tyr Arg Ala Glu Arg Ser Lys Thr Phe Thr Thr Trp Met Val Lys Asp
                260                 265                 270 ctc cag cat cac tgt gtc atc cac gac gcc tgg agc ggc ctg agg cac    864
Leu Gln His His Cys Val Ile His Asp Ala Trp Ser Gly Leu Arg His
            275                 280                 285 gtg gtg cag ctt cgt gcc cag gag gag ttc ggg caa ggc gag tgg agc    912
Val Val Gln Leu Arg Ala Gln Glu Glu Phe Gly Gln Gly Glu Trp Ser
        290                 295                 300 gag tgg agc ccg gag gcc atg ggc acg cct tgg aca gaa tcg cga tcg    960
Glu Trp Ser Pro Glu Ala Met Gly Thr Pro Trp Thr Glu Ser Arg Ser
305                 310                 315                 320 cct cca gct gag aac gag gtg tcc acc ccc atg gaa ctt cta gac cca    1008
Pro Pro Ala Glu Asn Glu Val Ser Thr Pro Met Glu Leu Leu Asp Pro
                    325                 330                 335 tgt ggt tat atc agt cct gaa tct cca gtt gta caa ctt cat tct aat    1056
Cys Gly Tyr Ile Ser Pro Glu Ser Pro Val Val Gln Leu His Ser Asn
                340                 345                 350 ttc act gca gtt tgt gtg cta aag gaa aaa tgt atg gat tat ttt cat    1104
Phe Thr Ala Val Cys Val Leu Lys Glu Lys Cys Met Asp Tyr Phe His
            355                 360                 365 gta aat gct aat tac att gtc tgg aaa aca aac cat ttt act att cct    1152
Val Asn Ala Asn Tyr Ile Val Trp Lys Thr Asn His Phe Thr Ile Pro
        370                 375                 380 aag gag caa tat act atc ata aac aga aca gca tcc agt gtc acc ttt    1200
Lys Glu Gln Tyr Thr Ile Ile Asn Arg Thr Ala Ser Ser Val Thr Phe
385                 390                 395                 400 aca gat ata gct tca tta aat att cag ctc act tgc aac att ctt aca    1248
Thr Asp Ile Ala Ser Leu Asn Ile Gln Leu Thr Cys Asn Ile Leu Thr
                    405                 410                 415 ttc gga cag ctt gaa cag aat gtt tat gga atc aca ata att tca ggc    1296
Phe Gly Gln Leu Glu Gln Asn Val Tyr Gly Ile Thr Ile Ile Ser Gly
                420                 425                 430 ttg cct cca gaa aaa cct aaa aat ttg agt tgc att gtg aac gag ggg    1344
Leu Pro Pro Glu Lys Pro Lys Asn Leu Ser Cys Ile Val Asn Glu Gly
            435                 440                 445 aag aaa atg agg tgt gag tgg gat ggt gga agg gaa aca cac ttg gag    1392
Lys Lys Met Arg Cys Glu Trp Asp Gly Gly Arg Glu Thr His Leu Glu
        450                 455                 460
```

-continued

| | | |
|---|---|---|
| aca aac ttc act tta aaa tct gaa tgg gca aca cac aag ttt gct gat<br>Thr Asn Phe Thr Leu Lys Ser Glu Trp Ala Thr His Lys Phe Ala Asp<br>465                         470                         475                         480 | | 1440 |
| tgc aaa gca aaa cgt gac acc ccc acc tca tgc act gtt gat tat tct<br>Cys Lys Ala Lys Arg Asp Thr Pro Thr Ser Cys Thr Val Asp Tyr Ser<br>                         485                         490                         495 | | 1488 |
| act gtg tat ttt gtc aac att gaa gtc tgg gta gaa gca gag aat gcc<br>Thr Val Tyr Phe Val Asn Ile Glu Val Trp Val Glu Ala Glu Asn Ala<br>              500                         505                         510 | | 1536 |
| ctt ggg aag gtt aca tca gat cat atc aat ttt gat cct gta tat aaa<br>Leu Gly Lys Val Thr Ser Asp His Ile Asn Phe Asp Pro Val Tyr Lys<br>                 515                       520                        525 | | 1584 |
| gtg aag ccc aat ccg cca cat aat tta tca gtg atc aac tca gag gaa<br>Val Lys Pro Asn Pro Pro His Asn Leu Ser Val Ile Asn Ser Glu Glu<br>530                         535                         540 | | 1632 |
| ctg tct agt atc tta aaa ttg aca tgg acc aac cca agt att aag agt<br>Leu Ser Ser Ile Leu Lys Leu Thr Trp Thr Asn Pro Ser Ile Lys Ser<br>545                         550                         555                         560 | | 1680 |
| gtt ata ata cta aaa tat aac att caa tat agg acc aaa gat gcc tca<br>Val Ile Ile Leu Lys Tyr Asn Ile Gln Tyr Arg Thr Lys Asp Ala Ser<br>                 565                       570                        575 | | 1728 |
| act tgg agc cag att cct cct gaa gac aca gca tcc acc cga tct tca<br>Thr Trp Ser Gln Ile Pro Pro Glu Asp Thr Ala Ser Thr Arg Ser Ser<br>              580                       585                        590 | | 1776 |
| ttc act gtc caa gac ctt aaa cct ttt aca gaa tat gtg ttt agg att<br>Phe Thr Val Gln Asp Leu Lys Pro Phe Thr Glu Tyr Val Phe Arg Ile<br>                 595                       600                        605 | | 1824 |
| cgc tgt atg aag gaa gat ggt aag gga tac tgg agt gac tgg agt gaa<br>Arg Cys Met Lys Glu Asp Gly Lys Gly Tyr Trp Ser Asp Trp Ser Glu<br>610                         615                         620 | | 1872 |
| gaa gca agt ggg atc acc tat gaa gat aga cca tct aaa gca cca agt<br>Glu Ala Ser Gly Ile Thr Tyr Glu Asp Arg Pro Ser Lys Ala Pro Ser<br>625                         630                         635                         640 | | 1920 |
| ttc tgg tat aaa ata gat cca tcc cat act caa ggc tac aga act gta<br>Phe Trp Tyr Lys Ile Asp Pro Ser His Thr Gln Gly Tyr Arg Thr Val<br>                 645                       650                        655 | | 1968 |
| caa ctc gtg tgg aag aca ttg cct cct ttt gaa gcc aat gga aaa atc<br>Gln Leu Val Trp Lys Thr Leu Pro Pro Phe Glu Ala Asn Gly Lys Ile<br>              660                       665                        670 | | 2016 |
| ttg gat tat gaa gtg act ctc aca aga tgg aaa tca cat tta caa aat<br>Leu Asp Tyr Glu Val Thr Leu Thr Arg Trp Lys Ser His Leu Gln Asn<br>               675                       680                        685 | | 2064 |
| tac aca gtt aat gcc aca aaa ctg aca gta aat ctc aca aat gat cgc<br>Tyr Thr Val Asn Ala Thr Lys Leu Thr Val Asn Leu Thr Asn Asp Arg<br>690                         695                         700 | | 2112 |
| tat cta gca acc tta aca gta aga aat ctt gtt ggc aaa tca gat gca<br>Tyr Leu Ala Thr Leu Thr Val Arg Asn Leu Val Gly Lys Ser Asp Ala<br>705                         710                         715                         720 | | 2160 |
| gct gtt tta act atc cct gcc tgt gac ttt caa gct act cac cct gta<br>Ala Val Leu Thr Ile Pro Ala Cys Asp Phe Gln Ala Thr His Pro Val<br>                        725                       730                        735 | | 2208 |
| atg gat ctt aaa gca ttc ccc aaa gat aac atg ctt tgg gtg gaa tgg<br>Met Asp Leu Lys Ala Phe Pro Lys Asp Asn Met Leu Trp Val Glu Trp<br>              740                       745                        750 | | 2256 |
| act act cca agg gaa tct gta aag aaa tat ata ctt gag tgg tgt gtg<br>Thr Thr Pro Arg Glu Ser Val Lys Lys Tyr Ile Leu Glu Trp Cys Val<br>                        755                       760                        765 | | 2304 |
| tta tca gat aaa gca ccc tgt atc aca gac tgg caa caa gaa gat ggt<br>Leu Ser Asp Lys Ala Pro Cys Ile Thr Asp Trp Gln Gln Glu Asp Gly<br>770                         775                         780 | | 2352 |

```
acc gtg cat cgc acc tat tta aga ggg aac tta gca gag agc aaa tgc      2400
Thr Val His Arg Thr Tyr Leu Arg Gly Asn Leu Ala Glu Ser Lys Cys
785                 790                 795                 800 tat ttg ata aca gtt act cca gta tat gct gat gga cca gga agc cct      2448
Tyr Leu Ile Thr Val Thr Pro Val Tyr Ala Asp Gly Pro Gly Ser Pro
            805                 810                 815 gaa tcc ata aag gca tac ctt aaa caa gct cca cct tcc aaa gga cct      2496
Glu Ser Ile Lys Ala Tyr Leu Lys Gln Ala Pro Pro Ser Lys Gly Pro
        820                 825                 830 act gtt cgg aca aaa aaa gta ggg aaa aac gaa gct gtc tta gag tgg      2544
Thr Val Arg Thr Lys Lys Val Gly Lys Asn Glu Ala Val Leu Glu Trp
    835                 840                 845 gac caa ctt cct gtt gat gtt cag aat gga ttt atc aga aat tat act      2592
Asp Gln Leu Pro Val Asp Val Gln Asn Gly Phe Ile Arg Asn Tyr Thr
850                 855                 860 ata ttt tat aga acc atc att gga aat gaa act gct gtg aat gtg gat      2640
Ile Phe Tyr Arg Thr Ile Ile Gly Asn Glu Thr Ala Val Asn Val Asp
865                 870                 875                 880 tct tcc cac aca gaa tat aca ttg tcc tct ttg act agt gac aca ttg      2688
Ser Ser His Thr Glu Tyr Thr Leu Ser Ser Leu Thr Ser Asp Thr Leu
                885                 890                 895 tac atg gta cga atg gca gca tac aca gat gaa ggt ggg aag gat ggt      2736
Tyr Met Val Arg Met Ala Ala Tyr Thr Asp Glu Gly Gly Lys Asp Gly
            900                 905                 910 cca gaa ttc act ttt act acc cca aag ttt gct caa gga gaa att gaa      2784
Pro Glu Phe Thr Phe Thr Thr Pro Lys Phe Ala Gln Gly Glu Ile Glu
        915                 920                 925 tcc ggg ggc gac aaa act cac aca tgc cca ccg tgc cca gca cct gaa      2832
Ser Gly Gly Asp Lys Thr His Thr Cys Pro Pro Cys Pro Ala Pro Glu
    930                 935                 940 ctc ctg ggg gga ccg tca gtc ttc ctc ttc ccc cca aaa ccc aag gac      2880
Leu Leu Gly Gly Pro Ser Val Phe Leu Phe Pro Pro Lys Pro Lys Asp
945                 950                 955                 960 acc ctc atg atc tcc cgg acc cct gag gtc aca tgc gtg gtg gtg gac      2928
Thr Leu Met Ile Ser Arg Thr Pro Glu Val Thr Cys Val Val Val Asp
                965                 970                 975 gtg agc cac gaa gac cct gag gtc aag ttc aac tgg tac gtg gac ggc      2976
Val Ser His Glu Asp Pro Glu Val Lys Phe Asn Trp Tyr Val Asp Gly
            980                 985                 990 gtg gag gtg cat aat gcc aag aca aag ccg cgg gag gag cag tac aac      3024
Val Glu Val His Asn Ala Lys Thr Lys Pro Arg Glu Glu Gln Tyr Asn
        995                 1000                1005 agc acg tac cgt gtg gtc agc gtc ctc acc gtc ctg cac cag gac tgg      3072
Ser Thr Tyr Arg Val Val Ser Val Leu Thr Val Leu His Gln Asp Trp
    1010                1015                1020 ctg aat ggc aag gag tac aag tgc aag gtc tcc aac aaa gcc ctc cca      3120
Leu Asn Gly Lys Glu Tyr Lys Cys Lys Val Ser Asn Lys Ala Leu Pro
1025                1030                1035                1040 gcc ccc atc gag aaa acc atc tcc aaa gcc aaa ggg cag ccc cga gaa      3168
Ala Pro Ile Glu Lys Thr Ile Ser Lys Ala Lys Gly Gln Pro Arg Glu
                1045                1050                1055 cca cag gtg tac acc ctg ccc cca tcc cgg gat gag ctg acc aag aac      3216
Pro Gln Val Tyr Thr Leu Pro Pro Ser Arg Asp Glu Leu Thr Lys Asn
            1060                1065                1070 cag gtc agc ctg acc tgc ctg gtc aaa ggc ttc tat ccc agc gac atc      3264
Gln Val Ser Leu Thr Cys Leu Val Lys Gly Phe Tyr Pro Ser Asp Ile
        1075                1080                1085 gcc gtg gag tgg gag agc aat ggg cag ccg gag aac aac tac aag acc      3312
Ala Val Glu Trp Glu Ser Asn Gly Gln Pro Glu Asn Asn Tyr Lys Thr
```

-continued

```
              1090                 1095                1100
acg cct ccc gtg ctg gac tcc gac ggc tcc ttc ttc ctc tac agc aag     3360
Thr Pro Pro Val Leu Asp Ser Asp Gly Ser Phe Phe Leu Tyr Ser Lys
1105                1110                1115                1120 ctc acc gtg gac aag agc agg tgg cag cag ggg aac gtc ttc tca tgc     3408
Leu Thr Val Asp Lys Ser Arg Trp Gln Gln Gly Asn Val Phe Ser Cys
                1125                1130                1135 tcc gtg atg cat gag gct ctg cac aac cac tac acg cag aag agc ctc     3456
Ser Val Met His Glu Ala Leu His Asn His Tyr Thr Gln Lys Ser Leu
            1140                1145                1150 tcc ctg tct ccg ggt aaa tga                                         3477
Ser Leu Ser Pro Gly Lys
        1155

<210> SEQ ID NO 26
<211> LENGTH: 1158
<212> TYPE: PRT
<213> ORGANISM: Homo sapiens

<400> SEQUENCE: 26

Met Val Ala Val Gly Cys Ala Leu Leu Ala Ala Leu Leu Ala Ala Pro
 1               5                  10                  15

Gly Ala Ala Leu Ala Pro Arg Arg Cys Pro Ala Gln Glu Val Ala Arg
            20                  25                  30

Gly Val Leu Thr Ser Leu Pro Gly Asp Ser Val Thr Leu Thr Cys Pro
        35                  40                  45

Gly Val Glu Pro Glu Asp Asn Ala Thr Val His Trp Val Leu Arg Lys
    50                  55                  60

Pro Ala Ala Gly Ser His Pro Ser Arg Trp Ala Gly Met Gly Arg Arg
65                  70                  75                  80

Leu Leu Leu Arg Ser Val Gln Leu His Asp Ser Gly Asn Tyr Ser Cys
                85                  90                  95

Tyr Arg Ala Gly Arg Pro Ala Gly Thr Val His Leu Leu Val Asp Val
            100                 105                 110

Pro Pro Glu Glu Pro Gln Leu Ser Cys Phe Arg Lys Ser Pro Leu Ser
        115                 120                 125

Asn Val Val Cys Glu Trp Gly Pro Arg Ser Thr Pro Ser Leu Thr Thr
    130                 135                 140

Lys Ala Val Leu Leu Val Arg Lys Phe Gln Asn Ser Pro Ala Glu Asp
145                 150                 155                 160

Phe Gln Glu Pro Cys Gln Tyr Ser Gln Glu Ser Gln Lys Phe Ser Cys
                165                 170                 175

Gln Leu Ala Val Pro Glu Gly Asp Ser Ser Phe Tyr Ile Val Ser Met
            180                 185                 190

Cys Val Ala Ser Ser Val Gly Ser Lys Phe Ser Lys Thr Gln Thr Phe
        195                 200                 205

Gln Gly Cys Gly Ile Leu Gln Pro Asp Pro Ala Asn Ile Thr Val
    210                 215                 220

Thr Ala Val Ala Arg Asn Pro Arg Trp Leu Ser Val Thr Trp Gln Asp
225                 230                 235                 240

Pro His Ser Trp Asn Ser Ser Phe Tyr Arg Leu Arg Phe Glu Leu Arg
                245                 250                 255

Tyr Arg Ala Glu Arg Ser Lys Thr Phe Thr Thr Trp Met Val Lys Asp
            260                 265                 270

Leu Gln His His Cys Val Ile His Asp Ala Trp Ser Gly Leu Arg His
        275                 280                 285
```

-continued

Val Val Gln Leu Arg Ala Gln Glu Glu Phe Gly Gln Gly Glu Trp Ser
290                 295                 300

Glu Trp Ser Pro Glu Ala Met Gly Thr Pro Trp Thr Glu Ser Arg Ser
305                 310                 315                 320

Pro Pro Ala Glu Asn Glu Val Ser Thr Pro Met Glu Leu Leu Asp Pro
            325                 330                 335

Cys Gly Tyr Ile Ser Pro Glu Ser Pro Val Val Gln Leu His Ser Asn
            340                 345                 350

Phe Thr Ala Val Cys Val Leu Lys Glu Lys Cys Met Asp Tyr Phe His
            355                 360                 365

Val Asn Ala Asn Tyr Ile Val Trp Lys Thr Asn His Phe Thr Ile Pro
370                 375                 380

Lys Glu Gln Tyr Thr Ile Ile Asn Arg Thr Ala Ser Ser Val Thr Phe
385                 390                 395                 400

Thr Asp Ile Ala Ser Leu Asn Ile Gln Leu Thr Cys Asn Ile Leu Thr
            405                 410                 415

Phe Gly Gln Leu Glu Gln Asn Val Tyr Gly Ile Thr Ile Ile Ser Gly
            420                 425                 430

Leu Pro Pro Glu Lys Pro Lys Asn Leu Ser Cys Ile Val Asn Glu Gly
            435                 440                 445

Lys Lys Met Arg Cys Glu Trp Asp Gly Gly Arg Glu Thr His Leu Glu
450                 455                 460

Thr Asn Phe Thr Leu Lys Ser Glu Trp Ala Thr His Lys Phe Ala Asp
465                 470                 475                 480

Cys Lys Ala Lys Arg Asp Thr Pro Thr Ser Cys Thr Val Asp Tyr Ser
            485                 490                 495

Thr Val Tyr Phe Val Asn Ile Glu Val Trp Val Glu Ala Glu Asn Ala
            500                 505                 510

Leu Gly Lys Val Thr Ser Asp His Ile Asn Phe Asp Pro Val Tyr Lys
            515                 520                 525

Val Lys Pro Asn Pro Pro His Asn Leu Ser Val Ile Asn Ser Glu Glu
530                 535                 540

Leu Ser Ser Ile Leu Lys Leu Thr Trp Thr Asn Pro Ser Ile Lys Ser
545                 550                 555                 560

Val Ile Ile Leu Lys Tyr Asn Ile Gln Tyr Arg Thr Lys Asp Ala Ser
            565                 570                 575

Thr Trp Ser Gln Ile Pro Pro Glu Asp Thr Ala Ser Thr Arg Ser Ser
            580                 585                 590

Phe Thr Val Gln Asp Leu Lys Pro Phe Thr Glu Tyr Val Phe Arg Ile
            595                 600                 605

Arg Cys Met Lys Glu Asp Gly Lys Gly Tyr Trp Ser Asp Trp Ser Glu
            610                 615                 620

Glu Ala Ser Gly Ile Thr Tyr Glu Asp Arg Pro Ser Lys Ala Pro Ser
625                 630                 635                 640

Phe Trp Tyr Lys Ile Asp Pro Ser His Thr Gln Gly Tyr Arg Thr Val
            645                 650                 655

Gln Leu Val Trp Lys Thr Leu Pro Pro Phe Glu Ala Asn Gly Lys Ile
            660                 665                 670

Leu Asp Tyr Glu Val Thr Leu Thr Arg Trp Lys Ser His Leu Gln Asn
            675                 680                 685

Tyr Thr Val Asn Ala Thr Lys Leu Thr Val Asn Leu Thr Asn Asp Arg
690                 695                 700

```
                                        -continued

Tyr Leu Ala Thr Leu Thr Val Arg Asn Leu Val Gly Lys Ser Asp Ala
705                 710                 715                 720

Ala Val Leu Thr Ile Pro Ala Cys Asp Phe Gln Ala Thr His Pro Val
                725                 730                 735

Met Asp Leu Lys Ala Phe Pro Lys Asp Asn Met Leu Trp Val Glu Trp
            740                 745                 750

Thr Thr Pro Arg Glu Ser Val Lys Lys Tyr Ile Leu Glu Trp Cys Val
        755                 760                 765

Leu Ser Asp Lys Ala Pro Cys Ile Thr Asp Trp Gln Gln Glu Asp Gly
    770                 775                 780

Thr Val His Arg Thr Tyr Leu Arg Gly Asn Leu Ala Glu Ser Lys Cys
785                 790                 795                 800

Tyr Leu Ile Thr Val Thr Pro Val Tyr Ala Asp Gly Pro Gly Ser Pro
                805                 810                 815

Glu Ser Ile Lys Ala Tyr Leu Lys Gln Ala Pro Pro Ser Lys Gly Pro
            820                 825                 830

Thr Val Arg Thr Lys Lys Val Gly Lys Asn Glu Ala Val Leu Glu Trp
        835                 840                 845

Asp Gln Leu Pro Val Asp Val Gln Asn Gly Phe Ile Arg Asn Tyr Thr
    850                 855                 860

Ile Phe Tyr Arg Thr Ile Ile Gly Asn Glu Thr Ala Val Asn Val Asp
865                 870                 875                 880

Ser Ser His Thr Glu Tyr Thr Leu Ser Ser Leu Thr Ser Asp Thr Leu
                885                 890                 895

Tyr Met Val Arg Met Ala Ala Tyr Thr Asp Glu Gly Gly Lys Asp Gly
            900                 905                 910

Pro Glu Phe Thr Phe Thr Thr Pro Lys Phe Ala Gln Gly Glu Ile Glu
        915                 920                 925

Ser Gly Gly Asp Lys Thr His Thr Cys Pro Pro Cys Pro Ala Pro Glu
    930                 935                 940

Leu Leu Gly Gly Pro Ser Val Phe Leu Phe Pro Pro Lys Pro Lys Asp
945                 950                 955                 960

Thr Leu Met Ile Ser Arg Thr Pro Glu Val Thr Cys Val Val Val Asp
                965                 970                 975

Val Ser His Glu Asp Pro Glu Val Lys Phe Asn Trp Tyr Val Asp Gly
            980                 985                 990

Val Glu Val His Asn Ala Lys Thr Lys Pro Arg Glu Glu Gln Tyr Asn
        995                 1000                1005

Ser Thr Tyr Arg Val Val Ser Val Leu Thr Val Leu His Gln Asp Trp
    1010                1015                1020

Leu Asn Gly Lys Glu Tyr Lys Cys Lys Val Ser Asn Lys Ala Leu Pro
1025                1030                1035                1040

Ala Pro Ile Glu Lys Thr Ile Ser Lys Ala Lys Gly Gln Pro Arg Glu
                1045                1050                1055

Pro Gln Val Tyr Thr Leu Pro Pro Ser Arg Asp Glu Leu Thr Lys Asn
            1060                1065                1070

Gln Val Ser Leu Thr Cys Leu Val Lys Gly Phe Tyr Pro Ser Asp Ile
        1075                1080                1085

Ala Val Glu Trp Glu Ser Asn Gly Gln Pro Glu Asn Asn Tyr Lys Thr
    1090                1095                1100

Thr Pro Pro Val Leu Asp Ser Asp Gly Ser Phe Phe Leu Tyr Ser Lys
1105                1110                1115                1120

Leu Thr Val Asp Lys Ser Arg Trp Gln Gln Gly Asn Val Phe Ser Cys
```

```
                    1125                1130                1135
Ser Val Met His Glu Ala Leu His Asn His Tyr Thr Gln Lys Ser Leu
            1140                1145                1150

Ser Leu Ser Pro Gly Lys
        1155

<210> SEQ ID NO 27
<211> LENGTH: 2733
<212> TYPE: DNA
<213> ORGANISM: Homo sapiens
<220> FEATURE:
<221> NAME/KEY: CDS
<222> LOCATION: (1)...(2730)

<400> SEQUENCE: 27 atg gtg ctt ctg tgg tgt gta gtg agt ctc tac ttt tat gga atc ctg      48
Met Val Leu Leu Trp Cys Val Val Ser Leu Tyr Phe Tyr Gly Ile Leu
  1               5                  10                  15 caa agt gat gcc tca gaa cgc tgc gat gac tgg gga cta gac acc atg      96
Gln Ser Asp Ala Ser Glu Arg Cys Asp Asp Trp Gly Leu Asp Thr Met
             20                  25                  30 agg caa atc caa gtg ttt gaa gat gag cca gct cgc atc aag tgc cca     144
Arg Gln Ile Gln Val Phe Glu Asp Glu Pro Ala Arg Ile Lys Cys Pro
         35                  40                  45 ctc ttt gaa cac ttc ttg aaa ttc aac tac agc aca gcc cat tca gct     192
Leu Phe Glu His Phe Leu Lys Phe Asn Tyr Ser Thr Ala His Ser Ala
     50                  55                  60 ggc ctt act ctg atc tgg tat tgg act agg cag gac cgg gac ctt gag     240
Gly Leu Thr Leu Ile Trp Tyr Trp Thr Arg Gln Asp Arg Asp Leu Glu
 65                  70                  75                  80 gag cca att aac ttc cgc ctc ccc gag aac cgc att agt aag gag aaa     288
Glu Pro Ile Asn Phe Arg Leu Pro Glu Asn Arg Ile Ser Lys Glu Lys
                 85                  90                  95 gat gtg ctg tgg ttc cgg ccc act ctc ctc aat gac act ggc aac tat     336
Asp Val Leu Trp Phe Arg Pro Thr Leu Leu Asn Asp Thr Gly Asn Tyr
            100                 105                 110 acc tgc atg tta agg aac act aca tat tgc agc aaa gtt gca ttt ccc     384
Thr Cys Met Leu Arg Asn Thr Thr Tyr Cys Ser Lys Val Ala Phe Pro
        115                 120                 125 ttg gaa gtt gtt caa aaa gac agc tgt ttc aat tcc ccc atg aaa ctc     432
Leu Glu Val Val Gln Lys Asp Ser Cys Phe Asn Ser Pro Met Lys Leu
    130                 135                 140 cca gtg cat aaa ctg tat ata gaa tat ggc att cag agg atc act tgt     480
Pro Val His Lys Leu Tyr Ile Glu Tyr Gly Ile Gln Arg Ile Thr Cys
145                 150                 155                 160 cca aat gta gat gga tat ttt cct tcc agt gtc aaa ccg act atc act     528
Pro Asn Val Asp Gly Tyr Phe Pro Ser Ser Val Lys Pro Thr Ile Thr
                165                 170                 175 tgg tat atg ggc tgt tat aaa ata cag aat ttt aat aat gta ata ccc     576
Trp Tyr Met Gly Cys Tyr Lys Ile Gln Asn Phe Asn Asn Val Ile Pro
            180                 185                 190 gaa ggt atg aac ttg agt ttc ctc att gcc tta att tca aat aat gga     624
Glu Gly Met Asn Leu Ser Phe Leu Ile Ala Leu Ile Ser Asn Asn Gly
        195                 200                 205 aat tac aca tgt gtt gtt aca tat cca gaa aat gga cgt acg ttt cat     672
Asn Tyr Thr Cys Val Val Thr Tyr Pro Glu Asn Gly Arg Thr Phe His
    210                 215                 220 ctc acc agg act ctg act gta aag gta gta ggc tct cca aaa aat gca     720
Leu Thr Arg Thr Leu Thr Val Lys Val Val Gly Ser Pro Lys Asn Ala
225                 230                 235                 240
```

-continued

| | |
|---|---|
| gtg ccc cct gtg atc cat tca cct aat gat cat gtg gtc tat gag aaa<br>Val Pro Pro Val Ile His Ser Pro Asn Asp His Val Val Tyr Glu Lys<br>245 250 255 | 768 |
| gaa cca gga gag gag cta ctc att ccc tgt acg gtc tat ttt agt ttt<br>Glu Pro Gly Glu Glu Leu Leu Ile Pro Cys Thr Val Tyr Phe Ser Phe<br>260 265 270 | 816 |
| ctg atg gat tct cgc aat gag gtt tgg tgg acc att gat gga aaa aaa<br>Leu Met Asp Ser Arg Asn Glu Val Trp Trp Thr Ile Asp Gly Lys Lys<br>275 280 285 | 864 |
| cct gat gac atc act att gat gtc acc att aac gaa agt ata agt cat<br>Pro Asp Asp Ile Thr Ile Asp Val Thr Ile Asn Glu Ser Ile Ser His<br>290 295 300 | 912 |
| agt aga aca gaa gat gaa aca aga act cag att ttg agc atc aag aaa<br>Ser Arg Thr Glu Asp Glu Thr Arg Thr Gln Ile Leu Ser Ile Lys Lys<br>305 310 315 320 | 960 |
| gtt acc tct gag gat ctc aag cgc agc tat gtc tgt cat gct aga agt<br>Val Thr Ser Glu Asp Leu Lys Arg Ser Tyr Val Cys His Ala Arg Ser<br>325 330 335 | 1008 |
| gcc aaa ggc gaa gtt gcc aaa gca gcc aag gtg aag cag aaa gtg cca<br>Ala Lys Gly Glu Val Ala Lys Ala Ala Lys Val Lys Gln Lys Val Pro<br>340 345 350 | 1056 |
| gct cca aga tac aca gtg tcc ggt ggc gcg cct atg ctg agc gag gct<br>Ala Pro Arg Tyr Thr Val Ser Gly Gly Ala Pro Met Leu Ser Glu Ala<br>355 360 365 | 1104 |
| gat aaa tgc aag gaa cgt gaa gaa aaa ata att tta gtg tca tct gca<br>Asp Lys Cys Lys Glu Arg Glu Glu Lys Ile Ile Leu Val Ser Ser Ala<br>370 375 380 | 1152 |
| aat gaa att gat gtt cgt ccc tgt cct ctt aac cca aat gaa cac aaa<br>Asn Glu Ile Asp Val Arg Pro Cys Pro Leu Asn Pro Asn Glu His Lys<br>385 390 395 400 | 1200 |
| ggc act ata act tgg tat aag gat gac agc aag aca cct gta tct aca<br>Gly Thr Ile Thr Trp Tyr Lys Asp Asp Ser Lys Thr Pro Val Ser Thr<br>405 410 415 | 1248 |
| gaa caa gcc tcc agg att cat caa cac aaa gag aaa ctt tgg ttt gtt<br>Glu Gln Ala Ser Arg Ile His Gln His Lys Glu Lys Leu Trp Phe Val<br>420 425 430 | 1296 |
| cct gct aag gtg gag gat tca gga cat tac tat tgc gtg gta aga aat<br>Pro Ala Lys Val Glu Asp Ser Gly His Tyr Tyr Cys Val Val Arg Asn<br>435 440 445 | 1344 |
| tca tct tac tgc ctc aga att aaa ata agt gca aaa ttt gtg gag aat<br>Ser Ser Tyr Cys Leu Arg Ile Lys Ile Ser Ala Lys Phe Val Glu Asn<br>450 455 460 | 1392 |
| gag cct aac tta tgt tat aat gca caa gcc ata ttt aag cag aaa cta<br>Glu Pro Asn Leu Cys Tyr Asn Ala Gln Ala Ile Phe Lys Gln Lys Leu<br>465 470 475 480 | 1440 |
| ccc gtt gca gga gac gga gga ctt gtg tgc cct tat atg gag ttt ttt<br>Pro Val Ala Gly Asp Gly Gly Leu Val Cys Pro Tyr Met Glu Phe Phe<br>485 490 495 | 1488 |
| aaa aat gaa aat aat gag tta cct aaa tta cag tgg tat aag gat tgc<br>Lys Asn Glu Asn Asn Glu Leu Pro Lys Leu Gln Trp Tyr Lys Asp Cys<br>500 505 510 | 1536 |
| aaa cct cta ctt ctt gac aat ata cac ttt agt gga gtc aaa gat agg<br>Lys Pro Leu Leu Leu Asp Asn Ile His Phe Ser Gly Val Lys Asp Arg<br>515 520 525 | 1584 |
| ctc atc gtg atg aat gtg gct gaa aag cat aga ggg aac tat act tgt<br>Leu Ile Val Met Asn Val Ala Glu Lys His Arg Gly Asn Tyr Thr Cys<br>530 535 540 | 1632 |
| cat gca tcc tac aca tac ttg ggc aag caa tat cct att acc cgg gta<br>His Ala Ser Tyr Thr Tyr Leu Gly Lys Gln Tyr Pro Ile Thr Arg Val<br>545 550 555 560 | 1680 |

```
ata gaa ttt att act cta gag gaa aac aaa ccc aca agg cct gtg att      1728
Ile Glu Phe Ile Thr Leu Glu Glu Asn Lys Pro Thr Arg Pro Val Ile
            565                 570                 575 gtg agc cca gct aat gag aca atg gaa gta gac ttg gga tcc cag ata      1776
Val Ser Pro Ala Asn Glu Thr Met Glu Val Asp Leu Gly Ser Gln Ile
        580                 585                 590 caa ttg atc tgt aat gtc acc ggc cag ttg agt gac att gct tac tgg      1824
Gln Leu Ile Cys Asn Val Thr Gly Gln Leu Ser Asp Ile Ala Tyr Trp
    595                 600                 605 aag tgg aat ggg tca gta att gat gaa gat gac cca gtg cta ggg gaa      1872
Lys Trp Asn Gly Ser Val Ile Asp Glu Asp Asp Pro Val Leu Gly Glu
610                 615                 620 gac tat tac agt gtg gaa aat cct gca aac aaa aga agg agt acc ctc      1920
Asp Tyr Tyr Ser Val Glu Asn Pro Ala Asn Lys Arg Arg Ser Thr Leu
625                 630                 635                 640 atc aca gtg ctt aat ata tcg gaa att gag agt aga ttt tat aaa cat      1968
Ile Thr Val Leu Asn Ile Ser Glu Ile Glu Ser Arg Phe Tyr Lys His
                645                 650                 655 cca ttt acc tgt ttt gcc aag aat aca cat ggt ata gat gca gca tat      2016
Pro Phe Thr Cys Phe Ala Lys Asn Thr His Gly Ile Asp Ala Ala Tyr
            660                 665                 670 atc cag tta ata tat cca gtc act aat tcc gga gac aaa act cac aca      2064
Ile Gln Leu Ile Tyr Pro Val Thr Asn Ser Gly Asp Lys Thr His Thr
        675                 680                 685 tgc cca ccg tgc cca gca cct gaa ctc ctg ggg gga ccg tca gtc ttc      2112
Cys Pro Pro Cys Pro Ala Pro Glu Leu Leu Gly Gly Pro Ser Val Phe
    690                 695                 700 ctc ttc ccc cca aaa ccc aag gac acc ctc atg atc tcc cgg acc cct      2160
Leu Phe Pro Pro Lys Pro Lys Asp Thr Leu Met Ile Ser Arg Thr Pro
705                 710                 715                 720 gag gtc aca tgc gtg gtg gtg gac gtg agc cac gaa gac cct gag gtc      2208
Glu Val Thr Cys Val Val Val Asp Val Ser His Glu Asp Pro Glu Val
                725                 730                 735 aag ttc aac tgg tac gtg gac ggc gtg gag gtg cat aat gcc aag aca      2256
Lys Phe Asn Trp Tyr Val Asp Gly Val Glu Val His Asn Ala Lys Thr
            740                 745                 750 aag ccg cgg gag gag cag tac aac agc acg tac cgt gtg gtc agc gtc      2304
Lys Pro Arg Glu Glu Gln Tyr Asn Ser Thr Tyr Arg Val Val Ser Val
        755                 760                 765 ctc acc gtc ctg cac cag gac tgg ctg aat ggc aag gag tac aag tgc      2352
Leu Thr Val Leu His Gln Asp Trp Leu Asn Gly Lys Glu Tyr Lys Cys
    770                 775                 780 aag gtc tcc aac aaa gcc ctc cca gcc ccc atc gag aaa acc atc tcc      2400
Lys Val Ser Asn Lys Ala Leu Pro Ala Pro Ile Glu Lys Thr Ile Ser
785                 790                 795                 800 aaa gcc aaa ggg cag ccc cga gaa cca cag gtg tac acc ctg ccc cca      2448
Lys Ala Lys Gly Gln Pro Arg Glu Pro Gln Val Tyr Thr Leu Pro Pro
                805                 810                 815 tcc cgg gag gag atg acc aag aac cag gtc agc ctg acc tgc ctg gtc      2496
Ser Arg Glu Glu Met Thr Lys Asn Gln Val Ser Leu Thr Cys Leu Val
            820                 825                 830 aaa ggc ttc tat ccc agc gac atc gcc gtg gag tgg gag agc aat ggg      2544
Lys Gly Phe Tyr Pro Ser Asp Ile Ala Val Glu Trp Glu Ser Asn Gly
        835                 840                 845 cag ccg gag aac aac tac aag acc acg cct ccc gtg ctg gac tcc gac      2592
Gln Pro Glu Asn Asn Tyr Lys Thr Thr Pro Pro Val Leu Asp Ser Asp
    850                 855                 860 ggc tcc ttc ttc ctc tat agc aag ctc acc gtg gac aag agc agg tgg      2640
Gly Ser Phe Phe Leu Tyr Ser Lys Leu Thr Val Asp Lys Ser Arg Trp
```

|  |  |  |  |  | 865 |  |  |  |  | 870 |  |  |  |  | 875 |  |  |  |  | 880 |  |  |
|---|---|---|---|---|---|---|---|---|---|---|---|---|---|---|---|---|---|---|---|---|---|---|---|

```
cag cag ggg aac gtc ttc tca tgc tcc gtg atg cat gag gct ctg cac         2688
Gln Gln Gly Asn Val Phe Ser Cys Ser Val Met His Glu Ala Leu His
                885                 890                 895 aac cac tac acg cag aag agc ctc tcc ctg tct ccg ggt aaa                 2730
Asn His Tyr Thr Gln Lys Ser Leu Ser Leu Ser Pro Gly Lys
            900                 905                 910 tga                                                                     2733

<210> SEQ ID NO 28
<211> LENGTH: 910
<212> TYPE: PRT
<213> ORGANISM: Homo sapiens

<400> SEQUENCE: 28

Met Val Leu Leu Trp Cys Val Val Ser Leu Tyr Phe Tyr Gly Ile Leu
 1               5                  10                  15

Gln Ser Asp Ala Ser Glu Arg Cys Asp Asp Trp Gly Leu Asp Thr Met
                20                  25                  30

Arg Gln Ile Gln Val Phe Glu Asp Glu Pro Ala Arg Ile Lys Cys Pro
            35                  40                  45

Leu Phe Glu His Phe Leu Lys Phe Asn Tyr Ser Thr Ala His Ser Ala
        50                  55                  60

Gly Leu Thr Leu Ile Trp Tyr Trp Thr Arg Gln Asp Arg Asp Leu Glu
65                  70                  75                  80

Glu Pro Ile Asn Phe Arg Leu Pro Glu Asn Arg Ile Ser Lys Glu Lys
                85                  90                  95

Asp Val Leu Trp Phe Arg Pro Thr Leu Leu Asn Asp Thr Gly Asn Tyr
            100                 105                 110

Thr Cys Met Leu Arg Asn Thr Thr Tyr Cys Ser Lys Val Ala Phe Pro
        115                 120                 125

Leu Glu Val Val Gln Lys Asp Ser Cys Phe Asn Ser Pro Met Lys Leu
    130                 135                 140

Pro Val His Lys Leu Tyr Ile Glu Tyr Gly Ile Gln Arg Ile Thr Cys
145                 150                 155                 160

Pro Asn Val Asp Gly Tyr Phe Pro Ser Val Lys Pro Thr Ile Thr
                165                 170                 175

Trp Tyr Met Gly Cys Tyr Lys Ile Gln Asn Phe Asn Asn Val Ile Pro
            180                 185                 190

Glu Gly Met Asn Leu Ser Phe Leu Ile Ala Leu Ile Ser Asn Asn Gly
        195                 200                 205

Asn Tyr Thr Cys Val Val Thr Tyr Pro Glu Asn Gly Arg Thr Phe His
    210                 215                 220

Leu Thr Arg Thr Leu Thr Val Lys Val Val Gly Ser Pro Lys Asn Ala
225                 230                 235                 240

Val Pro Pro Val Ile His Ser Pro Asn Asp His Val Val Tyr Glu Lys
                245                 250                 255

Glu Pro Gly Glu Glu Leu Leu Ile Pro Cys Thr Val Tyr Phe Ser Phe
            260                 265                 270

Leu Met Asp Ser Arg Asn Glu Val Trp Trp Thr Ile Asp Gly Lys Lys
        275                 280                 285

Pro Asp Asp Ile Thr Ile Asp Val Thr Ile Asn Glu Ser Ile Ser His
    290                 295                 300

Ser Arg Thr Glu Asp Glu Thr Arg Thr Gln Ile Leu Ser Ile Lys Lys
305                 310                 315                 320
```

-continued

Val Thr Ser Glu Asp Leu Lys Arg Ser Tyr Val Cys His Ala Arg Ser
            325                 330                 335

Ala Lys Gly Glu Val Ala Lys Ala Lys Val Lys Gln Lys Val Pro
        340                 345                 350

Ala Pro Arg Tyr Thr Val Ser Gly Ala Pro Met Leu Ser Glu Ala
        355                 360                 365

Asp Lys Cys Lys Glu Arg Glu Lys Ile Ile Leu Val Ser Ser Ala
    370                 375                 380

Asn Glu Ile Asp Val Arg Pro Cys Pro Leu Asn Pro Asn Glu His Lys
385                 390                 395                 400

Gly Thr Ile Thr Trp Tyr Lys Asp Asp Ser Lys Thr Pro Val Ser Thr
                405                 410                 415

Glu Gln Ala Ser Arg Ile His Gln His Lys Glu Lys Leu Trp Phe Val
                420                 425                 430

Pro Ala Lys Val Glu Asp Ser Gly His Tyr Tyr Cys Val Val Arg Asn
            435                 440                 445

Ser Ser Tyr Cys Leu Arg Ile Lys Ile Ser Ala Lys Phe Val Glu Asn
450                 455                 460

Glu Pro Asn Leu Cys Tyr Asn Ala Gln Ala Ile Phe Lys Gln Lys Leu
465                 470                 475                 480

Pro Val Ala Gly Asp Gly Gly Leu Val Cys Pro Tyr Met Glu Phe Phe
                485                 490                 495

Lys Asn Glu Asn Asn Glu Leu Pro Lys Leu Gln Trp Tyr Lys Asp Cys
            500                 505                 510

Lys Pro Leu Leu Leu Asp Asn Ile His Phe Ser Gly Val Lys Asp Arg
        515                 520                 525

Leu Ile Val Met Asn Val Ala Glu Lys His Arg Gly Asn Tyr Thr Cys
        530                 535                 540

His Ala Ser Tyr Thr Tyr Leu Gly Lys Gln Tyr Pro Ile Thr Arg Val
545                 550                 555                 560

Ile Glu Phe Ile Thr Leu Glu Glu Asn Lys Pro Thr Arg Pro Val Ile
                565                 570                 575

Val Ser Pro Ala Asn Glu Thr Met Glu Val Asp Leu Gly Ser Gln Ile
            580                 585                 590

Gln Leu Ile Cys Asn Val Thr Gly Gln Leu Ser Asp Ile Ala Tyr Trp
        595                 600                 605

Lys Trp Asn Gly Ser Val Ile Asp Glu Asp Pro Val Leu Gly Glu
        610                 615                 620

Asp Tyr Tyr Ser Val Glu Asn Pro Ala Asn Lys Arg Arg Ser Thr Leu
625                 630                 635                 640

Ile Thr Val Leu Asn Ile Ser Glu Ile Glu Ser Arg Phe Tyr Lys His
                645                 650                 655

Pro Phe Thr Cys Phe Ala Lys Asn Thr His Gly Ile Asp Ala Ala Tyr
            660                 665                 670

Ile Gln Leu Ile Tyr Pro Val Thr Asn Ser Gly Asp Lys Thr His Thr
        675                 680                 685

Cys Pro Pro Cys Pro Ala Pro Glu Leu Leu Gly Gly Pro Ser Val Phe
690                 695                 700

Leu Phe Pro Pro Lys Pro Lys Asp Thr Leu Met Ile Ser Arg Thr Pro
705                 710                 715                 720

Glu Val Thr Cys Val Val Val Asp Val Ser His Glu Asp Pro Glu Val
                725                 730                 735

-continued

```
Lys Phe Asn Trp Tyr Val Asp Gly Val Glu Val His Asn Ala Lys Thr
                740                 745                 750
Lys Pro Arg Glu Glu Gln Tyr Asn Ser Thr Tyr Arg Val Val Ser Val
            755                 760                 765
Leu Thr Val Leu His Gln Asp Trp Leu Asn Gly Lys Glu Tyr Lys Cys
    770                 775                 780
Lys Val Ser Asn Lys Ala Leu Pro Ala Pro Ile Glu Lys Thr Ile Ser
785                 790                 795                 800
Lys Ala Lys Gly Gln Pro Arg Glu Pro Gln Val Tyr Thr Leu Pro Pro
                805                 810                 815
Ser Arg Glu Glu Met Thr Lys Asn Gln Val Ser Leu Thr Cys Leu Val
            820                 825                 830
Lys Gly Phe Tyr Pro Ser Asp Ile Ala Val Glu Trp Glu Ser Asn Gly
    835                 840                 845
Gln Pro Glu Asn Asn Tyr Lys Thr Thr Pro Pro Val Leu Asp Ser Asp
850                 855                 860
Gly Ser Phe Phe Leu Tyr Ser Lys Leu Thr Val Asp Lys Ser Arg Trp
865                 870                 875                 880
Gln Gln Gly Asn Val Phe Ser Cys Ser Val Met His Glu Ala Leu His
                885                 890                 895
Asn His Tyr Thr Gln Lys Ser Leu Ser Leu Ser Pro Gly Lys
            900                 905                 910

<210> SEQ ID NO 29
<211> LENGTH: 2355
<212> TYPE: DNA
<213> ORGANISM: Homo sapiens
<220> FEATURE:
<221> NAME/KEY: CDS
<222> LOCATION: (1)...(2352)

<400> SEQUENCE: 29 atg gtg tgg ctt tgc tct ggg ctc ctg ttc cct gtg agc tgc ctg gtc     48
Met Val Trp Leu Cys Ser Gly Leu Leu Phe Pro Val Ser Cys Leu Val
1               5                   10                  15 ctg ctg cag gtg gca agc tct ggg aac atg aag gtc ttg cag gag ccc     96
Leu Leu Gln Val Ala Ser Ser Gly Asn Met Lys Val Leu Gln Glu Pro
            20                  25                  30 acc tgc gtc tcc gac tac atg agc atc tct act tgc gag tgg aag atg    144
Thr Cys Val Ser Asp Tyr Met Ser Ile Ser Thr Cys Glu Trp Lys Met
        35                  40                  45 aat ggt ccc acc aat tgc agc acc gag ctc cgc ctg ttg tac cag ctg    192
Asn Gly Pro Thr Asn Cys Ser Thr Glu Leu Arg Leu Leu Tyr Gln Leu
    50                  55                  60 gtt ttt ctg ctc tcc gaa gcc cac acg tgt atc cct gag aac aac gga    240
Val Phe Leu Leu Ser Glu Ala His Thr Cys Ile Pro Glu Asn Asn Gly
65                  70                  75                  80 ggc gcg ggg tgc gtg tgc cac ctg ctc atg gat gac gtg gtc agt gcg    288
Gly Ala Gly Cys Val Cys His Leu Leu Met Asp Asp Val Val Ser Ala
                85                  90                  95 gat aac tat aca ctg gac ctg tgg gct ggg cag cag ctg ctg tgg aag    336
Asp Asn Tyr Thr Leu Asp Leu Trp Ala Gly Gln Gln Leu Leu Trp Lys
            100                 105                 110 ggc tcc ttc aag ccc agc gag cat gtg aaa ccc agg gcc cca gga aac    384
Gly Ser Phe Lys Pro Ser Glu His Val Lys Pro Arg Ala Pro Gly Asn
        115                 120                 125 ctg aca gtt cac acc aat gtc tcc gac act ctg ctg ctg acc tgg agc    432
Leu Thr Val His Thr Asn Val Ser Asp Thr Leu Leu Leu Thr Trp Ser
    130                 135                 140
```

-continued

| | | |
|---|---|---|
| aac ccg tat ccc cct gac aat tac ctg tat aat cat ctc acc tat gca<br>Asn Pro Tyr Pro Pro Asp Asn Tyr Leu Tyr Asn His Leu Thr Tyr Ala<br>145                      150                        155                        160 | 480 |

```
aac ccg tat ccc cct gac aat tac ctg tat aat cat ctc acc tat gca       480
Asn Pro Tyr Pro Pro Asp Asn Tyr Leu Tyr Asn His Leu Thr Tyr Ala
145                 150                 155                 160 gtc aac att tgg agt gaa aac gac ccg gca gat ttc aga atc tat aac       528
Val Asn Ile Trp Ser Glu Asn Asp Pro Ala Asp Phe Arg Ile Tyr Asn
                165                 170                 175 gtg acc tac cta gaa ccc tcc ctc cgc atc gca gcc agc acc ctg aag       576
Val Thr Tyr Leu Glu Pro Ser Leu Arg Ile Ala Ala Ser Thr Leu Lys
            180                 185                 190 tct ggg att tcc tac agg gca cgg gtg agg gcc tgg gct cag agc tat       624
Ser Gly Ile Ser Tyr Arg Ala Arg Val Arg Ala Trp Ala Gln Ser Tyr
        195                 200                 205 aac acc acc tgg agt gag tgg agc ccc agc acc aag tgg cac aac tcc       672
Asn Thr Thr Trp Ser Glu Trp Ser Pro Ser Thr Lys Trp His Asn Ser
    210                 215                 220 tac agg gag ccc ttc gag cag tcc ggt ggg ggc ggg ggc gcc gcg cct       720
Tyr Arg Glu Pro Phe Glu Gln Ser Gly Gly Gly Gly Gly Ala Ala Pro
225                 230                 235                 240 acg gaa act cag cca cct gtg aca aat ttg agt gtc tct gtt gaa aac       768
Thr Glu Thr Gln Pro Pro Val Thr Asn Leu Ser Val Ser Val Glu Asn
                245                 250                 255 ctc tgc aca gta ata tgg aca tgg aat cca ccc gag gga gcc agc tca       816
Leu Cys Thr Val Ile Trp Thr Trp Asn Pro Pro Glu Gly Ala Ser Ser
            260                 265                 270 aat tgt agt cta tgg tat ttt agt cat ttt ggc gac aaa caa gat aag       864
Asn Cys Ser Leu Trp Tyr Phe Ser His Phe Gly Asp Lys Gln Asp Lys
        275                 280                 285 aaa ata gct ccg gaa act cgt cgt tca ata gaa gta ccc ctg aat gag       912
Lys Ile Ala Pro Glu Thr Arg Arg Ser Ile Glu Val Pro Leu Asn Glu
    290                 295                 300 agg att tgt ctg caa gtg ggg tcc cag tgt agc acc aat gag agt gag       960
Arg Ile Cys Leu Gln Val Gly Ser Gln Cys Ser Thr Asn Glu Ser Glu
305                 310                 315                 320 aag cct agc att ttg gtt gaa aaa tgc atc tca ccc cca gaa ggt gat      1008
Lys Pro Ser Ile Leu Val Glu Lys Cys Ile Ser Pro Pro Glu Gly Asp
                325                 330                 335 cct gag tct gct gtg act gag ctt caa tgc att tgg cac aac ctg agc      1056
Pro Glu Ser Ala Val Thr Glu Leu Gln Cys Ile Trp His Asn Leu Ser
            340                 345                 350 tac atg aag tgt tct tgg ctc cct gga agg aat acc agt ccc gac act      1104
Tyr Met Lys Cys Ser Trp Leu Pro Gly Arg Asn Thr Ser Pro Asp Thr
        355                 360                 365 aac tat act ctc tac tat tgg cac aga agc ctg gaa aaa att cat caa      1152
Asn Tyr Thr Leu Tyr Tyr Trp His Arg Ser Leu Glu Lys Ile His Gln
    370                 375                 380 tgt gaa aac atc ttt aga gaa ggc caa tac ttt ggt tgt tcc ttt gat      1200
Cys Glu Asn Ile Phe Arg Glu Gly Gln Tyr Phe Gly Cys Ser Phe Asp
385                 390                 395                 400 ctg acc aaa gtg aag gat tcc agt ttt gaa caa cac agt gtc caa ata      1248
Leu Thr Lys Val Lys Asp Ser Ser Phe Glu Gln His Ser Val Gln Ile
                405                 410                 415 atg gtc aag gat aat gca gga aaa att aaa cca tcc ttc aat ata gtg      1296
Met Val Lys Asp Asn Ala Gly Lys Ile Lys Pro Ser Phe Asn Ile Val
            420                 425                 430 cct tta act tcc cgt gtg aaa cct gat cct cca cat att aaa aac ctc      1344
Pro Leu Thr Ser Arg Val Lys Pro Asp Pro Pro His Ile Lys Asn Leu
        435                 440                 445 tcc ttc cac aat gat gac cta tat gtg caa tgg gag aat cca cag aat      1392
Ser Phe His Asn Asp Asp Leu Tyr Val Gln Trp Glu Asn Pro Gln Asn
```

-continued

| | | | | | | | | | | | | | | | | |
|---|---|---|---|---|---|---|---|---|---|---|---|---|---|---|---|---|
| | | 450 | | | | | 455 | | | | | 460 | | | | |
| ttt | att | agc | aga | tgc | cta | ttt | tat | gaa | gta | gaa | gtc | aat | aac | agc | caa | 1440 |
| Phe | Ile | Ser | Arg | Cys | Leu | Phe | Tyr | Glu | Val | Glu | Val | Asn | Asn | Ser | Gln | |
| 465 | | | | 470 | | | | | 475 | | | | | 480 | | |
| act | gag | aca | cat | aat | gtt | ttc | tac | gtc | caa | gag | gct | aaa | tgt | gag | aat | 1488 |
| Thr | Glu | Thr | His | Asn | Val | Phe | Tyr | Val | Gln | Glu | Ala | Lys | Cys | Glu | Asn | |
| | | | | 485 | | | | | 490 | | | | | 495 | | |
| cca | gaa | ttt | gag | aga | aat | gtg | gag | aat | aca | tct | tgt | ttc | atg | gtc | cct | 1536 |
| Pro | Glu | Phe | Glu | Arg | Asn | Val | Glu | Asn | Thr | Ser | Cys | Phe | Met | Val | Pro | |
| | | | 500 | | | | | 505 | | | | | 510 | | | |
| ggt | gtt | ctt | cct | gat | act | ttg | aac | aca | gtc | aga | ata | aga | gtc | aaa | aca | 1584 |
| Gly | Val | Leu | Pro | Asp | Thr | Leu | Asn | Thr | Val | Arg | Ile | Arg | Val | Lys | Thr | |
| | | 515 | | | | | 520 | | | | | 525 | | | | |
| aat | aag | tta | tgc | tat | gag | gat | gac | aaa | ctc | tgg | agt | aat | tgg | agc | caa | 1632 |
| Asn | Lys | Leu | Cys | Tyr | Glu | Asp | Asp | Lys | Leu | Trp | Ser | Asn | Trp | Ser | Gln | |
| 530 | | | | | 535 | | | | | 540 | | | | | | |
| gaa | atg | agt | ata | ggt | aag | aag | cgc | aat | tcc | aca | acc | gga | gac | aaa | act | 1680 |
| Glu | Met | Ser | Ile | Gly | Lys | Lys | Arg | Asn | Ser | Thr | Thr | Gly | Asp | Lys | Thr | |
| 545 | | | | 550 | | | | | 555 | | | | | 560 | | |
| cac | aca | tgc | cca | ccg | tgc | cca | gca | cct | gaa | ctc | ctg | ggg | gga | ccg | tca | 1728 |
| His | Thr | Cys | Pro | Pro | Cys | Pro | Ala | Pro | Glu | Leu | Leu | Gly | Gly | Pro | Ser | |
| | | | | 565 | | | | | 570 | | | | | 575 | | |
| gtc | ttc | ctc | ttc | ccc | cca | aaa | ccc | aag | gac | acc | ctc | atg | atc | tcc | cgg | 1776 |
| Val | Phe | Leu | Phe | Pro | Pro | Lys | Pro | Lys | Asp | Thr | Leu | Met | Ile | Ser | Arg | |
| | | | 580 | | | | | 585 | | | | | 590 | | | |
| acc | cct | gag | gtc | aca | tgc | gtg | gtg | gtg | gac | gtg | agc | cac | gaa | gac | cct | 1824 |
| Thr | Pro | Glu | Val | Thr | Cys | Val | Val | Val | Asp | Val | Ser | His | Glu | Asp | Pro | |
| | | 595 | | | | | 600 | | | | | 605 | | | | |
| gag | gtc | aag | ttc | aac | tgg | tac | gtg | gac | ggc | gtg | gag | gtg | cat | aat | gcc | 1872 |
| Glu | Val | Lys | Phe | Asn | Trp | Tyr | Val | Asp | Gly | Val | Glu | Val | His | Asn | Ala | |
| | 610 | | | | | 615 | | | | | 620 | | | | | |
| aag | aca | aag | ccg | cgg | gag | gag | cag | tac | aac | agc | acg | tac | cgt | gtg | gtc | 1920 |
| Lys | Thr | Lys | Pro | Arg | Glu | Glu | Gln | Tyr | Asn | Ser | Thr | Tyr | Arg | Val | Val | |
| 625 | | | | 630 | | | | | 635 | | | | | 640 | | |
| agc | gtc | ctc | acc | gtc | ctg | cac | cag | gac | tgg | ctg | aat | ggc | aag | gag | tac | 1968 |
| Ser | Val | Leu | Thr | Val | Leu | His | Gln | Asp | Trp | Leu | Asn | Gly | Lys | Glu | Tyr | |
| | | | 645 | | | | | 650 | | | | | 655 | | | |
| aag | tgc | aag | gtc | tcc | aac | aaa | gcc | ctc | cca | gcc | ccc | atc | gag | aaa | acc | 2016 |
| Lys | Cys | Lys | Val | Ser | Asn | Lys | Ala | Leu | Pro | Ala | Pro | Ile | Glu | Lys | Thr | |
| | | 660 | | | | | 665 | | | | | 670 | | | | |
| atc | tcc | aaa | gcc | aaa | ggg | cag | ccc | cga | gaa | cca | cag | gtg | tac | acc | ctg | 2064 |
| Ile | Ser | Lys | Ala | Lys | Gly | Gln | Pro | Arg | Glu | Pro | Gln | Val | Tyr | Thr | Leu | |
| | 675 | | | | | 680 | | | | | 685 | | | | | |
| ccc | cca | tcc | cgg | gag | gag | atg | acc | aag | aac | cag | gtc | agc | ctg | acc | tgc | 2112 |
| Pro | Pro | Ser | Arg | Glu | Glu | Met | Thr | Lys | Asn | Gln | Val | Ser | Leu | Thr | Cys | |
| 690 | | | | 695 | | | | | 700 | | | | | | | |
| ctg | gtc | aaa | ggc | ttc | tat | ccc | agc | gac | atc | gcc | gtg | gag | tgg | gag | agc | 2160 |
| Leu | Val | Lys | Gly | Phe | Tyr | Pro | Ser | Asp | Ile | Ala | Val | Glu | Trp | Glu | Ser | |
| 705 | | | | 710 | | | | | 715 | | | | | 720 | | |
| aat | ggg | cag | ccg | gag | aac | aac | tac | aag | acc | acg | cct | ccc | gtg | ctg | gac | 2208 |
| Asn | Gly | Gln | Pro | Glu | Asn | Asn | Tyr | Lys | Thr | Thr | Pro | Pro | Val | Leu | Asp | |
| | | | 725 | | | | | 730 | | | | | 735 | | | |
| tcc | gac | ggc | tcc | ttc | ttc | ctc | tat | agc | aag | ctc | acc | gtg | gac | aag | agc | 2256 |
| Ser | Asp | Gly | Ser | Phe | Phe | Leu | Tyr | Ser | Lys | Leu | Thr | Val | Asp | Lys | Ser | |
| | | 740 | | | | | 745 | | | | | 750 | | | | |
| agg | tgg | cag | cag | ggg | aac | gtc | ttc | tca | tgc | tcc | gtg | atg | cat | gag | gct | 2304 |
| Arg | Trp | Gln | Gln | Gly | Asn | Val | Phe | Ser | Cys | Ser | Val | Met | His | Glu | Ala | |
| | 755 | | | | | 760 | | | | | 765 | | | | | |
| ctg | cac | aac | cac | tac | acg | cag | aag | agc | ctc | tcc | ctg | tct | ccg | ggt | aaa | 2352 |

```
Leu His Asn His Tyr Thr Gln Lys Ser Leu Ser Leu Ser Pro Gly Lys
    770                 775                 780 tga                                                                    2355

<210> SEQ ID NO 30
<211> LENGTH: 784
<212> TYPE: PRT
<213> ORGANISM: Homo sapiens

<400> SEQUENCE: 30

Met Val Trp Leu Cys Ser Gly Leu Leu Phe Pro Val Ser Cys Leu Val
 1               5                  10                  15

Leu Leu Gln Val Ala Ser Ser Gly Asn Met Lys Val Leu Gln Glu Pro
            20                  25                  30

Thr Cys Val Ser Asp Tyr Met Ser Ile Ser Thr Cys Glu Trp Lys Met
        35                  40                  45

Asn Gly Pro Thr Asn Cys Ser Thr Glu Leu Arg Leu Leu Tyr Gln Leu
    50                  55                  60

Val Phe Leu Leu Ser Glu Ala His Thr Cys Ile Pro Glu Asn Asn Gly
 65                  70                  75                  80

Gly Ala Gly Cys Val Cys His Leu Leu Met Asp Asp Val Val Ser Ala
                85                  90                  95

Asp Asn Tyr Thr Leu Asp Leu Trp Ala Gly Gln Gln Leu Leu Trp Lys
            100                 105                 110

Gly Ser Phe Lys Pro Ser Glu His Val Lys Pro Arg Ala Pro Gly Asn
        115                 120                 125

Leu Thr Val His Thr Asn Val Ser Asp Thr Leu Leu Leu Thr Trp Ser
    130                 135                 140

Asn Pro Tyr Pro Pro Asp Asn Tyr Leu Tyr Asn His Leu Thr Tyr Ala
145                 150                 155                 160

Val Asn Ile Trp Ser Glu Asn Asp Pro Ala Asp Phe Arg Ile Tyr Asn
                165                 170                 175

Val Thr Tyr Leu Glu Pro Ser Leu Arg Ile Ala Ala Ser Thr Leu Lys
            180                 185                 190

Ser Gly Ile Ser Tyr Arg Ala Arg Val Arg Ala Trp Ala Gln Ser Tyr
        195                 200                 205

Asn Thr Thr Trp Ser Glu Trp Ser Pro Ser Thr Lys Trp His Asn Ser
    210                 215                 220

Tyr Arg Glu Pro Phe Glu Gln Ser Gly Gly Gly Gly Ala Ala Pro
225                 230                 235                 240

Thr Glu Thr Gln Pro Pro Val Thr Asn Leu Ser Val Ser Val Glu Asn
                245                 250                 255

Leu Cys Thr Val Ile Trp Thr Trp Asn Pro Pro Glu Gly Ala Ser Ser
            260                 265                 270

Asn Cys Ser Leu Trp Tyr Phe Ser His Phe Gly Asp Lys Gln Asp Lys
        275                 280                 285

Lys Ile Ala Pro Glu Thr Arg Arg Ser Ile Glu Val Pro Leu Asn Glu
    290                 295                 300

Arg Ile Cys Leu Gln Val Gly Ser Gln Cys Ser Thr Asn Glu Ser Glu
305                 310                 315                 320

Lys Pro Ser Ile Leu Val Glu Lys Cys Ile Ser Pro Pro Glu Gly Asp
                325                 330                 335

Pro Glu Ser Ala Val Thr Glu Leu Gln Cys Ile Trp His Asn Leu Ser
            340                 345                 350
```

-continued

```
Tyr Met Lys Cys Ser Trp Leu Pro Gly Arg Asn Thr Ser Pro Asp Thr
        355                 360                 365
Asn Tyr Thr Leu Tyr Tyr Trp His Arg Ser Leu Glu Lys Ile His Gln
        370                 375                 380
Cys Glu Asn Ile Phe Arg Glu Gly Gln Tyr Phe Gly Cys Ser Phe Asp
385                 390                 395                 400
Leu Thr Lys Val Lys Asp Ser Ser Phe Glu Gln His Ser Val Gln Ile
                405                 410                 415
Met Val Lys Asp Asn Ala Gly Lys Ile Lys Pro Ser Phe Asn Ile Val
            420                 425                 430
Pro Leu Thr Ser Arg Val Lys Pro Asp Pro His Ile Lys Asn Leu
        435                 440                 445
Ser Phe His Asn Asp Asp Leu Tyr Val Gln Trp Glu Asn Pro Gln Asn
450                 455                 460
Phe Ile Ser Arg Cys Leu Phe Tyr Glu Val Glu Val Asn Asn Ser Gln
465                 470                 475                 480
Thr Glu Thr His Asn Val Phe Tyr Val Gln Glu Ala Lys Cys Glu Asn
                485                 490                 495
Pro Glu Phe Glu Arg Asn Val Glu Asn Thr Ser Cys Phe Met Val Pro
                500                 505                 510
Gly Val Leu Pro Asp Thr Leu Asn Thr Val Arg Ile Arg Val Lys Thr
            515                 520                 525
Asn Lys Leu Cys Tyr Glu Asp Asp Lys Leu Trp Ser Asn Trp Ser Gln
530                 535                 540
Glu Met Ser Ile Gly Lys Lys Arg Asn Ser Thr Thr Gly Asp Lys Thr
545                 550                 555                 560
His Thr Cys Pro Pro Cys Pro Ala Pro Glu Leu Leu Gly Gly Pro Ser
                565                 570                 575
Val Phe Leu Phe Pro Pro Lys Pro Lys Asp Thr Leu Met Ile Ser Arg
            580                 585                 590
Thr Pro Glu Val Thr Cys Val Val Val Asp Val Ser His Glu Asp Pro
        595                 600                 605
Glu Val Lys Phe Asn Trp Tyr Val Asp Gly Val Glu Val His Asn Ala
    610                 615                 620
Lys Thr Lys Pro Arg Glu Glu Gln Tyr Asn Ser Thr Tyr Arg Val Val
625                 630                 635                 640
Ser Val Leu Thr Val Leu His Gln Asp Trp Leu Asn Gly Lys Glu Tyr
                645                 650                 655
Lys Cys Lys Val Ser Asn Lys Ala Leu Pro Ala Pro Ile Glu Lys Thr
                660                 665                 670
Ile Ser Lys Ala Lys Gly Gln Pro Arg Glu Pro Gln Val Tyr Thr Leu
            675                 680                 685
Pro Pro Ser Arg Glu Glu Met Thr Lys Asn Gln Val Ser Leu Thr Cys
        690                 695                 700
Leu Val Lys Gly Phe Tyr Pro Ser Asp Ile Ala Val Glu Trp Glu Ser
705                 710                 715                 720
Asn Gly Gln Pro Glu Asn Asn Tyr Lys Thr Thr Pro Pro Val Leu Asp
                725                 730                 735
Ser Asp Gly Ser Phe Phe Leu Tyr Ser Lys Leu Thr Val Asp Lys Ser
            740                 745                 750
Arg Trp Gln Gln Gly Asn Val Phe Ser Cys Ser Val Met His Glu Ala
        755                 760                 765
Leu His Asn His Tyr Thr Gln Lys Ser Leu Ser Leu Ser Pro Gly Lys
```

<210> SEQ ID NO 31
<211> LENGTH: 2382
<212> TYPE: DNA
<213> ORGANISM: Homo sapiens
<220> FEATURE:
<221> NAME/KEY: CDS
<222> LOCATION: (1)...(2379)

<400> SEQUENCE: 31

| | | | | | | | | | | | | | | | | |
|---|---|---|---|---|---|---|---|---|---|---|---|---|---|---|---|---|
| atg | gtg | tgg | ccg | gcg | cgg | ctc | tgc | ggg | ctg | tgg | gcg | ctg | ctg | ctc | tgc | 48 |
| Met | Val | Trp | Pro | Ala | Arg | Leu | Cys | Gly | Leu | Trp | Ala | Leu | Leu | Leu | Cys | |
| 1 | | | 5 | | | | 10 | | | | | 15 | | | | |

| | | | | | | | | | | | | | | | | |
|---|---|---|---|---|---|---|---|---|---|---|---|---|---|---|---|---|
| gcc | ggc | ggc | ggg | ggc | ggg | ggc | ggg | ggc | gcc | gcg | cct | acg | gaa | act | cag | 96 |
| Ala | Gly | Gly | Gly | Gly | Gly | Gly | Gly | Gly | Ala | Ala | Pro | Thr | Glu | Thr | Gln | |
| | | 20 | | | | | 25 | | | | | 30 | | | | |

| | | | | | | | | | | | | | | | | |
|---|---|---|---|---|---|---|---|---|---|---|---|---|---|---|---|---|
| cca | cct | gtg | aca | aat | ttg | agt | gtc | tct | gtt | gaa | aac | ctc | tgc | aca | gta | 144 |
| Pro | Pro | Val | Thr | Asn | Leu | Ser | Val | Ser | Val | Glu | Asn | Leu | Cys | Thr | Val | |
| | | | 35 | | | | | 40 | | | | | 45 | | | |

| | | | | | | | | | | | | | | | | |
|---|---|---|---|---|---|---|---|---|---|---|---|---|---|---|---|---|
| ata | tgg | aca | tgg | aat | cca | ccc | gag | gga | gcc | agc | tca | aat | tgt | agt | cta | 192 |
| Ile | Trp | Thr | Trp | Asn | Pro | Pro | Glu | Gly | Ala | Ser | Ser | Asn | Cys | Ser | Leu | |
| 50 | | | | | 55 | | | | | 60 | | | | | | |

| | | | | | | | | | | | | | | | | |
|---|---|---|---|---|---|---|---|---|---|---|---|---|---|---|---|---|
| tgg | tat | ttt | agt | cat | ttt | ggc | gac | aaa | caa | gat | aag | aaa | ata | gct | ccg | 240 |
| Trp | Tyr | Phe | Ser | His | Phe | Gly | Asp | Lys | Gln | Asp | Lys | Lys | Ile | Ala | Pro | |
| 65 | | | | | 70 | | | | | 75 | | | | | 80 | |

| | | | | | | | | | | | | | | | | |
|---|---|---|---|---|---|---|---|---|---|---|---|---|---|---|---|---|
| gaa | act | cgt | cgt | tca | ata | gaa | gta | ccc | ctg | aat | gag | agg | att | tgt | ctg | 288 |
| Glu | Thr | Arg | Arg | Ser | Ile | Glu | Val | Pro | Leu | Asn | Glu | Arg | Ile | Cys | Leu | |
| | | | | 85 | | | | | 90 | | | | | 95 | | |

| | | | | | | | | | | | | | | | | |
|---|---|---|---|---|---|---|---|---|---|---|---|---|---|---|---|---|
| caa | gtg | ggg | tcc | cag | tgt | agc | acc | aat | gag | agt | gag | aag | cct | agc | att | 336 |
| Gln | Val | Gly | Ser | Gln | Cys | Ser | Thr | Asn | Glu | Ser | Glu | Lys | Pro | Ser | Ile | |
| | | | 100 | | | | | 105 | | | | | 110 | | | |

| | | | | | | | | | | | | | | | | |
|---|---|---|---|---|---|---|---|---|---|---|---|---|---|---|---|---|
| ttg | gtt | gaa | aaa | tgc | atc | tca | ccc | cca | gaa | ggt | gat | cct | gag | tct | gct | 384 |
| Leu | Val | Glu | Lys | Cys | Ile | Ser | Pro | Pro | Glu | Gly | Asp | Pro | Glu | Ser | Ala | |
| | | 115 | | | | | 120 | | | | | 125 | | | | |

| | | | | | | | | | | | | | | | | |
|---|---|---|---|---|---|---|---|---|---|---|---|---|---|---|---|---|
| gtg | act | gag | ctt | caa | tgc | att | tgg | cac | aac | ctg | agc | tac | atg | aag | tgt | 432 |
| Val | Thr | Glu | Leu | Gln | Cys | Ile | Trp | His | Asn | Leu | Ser | Tyr | Met | Lys | Cys | |
| | 130 | | | | | 135 | | | | | 140 | | | | | |

| | | | | | | | | | | | | | | | | |
|---|---|---|---|---|---|---|---|---|---|---|---|---|---|---|---|---|
| tct | tgg | ctc | cct | gga | agg | aat | acc | agt | ccc | gac | act | aac | tat | act | ctc | 480 |
| Ser | Trp | Leu | Pro | Gly | Arg | Asn | Thr | Ser | Pro | Asp | Thr | Asn | Tyr | Thr | Leu | |
| 145 | | | | | 150 | | | | | 155 | | | | | 160 | |

| | | | | | | | | | | | | | | | | |
|---|---|---|---|---|---|---|---|---|---|---|---|---|---|---|---|---|
| tac | tat | tgg | cac | aga | agc | ctg | gaa | aaa | att | cat | caa | tgt | gaa | aac | atc | 528 |
| Tyr | Tyr | Trp | His | Arg | Ser | Leu | Glu | Lys | Ile | His | Gln | Cys | Glu | Asn | Ile | |
| | | | | 165 | | | | | 170 | | | | | 175 | | |

| | | | | | | | | | | | | | | | | |
|---|---|---|---|---|---|---|---|---|---|---|---|---|---|---|---|---|
| ttt | aga | gaa | ggc | caa | tac | ttt | ggt | tgt | tcc | ttt | gat | ctg | acc | aaa | gtg | 576 |
| Phe | Arg | Glu | Gly | Gln | Tyr | Phe | Gly | Cys | Ser | Phe | Asp | Leu | Thr | Lys | Val | |
| | | | 180 | | | | | 185 | | | | | 190 | | | |

| | | | | | | | | | | | | | | | | |
|---|---|---|---|---|---|---|---|---|---|---|---|---|---|---|---|---|
| aag | gat | tcc | agt | ttt | gaa | caa | cac | agt | gtc | caa | ata | atg | gtc | aag | gat | 624 |
| Lys | Asp | Ser | Ser | Phe | Glu | Gln | His | Ser | Val | Gln | Ile | Met | Val | Lys | Asp | |
| | | 195 | | | | | 200 | | | | | 205 | | | | |

| | | | | | | | | | | | | | | | | |
|---|---|---|---|---|---|---|---|---|---|---|---|---|---|---|---|---|
| aat | gca | gga | aaa | att | aaa | cca | tcc | ttc | aat | ata | gtg | cct | tta | act | tcc | 672 |
| Asn | Ala | Gly | Lys | Ile | Lys | Pro | Ser | Phe | Asn | Ile | Val | Pro | Leu | Thr | Ser | |
| | 210 | | | | | 215 | | | | | 220 | | | | | |

| | | | | | | | | | | | | | | | | |
|---|---|---|---|---|---|---|---|---|---|---|---|---|---|---|---|---|
| cgt | gtg | aaa | cct | gat | cct | cca | cat | att | aaa | aac | ctc | tcc | ttc | cac | aat | 720 |
| Arg | Val | Lys | Pro | Asp | Pro | Pro | His | Ile | Lys | Asn | Leu | Ser | Phe | His | Asn | |
| 225 | | | | | 230 | | | | | 235 | | | | | 240 | |

| | | | | | | | | | | | | | | | | |
|---|---|---|---|---|---|---|---|---|---|---|---|---|---|---|---|---|
| gat | gac | cta | tat | gtg | caa | tgg | gag | aat | cca | cag | aat | ttt | att | agc | aga | 768 |
| Asp | Asp | Leu | Tyr | Val | Gln | Trp | Glu | Asn | Pro | Gln | Asn | Phe | Ile | Ser | Arg | |
| | | | | 245 | | | | | 250 | | | | | 255 | | |

| | | | | | | | | | | | | | | | | |
|---|---|---|---|---|---|---|---|---|---|---|---|---|---|---|---|---|
| tgc | cta | ttt | tat | gaa | gta | gaa | gtc | aat | aac | agc | caa | act | gag | aca | cat | 816 |
| Cys | Leu | Phe | Tyr | Glu | Val | Glu | Val | Asn | Asn | Ser | Gln | Thr | Glu | Thr | His | |

-continued

```
                260                 265                 270
aat gtt ttc tac gtc caa gag gct aaa tgt gag aat cca gaa ttt gag          864
Asn Val Phe Tyr Val Gln Glu Ala Lys Cys Glu Asn Pro Glu Phe Glu
        275                 280                 285 aga aat gtg gag aat aca tct tgt ttc atg gtc cct ggt gtt ctt cct          912
Arg Asn Val Glu Asn Thr Ser Cys Phe Met Val Pro Gly Val Leu Pro
    290                 295                 300 gat act ttg aac aca gtc aga ata aga gtc aaa aca aat aag tta tgc          960
Asp Thr Leu Asn Thr Val Arg Ile Arg Val Lys Thr Asn Lys Leu Cys
305                 310                 315                 320 tat gag gat gac aaa ctc tgg agt aat tgg agc caa gaa atg agt ata         1008
Tyr Glu Asp Asp Lys Leu Trp Ser Asn Trp Ser Gln Glu Met Ser Ile
                325                 330                 335 ggt aag aag cgc aat tcc aca ggc gcg cct agt ggt gga ggt ggc cgg         1056
Gly Lys Lys Arg Asn Ser Thr Gly Ala Pro Ser Gly Gly Gly Gly Arg
            340                 345                 350 ccc gca agc tct ggg aac atg aag gtc ttg cag gag ccc acc tgc gtc         1104
Pro Ala Ser Ser Gly Asn Met Lys Val Leu Gln Glu Pro Thr Cys Val
        355                 360                 365 tcc gac tac atg agc atc tct act tgc gag tgg aag atg aat ggt ccc         1152
Ser Asp Tyr Met Ser Ile Ser Thr Cys Glu Trp Lys Met Asn Gly Pro
    370                 375                 380 acc aat tgc agc acc gag ctc cgc ctg ttg tac cag ctg gtt ttt ctg         1200
Thr Asn Cys Ser Thr Glu Leu Arg Leu Leu Tyr Gln Leu Val Phe Leu
385                 390                 395                 400 ctc tcc gaa gcc cac acg tgt atc cct gag aac aac gga ggc gcg ggg         1248
Leu Ser Glu Ala His Thr Cys Ile Pro Glu Asn Asn Gly Gly Ala Gly
                405                 410                 415 tgc gtg tgc cac ctg ctc atg gat gac gtg gtc agt gcg gat aac tat         1296
Cys Val Cys His Leu Leu Met Asp Asp Val Val Ser Ala Asp Asn Tyr
            420                 425                 430 aca ctg gac ctg tgg gct ggg cag cag ctg ctg tgg aag ggc tcc ttc         1344
Thr Leu Asp Leu Trp Ala Gly Gln Gln Leu Leu Trp Lys Gly Ser Phe
        435                 440                 445 aag ccc agc gag cat gtg aaa ccc agg gcc cca gga aac ctg aca gtt         1392
Lys Pro Ser Glu His Val Lys Pro Arg Ala Pro Gly Asn Leu Thr Val
    450                 455                 460 cac acc aat gtc tcc gac act ctg ctg ctg acc tgg agc aac ccg tat         1440
His Thr Asn Val Ser Asp Thr Leu Leu Leu Thr Trp Ser Asn Pro Tyr
465                 470                 475                 480 ccc cct gac aat tac ctg tat aat cat ctc acc tat gca gtc aac att         1488
Pro Pro Asp Asn Tyr Leu Tyr Asn His Leu Thr Tyr Ala Val Asn Ile
                485                 490                 495 tgg agt gaa aac gac ccg gca gat ttc aga atc tat aac gtg acc tac         1536
Trp Ser Glu Asn Asp Pro Ala Asp Phe Arg Ile Tyr Asn Val Thr Tyr
            500                 505                 510 cta gaa ccc tcc ctc cgc atc gca gcc agc acc ctg aag tct ggg att         1584
Leu Glu Pro Ser Leu Arg Ile Ala Ala Ser Thr Leu Lys Ser Gly Ile
        515                 520                 525 tcc tac agg gca cgg gtg agg gcc tgg gct cag tgc tat aac acc acc         1632
Ser Tyr Arg Ala Arg Val Arg Ala Trp Ala Gln Cys Tyr Asn Thr Thr
    530                 535                 540 tgg agt gag tgg agc ccc agc acc aag tgg cac aac tcc tac agg gag         1680
Trp Ser Glu Trp Ser Pro Ser Thr Lys Trp His Asn Ser Tyr Arg Glu
545                 550                 555                 560 ccc ttc gag cag tcc gga gac aaa act cac aca tgc cca ccg tgc cca         1728
Pro Phe Glu Gln Ser Gly Asp Lys Thr His Thr Cys Pro Pro Cys Pro
                565                 570                 575 gca cct gaa ctc ctg ggg gga ccg tca gtc ttc ctc ttc ccc cca aaa         1776
```

-continued

| | | |
|---|---|---|
| Ala Pro Glu Leu Leu Gly Gly Pro Ser Val Phe Leu Phe Pro Pro Lys<br>580 585 590 | | |
| ccc aag gac acc ctc atg atc tcc cgg acc cct gag gtc aca tgc gtg<br>Pro Lys Asp Thr Leu Met Ile Ser Arg Thr Pro Glu Val Thr Cys Val<br>595 600 605 | 1824 | |
| gtg gtg gac gtg agc cac gaa gac cct gag gtc aag ttc aac tgg tac<br>Val Val Asp Val Ser His Glu Asp Pro Glu Val Lys Phe Asn Trp Tyr<br>610 615 620 | 1872 | |
| gtg gac ggc gtg gag gtg cat aat gcc aag aca aag ccg cgg gag gag<br>Val Asp Gly Val Glu Val His Asn Ala Lys Thr Lys Pro Arg Glu Glu<br>625 630 635 640 | 1920 | |
| cag tac aac agc acg tac cgt gtg gtc agc gtc ctc acc gtc ctg cac<br>Gln Tyr Asn Ser Thr Tyr Arg Val Val Ser Val Leu Thr Val Leu His<br>645 650 655 | 1968 | |
| cag gac tgg ctg aat ggc aag gag tac aag tgc aag gtc tcc aac aaa<br>Gln Asp Trp Leu Asn Gly Lys Glu Tyr Lys Cys Lys Val Ser Asn Lys<br>660 665 670 | 2016 | |
| gcc ctc cca gcc ccc atc gag aaa acc atc tcc aaa gcc aaa ggg cag<br>Ala Leu Pro Ala Pro Ile Glu Lys Thr Ile Ser Lys Ala Lys Gly Gln<br>675 680 685 | 2064 | |
| ccc cga gaa cca cag gtg tac acc ctg ccc cca tcc cgg gag gag atg<br>Pro Arg Glu Pro Gln Val Tyr Thr Leu Pro Pro Ser Arg Glu Glu Met<br>690 695 700 | 2112 | |
| acc aag aac cag gtc agc ctg acc tgc ctg gtc aaa ggc ttc tat ccc<br>Thr Lys Asn Gln Val Ser Leu Thr Cys Leu Val Lys Gly Phe Tyr Pro<br>705 710 715 720 | 2160 | |
| agc gac atc gcc gtg gag tgg gag agc aat ggg cag ccg gag aac aac<br>Ser Asp Ile Ala Val Glu Trp Glu Ser Asn Gly Gln Pro Glu Asn Asn<br>725 730 735 | 2208 | |
| tac aag acc acg cct ccc gtg ctg gac tcc gac ggc tcc ttc ttc ctc<br>Tyr Lys Thr Thr Pro Pro Val Leu Asp Ser Asp Gly Ser Phe Phe Leu<br>740 745 750 | 2256 | |
| tat agc aag ctc acc gtg gac aag agc agg tgg cag cag ggg aac gtc<br>Tyr Ser Lys Leu Thr Val Asp Lys Ser Arg Trp Gln Gln Gly Asn Val<br>755 760 765 | 2304 | |
| ttc tca tgc tcc gtg atg cat gag gct ctg cac aac cac tac acg cag<br>Phe Ser Cys Ser Val Met His Glu Ala Leu His Asn His Tyr Thr Gln<br>770 775 780 | 2352 | |
| aag agc ctc tcc ctg tct ccg ggt aaa tga<br>Lys Ser Leu Ser Leu Ser Pro Gly Lys<br>785 790 | 2382 | |

<210> SEQ ID NO 32
<211> LENGTH: 793
<212> TYPE: PRT
<213> ORGANISM: Homo sapiens

<400> SEQUENCE: 32

Met Val Trp Pro Ala Arg Leu Cys Gly Leu Trp Ala Leu Leu Leu Cys
1               5                   10                  15

Ala Gly Gly Gly Gly Gly Gly Gly Ala Ala Pro Thr Glu Thr Gln
        20                  25                  30

Pro Pro Val Thr Asn Leu Ser Val Ser Val Glu Asn Leu Cys Thr Val
            35                  40                  45

Ile Trp Thr Trp Asn Pro Pro Glu Gly Ala Ser Ser Asn Cys Ser Leu
        50                  55                  60

Trp Tyr Phe Ser His Phe Gly Asp Lys Gln Asp Lys Lys Ile Ala Pro
65                  70                  75                  80

Glu Thr Arg Arg Ser Ile Glu Val Pro Leu Asn Glu Arg Ile Cys Leu

-continued

```
                 85                  90                  95
Gln Val Gly Ser Gln Cys Ser Thr Asn Glu Ser Glu Lys Pro Ser Ile
            100                 105                 110
Leu Val Glu Lys Cys Ile Ser Pro Glu Gly Asp Pro Glu Ser Ala
            115                 120                 125
Val Thr Glu Leu Gln Cys Ile Trp His Asn Leu Ser Tyr Met Lys Cys
            130                 135                 140
Ser Trp Leu Pro Gly Arg Asn Thr Ser Pro Asp Thr Asn Tyr Thr Leu
145                 150                 155                 160
Tyr Tyr Trp His Arg Ser Leu Glu Lys Ile His Gln Cys Glu Asn Ile
                165                 170                 175
Phe Arg Glu Gly Gln Tyr Phe Gly Cys Ser Phe Asp Leu Thr Lys Val
            180                 185                 190
Lys Asp Ser Ser Phe Glu Gln His Ser Val Gln Ile Met Val Lys Asp
            195                 200                 205
Asn Ala Gly Lys Ile Lys Pro Ser Phe Asn Ile Val Pro Leu Thr Ser
210                 215                 220
Arg Val Lys Pro Asp Pro Pro His Ile Lys Asn Leu Ser Phe His Asn
225                 230                 235                 240
Asp Asp Leu Tyr Val Gln Trp Glu Asn Pro Gln Asn Phe Ile Ser Arg
            245                 250                 255
Cys Leu Phe Tyr Glu Val Glu Val Asn Asn Ser Gln Thr Glu Thr His
            260                 265                 270
Asn Val Phe Tyr Val Gln Glu Ala Lys Cys Glu Asn Pro Glu Phe Glu
            275                 280                 285
Arg Asn Val Glu Asn Thr Ser Cys Phe Met Val Pro Gly Val Leu Pro
290                 295                 300
Asp Thr Leu Asn Thr Val Arg Ile Arg Val Lys Thr Asn Lys Leu Cys
305                 310                 315                 320
Tyr Glu Asp Asp Lys Leu Trp Ser Asn Trp Ser Gln Glu Met Ser Ile
            325                 330                 335
Gly Lys Lys Arg Asn Ser Thr Gly Ala Pro Ser Gly Gly Gly Arg
            340                 345                 350
Pro Ala Ser Ser Gly Asn Met Lys Val Leu Gln Glu Pro Thr Cys Val
            355                 360                 365
Ser Asp Tyr Met Ser Ile Ser Thr Cys Glu Trp Lys Met Asn Gly Pro
            370                 375                 380
Thr Asn Cys Ser Thr Glu Leu Arg Leu Leu Tyr Gln Leu Val Phe Leu
385                 390                 395                 400
Leu Ser Glu Ala His Thr Cys Ile Pro Glu Asn Asn Gly Gly Ala Gly
            405                 410                 415
Cys Val Cys His Leu Leu Met Asp Asp Val Val Ser Ala Asp Asn Tyr
            420                 425                 430
Thr Leu Asp Leu Trp Ala Gly Gln Gln Leu Leu Trp Lys Gly Ser Phe
            435                 440                 445
Lys Pro Ser Glu His Val Lys Pro Arg Ala Pro Gly Asn Leu Thr Val
            450                 455                 460
His Thr Asn Val Ser Asp Thr Leu Leu Leu Thr Trp Ser Asn Pro Tyr
465                 470                 475                 480
Pro Pro Asp Asn Tyr Leu Tyr Asn His Leu Thr Tyr Ala Val Asn Ile
            485                 490                 495
Trp Ser Glu Asn Asp Pro Ala Asp Phe Arg Ile Tyr Asn Val Thr Tyr
            500                 505                 510
```

Leu Glu Pro Ser Leu Arg Ile Ala Ala Ser Thr Leu Lys Ser Gly Ile
            515                 520                 525

Ser Tyr Arg Ala Arg Val Arg Ala Trp Ala Gln Cys Tyr Asn Thr Thr
        530                 535                 540

Trp Ser Glu Trp Ser Pro Ser Thr Lys Trp His Asn Ser Tyr Arg Glu
545                 550                 555                 560

Pro Phe Glu Gln Ser Gly Asp Lys Thr His Thr Cys Pro Pro Cys Pro
                565                 570                 575

Ala Pro Glu Leu Leu Gly Gly Pro Ser Val Phe Leu Phe Pro Pro Lys
            580                 585                 590

Pro Lys Asp Thr Leu Met Ile Ser Arg Thr Pro Glu Val Thr Cys Val
        595                 600                 605

Val Val Asp Val Ser His Glu Asp Pro Glu Val Lys Phe Asn Trp Tyr
610                 615                 620

Val Asp Gly Val Glu Val His Asn Ala Lys Thr Lys Pro Arg Glu Glu
625                 630                 635                 640

Gln Tyr Asn Ser Thr Tyr Arg Val Val Ser Val Leu Thr Val Leu His
                645                 650                 655

Gln Asp Trp Leu Asn Gly Lys Glu Tyr Lys Cys Lys Val Ser Asn Lys
            660                 665                 670

Ala Leu Pro Ala Pro Ile Glu Lys Thr Ile Ser Lys Ala Lys Gly Gln
        675                 680                 685

Pro Arg Glu Pro Gln Val Tyr Thr Leu Pro Pro Ser Arg Glu Glu Met
    690                 695                 700

Thr Lys Asn Gln Val Ser Leu Thr Cys Leu Val Lys Gly Phe Tyr Pro
705                 710                 715                 720

Ser Asp Ile Ala Val Glu Trp Glu Ser Asn Gly Gln Pro Glu Asn Asn
                725                 730                 735

Tyr Lys Thr Thr Pro Pro Val Leu Asp Ser Asp Gly Ser Phe Phe Leu
            740                 745                 750

Tyr Ser Lys Leu Thr Val Asp Lys Ser Arg Trp Gln Gln Gly Asn Val
        755                 760                 765

Phe Ser Cys Ser Val Met His Glu Ala Leu His Asn His Tyr Thr Gln
    770                 775                 780

Lys Ser Leu Ser Leu Ser Pro Gly Lys
785                 790

<210> SEQ ID NO 33
<211> LENGTH: 2343
<212> TYPE: DNA
<213> ORGANISM: Homo sapiens

<400> SEQUENCE: 33
atggtgtggc cggcgcggct ctgcgggctg tgggcgctgc tgctctgcgc cggcggcggg      60
ggcgggggcg ggggcgccgc gcctacggaa actcagccac ctgtgacaaa tttgagtgtc     120
tctgttgaaa acctctgcac agtaatatgg acatggaatc cacccgaggg agccagctca     180
aattgtagtc tatggtattt tagtcatttt ggcgacaaac aagataagaa aatagctccg     240
gaaactcgtc gttcaataga agtacccctg aatgagagga tttgtctgca agtgggtcc     300 cagtgtagca ccaatgagag tgagaagcct agcattttgg ttgaaaaatg catctcaccc     360
ccagaaggtg atcctgagtc tgctgtgact gagcttcaat gcatttggca caacctgagc     420
tacatgaagt gttcttggct ccctggaagg aataccagtc ccgacactaa ctatactctc     480

-continued

```
tactattggc acagaagcct ggaaaaaatt catcaatgtg aaaacatctt tagagaaggc     540
caatactttg gttgttcctt tgatctgacc aaagtgaagg attccagttt tgaacaacac     600
agtgtccaaa taatggtcaa ggataatgca ggaaaaatta aaccatcctt caatatagtg     660
cctttaactt cccgtgtgaa acctgatcct ccacatatta aaaacctctc cttccacaat     720
gatgacctat atgtgcaatg ggagaatcca cagaattta ttagcagatg cctatttat     780
gaagtagaag tcaataacag ccaaactgag acacataatg ttttctacgt ccaagaggct     840
aaatgtgaga atccagaatt tgagagaaat gtggagaata catcttgttt catggtccct     900
ggtgttcttc ctgatacttt gaacacagtc agaataagag tcaaaacaaa taagttatgc     960
tatgaggatg acaaactctg gagtaattgg agccaagaaa tgagtatagg taagaagcgc    1020
aattccacag gaacatgaa ggtcttgcag gagcccacct gcgtctccga ctacatgagc    1080
atctctactt gcgagtggaa gatgaatggt cccaccaatt gcagcaccga gctccgcctg    1140
ttgtaccagc tggtttttct gctctccgaa gcccacacgt gtatccctga gaacaacgga    1200
ggcgcgggt gcgtgtgcca cctgctcatg gatgacgtgg tcagtgcgga taactataca    1260
ctggacctgt gggctgggca gcagctgctg tggaagggct ccttcaagcc cagcgagcat    1320
gtgaaaccca gggccccagg aaacctgaca gttcacacca atgtctccga cactctgctg    1380
ctgacctgga gcaacccgta tccccctgac aattacctgt ataatcatct cacctatgca    1440
gtcaacattt ggagtgaaaa cgaccccgca gatttcagaa tctataacgt gacctaccta    1500
gaaccctccc tccgcatcgc agccagcacc ctgaagtctg ggatttccta cagggcacgc    1560
gtacgggcct gggctcagag ctataacacc acctggagtg agtggagccc cagcaccaag    1620
tggcacaact cctacaggga gcccttcgag cagtccggag acaaaactca cacatgccca    1680
ccgtgcccag cacctgaact cctgggggga ccgtcagtct tcctcttccc cccaaaaccc    1740
aaggacaccc tcatgatctc ccggacccct gaggtcacat gcgtggtggt ggacgtgagc    1800
cacgaagacc ctgaggtcaa gttcaactgg tacgtggacg gcgtggaggt gcataatgcc    1860
aagacaaagc cgcgggagga gcagtacaac agcacgtacc gtgtggtcag cgtcctcacc    1920
gtcctgcacc aggactggct gaatggcaag gagtacaagt gcaaggtctc caacaaagcc    1980
ctcccagccc ccatcgagaa aaccatctcc aaagccaaag gcagccccg agaaccacag    2040
gtgtacaccc tgcccccatc ccgggatgag ctgaccaaga accaggtcag cctgacctgc    2100
ctggtcaaag gcttctatcc cagcgacatc gccgtggagt gggagagcaa tgggcagccg    2160
gagaacaact acaagaccac gcctcccgtg ctggactccg acggctcctt cttcctctac    2220
agcaagctca ccgtggacaa gagcaggtgg cagcagggga acgtcttctc atgctccgtg    2280
atgcatgagg ctctgcacaa ccactacacg cagaagagcc tctccctgtc tccgggtaaa    2340
tga                                                                 2343
```

<210> SEQ ID NO 34
<211> LENGTH: 780
<212> TYPE: PRT
<213> ORGANISM: Homo sapiens

<400> SEQUENCE: 34

Met Val Trp Pro Ala Arg Leu Cys Gly Leu Trp Ala Leu Leu Leu Cys
1               5                   10                  15

Ala Gly Gly Gly Gly Gly Gly Gly Ala Ala Pro Thr Glu Thr Gln
            20                  25                  30

Pro Pro Val Thr Asn Leu Ser Val Ser Val Glu Asn Leu Cys Thr Val

-continued

```
                35                  40                  45
Ile Trp Thr Trp Asn Pro Pro Glu Gly Ala Ser Ser Asn Cys Ser Leu
 50                  55                  60
Trp Tyr Phe Ser His Phe Gly Asp Lys Gln Asp Lys Lys Ile Ala Pro
 65                  70                  75                  80
Glu Thr Arg Arg Ser Ile Glu Val Pro Leu Asn Glu Arg Ile Cys Leu
                 85                  90                  95
Gln Val Gly Ser Gln Cys Ser Thr Asn Glu Ser Glu Lys Pro Ser Ile
                100                 105                 110
Leu Val Glu Lys Cys Ile Ser Pro Pro Glu Gly Asp Pro Glu Ser Ala
                115                 120                 125
Val Thr Glu Leu Gln Cys Ile Trp His Asn Leu Ser Tyr Met Lys Cys
                130                 135                 140
Ser Trp Leu Pro Gly Arg Asn Thr Ser Pro Asp Thr Asn Tyr Thr Leu
145                 150                 155                 160
Tyr Tyr Trp His Arg Ser Leu Glu Lys Ile His Gln Cys Glu Asn Ile
                165                 170                 175
Phe Arg Glu Gly Gln Tyr Phe Gly Cys Ser Phe Asp Leu Thr Lys Val
                180                 185                 190
Lys Asp Ser Ser Phe Glu Gln His Ser Val Gln Ile Met Val Lys Asp
                195                 200                 205
Asn Ala Gly Lys Ile Lys Pro Ser Phe Asn Ile Val Pro Leu Thr Ser
                210                 215                 220
Arg Val Lys Pro Asp Pro Pro His Ile Lys Asn Leu Ser Phe His Asn
225                 230                 235                 240
Asp Asp Leu Tyr Val Gln Trp Glu Asn Pro Gln Asn Phe Ile Ser Arg
                245                 250                 255
Cys Leu Phe Tyr Glu Val Glu Val Asn Asn Ser Gln Thr Glu Thr His
                260                 265                 270
Asn Val Phe Tyr Val Gln Glu Ala Lys Cys Glu Asn Pro Glu Phe Glu
                275                 280                 285
Arg Asn Val Glu Asn Thr Ser Cys Phe Met Val Pro Gly Val Leu Pro
                290                 295                 300
Asp Thr Leu Asn Thr Val Arg Ile Arg Val Lys Thr Asn Lys Leu Cys
305                 310                 315                 320
Tyr Glu Asp Asp Lys Leu Trp Ser Asn Trp Ser Gln Glu Met Ser Ile
                325                 330                 335
Gly Asn Met Lys Val Leu Gln Gly Lys Lys Arg Asn Ser Thr Glu Pro
                340                 345                 350
Thr Cys Val Ser Asp Tyr Met Ser Ile Ser Thr Cys Glu Trp Lys Met
                355                 360                 365
Asn Gly Pro Thr Asn Cys Ser Thr Glu Leu Arg Leu Leu Tyr Gln Leu
                370                 375                 380
Val Phe Leu Leu Ser Glu Ala His Thr Cys Ile Pro Glu Asn Asn Gly
385                 390                 395                 400
Gly Ala Gly Cys Val Cys His Leu Leu Met Asp Asp Val Val Ser Ala
                405                 410                 415
Asp Asn Tyr Thr Leu Asp Leu Trp Ala Gly Gln Gln Leu Leu Trp Lys
                420                 425                 430
Gly Ser Phe Lys Pro Ser Glu His Val Lys Pro Arg Ala Pro Gly Asn
                435                 440                 445
Leu Thr Val His Thr Asn Val Ser Asp Thr Leu Leu Leu Thr Trp Ser
450                 455                 460
```

-continued

```
Asn Pro Tyr Pro Pro Asp Asn Tyr Leu Tyr Asn His Leu Thr Tyr Ala
465                 470                 475                 480

Val Asn Ile Trp Ser Glu Asn Asp Pro Ala Asp Phe Arg Ile Tyr Asn
                485                 490                 495

Val Thr Tyr Leu Glu Pro Ser Leu Arg Ile Ala Ala Ser Thr Leu Lys
            500                 505                 510

Ser Gly Ile Ser Tyr Arg Ala Arg Val Arg Ala Trp Ala Gln Ser Tyr
        515                 520                 525

Asn Thr Thr Trp Ser Glu Trp Ser Pro Ser Thr Lys Trp His Asn Ser
    530                 535                 540

Tyr Arg Glu Pro Phe Glu Gln Ser Gly Asp Lys Thr His Thr Cys Pro
545                 550                 555                 560

Pro Cys Pro Ala Pro Glu Leu Leu Gly Gly Pro Ser Val Phe Leu Phe
                565                 570                 575

Pro Pro Lys Pro Lys Asp Thr Leu Met Ile Ser Arg Thr Pro Glu Val
            580                 585                 590

Thr Cys Val Val Val Asp Val Ser His Glu Asp Pro Glu Val Lys Phe
        595                 600                 605

Asn Trp Tyr Val Asp Gly Val Glu Val His Asn Ala Lys Thr Lys Pro
    610                 615                 620

Arg Glu Glu Gln Tyr Asn Ser Thr Tyr Arg Val Val Ser Val Leu Thr
625                 630                 635                 640

Val Leu His Gln Asp Trp Leu Asn Gly Lys Glu Tyr Lys Cys Lys Val
                645                 650                 655

Ser Asn Lys Ala Leu Pro Ala Pro Ile Glu Lys Thr Ile Ser Lys Ala
            660                 665                 670

Lys Gly Gln Pro Arg Glu Pro Gln Val Tyr Thr Leu Pro Pro Ser Arg
        675                 680                 685

Asp Glu Leu Thr Lys Asn Gln Val Ser Leu Thr Cys Leu Val Lys Gly
    690                 695                 700

Phe Tyr Pro Ser Asp Ile Ala Val Glu Trp Glu Ser Asn Gly Gln Pro
705                 710                 715                 720

Glu Asn Asn Tyr Lys Thr Thr Pro Pro Val Leu Asp Ser Asp Gly Ser
                725                 730                 735

Phe Phe Leu Tyr Ser Lys Leu Thr Val Asp Lys Ser Arg Trp Gln Gln
            740                 745                 750

Gly Asn Val Phe Ser Cys Ser Val Met His Glu Ala Leu His Asn His
        755                 760                 765

Tyr Thr Gln Lys Ser Leu Ser Leu Ser Pro Gly Lys
    770                 775                 780
```

<210> SEQ ID NO 35
<211> LENGTH: 2331
<212> TYPE: DNA
<213> ORGANISM: Homo sapiens

<400> SEQUENCE: 35

| | | | | | |
|---|---|---|---|---|---|
| atggtgtggc | tttgctctgg | gctcctgttc | cctgtgagct | gcctggtcct | gctgcaggtg | 60 |
| gcaagctctg | ggaacatgaa | ggtcttgcag | gagcccacct | gcgtctccga | ctacatgagc | 120 |
| atctctactt | gcgagtggaa | gatgaatggt | cccaccaatt | gcagcaccga | gctccgcctg | 180 |
| ttgtaccagc | tggttttcct | gctctccgaa | gcccacacgt | gtatccctga | gaacaacgga | 240 |
| ggcgcgggt | gcgtgtgcca | cctgctcatg | gatgacgtgg | tcagtgcgga | taactataca | 300 |

-continued

```
ctggacctgt gggctgggca gcagctgctg tggaagggct ccttcaagcc cagcgagcat      360
gtgaaaccca gggccccagg aaacctgaca gttcacacca atgtctccga cactctgctg      420
ctgacctgga gcaacccgta tccccctgac aattacctgt ataatcatct cacctatgca      480
gtcaacattt ggagtgaaaa cgaccccgca gatttcagaa tctataacgt gacctaccta      540
gaaccctccc tccgcatcgc agccagcacc ctgaagtctg ggatttccta cagggcacgc      600
gtacgggcct gggctcagag ctataacacc acctggagtg agtggagccc cagcaccaag      660
tggcacaact cctacaggga gcccttcgag caggcgccta cggaaactca gccacctgtg      720
acaaatttga gtgtctctgt tgaaaacctc agcacagtaa tatggacatg aatccaccc       780
gagggagcca gctcaaattg tagtctatgg tattttagtc attttggcga caaacaagat      840
aagaaaatag ctccggaaac tcgtcgttca atagaagtac ccctgaatga gaggatttgt      900
ctgcaagtgg ggtcccagtg tagcaccaat gagagtgaga agcctagcat tttggttgaa      960
aaatgcatct caccccagaa aggtgatcct gagtctgctg tgactgagct tcaatgcatt      1020
tggcacaacc tgagctacat gaagtgttct tggctccctg aaggaatac cagtcccgac       1080
actaactata ctctctacta ttggcacaga agcctggaaa aaattcatca atgtgaaaac      1140
atctttagag aaggccaata ctttggttgt tcctttgatc tgaccaaagt gaaggattcc      1200
agttttgaac aacacagtgt ccaaataatg gtcaaggata tgcaggaaaa aattaaacca      1260
tccttcaata tagtgccttt aacttcccgt gtgaaacctg atcctccaca tattaaaaac      1320
ctctccttcc acaatgatga cctatatgtg caatgggaga atccacagaa ttttattagc      1380
agatgcctat tttatgaagt agaagtcaat aacagccaaa ctgagacaca taatgttttc      1440
tacgtccaag aggctaaatg tgagaatcca gaatttgaga gaaatgtgga gaatacatct      1500
tgtttcatgg tccctggtgt tcttcctgat actttgaaca cagtcagaat aagagtcaaa      1560
acaaataagt tatgctatga ggatgacaaa ctctggagta attggagcca agaaatgagt      1620
ataggtaaga agcgcaattc caccggtgac aaaactcaca catgcccacc gtgcccagca      1680
cctgaactcc tggggggacc gtcagtcttc ctcttccccc caaaacccaa ggacaccctc      1740
atgatctccc ggacccctga ggtcacatgc gtggtggtgg acgtgagcca cgaagaccct      1800
gaggtcaagt tcaactggta cgtggacggc gtggaggtgc ataatgccaa gacaaagccg      1860
cgggaggagc agtacaacag cacgtaccgt gtggtcagcg tcctcaccgt cctgcaccag      1920
gactggctga atggcaagga gtacaagtgc aaggtctcca acaaagccct cccagccccc      1980
atcgagaaaa ccatctccaa agccaaaggg cagccccgag aaccacaggt gtacaccctg      2040
cccccatccc gggatgagct gaccaagaac caggtcagcc tgacctgcct ggtcaaaggc      2100
ttctatccca gcgacatcgc cgtggagtgg gagagcaatg gcagccgga gaacaactac       2160
aagaccacgc ctcccgtgct ggactccgac ggctccttct tcctctacag caagctcacc      2220
gtggacaaga gcaggtggca gcaggggaac gtcttctcat gctccgtgat gcatgaggct      2280
ctgcacaacc actacacgca gaagagcctc tccctgtctc cgggtaaatg a               2331
```

<210> SEQ ID NO 36
<211> LENGTH: 776
<212> TYPE: PRT
<213> ORGANISM: Homo sapiens

<400> SEQUENCE: 36

```
Met Val Trp Leu Cys Ser Gly Leu Leu Phe Pro Val Ser Cys Leu Val
1               5                   10                  15
```

```
Gly Asn Met Lys Val Leu Gln Glu Pro Leu Leu Gln Val Ala Ser Ser
             20                  25                  30

Thr Cys Val Ser Asp Tyr Met Ser Ile Ser Thr Cys Glu Trp Lys Met
         35                  40                  45

Asn Gly Pro Thr Asn Cys Ser Thr Glu Leu Arg Leu Leu Tyr Gln Leu
 50                  55                  60

Val Phe Leu Leu Ser Glu Ala His Thr Cys Ile Pro Glu Asn Asn Gly
 65                  70                  75                  80

Gly Ala Gly Cys Val Cys His Leu Leu Met Asp Asp Val Val Ser Ala
             85                  90                  95

Asp Asn Tyr Thr Leu Asp Leu Trp Ala Gly Gln Gln Leu Leu Trp Lys
            100                 105                 110

Gly Ser Phe Lys Pro Ser Glu His Val Lys Pro Arg Ala Pro Gly Asn
            115                 120                 125

Leu Thr Val His Thr Asn Val Ser Asp Thr Leu Leu Leu Thr Trp Ser
130                 135                 140

Asn Pro Tyr Pro Pro Asp Asn Tyr Leu Tyr Asn His Leu Thr Tyr Ala
145                 150                 155                 160

Val Asn Ile Trp Ser Glu Asn Asp Pro Ala Asp Phe Arg Ile Tyr Asn
            165                 170                 175

Val Thr Tyr Leu Glu Pro Ser Leu Arg Ile Ala Ala Ser Thr Leu Lys
            180                 185                 190

Ser Gly Ile Ser Tyr Arg Ala Arg Val Arg Ala Trp Ala Gln Ser Tyr
            195                 200                 205

Asn Thr Thr Trp Ser Glu Trp Ser Pro Ser Thr Lys Trp His Asn Ser
            210                 215                 220

Tyr Arg Glu Pro Phe Glu Gln Ala Pro Thr Glu Thr Gln Pro Pro Val
225                 230                 235                 240

Thr Asn Leu Ser Val Ser Val Glu Asn Leu Ser Thr Val Ile Trp Thr
            245                 250                 255

Trp Asn Pro Pro Glu Gly Ala Ser Ser Asn Cys Ser Leu Trp Tyr Phe
            260                 265                 270

Ser His Phe Gly Asp Lys Gln Asp Lys Lys Ile Ala Pro Glu Thr Arg
            275                 280                 285

Arg Ser Ile Glu Val Pro Leu Asn Glu Arg Ile Cys Leu Gln Val Gly
            290                 295                 300

Ser Gln Cys Ser Thr Asn Glu Ser Glu Lys Pro Ser Ile Leu Val Glu
305                 310                 315                 320

Lys Cys Ile Ser Pro Pro Glu Gly Asp Pro Glu Ser Ala Val Thr Glu
            325                 330                 335

Leu Gln Cys Ile Trp His Asn Leu Ser Tyr Met Lys Cys Ser Trp Leu
            340                 345                 350

Pro Gly Arg Asn Thr Ser Pro Asp Thr Asn Tyr Thr Leu Tyr Tyr Trp
            355                 360                 365

His Arg Ser Leu Glu Lys Ile His Gln Cys Glu Asn Ile Phe Arg Glu
            370                 375                 380

Gly Gln Tyr Phe Gly Cys Ser Phe Asp Leu Thr Lys Val Lys Asp Ser
385                 390                 395                 400

Ser Phe Glu Gln His Ser Val Gln Ile Met Val Lys Asp Asn Ala Gly
            405                 410                 415

Lys Ile Lys Pro Ser Phe Asn Ile Val Pro Leu Thr Ser Arg Val Lys
            420                 425                 430

Pro Asp Pro Pro His Ile Lys Asn Leu Ser Phe His Asn Asp Asp Leu
```

```
                  435                 440                 445
Tyr Val Gln Trp Glu Asn Pro Gln Asn Phe Ile Ser Arg Cys Leu Phe
    450                 455                 460
Tyr Glu Val Glu Val Asn Asn Ser Gln Thr Glu Thr His Asn Val Phe
465                 470                 475                 480
Tyr Val Gln Glu Ala Lys Cys Glu Asn Pro Glu Phe Glu Arg Asn Val
                485                 490                 495
Glu Asn Thr Ser Cys Phe Met Val Pro Gly Val Leu Pro Asp Thr Leu
            500                 505                 510
Asn Thr Val Arg Ile Arg Val Lys Thr Asn Lys Leu Cys Tyr Glu Asp
        515                 520                 525
Asp Lys Leu Trp Ser Asn Trp Ser Gln Glu Met Ser Ile Gly Lys Lys
    530                 535                 540
Gly Asp Lys Thr His Thr Cys Pro Pro Cys Pro Ala Arg Asn Ser Thr
545                 550                 555                 560
Pro Glu Leu Leu Gly Gly Pro Ser Val Phe Leu Phe Pro Pro Lys Pro
                565                 570                 575
Lys Asp Thr Leu Met Ile Ser Arg Thr Pro Glu Val Thr Cys Val Val
            580                 585                 590
Val Asp Val Ser His Glu Asp Pro Glu Val Lys Phe Asn Trp Tyr Val
        595                 600                 605
Asp Gly Val Glu Val His Asn Ala Lys Thr Lys Pro Arg Glu Glu Gln
    610                 615                 620
Tyr Asn Ser Thr Tyr Arg Val Val Ser Val Leu Thr Val Leu His Gln
625                 630                 635                 640
Asp Trp Leu Asn Gly Lys Glu Tyr Lys Cys Lys Val Ser Asn Lys Ala
                645                 650                 655
Leu Pro Ala Pro Ile Glu Lys Thr Ile Ser Lys Ala Lys Gly Gln Pro
            660                 665                 670
Arg Glu Pro Gln Val Tyr Thr Leu Pro Pro Ser Arg Asp Glu Leu Thr
        675                 680                 685
Lys Asn Gln Val Ser Leu Thr Cys Leu Val Lys Gly Phe Tyr Pro Ser
    690                 695                 700
Asp Ile Ala Val Glu Trp Glu Ser Asn Gly Gln Pro Glu Asn Asn Tyr
705                 710                 715                 720
Lys Thr Thr Pro Pro Val Leu Asp Ser Asp Gly Ser Phe Phe Leu Tyr
                725                 730                 735
Ser Lys Leu Thr Val Asp Lys Ser Arg Trp Gln Gln Gly Asn Val Phe
            740                 745                 750
Ser Cys Ser Val Met His Glu Ala Leu His Asn His Tyr Thr Gln Lys
        755                 760                 765
Ser Leu Ser Leu Ser Pro Gly Lys
    770                 775

<210> SEQ ID NO 37
<211> LENGTH: 2343
<212> TYPE: DNA
<213> ORGANISM: Homo sapiens

<400> SEQUENCE: 37
atggtgtggc cggcgcggct ctgcgggctg tgggcgctgc tgctctgcgc cggcggcggg      60
ggcgggggcg gggcgccgc gcctacggaa actcagccac tgtgacaaa tttgagtgtc      120 tctgttgaaa acctcagcac agtaatatgg acatggaatc cacccgaggg agccagctca     180
```

-continued

```
aattgtagtc tatggtatttt tagtcattttt ggcgacaaac aagataagaa aatagctccg    240
gaaactcgtc gttcaataga agtaccctg  aatgagagga tttgtctgca agtggggtcc     300
cagtgtagca ccaatgagag tgagaagcct agcattttgg ttgaaaaatg catctcaccc     360
ccagaaggtg atcctgagtc tgctgtgact gagcttcaat gcatttggca caacctgagc    420
tacatgaagt gttcttggct ccctggaagg aataccagtc ccgacactaa ctatactctc    480
tactattggc acagaagcct ggaaaaaatt catcaatgtg aaaacatctt tagagaaggc    540
caatactttg gttgttcctt tgatctgacc aaagtgaagg attccagttt tgaacaacac    600
agtgtccaaa taatggtcaa ggataatgca ggaaaaatta accatcctt  caatatagtg    660
cctttaactt cccgtgtgaa acctgatcct ccacatatta aaaacctctc cttccacaat    720
gatgacctat atgtgcaatg ggagaatcca cagaatttta ttagcagatg cctattttat    780
gaagtagaag tcaataacag ccaaactgag acacataatg ttttctacgt ccaagaggct    840
aaatgtgaga atccagaatt tgagagaaat gtggagaata catcttgttt catggtccct    900
ggtgttcttc ctgatacttt gaacacagtc agaataagag tcaaaacaaa taagttatgc    960
tatgaggatg acaaactctg gagtaattgg agccaagaaa tgagtatagg taagaagcgc   1020
aattccacag ggaacatgaa ggtcttgcag gagcccacct gcgtctccga ctacatgagc   1080
atctctactt gcgagtggaa gatgaatggt cccaccaatt gcagcaccga gctccgcctg   1140
ttgtaccagc tggttttttct gctctccgaa gcccacacgt gtatccctga gaacaacgga  1200
ggcgcgggt  gcgtgtgcca cctgctcatg gatgacgtgg tcagtgcgga taactataca   1260
ctggacctgt gggctgggca gcagctgctg tggaagggct ccttcaagcc cagcgagcat   1320
gtgaaaccca gggccccagg aaacctgaca gttcacacca atgtctccga cactctgctg   1380
ctgacctgga gcaacccgta tccccctgac aattacctgt ataatcatct cacctatgca   1440
gtcaacattt ggagtgaaaa cgacccggca gatttcagaa tctataacgt gacctaccta   1500
gaaccctccc tccgcatcgc agccagcacc ctgaagtctg ggatttccta cagggcacgc   1560
gtacgggcct gggctcagag ctataacacc acctggagtg agtggagccc cagcaccaag   1620
tggcacaact cctacaggga gcccttcgag cagtccggag acaaaactca cacatgccca   1680
ccgtgcccag cacctgaact cctgggggga ccgtcagtct tcctcttccc cccaaaaccc   1740
aaggacaccc tcatgatctc ccggaccct  gaggtcacat gcgtggtggt ggacgtgagc   1800
cacgaagacc ctgaggtcaa gttcaactgg tacgtggacg gcgtggaggt gcataatgcc   1860
aagacaaagc cgcgggagga gcagtacaac agcacgtacc gtgtggtcag cgtcctcacc   1920
gtcctgcacc aggactggct gaatggcaag gagtacaagt gcaaggtctc caacaaagcc   1980
ctcccagccc ccatcgagaa aaccatctcc aaagccaaag gcagccccg  agaaccacag   2040
gtgtacaccc tgcccccatc ccgggatgag ctgaccaaga accaggtcag cctgacctgc   2100
ctggtcaaag gcttctatcc cagcgacatc gccgtggagt gggagagcaa tgggcagccg   2160
gagaacaact acaagaccac gcctcccgtg ctggactccg acggctcctt cttcctctac   2220
agcaagctca ccgtggacaa gagcaggtgg cagcagggga acgtcttctc atgctccgtg   2280
atgcatgagg ctctgcacaa ccactacacg cagaagagcc tctccctgtc tccgggtaaa   2340
tga                                                                 2343
```

<210> SEQ ID NO 38
<211> LENGTH: 780
<212> TYPE: PRT
<213> ORGANISM: Homo sapiens

<400> SEQUENCE: 38

```
Met Val Trp Pro Ala Arg Leu Cys Gly Leu Trp Ala Leu Leu Leu Cys
1               5                   10                  15

Ala Gly Gly Gly Gly Gly Gly Gly Ala Ala Pro Thr Glu Thr Gln
            20                  25                  30

Pro Pro Val Thr Asn Leu Ser Val Ser Val Glu Asn Leu Ser Thr Val
            35                  40                  45

Ile Trp Thr Trp Asn Pro Pro Glu Gly Ala Ser Ser Asn Cys Ser Leu
    50                  55                  60

Trp Tyr Phe Ser His Phe Gly Asp Lys Gln Asp Lys Lys Ile Ala Pro
65                  70                  75                  80

Glu Thr Arg Arg Ser Ile Glu Val Pro Leu Asn Glu Arg Ile Cys Leu
                85                  90                  95

Gln Val Gly Ser Gln Cys Ser Thr Asn Glu Ser Glu Lys Pro Ser Ile
            100                 105                 110

Leu Val Glu Lys Cys Ile Ser Pro Pro Glu Gly Asp Pro Glu Ser Ala
            115                 120                 125

Val Thr Glu Leu Gln Cys Ile Trp His Asn Leu Ser Tyr Met Lys Cys
130                 135                 140

Ser Trp Leu Pro Gly Arg Asn Thr Ser Pro Asp Thr Asn Tyr Thr Leu
145                 150                 155                 160

Tyr Tyr Trp His Arg Ser Leu Glu Lys Ile His Gln Cys Glu Asn Ile
                165                 170                 175

Phe Arg Glu Gly Gln Tyr Phe Gly Cys Ser Phe Asp Leu Thr Lys Val
            180                 185                 190

Lys Asp Ser Ser Phe Glu Gln His Ser Val Gln Ile Met Val Lys Asp
            195                 200                 205

Asn Ala Gly Lys Ile Lys Pro Ser Phe Asn Ile Val Pro Leu Thr Ser
    210                 215                 220

Arg Val Lys Pro Asp Pro Pro His Ile Lys Asn Leu Ser Phe His Asn
225                 230                 235                 240

Asp Asp Leu Tyr Val Gln Trp Glu Asn Pro Gln Asn Phe Ile Ser Arg
                245                 250                 255

Cys Leu Phe Tyr Glu Val Glu Val Asn Asn Ser Gln Thr Glu Thr His
            260                 265                 270

Asn Val Phe Tyr Val Gln Glu Ala Lys Cys Glu Asn Pro Glu Phe Glu
            275                 280                 285

Arg Asn Val Glu Asn Thr Ser Cys Phe Met Val Pro Gly Val Leu Pro
290                 295                 300

Asp Thr Leu Asn Thr Val Arg Ile Arg Val Lys Thr Asn Lys Leu Cys
305                 310                 315                 320

Tyr Glu Asp Asp Lys Leu Trp Ser Asn Trp Ser Gln Glu Met Ser Ile
                325                 330                 335

Gly Asn Met Lys Val Leu Gln Gly Lys Lys Arg Asn Ser Thr Glu Pro
            340                 345                 350

Thr Cys Val Ser Asp Tyr Met Ser Ile Ser Thr Cys Glu Trp Lys Met
            355                 360                 365

Asn Gly Pro Thr Asn Cys Ser Thr Glu Leu Arg Leu Leu Tyr Gln Leu
    370                 375                 380

Val Phe Leu Leu Ser Glu Ala His Thr Cys Ile Pro Glu Asn Asn Gly
385                 390                 395                 400

Gly Ala Gly Cys Val Cys His Leu Leu Met Asp Asp Val Val Ser Ala
```

```
                405                 410                 415
Asp Asn Tyr Thr Leu Asp Leu Trp Ala Gly Gln Gln Leu Leu Trp Lys
                420                 425                 430

Gly Ser Phe Lys Pro Ser Glu His Val Lys Pro Arg Ala Pro Gly Asn
            435                 440                 445

Leu Thr Val His Thr Asn Val Ser Asp Thr Leu Leu Leu Thr Trp Ser
        450                 455                 460

Asn Pro Tyr Pro Pro Asp Asn Tyr Leu Tyr Asn His Leu Thr Tyr Ala
465                 470                 475                 480

Val Asn Ile Trp Ser Glu Asn Asp Pro Ala Asp Phe Arg Ile Tyr Asn
                485                 490                 495

Val Thr Tyr Leu Glu Pro Ser Leu Arg Ile Ala Ala Ser Thr Leu Lys
            500                 505                 510

Ser Gly Ile Ser Tyr Arg Ala Arg Val Arg Ala Trp Ala Gln Ser Tyr
        515                 520                 525

Asn Thr Thr Trp Ser Glu Trp Ser Pro Ser Thr Lys Trp His Asn Ser
    530                 535                 540

Tyr Arg Glu Pro Phe Glu Gln Ser Gly Asp Lys Thr His Thr Cys Pro
545                 550                 555                 560

Pro Cys Pro Ala Pro Glu Leu Leu Gly Gly Pro Ser Val Phe Leu Phe
                565                 570                 575

Pro Pro Lys Pro Lys Asp Thr Leu Met Ile Ser Arg Thr Pro Glu Val
            580                 585                 590

Thr Cys Val Val Val Asp Val Ser His Glu Asp Pro Glu Val Lys Phe
        595                 600                 605

Asn Trp Tyr Val Asp Gly Val Glu Val His Asn Ala Lys Thr Lys Pro
    610                 615                 620

Arg Glu Glu Gln Tyr Asn Ser Thr Tyr Arg Val Val Ser Val Leu Thr
625                 630                 635                 640

Val Leu His Gln Asp Trp Leu Asn Gly Lys Glu Tyr Lys Cys Lys Val
                645                 650                 655

Ser Asn Lys Ala Leu Pro Ala Pro Ile Glu Lys Thr Ile Ser Lys Ala
            660                 665                 670

Lys Gly Gln Pro Arg Glu Pro Gln Val Tyr Thr Leu Pro Pro Ser Arg
        675                 680                 685

Asp Glu Leu Thr Lys Asn Gln Val Ser Leu Thr Cys Leu Val Lys Gly
    690                 695                 700

Phe Tyr Pro Ser Asp Ile Ala Val Glu Trp Glu Ser Asn Gly Gln Pro
705                 710                 715                 720

Glu Asn Asn Tyr Lys Thr Thr Pro Pro Val Leu Asp Ser Asp Gly Ser
                725                 730                 735

Phe Phe Leu Tyr Ser Lys Leu Thr Val Asp Lys Ser Arg Trp Gln Gln
            740                 745                 750

Gly Asn Val Phe Ser Cys Ser Val Met His Glu Ala Leu His Asn His
        755                 760                 765

Tyr Thr Gln Lys Ser Leu Ser Leu Ser Pro Gly Lys
    770                 775                 780

<210> SEQ ID NO 39
<211> LENGTH: 2331
<212> TYPE: DNA
<213> ORGANISM: Homo sapiens

<400> SEQUENCE: 39
```

-continued

```
atggtgtggc tttgctctgg gctcctgttc cctgtgagct gcctggtcct gctgcaggtg    60
gcaagctctg ggaacatgaa ggtcttgcag gagcccacct gcgtctccga ctacatgagc   120
atctctactt gcgagtggaa gatgaatggt cccaccaatt gcagcaccga gctccgcctg   180
ttgtaccagc tggtttttct gctctccgaa gcccacacgt gtatccctga gaacaacgga   240
ggcgcgggt gcgtgtgcca cctgctcatg gatgacgtgg tcagtgcgga taactataca   300
ctggacctgt gggctgggca gcagctgctg tggaagggcc ccttcaagcc cagcgagcat   360
gtgaaaccca gggccccagg aaacctgaca gttcacacca atgtctccga cactctgctg   420
ctgacctgga gcaacccgta tccccctgac aattacctgt ataatcatct cacctatgca   480
gtccacattt ggagtgaaaa cgacccggca gatttcagaa tctataacgt gacctaccta   540
gaaccctccc tccgcatcgc agccagcacc ctgaagtctg ggatttccta cagggcacgc   600
gtacgggcct gggctcagag ctataacacc acctggagtg agtggagccc cagcaccaag   660
tggcacaact cctacaggga gcccttcgag caggcgccta cggaaactca gccacctgtg   720
acaaatttga gtgtctctgt tgaaaacctc tgcacagtaa tatggacatg gaatccaccc   780
gagggagcca gctcaaattg tagtctatgg tattttagtc attttggcga caaacaagat   840
aagaaaatag ctccggaaac tcgtcgttca atagaagtac ccctgaatga gaggatttgt   900
ctgcaagtgg ggtcccagtg tagcaccaat gagagtgaga agcctagcat tttggttgaa   960
aaatgcatct caccccagag aggtgatcct gagtctgctg tgactgagct tcaatgcatt  1020
tggcacaacc tgagctacat gaagtgttct tggctccctg gaaggaatac cagtcccgac  1080
actaactata ctctctacta ttggcacaga agcctggaaa aaattcatca atgtgaaaac  1140
atctttagag aaggccaata ctttggttgt tcctttgatc tgaccaaagt gaaggattcc  1200
agtttttgaac aacacagtgt ccaaataatg gtcaaggata atgcaggaaa aattaaacca  1260
tccttcaata tagtgccttt aacttcccgt gtgaaacctg atcctccaca tattaaaaac  1320
ctctccttcc acaatgatga cctatatgtg caatgggaga atccacagaa ttttattagc  1380
agatgcctat tttatgaagt agaagtcaat aacagccaaa ctgagacaca taatgttttc  1440
tacgtccaag aggctaaatg tgagaatcca gaatttgaga gaaatgtgga gaatacatct  1500
tgtttcatgg tccctggtgt tcttcctgat actttgaaca cagtcagaat aagagtcaaa  1560
acaaataagt tatgctatga ggatgacaaa ctctggagta attggagcca agaaatgagt  1620
ataggtaaga agcgcaattc caccggtgac aaaactcaca catgcccacc gtgcccagca  1680
cctgaactcc tggggggacc gtcagtcttc ctcttccccc caaaacccaa ggacaccctc  1740
atgatctccc ggacccctga ggtcacatgc gtggtggtgg acgtgagcca cgaagaccct  1800
gaggtcaagt tcaactggta cgtggacggc gtggaggtgc ataatgccaa gacaaagccg  1860
cgggaggagc agtacaacag cacgtaccgt gtggtcagcg tcctcaccgt cctgcaccag  1920
gactggctga atggcaagga gtacaagtgc aaggtctcca acaaagccct cccagccccc  1980
atcgagaaaa ccatctccaa agccaaaggg cagccccgag aaccacaggt gtacaccctg  2040
cccccatccc gggatgagct gaccaagaac caggtcagcc tgacctgcct ggtcaaaggc  2100
ttctatccca gcgacatcgc cgtggagtgg gagagcaatg ggcagccgga gaacaactac  2160
aagaccacgc ctcccgtgct ggactccgac ggctccttct tcctctacag caagctcacc  2220
gtggacaaga gcaggtggca gcagggggaac gtcttctcat gctccgtgat gcatgaggct  2280
ctgcacaacc actacacgca gaagagcctc tccctgtctc cgggtaaatg a           2331
```

<210> SEQ ID NO 40
<211> LENGTH: 776
<212> TYPE: PRT
<213> ORGANISM: Homo sapiens

<400> SEQUENCE: 40

```
Met Val Trp Leu Cys Ser Gly Leu Leu Phe Pro Val Ser Cys Leu Val
 1               5                  10                  15

Gly Asn Met Lys Val Leu Gln Glu Pro Leu Leu Gln Val Ala Ser Ser
             20                  25                  30

Thr Cys Val Ser Asp Tyr Met Ser Ile Ser Thr Cys Glu Trp Lys Met
         35                  40                  45

Asn Gly Pro Thr Asn Cys Ser Thr Glu Leu Arg Leu Leu Tyr Gln Leu
     50                  55                  60

Val Phe Leu Leu Ser Glu Ala His Thr Cys Ile Pro Glu Asn Asn Gly
 65                  70                  75                  80

Gly Ala Gly Cys Val Cys His Leu Leu Met Asp Asp Val Val Ser Ala
                 85                  90                  95

Asp Asn Tyr Thr Leu Asp Leu Trp Ala Gly Gln Gln Leu Leu Trp Lys
            100                 105                 110

Gly Ser Phe Lys Pro Ser Glu His Val Lys Pro Arg Ala Pro Gly Asn
        115                 120                 125

Leu Thr Val His Thr Asn Val Ser Asp Thr Leu Leu Leu Thr Trp Ser
    130                 135                 140

Asn Pro Tyr Pro Pro Asp Asn Tyr Leu Tyr Asn His Leu Thr Tyr Ala
145                 150                 155                 160

Val Asn Ile Trp Ser Glu Asn Asp Pro Ala Asp Phe Arg Ile Tyr Asn
                165                 170                 175

Val Thr Tyr Leu Glu Pro Ser Leu Arg Ile Ala Ala Ser Thr Leu Lys
            180                 185                 190

Ser Gly Ile Ser Tyr Arg Ala Arg Val Arg Ala Trp Ala Gln Ser Tyr
        195                 200                 205

Asn Thr Thr Trp Ser Glu Trp Ser Pro Ser Thr Lys Trp His Asn Ser
    210                 215                 220

Tyr Arg Glu Pro Phe Glu Gln Ala Pro Thr Glu Thr Gln Pro Pro Val
225                 230                 235                 240

Thr Asn Leu Ser Val Ser Val Glu Asn Leu Cys Thr Val Ile Trp Thr
                245                 250                 255

Trp Asn Pro Pro Glu Gly Ala Ser Ser Asn Cys Ser Leu Trp Tyr Phe
            260                 265                 270

Ser His Phe Gly Asp Lys Gln Asp Lys Lys Ile Ala Pro Glu Thr Arg
        275                 280                 285

Arg Ser Ile Glu Val Pro Leu Asn Glu Arg Ile Cys Leu Gln Val Gly
    290                 295                 300

Ser Gln Cys Ser Thr Asn Glu Ser Glu Lys Pro Ser Ile Leu Val Glu
305                 310                 315                 320

Lys Cys Ile Ser Pro Pro Glu Gly Asp Pro Glu Ser Ala Val Thr Glu
                325                 330                 335

Leu Gln Cys Ile Trp His Asn Leu Ser Tyr Met Lys Cys Ser Trp Leu
            340                 345                 350

Pro Gly Arg Asn Thr Ser Pro Asp Thr Asn Tyr Thr Leu Tyr Tyr Trp
        355                 360                 365

His Arg Ser Leu Glu Lys Ile His Gln Cys Glu Asn Ile Phe Arg Glu
    370                 375                 380
```

```
Gly Gln Tyr Phe Gly Cys Ser Phe Asp Leu Thr Lys Val Lys Asp Ser
385                 390                 395                 400

Ser Phe Glu Gln His Ser Val Gln Ile Met Val Lys Asp Asn Ala Gly
            405                 410                 415

Lys Ile Lys Pro Ser Phe Asn Ile Val Pro Leu Thr Ser Arg Val Lys
        420                 425                 430

Pro Asp Pro His Ile Lys Asn Leu Ser Phe His Asn Asp Asp Leu
    435                 440                 445

Tyr Val Gln Trp Glu Asn Pro Gln Asn Phe Ile Ser Arg Cys Leu Phe
450                 455                 460

Tyr Glu Val Glu Val Asn Asn Ser Gln Thr Glu Thr His Asn Val Phe
465                 470                 475                 480

Tyr Val Gln Glu Ala Lys Cys Glu Asn Pro Glu Phe Glu Arg Asn Val
                485                 490                 495

Glu Asn Thr Ser Cys Phe Met Val Pro Gly Val Leu Pro Asp Thr Leu
            500                 505                 510

Asn Thr Val Arg Ile Arg Val Lys Thr Asn Lys Leu Cys Tyr Glu Asp
        515                 520                 525

Asp Lys Leu Trp Ser Asn Trp Ser Gln Glu Met Ser Ile Gly Lys Lys
530                 535                 540

Gly Asp Lys Thr His Thr Cys Pro Pro Cys Pro Ala Arg Asn Ser Thr
545                 550                 555                 560

Pro Glu Leu Leu Gly Gly Pro Ser Val Phe Leu Phe Pro Pro Lys Pro
                565                 570                 575

Lys Asp Thr Leu Met Ile Ser Arg Thr Pro Glu Val Thr Cys Val Val
            580                 585                 590

Val Asp Val Ser His Glu Asp Pro Glu Val Lys Phe Asn Trp Tyr Val
        595                 600                 605

Asp Gly Val Glu Val His Asn Ala Lys Thr Lys Pro Arg Glu Glu Gln
610                 615                 620

Tyr Asn Ser Thr Tyr Arg Val Val Ser Val Leu Thr Val Leu His Gln
625                 630                 635                 640

Asp Trp Leu Asn Gly Lys Glu Tyr Lys Cys Lys Val Ser Asn Lys Ala
                645                 650                 655

Leu Pro Ala Pro Ile Glu Lys Thr Ile Ser Lys Ala Lys Gly Gln Pro
            660                 665                 670

Arg Glu Pro Gln Val Tyr Thr Leu Pro Pro Ser Arg Asp Glu Leu Thr
        675                 680                 685

Lys Asn Gln Val Ser Leu Thr Cys Leu Val Lys Gly Phe Tyr Pro Ser
690                 695                 700

Asp Ile Ala Val Glu Trp Glu Ser Asn Gly Gln Pro Glu Asn Asn Tyr
705                 710                 715                 720

Lys Thr Thr Pro Pro Val Leu Asp Ser Asp Gly Ser Phe Phe Leu Tyr
                725                 730                 735

Ser Lys Leu Thr Val Asp Lys Ser Arg Trp Gln Gln Gly Asn Val Phe
            740                 745                 750

Ser Cys Ser Val Met His Glu Ala Leu His Asn His Tyr Thr Gln Lys
        755                 760                 765

Ser Leu Ser Leu Ser Pro Gly Lys
770                 775

<210> SEQ ID NO 41
<211> LENGTH: 2343
<212> TYPE: DNA
```

<213> ORGANISM: Homo sapiens

<400> SEQUENCE: 41

```
atggtgtggc cggcgcggct ctgcgggctg tgggcgctgc tgctctgcgc cggcggcggg      60
ggcggggggcg gggcgccgc gcctacggaa actcagccac ctgtgacaaa tttgagtgtc     120
tctgttgaaa acctcgcgac agtaatatgg acatggaatc cacccgaggg agccagctca     180
aattgtagtc tatggtattt tagtcatttt ggcgacaaac aagataagaa aatagctccg     240
gaaactcgtc gttcaataga agtaccctg aatgagagga tttgtctgca agtggggtcc      300
cagtgtagca ccaatgagag tgagaagcct agcattttgg ttgaaaaatg catctcaccc     360
ccagaaggtg atcctgagtc tgctgtgact gagcttcaat gcatttggca aacctgagc      420
tacatgaagt gttcttggct ccctggaagg aataccagtc ccgacactaa ctatactctc     480
tactattggc acagaagcct ggaaaaaatt catcaatgtg aaaacatctt tagagaaggc     540
caatactttg gttgttcctt tgatctgacc aaagtgaagg attccagttt tgaacaacac     600
agtgtccaaa taatggtcaa ggataatgca ggaaaaatta accatccttt caatatagtg     660
cctttaactt cccgtgtgaa acctgatcct ccacatatta aaaacctctc cttccacaat     720
gatgacctat atgtgcaatg ggagaatcca cagaattttta ttagcagatg cctatttttat  780
gaagtagaag tcaataacag ccaaactgag acacataatg ttttctacgt ccaagaggct     840
aaatgtgaga atccagaatt tgagagaaat gtggagaata catcttgttt catggtccct     900
ggtgttcttc ctgatacttt gaacacagtc agaataagag tcaaaacaaa taagttatgc     960
tatgaggatg acaaactctg gagtaattgg agccaagaaa tgagtatagg taagaagcgc    1020
aattccacag ggaacatgaa ggtcttgcag gagcccacct gcgtctccga ctacatgagc    1080
atctctactt gcgagtggaa gatgaatggt cccaccaatt gcagcaccga gctccgcctg    1140
ttgtaccagc tggtttttct gctctccgaa gcccacacgt gtatccctga gaacaacgga    1200
ggcgcgggt gcgtgtgcca cctgctcatg gatgacgtgg tcagtgcgga taactataca    1260
ctggacctgt gggctgggca gcagctgctg tggaagggct ccttcaagcc cagcgagcat    1320
gtgaaaccca gggccccagg aaacctgaca gttcacacca atgtctccga cactctgctg    1380
ctgacctgga gcaacccgta tccccctgac aattacctgt ataatcatct cacctatgca    1440
gtcaacattt ggagtgaaaa cgaccccgca gatttcagaa tctataacgt gacctaccta    1500
gaaccctccc tccgcatcgc agccagcacc ctgaagtctg ggatttccta cagggcacgc    1560
gtacgggcct gggctcagag ctataacacc acctggagtg agtggagccc cagcaccaag    1620
tggcacaact cctacaggga gcccttcgag cagtccggag acaaaactca cacatgccca    1680
ccgtgcccag cacctgaact cctgggggga ccgtcagtct tcctcttccc cccaaaaccc    1740
aaggacaccc tcatgatctc ccggacccct gaggtcacat gcgtggtggt ggacgtgagc    1800
cacgaagacc ctgaggtcaa gttcaactgg tacgtggacg gcgtggaggt gcataatgcc    1860
aagacaaagc cgcgggagga gcagtacaac agcacgtacc gtgtggtcag cgtcctcacc    1920
gtcctgcacc aggactggct gaatggcaag gagtacaagt gcaaggtctc caacaaagcc    1980
ctcccagccc ccatcgagaa aaccatctcc aaagccaaag gcagccccg agaaccacag    2040
gtgtacaccc tgcccccatc ccgggatgag ctgaccaaga accaggtcag cctgacctgc    2100
ctggtcaaag gcttctatcc cagcgacatc gccgtggagt gggagagcaa tgggcagccg    2160
gagaacaact acaagaccac gcctcccgtg ctggactccg acggctcctt cttcctctac    2220
agcaagctca ccgtggacaa gagcaggtgg cagcagggga acgtcttctc atgctccgtg    2280
```

```
atgcatgagg ctctgcacaa ccactacacg cagaagagcc tctccctgtc tccgggtaaa   2340
tga                                                                 2343
```

<210> SEQ ID NO 42
<211> LENGTH: 780
<212> TYPE: PRT
<213> ORGANISM: Homo sapiens

<400> SEQUENCE: 42

```
Met Val Trp Pro Ala Arg Leu Cys Gly Leu Trp Ala Leu Leu Leu Cys
 1               5                  10                  15

Ala Gly Gly Gly Gly Gly Gly Gly Ala Ala Pro Thr Glu Thr Gln
                20                  25                  30

Pro Pro Val Thr Asn Leu Ser Val Ser Val Glu Asn Leu Ala Thr Val
                35                  40                  45

Ile Trp Thr Trp Asn Pro Pro Glu Gly Ala Ser Ser Asn Cys Ser Leu
 50                  55                  60

Trp Tyr Phe Ser His Phe Gly Asp Lys Gln Asp Lys Lys Ile Ala Pro
65                   70                  75                  80

Glu Thr Arg Arg Ser Ile Glu Val Pro Leu Asn Glu Arg Ile Cys Leu
                85                  90                  95

Gln Val Gly Ser Gln Cys Ser Thr Asn Glu Ser Glu Lys Pro Ser Ile
                100                 105                 110

Leu Val Glu Lys Cys Ile Ser Pro Pro Glu Gly Asp Pro Glu Ser Ala
                115                 120                 125

Val Thr Glu Leu Gln Cys Ile Trp His Asn Leu Ser Tyr Met Lys Cys
                130                 135                 140

Ser Trp Leu Pro Gly Arg Asn Thr Ser Pro Asp Thr Asn Tyr Thr Leu
145                 150                 155                 160

Tyr Tyr Trp His Arg Ser Leu Glu Lys Ile His Gln Cys Glu Asn Ile
                165                 170                 175

Phe Arg Glu Gly Gln Tyr Phe Gly Cys Ser Phe Asp Leu Thr Lys Val
                180                 185                 190

Lys Asp Ser Ser Phe Glu Gln His Ser Val Gln Ile Met Val Lys Asp
                195                 200                 205

Asn Ala Gly Lys Ile Lys Pro Ser Phe Asn Ile Val Pro Leu Thr Ser
                210                 215                 220

Arg Val Lys Pro Asp Pro Pro His Ile Lys Asn Leu Ser Phe His Asn
225                 230                 235                 240

Asp Asp Leu Tyr Val Gln Trp Glu Asn Pro Gln Asn Phe Ile Ser Arg
                245                 250                 255

Cys Leu Phe Tyr Glu Val Glu Val Asn Asn Ser Gln Thr Glu Thr His
                260                 265                 270

Asn Val Phe Tyr Val Gln Glu Ala Lys Cys Glu Asn Pro Glu Phe Glu
                275                 280                 285

Arg Asn Val Glu Asn Thr Ser Cys Phe Met Val Pro Gly Val Leu Pro
                290                 295                 300

Asp Thr Leu Asn Thr Val Arg Ile Arg Val Lys Thr Asn Lys Leu Cys
305                 310                 315                 320

Tyr Glu Asp Asp Lys Leu Trp Ser Asn Trp Ser Gln Glu Met Ser Ile
                325                 330                 335

Gly Asn Met Lys Val Leu Gln Gly Lys Lys Arg Asn Ser Thr Glu Pro
                340                 345                 350
```

```
Thr Cys Val Ser Asp Tyr Met Ser Ile Ser Thr Cys Glu Trp Lys Met
            355                 360                 365

Asn Gly Pro Thr Asn Cys Ser Thr Glu Leu Arg Leu Leu Tyr Gln Leu
            370                 375                 380

Val Phe Leu Leu Ser Glu Ala His Thr Cys Ile Pro Glu Asn Asn Gly
385                 390                 395                 400

Gly Ala Gly Cys Val Cys His Leu Leu Met Asp Asp Val Val Ser Ala
                    405                 410                 415

Asp Asn Tyr Thr Leu Asp Leu Trp Ala Gly Gln Leu Leu Trp Lys
            420                 425                 430

Gly Ser Phe Lys Pro Ser Glu His Val Lys Pro Arg Ala Pro Gly Asn
            435                 440                 445

Leu Thr Val His Thr Asn Val Ser Asp Thr Leu Leu Leu Thr Trp Ser
            450                 455                 460

Asn Pro Tyr Pro Pro Asp Asn Tyr Leu Tyr Asn His Leu Thr Tyr Ala
465                 470                 475                 480

Val Asn Ile Trp Ser Glu Asn Asp Pro Ala Asp Phe Arg Ile Tyr Asn
                    485                 490                 495

Val Thr Tyr Leu Glu Pro Ser Leu Arg Ile Ala Ala Ser Thr Leu Lys
            500                 505                 510

Ser Gly Ile Ser Tyr Arg Ala Arg Val Arg Ala Trp Ala Gln Ser Tyr
            515                 520                 525

Asn Thr Thr Trp Ser Glu Trp Ser Pro Ser Thr Lys Trp His Asn Ser
            530                 535                 540

Tyr Arg Glu Pro Phe Glu Gln Ser Gly Asp Lys Thr His Thr Cys Pro
545                 550                 555                 560

Pro Cys Pro Ala Pro Glu Leu Leu Gly Gly Pro Ser Val Phe Leu Phe
                    565                 570                 575

Pro Pro Lys Pro Lys Asp Thr Leu Met Ile Ser Arg Thr Pro Glu Val
            580                 585                 590

Thr Cys Val Val Val Asp Val Ser His Glu Asp Pro Glu Val Lys Phe
            595                 600                 605

Asn Trp Tyr Val Asp Gly Val Glu Val His Asn Ala Lys Thr Lys Pro
610                 615                 620

Arg Glu Glu Gln Tyr Asn Ser Thr Tyr Arg Val Val Ser Val Leu Thr
625                 630                 635                 640

Val Leu His Gln Asp Trp Leu Asn Gly Lys Glu Tyr Lys Cys Lys Val
            645                 650                 655

Ser Asn Lys Ala Leu Pro Ala Pro Ile Glu Lys Thr Ile Ser Lys Ala
            660                 665                 670

Lys Gly Gln Pro Arg Glu Pro Gln Val Tyr Thr Leu Pro Pro Ser Arg
            675                 680                 685

Asp Glu Leu Thr Lys Asn Gln Val Ser Leu Thr Cys Leu Val Lys Gly
            690                 695                 700

Phe Tyr Pro Ser Asp Ile Ala Val Glu Trp Glu Ser Asn Gly Gln Pro
705                 710                 715                 720

Glu Asn Asn Tyr Lys Thr Thr Pro Pro Val Leu Asp Ser Asp Gly Ser
                    725                 730                 735

Phe Phe Leu Tyr Ser Lys Leu Thr Val Asp Lys Ser Arg Trp Gln Gln
                    740                 745                 750

Gly Asn Val Phe Ser Cys Ser Val Met His Glu Ala Leu His Asn His
            755                 760                 765

Tyr Thr Gln Lys Ser Leu Ser Leu Ser Pro Gly Lys
```

-continued

<210> SEQ ID NO 43
<211> LENGTH: 2331
<212> TYPE: DNA
<213> ORGANISM: Homo sapiens

<400> SEQUENCE: 43

| | | | | | |
|---|---|---|---|---|---|
| atggtgtggc | tttgctctgg | gctcctgttc | cctgtgagct | gcctggtcct | gctgcaggtg | 60 |
| gcaagctctg | ggaacatgaa | ggtcttgcag | gagcccacct | gcgtctccga | ctacatgagc | 120 |
| atctctactt | gcgagtggaa | gatgaatggt | cccaccaatt | gcagcaccga | gctccgcctg | 180 |
| ttgtaccagc | tggttttttct | gctctccgaa | gcccacacgt | gtatccctga | gaacaacgga | 240 |
| ggcgcgggt | gcgtgtgcca | cctgctcatg | gatgacgtgg | tcagtgcgga | taactataca | 300 |
| ctggacctgt | gggctgggca | gcagctgctg | tggaagggct | ccttcaagcc | cagcgagcat | 360 |
| gtgaaaccca | gggccccagg | aaacctgaca | gttcacacca | tgtctccga | cactctgctg | 420 |
| ctgacctgga | gcaacccgta | tccccctgac | aattacctgt | ataatcatct | cacctatgca | 480 |
| gtcaacattt | ggagtgaaaa | cgacccggca | gatttcagaa | tctataacgt | gacctaccta | 540 |
| gaaccctccc | tccgcatcgc | agccagcacc | ctgaagtctg | ggatttccta | cagggcacgc | 600 |
| gtacgggcct | gggctcagag | ctataacacc | cctggagtg | agtggagccc | cagcaccaag | 660 |
| tggcacaact | cctacaggga | gcccttcgag | caggcgccta | cggaaactca | gccacctgtg | 720 |
| acaaatttga | gtgtctctgt | tgaaaacctc | gcgacagtaa | tatggacatg | gaatccaccc | 780 |
| gagggagcca | gctcaaattg | tagtctatgg | tattttagtc | attttggcga | caaacaagat | 840 |
| aagaaaatag | ctccggaaac | tcgtcgttca | atagaagtac | ccctgaatga | gaggatttgt | 900 |
| ctgcaagtgg | ggtcccagtg | tagcaccaat | gagagtgaga | agcctagcat | tttggttgaa | 960 |
| aaatgcatct | cacccccaga | aggtgatcct | gagtctgctg | tgactgagct | tcaatgcatt | 1020 |
| tggcacaacc | tgagctacat | gaagtgttct | tggctccctg | gaaggaatac | cagtcccgac | 1080 |
| actaactata | ctctctacta | ttggcacaga | agcctggaaa | aaattcatca | atgtgaaaac | 1140 |
| atctttagag | aaggccaata | ctttggttgt | tcctttgatc | tgaccaaagt | gaaggattcc | 1200 |
| agttttgaac | aacacagtgt | ccaaataatg | gtcaaggata | atgcaggaaa | aattaaacca | 1260 |
| tccttcaata | tagtgccttt | aacttcccgt | gtgaaacctg | atcctccaca | tattaaaaac | 1320 |
| ctctccttcc | acaatgatga | cctatatgtg | caatgggaga | atccacagaa | ttttattagc | 1380 |
| agatgcctat | tttatgaagt | agaagtcaat | aacagccaaa | ctgagacaca | taatgttttc | 1440 |
| tacgtccaag | aggctaaatg | tgagaatcca | gaatttgaga | gaaatgtgga | gaatacatct | 1500 |
| tgtttcatgg | tccctggtgt | tcttcctgat | actttgaaca | cagtcagaat | aagagtcaaa | 1560 |
| acaaataagt | tatgctatga | ggatgacaaa | ctctggagta | attggagcca | agaaatgagt | 1620 |
| ataggtaaga | agcgcaattc | caccggtgac | aaaactcaca | catgcccacc | gtgcccagca | 1680 |
| cctgaactcc | tggggggacc | gtcagtcttc | ctcttccccc | caaaacccaa | ggacaccctc | 1740 |
| atgatctccc | ggacccctga | ggtcacatgc | gtggtggtgg | acgtgagcca | cgaagaccct | 1800 |
| gaggtcaagt | tcaactggta | cgtggacggc | gtggaggtgc | ataatgccaa | gacaaagccg | 1860 |
| cgggaggagc | agtacaacag | cacgtaccgt | gtggtcagcg | tcctcaccgt | cctgcaccag | 1920 |
| gactggctga | atggcaagga | gtacaagtgc | aaggtctcca | acaaagccct | cccagccccc | 1980 |
| atcgagaaaa | ccatctccaa | agccaaaggg | cagccccgag | aaccacaggt | gtacaccctg | 2040 |
| cccccatccc | gggatgagct | gaccaagaac | caggtcagcc | tgacctgcct | ggtcaaaggc | 2100 |

```
ttctatccca gcgacatcgc cgtggagtgg gagagcaatg ggcagccgga gaacaactac    2160
aagaccacgc ctcccgtgct ggactccgac ggctccttct tcctctacag caagctcacc    2220
gtggacaaga gcaggtggca gcagggggaac gtcttctcat gctccgtgat gcatgaggct    2280
ctgcacaacc actacacgca gaagagcctc tccctgtctc cgggtaaatg a             2331
```

<210> SEQ ID NO 44
<211> LENGTH: 776
<212> TYPE: PRT
<213> ORGANISM: Homo sapiens

<400> SEQUENCE: 44

```
Met Val Trp Leu Cys Ser Gly Leu Leu Phe Pro Val Ser Cys Leu Val
 1               5                  10                  15

Gly Asn Met Lys Val Leu Gln Glu Pro Leu Leu Gln Val Ala Ser Ser
            20                  25                  30

Thr Cys Val Ser Asp Tyr Met Ser Ile Ser Thr Cys Glu Trp Lys Met
        35                  40                  45

Asn Gly Pro Thr Asn Cys Ser Thr Glu Leu Arg Leu Leu Tyr Gln Leu
    50                  55                  60

Val Phe Leu Leu Ser Glu Ala His Thr Cys Ile Pro Glu Asn Asn Gly
65                  70                  75                  80

Gly Ala Gly Cys Val Cys His Leu Leu Met Asp Asp Val Val Ser Ala
                85                  90                  95

Asp Asn Tyr Thr Leu Asp Leu Trp Ala Gly Gln Gln Leu Leu Trp Lys
           100                 105                 110

Gly Ser Phe Lys Pro Ser Glu His Val Lys Pro Arg Ala Pro Gly Asn
       115                 120                 125

Leu Thr Val His Thr Asn Val Ser Asp Thr Leu Leu Leu Thr Trp Ser
130                 135                 140

Asn Pro Tyr Pro Pro Asp Asn Tyr Leu Tyr Asn His Leu Thr Tyr Ala
145                 150                 155                 160

Val Asn Ile Trp Ser Glu Asn Asp Pro Ala Asp Phe Arg Ile Tyr Asn
                165                 170                 175

Val Thr Tyr Leu Glu Pro Ser Leu Arg Ile Ala Ala Ser Thr Leu Lys
            180                 185                 190

Ser Gly Ile Ser Tyr Arg Ala Arg Val Arg Ala Trp Ala Gln Ser Tyr
        195                 200                 205

Asn Thr Thr Trp Ser Glu Trp Ser Pro Ser Thr Lys Trp His Asn Ser
    210                 215                 220

Tyr Arg Glu Pro Phe Glu Gln Ala Pro Thr Glu Thr Gln Pro Pro Val
225                 230                 235                 240

Thr Asn Leu Ser Val Ser Val Glu Asn Leu Ala Thr Val Ile Trp Thr
                245                 250                 255

Trp Asn Pro Pro Glu Gly Ala Ser Ser Asn Cys Ser Leu Trp Tyr Phe
            260                 265                 270

Ser His Phe Gly Asp Lys Gln Asp Lys Lys Ile Ala Pro Glu Thr Arg
        275                 280                 285

Arg Ser Ile Glu Val Pro Leu Asn Glu Arg Ile Cys Leu Gln Val Gly
    290                 295                 300

Ser Gln Cys Ser Thr Asn Glu Ser Glu Lys Pro Ser Ile Leu Val Glu
305                 310                 315                 320

Lys Cys Ile Ser Pro Pro Glu Gly Asp Pro Glu Ser Ala Val Thr Glu
                325                 330                 335
```

-continued

```
Leu Gln Cys Ile Trp His Asn Leu Ser Tyr Met Lys Cys Ser Trp Leu
            340                 345                 350
Pro Gly Arg Asn Thr Ser Pro Asp Thr Asn Tyr Thr Leu Tyr Tyr Trp
            355                 360                 365
His Arg Ser Leu Glu Lys Ile His Gln Cys Glu Asn Ile Phe Arg Glu
            370                 375                 380
Gly Gln Tyr Phe Gly Cys Ser Phe Asp Leu Thr Lys Val Lys Asp Ser
385                 390                 395                 400
Ser Phe Glu Gln His Ser Val Gln Ile Met Val Lys Asp Asn Ala Gly
                405                 410                 415
Lys Ile Lys Pro Ser Phe Asn Ile Val Pro Leu Thr Ser Arg Val Lys
            420                 425                 430
Pro Asp Pro Pro His Ile Lys Asn Leu Ser Phe His Asn Asp Asp Leu
            435                 440                 445
Tyr Val Gln Trp Glu Asn Pro Gln Asn Phe Ile Ser Arg Cys Leu Phe
450                 455                 460
Tyr Glu Val Glu Val Asn Asn Ser Gln Thr Glu Thr His Asn Val Phe
465                 470                 475                 480
Tyr Val Gln Glu Ala Lys Cys Glu Asn Pro Glu Phe Glu Arg Asn Val
                485                 490                 495
Glu Asn Thr Ser Cys Phe Met Val Pro Gly Val Leu Pro Asp Thr Leu
            500                 505                 510
Asn Thr Val Arg Ile Arg Val Lys Thr Asn Lys Leu Cys Tyr Glu Asp
            515                 520                 525
Asp Lys Leu Trp Ser Asn Trp Ser Gln Glu Met Ser Ile Gly Lys Lys
            530                 535                 540
Gly Asp Lys Thr His Thr Cys Pro Pro Cys Pro Ala Arg Asn Ser Thr
545                 550                 555                 560
Pro Glu Leu Leu Gly Gly Pro Ser Val Phe Leu Phe Pro Pro Lys Pro
                565                 570                 575
Lys Asp Thr Leu Met Ile Ser Arg Thr Pro Glu Val Thr Cys Val Val
            580                 585                 590
Val Asp Val Ser His Glu Asp Pro Glu Val Lys Phe Asn Trp Tyr Val
            595                 600                 605
Asp Gly Val Glu Val His Asn Ala Lys Thr Lys Pro Arg Glu Glu Gln
            610                 615                 620
Tyr Asn Ser Thr Tyr Arg Val Val Ser Val Leu Thr Val Leu His Gln
625                 630                 635                 640
Asp Trp Leu Asn Gly Lys Glu Tyr Lys Cys Lys Val Ser Asn Lys Ala
                645                 650                 655
Leu Pro Ala Pro Ile Glu Lys Thr Ile Ser Lys Ala Lys Gly Gln Pro
            660                 665                 670
Arg Glu Pro Gln Val Tyr Thr Leu Pro Pro Ser Arg Asp Glu Leu Thr
            675                 680                 685
Lys Asn Gln Val Ser Leu Thr Cys Leu Val Lys Gly Phe Tyr Pro Ser
            690                 695                 700
Asp Ile Ala Val Glu Trp Glu Ser Asn Gly Gln Pro Glu Asn Asn Tyr
705                 710                 715                 720
Lys Thr Thr Pro Pro Val Leu Asp Ser Asp Gly Ser Phe Phe Leu Tyr
                725                 730                 735
Ser Lys Leu Thr Val Asp Lys Ser Arg Trp Gln Gln Gly Asn Val Phe
            740                 745                 750
```

```
Ser Cys Ser Val Met His Glu Ala Leu His Asn His Tyr Thr Gln Lys
        755                 760                 765
Ser Leu Ser Leu Ser Pro Gly Lys
        770                 775

<210> SEQ ID NO 45
<211> LENGTH: 2337
<212> TYPE: DNA
<213> ORGANISM: Homo sapiens

<400> SEQUENCE: 45
atggtgtggc tttgctctgg gctcctgttc cctgtgagct gcctggtcct gctgcaggtg      60
gcaagctctg ggaacatgaa ggtcttgcag gagcccacct gcgtctccga ctacatgagc     120
atctctactt gcgagtggaa gatgaatggt cccaccaatt gcagcaccga gctccgcctg     180
ttgtaccagc tggttttttct gctctccgaa gcccacacgt gtatccctga gaacaacgga     240 ggcgcgggt gcgtgtgcca cctgctcatg gatgacgtgg tcagtgcgga taactataca     300
ctggacctgt gggctgggca gcagctgctg tggaagggct ccttcaagcc cagcgagcat     360
gtgaaaccca gggccccagg aaacctgaca gttcacacca tgtctccga cactctgctg     420 ctgacctgga gcaacccgta tccccctgac aattacctgt ataatcatct cacctatgca     480
gtcaacattt ggagtgaaaa cgacccggca gatttcagaa tctataacgt gacctaccta     540
gaaccctccc tccgcatcgc agccagcacc ctgaagtctg ggatttccta cagggcacgc     600
gtacgggcct gggctcagag ctataacacc acctggagtg agtggagccc cagcaccaag     660
tggcacaact cctacaggga gcccttcgag caggcgccta cggaaactca gccacctgtg     720
acaaatttga gtgtctctgt tgaaaacctc gcgacagtaa tatggacatg aatccaccc     780 gagggagcca gctcaaattg tagtctatgg tattttagtc attttggcga caaacaagat     840
aagaaaatag ctccggaaac tcgtcgttca atagaagtac ccctgaatga gaggatttgt     900
ctgcaagtgg ggtcccagtg tagcaccaat gagagtgaga agcctagcat tttggttgaa     960
aaatgcatct cacccccaga aggtgatcct gagtctgctg tgactgagct tcaatgcatt    1020
tggcacaacc tgagctacat gaagtgttct tggctccctg aaggaataac cagtcccgac    1080
actaactata ctctctacta ttggcacaga agcctggaaa aaattcatca atgtgaaaac    1140
atctttagag aaggccaata ctttggttgt tcctttgatc tgaccaaagt gaaggattcc    1200
agttttgaac aacacagtgt ccaaataatg gtcaaggata tgcaggaaa aattaaacca    1260 tccttcaata tagtgccttt aacttcccgt gtgaaacctg atcctccaca tattaaaaac    1320
ctctccttcc acaatgatga cctatatgtg caatgggaga atccacagaa ttttattagc    1380
agatgcctat tttatgaagt agaagtcaat aacagccaaa ctgagacaca taatgttttc    1440
tacgtccaag aggctaaatg tgagaatcca gaatttgaga gaaatgtgga aatacatct    1500 tgtttcatgg tccctggtgt tcttcctgat actttgaaca cagtcagaat aagagtcaaa    1560
acaaataagt tatgctatga ggatgacaaa ctctggagta attggagcca agaaatgagt    1620
ataggtaaga agcgcaattc caccggagag tccaaatacg gtccgccatg ccatcatgc    1680 ccagcacctg agttcctggg gggaccatca gtcttcctgt tccccccaaa acccaaggac    1740
actctcatga tctcccggac ccctgaggtc acgtgcgtgg tggtggacgt gagccaggaa    1800
gaccccgagg tccagttcaa ctggtacgtg gatggcgtgg aggtgcataa tgccaagaca    1860
aagccgcggg aggagcagtt caacagcacg taccgtgtgg tcagcgtcct caccgtcctg    1920
caccaggact ggctgaacgg caaggagtac aagtgcaagg tctccaacaa aggcctcccg    1980
```

```
tcctccatcg agaaaaccat ctccaaagcc aaagggcagc cccgagagcc acaggtgtac      2040
accctgcccc catcccagga ggagatgacc aagaaccagg tcagcctgac ctgcctggtc      2100
aaaggcttct accccagcga catcgccgtg gagtgggaga gcaatgggca gccggagaac      2160
aactacaaga ccacgcctcc cgtgctggac tccgacggct ccttcttcct ctacagcagg      2220
ctaaccgtgg acaagagcag gtggcaggag gggaatgtct tctcatgctc cgtgatgcat      2280
gaggctctgc acaaccacta cacacagaag agcctctccc tgtctctggg taaatga        2337
```

<210> SEQ ID NO 46
<211> LENGTH: 778
<212> TYPE: PRT
<213> ORGANISM: Homo sapiens

<400> SEQUENCE: 46

```
Met Val Trp Leu Cys Ser Gly Leu Leu Phe Pro Val Ser Cys Leu Val
  1               5                  10                  15

Leu Leu Gln Val Ala Ser Ser Gly Asn Met Lys Val Leu Gln Glu Pro
             20                  25                  30

Thr Cys Val Ser Asp Tyr Met Ser Ile Ser Thr Cys Glu Trp Lys Met
         35                  40                  45

Asn Gly Pro Thr Asn Cys Ser Thr Glu Leu Arg Leu Leu Tyr Gln Leu
     50                  55                  60

Val Phe Leu Leu Ser Glu Ala His Thr Cys Ile Pro Glu Asn Asn Gly
 65                  70                  75                  80

Gly Ala Gly Cys Val Cys His Leu Leu Met Asp Asp Val Val Ser Ala
                 85                  90                  95

Asp Asn Tyr Thr Leu Asp Leu Trp Ala Gly Gln Gln Leu Leu Trp Lys
            100                 105                 110

Gly Ser Phe Lys Pro Ser Glu His Val Lys Pro Arg Ala Pro Gly Asn
        115                 120                 125

Leu Thr Val His Thr Asn Val Ser Asp Thr Leu Leu Leu Thr Trp Ser
    130                 135                 140

Asn Pro Tyr Pro Pro Asp Asn Tyr Leu Tyr Asn His Leu Thr Tyr Ala
145                 150                 155                 160

Val Asn Ile Trp Ser Glu Asn Asp Pro Ala Asp Phe Arg Ile Tyr Asn
                165                 170                 175

Val Thr Tyr Leu Glu Pro Ser Leu Arg Ile Ala Ala Ser Thr Leu Lys
            180                 185                 190

Ser Gly Ile Ser Tyr Arg Ala Arg Val Arg Ala Trp Ala Gln Ser Tyr
        195                 200                 205

Asn Thr Thr Trp Ser Glu Trp Ser Pro Ser Thr Lys Trp His Asn Ser
    210                 215                 220

Tyr Arg Glu Pro Phe Glu Gln Ala Pro Thr Glu Thr Gln Pro Pro Val
225                 230                 235                 240

Thr Asn Leu Ser Val Ser Val Glu Asn Leu Ala Thr Val Ile Trp Thr
                245                 250                 255

Trp Asn Pro Pro Glu Gly Ala Ser Ser Asn Cys Ser Leu Trp Tyr Phe
            260                 265                 270

Ser His Phe Gly Asp Lys Gln Asp Lys Lys Ile Ala Pro Glu Thr Arg
        275                 280                 285

Arg Ser Ile Glu Val Pro Leu Asn Glu Arg Ile Cys Leu Gln Val Gly
    290                 295                 300

Ser Gln Cys Ser Thr Asn Glu Ser Glu Lys Pro Ser Ile Leu Val Glu
```

```
                305                 310                 315                 320
Lys Cys Ile Pro Pro Glu Gly Asp Pro Glu Ser Ala Val Thr Glu
                325                 330                 335

Leu Gln Cys Ile Trp His Asn Leu Ser Tyr Met Lys Cys Ser Trp Leu
            340                 345                 350

Pro Gly Arg Asn Thr Ser Pro Asp Thr Asn Tyr Thr Leu Tyr Tyr Trp
            355                 360                 365

His Arg Ser Leu Glu Lys Ile His Gln Cys Glu Asn Ile Phe Arg Glu
        370                 375                 380

Gly Gln Tyr Phe Gly Cys Ser Phe Asp Leu Thr Lys Val Lys Asp Ser
385                 390                 395                 400

Ser Phe Glu Gln His Ser Val Gln Ile Met Val Lys Asp Asn Ala Gly
                405                 410                 415

Lys Ile Lys Pro Ser Phe Asn Ile Val Pro Leu Thr Ser Arg Val Lys
            420                 425                 430

Pro Asp Pro Pro His Ile Lys Asn Leu Ser Phe His Asn Asp Asp Leu
        435                 440                 445

Tyr Val Gln Trp Glu Asn Pro Gln Asn Phe Ile Ser Arg Cys Leu Phe
    450                 455                 460

Tyr Glu Val Glu Val Asn Asn Ser Gln Thr Glu Thr His Asn Val Phe
465                 470                 475                 480

Tyr Val Gln Glu Ala Lys Cys Glu Asn Pro Glu Phe Glu Arg Asn Val
                485                 490                 495

Glu Asn Thr Ser Cys Phe Met Val Pro Gly Val Leu Pro Asp Thr Leu
            500                 505                 510

Asn Thr Val Arg Ile Arg Val Lys Thr Asn Lys Leu Cys Tyr Glu Asp
        515                 520                 525

Asp Lys Leu Trp Ser Asn Trp Ser Gln Glu Met Ser Ile Gly Lys Lys
    530                 535                 540

Arg Asn Ser Thr Gly Glu Ser Lys Tyr Gly Pro Cys Pro Ser Cys
545                 550                 555                 560

Pro Ala Pro Glu Phe Leu Gly Gly Pro Ser Val Phe Leu Phe Pro Pro
                565                 570                 575

Lys Pro Lys Asp Thr Leu Met Ile Ser Arg Thr Pro Glu Val Thr Cys
            580                 585                 590

Val Val Val Asp Val Ser Gln Glu Asp Pro Glu Val Gln Phe Asn Trp
        595                 600                 605

Tyr Val Asp Gly Val Glu Val His Asn Ala Lys Thr Lys Pro Arg Glu
    610                 615                 620

Glu Gln Phe Asn Ser Thr Tyr Arg Val Val Ser Val Leu Thr Val Leu
625                 630                 635                 640

His Gln Asp Trp Leu Asn Gly Lys Glu Tyr Lys Cys Lys Val Ser Asn
                645                 650                 655

Lys Gly Leu Pro Ser Ser Ile Glu Lys Thr Ile Ser Lys Ala Lys Gly
            660                 665                 670

Gln Pro Arg Glu Pro Gln Val Tyr Thr Leu Pro Pro Ser Gln Glu Glu
        675                 680                 685

Met Thr Lys Asn Gln Val Ser Leu Thr Cys Leu Val Lys Gly Phe Tyr
    690                 695                 700

Pro Ser Asp Ile Ala Val Glu Trp Glu Ser Asn Gly Gln Pro Glu Asn
705                 710                 715                 720

Asn Tyr Lys Thr Thr Pro Pro Val Leu Asp Ser Asp Gly Ser Phe Phe
                725                 730                 735
```

Leu Tyr Ser Arg Leu Thr Val Asp Lys Ser Arg Trp Gln Glu Gly Asn
        740                 745                 750

Val Phe Ser Cys Ser Val Met His Glu Ala Leu His Asn His Tyr Thr
        755                 760                 765

Gln Lys Ser Leu Ser Leu Ser Leu Gly Lys
        770                 775

<210> SEQ ID NO 47
<211> LENGTH: 2349
<212> TYPE: DNA
<213> ORGANISM: Homo sapiens

<400> SEQUENCE: 47

| | | | | |
|---|---|---|---|---|
| atggtgtggc | cggcgcggct | ctgcgggctg | tgggcgctgc | tgctctgcgc cggcggcggg | 60 |
| ggcgggggcg | gggcgccgc | gcctacggaa | actcagccac | ctgtgacaaa tttgagtgtc | 120 |
| tctgttgaaa | acctcgcgac | agtaatatgg | acatggaatc | cacccgaggg agccagctca | 180 |
| aattgtagtc | tatggtattt | tagtcatttt | ggcgacaaac | aagataagaa atagctccg | 240 |
| gaaactcgtc | gttcaataga | agtacccctg | aatgagagga | tttgtctgca agtggggtcc | 300 |
| cagtgtagca | ccaatgagag | tgagaagcct | agcattttgg | ttgaaaaatg catctcaccc | 360 |
| ccagaaggtg | atcctgagtc | tgctgtgact | gagcttcaat | gcatttggca caacctgagc | 420 |
| tacatgaagt | gttcttggct | ccctggaagg | aataccagtc | ccgacactaa ctatactctc | 480 |
| tactattggc | acagaagcct | ggaaaaaatt | catcaatgtg | aaaacatctt tagagaaggc | 540 |
| caatactttg | gttgttcctt | tgatctgacc | aaagtgaagg | attccagttt tgaacaacac | 600 |
| agtgtccaaa | taatggtcaa | ggataatgca | ggaaaaatta | accatccttc caatatagtg | 660 |
| cctttaactt | cccgtgtgaa | acctgatcct | ccacatatta | aaaacctctc cttccacaat | 720 |
| gatgacctat | atgtgcaatg | ggagaatcca | cagaatttta | ttagcagatg cctattttat | 780 |
| gaagtagaag | tcaataacag | ccaaactgag | acacataatg | ttttctacgt ccaagaggct | 840 |
| aaatgtgaga | atccagaatt | tgagagaaat | gtggagaata | catcttgttt catggtccct | 900 |
| ggtgttcttc | ctgatacttt | gaacacagtc | agaataagag | tcaaaacaaa taagttatgc | 960 |
| tatgaggatg | acaaactctg | gagtaattgg | agccaagaaa | tgagtatagg taagaagcgc | 1020 |
| aattccacag | gaacatgaa | ggtcttgcag | gagcccacct | gcgtctccga ctacatgagc | 1080 |
| atctctactt | gcgagtggaa | gatgaatggt | cccaccaatt | gcagcaccga gctccgcctg | 1140 |
| ttgtaccagc | tggttttttct | gctctccgaa | gcccacacgt | gtatccctga aacaacgga | 1200 |
| ggcgcgggt | gcgtgtgcca | cctgctcatg | gatgacgtgg | tcagtgcgga taactataca | 1260 |
| ctggacctgt | gggctgggca | gcagctgctg | tggaagggct | ccttcaagcc cagcgagcat | 1320 |
| gtgaaaccca | gggcccccagg | aaacctgaca | gttcacacca | atgtctccga cactctgctg | 1380 |
| ctgacctgga | gcaacccgta | tccccctgac | aattacctgt | ataatcatct cacctatgca | 1440 |
| gtcaacattt | ggagtgaaaa | cgacccggca | gatttcagaa | tctataacgt gacctaccta | 1500 |
| gaaccctccc | tccgcatcgc | agccagcacc | ctgaagtctg | gatttcctca gggcacgc | 1560 |
| gtacgggcct | gggctcagag | ctataacacc | acctggagtg | agtggagccc cagcaccaag | 1620 |
| tggcacaact | cctacaggga | gcccttcgag | cagaccggag | agtccaaata cggtccgcca | 1680 |
| tgcccatcat | gcccagcacc | tgagttcctg | ggggaccat | cagtcttcct gttccccca | 1740 |
| aaacccaagg | acactctcat | gatctcccgg | acccctgagg | tcacgtgcgt ggtggtggac | 1800 |
| gtgagccagg | aagaccccga | ggtccagttc | aactggtacg | tggatggcgt ggaggtgcat | 1860 |

-continued

```
aatgccaaga caaagccgcg ggaggagcag ttcaacagca cgtaccgtgt ggtcagcgtc    1920
ctcaccgtcc tgcaccagga ctggctgaac ggcaaggagt acaagtgcaa ggtctccaac    1980
aaaggcctcc cgtcctccat cgagaaaacc atctccaaag ccaagggca gccccgagag     2040 ccacaggtgt acaccctgcc cccatcccag gaggagatga ccaagaacca ggtcagcctg    2100
acctgcctgg tcaaaggctt ctaccccagc gacatcgccg tggagtggga gagcaatggg    2160
cagccggaga caactacaa gaccacgcct cccgtgctgg actccgacgg ctccttcttc     2220
ctctacagca ggctaaccgt ggacaagagc aggtggcagg aggggaatgt cttctcatgc    2280
tccgtgatgc atgaggctct gcacaaccac tacacacaga gagcctctc cctgtctctg     2340 ggtaaatga                                                             2349
```

<210> SEQ ID NO 48
<211> LENGTH: 782
<212> TYPE: PRT
<213> ORGANISM: Homo sapiens

<400> SEQUENCE: 48

```
Met Val Trp Pro Ala Arg Leu Cys Gly Leu Trp Ala Leu Leu Leu Cys
1               5                   10                  15

Ala Gly Gly Gly Gly Gly Gly Gly Ala Ala Pro Thr Glu Thr Gln
            20                  25                  30

Pro Pro Val Thr Asn Leu Ser Val Ser Val Glu Asn Leu Ala Thr Val
            35                  40                  45

Ile Trp Thr Trp Asn Pro Pro Glu Gly Ala Ser Ser Asn Cys Ser Leu
    50                  55                  60

Trp Tyr Phe Ser His Phe Gly Asp Lys Gln Asp Lys Lys Ile Ala Pro
65                  70                  75                  80

Glu Thr Arg Arg Ser Ile Glu Val Pro Leu Asn Glu Arg Ile Cys Leu
                85                  90                  95

Gln Val Gly Ser Gln Cys Ser Thr Asn Glu Ser Glu Lys Pro Ser Ile
            100                 105                 110

Leu Val Glu Lys Cys Ile Ser Pro Pro Glu Gly Asp Pro Glu Ser Ala
        115                 120                 125

Val Thr Glu Leu Gln Cys Ile Trp His Asn Leu Ser Tyr Met Lys Cys
    130                 135                 140

Ser Trp Leu Pro Gly Arg Asn Thr Ser Pro Asp Thr Asn Tyr Thr Leu
145                 150                 155                 160

Tyr Tyr Trp His Arg Ser Leu Glu Lys Ile His Gln Cys Glu Asn Ile
                165                 170                 175

Phe Arg Glu Gly Gln Tyr Phe Gly Cys Ser Phe Asp Leu Thr Lys Val
            180                 185                 190

Lys Asp Ser Ser Phe Glu Gln His Ser Val Gln Ile Met Val Lys Asp
        195                 200                 205

Asn Ala Gly Lys Ile Lys Pro Ser Phe Asn Ile Val Pro Leu Thr Ser
    210                 215                 220

Arg Val Lys Pro Asp Pro Pro His Ile Lys Asn Leu Ser Phe His Asn
225                 230                 235                 240

Asp Asp Leu Tyr Val Gln Trp Glu Asn Pro Gln Asn Phe Ile Ser Arg
                245                 250                 255

Cys Leu Phe Tyr Glu Val Glu Val Asn Asn Ser Gln Thr Glu Thr His
            260                 265                 270

Asn Val Phe Tyr Val Gln Glu Ala Lys Cys Glu Asn Pro Glu Phe Glu
```

275                 280                 285
Arg Asn Val Glu Asn Thr Ser Cys Phe Met Val Pro Gly Val Leu Pro
    290                 295                 300

Asp Thr Leu Asn Thr Val Arg Ile Arg Val Lys Thr Asn Lys Leu Cys
305                 310                 315                 320

Tyr Glu Asp Asp Lys Leu Trp Ser Asn Trp Ser Gln Glu Met Ser Ile
                325                 330                 335

Gly Asn Met Lys Val Leu Gln Gly Lys Lys Arg Asn Ser Thr Glu Pro
            340                 345                 350

Thr Cys Val Ser Asp Tyr Met Ser Ile Ser Thr Cys Glu Trp Lys Met
        355                 360                 365

Asn Gly Pro Thr Asn Cys Ser Thr Glu Leu Arg Leu Leu Tyr Gln Leu
    370                 375                 380

Val Phe Leu Leu Ser Glu Ala His Thr Cys Ile Pro Glu Asn Asn Gly
385                 390                 395                 400

Gly Ala Gly Cys Val Cys His Leu Leu Met Asp Asp Val Val Ser Ala
                405                 410                 415

Asp Asn Tyr Thr Leu Asp Leu Trp Ala Gly Gln Gln Leu Leu Trp Lys
            420                 425                 430

Gly Ser Phe Lys Pro Ser Glu His Val Lys Pro Arg Ala Pro Gly Asn
        435                 440                 445

Leu Thr Val His Thr Asn Val Ser Asp Thr Leu Leu Leu Thr Trp Ser
    450                 455                 460

Asn Pro Tyr Pro Pro Asp Asn Tyr Leu Tyr Asn His Leu Thr Tyr Ala
465                 470                 475                 480

Val Asn Ile Trp Ser Glu Asn Asp Pro Ala Asp Phe Arg Ile Tyr Asn
                485                 490                 495

Val Thr Tyr Leu Glu Pro Ser Leu Arg Ile Ala Ala Ser Thr Leu Lys
            500                 505                 510

Ser Gly Ile Ser Tyr Arg Ala Arg Val Arg Ala Trp Ala Gln Ser Tyr
        515                 520                 525

Asn Thr Thr Trp Ser Glu Trp Ser Pro Ser Thr Lys Trp His Asn Ser
    530                 535                 540

Tyr Arg Thr Gly Glu Pro Phe Glu Gln Glu Ser Lys Tyr Gly Pro Pro
545                 550                 555                 560

Cys Pro Ser Cys Pro Ala Pro Glu Phe Leu Gly Gly Pro Ser Val Phe
                565                 570                 575

Leu Phe Pro Pro Lys Pro Lys Asp Thr Leu Met Ile Ser Arg Thr Pro
            580                 585                 590

Glu Val Thr Cys Val Val Val Asp Val Ser Gln Glu Asp Pro Glu Val
        595                 600                 605

Gln Phe Asn Trp Tyr Val Asp Gly Val Glu Val His Asn Ala Lys Thr
    610                 615                 620

Lys Pro Arg Glu Glu Gln Phe Asn Ser Thr Tyr Arg Val Val Ser Val
625                 630                 635                 640

Leu Thr Val Leu His Gln Asp Trp Leu Asn Gly Lys Glu Tyr Lys Cys
                645                 650                 655

Lys Val Ser Asn Lys Gly Leu Pro Ser Ser Ile Glu Lys Thr Ile Ser
            660                 665                 670

Lys Ala Lys Gly Gln Pro Arg Glu Pro Gln Val Tyr Thr Leu Pro Pro
        675                 680                 685

Ser Gln Glu Glu Met Thr Lys Asn Gln Val Ser Leu Thr Cys Leu Val
    690                 695                 700

```
Lys Gly Phe Tyr Pro Ser Asp Ile Ala Val Glu Trp Glu Ser Asn Gly
705                 710                 715                 720
Gln Pro Glu Asn Asn Tyr Lys Thr Thr Pro Pro Val Leu Asp Ser Asp
            725                 730                 735
Gly Ser Phe Phe Leu Tyr Ser Arg Leu Thr Val Asp Lys Ser Arg Trp
        740                 745                 750
Gln Glu Gly Asn Val Phe Ser Cys Ser Val Met His Glu Ala Leu His
    755                 760                 765
Asn His Tyr Thr Gln Lys Ser Leu Ser Leu Ser Leu Gly Lys
770                 775                 780

<210> SEQ ID NO 49
<211> LENGTH: 2337
<212> TYPE: DNA
<213> ORGANISM: Homo sapiens

<400> SEQUENCE: 49
atggtgtggc tttgctctgg gctcctgttc cctgtgagct gcctggtcct gctgcaggtg     60
gcaagctctg ggaacatgaa ggtcttgcag gagcccacct gcgtctccga ctacatgagc    120
atctctactt gcgagtggaa gatgaatggt cccaccaatt gcagcaccga gctccgcctg    180
ttgtaccagc tggtttttct gctctccgaa gcccacacgt gtatccctga acaacggat    240 ggcgcgggt gcgtgtgcca cctgctcatg gatgacgtgg tcagtgcgga taactataca    300
ctggacctgt gggctgggca gcagctgctg tggaagggct ccttcaagcc cagcgagcat    360
gtgaaaccca gggccccagg aaacctgaca gttcacacca atgtctccga cactctgctg    420
ctgacctgga gcaaccogta tccccctgac aattacctgt ataatcatct cacctatgca    480
gtcaacattt ggagtgaaaa cgaccoggca gatttcagaa tctataacgt gacctaccta    540
gaaccctccc tccgcatcgc agccagcacc ctgaagtctg ggatttccta cagggcacgc    600
gtacgggcct gggctcagag ctataacacc acctggagtg agtggagccc cagcaccaag    660
tggcacaact cctacaggga gcccttcgag caggcgccta cggaaactca gccacctgtg    720
acaaatttga gtgtctctgt tgaaaacctc agcacagtaa tatggacatg gaatccaccc    780
gagggagcca gctcaaattg tagtctatgg tattttagtc attttggcga caaacaagat    840
aagaaaatag ctccggaaac tcgtcgttca atagaagtac ccctgaatga gaggatttgt    900
ctgcaagtgg ggtcccagtg tagcaccaat gagagtgaga agcctagcat tttggttgaa    960
aaatgcatct caccccaga aggtgatcct gagtctgctg tgactgagct tcaatgcatt   1020
tggcacaacc tgagctacat gaagtgttct tggctccctg aaggaatac cagtcccgac   1080 actaactata ctctctacta ttggcacaga agcctggaaa aaattcatca atgtgaaaac   1140
atctttagag aaggccaata ctttggttgt tcctttgatc tgaccaaagt gaaggattcc   1200
agttttgaac aacacagtgt ccaaataatg gtcaaggata tgcaggaaa attaaaacca   1260 tccttcaata tagtgccttt aacttcccgt gtgaaacctg atcctccaca tattaaaaac   1320
ctctccttcc acaatgatga cctatatgtg caatgggaga atccacagaa ttttattagc   1380
agatgcctat tttatgaagt agaagtcaat aacagccaaa ctgagacaca taatgttttc   1440
tacgtccaag aggctaaatg tgagaatcca gaatttgaga gaatgtgga gaatacatct   1500 tgtttcatgg tccctggtgt tcttcctgat actttgaaca cagtcagaat aagagtcaaa   1560
acaaataagt tatgctatga ggatgacaaa ctctggagta attggagcca agaaatgagt   1620
ataggtaaga agcgcaattc caccggagag tccaaatacg gtccgccatg cccatcatgc   1680
```

-continued

```
ccagcacctg agttcctggg gggaccatca gtcttcctgt tcccccccaaa acccaaggac    1740 actctcatga tctcccggac ccctgaggtc acgtgcgtgg tggtggacgt gagccaggaa    1800
gaccccgagg tccagttcaa ctggtacgtg gatggcgtgg aggtgcataa tgccaagaca    1860
aagccgcggg aggagcagtt caacagcacg taccgtgtgg tcagcgtcct caccgtcctg    1920
caccaggact ggctgaacgg caaggagtac aagtgcaagg tctccaacaa aggcctcccg    1980
tcctccatcg agaaaaccat ctccaaagcc aaagggcagc ccgagagcc acaggtgtac     2040 accctgcccc catcccagga ggagatgacc aagaaccagg tcagcctgac ctgcctggtc    2100
aaaggcttct accccagcga catcgccgtg gagtgggaga gcaatgggca gccggagaac    2160
aactacaaga ccacgcctcc cgtgctggac tccgacggct ccttcttcct ctacagcagg    2220
ctaaccgtgg acaagagcag gtggcaggag gggaatgtct tctcatgctc cgtgatgcat    2280
gaggctctgc acaaccacta cacacagaag agcctctccc tgtctctggg taaatga       2337
```

<210> SEQ ID NO 50
<211> LENGTH: 778
<212> TYPE: PRT
<213> ORGANISM: Homo sapiens

<400> SEQUENCE: 50

```
Met Val Trp Leu Cys Ser Gly Leu Leu Phe Pro Val Ser Cys Leu Val
  1               5                  10                  15

Leu Leu Gln Val Ala Ser Ser Gly Asn Met Lys Val Leu Gln Glu Pro
             20                  25                  30

Thr Cys Val Ser Asp Tyr Met Ser Ile Ser Thr Cys Glu Trp Lys Met
         35                  40                  45

Asn Gly Pro Thr Asn Cys Ser Thr Glu Leu Arg Leu Leu Tyr Gln Leu
     50                  55                  60

Val Phe Leu Leu Ser Glu Ala His Thr Cys Ile Pro Glu Asn Asn Gly
 65                  70                  75                  80

Gly Ala Gly Cys Val Cys His Leu Leu Met Asp Asp Val Val Ser Ala
                 85                  90                  95

Asp Asn Tyr Thr Leu Asp Leu Trp Ala Gly Gln Gln Leu Leu Trp Lys
            100                 105                 110

Gly Ser Phe Lys Pro Ser Glu His Val Lys Pro Arg Ala Pro Gly Asn
        115                 120                 125

Leu Thr Val His Thr Asn Val Ser Asp Thr Leu Leu Leu Thr Trp Ser
    130                 135                 140

Asn Pro Tyr Pro Pro Asp Asn Tyr Leu Tyr Asn His Leu Thr Tyr Ala
145                 150                 155                 160

Val Asn Ile Trp Ser Glu Asn Asp Pro Ala Asp Phe Arg Ile Tyr Asn
                165                 170                 175

Val Thr Tyr Leu Glu Pro Ser Leu Arg Ile Ala Ala Ser Thr Leu Lys
            180                 185                 190

Ser Gly Ile Ser Tyr Arg Ala Arg Val Arg Ala Trp Ala Gln Ser Tyr
        195                 200                 205

Asn Thr Thr Trp Ser Glu Trp Ser Pro Ser Thr Lys Trp His Asn Ser
    210                 215                 220

Tyr Arg Glu Pro Phe Glu Gln Ala Pro Thr Gly Thr Gln Pro Pro Val
225                 230                 235                 240

Thr Asn Leu Ser Val Ser Val Glu Asn Leu Ser Thr Val Ile Trp Thr
                245                 250                 255
```

-continued

```
Trp Asn Pro Pro Glu Gly Ala Ser Ser Asn Cys Ser Leu Trp Tyr Phe
            260                 265                 270

Ser His Phe Gly Asp Lys Gln Asp Lys Lys Ile Ala Pro Glu Thr Arg
            275                 280                 285

Arg Ser Ile Glu Val Pro Leu Asn Glu Arg Ile Cys Leu Gln Val Gly
            290                 295                 300

Ser Gln Cys Ser Thr Asn Glu Ser Glu Lys Pro Ser Ile Leu Val Glu
305                 310                 315                 320

Lys Cys Ile Ser Pro Pro Glu Gly Asp Pro Glu Ser Ala Val Thr Glu
            325                 330                 335

Leu Gln Cys Ile Trp His Asn Leu Ser Tyr Met Lys Cys Ser Trp Leu
            340                 345                 350

Pro Gly Arg Asn Thr Ser Pro Asp Thr Asn Tyr Thr Leu Tyr Tyr Trp
            355                 360                 365

His Arg Ser Leu Glu Lys Ile His Gln Cys Glu Asn Ile Phe Arg Glu
            370                 375                 380

Gly Gln Tyr Phe Gly Cys Ser Phe Asp Leu Thr Lys Val Lys Asp Ser
385                 390                 395                 400

Ser Phe Glu Gln His Ser Val Gln Ile Met Val Lys Asp Asn Ala Gly
            405                 410                 415

Lys Ile Lys Pro Ser Phe Asn Ile Val Pro Leu Thr Ser Arg Val Lys
            420                 425                 430

Pro Asp Pro Pro His Ile Lys Asn Leu Ser Phe His Asn Asp Asp Leu
            435                 440                 445

Tyr Val Gln Trp Glu Asn Pro Gln Asn Phe Ile Ser Arg Cys Leu Phe
            450                 455                 460

Tyr Glu Val Glu Val Asn Asn Ser Gln Thr Glu Thr His Asn Val Phe
465                 470                 475                 480

Tyr Val Gln Glu Ala Lys Cys Glu Asn Pro Glu Phe Glu Arg Asn Val
            485                 490                 495

Glu Asn Thr Ser Cys Phe Met Val Pro Gly Val Leu Pro Asp Thr Leu
            500                 505                 510

Asn Thr Val Arg Ile Arg Val Lys Thr Asn Lys Leu Cys Tyr Glu Asp
            515                 520                 525

Asp Lys Leu Trp Ser Asn Trp Ser Gln Glu Met Ser Ile Gly Lys Lys
            530                 535                 540

Arg Asn Ser Thr Gly Glu Ser Lys Tyr Gly Pro Pro Cys Pro Ser Cys
545                 550                 555                 560

Pro Ala Pro Glu Phe Leu Gly Gly Pro Ser Val Phe Leu Phe Pro Pro
            565                 570                 575

Lys Pro Lys Asp Thr Leu Met Ile Ser Arg Thr Pro Glu Val Thr Cys
            580                 585                 590

Val Val Val Asp Val Ser Gln Glu Asp Pro Glu Val Gln Phe Asn Trp
            595                 600                 605

Tyr Val Asp Gly Val Glu Val His Asn Ala Lys Thr Lys Pro Arg Glu
            610                 615                 620

Glu Gln Phe Asn Ser Thr Tyr Arg Val Val Ser Val Leu Thr Val Leu
625                 630                 635                 640

His Gln Asp Trp Leu Asn Gly Lys Glu Tyr Lys Cys Lys Val Ser Asn
            645                 650                 655

Lys Gly Leu Pro Ser Ser Ile Glu Lys Thr Ile Ser Lys Ala Lys Gly
            660                 665                 670

Gln Pro Arg Glu Pro Gln Val Tyr Thr Leu Pro Pro Ser Gln Glu Glu
```

```
              675              680              685
Met Thr Lys Asn Gln Val Ser Leu Thr Cys Leu Val Lys Gly Phe Tyr
            690              695              700

Pro Ser Asp Ile Ala Val Glu Trp Glu Ser Asn Gly Gln Pro Glu Asn
705              710              715              720

Asn Tyr Lys Thr Thr Pro Pro Val Leu Asp Ser Asp Gly Ser Phe Phe
                725              730              735

Leu Tyr Ser Arg Leu Thr Val Asp Lys Ser Arg Trp Gln Glu Gly Asn
            740              745              750

Val Phe Ser Cys Ser Val Met His Glu Ala Leu His Asn His Tyr Thr
            755              760              765

Gln Lys Ser Leu Ser Leu Ser Leu Gly Lys
    770              775

<210> SEQ ID NO 51
<211> LENGTH: 2349
<212> TYPE: DNA
<213> ORGANISM: Homo sapiens

<400> SEQUENCE: 51
atggtgtggc cggcgcggct ctgcgggctg tgggcgctgc tgctctgcgc cggcggcggg      60
ggcgggggcg gggcgccgc gcctacggaa actcagccac ctgtgacaaa tttgagtgtc     120
tctgttgaaa acctcagcac agtaatatgg acatggaatc cacccgaggg agccagctca     180
aattgtagtc tatggtattt tagtcatttt ggcgacaaac aagataagaa atagctccg     240 gaaactcgtc gttcaataga gtacccctg aatgagagga tttgtctgca gtggggtcc     300 cagtgtagca ccaatgagag tgagaagcct agcattttgg ttgaaaaatg catctcaccc     360
ccagaaggtg atcctgagtc tgctgtgact gagcttcaat gcatttggca acctgagc      420 tacatgaagt gttcttggct ccctggaagg aataccagtc cgacactaa ctatactctc      480 tactattggc acagaagcct ggaaaaaatt catcaatgtg aaaacatctt tagagaaggc     540
caatactttg gttgttcctt tgatctgacc aaagtgaagg attccagttt tgaacaacac     600
agtgtccaaa taatggtcaa ggataatgca ggaaaaatta accatccttt caatatagtg     660
cctttaactt cccgtgtgaa acctgatcct ccacatatta aaaacctctc cttccacaat     720
gatgacctat atgtgcaatg ggagaatcca cagaatttta ttagcagatg cctatttat      780 gaagtagaag tcaataacag ccaaactgag cacacataatg ttttctacgt ccaagaggct     840
aaatgtgaga tccagaatt tgagagaaat gtggagaata catcttgttt catggtccct     900
ggtgttcttc ctgatacttt gaacacagtc agaataagag tcaaaacaaa taagttatgc     960
tatgaggatg acaaactctg gagtaattgg agccaagaaa tgagtatagg taagaagcgc    1020
aattccacag ggaacatgaa ggtcttgcag gagcccacct gcgtctccga ctacatgagc    1080
atctctactt gcgagtggaa gatgaatggt cccaccaatt gcagcaccga gctccgcctg    1140
ttgtaccagc tggttttct gctctccgaa gcccacacgt gtatccctga gaacaacgga    1200
ggcgcggggt gcgtgtgcca cctgctcatg gatgacgtgg tcagtgcgga taactataca    1260
ctggacctgt gggctgggca gcagctgctg tggaagggct ccttcaagcc cagcgagcat    1320
gtgaaaccca gggccccagg aaaacctgaca gttcacacca atgtctccga cactctgctg    1380
ctgacctgga gcaacccgta tccccctgac aattacctgt ataatcatct cacctatgca    1440
gtcaacattt ggagtgaaaa cgaccccggca gatttcagaa tctataacgt gacctaccta    1500
gaaccctccc tccgcatcgc agccagcacc ctgaagtctg ggatttccta caggcacgc    1560
```

-continued

```
gtacgggcct gggctcagag ctataacacc acctggagtg agtggagccc cagcaccaag    1620
tggcacaact cctacaggga gcccttcgag cagaccggag agtccaaata cggtccgcca    1680
tgcccatcat gcccagcacc tgagttcctg gggggaccat cagtcttcct gttcccccca    1740
aaacccaagg acactctcat gatctcccgg acccctgagg tcacgtgcgt ggtggtggac    1800
gtgagccagg aagaccccga ggtccagttc aactggtacg tggatggcgt ggaggtgcat    1860
aatgccaaga caaagccgcg ggaggagcag ttcaacagca cgtaccgtgt ggtcagcgtc    1920
ctcaccgtcc tgcaccagga ctggctgaac ggcaaggagt acaagtgcaa ggtctccaac    1980
aaaggcctcc cgtcctccat cgagaaaacc atctccaaag ccaaagggca gccccgagag    2040
ccacaggtgt acaccctgcc cccatcccag gaggagatga ccaagaacca ggtcagcctg    2100
acctgcctgg tcaaaggctt ctaccccagc gacatcgccg tggagtggga gagcaatggg    2160
cagccggaga acaactacaa gaccacgcct cccgtgctgg actccgacgg ctccttcttc    2220
ctctacagca ggctaaccgt ggacaagagc aggtggcagg aggggaatgt cttctcatgc    2280
tccgtgatgc atgaggctct gcacaaccac tacacacaga gagcctctcc cctgtctctg    2340
ggtaaatga                                                           2349
```

<210> SEQ ID NO 52
<211> LENGTH: 782
<212> TYPE: PRT
<213> ORGANISM: Homo sapiens

<400> SEQUENCE: 52

```
Met Val Trp Pro Ala Arg Leu Cys Gly Leu Trp Ala Leu Leu Leu Cys
 1               5                  10                  15

Ala Gly Gly Gly Gly Gly Gly Gly Ala Ala Pro Thr Glu Thr Gln
             20                  25                  30

Pro Pro Val Thr Asn Leu Ser Val Ser Val Glu Asn Leu Ser Thr Val
         35                  40                  45

Ile Trp Thr Trp Asn Pro Pro Glu Gly Ala Ser Ser Asn Cys Ser Leu
     50                  55                  60

Trp Tyr Phe Ser His Phe Gly Asp Lys Gln Asp Lys Lys Ile Ala Pro
 65                  70                  75                  80

Glu Thr Arg Arg Ser Ile Glu Val Pro Leu Asn Glu Arg Ile Cys Leu
                 85                  90                  95

Gln Val Gly Ser Gln Cys Ser Thr Asn Glu Ser Glu Lys Pro Ser Ile
            100                 105                 110

Leu Val Glu Lys Cys Ile Ser Pro Pro Glu Gly Asp Pro Glu Ser Ala
        115                 120                 125

Val Thr Glu Leu Gln Cys Ile Trp His Asn Leu Ser Tyr Met Lys Cys
    130                 135                 140

Ser Trp Leu Pro Gly Arg Asn Thr Ser Pro Asp Thr Asn Tyr Thr Leu
145                 150                 155                 160

Tyr Tyr Trp His Arg Ser Leu Glu Lys Ile His Gln Cys Glu Asn Ile
                165                 170                 175

Phe Arg Glu Gly Gln Tyr Phe Gly Cys Ser Phe Asp Leu Thr Lys Val
            180                 185                 190

Lys Asp Ser Ser Phe Glu Gln His Ser Val Gln Ile Met Val Lys Asp
        195                 200                 205

Asn Ala Gly Lys Ile Lys Pro Ser Phe Asn Ile Val Pro Leu Thr Ser
    210                 215                 220
```

```
Arg Val Lys Pro Asp Pro His Ile Lys Asn Leu Ser Phe His Asn
225                 230                 235                 240

Asp Asp Leu Tyr Val Gln Trp Glu Asn Pro Gln Asn Phe Ile Ser Arg
                245                 250                 255

Cys Leu Phe Tyr Glu Val Glu Val Asn Asn Ser Gln Thr Glu Thr His
            260                 265                 270

Asn Val Phe Tyr Val Gln Glu Ala Lys Cys Glu Asn Pro Glu Phe Glu
            275                 280                 285

Arg Asn Val Glu Asn Thr Ser Cys Phe Met Val Pro Gly Val Leu Pro
290                 295                 300

Asp Thr Leu Asn Thr Val Arg Ile Arg Val Lys Thr Asn Lys Leu Cys
305                 310                 315                 320

Tyr Glu Asp Asp Lys Leu Trp Ser Asn Trp Ser Gln Glu Met Ser Ile
                325                 330                 335

Gly Asn Met Lys Val Leu Gln Gly Lys Lys Arg Asn Ser Thr Glu Pro
            340                 345                 350

Thr Cys Val Ser Asp Tyr Met Ser Ile Ser Thr Cys Glu Trp Lys Met
        355                 360                 365

Asn Gly Pro Thr Asn Cys Ser Thr Glu Leu Arg Leu Leu Tyr Gln Leu
370                 375                 380

Val Phe Leu Leu Ser Glu Ala His Thr Cys Ile Pro Glu Asn Asn Gly
385                 390                 395                 400

Gly Ala Gly Cys Val Cys His Leu Leu Met Asp Asp Val Val Ser Ala
                405                 410                 415

Asp Asn Tyr Thr Leu Asp Leu Trp Ala Gly Gln Gln Leu Leu Trp Lys
            420                 425                 430

Gly Ser Phe Lys Pro Ser Glu His Val Lys Pro Arg Ala Pro Gly Asn
            435                 440                 445

Leu Thr Val His Thr Asn Val Ser Asp Thr Leu Leu Leu Thr Trp Ser
    450                 455                 460

Asn Pro Tyr Pro Pro Asp Asn Tyr Leu Tyr Asn His Leu Thr Tyr Ala
465                 470                 475                 480

Val Asn Ile Trp Ser Glu Asn Asp Pro Ala Asp Phe Arg Ile Tyr Asn
                485                 490                 495

Val Thr Tyr Leu Glu Pro Ser Leu Arg Ile Ala Ala Ser Thr Leu Lys
            500                 505                 510

Ser Gly Ile Ser Tyr Arg Ala Arg Val Arg Ala Trp Ala Gln Ser Tyr
        515                 520                 525

Asn Thr Thr Trp Ser Glu Trp Ser Pro Ser Thr Lys Trp His Asn Ser
        530                 535                 540

Tyr Arg Glu Pro Phe Glu Gln Thr Gly Glu Ser Lys Tyr Gly Pro Pro
545                 550                 555                 560

Cys Pro Ser Cys Pro Ala Pro Glu Phe Leu Gly Gly Pro Ser Val Phe
                565                 570                 575

Leu Phe Pro Pro Lys Pro Lys Asp Thr Leu Met Ile Ser Arg Thr Pro
            580                 585                 590

Glu Val Thr Cys Val Val Val Asp Val Ser Gln Glu Asp Pro Glu Val
        595                 600                 605

Gln Phe Asn Trp Tyr Val Asp Gly Val Glu Val His Asn Ala Lys Thr
        610                 615                 620

Lys Pro Arg Glu Glu Gln Phe Asn Ser Thr Tyr Arg Val Val Ser Val
625                 630                 635                 640

Leu Thr Val Leu His Gln Asp Trp Leu Asn Gly Lys Glu Tyr Lys Cys
```

```
                      645                 650                 655
Lys Val Ser Asn Lys Gly Leu Pro Ser Ser Ile Glu Lys Thr Ile Ser
                660                 665                 670

Lys Ala Lys Gly Gln Pro Arg Glu Pro Gln Val Tyr Thr Leu Pro Pro
            675                 680                 685

Ser Gln Glu Glu Met Thr Lys Asn Gln Val Ser Leu Thr Cys Leu Val
        690                 695                 700

Lys Gly Phe Tyr Pro Ser Asp Ile Ala Val Glu Trp Glu Ser Asn Gly
705                 710                 715                 720

Gln Pro Glu Asn Asn Tyr Lys Thr Thr Pro Pro Val Leu Asp Ser Asp
                725                 730                 735

Gly Ser Phe Phe Leu Tyr Ser Arg Leu Thr Val Asp Lys Ser Arg Trp
            740                 745                 750

Gln Glu Gly Asn Val Phe Ser Cys Ser Val Met His Glu Ala Leu His
        755                 760                 765

Asn His Tyr Thr Gln Lys Ser Leu Ser Leu Ser Leu Gly Lys
    770                 775                 780
```

<210> SEQ ID NO 53
<211> LENGTH: 2349
<212> TYPE: DNA
<213> ORGANISM: Homo sapiens

<400> SEQUENCE: 53

```
atggtgtggc cggcgcggct ctgcgggctg tgggcgctgc tgctctgcgc cggcggcggg    60
ggcgggggcg ggggcgccgc gcctacggaa actcagccac ctgtgacaaa tttgagtgtc   120
tctgttgaaa acctcgcgac agtaatatgg acatggaatc cacccgaggg agccagctca   180
aattgtagtc tatggtattt tagtcatttt ggcgacaaac aagataagaa aatagctccg   240
gaaactcgtc gttcaataga gtacccctga atgagagga tttgtctgca agtggggtcc   300
cagtgtagca ccaatgagag tgagaagcct agcattttgg ttgaaaaatg catctcaccc   360
ccagaaggtg atcctgagtc tgctgtgact gagcttcaat gcatttggca caacctgagc   420
tacatgaagt gttcttggct ccctggaagg aataccagtc ccgacactaa ctatactctc   480
tactattggc acagaagcct ggaaaaaatt catcaatgtg aaaacatctt tagagaaggc   540
caatactttg gttgttcctt tgatctgacc aaagtgaagg attccagttt tgaacaacac   600
agtgtccaaa taatggtcaa ggataatgca ggaaaaatta accatcctt caatatagtg   660
cctttaactt cccgtgtgaa acctgatcct ccacatatta aaaacctctc cttccacaat   720
gatgacctat atgtgcaatg ggagaatcca cagaatttta ttagcagatg cctattttat   780
gaagtagaag tcaataacag ccaaactgag acacataatg tttttctacgt ccaagaggct   840
aaatgtgaga tccagaatt tgagagaaat gtggagaata catcttgttt catggtccct   900
ggtgttcttc ctgatacttt gaacacagtc agaataagg tcaaaacaaa taagttatgc   960
tatgaggatg acaaactctg gagtaattgg agccaagaaa tgagtatagg taagaagcgc  1020
aattccacag ggaacatgaa ggtcttgcag gagcccacct cgtctccga ctacatgagc  1080
atctctactt gcgagtggaa gatgaatggt cccaccaatt gcagcaccga gctccgcctg  1140
ttgtaccagc tggtttttct gctctccgaa gcccacacgt gtatccctga acaacgga   1200
ggcgcgggt gcgtgtgcca cctgctcatg gatgacgtgg tcagtgcgga taactataca  1260
ctggacctgt gggctgggca gcagctgctg tggaagggct ccttcaagcc cagcgagcat  1320
gtgaaaccca gggccccagg aaacctgaca gttcacacca atgtctccga cactctgctg  1380
```

-continued

```
ctgacctgga gcaacccgta tccccctgac aattacctgt ataatcatct cacctatgca   1440
gtcaacattt ggagtgaaaa cgacccggca gatttcagaa tctataacgt gacctaccta   1500
gaaccctccc tccgcatcgc agccagcacc ctgaagtctg ggatttccta cagggcacgc   1560
gtacgggcct gggctcagag ctataacacc acctggagtg agtggagccc cagcaccaag   1620
tggcacaact cctacaggga gcccttcgag cagaccggag agtccaaata cggtccgcca   1680
tgcccaccat gcccagcacc tgagttcctg ggggaccat cagtcttcct gttccccca    1740 aaacccaagg acactctcat gatctcccgg acccctgagg tcacgtgcgt ggtggtggac   1800
gtgagccagg aagaccccga ggtccagttc aactggtacg tggatggcgt ggaggtgcat   1860
aatgccaaga caaagccgcg ggaggagcag ttcaacagca cgtaccgtgt ggtcagcgtc   1920
ctcaccgtcc tgcaccagga ctggctgaac ggcaaggagt acaagtgcaa ggtctccaac   1980
aaaggcctcc cgtcctccat cgagaaaacc atctccaaag ccaaagggca gccccgagag   2040
ccacaggtgt acaccctgcc cccatcccag gaggagatga ccaagaacca ggtcagcctg   2100
acctgcctgg tcaaaggctt ctaccccagc gacatcgccg tggagtggga gagcaatggg   2160
cagccggaga acaactacaa gaccacgcct cccgtgctgg actccgacgg ctccttcttc   2220
ctctacagca ggctaaccgt ggacaagagc aggtggcagg aggggaatgt cttctcatgc   2280
tccgtgatgc atgaggctct gcacaaccac tacacacaga gagcctctc cctgtctctg   2340 ggtaaatga                                                           2349
```

<210> SEQ ID NO 54
<211> LENGTH: 782
<212> TYPE: PRT
<213> ORGANISM: Homo sapiens

<400> SEQUENCE: 54

```
Met Val Trp Pro Ala Arg Leu Cys Gly Leu Trp Ala Leu Leu Leu Cys
  1               5                  10                  15

Ala Gly Gly Gly Gly Gly Gly Gly Ala Ala Pro Thr Glu Thr Gln
             20                  25                  30

Pro Pro Val Thr Asn Leu Ser Val Ser Val Glu Asn Leu Ala Thr Val
         35                  40                  45

Ile Trp Thr Trp Asn Pro Pro Glu Gly Ala Ser Ser Asn Cys Ser Leu
     50                  55                  60

Trp Tyr Phe Ser His Phe Gly Asp Lys Gln Asp Lys Lys Ile Ala Pro
 65                  70                  75                  80

Glu Thr Arg Arg Ser Ile Glu Val Pro Leu Asn Glu Arg Ile Cys Leu
                 85                  90                  95

Gln Val Gly Ser Gln Cys Ser Thr Asn Glu Ser Glu Lys Pro Ser Ile
            100                 105                 110

Leu Val Glu Lys Cys Ile Ser Pro Pro Glu Gly Asp Pro Glu Ser Ala
        115                 120                 125

Val Thr Glu Leu Gln Cys Ile Trp His Asn Leu Ser Tyr Met Lys Cys
    130                 135                 140

Ser Trp Leu Pro Gly Arg Asn Thr Ser Pro Asp Thr Asn Tyr Thr Leu
145                 150                 155                 160

Tyr Tyr Trp His Arg Ser Leu Glu Lys Ile His Gln Cys Glu Asn Ile
                165                 170                 175

Phe Arg Glu Gly Gln Tyr Phe Gly Cys Ser Phe Asp Leu Thr Lys Val
            180                 185                 190
```

-continued

```
Lys Asp Ser Ser Phe Glu Gln His Ser Val Gln Ile Met Val Lys Asp
            195                 200                 205

Asn Ala Gly Lys Ile Lys Pro Ser Phe Asn Ile Val Pro Leu Thr Ser
    210                 215                 220

Arg Val Lys Pro Asp Pro His Ile Lys Asn Leu Ser Phe His Asn
225                 230                 235                 240

Asp Asp Leu Tyr Val Gln Trp Glu Asn Pro Gln Asn Phe Ile Ser Arg
                245                 250                 255

Cys Leu Phe Tyr Glu Val Val Asn Asn Ser Gln Thr Glu Thr His
                260                 265                 270

Asn Val Phe Tyr Val Gln Glu Ala Lys Cys Glu Asn Pro Glu Phe Glu
            275                 280                 285

Arg Asn Val Glu Asn Thr Ser Cys Phe Met Val Pro Gly Val Leu Pro
            290                 295                 300

Asp Thr Leu Asn Thr Val Arg Ile Arg Val Lys Thr Asn Lys Leu Cys
305                 310                 315                 320

Tyr Glu Asp Asp Lys Leu Trp Ser Asn Trp Ser Gln Glu Met Ser Ile
                325                 330                 335

Gly Asn Met Lys Val Leu Gln Gly Lys Lys Arg Asn Ser Thr Glu Pro
            340                 345                 350

Thr Cys Val Ser Asp Tyr Met Ser Ile Ser Thr Cys Glu Trp Lys Met
            355                 360                 365

Asn Gly Pro Thr Asn Cys Ser Thr Glu Leu Arg Leu Leu Tyr Gln Leu
    370                 375                 380

Val Phe Leu Leu Ser Glu Ala His Thr Cys Ile Pro Glu Asn Asn Gly
385                 390                 395                 400

Gly Ala Gly Cys Val Cys His Leu Leu Met Asp Asp Val Val Ser Ala
                405                 410                 415

Asp Asn Tyr Thr Leu Asp Leu Trp Ala Gly Gln Gln Leu Leu Trp Lys
            420                 425                 430

Gly Ser Phe Lys Pro Ser Glu His Val Lys Pro Arg Ala Pro Gly Asn
        435                 440                 445

Leu Thr Val His Thr Asn Val Ser Asp Thr Leu Leu Leu Thr Trp Ser
    450                 455                 460

Asn Pro Tyr Pro Pro Asp Asn Tyr Leu Tyr Asn His Leu Thr Tyr Ala
465                 470                 475                 480

Val Asn Ile Trp Ser Glu Asn Asp Pro Ala Asp Phe Arg Ile Tyr Asn
                485                 490                 495

Val Thr Tyr Leu Glu Pro Ser Leu Arg Ile Ala Ala Ser Thr Leu Lys
            500                 505                 510

Ser Gly Ile Ser Tyr Arg Ala Arg Val Arg Ala Trp Ala Gln Ser Tyr
        515                 520                 525

Asn Thr Thr Trp Ser Glu Trp Ser Pro Ser Thr Lys Trp His Asn Ser
    530                 535                 540

Tyr Arg Thr Gly Glu Ser Lys Tyr Gly Pro Pro Glu Pro Phe Glu Gln
545                 550                 555                 560

Cys Pro Pro Cys Pro Ala Pro Glu Phe Leu Gly Gly Pro Ser Val Phe
                565                 570                 575

Leu Phe Pro Pro Lys Pro Lys Asp Thr Leu Met Ile Ser Arg Thr Pro
            580                 585                 590

Glu Val Thr Cys Val Val Val Asp Val Ser Gln Glu Asp Pro Glu Val
            595                 600                 605

Gln Phe Asn Trp Tyr Val Asp Gly Val Glu Val His Asn Ala Lys Thr
```

```
                   610                 615                 620
Lys Pro Arg Glu Glu Gln Phe Asn Ser Thr Tyr Arg Val Val Ser Val
625                 630                 635                 640

Leu Thr Val Leu His Gln Asp Trp Leu Asn Gly Lys Glu Tyr Lys Cys
                645                 650                 655

Lys Val Ser Asn Lys Gly Leu Pro Ser Ser Ile Glu Lys Thr Ile Ser
                660                 665                 670

Lys Ala Lys Gly Gln Pro Arg Glu Pro Gln Val Tyr Thr Leu Pro Pro
            675                 680                 685

Ser Gln Glu Glu Met Thr Lys Asn Gln Val Ser Leu Thr Cys Leu Val
        690                 695                 700

Lys Gly Phe Tyr Pro Ser Asp Ile Ala Val Glu Trp Glu Ser Asn Gly
705                 710                 715                 720

Gln Pro Glu Asn Asn Tyr Lys Thr Thr Pro Pro Val Leu Asp Ser Asp
                725                 730                 735

Gly Ser Phe Phe Leu Tyr Ser Arg Leu Thr Val Asp Lys Ser Arg Trp
                740                 745                 750

Gln Glu Gly Asn Val Phe Ser Cys Ser Val Met His Glu Ala Leu His
            755                 760                 765

Asn His Tyr Thr Gln Lys Ser Leu Ser Leu Ser Leu Gly Lys
770                 775                 780

<210> SEQ ID NO 55
<211> LENGTH: 2337
<212> TYPE: DNA
<213> ORGANISM: Homo sapiens

<400> SEQUENCE: 55
atggtgtggc tttgctctgg gctcctgttc cctgtgagct gcctggtcct gctgcaggtg      60
gcaagctctg ggaacatgaa ggtcttgcag gagcccacct gcgtctccga ctacatgagc     120
atctctactt gcgagtggaa gatgaatggt cccaccaatt gcagcaccga gctccgcctg     180
ttgtaccagc tggttttttct gctctccgaa gcccacacgt gtatccctga aacaacgga     240 ggcgcggggt gcgtgtgcca cctgctcatg gatgacgtgg tcagtgcgga taactataca     300
ctggacctgt gggctgggca gcagctgctg tggaagggct ccttcaagcc cagcgagcat     360
gtgaaaccca gggccccagg aaacctgaca gttcacacca tgtctccga cactctgctg     420 ctgacctgga gcaacccgta tcccctgac aattacctgt ataatcatct cacctatgca     480
gtcaacattt ggagtgaaaa cgaccgcca gatttcagaa tctataacgt gacctaccta     540
gaaccctccc tccgcatcgc agccagcacc ctgaagtctg ggatttccta cagggcacgc     600
gtacgggcct gggctcagag ctataacacc acctggagtg agtggagccc cagcaccaag     660
tggcacaact cctacaggga gcccttcgag caggcgccta cggaaactca gccacctgtg     720
acaaatttga gtgtctctgt tgaaaacctc agcacagtaa tatggacatg aatccaccc     780 gagggagcca gctcaaattg tagtctatgg tattttagtc attttggcga caaacaagat     840 aagaaaaatag ctccggaaac tcgtcgttca atagaagtac ccctgaatga gaggatttgt     900
ctgcaagtgg ggtcccagtg tagcaccaat gagagtgaga agcctagcat tttggttgaa     960
aaatgcatct cacccccaga aggtgatcct gagtctgctg tgactgagct tcaatgcatt    1020
tggcacaacc tgagctacat gaagtgttct tggctccctg aaggaatac cagtcccgac    1080 actaactata ctctctacta ttggcacaga agcctggaaa aaattcatca atgtgaaaac    1140
atctttagag aaggccaata ctttggttgt tcctttgatc tgaccaaagt gaaggattcc    1200
```

```
agttttgaac aacacagtgt ccaaataatg gtcaaggata atgcaggaaa aattaaacca    1260
tccttcaata tagtgccttt aacttcccgt gtgaaacctg atcctccaca tattaaaaac    1320
ctctccttcc acaatgatga cctatatgtg caatgggaga atccacagaa ttttattagc    1380
agatgcctat tttatgaagt agaagtcaat aacagccaaa ctgagacaca taatgttttc    1440
tacgtccaag aggctaaatg tgagaatcca gaatttgaga gaaatgtgga gaatacatct    1500
tgtttcatgg tccctggtgt tcttcctgat actttgaaca cagtcagaat aagagtcaaa    1560
acaaataagt tatgctatga ggatgacaaa ctctggagta attggagcca agaaatgagt    1620
ataggtaaga agcgcaattc caccggagag tccaaatacg gtccgccatg cccaccatgc    1680
ccagcacctg agttcctggg gggaccatca gtcttcctgt tccccccaaa acccaaggac    1740
actctcatga tctcccggac ccctgaggtc acgtgcgtgg tggtggacgt gagccaggaa    1800
gaccccgagg tccagttcaa ctggtacgtg gatggcgtgg aggtgcataa tgccaagaca    1860
aagccgcggg aggagcagtt caacagcacg taccgtgtgg tcagcgtcct caccgtcctg    1920
caccaggact ggctgaacgg caaggagtac aagtgcaagg tctccaacaa aggcctcccg    1980
tcctccatcg agaaaaccat ctccaaagcc aaagggcagc cccgagagcc acaggtgtac    2040
accctgcccc catcccagga ggagatgacc aagaaccagg tcagcctgac ctgcctggtc    2100
aaaggcttct accccagcga catcgccgtg gagtgggaga gcaatgggca gccggagaac    2160
aactacaaga ccacgcctcc cgtgctggac tccgacggct ccttcttcct ctacagcagg    2220
ctaaccgtgg acaagagcag gtggcaggag gggaatgtct tctcatgctc cgtgatgcat    2280
gaggctctgc acaaccacta cacacagaag agcctctccc tgtctctggg taaatga      2337
```

<210> SEQ ID NO 56
<211> LENGTH: 778
<212> TYPE: PRT
<213> ORGANISM: Homo sapiens

<400> SEQUENCE: 56

```
Met Val Trp Leu Cys Ser Gly Leu Leu Phe Pro Val Ser Cys Leu Val
 1               5                  10                  15

Leu Leu Gln Val Ala Ser Ser Gly Asn Met Lys Val Leu Gln Glu Pro
            20                  25                  30

Thr Cys Val Ser Asp Tyr Met Ser Ile Ser Thr Cys Glu Trp Lys Met
        35                  40                  45

Asn Gly Pro Thr Asn Cys Ser Thr Glu Leu Arg Leu Leu Tyr Gln Leu
    50                  55                  60

Val Phe Leu Leu Ser Glu Ala His Thr Cys Ile Pro Glu Asn Asn Gly
65                  70                  75                  80

Gly Ala Gly Cys Val Cys His Leu Leu Met Asp Asp Val Val Ser Ala
                85                  90                  95

Asp Asn Tyr Thr Leu Asp Leu Trp Ala Gly Gln Gln Leu Leu Trp Lys
            100                 105                 110

Gly Ser Phe Lys Pro Ser Glu His Val Lys Pro Arg Ala Pro Gly Asn
        115                 120                 125

Leu Thr Val His Thr Asn Val Ser Asp Thr Leu Leu Leu Thr Trp Ser
    130                 135                 140

Asn Pro Tyr Pro Pro Asp Asn Tyr Leu Tyr Asn His Leu Thr Tyr Ala
145                 150                 155                 160

Val Asn Ile Trp Ser Glu Asn Asp Pro Ala Asp Phe Arg Ile Tyr Asn
                165                 170                 175
```

-continued

```
Val Thr Tyr Leu Glu Pro Ser Leu Arg Ile Ala Ala Ser Thr Leu Lys
            180                 185                 190

Ser Gly Ile Ser Tyr Arg Ala Arg Val Arg Ala Trp Ala Gln Ser Tyr
            195                 200                 205

Asn Thr Thr Trp Ser Glu Trp Ser Pro Ser Thr Lys Trp His Asn Ser
            210                 215                 220

Tyr Arg Glu Pro Phe Glu Gln Ala Pro Thr Glu Thr Gln Pro Pro Val
225                 230                 235                 240

Thr Asn Leu Ser Val Ser Val Glu Asn Leu Ser Thr Val Ile Trp Thr
                245                 250                 255

Trp Asn Pro Pro Glu Gly Ala Ser Ser Asn Cys Ser Leu Trp Tyr Phe
                260                 265                 270

Ser His Phe Gly Asp Lys Gln Asp Lys Lys Ile Ala Pro Glu Thr Arg
            275                 280                 285

Arg Ser Ile Glu Val Pro Leu Asn Glu Arg Ile Cys Leu Gln Val Gly
            290                 295                 300

Ser Gln Cys Ser Thr Asn Glu Ser Glu Lys Pro Ser Ile Leu Val Glu
305                 310                 315                 320

Lys Cys Ile Ser Pro Pro Glu Gly Asp Pro Glu Ser Ala Val Thr Glu
                325                 330                 335

Leu Gln Cys Ile Trp His Asn Leu Ser Tyr Met Lys Cys Ser Trp Leu
            340                 345                 350

Pro Gly Arg Asn Thr Ser Pro Asp Thr Asn Tyr Thr Leu Tyr Tyr Trp
            355                 360                 365

His Arg Ser Leu Glu Lys Ile His Gln Cys Glu Asn Ile Phe Arg Glu
            370                 375                 380

Gly Gln Tyr Phe Gly Cys Ser Phe Asp Leu Thr Lys Val Lys Asp Ser
385                 390                 395                 400

Ser Phe Glu Gln His Ser Val Gln Ile Met Val Lys Asp Asn Ala Gly
                405                 410                 415

Lys Ile Lys Pro Ser Phe Asn Ile Val Pro Leu Thr Ser Arg Val Lys
            420                 425                 430

Pro Asp Pro Pro His Ile Lys Asn Leu Ser Phe His Asn Asp Asp Leu
            435                 440                 445

Tyr Val Gln Trp Glu Asn Pro Gln Asn Phe Ile Ser Arg Cys Leu Phe
            450                 455                 460

Tyr Glu Val Glu Val Asn Asn Ser Gln Thr Glu Thr His Asn Val Phe
465                 470                 475                 480

Tyr Val Gln Glu Ala Lys Cys Glu Asn Pro Glu Phe Glu Arg Asn Val
                485                 490                 495

Glu Asn Thr Ser Cys Phe Met Val Pro Gly Val Leu Pro Asp Thr Leu
            500                 505                 510

Asn Thr Val Arg Ile Arg Val Lys Thr Asn Lys Leu Cys Tyr Glu Asp
            515                 520                 525

Asp Lys Leu Trp Ser Asn Trp Ser Gln Glu Met Ser Ile Gly Lys Lys
530                 535                 540

Arg Asn Ser Thr Gly Glu Ser Lys Tyr Gly Pro Pro Cys Pro Pro Cys
545                 550                 555                 560

Pro Ala Pro Glu Phe Leu Gly Gly Pro Ser Val Phe Leu Phe Pro Pro
                565                 570                 575

Lys Pro Lys Asp Thr Leu Met Ile Ser Arg Thr Pro Glu Val Thr Cys
            580                 585                 590
```

-continued

| | | | | | | | | | | | | | | |
|---|---|---|---|---|---|---|---|---|---|---|---|---|---|---|
|Val|Val|Val|Asp|Val|Ser|Gln|Glu|Asp|Pro|Glu|Val|Gln|Phe|Asn|Trp|
| | |595| | | |600| | | |605| | | | |

Tyr Val Asp Gly Val Glu Val His Asn Ala Lys Thr Lys Pro Arg Glu
                610                 615                 620

Glu Gln Phe Asn Ser Thr Tyr Arg Val Val Ser Val Leu Thr Val Leu
625                 630                 635                 640

His Gln Asp Trp Leu Asn Gly Lys Glu Tyr Lys Cys Lys Val Ser Asn
                645                 650                 655

Lys Gly Leu Pro Ser Ser Ile Glu Lys Thr Ile Ser Lys Ala Lys Gly
                660                 665                 670

Gln Pro Arg Glu Pro Gln Val Tyr Thr Leu Pro Pro Ser Gln Glu Glu
                675                 680                 685

Met Thr Lys Asn Gln Val Ser Leu Thr Cys Leu Val Lys Gly Phe Tyr
        690                 695                 700

Pro Ser Asp Ile Ala Val Glu Trp Glu Ser Asn Gly Gln Pro Glu Asn
705                 710                 715                 720

Asn Tyr Lys Thr Thr Pro Pro Val Leu Asp Ser Asp Gly Ser Phe Phe
                725                 730                 735

Leu Tyr Ser Arg Leu Thr Val Asp Lys Ser Arg Trp Gln Glu Gly Asn
                740                 745                 750

Val Phe Ser Cys Ser Val Met His Glu Ala Leu His Asn His Tyr Thr
            755                 760                 765

Gln Lys Ser Leu Ser Leu Ser Leu Gly Lys
    770                 775

<210> SEQ ID NO 57
<211> LENGTH: 2349
<212> TYPE: DNA
<213> ORGANISM: Homo sapiens

<400> SEQUENCE: 57

```
atggtgtggc cggcgcggct ctgcgggctg tgggcgctgc tgctctgcgc cggcggcggg      60
ggcgggggcg ggggcgccgc gcctacggaa actcagccac tgtgacaaa tttgagtgtc      120
tctgttgaaa acctcagcac agtaatatgg acatggaatc caccgaggg agccagctca      180
aattgtagtc tatggtattt tagtcatttt ggcgacaaac aagataagaa atagctccg      240
gaaactcgtc gttcaataga agtaccctg aatgagagga tttgtctgca agtggggtcc      300
cagtgtagca ccaatgagag tgagaagcct agcatttgg ttgaaaatg catctcaccc      360
ccagaaggtg atcctgagtc tgctgtgact gagcttcaat gcatttggca caacctgagc      420
tacatgaagt gttcttggct ccctggaagg aataccagtc ccgacactaa ctatactctc      480
tactattggc acagaagcct ggaaaaaatt catcaatgtg aaaacatctt tagagaaggc      540
caatactttg gttgttcctt tgatctgacc aaagtgaagg attccagttt tgaacaacac      600
agtgtccaaa taatggtcaa ggataatgca ggaaaaatta accatccctt caatatagtg      660
cctttaactt cccgtgtgaa acctgatcct ccacatatta aaaacctctc cttccacaat      720
gatgacctat atgtgcaatg ggagaatcca cagaatttta ttagcagatg cctatttta      780
gaagtagaag tcaataacag ccaaactgag acacataatg ttttctacgt ccaagaggct      840
aaatgtgaga atccagaatt tgagagaaat gtggagaata catcttgttt catggtccct      900
ggtgttcttc ctgatacttt gaacacagtc agaataagag tcaaaacaaa taagttatgc      960
tatgaggatg acaaactctg gagtaattgg agccaagaaa tgagtatagg taagaagcgc     1020
aattccacag ggaacatgaa ggtcttgcag gagcccacct gcgtctccga ctacatgagc     1080
```

-continued

```
atctctactt gcgagtggaa gatgaatggt cccaccaatt gcagcaccga gctccgcctg    1140
ttgtaccagc tggtttttct gctctccgaa gcccacacgt gtatccctga acaacgga     1200 ggcgcgggt gcgtgtgcca cctgctcatg gatgacgtgg tcagtgcgga taactataca   1260
ctggacctgt gggctgggca gcagctgctg tggaagggct ccttcaagcc cagcgagcat  1320
gtgaaaccca gggccccagg aaacctgaca gttcacacca atgtctccga cactctgctg   1380
ctgacctgga gcaacccgta tcccctgac aattacctgt ataatcatct cacctatgca   1440
gtcaacattt ggagtgaaaa cgacccggca gatttcagaa tctataacgt gacctaccta   1500
gaaccctccc tccgcatcgc agccagcacc ctgaagtctg ggatttccta cagggcacgc   1560
gtacgggcct gggctcagag ctataacacc acctggagtg agtggagccc cagcaccaag   1620
tggcacaact cctacaggga gcccttcgag cagaccggag agtccaaata cggtccgcca   1680 tgccaccat gcccagcacc tgagttcctg gggggaccat cagtcttcct gttcccccca    1740
aaacccaagg acactctcat gatctcccgg acccctgagg tcacgtgcgt ggtggtggac   1800
gtgagccagg aagaccccga ggtccagttc aactggtacg tggatggcgt ggaggtgcat   1860
aatgccaaga caaagccgcg ggaggagcag ttcaacagca cgtaccgtgt ggtcagcgtc   1920
ctcaccgtcc tgcaccagga ctggctgaac ggcaaggagt acaagtgcaa ggtctccaac   1980
aaaggcctcc cgtcctccat cgagaaaacc atctccaaag ccaaagggca gccccgagag   2040
ccacaggtgt acaccctgcc cccatcccag gaggagatga ccaagaacca ggtcagcctg   2100
acctgcctgg tcaaaggctt ctaccccagc gacatcgccg tggagtggga gagcaatggg   2160
cagccggaga acaactacaa gaccacgcct cccgtgctgg actccgacgg ctccttcttc   2220
ctctacagca ggctaaccgt ggacaagagc aggtggcagg aggggaatgt cttctcatgc   2280
tccgtgatgc atgaggctct gcacaaccac tacacacaga gagcctctc cctgtctctg     2340 ggtaaatga                                                              2349
```

<210> SEQ ID NO 58
<211> LENGTH: 782
<212> TYPE: PRT
<213> ORGANISM: Homo sapiens

<400> SEQUENCE: 58

```
Met Val Trp Pro Ala Arg Leu Cys Gly Leu Trp Ala Leu Leu Leu Cys
 1               5                  10                  15

Ala Gly Gly Gly Gly Gly Gly Gly Ala Ala Pro Thr Glu Thr Gln
            20                  25                  30

Pro Pro Val Thr Asn Leu Ser Val Ser Val Glu Asn Leu Ser Thr Val
        35                  40                  45

Ile Trp Thr Trp Asn Pro Pro Glu Gly Ala Ser Ser Asn Cys Ser Leu
    50                  55                  60

Trp Tyr Phe Ser His Phe Gly Asp Lys Gln Asp Lys Lys Ile Ala Pro
65                  70                  75                  80

Glu Thr Arg Arg Ser Ile Glu Val Pro Leu Asn Glu Arg Ile Cys Leu
                85                  90                  95

Gln Val Gly Ser Gln Cys Ser Thr Asn Glu Ser Glu Lys Pro Ser Ile
            100                 105                 110

Leu Val Glu Lys Cys Ile Ser Pro Pro Glu Gly Asp Pro Glu Ser Ala
        115                 120                 125

Val Thr Glu Leu Gln Cys Ile Trp His Asn Leu Ser Tyr Met Lys Cys
    130                 135                 140
```

```
Ser Trp Leu Pro Gly Arg Asn Thr Ser Pro Asp Thr Asn Tyr Thr Leu
145                 150                 155                 160

Tyr Tyr Trp His Arg Ser Leu Glu Lys Ile His Gln Cys Glu Asn Ile
            165                 170                 175

Phe Arg Glu Gly Gln Tyr Phe Gly Cys Ser Phe Asp Leu Thr Lys Val
        180                 185                 190

Lys Asp Ser Ser Phe Glu Gln His Ser Val Gln Ile Met Val Lys Asp
    195                 200                 205

Asn Ala Gly Lys Ile Lys Pro Ser Phe Asn Ile Val Pro Leu Thr Ser
210                 215                 220

Arg Val Lys Pro Asp Pro His Ile Lys Asn Leu Ser Phe His Asn
225                 230                 235                 240

Asp Asp Leu Tyr Val Gln Trp Glu Asn Pro Gln Asn Phe Ile Ser Arg
            245                 250                 255

Cys Leu Phe Tyr Glu Val Glu Val Asn Asn Ser Gln Thr Glu Thr His
            260                 265                 270

Asn Val Phe Tyr Val Gln Glu Ala Lys Cys Glu Asn Pro Glu Phe Glu
        275                 280                 285

Arg Asn Val Glu Asn Thr Ser Cys Phe Met Val Pro Gly Val Leu Pro
        290                 295                 300

Asp Thr Leu Asn Thr Val Arg Ile Arg Val Lys Thr Asn Lys Leu Cys
305                 310                 315                 320

Tyr Glu Asp Asp Lys Leu Trp Ser Asn Trp Ser Gln Glu Met Ser Ile
            325                 330                 335

Gly Asn Met Lys Val Leu Gln Gly Lys Lys Arg Asn Ser Thr Glu Pro
            340                 345                 350

Thr Cys Val Ser Asp Tyr Met Ser Ile Ser Thr Cys Glu Trp Lys Met
            355                 360                 365

Asn Gly Pro Thr Asn Cys Ser Thr Glu Leu Arg Leu Leu Tyr Gln Leu
        370                 375                 380

Val Phe Leu Leu Ser Glu Ala His Thr Cys Ile Pro Glu Asn Asn Gly
385                 390                 395                 400

Gly Ala Gly Cys Val Cys His Leu Leu Met Asp Asp Val Val Ser Ala
                405                 410                 415

Asp Asn Tyr Thr Leu Asp Leu Trp Ala Gly Gln Gln Leu Leu Trp Lys
            420                 425                 430

Gly Ser Phe Lys Pro Ser Glu His Val Lys Pro Arg Ala Pro Gly Asn
        435                 440                 445

Leu Thr Val His Thr Asn Val Ser Asp Thr Leu Leu Leu Thr Trp Ser
450                 455                 460

Asn Pro Tyr Pro Pro Asp Asn Tyr Leu Tyr Asn His Leu Thr Tyr Ala
465                 470                 475                 480

Val Asn Ile Trp Ser Glu Asn Asp Pro Ala Asp Phe Arg Ile Tyr Asn
            485                 490                 495

Val Thr Tyr Leu Glu Pro Ser Leu Arg Ile Ala Ala Ser Thr Leu Lys
        500                 505                 510

Ser Gly Ile Ser Tyr Arg Ala Arg Val Arg Ala Trp Ala Gln Ser Tyr
        515                 520                 525

Asn Thr Thr Trp Ser Glu Trp Ser Pro Ser Thr Lys Trp His Asn Ser
        530                 535                 540

Tyr Arg Thr Gly Glu Pro Phe Glu Gln Glu Ser Lys Tyr Gly Pro Pro
545                 550                 555                 560
```

```
Cys Pro Pro Cys Pro Ala Pro Glu Phe Leu Gly Gly Pro Ser Val Phe
                565                 570                 575
Leu Phe Pro Pro Lys Pro Lys Asp Thr Leu Met Ile Ser Arg Thr Pro
            580                 585                 590
Glu Val Thr Cys Val Val Val Asp Val Ser Gln Glu Asp Pro Glu Val
        595                 600                 605
Gln Phe Asn Trp Tyr Val Asp Gly Val Glu Val His Asn Ala Lys Thr
    610                 615                 620
Lys Pro Arg Glu Glu Gln Phe Asn Ser Thr Tyr Arg Val Val Ser Val
625                 630                 635                 640
Leu Thr Val Leu His Gln Asp Trp Leu Asn Gly Lys Glu Tyr Lys Cys
                645                 650                 655
Lys Val Ser Asn Lys Gly Leu Pro Ser Ser Ile Glu Lys Thr Ile Ser
            660                 665                 670
Lys Ala Lys Gly Gln Pro Arg Glu Pro Gln Val Tyr Thr Leu Pro Pro
        675                 680                 685
Ser Gln Glu Glu Met Thr Lys Asn Gln Val Ser Leu Thr Cys Leu Val
    690                 695                 700
Lys Gly Phe Tyr Pro Ser Asp Ile Ala Val Glu Trp Glu Ser Asn Gly
705                 710                 715                 720
Gln Pro Glu Asn Asn Tyr Lys Thr Thr Pro Pro Val Leu Asp Ser Asp
                725                 730                 735
Gly Ser Phe Phe Leu Tyr Ser Arg Leu Thr Val Asp Lys Ser Arg Trp
            740                 745                 750
Gln Glu Gly Asn Val Phe Ser Cys Ser Val Met His Glu Ala Leu His
        755                 760                 765
Asn His Tyr Thr Gln Lys Ser Leu Ser Leu Ser Leu Gly Lys
    770                 775                 780

<210> SEQ ID NO 59
<211> LENGTH: 2337
<212> TYPE: DNA
<213> ORGANISM: Homo sapiens

<400> SEQUENCE: 59
atggtgtggc tttgctctgg gctcctgttc cctgtgagct gcctggtcct gctgcaggtg      60
gcaagctctg ggaacatgaa ggtcttgcag gagcccacct gcgtctccga ctacatgagc     120
atctctactt gcgagtggaa gatgaatggt cccaccaatt gcagcaccga gctccgcctg     180
ttgtaccagc tggtttttct gctctccgaa gcccacacgt gtatccctga aacaacggga     240
ggcgcgggt gcgtgtgcca cctgctcatg gatgacgtgg tcagtgcgga taactataca      300
ctggacctgt gggctgggca gcagctgctg tggaagggcc cttcaagcc cagcgagcat      360
gtgaaaccca gggccccagg aaacctgaca gttcacacca tgtctccga cactctgctg      420
ctgacctgga gcaacccgta tcccctgac aattacctgt ataatcatct caccatgtgca    480
gtcaacattt ggagtgaaaa cgacccggca gatttcagaa tctataacgt gacctaccta     540
gaaccctccc tccgcatcgc agccagcacc ctgaagtctg ggatttccta cagggcacgc     600
gtacgggcct gggctcagag ctataacacc acctggagtg agtggagccc cagcaccaag     660
tggcacaact cctacaggga gcccttcgag caggcgccta cggaaactca gccacctgtg     720
acaaatttga gtgtctctgt tgaaaacctc gcgacagtaa tatggacatg aatccaccc     780
gagggagcca gctcaaattg tagtctatgg tattttagtc attttggcga caaacaagat    840
aagaaaatag ctccggaaac tcgtcgttca atagaagtac ccctgaatga gaggatttgt     900
```

```
ctgcaagtgg ggtcccagtg tagcaccaat gagagtgaga agcctagcat tttggttgaa    960
aaatgcatct caccccagaa aggtgatcct gagtctgctg tgactgagct tcaatgcatt   1020
tggcacaacc tgagctacat gaagtgttct tggctccctg aaggaatac cagtcccgac   1080
actaactata ctctctacta ttggcacaga agcctggaaa aaattcatca atgtgaaaac   1140
atctttagag aaggccaata ctttggttgt tcctttgatc tgaccaaagt gaaggattcc   1200
agttttgaac aacacagtgt ccaaataatg gtcaaggata atgcaggaaa aattaaacca   1260
tccttcaata tagtgccttt aacttcccgt gtgaaacctg atcctccaca tattaaaaac   1320
ctctccttcc acaatgatga cctatatgtg caatgggaga atccacagaa ttttattagc   1380
agatgcctat tttatgaagt agaagtcaat aacagccaaa ctgagacaca taatgttttc   1440
tacgtccaag aggctaaatg tgagaatcca gaatttgaga gaaatgtgga gaatacatct   1500
tgtttcatgg tccctggtgt tcttcctgat actttgaaca cagtcagaat aagagtcaaa   1560
acaaataagt tatgctatga ggatgacaaa ctctggagta attggagcca agaaatgagt   1620
ataggtaaga agcgcaattc caccggagag tccaaatacg gtccgccatg cccaccatgc   1680
ccagcacctg agttcctggg gggaccatca gtcttcctgt tccccccaaa acccaaggac   1740
actctcatga tctcccggac ccctgaggtc acgtgcgtgg tggtggacgt gagccaggaa   1800
gaccccgagg tccagttcaa ctggtacgtg gatggcgtgg aggtgcataa tgccaagaca   1860
aagccgcggg aggagcagtt caacagcacg taccgtgtgg tcagcgtcct caccgtcctg   1920
caccaggact ggctgaacgg caaggagtac aagtgcaagg tctccaacaa aggcctcccg   1980
tcctccatcg agaaaaccat ctccaaagcc aaagggcagc cccgagagcc acaggtgtac   2040
accctgcccc catcccagga ggagatgacc aagaaccagg tcagcctgac ctgcctggtc   2100
aaaggcttct accccagcga catcgccgtg gagtgggaga gcaatgggca gccggagaac   2160
aactacaaga ccacgcctcc cgtgctggac tccgacggct ccttcttcct ctacagcagg   2220
ctaaccgtgg acaagagcag gtggcaggag gggaatgtct tctcatgctc cgtgatgcat   2280
gaggctctgc acaaccacta cacacagaag agcctctccc tgtctctggg taaatga     2337
```

<210> SEQ ID NO 60
<211> LENGTH: 778
<212> TYPE: PRT
<213> ORGANISM: Homo sapiens

<400> SEQUENCE: 60

```
Met Val Trp Leu Cys Ser Gly Leu Leu Phe Pro Val Ser Cys Leu Val
 1               5                  10                  15

Leu Leu Gln Val Ala Ser Ser Gly Asn Met Lys Val Leu Gln Glu Pro
            20                  25                  30

Thr Cys Val Ser Asp Tyr Met Ser Ile Ser Thr Cys Glu Trp Lys Met
        35                  40                  45

Asn Gly Pro Thr Asn Cys Ser Thr Glu Leu Arg Leu Leu Tyr Gln Leu
    50                  55                  60

Val Phe Leu Leu Ser Glu Ala His Thr Cys Ile Pro Glu Asn Asn Gly
65                  70                  75                  80

Gly Ala Gly Cys Val Cys His Leu Leu Met Asp Asp Val Val Ser Ala
                85                  90                  95

Asp Asn Tyr Thr Leu Asp Leu Trp Ala Gly Gln Gln Leu Leu Trp Lys
            100                 105                 110

Gly Ser Phe Lys Pro Ser Glu His Val Lys Pro Arg Ala Pro Gly Asn
```

```
                115                 120                 125
Leu Thr Val His Thr Asn Val Ser Asp Thr Leu Leu Thr Trp Ser
    130                 135                 140
Asn Pro Tyr Pro Pro Asp Asn Tyr Leu Tyr Asn His Leu Thr Tyr Ala
145                 150                 155                 160
Val Asn Ile Trp Ser Glu Asn Asp Pro Ala Asp Phe Arg Ile Tyr Asn
                165                 170                 175
Val Thr Tyr Leu Glu Pro Ser Leu Arg Ile Ala Ala Ser Thr Leu Lys
                180                 185                 190
Ser Gly Ile Ser Tyr Arg Ala Arg Val Arg Ala Trp Ala Gln Ser Tyr
                195                 200                 205
Asn Thr Thr Trp Ser Glu Trp Ser Pro Ser Thr Lys Trp His Asn Ser
    210                 215                 220
Tyr Arg Glu Pro Phe Glu Gln Ala Pro Thr Glu Thr Gln Pro Pro Val
225                 230                 235                 240
Thr Asn Leu Ser Val Ser Val Glu Asn Leu Ala Thr Val Ile Trp Thr
                245                 250                 255
Trp Asn Pro Pro Glu Gly Ala Ser Ser Asn Cys Ser Leu Trp Tyr Phe
                260                 265                 270
Ser His Phe Gly Asp Lys Gln Asp Lys Lys Ile Ala Pro Glu Thr Arg
            275                 280                 285
Arg Ser Ile Glu Val Pro Leu Asn Glu Arg Ile Cys Leu Gln Val Gly
            290                 295                 300
Ser Gln Cys Ser Thr Asn Glu Ser Glu Lys Pro Ser Ile Leu Val Glu
305                 310                 315                 320
Lys Cys Ile Ser Pro Pro Glu Gly Asp Pro Glu Ser Ala Val Thr Glu
                325                 330                 335
Leu Gln Cys Ile Trp His Asn Leu Ser Tyr Met Lys Cys Ser Trp Leu
                340                 345                 350
Pro Gly Arg Asn Thr Ser Pro Asp Thr Asn Tyr Thr Leu Tyr Tyr Trp
            355                 360                 365
His Arg Ser Leu Glu Lys Ile His Gln Cys Glu Asn Ile Phe Arg Glu
    370                 375                 380
Gly Gln Tyr Phe Gly Cys Ser Phe Asp Leu Thr Lys Val Lys Asp Ser
385                 390                 395                 400
Ser Phe Glu Gln His Ser Val Gln Ile Met Val Lys Asp Asn Ala Gly
                405                 410                 415
Lys Ile Lys Pro Ser Phe Asn Ile Val Pro Leu Thr Ser Arg Val Lys
            420                 425                 430
Pro Asp Pro Pro His Ile Lys Asn Leu Ser Phe His Asn Asp Asp Leu
            435                 440                 445
Tyr Val Gln Trp Glu Asn Pro Gln Asn Phe Ile Ser Arg Cys Leu Phe
    450                 455                 460
Tyr Glu Val Glu Val Asn Asn Ser Gln Thr Glu Thr His Asn Val Phe
465                 470                 475                 480
Tyr Val Gln Glu Ala Lys Cys Glu Asn Pro Glu Phe Glu Arg Asn Val
                485                 490                 495
Glu Asn Thr Ser Cys Phe Met Val Pro Gly Val Leu Pro Asp Thr Leu
            500                 505                 510
Asn Thr Val Arg Ile Arg Val Lys Thr Asn Lys Leu Cys Tyr Glu Asp
            515                 520                 525
Asp Lys Leu Trp Ser Asn Trp Ser Gln Glu Met Ser Ile Gly Lys Lys
    530                 535                 540
```

-continued

```
Arg Asn Ser Thr Gly Glu Ser Lys Tyr Gly Pro Pro Cys Pro Pro Cys
545                 550                 555                 560

Pro Ala Pro Glu Phe Leu Gly Gly Pro Ser Val Phe Leu Phe Pro Pro
                565                 570                 575

Lys Pro Lys Asp Thr Leu Met Ile Ser Arg Thr Pro Glu Val Thr Cys
            580                 585                 590

Val Val Val Asp Val Ser Gln Glu Asp Pro Glu Val Gln Phe Asn Trp
        595                 600                 605

Tyr Val Asp Gly Val Glu Val His Asn Ala Lys Thr Lys Pro Arg Glu
    610                 615                 620

Glu Gln Phe Asn Ser Thr Tyr Arg Val Val Ser Val Leu Thr Val Leu
625                 630                 635                 640

His Gln Asp Trp Leu Asn Gly Lys Glu Tyr Lys Cys Lys Val Ser Asn
                645                 650                 655

Lys Gly Leu Pro Ser Ser Ile Glu Lys Thr Ile Ser Lys Ala Lys Gly
            660                 665                 670

Gln Pro Arg Glu Pro Gln Val Tyr Thr Leu Pro Pro Ser Gln Glu Glu
        675                 680                 685

Met Thr Lys Asn Gln Val Ser Leu Thr Cys Leu Val Lys Gly Phe Tyr
    690                 695                 700

Pro Ser Asp Ile Ala Val Glu Trp Glu Ser Asn Gly Gln Pro Glu Asn
705                 710                 715                 720

Asn Tyr Lys Thr Thr Pro Pro Val Leu Asp Ser Asp Gly Ser Phe Phe
                725                 730                 735

Leu Tyr Ser Arg Leu Thr Val Asp Lys Ser Arg Trp Gln Glu Gly Asn
            740                 745                 750

Val Phe Ser Cys Ser Val Met His Glu Ala Leu His Asn His Tyr Thr
        755                 760                 765

Gln Lys Ser Leu Ser Leu Ser Leu Gly Lys
770                 775
```

We claim:

1. A fusion polypeptide having the amino acid sequence of SEQ ID NO: 30, wherein the fusion polypeptide forms a multimer capable of binding interleukin-4 (IL-4) and/or IL-13 to form a nonfunctional complex.

2. An isolated nucleic acid molecule encoding the fusion polypeptide of claim 1.

3. The isolated nucleic acid of claim 2, wherein the nucleic acid molecule comprises the sequence of SEQ ID NO:29.

4. A fusion polypeptide having the amino acid sequence of SEQ ID NO: 32, wherein the fusion polypeptide forms a multimer capable of binding interleukin-4 (IL-4) and/or IL-13to form a nonfunctional complex.

5. An isolated nucleic acid molecule encoding the fusion polypeptide of claim 4.

6. The isolated nucleic acid of claim 5, wherein the nucleic acid molecule comprises the sequence of SEQ ID NO:31.

7. A fusion polypeptide having the amino acid sequence of SEQ ID NO:34, wherein the fusion polypeptide forms a multimer capable of binding interleukin-4 (IL-4) and/or IL-13to form a nonfunctional complex.

8. An isolated nucleic acid molecule encoding the fusion polypeptide of claim 7.

9. The isolated nucleic acid of claim 8, wherein the nucleic acid molecule comprises the sequence of SEQ ID NO:33.

10. The isolated nucleic acid of claim 9, wherein nucleotide 311 is changed from C to T.

11. The isolated nucleic acid of claim 9, wherein nucleotide 1105 is changed from A to G.

12. The isolated nucleic acid of claim 9, wherein nucleotides TCCGGA are inserted between nucleotides 951 and 952.

13. The isolated nucleic acid of claim 9, wherein nucleotides TCCGGA are inserted between nucleotides 951 and 952, nucleotide 311 is changed from C to T, and nucleotide 1105 is changed from A to G.

14. A fusion polypeptide having the amino acid sequence of SEQ ID NO:36, wherein the fusion polypeptide forms a multimer capable of binding interleukin-4 (IL-4) and/or IL-13to form a nonfunctional complex.

15. An isolated nucleic acid molecule encoding the fusion polypeptide of claim 14.

16. The isolated nucleic acid of claim 15, wherein the nucleic acid molecule comprises the sequence of SEQ ID NO:35.

17. The isolated nucleic acid of claim 16, wherein nucleotide 935 is changed from C to T.

18. The isolated nucleic acid of claim 16, wherein nucleotides TCCGGA are inserted between nucleotides 624 and 625.

19. The isolated nucleic acid of claim 16, wherein nucleotide 154 is changed from A to G.

20. The isolated nucleic acid of claim 16, wherein nucleotide 935 is changed from C to T, nucleotides TCCGGA are inserted between nucleotides 624 and 625, and nucleotide 154 is changed from A to G.

21. A fusion polypeptide having the amino acid sequence of SEQ ID NO:38, wherein the fusion polypeptide forms a multimer capable of binding interleukin-4 (IL-4) and IL-13to form a nonfunctional complex.

22. An isolated nucleic acid molecule encoding the fusion polypeptide of claim 21.

23. The isolated nucleic acid of claim 22, wherein the nucleic acid molecule comprises the sequence of SEQ ID NO:37.

24. The isolated nucleic acid of claim 23, wherein nucleotide 311 is changed from C to T.

25. The isolated nucleic acid of claim 23, wherein nucleotide 1105 is changed from A to G.

26. The isolated nucleic acid of claim 23, wherein nucleotides TCCGGA are inserted between nucleotides 951 and 952.

27. The isolated nucleic acid of claim 23, wherein nucleotides TCCGGA are inserted between nucleotides 951 and 952, nucleotide 311 is changed from C to T, and nucleotide 1105 is changed from A to G.

28. A fusion polypeptide having the amino acid sequence of SEQ ID NO:40, wherein the fusion polypeptide forms a multimer capable of binding interleukin-4 (IL-4) and/or IL-13to form a nonfunctional complex.

29. An isolated nucleic acid molecule encoding the fusion polypeptide of claim 28.

30. The isolated nucleic acid of claim 29, wherein the nucleic acid molecule comprises the sequence of SEQ ID NO:39.

31. The isolated nucleic acid of claim 30, wherein nucleotide 935 is changed from C to T.

32. The isolated nucleic acid of claim 30, wherein nucleotides TCCGGA are inserted between nucleotides 624 and 625.

33. The isolated nucleic acid of claim 30, wherein nucleotide 154 is changed from A to G.

34. The isolated nucleic acid of claim 30, wherein nucleotide 935 is changed from C to T, nucleotides TCCGGA are inserted between nucleotides 624 and 625, and nucleotide 154 is changed from A to G.

35. A fusion polypeptide having the amino acid sequence of SEQ ID NO:42, wherein the fusion polypeptide forms a multimer capable of binding interleukin-4 (IL-4) and/or IL-13 to form a nonfunctional complex.

36. An isolated nucleic acid molecule encoding the fusion polypeptide of claim 35.

37. The isolated nucleic acid of claim 36, wherein the nucleic acid molecule comprises the sequence of SEQ ID NO:41.

38. The isolated nucleic acid of claim 37, wherein nucleotide 311 is changed from C to T.

39. The isolated nucleic acid of claim 37, wherein nucleotide 1105 is changed from A to G.

40. The isolated nucleic acid of claim 37, wherein nucleotides TCCGGA are inserted between nucleotides 951 and 952.

41. The isolated nucleic acid of claim 37, wherein nucleotides TCCGGA are inserted between nucleotides 951 and 952, nucleotide 311 is changed from C to T, and nucleotide 1105 is changed from A to G.

42. A fusion polypeptide having the amino acid sequence of SEQ ID NO:44, wherein the fusion polypeptide forms a multimer capable of binding interleukin-4 (IL-4) and/or IL-13 to form a nonfunctional complex.

43. An isolated nucleic acid molecule encoding the fusion polypeptide of claim 42.

44. The isolated nucleic acid of claim 43, wherein the nucleic acid molecule comprises the sequence of SEQ ID NO:43.

45. The isolated nucleic acid of claim 44, wherein nucleotide 935 is changed from C to T.

46. The isolated nucleic acid of claim 44, wherein nucleotides TCCGGA are inserted between nucleotides 624 and 625.

47. The isolated nucleic acid of claim 44, wherein nucleotide 154 is changed from A to G.

48. The isolated nucleic acid of claim 44, wherein nucleotide 935 is changed from C to T, nucleotides TCCGGA are inserted between nucleotides 624 and 625, and nucleotide 154 is changed from A to G.

49. A fusion polypeptide having the amino acid sequence of SEQ ID NO:46, wherein the fusion polypeptide forms a multimer capable of binding interleukin-4 (IL-4) and/or IL-13 to form a nonfunctional complex.

50. An isolated nucleic acid molecule encoding the fusion polypeptide of claim 49.

51. The isolated nucleic acid of claim 50, wherein the nucleic acid molecule comprises the sequence of SEQ ID NO:45.

52. A fusion polypeptide having the amino acid sequence of SEQ ID NO:48, wherein the fusion polypeptide forms a multimer capable of binding interleukin-4 (IL-4) and/or IL-13 to form a nonfunctional complex.

53. An isolated nucleic acid molecule encoding the fusion polypeptide of claim 52.

54. The isolated nucleic acid of claim 53, wherein the nucleic acid molecule comprises the sequence of SEQ ID NO:47.

55. A fusion polypeptide having the amino acid sequence of SEQ ID NO:50, wherein the fusion polypeptide forms a multimer capable of binding interleukin-4 (IL-4) and/or IL-13 to form a nonfunctional complex.

56. An isolated nucleic acid molecule encoding the fusion polypeptide of claim 55.

57. The isolated nucleic acid of claim 56, wherein the nucleic acid molecule comprises the sequence of SEQ ID NO:49.

58. A fusion polypeptide having the amino acid sequence of SEQ ID NO:52, wherein the fusion polypeptide forms a multimer capable of binding interleukin-4 (IL-4) and/or IL-13 to form a nonfunctional complex.

59. An isolated nucleic acid molecule encoding the fusion polypeptide of claim 58.

60. The isolated nucleic acid of claim 59, wherein the nucleic acid molecule comprises the sequence of SEQ ID NO:51.

61. A fusion polypeptide having the amino acid sequence of SEQ ID NO:54, wherein the fusion polypeptide forms a multimer capable of binding interleukin-4 (IL-4) and/or IL-13 to form a nonfunctional complex.

62. An isolated nucleic acid molecule encoding the fusion polypeptide of claim 61.

63. The isolated nucleic acid of claim 62, wherein the nucleic acid molecule comprises the sequence of SEQ ID NO:53.

64. A fusion polypeptide having the amino acid sequence of SEQ ID NO:56, wherein the fusion polypeptide forms a multimer capable of binding interleukin-4 (IL-4) and/or IL-13 to form a nonfunctional complex.

65. An isolated nucleic acid molecule encoding the fusion polypeptide of claim 64.

66. The isolated nucleic acid of claim 65, wherein the nucleic acid molecule comprises the sequence of SEQ ID NO:55.

67. A fusion polypeptide having the amino acid sequence of SEQ ID NO:58, wherein the fusion polypeptide forms a multimer capable of binding interleukin-4 (IL-4) and/or IL-13 to form a nonfunctional complex.

68. An isolated nucleic acid molecule encoding the fusion polypeptide of claim 67.

69. The isolated nucleic acid of claim 68, wherein the nucleic acid molecule comprises the sequence of SEQ ID NO:57.

70. A fusion polypeptide having the amino acid sequence of SEQ ID NO:60, wherein the fusion polypeptide forms a multimer capable of binding interleukin-4 (IL-4) and/or IL-13 to form a nonfunctional complex.

71. An isolated nucleic acid molecule encoding the fusion polypeptide of claim 70.

72. The isolated nucleic acid of claim 71, wherein the nucleic acid molecule comprises the sequence of SEQ ID NO:59.

73. A pharmaceutical composition comprising a multimer of the fusion polypeptide of any one of claims 1, 4, 7, 14, 21, 28, 35, 42, 49, 52, 55, 58, 61, 64, 67 or 70, and a pharmaceutically acceptable carrier.

74. The pharmaceutical composition of claim 73, wherein the multimer is a dimer.

75. An isolated nucleic acid selected from the group consisting of SEQ ID NO: 29, 31, 33, 35, 37, 39, 41, 43, 45, 47, 49, 51, 53, 55, 57 and 59.

76. A vector that comprises the isolated nucleic acid molecule of claim 75.

77. The vector of claim 76, wherein the isolated nucleic acid molecule is operatively linked to an expression control sequence.

78. A host-vector system for the production of a fusion polypeptide, comprising the vector of claim 77, in a suitable host cell.

79. The host-vector system of claim 78, wherein the suitable host cell is a bacterial cell, yeast cell, insect cell, or mammalian cell.

80. The host-vector system of claim 79, wherein the suitable host cell is a CHO cell.

81. A method of producing a fusion polypeptide that comprises growing cells of the host-vector system of claim 78, under conditions permitting production of the fusion polypeptide and recovering the fusion polypeptide so produced.

* * * * *